(12) United States Patent
Peled Kamar et al.

(10) Patent No.: US 12,252,547 B2
(45) Date of Patent: Mar. 18, 2025

(54) AFFINITY ENTITIES COMPRISING A TCR-LIKE ANTIBODY BINDING DOMAIN WITH HIGH AFFINITY AND FINE SPECIFICITY AND USES OF SAME

(71) Applicant: ADICET THERAPEUTICS, INC., Redwood City, CA (US)

(72) Inventors: Mira Peled Kamar, Herzlia (IL); Galit Denkberg, Nofit (IL); Yoram Reiter, Haifa (IL); Ilan Beer, Haifa (IL); Keren Sinik, Ramat-Yishai (IL); Yael Teboul (Elbaz), Haifa (IL); Yael Shperber (Sery), Kfar-Vradim (IL); Reut Erel Segal, Haifa (IL); Ravit Oren, Haifa (IL); Dror Shmuel Alishekevitz, Kiryat-Tivon (IL)

(73) Assignee: ADICET THERAPEUTICS, INC., Redwood City, CA (US)

( * ) Notice: Subject to any disclaimer, the term of this patent is extended or adjusted under 35 U.S.C. 154(b) by 829 days.

(21) Appl. No.: 17/317,824

(22) Filed: May 11, 2021

(65) Prior Publication Data
US 2021/0388111 A1    Dec. 16, 2021

Related U.S. Application Data

(62) Division of application No. 15/579,616, filed as application No. PCT/IL2016/050600 on Jun. 8, 2016, now Pat. No. 11,001,642.

(30) Foreign Application Priority Data

Jun. 8, 2015 (NL) .................................. N2014935

(51) Int. Cl.
*C07K 16/30* (2006.01)
*A61P 35/00* (2006.01)
*C07K 16/28* (2006.01)
*C07K 16/40* (2006.01)
*G01N 33/574* (2006.01)
*A61K 39/00* (2006.01)

(52) U.S. Cl.
CPC .......... *C07K 16/3053* (2013.01); *A61P 35/00* (2018.01); *C07K 16/2809* (2013.01); *C07K 16/2833* (2013.01); *C07K 16/30* (2013.01); *C07K 16/40* (2013.01); *G01N 33/5743* (2013.01); *A61K 2039/505* (2013.01); *C07K 2317/21* (2013.01); *C07K 2317/31* (2013.01); *C07K 2317/32* (2013.01); *C07K 2317/34* (2013.01); *C07K 2317/55* (2013.01); *C07K 2317/622* (2013.01); *C07K 2317/73* (2013.01); *C07K 2317/92* (2013.01); *C07K 2319/00* (2013.01); *G01N 33/57492* (2013.01)

(58) Field of Classification Search
None
See application file for complete search history.

(56) References Cited

U.S. PATENT DOCUMENTS

2004/0185033 A1* 9/2004 Chaux ................ C07K 14/4748
424/93.71

* cited by examiner

*Primary Examiner* — Brad Duffy
(74) *Attorney, Agent, or Firm* — Todd Lorenz

(57) ABSTRACT

Affinity binding entities having TCRL binding domain and methods of their use are provided. More specifically these compositions bind HLA-A2/WT1+, HLA-A2/MAGE-A4, HLA-A2/MAGE-A9, HLA-A2/PAP or HLA-A2/TyrD+ cells and as such can be used in diagnostics and therapy.

16 Claims, 108 Drawing Sheets
Specification includes a Sequence Listing.

Figure 3:
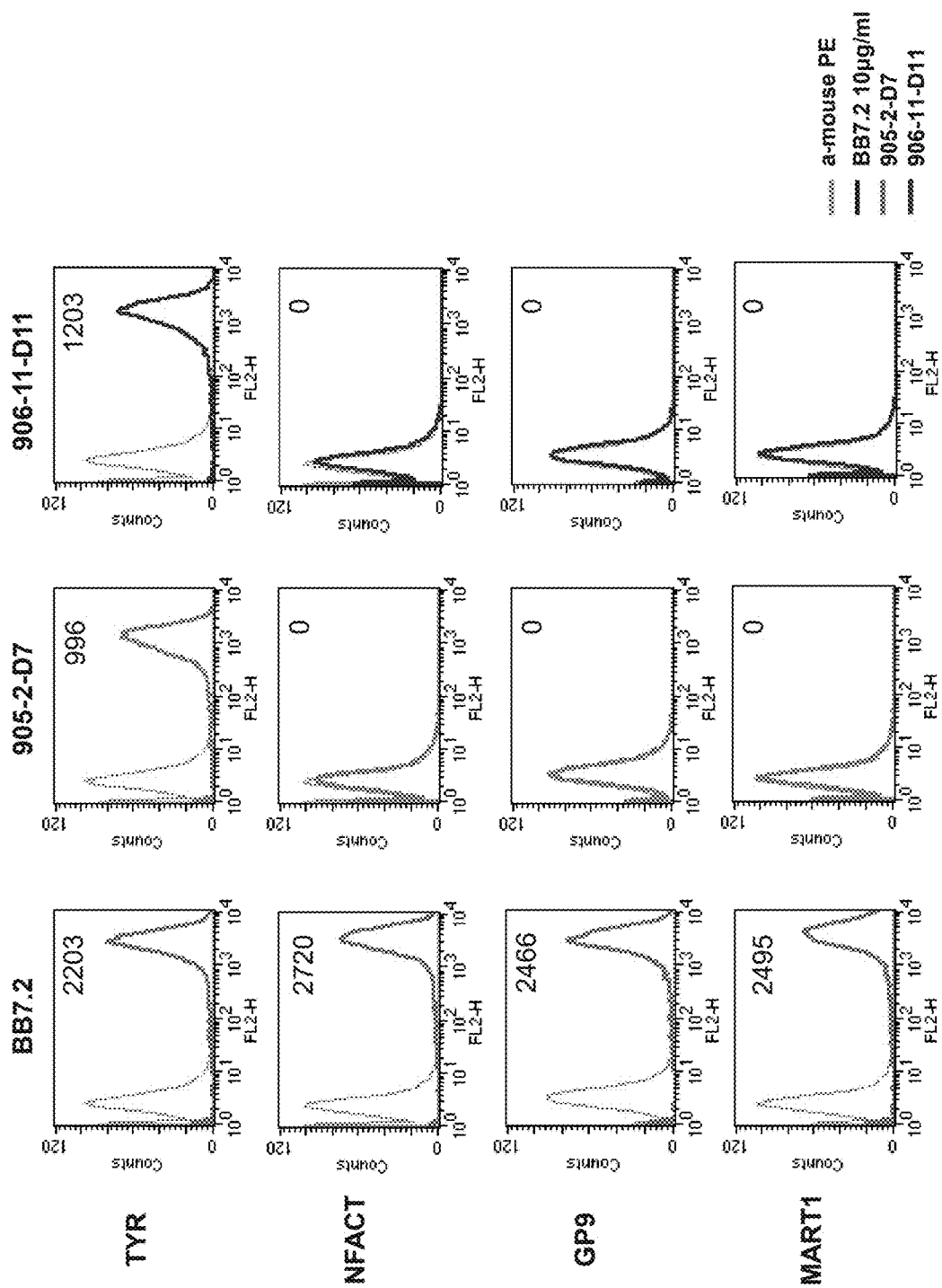

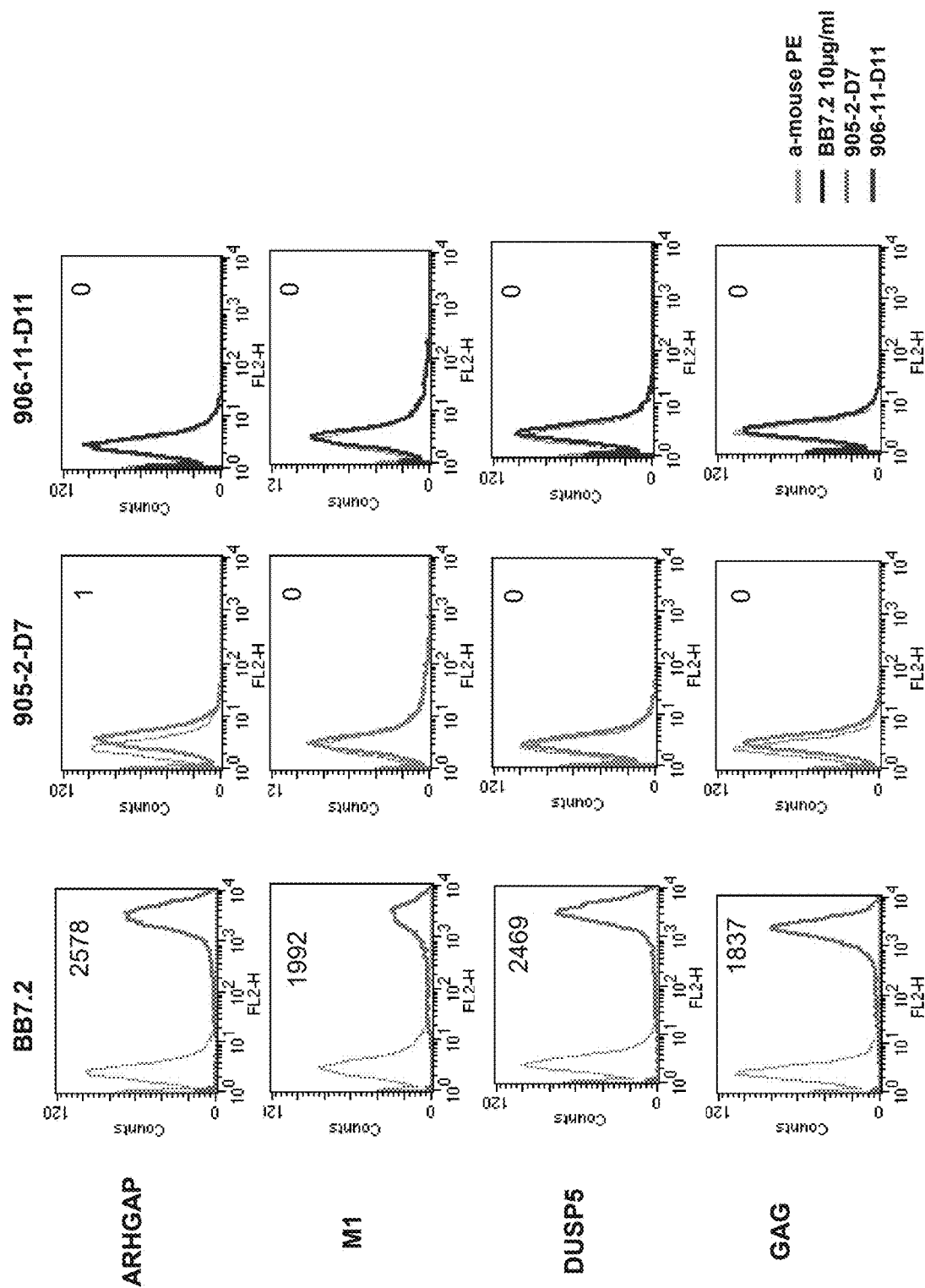
Fig. 3 - continued

Figure 4:
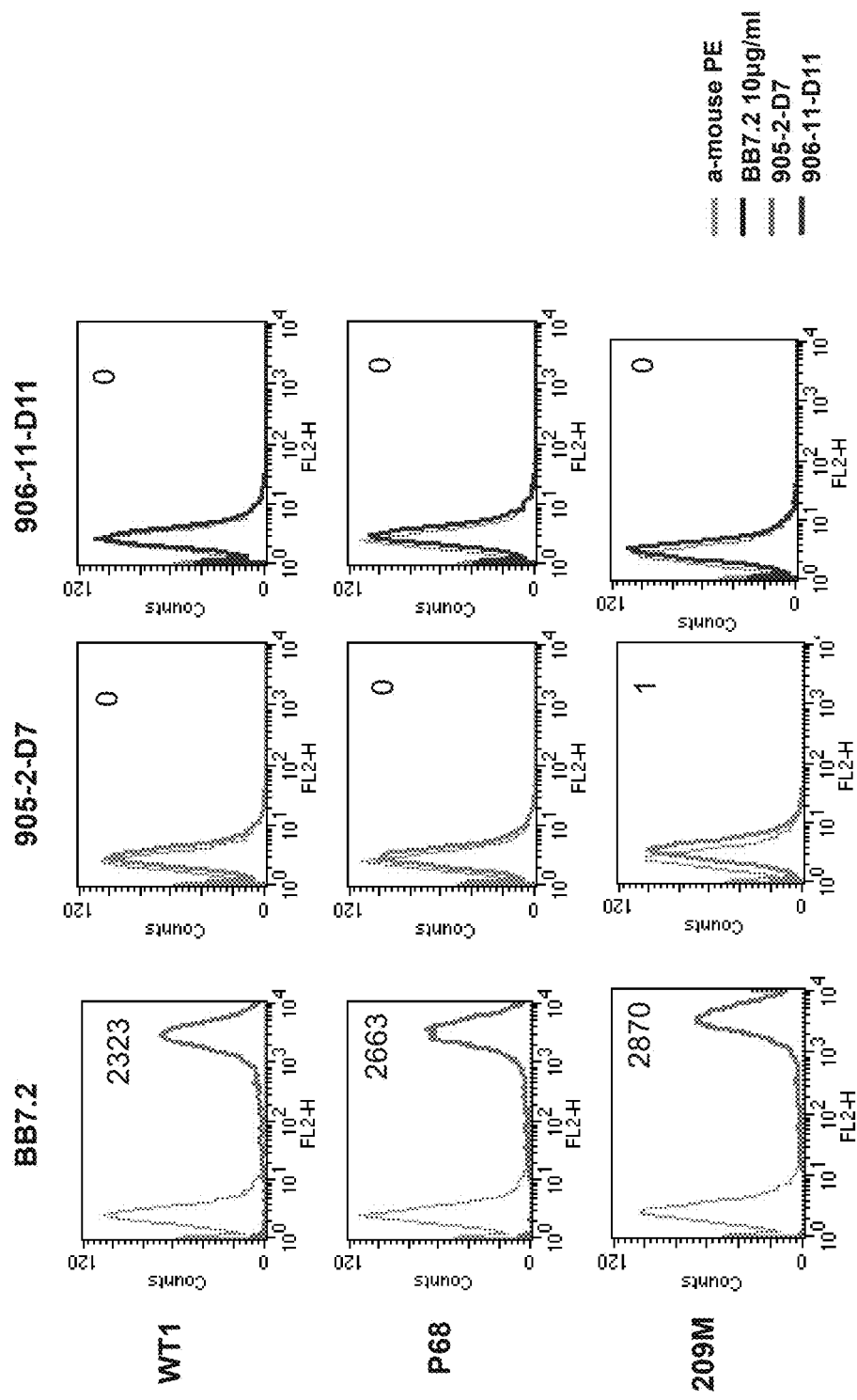

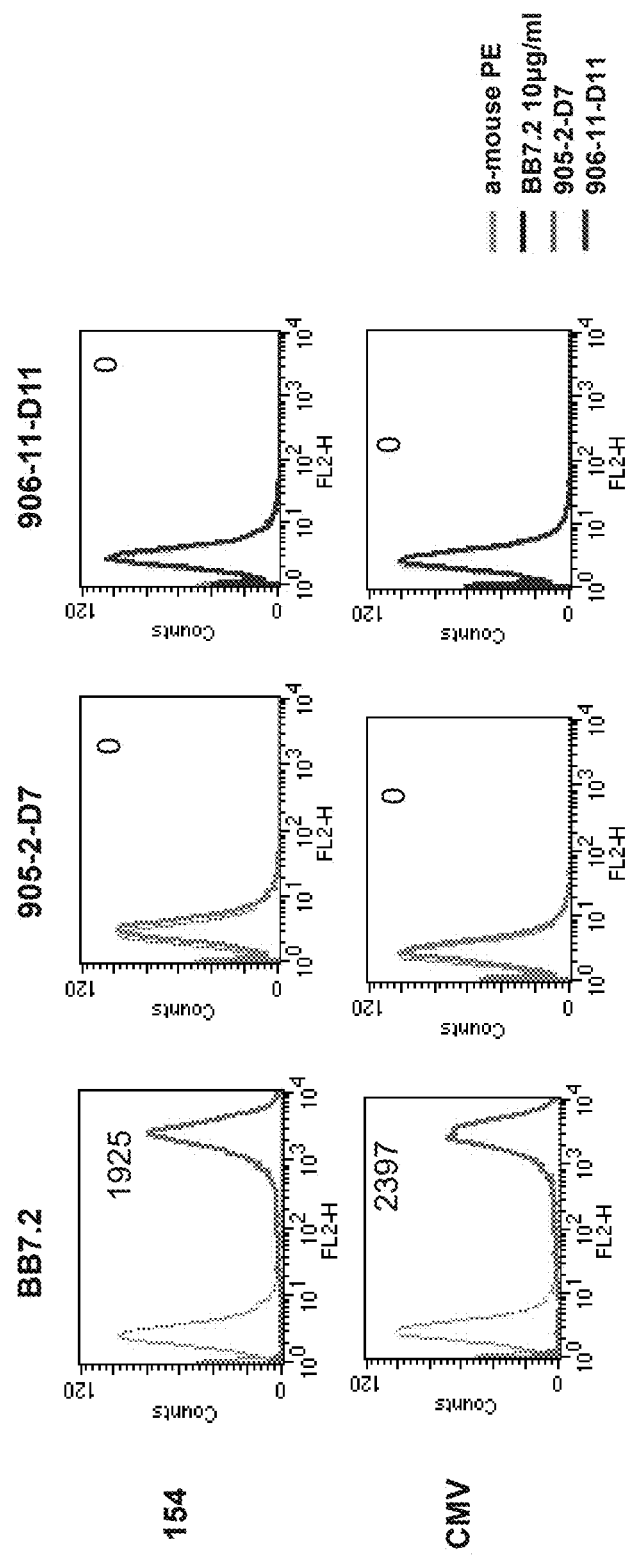
Fig. 4 - continued

Figure 5:
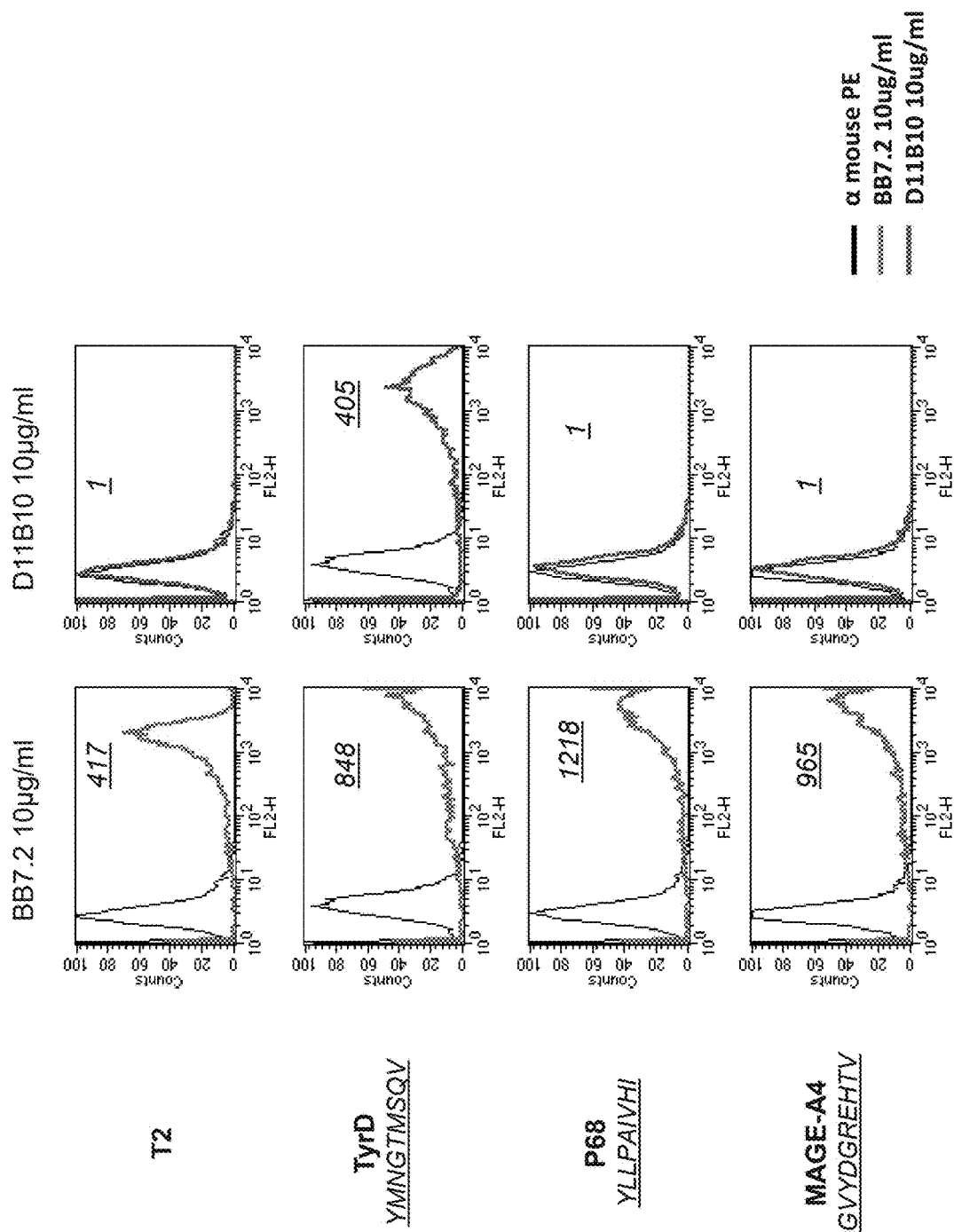

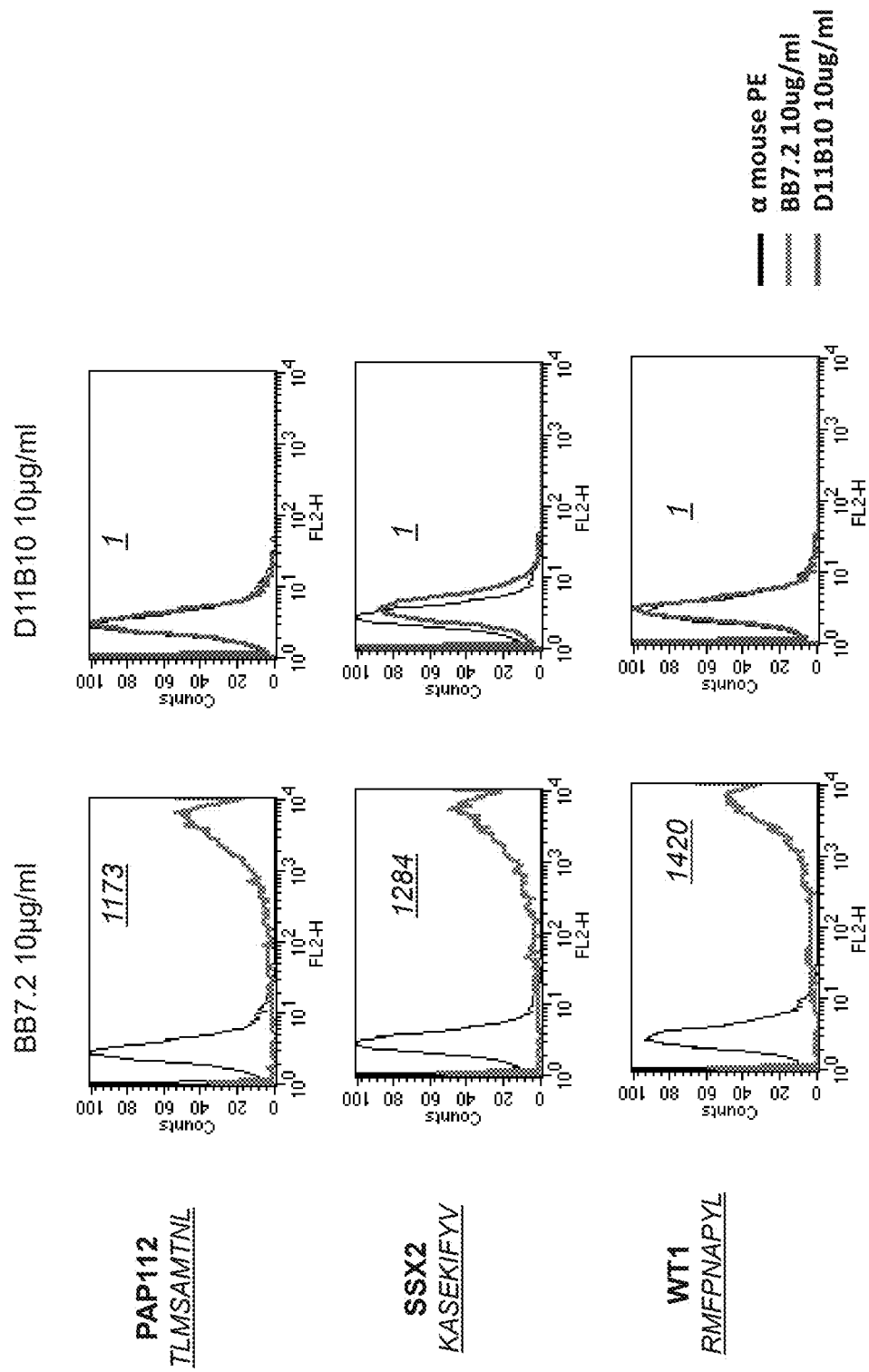
Fig. 5 - continued

Figure 6:
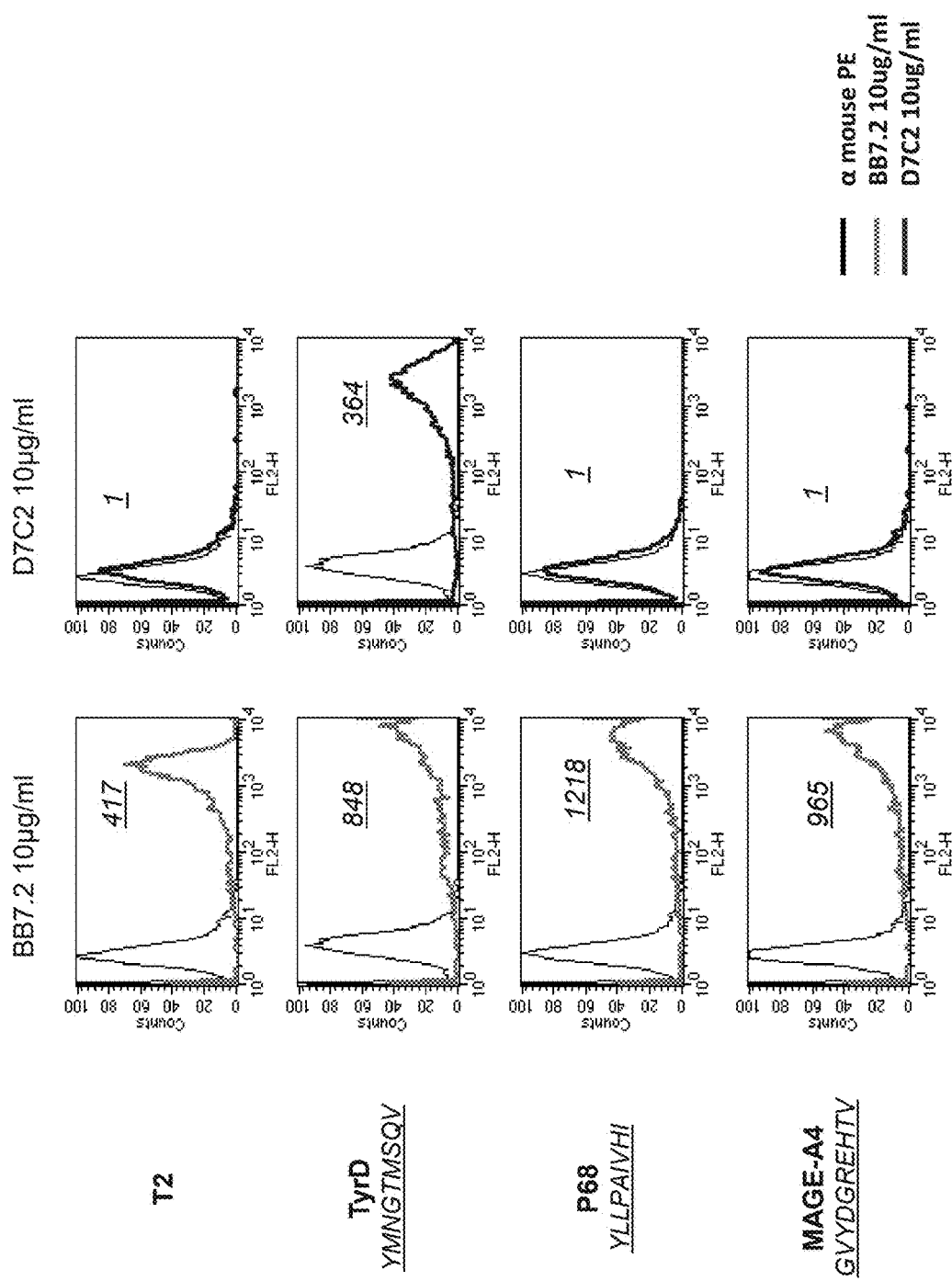

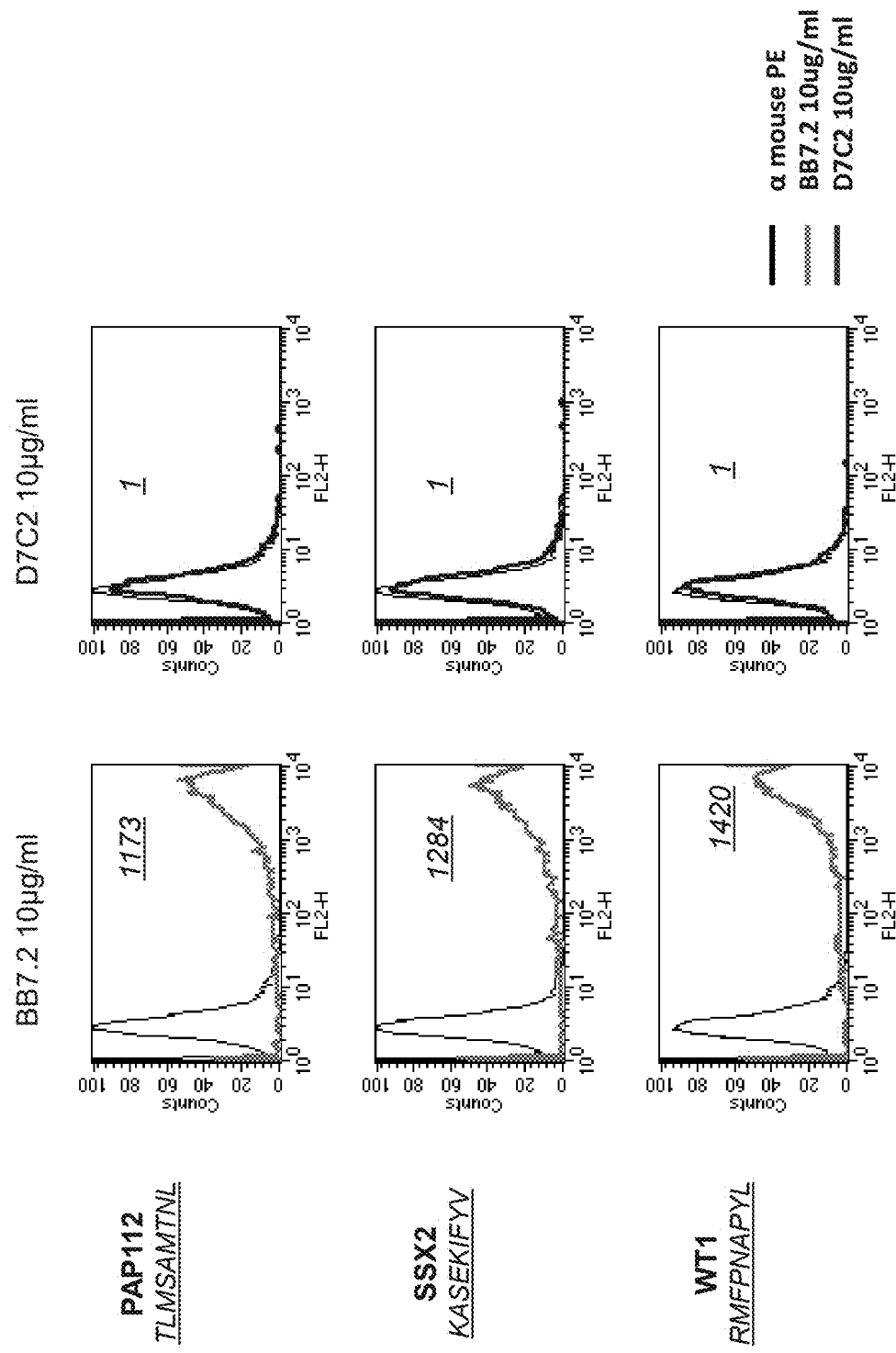
Fig. 6 - continued

Figure 7:
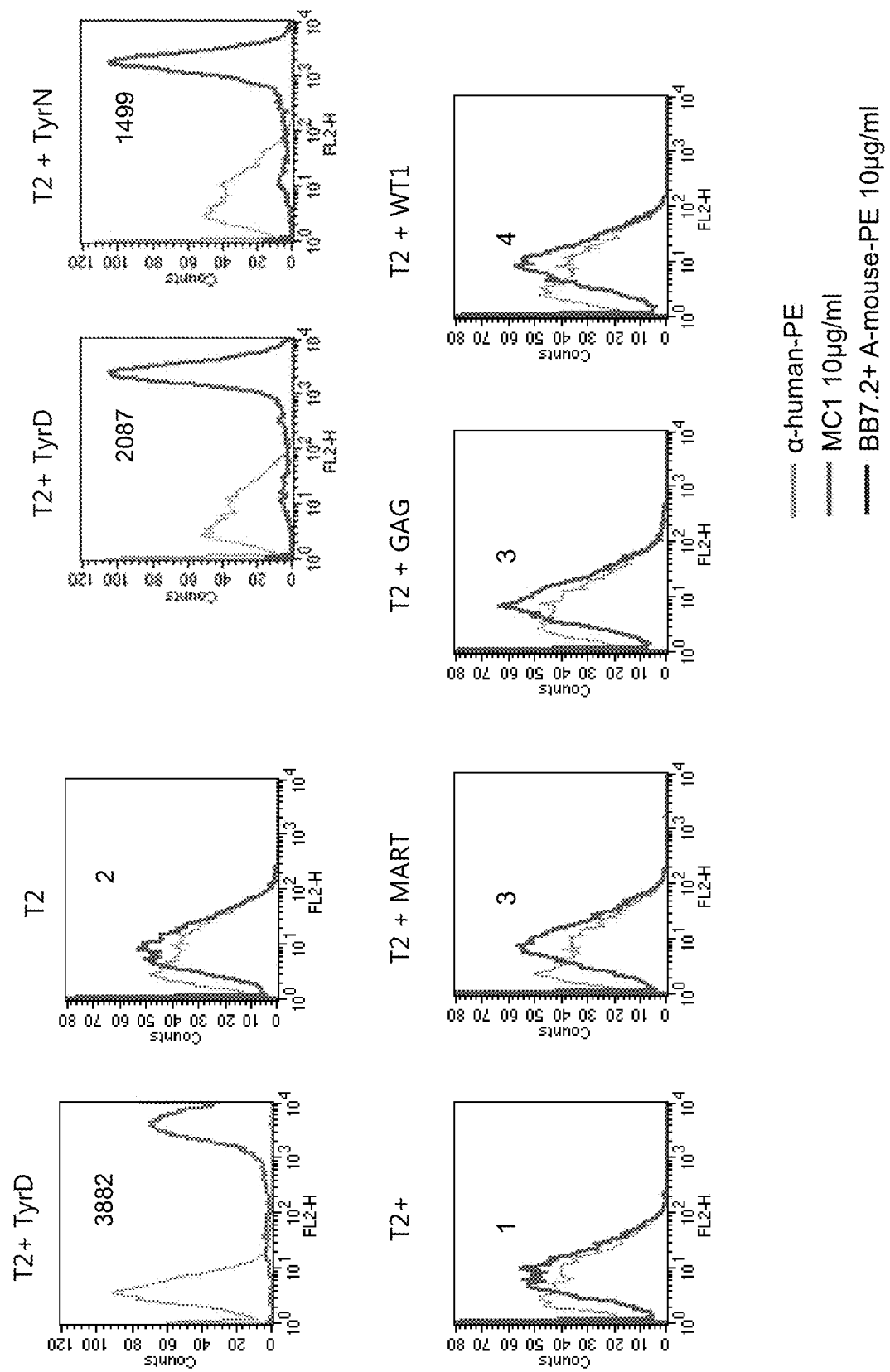

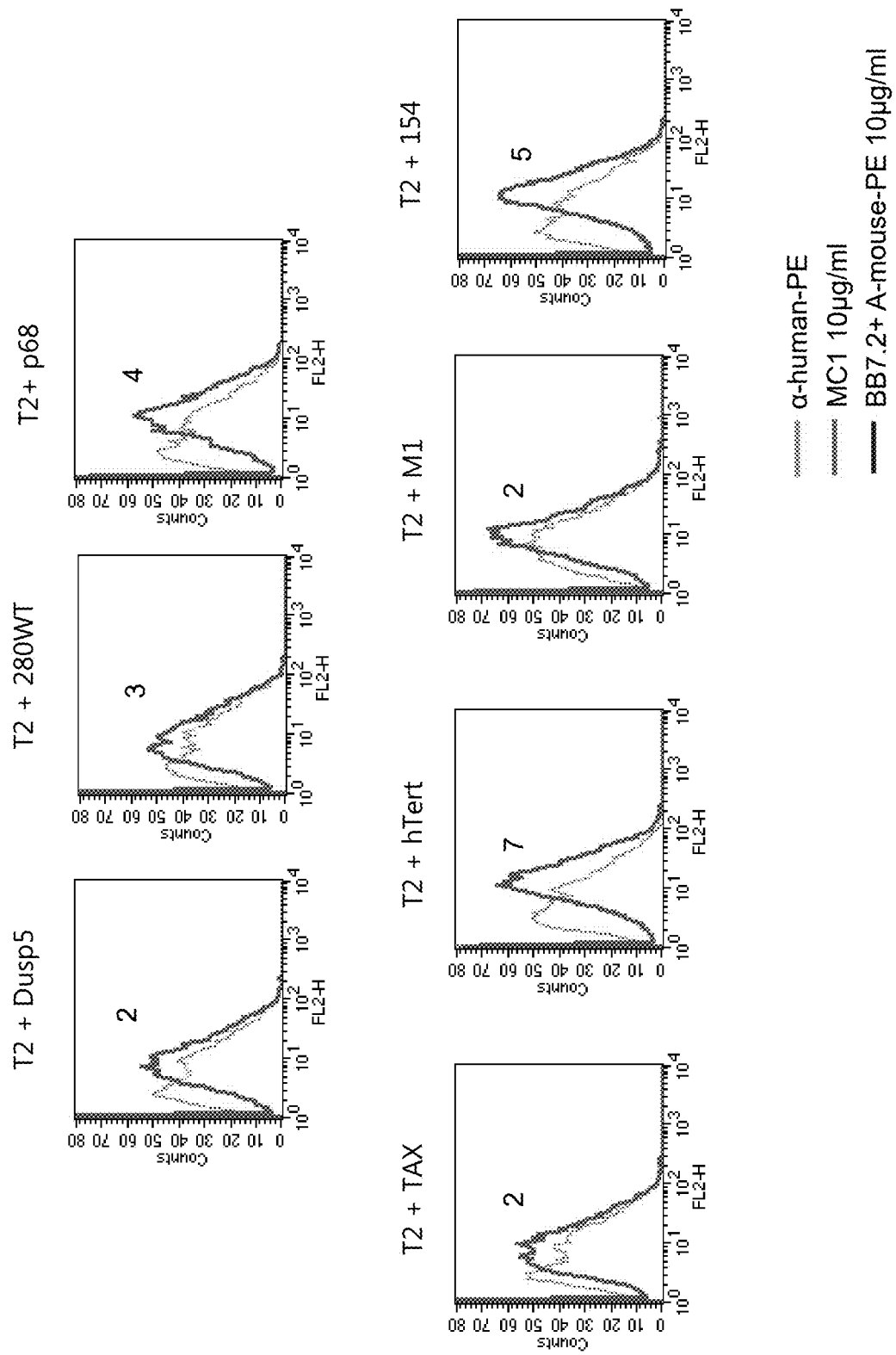
Fig. 7 - continued

Figure 8:
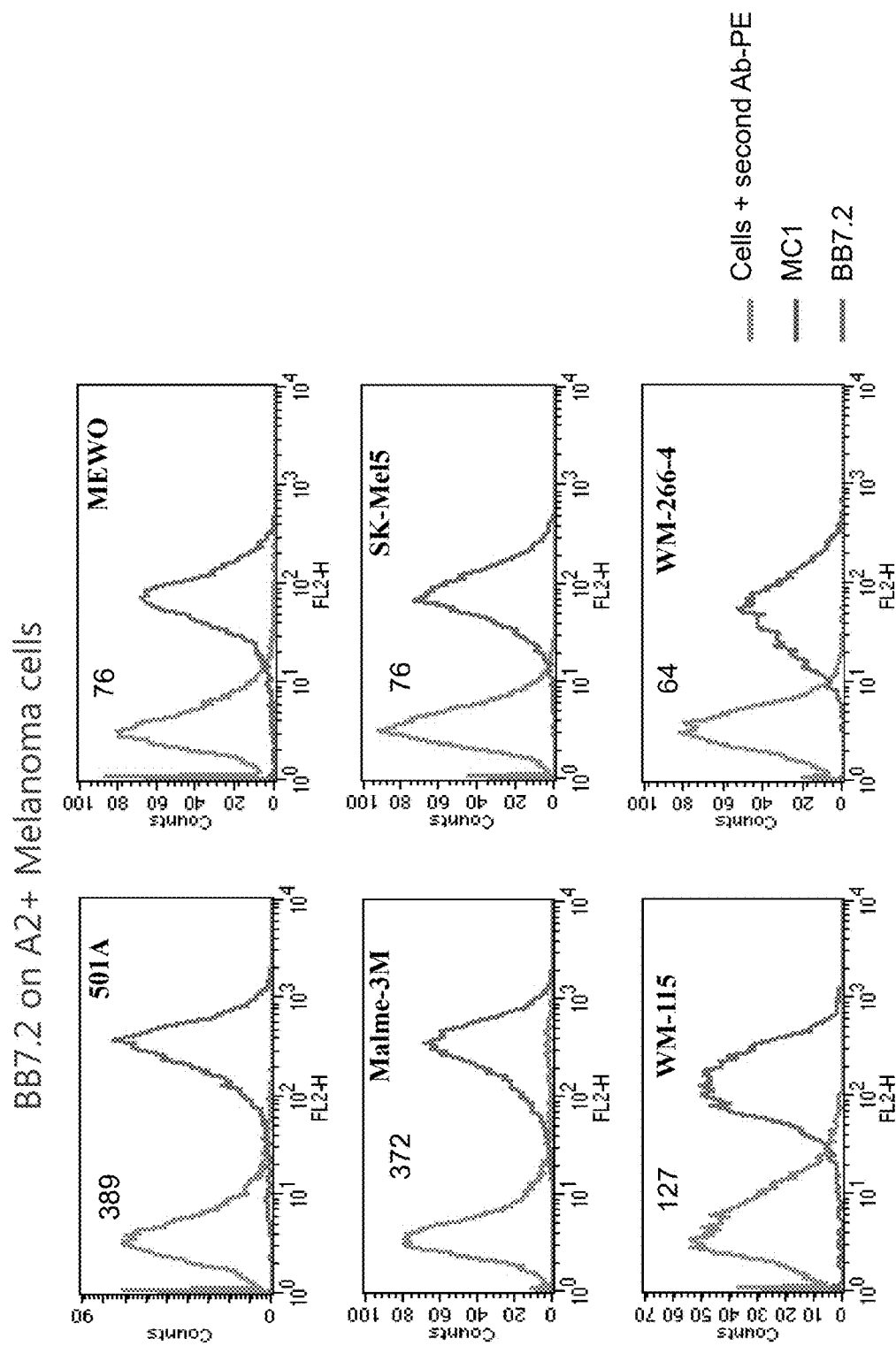

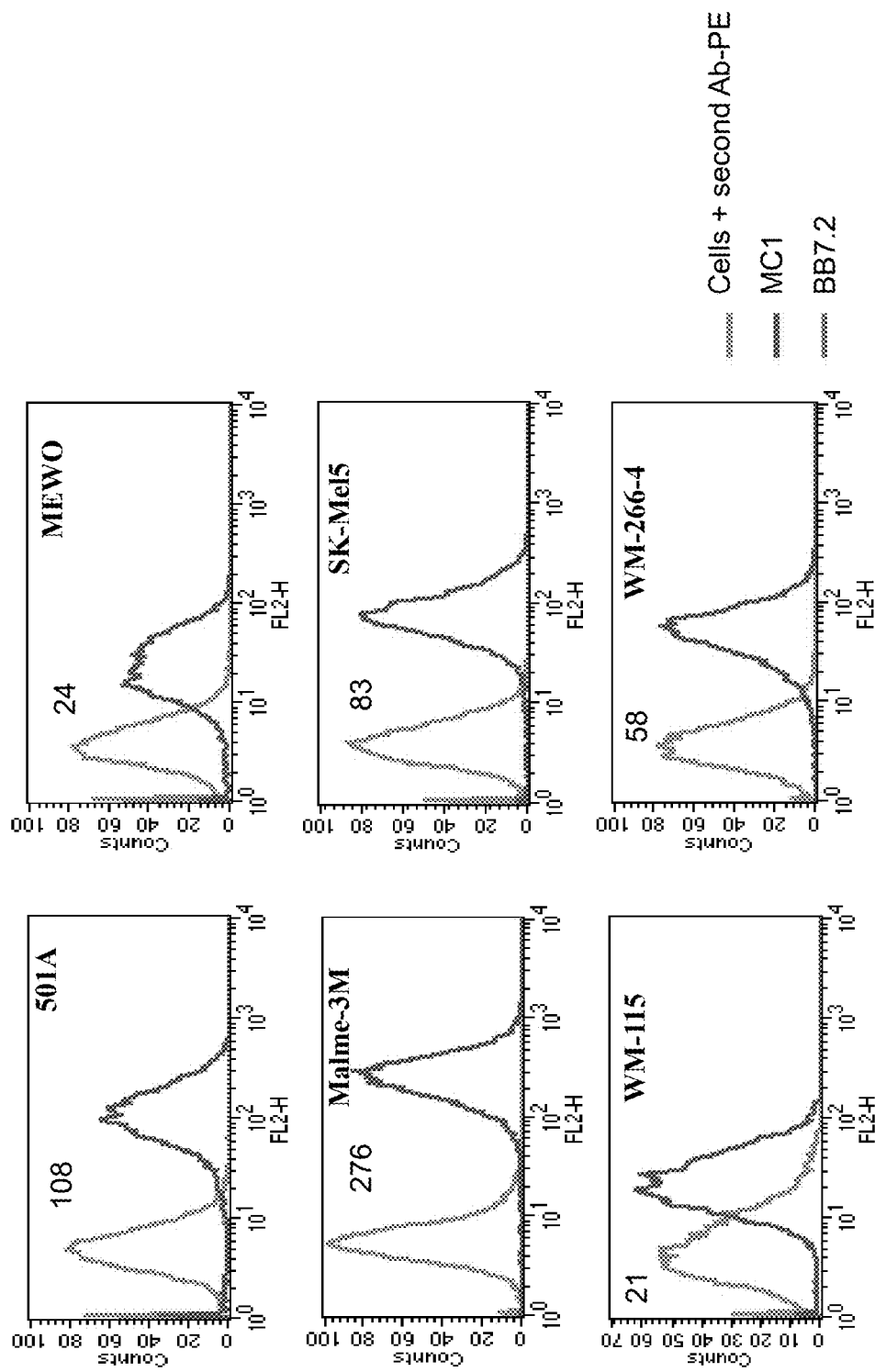
Fig. 8 - continued

Figure 9:
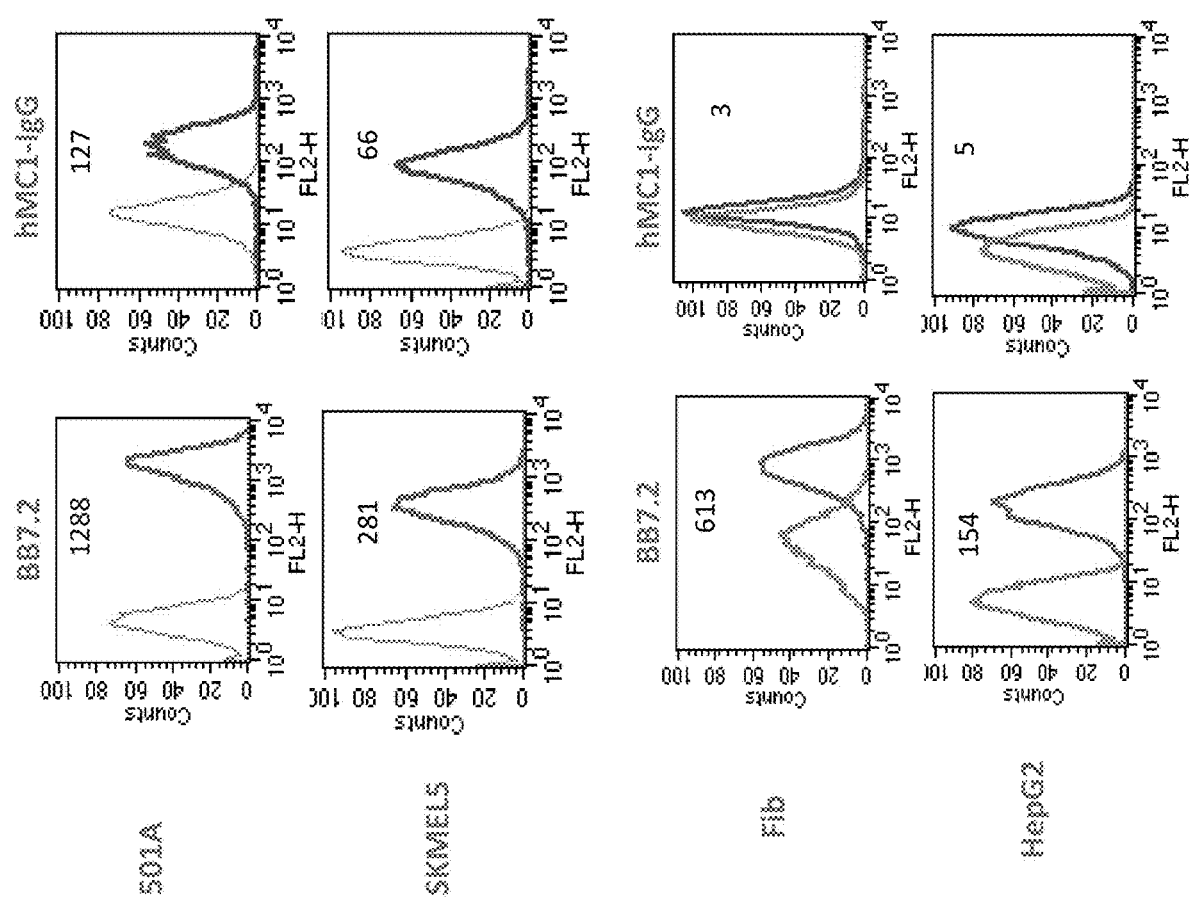

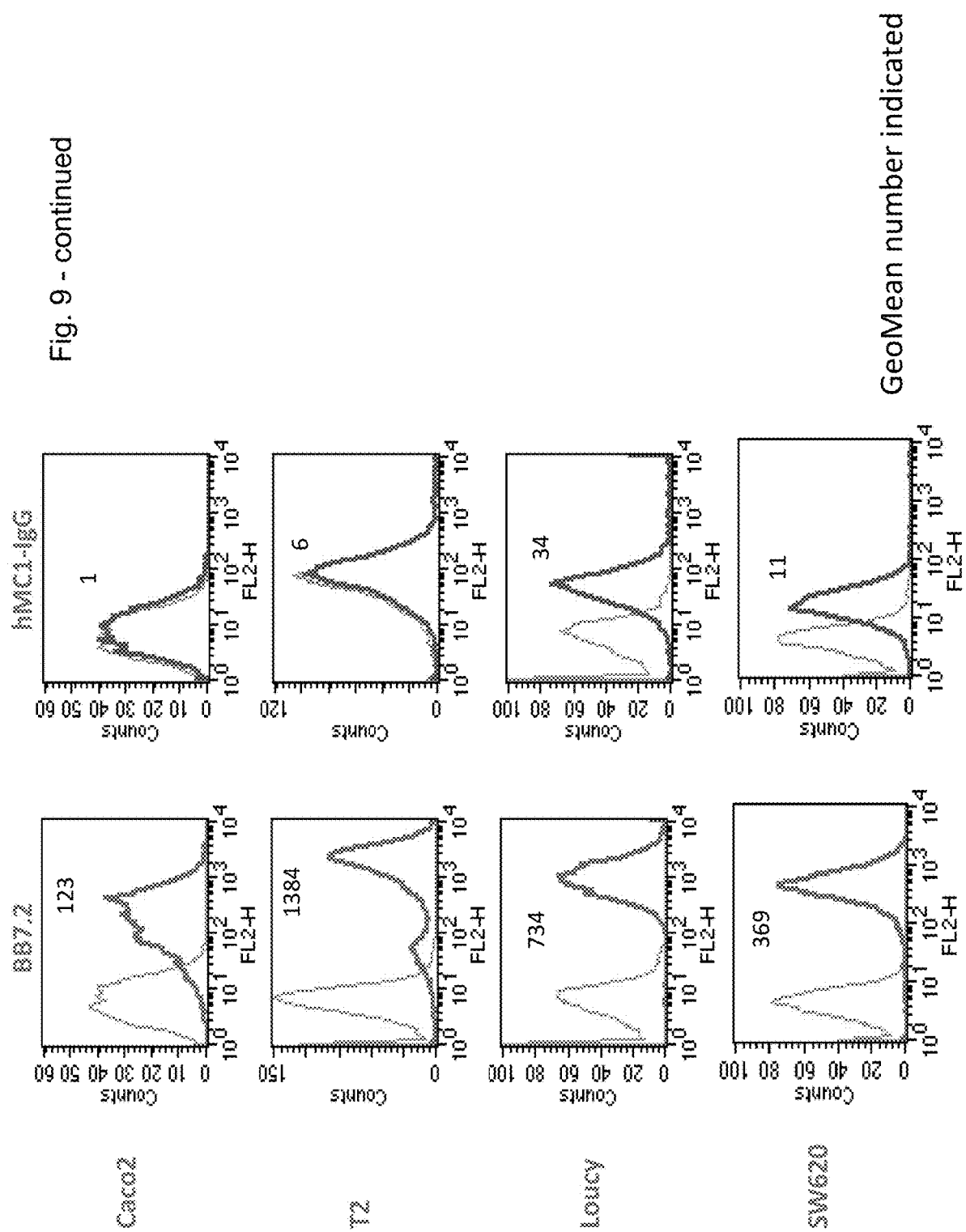
Fig. 9 - continued

Figure 10:
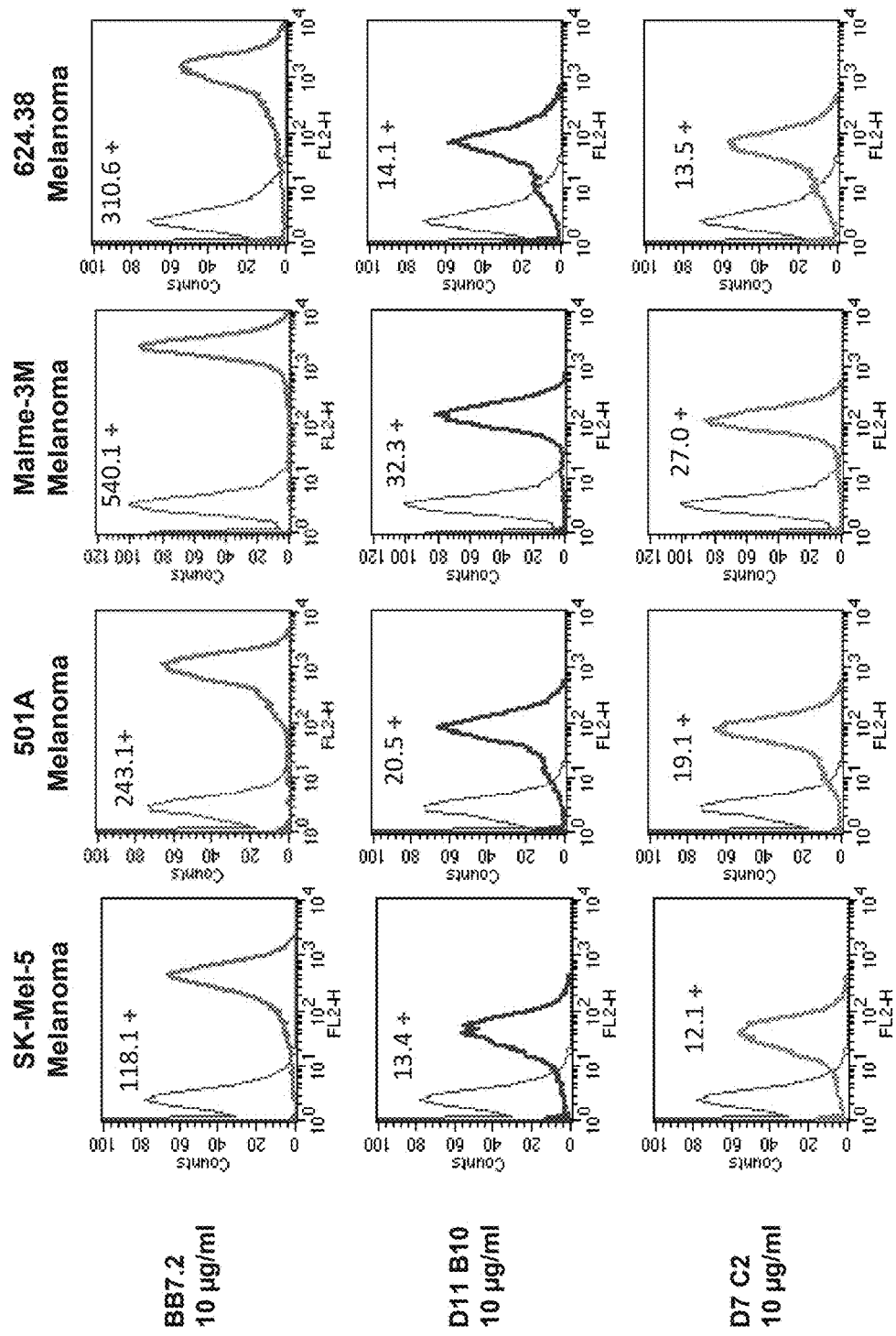

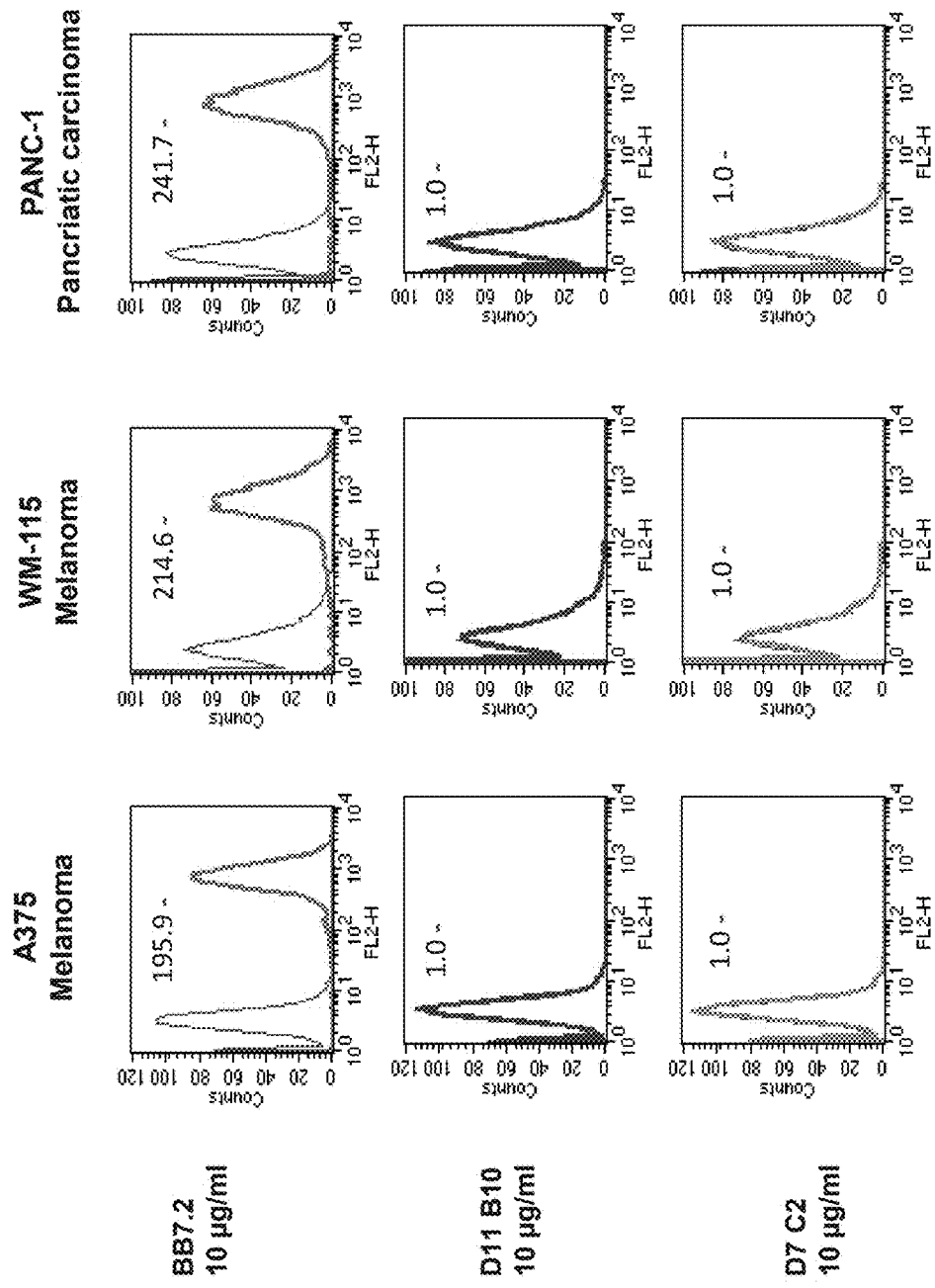
Fig. 10 - continued

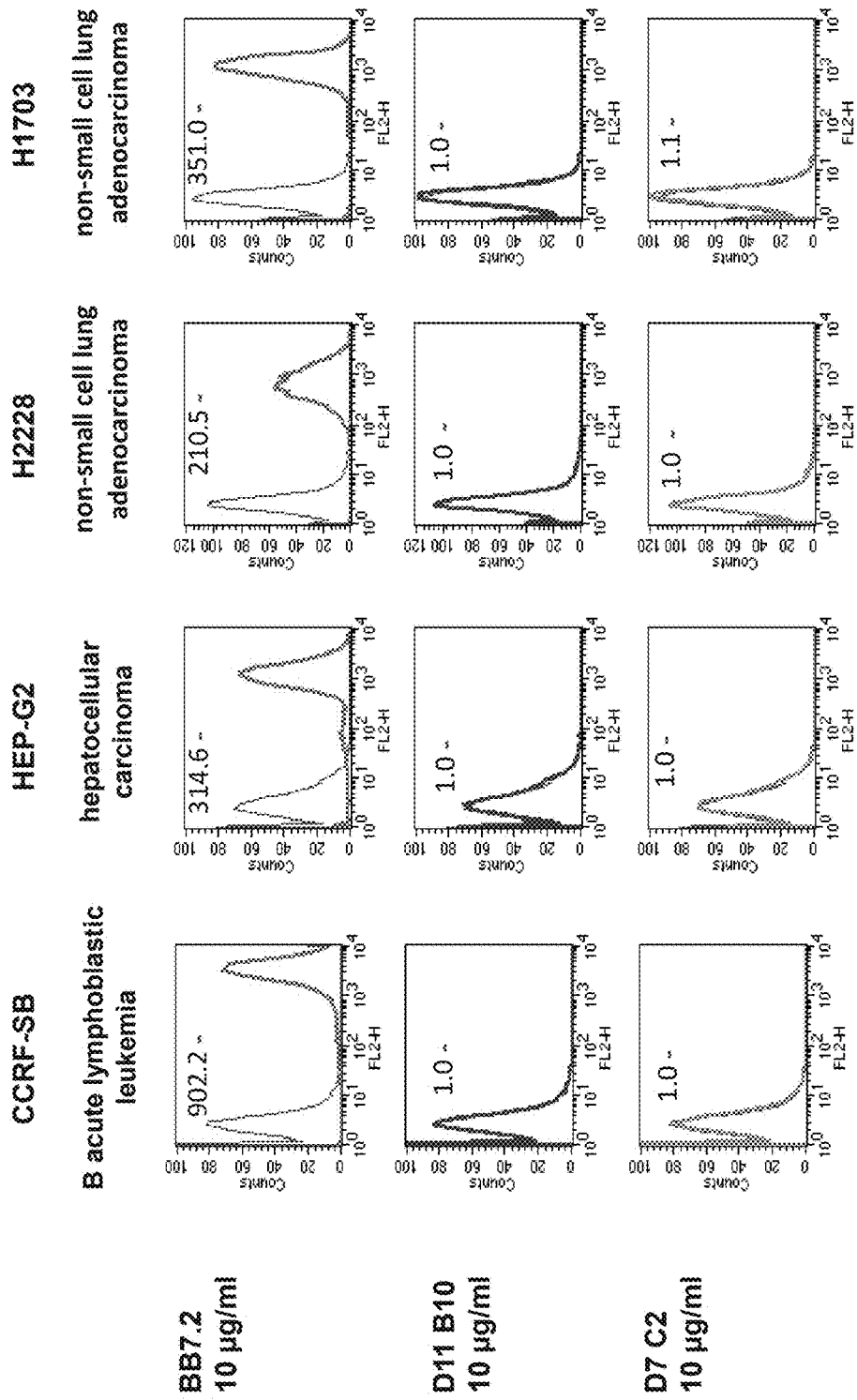
Fig. 10 - continued

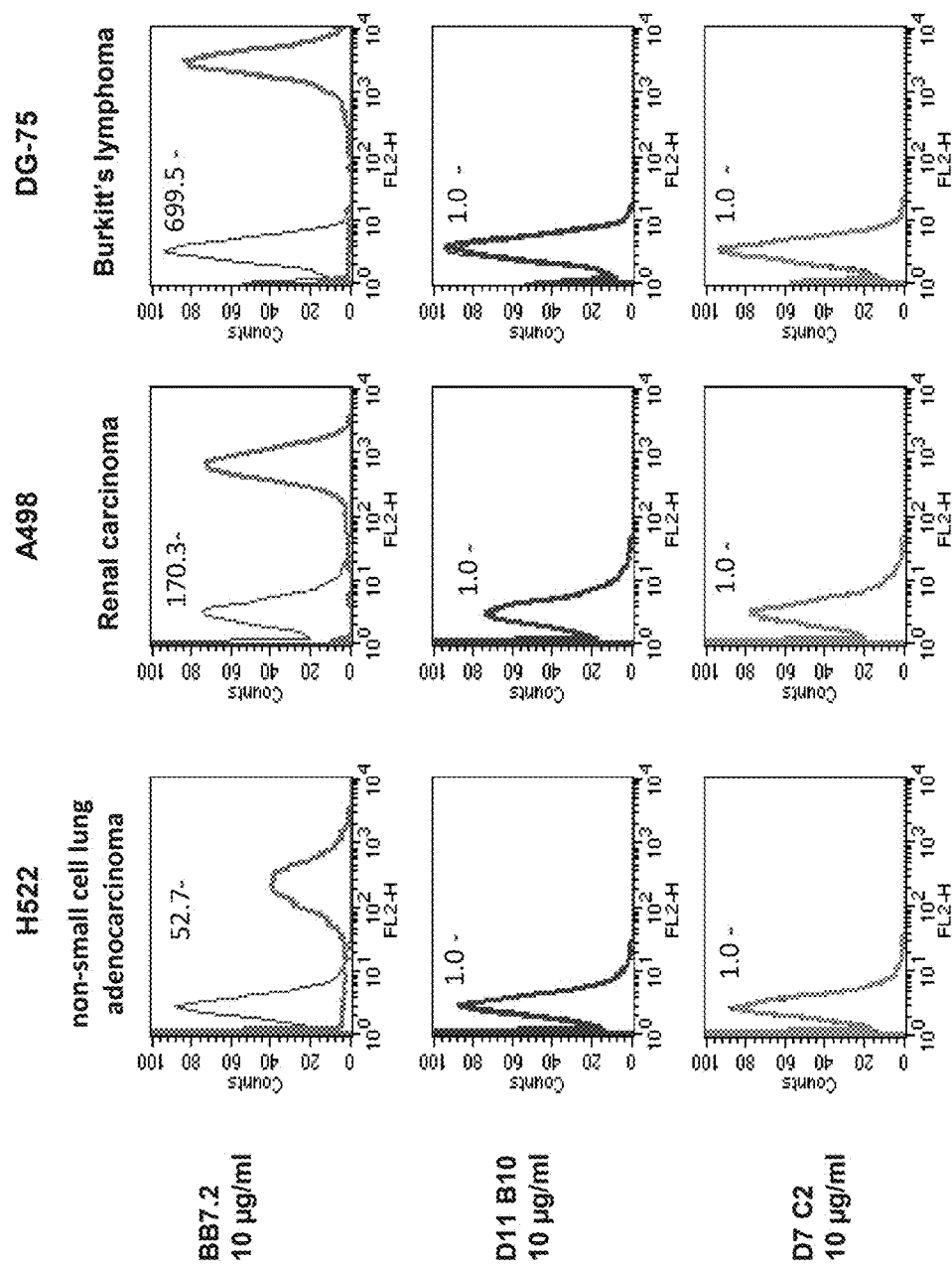
Fig. 10 - continued

Figure 12:
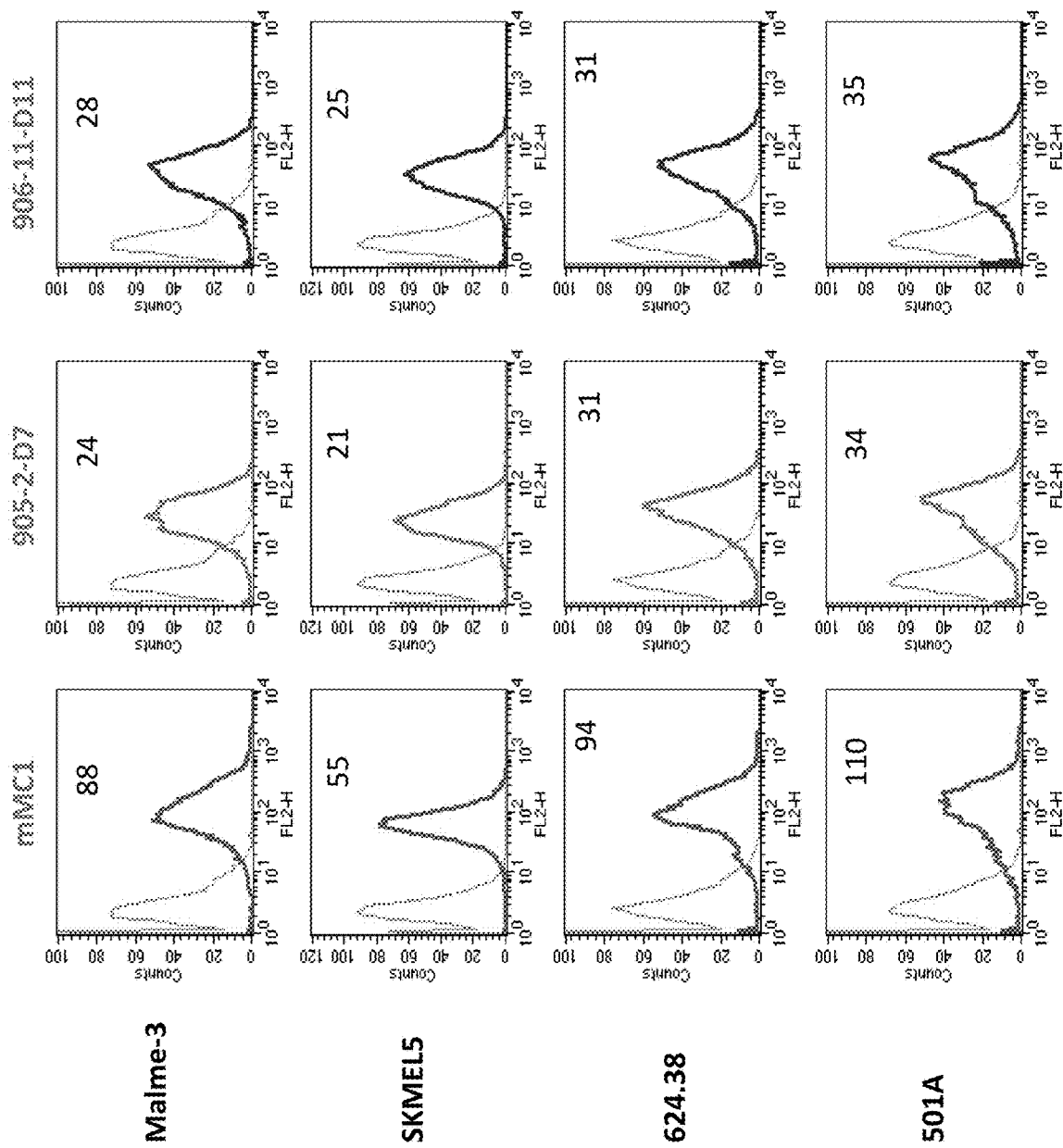

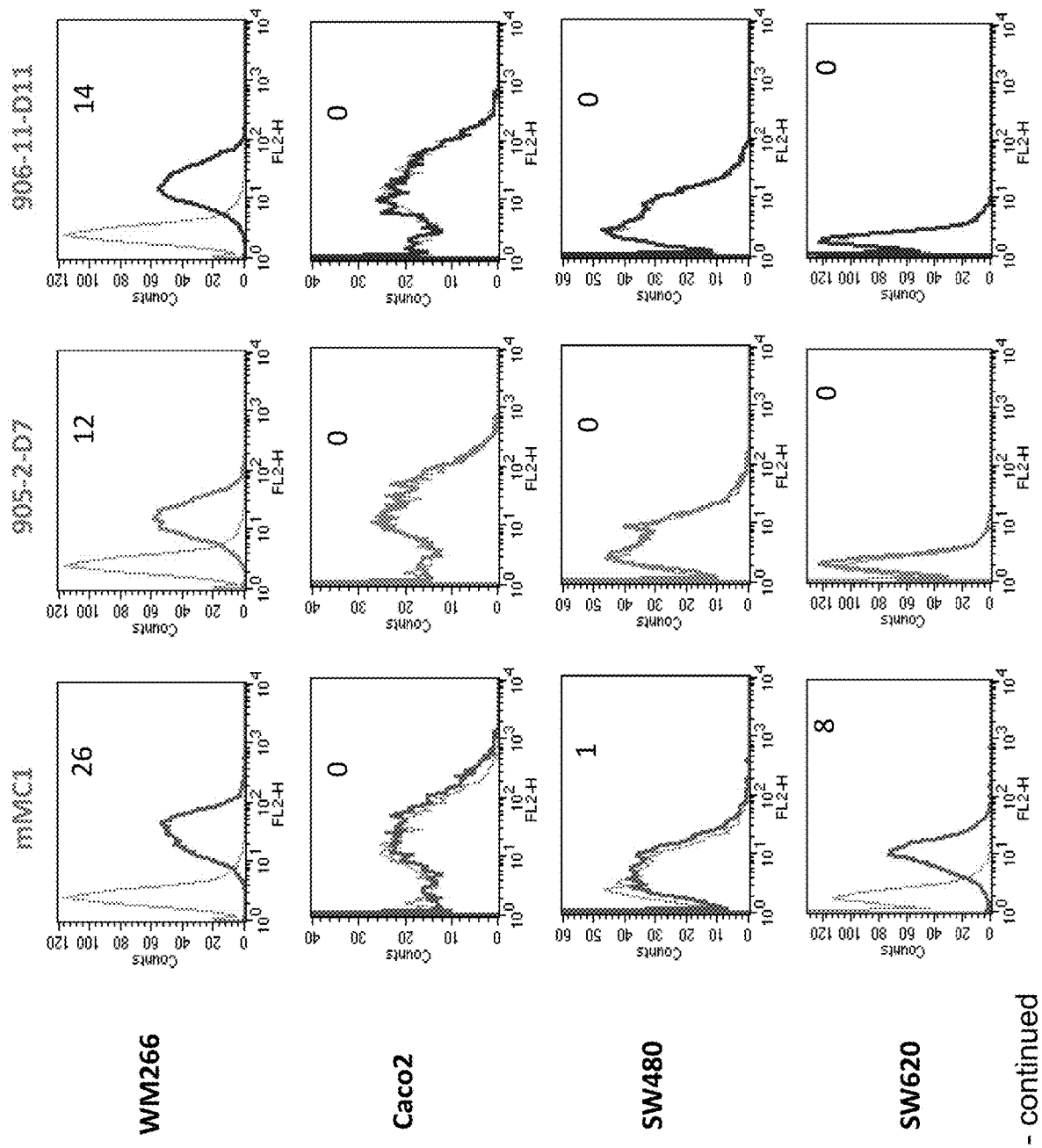
Fig. 12 - continued

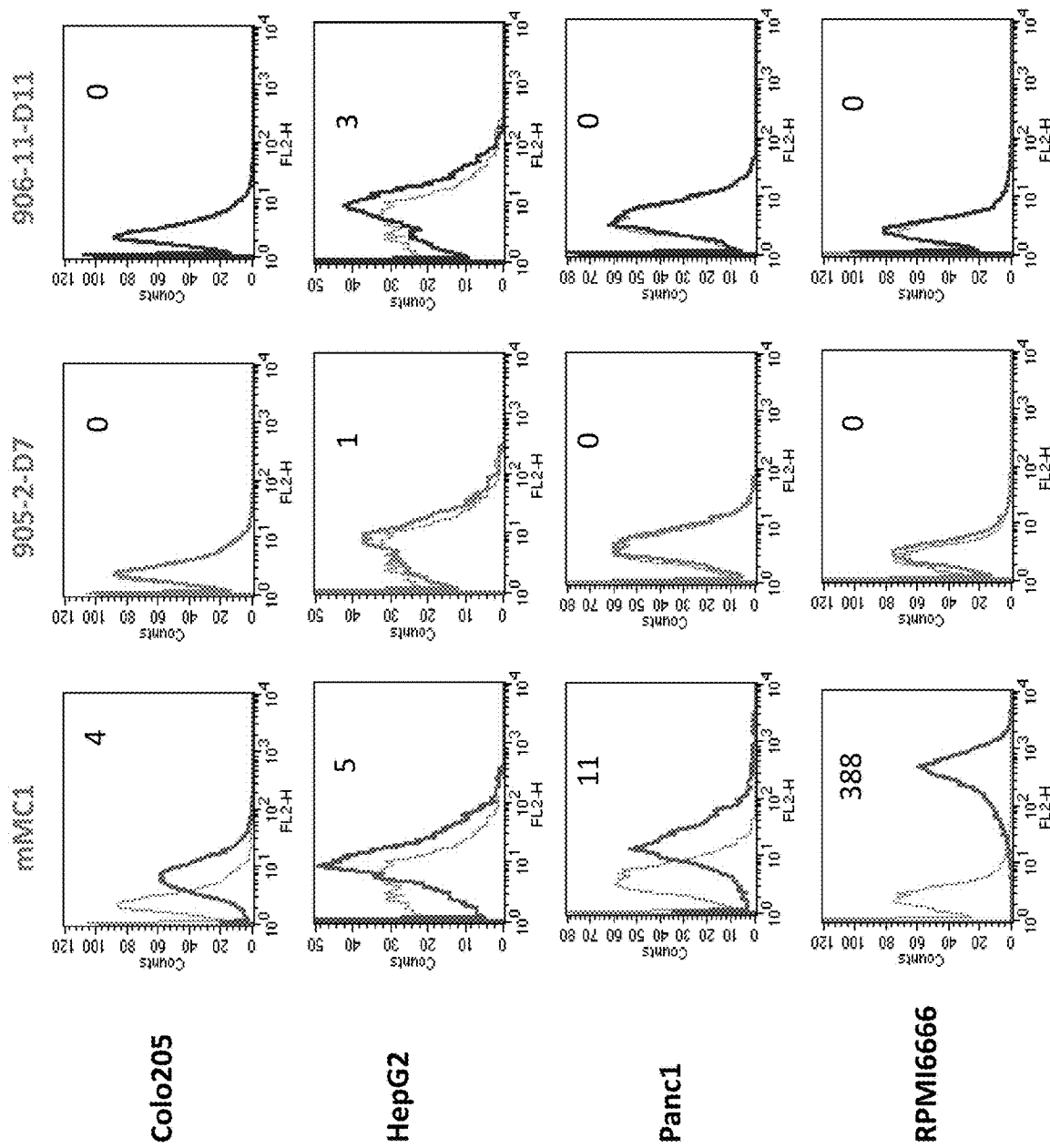
Fig. 12 - continued

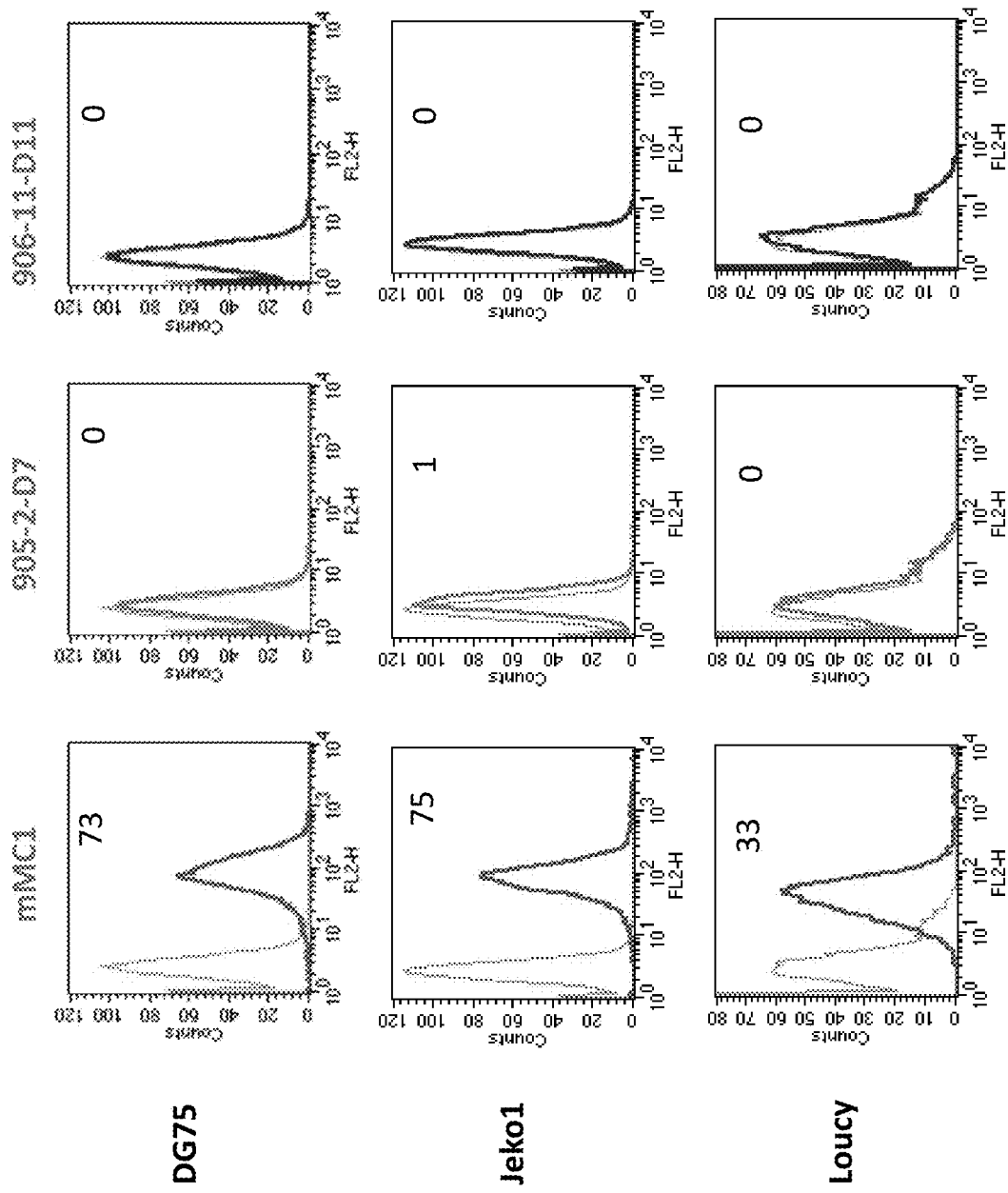
Fig. 12 - continued

Figure 13:
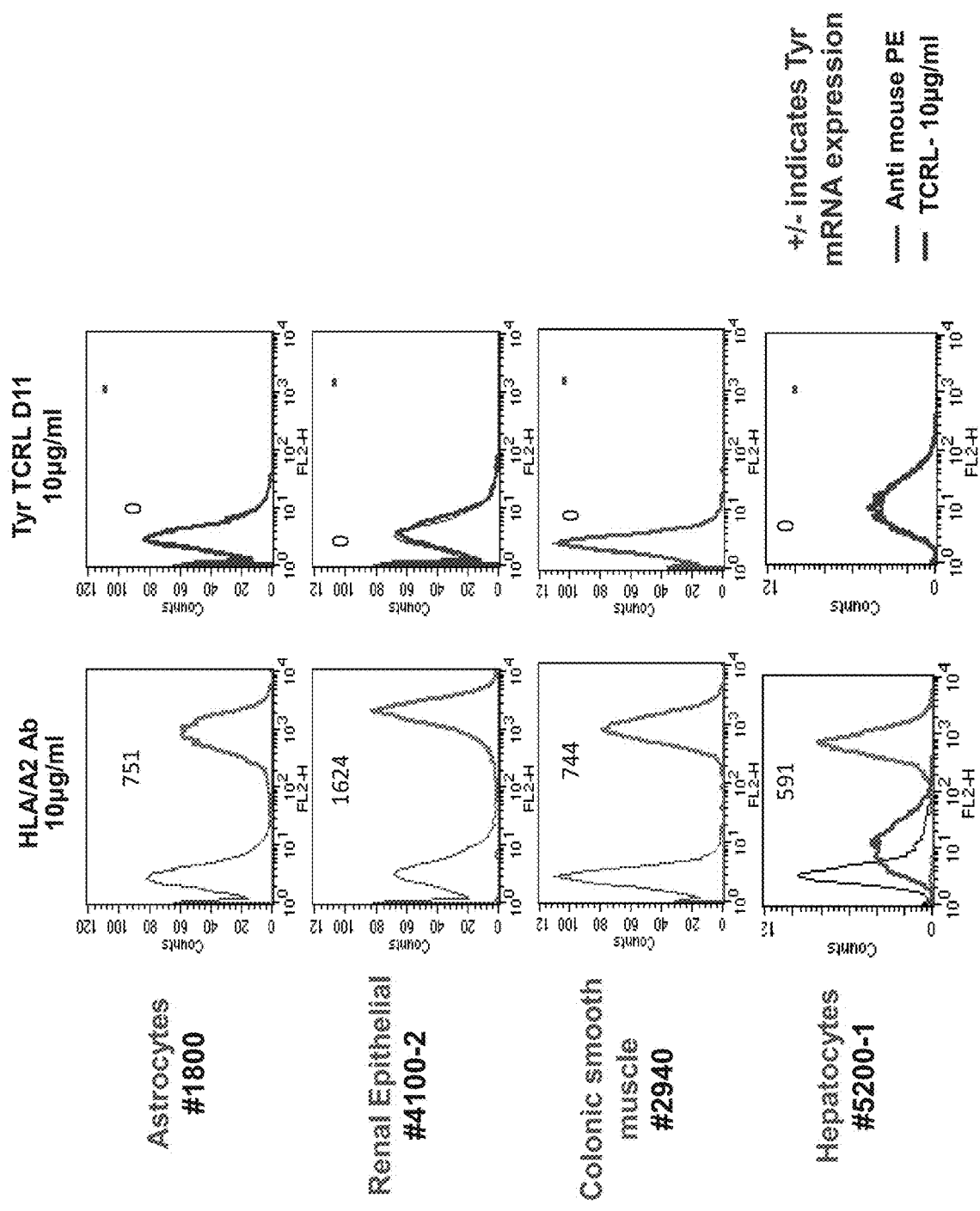

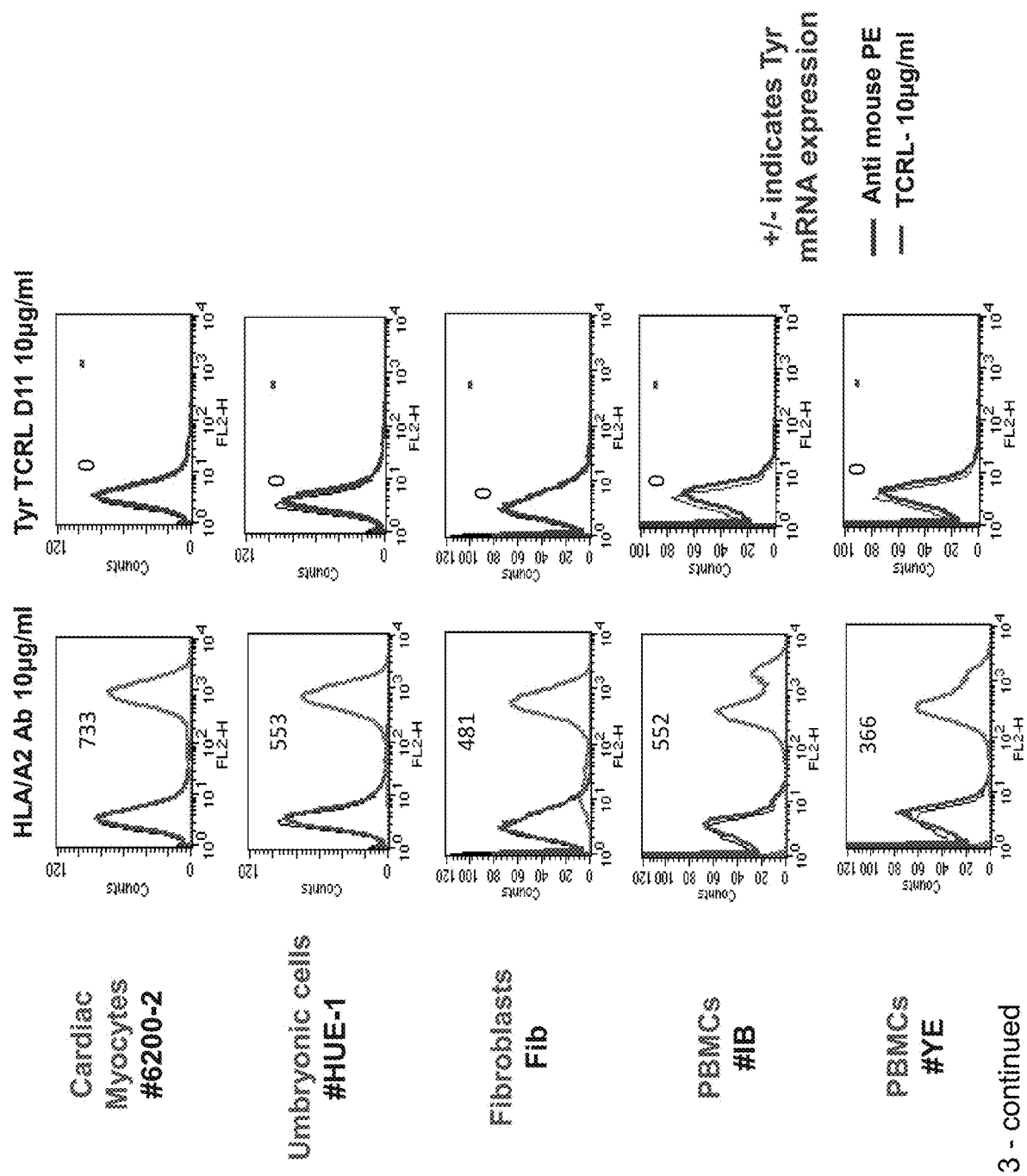
Fig. 13 - continued

Figure 17:
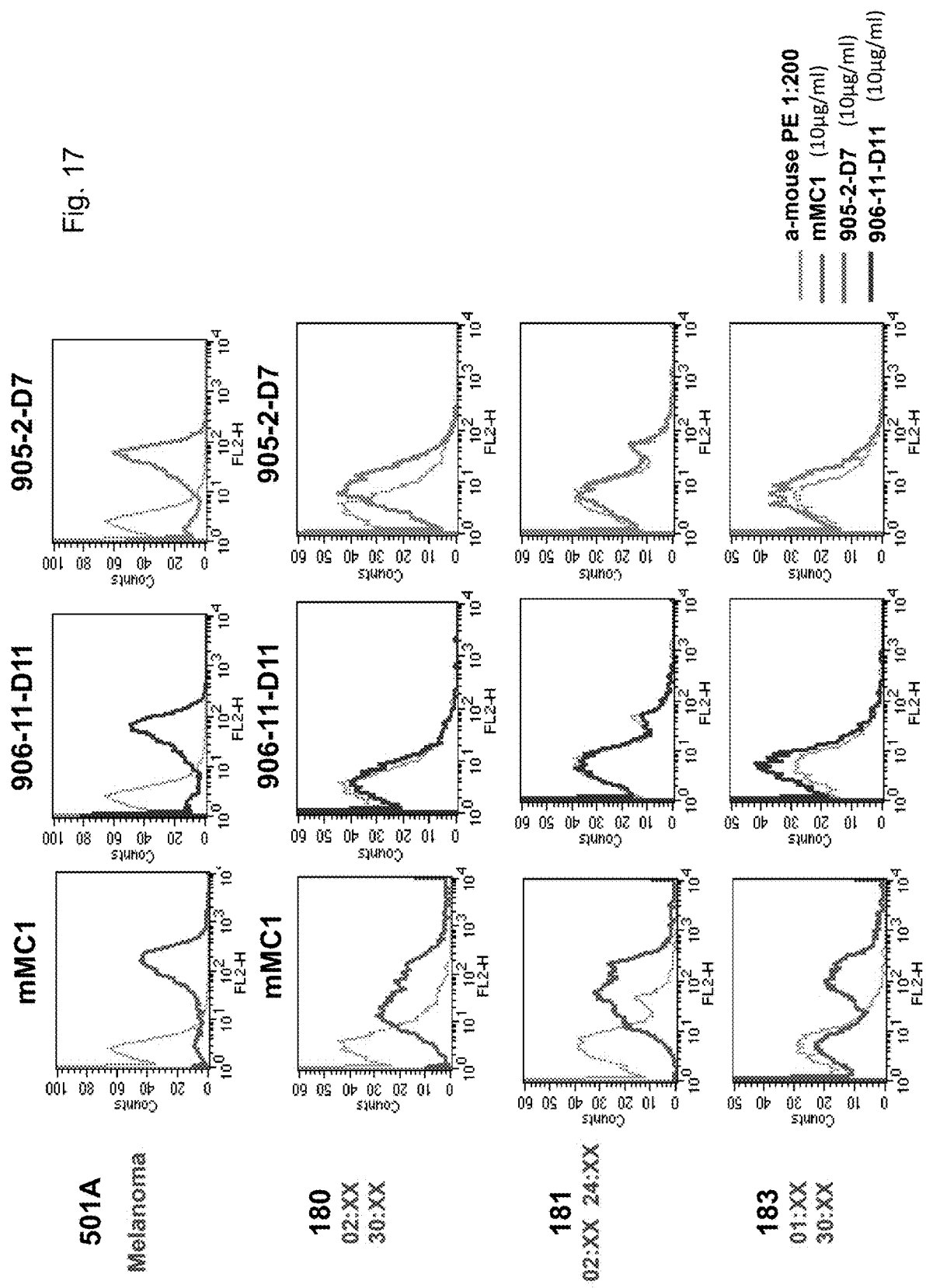

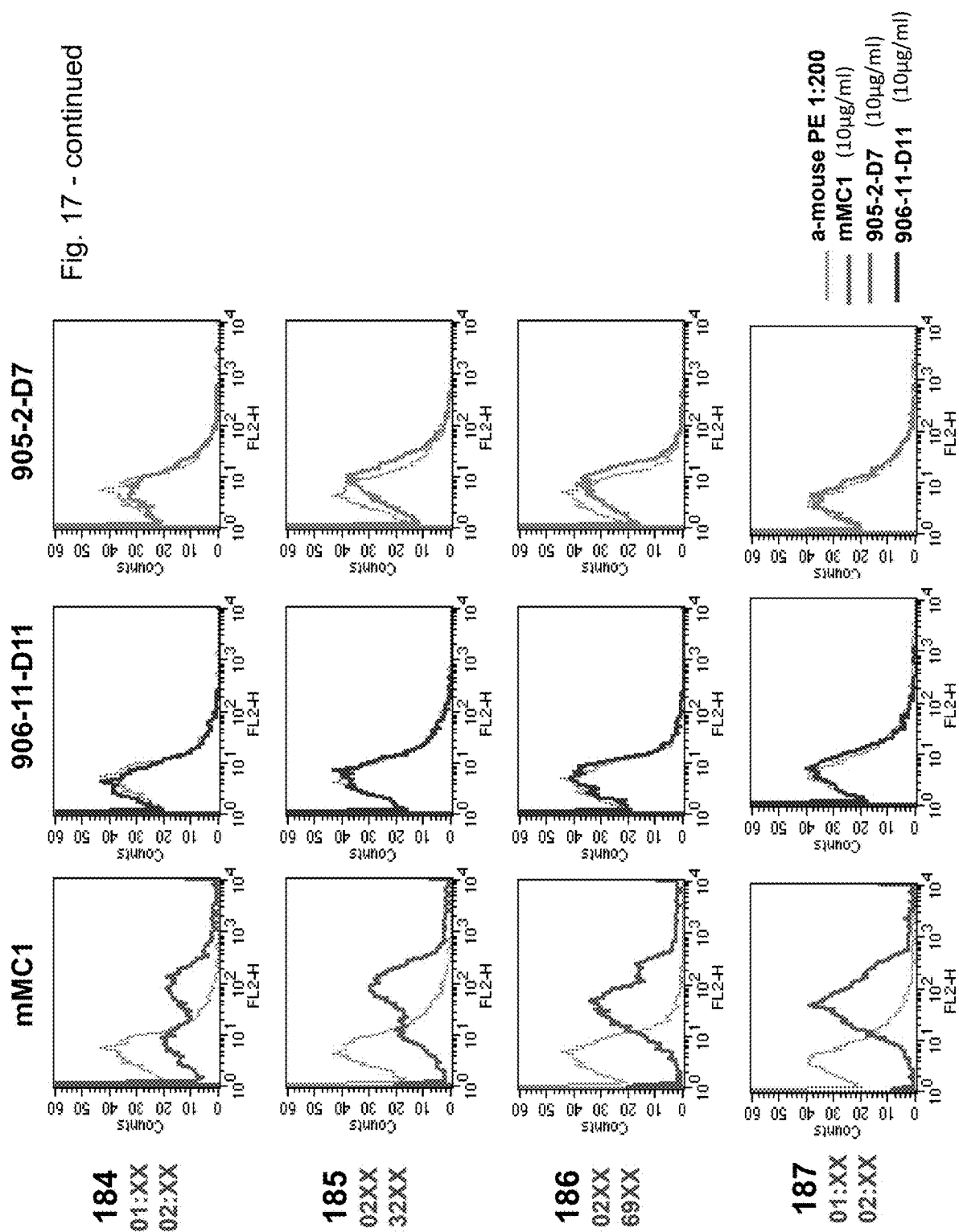
Fig. 17 - continued

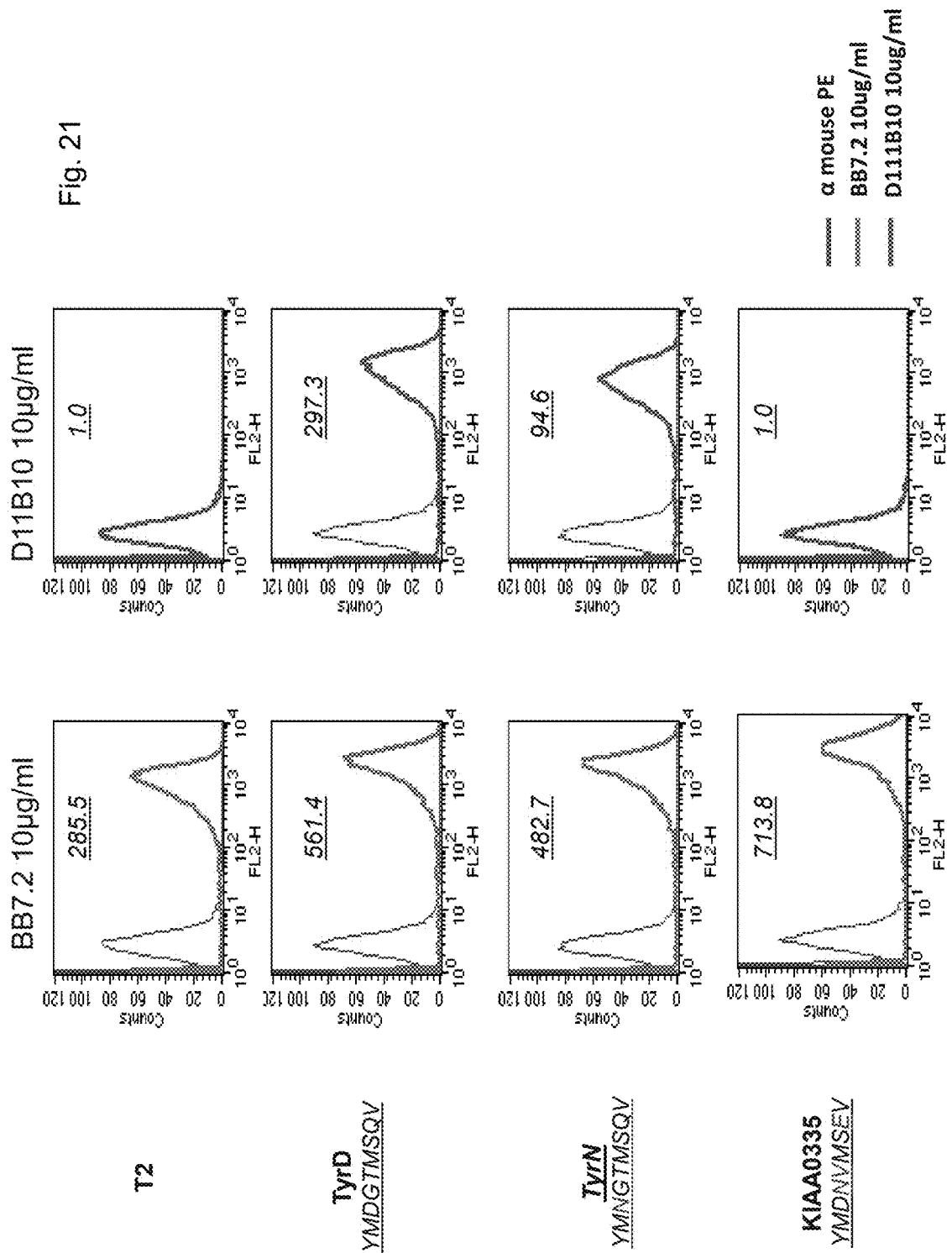

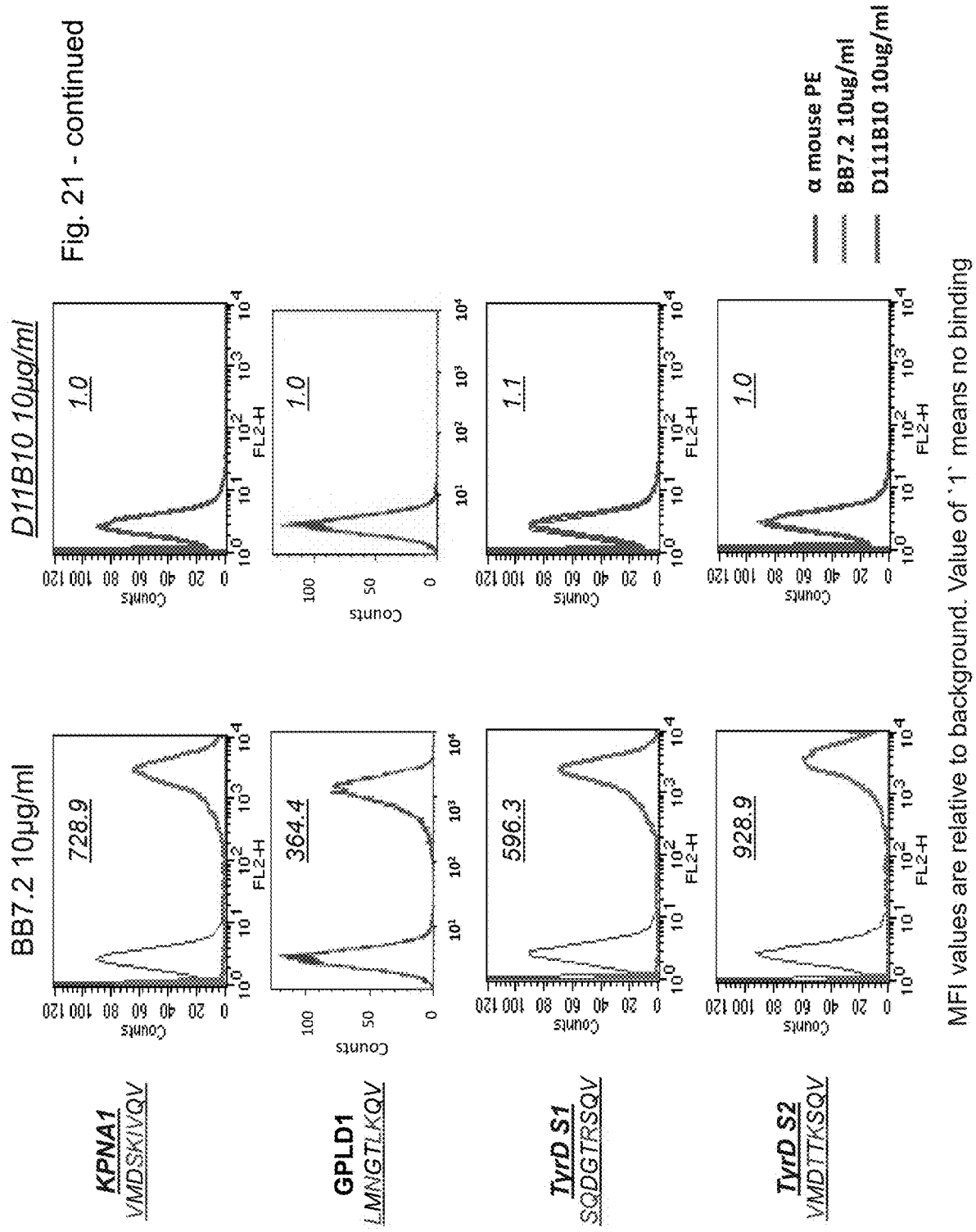

Figure 22:
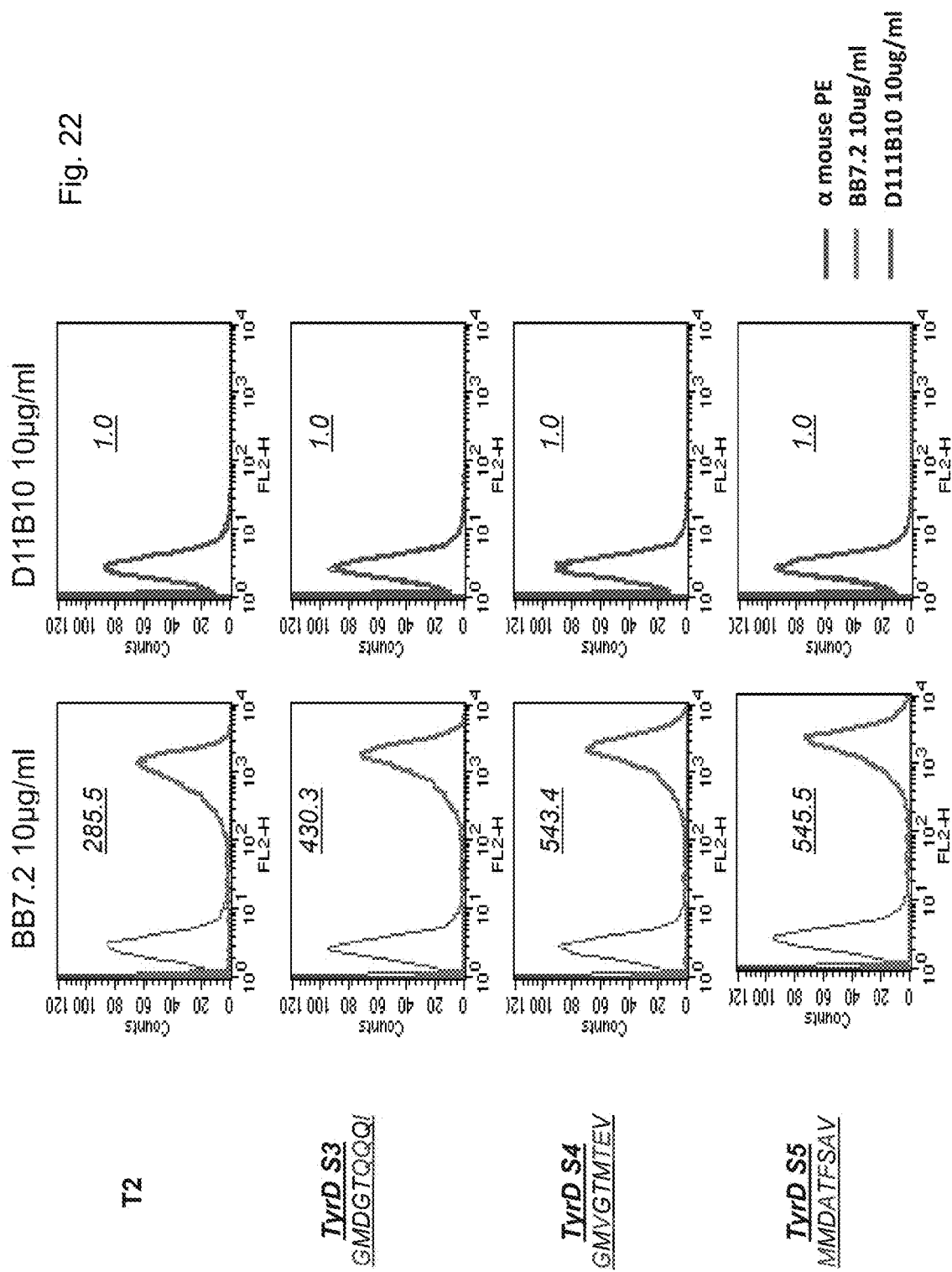

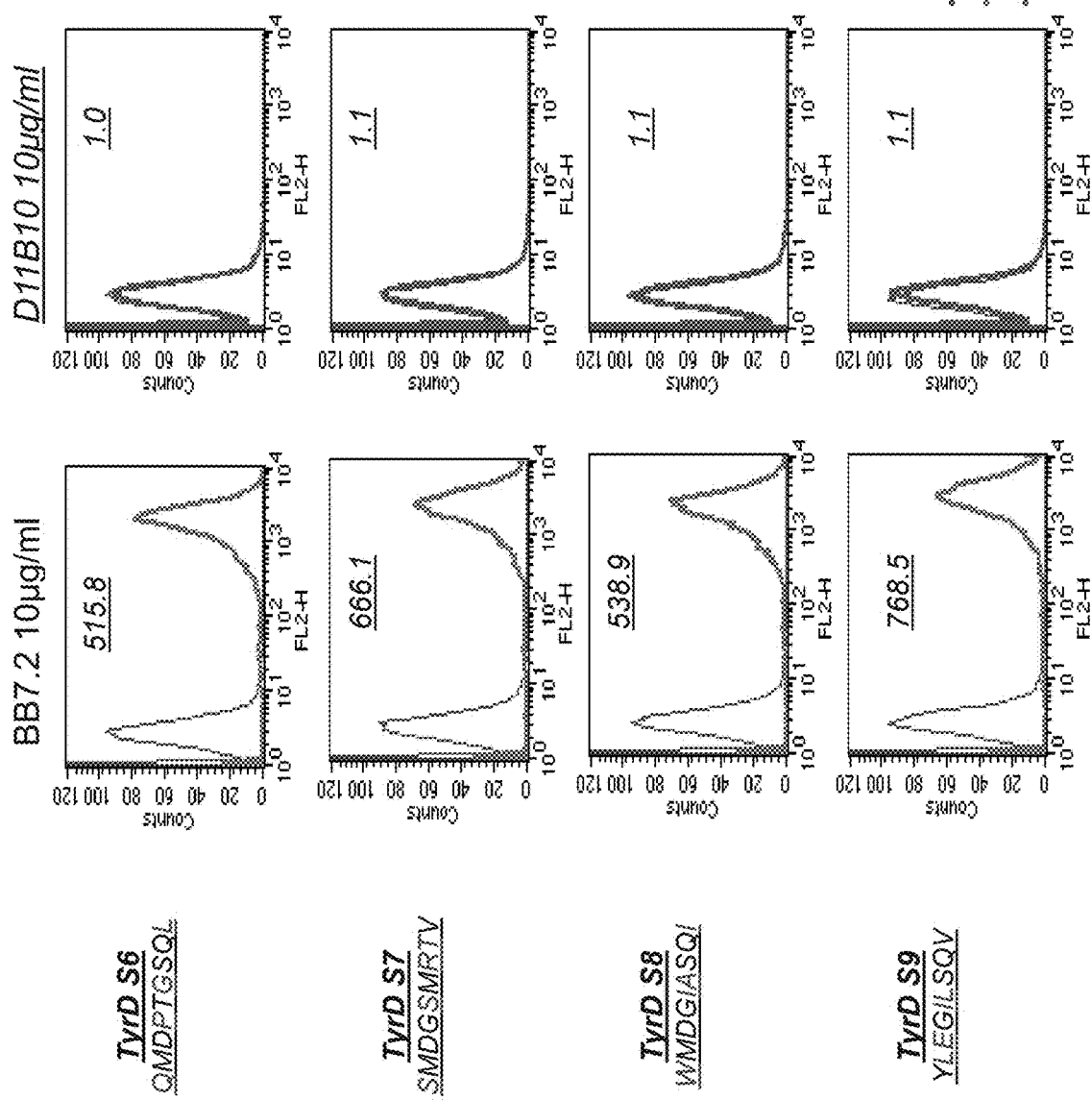
Fig. 22 - continued

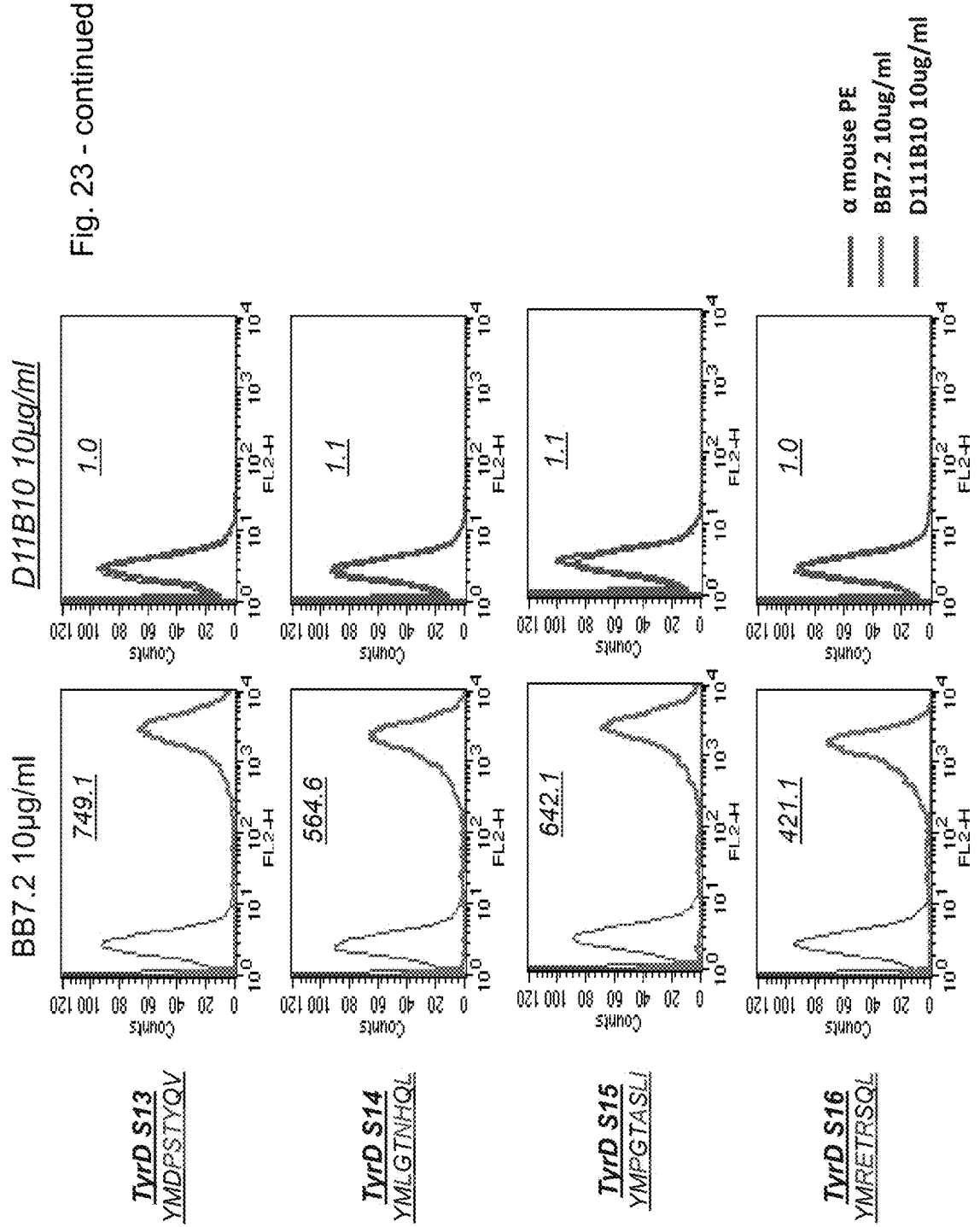

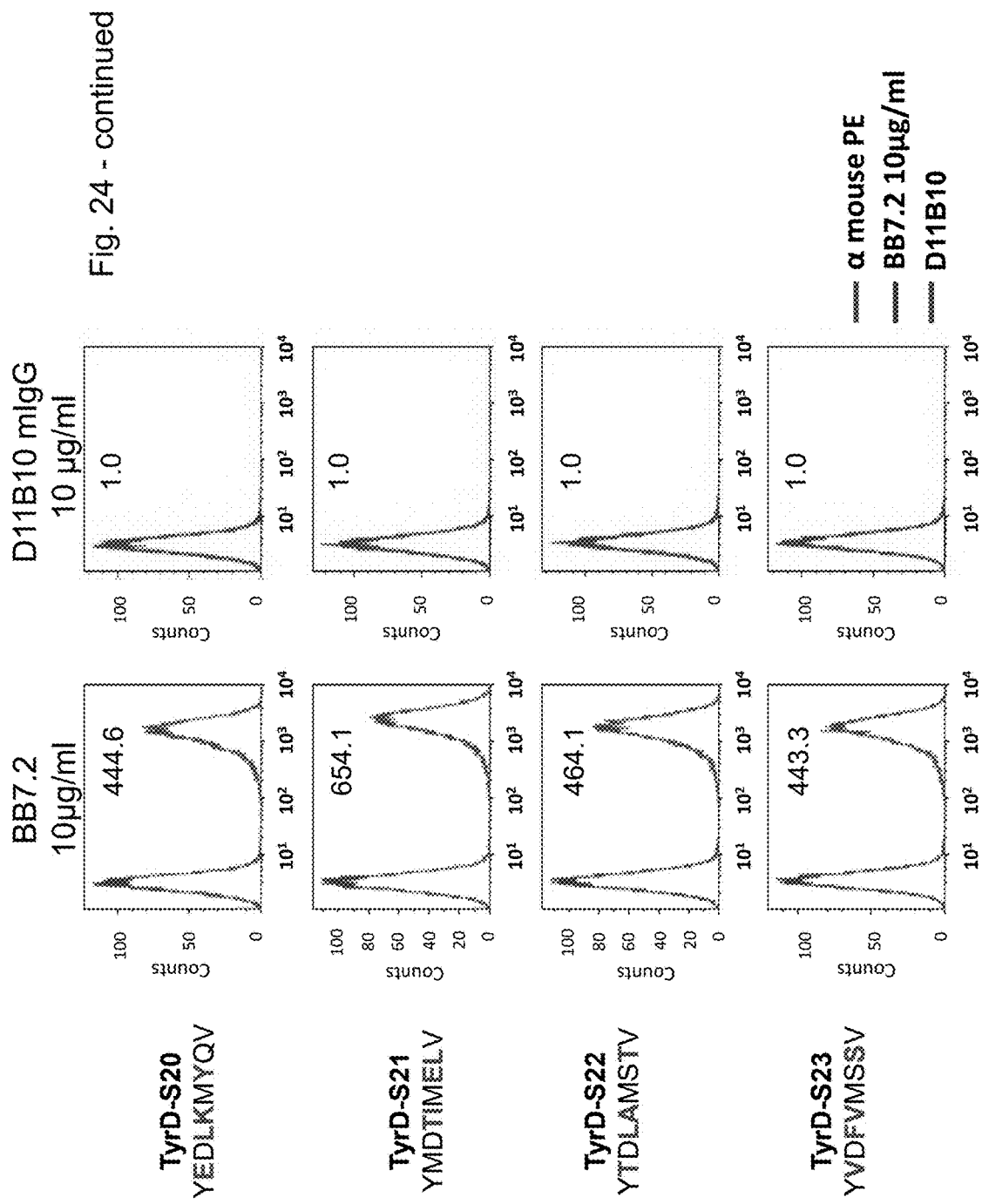

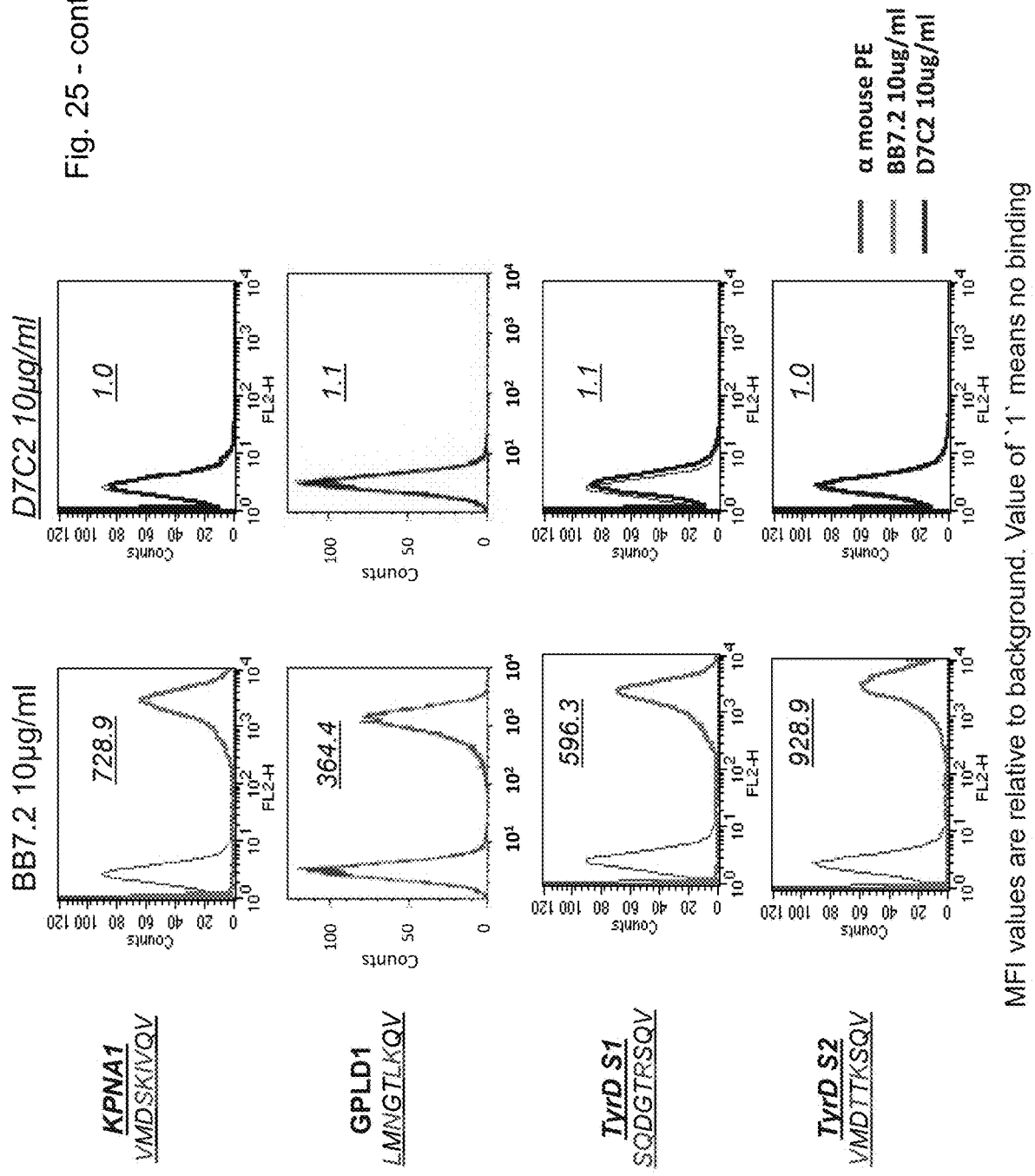

Figure 26:
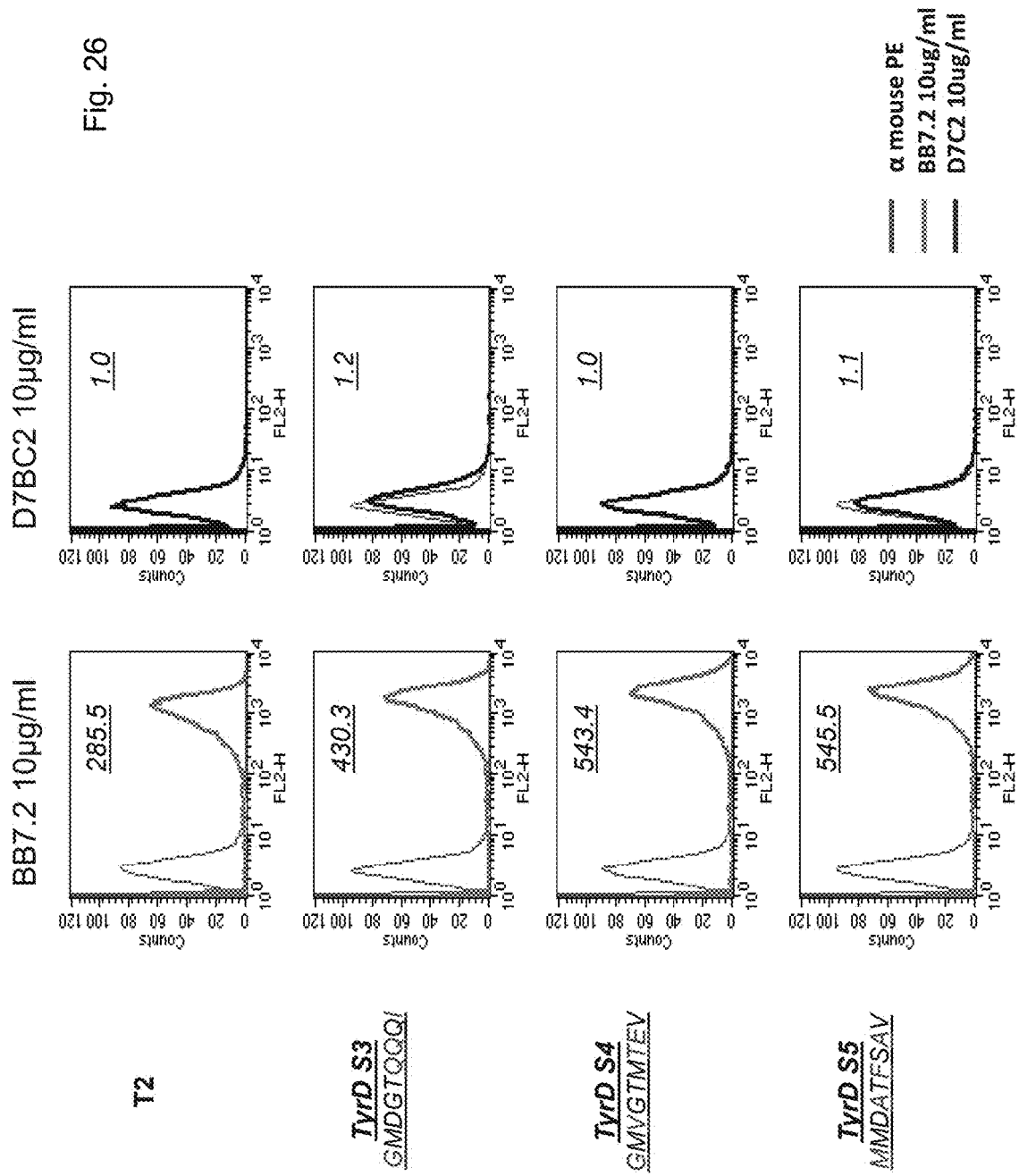

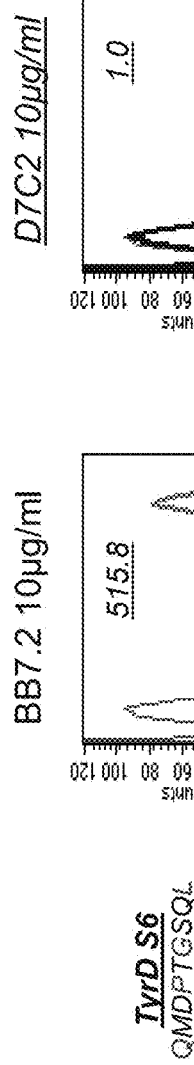
Fig. 26 - continued

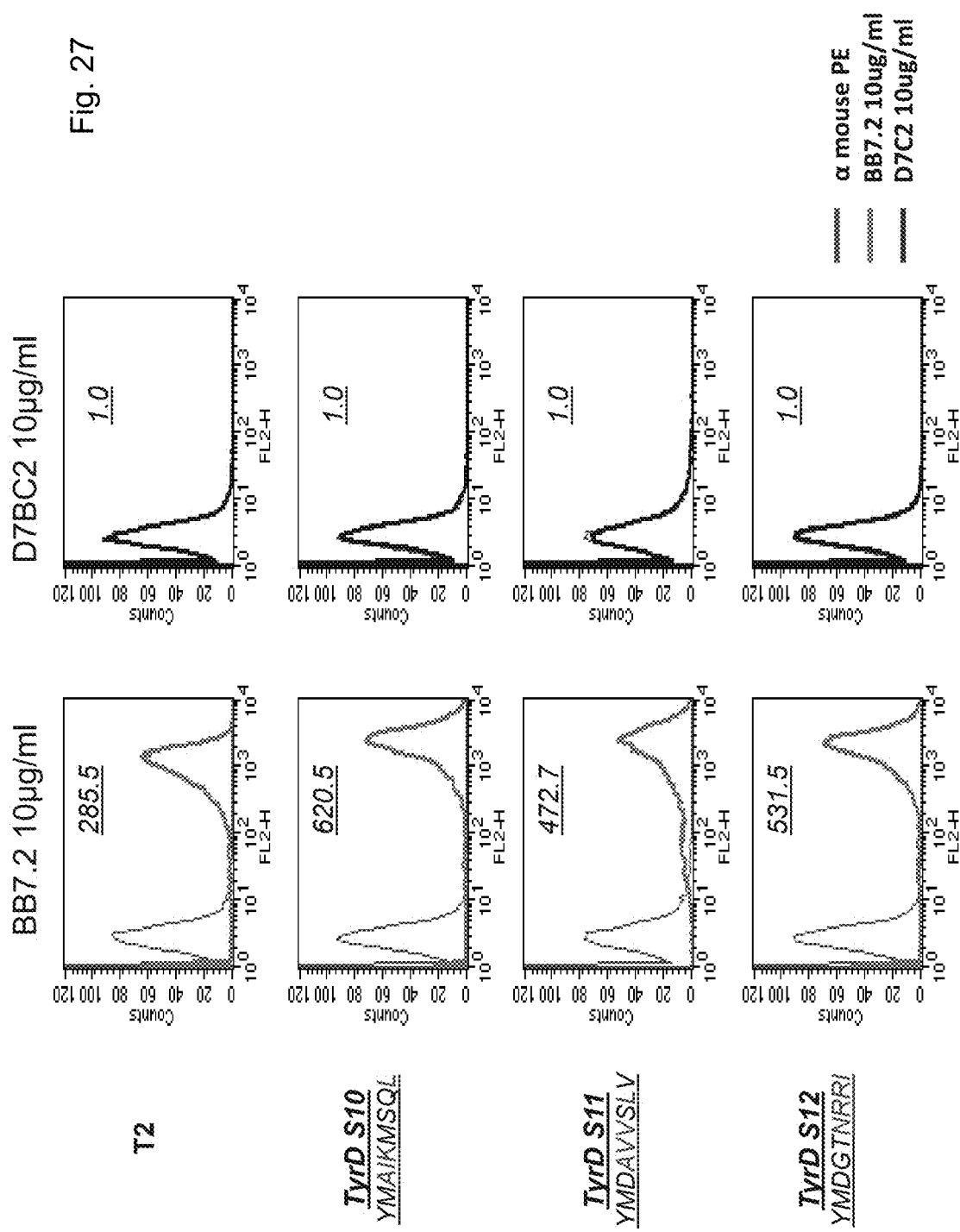

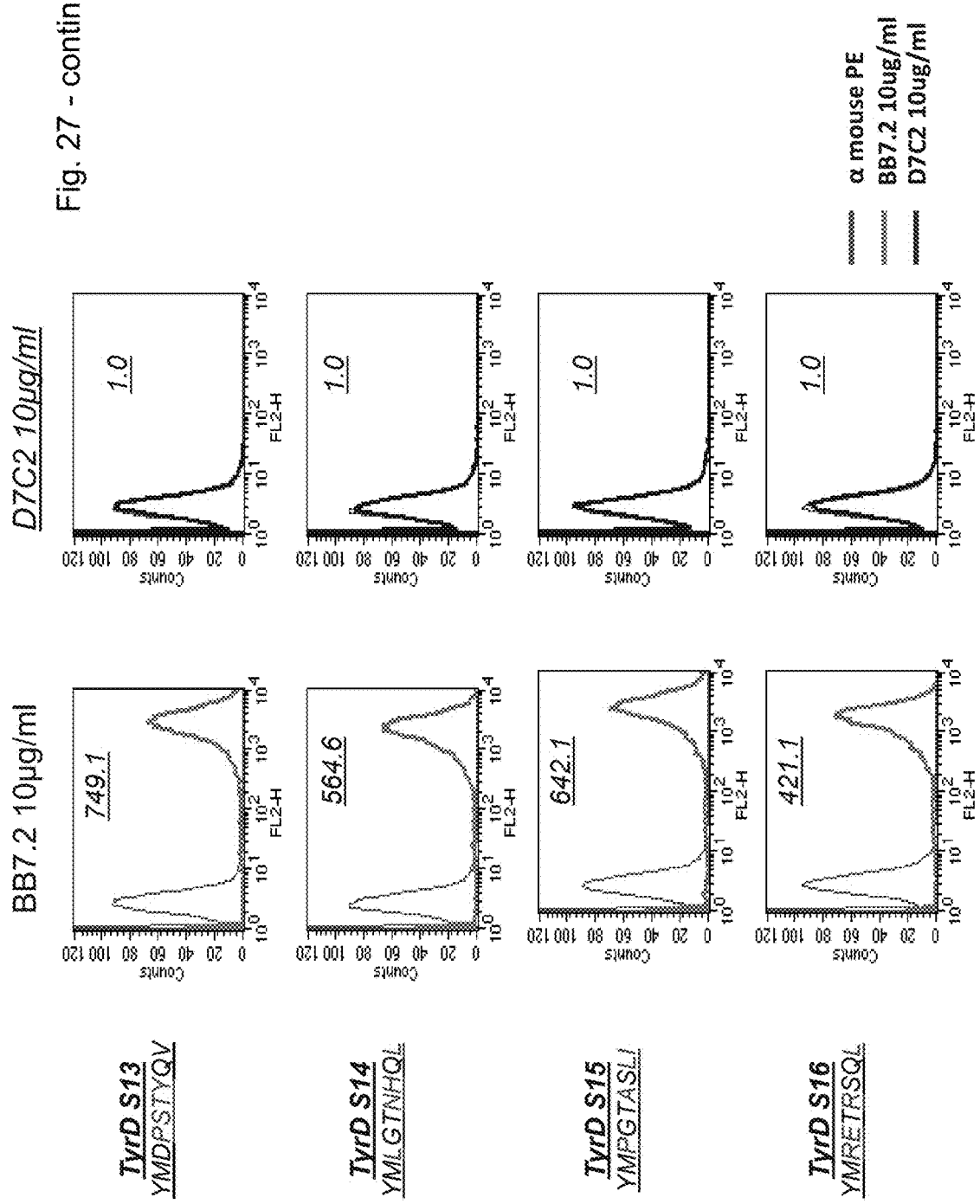

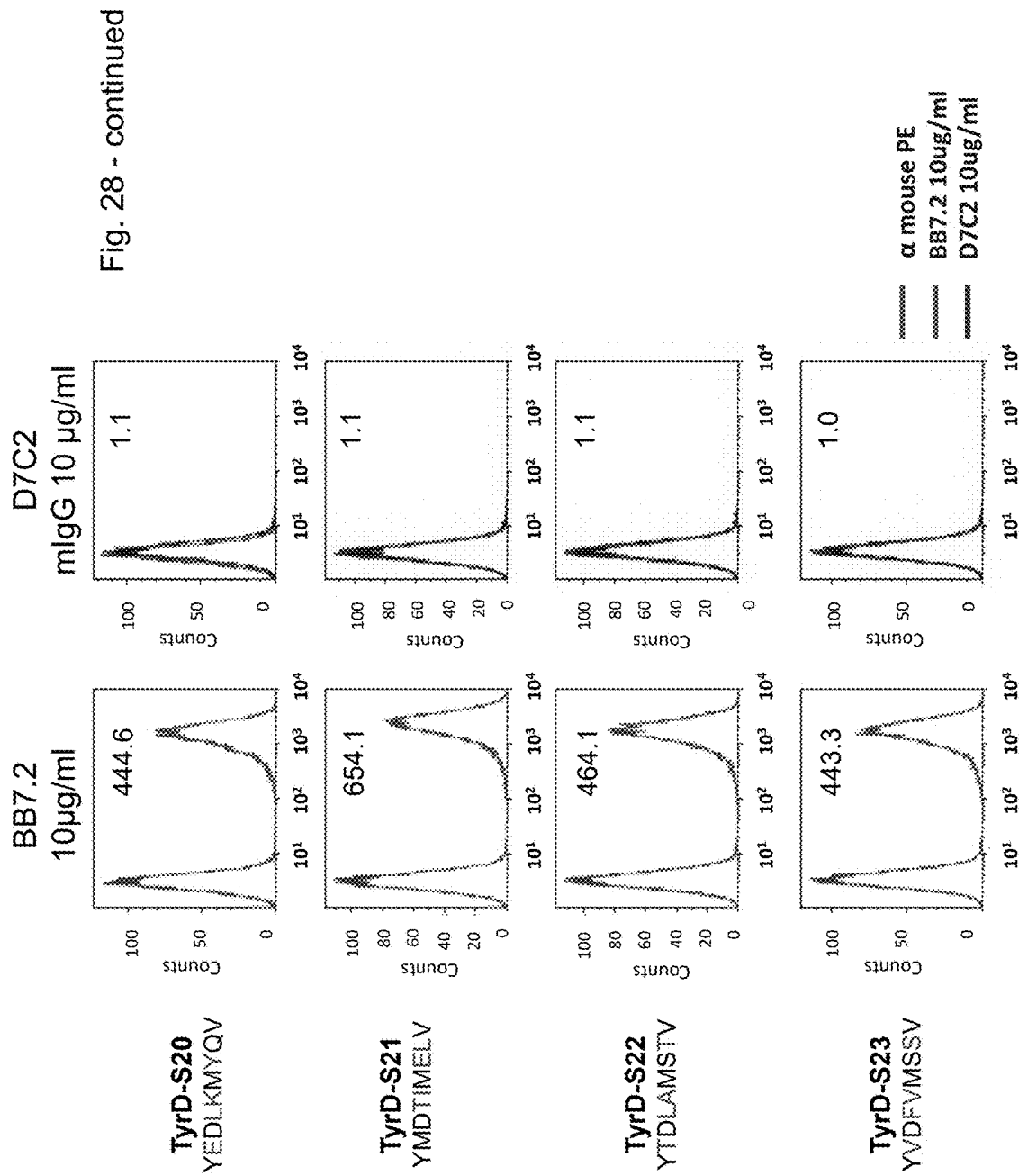

Figure 31:
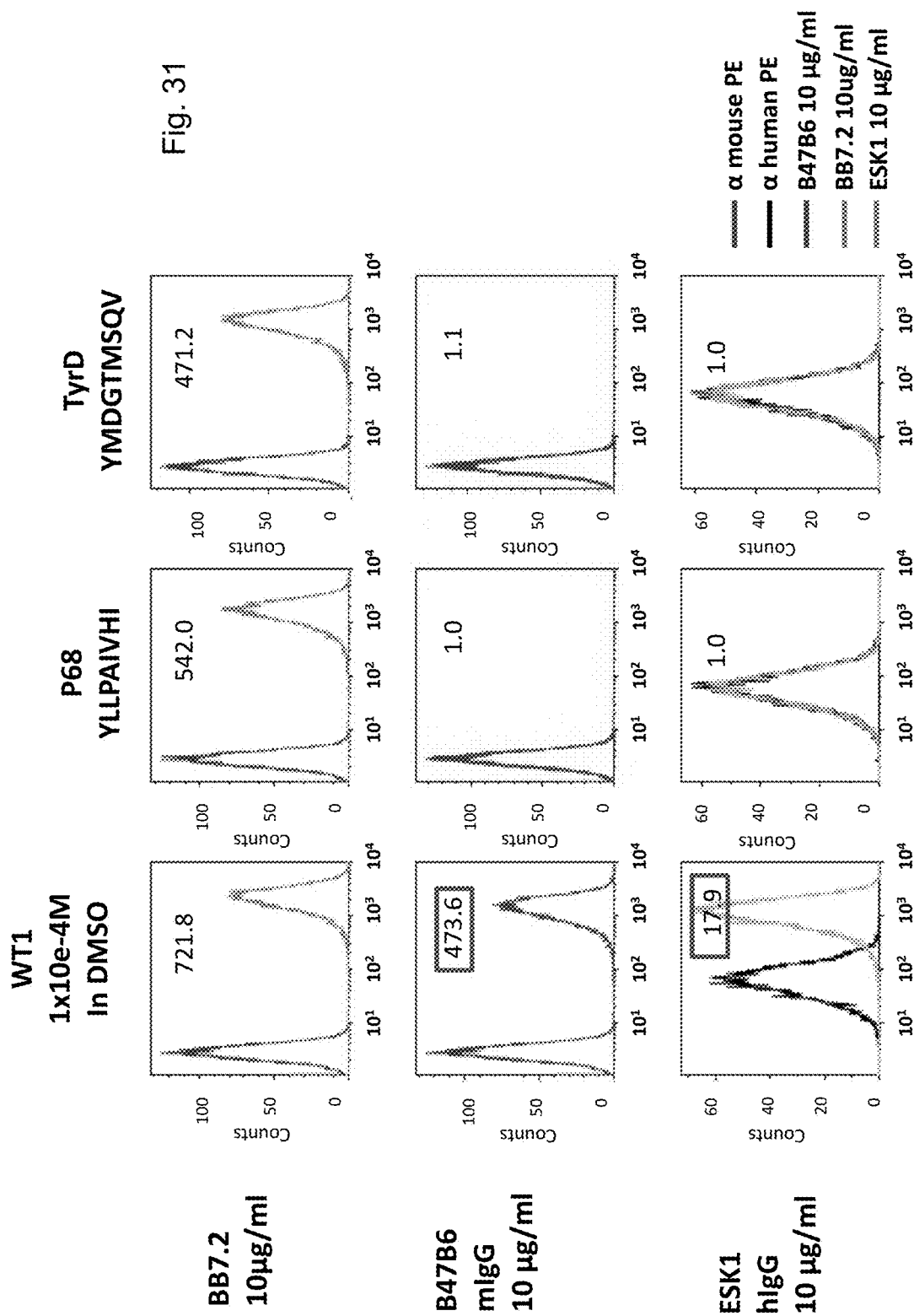

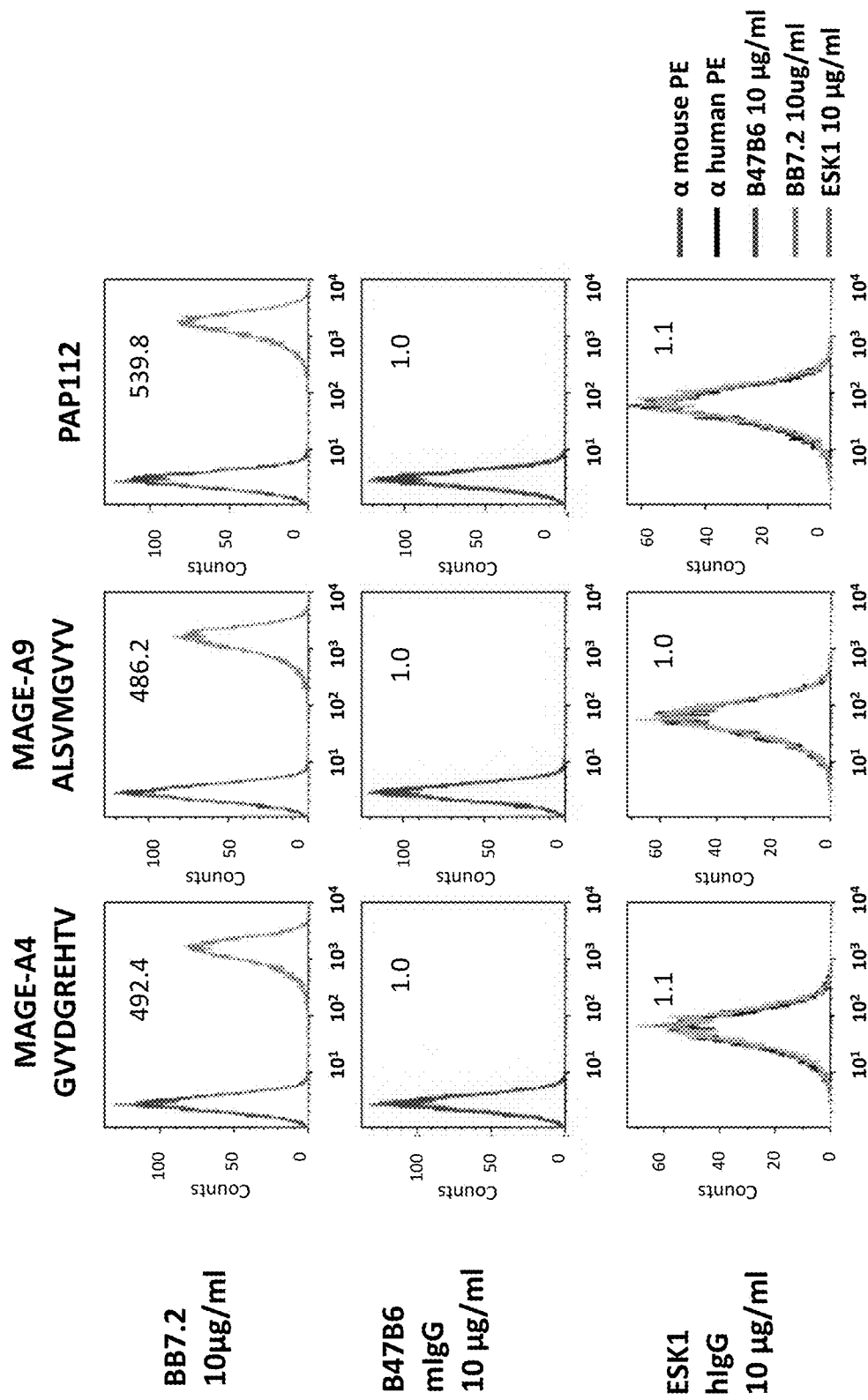
Fig. 31 - continued

Figure 32:
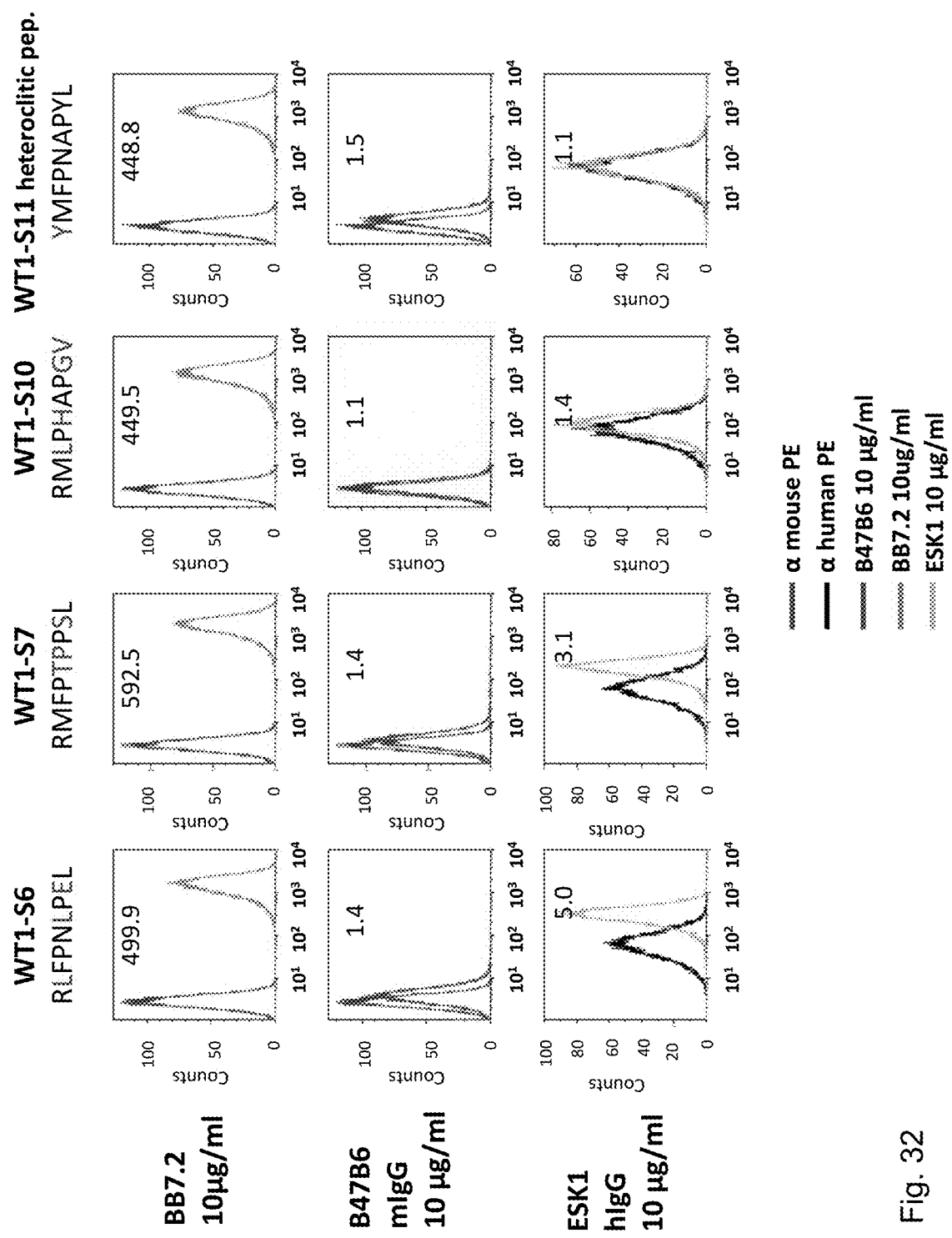

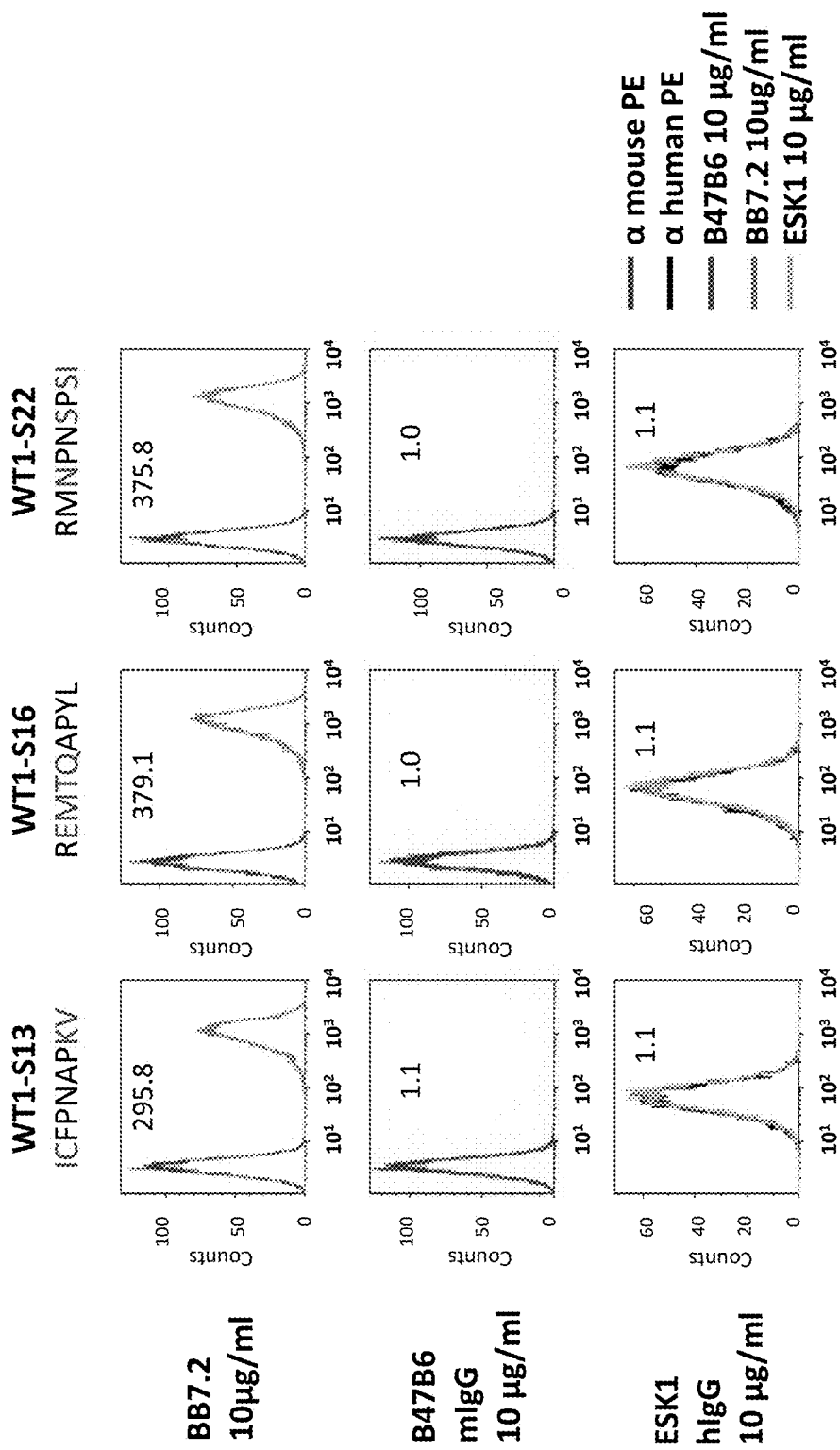
Fig. 32 - continued

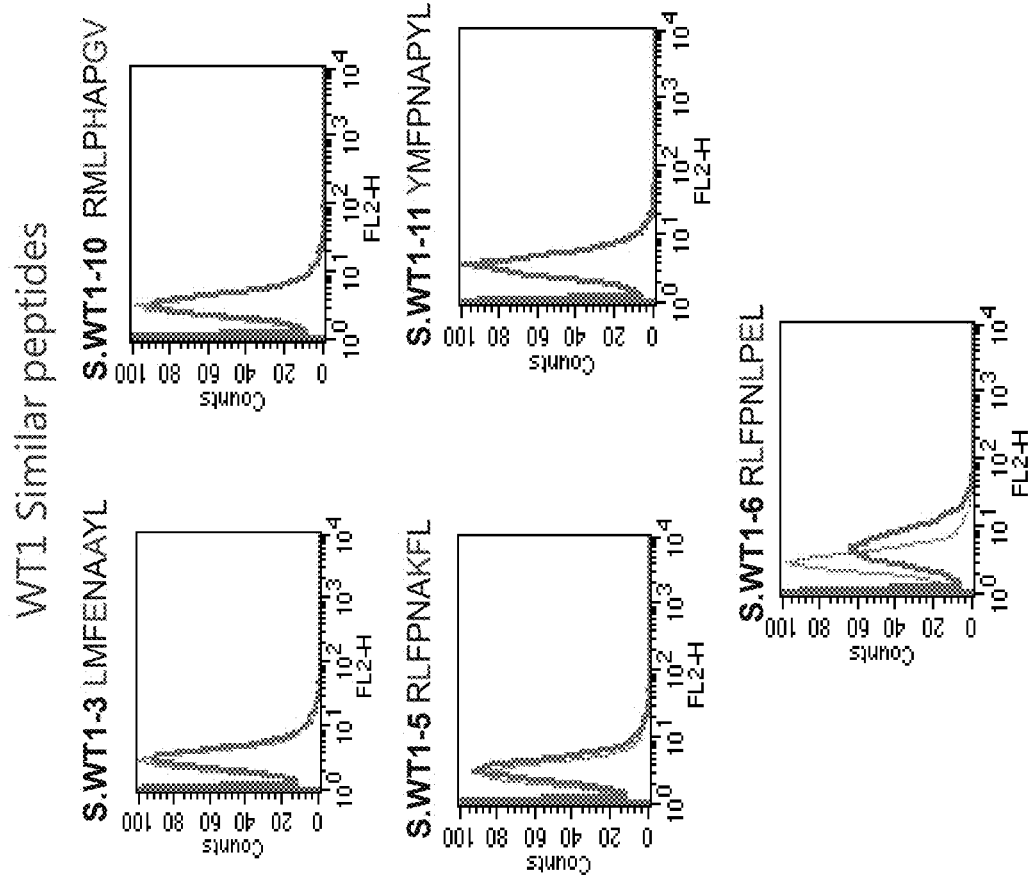

Figure 34:
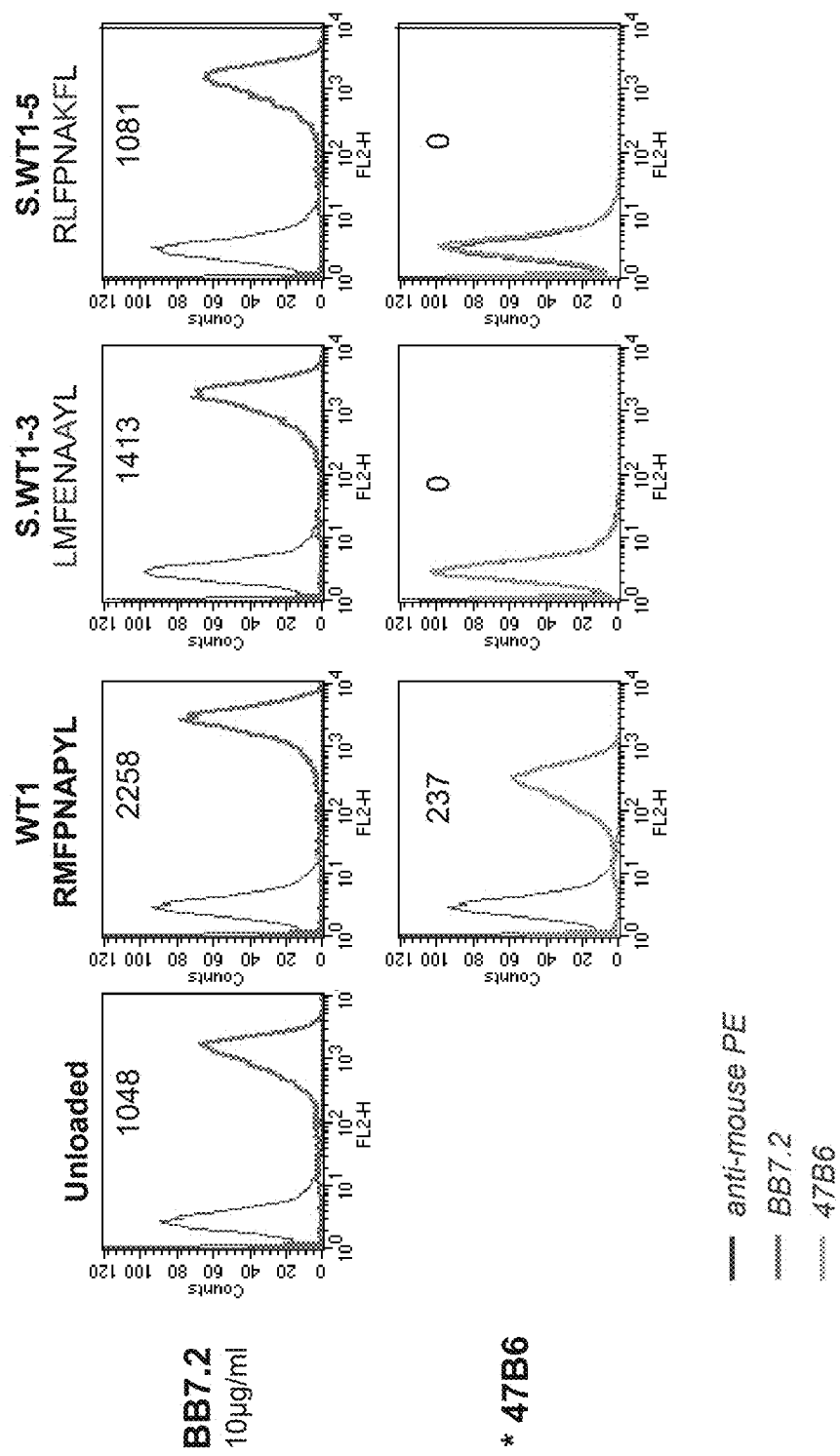

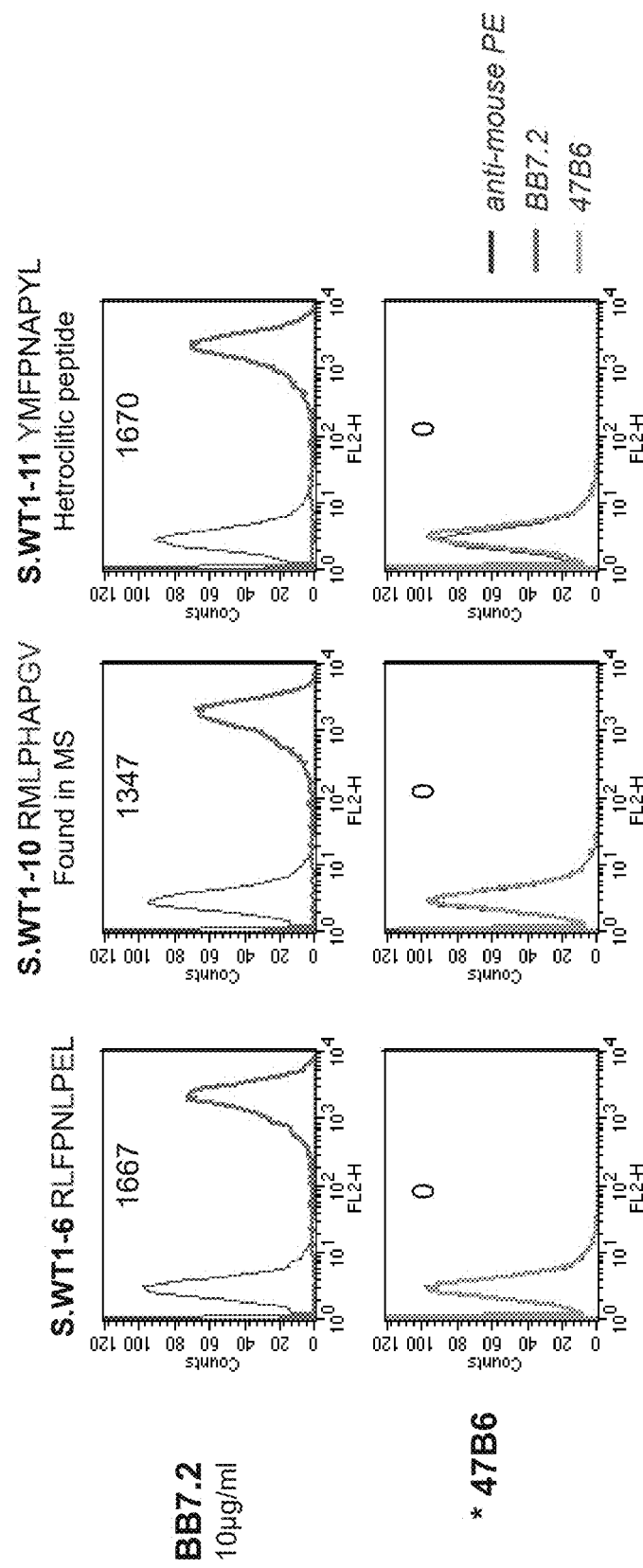
Fig. 34 - continued

Figure 35:
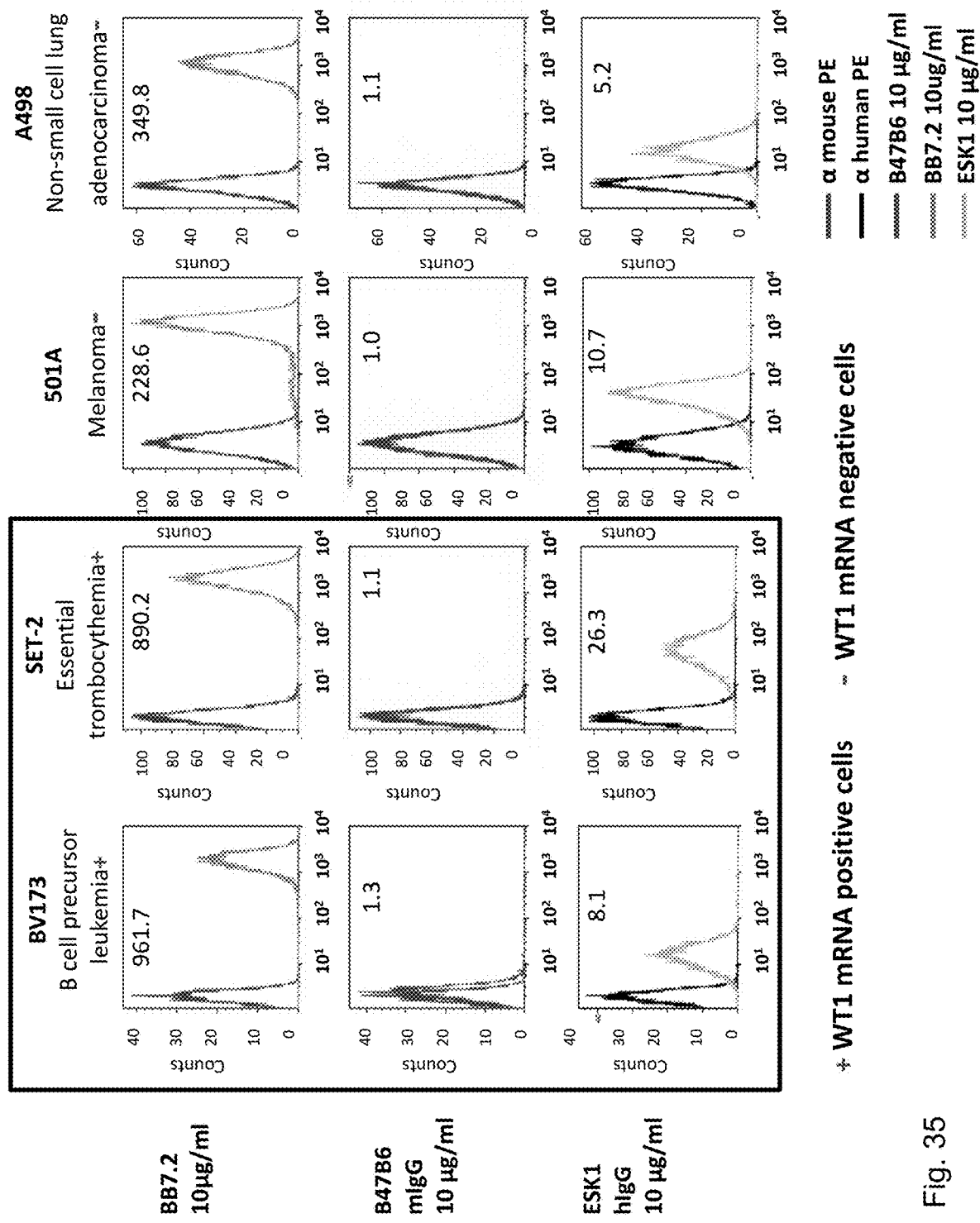

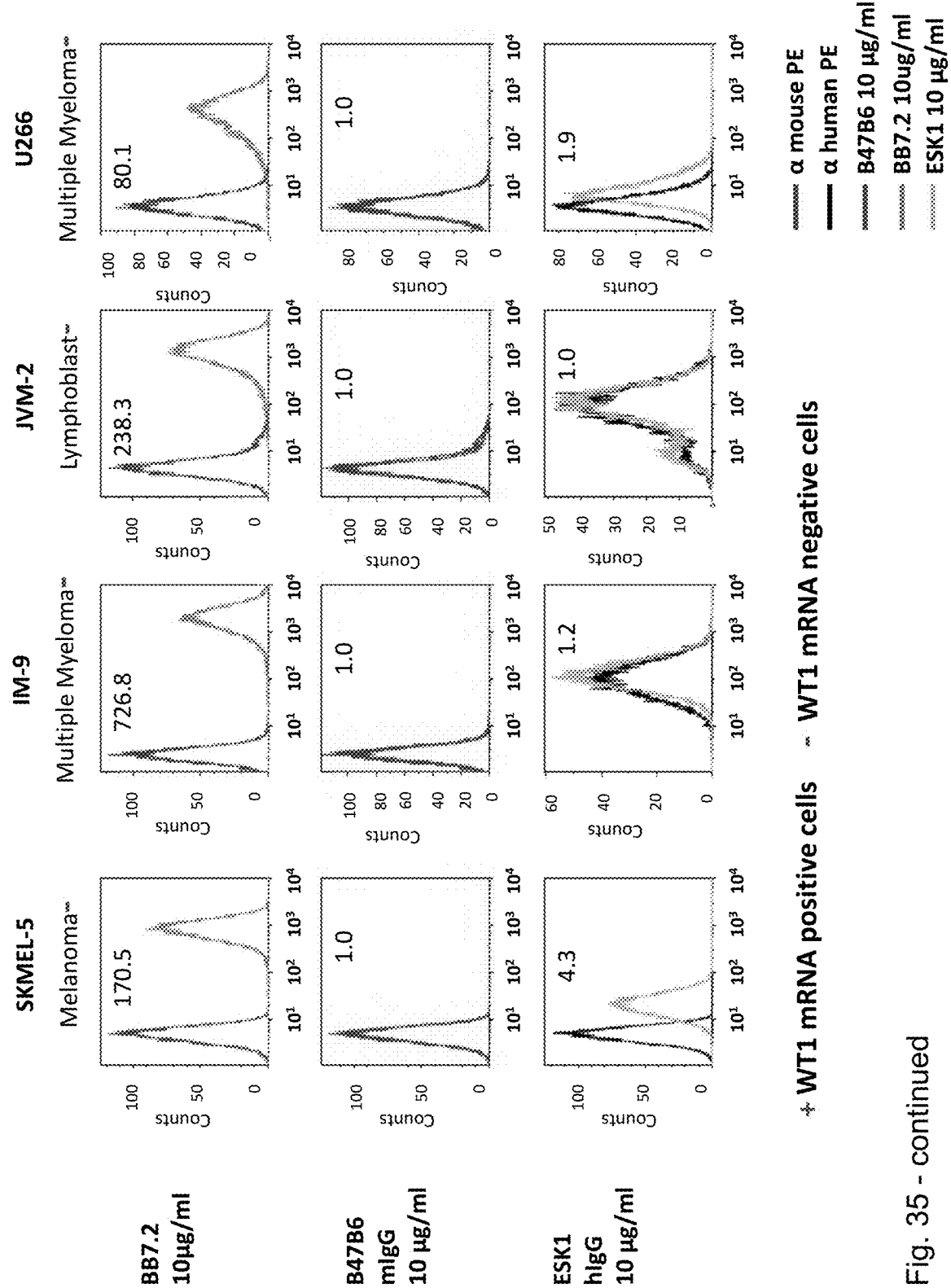
Fig. 35 - continued

** WT1-loaded T2 serve as positive control. Actual MFI reaches 1300.

Fig. 37

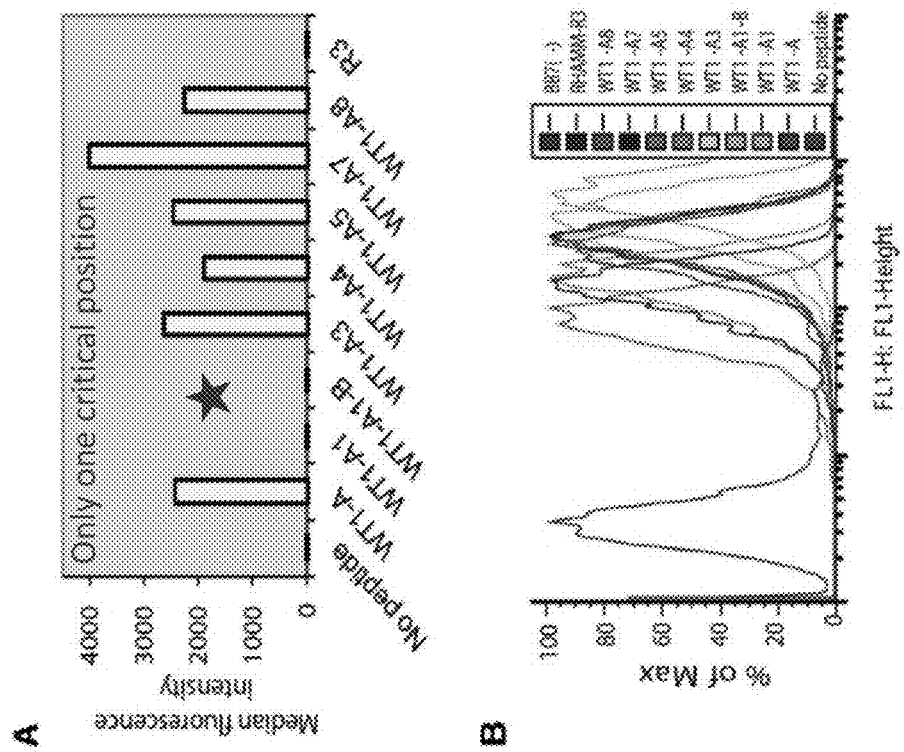

Figure S1. Epitope specificity. The RMF peptide sequence was substituted with alanine at positions 1, 3, 4, 5, 7, or 8, or with tyrosine (WT1-A1B) at position 1 (sequences in table S1). (A) T2 cells were pulsed with indicated peptides at 50 μg/ml and the binding of ESK1 was measured by flow cytometry. (B) In order to show that the analog peptides still bound to HLA-A0201, cells were simultaneously stained with anti-HLA-A2 mAb, clone BB7.2 to measure the relative binding of the peptides to HLA-A2 molecule.

Tao Dao et al. *Sci Transl Med* 5, 176ra33 (2013)

* Found by MS in normal tissues

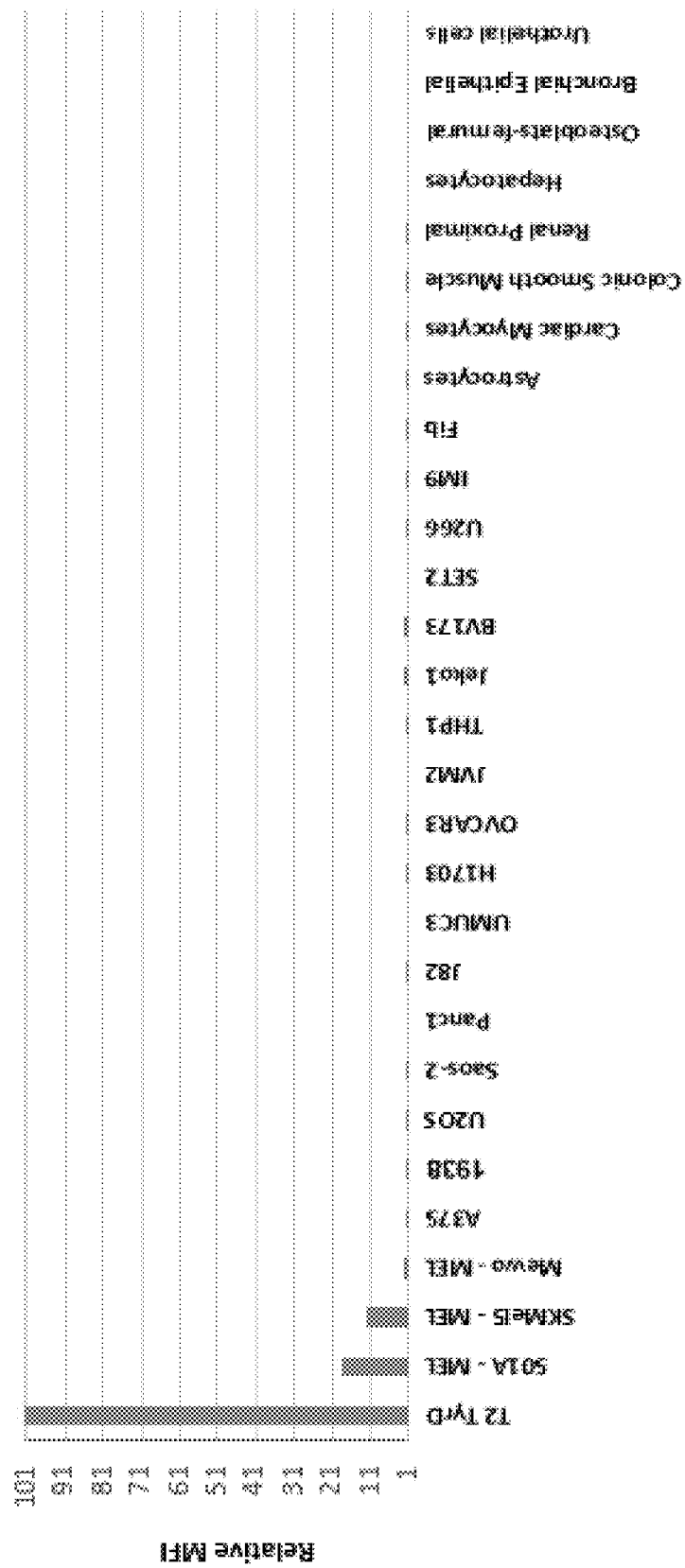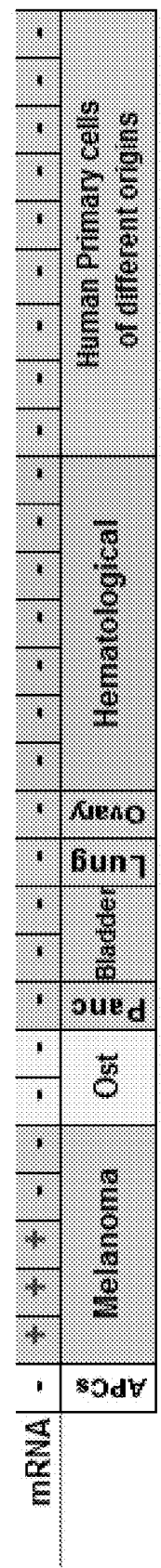
Fig. 40B

906-11-D11
Heavy chain: DNA sequence (1398 bp)
Leader sequence-FR1-CDR1-FR2-CDR2-FR3-CDR3-FR4-Constant region-Stop codon
ATGGACAGGCTTACTTCCTCATTCCTGCTGCTGATTGTCCCTGCATATGTCCTTTCCCAGGTAACTC
TGAAAGAGTCTGGCCCTGGGATATTGCAGCCCTCCCAGACCCTCAGTCTGACTTGTTCTTTCTCTGG
GTTTTCACTGACCACTTCTGGTATGGGTGTGAGCTGGATTCGTCAGCCTTCAGGAAAGGGTCTGGAG
TGGCTGGCACACATTTACTGGGATGATGACAAGCGCTATAACCCATCCCTGAAGAGCCGACTCACAA
TCTCCAAGGATACCTCCAGAAACCAGGTATTCCTCAAGATCACCAGTGTGGACGCTGCAGATACTGC
CACATACTACTGTGCTCGAAAGGACTACGGTAGTAGCTTCTATGCTATGCACTACTGGGGTCAAGGA
ACCTCAGTCACCGTCTCCTCAGCCAAAACGACACCCCCATCTGTCTATCCACTGGCCCCTGGATCTG
CTGCCCAAACTAACTCCATGGTGACCCTGGGATGCCTGGTCAAGGGCTATTTCCCTGAGCCAGTGAC
AGTGACCTGGAACTCTGGATCCCTGTCCAGCGGTGTGCACACCTTCCCAGCTGTCCTGCAGTCTGAC
CTCTACACTCTGAGCAGCTCAGTGACTGTCCCCTCCAGCACCTGGCCCAGCGAGACCGTCACCTGCA
ACGTTGCCCACCCGGCCAGCAGCACCAAGGTGGACAAGAAAATTGTGCCCAGGGATTGTGGTTGTAA
GCCTTGCATATGTACAGTCCCAGAAGTATCATCTGTCTTCATCTTCCCCCAAAGCTCAAGGATGTG
CTCACCATTACTCTGACTCCTAAGGTCACGTGTGTTGTGGTAGACATCAGCAAGGATGATCCCGAGG
TCCAGTTCAGCTGGTTTGTAGATGATGTGGAGGTGCACACAGCTCAGACGCAACCCCGGGAGGAGCA
GTTCAACAGCACTTTCCGCTCAGTCAGTGAACTTCCCATCATGCACCAGGACTGGCTCAATGGCAAG
GAGTTCAAATGCAGGGTCAACAGTGCAGCTTTCCCTGCCCCCATCGAGAAAACCATCTCCAAAACCA
AAGGCAGACCGAAGGCTCCACAGGTGTACACCATTCCACCTCCCAAGGAGCAGATGGCCAAGGATAA
AGTCAGTCTGACCTGCATGATAACAGACTTCTTCCCTGAAGACATTACTGTGGAGTGGCAGTGGAAT
GGGCAGCCAGCGGAGAACTACAAGAACACTCAGCCCATCATGGACACAGATGGCTCTTACTTCGTCT
ACAGCAAGCTCAATGTGCAGAAGAGCAACTGGGAGGCAGGAAATACTTTCACCTGCTCTGTGTTACA
TGAGGGCCTGCACAACCACCATACTGAGAAGAGCCTCTCCCACTCTCCTGGTAAATGA
Heavy chain: Amino acids sequence (465 AA)
Leader sequence-FR1-CDR1-FR2-CDR2-FR3-CDR3-FR4-Constant region-Stop codon
MDRLTSSFLLLIVPAYVLSQVTLKESGPGILQPSQTLSLTCSFSGFSLTTSGMGVSWIRQPSGKGLE
WLAHIYWDDDKRYNPSLKSRLTISKDTSRNQVFLKITSVDAADTATYYCARKDYGSSFYAMHYWGQG
TSVTVSSAKTTPPSVYPLAPGSAAQTNSMVTLGCLVKGYFPEPVTVTWNSGSLSSGVHTFPAVLQSD
LYTLSSSVTVPSSTWPSETVTCNVAHPASSTKVDKKIVPRDCGCKPCICTVPEVSSVFIFPPKPKDV
LTITLTPKVTCVVVDISKDDPEVQFSWFVDDVEVHTAQTQPREEQFNSTFRSVSELPIMHQDWLNGK
EFKCRVNSAAFPAPIEKTISKTKGRPKAPQVYTIPPPKEQMAKDKVSLTCMITDFFPEDITVEWQWN
GQPAENYKNTQPIMDTDGSYFVYSKLNVQKSNWEAGNTFTCSVLHEGLHNHHTEKSLSHSPGK
Light chain: DNA sequence (702 bp)
Leader sequence-FR1-CDR1-FR2-CDR2-FR3-CDR3-FR4-Constant region-Stop codon
ATGAGACCGTCTATTCAGTTCCTGGGGCTCTTGTTGTTCTGGCTTCATGGTGCTCAGTGTGACATCC
AGATGACACAGTCTCCATCCTCACTGTCTGCATCTCTGGGAGGCAAAGTCACCATCACATGCAAGGC
AAGCCAAGACATTCACAACTATATAGCTTGGTACCAACACAAGCCTGTAAAAGGTCCTAGGCTGCTC
ATACATTACACATCTACATTACAGCCAGGCACCCATCAAGGTTCAGTGGAAGTGGGTCTGGGAGAG
ATTATTCCTTCAGCATCAGCAACCTGGAGCCTGAAGATATTGCAACTTATTATTGTCTACAGTATGA
TAATCTGTGGACGTTCGGTGGAGGCACCAAGCTGGAAATCAAACGGGCTGATGCTGCACCAACTGTA
TCCATCTTCCCACCATCCAGTGAGCAGTTAACATCTGGAGGTGCCTCAGTCGTGTGCTTCTTGAACA
ACTTCTACCCCAAAGACATCAATGTCAAGTGGAAGATTGATGGCAGTGAACGACAAAATGGCGTCCT
GAACAGTTGGACTGATCAGGACAGCAAAGACAGCACCTACAGCATGAGCAGCACCCTCACGTTGACC
AAGGACGAGTATGAACGACATAACAGCTATACCTGTGAGGCCACTCACAAGACATCAACTTCACCCA
TTGTCAAGAGCTTCAACAGGAATGAGTGTTAG
Light chain: Amino acids sequence (233 AA)
Leader sequence-FR1-CDR1-FR2-CDR2-FR3-CDR3-FR4-Constant region-Stop codon
MRPSIQFLGLLLFWLHGAQCDIQMTQSPSSLSASLGGKVTITCKASQDIHNYIAWYQHKPVKGPRLL
IHYTSTLQPGTPSRFSGSGSGRDYSFSISNLEPEDIATYYCLQYDNLWTFGGGTKLEIKRADAAPTV
SIFPPSSEQLTSGGASVVCFLNNFYPKDINVKWKIDGSERQNGVLNSWTDQDSKDSTYSMSSTLTLT
KDEYERHNSYTCEATHKTSTSPIVKSFNRNEC

Fig. 68

Heavy chain: DNA sequence (1380 bp)
Leader sequence-FR1-CDR1-FR2-CDR2-FR3-CDR3-FR4-Constant region-Stop codon
ATGGCTGTCCTGGTGCTGTTCCTCTGCCTGGTTGCATTTCCAAGCTGTGTCCTGTCCCAGGTGCAAC
TGAAGGAATCAGGACCTGGTCTGGTGGCGCCCTCACAGAGCCTGTCCATCACTTGCACTGTCTCTGG
GTTTTCATTAACCAGCTATGGTGTACACTGGGTTCGCCAGCCTCCAGGAAAGGGTCTGGAGTGGCTG
GGAGTAATATGGGCTGGTGGAACCACAAATTATAATTCGGCTCTCATGTCCAGACTGAGCATCAGCA
GAGACAACTCCAAGAGCCAAGTTTTCTTAGAAATGAACAGTCTGCAAACTGATGACACAGCCATTTA
CTACTGTGCCAGAGATGGTCACTTCCACTTTGACTTCTGGGGCCAAGGCACCACTCTCACAGTCTCC
TCAGCCAAAACGACACCCCCATCTGTCTATCCACTGGCCCCTGGATCTGCTGCCCAAACTAACTCCA
TGGTGACCCTGGGATGCCTGGTCAAGGGCTATTTCCCTGAGCCAGTGACAGTGACCTGGAACTCTGG
ATCCCTGTCCAGCGGTGTGCACACCTTCCCAGCTGTCCTGCAGTCTGACCTCTACACTCTGAGCAGC
TCAGTGACTGTCCCCTCCAGCACCTGGCCCAGCGAGACCGTCACCTGCAACGTTGCCCACCCGGCCA
GCAGCACCAAGGTGGACAAGAAAATTGTGCCCAGGGATTGTGGTTGTAAGCCTTGCATATGTACAGT
CCCAGAAGTATCATCTGTCTTCATCTTCCCCCCAAAGCCCAAGGATGTGCTCACCATTACTCTGACT
CCTAAGGTCACGTGTGTTGTGGTAGACATCAGCAAGGATGATCCCGAGGTCCAGTTCAGCTGGTTTG
TAGATGATGTGGAGGTGCACACAGCTCAGACGCAACCCCGGGAGGAGCAGTTCAACAGCACTTTCCG
CTCAGTCAGTGAACTTCCCATCATGCACCAGGACTGGCTCAATGGCAAGGAGTTCAAATGCAGGGTC
AACAGTGCAGCTTTCCCTGCCCCCATCGAGAAAACCATCTCCAAAACCAAAGGCAGACCGAAGGCTC
CACAGGTGTACACCATTCCACCTCCCAAGGAGCAGATGGCCAAGGATAAAGTCAGTCTGACCTGCAT
GATAACAGACTTCTTCCCTGAAGACATTACTGTGGAGTGGCAGTGGAATGGGCAGCCAGCGGAGAAC
TACAAGAACACTCAGCCCATCATGGACACAGATGGCTCTTACTTCGTCTACAGCAAGCTCAATGTGC
AGAAGAGCAACTGGGAGGCAGGAAATACTTTCACCTGCTCTGTGTTACATGAGGGCCTGCACAACCA
CCATACTGAGAAGAGCCTCTCCCACTCTCCTGGTAAATGA

Heavy chain: Amino acids sequence (459 AA)
Leader sequence-FR1-CDR1-FR2-CDR2-FR3-CDR3-FR4-Constant region-Stop codon
MAVLVLFLCLVAFPSCVLSQVQLKESGPGLVAPSQSLSITCTVSGFSLTSYGVHWVRQPPGKGLEWL
GVIWAGGTTNYNSALMSRLSISRDNSKSQVFLEMNSLQTDDTAIYYCARDGHFHFDFWGQGTTLTVS
SAKTTPPSVYPLAPGSAAQTNSMVTLGCLVKGYFPEPVTVTWNSGSLSSGVHTFPAVLQSDLYTLSS
SVTVPSSTWPSETVTCNVAHPASSTKVDKKIVPRDCGCKPCICTVPEVSSVFIFPPKPKDVLTITLT
PKVTCVVVDISKDDPEVQFSWFVDDVEVHTAQTQPREEQFNSTFRSVSELPIMHQDWLNGKEFKCRV
NSAAFPAPIEKTISKTKGRPKAPQVYTIPPPKEQMAKDKVSLTCMITDFFPEDITVEWQWNGQPAEN
YKNTQPIMDTDGSYFVYSKLNVQKSNWEAGNTFTCSVLHEGLHNHHTEKSLSHSPGK

Light chain: DNA sequence (705 bp)
Leader sequence-FR1-CDR1-FR2-CDR2-FR3-CDR3-FR4-Constant region-Stop codon
ATGAGTGTGCCCACTCAGGTCCTGGGGTTGCTGCTGCTGTGGCTTACAGATGCCAGATGTGACATCC
AGATGACTCAGTCTCCAGCCTCCCTATCTGTATCTGTGGGAGAAACTGTCACCATCACATGTCGAGC
AAGTGATATTATTTACAGTAATTTAGCATGGTATCAGCAGAAACAGGGAAAATCTCCTCAGCTCCTG
GTCTATGCTGCAACAAACTTAGCAGCTGGTGTGCCATCAAGGTTCAGTGGCAGTGGATCAGGCACAC
AGTATTCCCTCAAGATCAATAGCCTGCAGTCTGAAGATTTTGGGACTTATTACTGTCAACATTTTTG
GGGTAGTTCAATCTCGTTCGGCTCGGGGACAAAGTTGGAAATAAAACGGGCTGATGCTGCACCAACT
GTATCCATCTTCCCACCATCCAGTGAGCAGTTAACATCTGGAGGTGCCCTCAGTCGTGTGCTTCTTGA
ACAACTTCTACCCCAAAGACATCAATGTCAAGTGGAAGATTGATGGCAGTGAACGACAAAATGGCGT
CCTGAACAGTTGGACTGATCAGGACAGCAAAGACAGCACCTACAGCATGAGCAGCACCCTCACGTTG
ACCAAGGACGAGTATGAACGACATAACAGCTATACCTGTGAGGCCACTCACAAGACATCAACTTCAC
CCATTGTCAAGAGCTTCAACAGGAATGAGTGTTAG

Light chain: Amino acids sequence (234 AA)
Leader sequence-FR1-CDR1-FR2-CDR2-FR3-CDR3-FR4-Constant region-Stop codon
MSVPTQVLGLLLLWLTDARCDIQMTQSPASLSVSVGETVTITCRASDIIYSNLAWYQQKQGKSPQLL
VYAATNLAAGVPSRFSGSGSGTQYSLKINSLQSEDFGTYYCQHFWGSSISFGSGTKLEIKRADAAPT
VSIFPPSSEQLTSGGASVVCFLNNFYPKDINVKWKIDGSERQNGVLNSWTDQDSKDSTYSMSSTLTL
TKDEYERHNSYTCEATHKTSTSPIVKSFNRNEC

Fig. 69

WT1 B47B6 TCRL SEQUENCE

Heavy chain: DNA sequence

FR1-CDR1-FR2-CDR2-FR3-CDR3-FR4-Constant region

```
GAAGTGCAGTTGGTGGAGTCGGGGGGAGGCTTAGTGAAGCCTGGAGGGTCCCTGAAACTCTCCTGTGCAGCCTC
TGGATTCGTTTTCAGTAGCTATGACATGTCTTGGGTTCGCCAGGCTCAGGAGAAGAGGCTGGAGTGGGTCGCATA
CATGAGTAGTGGTGGCGGCACCTACTATCCAGACACTGTGAAGGGCCGATTCACCATCTCCAGAGACAATGCCAA
GAACACCCTGCACCTGCAAATGAGCAGCCTGAAGTCTGAGGACACAGCCATGTATTACTGTGCAAGACATGATGA
GATTACTAACTTTGACTACTGGGGCCAAGGCACCACTCTCACAGTCTCCTCAGCCAAAACGACACCCCCATCTGT
CTATCCACTGGCCCTGGATCTGCTGCCCAAACTAACTCCATGGTGACCCTGGGATGCCTGGTCAAGGGC
TATTTCCCTGAGCCAGTGACAGTGACCTGGAACTCTGGATCCCTGTCCAGCGGTGTGCACACCTTCCCAG
CTGTCCTGCAGTCTGACCTCTACACTCTGAGCAGCTCAGTGACTGTCCCCTCCAGCACCTGGCCCAGCGA
GACCGTCACCTGCAACGTTGCCCACCCGGCCAGCAGCACCAAGGTGGACAAGAAAATTGTGCCCAGGGAT
TGTGGTTGTAAGCCTTGCATATGTACAGTCCCAGAAGTATCATCTGTCTTCATCTTCCCCCCAAAAGCCCA
AGGATGTGCTCACCATTACTCTGACTCCTAAGGTCACGTGTGTTGTGGTAGACATCAGCAAGGATGATCC
CGAGGTCCAGTTCAGCTGGTTTGTAGATGATGTGGAGGTGCACACAGCTCAGACGCAACCCCGGGAGGAG
CAGTTCAACAGCACTTTCCGCTCAGTCAGTGAACTTCCCATCATGCACCAGGACTGGCTCAATGGCAAG
GAGTTCAAATGCAGGGTCAACAGTGCAGCTTTCCCTGCCCCCATCGAGAAAACCATCTCCAAAACCAAAG
GCAGACCGAAGGCTCCACAGGTGTACACCATTCCACCTCCCAAGGAGCAGATGGCCAAGGATAAAGTCAG
TCTGACCTGCATGATAACAGACTTCTTCCCTGAAGACATTACTGTGGAGTGGCAGTGGAATGGGCAGCCA
GCGGAGAACTACAAGAACACTCAGCCCATCATGGACACAGATGGCTCTTACTTCGTCTACAGCAAGCTCA
ATGTGCAGAAGAGCAACTGGGAGGCAGGAAATACTTTCACCTGCTCTGTGTTACATGAGGGCCTGCACAA
CCACCATACTGAGAAGAGCCTCTCCCACTCTCCTGGTAAA
```

```
EVQLVESGGGLVKPGGSLKLSCAASGFVFSSYDMSWVRQAQEKRLEWVAYMSSGGGTYYPDTVKGRFTISRDNAKNT
LHLQMSSLKSEDTAMYYCARHDEITNFDYWGQGTTLTVSSAKTTPPSVYPLAPGSAAQTNSMVTLGCLVKGYFP
EPVTVTWNSGSLSSGVHTFPAVLQSDLYTLSSSVTVPSSTWPSETVTCNVAHPASSTKVDKKIVPRDCGC
KPCICTVPEVSSVFIFPPKPKDVLTITLTPKVTCVVVDISKDDPEVQFSWFVDDVEVHTAQTQPREEQFN
STFRSVSELPIMHQDWLNGKEFKCRVNSAAFPAPIEKTISKTKGRPKAPQVYTIPPPKEQMAKDKVSLTC
MITDFFPEDITVEWQWNGQPAENYKNTQPIMDTDGSYFVYSKLNVQKSNWEAGNTFTCSVLHEGLHNHHT
EKSLSHSPGK
```

Light chain: DNA sequence
FR1-CDR1-FR2-CDR2-FR3-CDR3-FR4-Constant region

```
GATATTGTGCTCACTCAGTCTCCAGCCACCCTGTCTGTGAGTCCAGGAGATAGCGTCAGTCTTTCCTGCAGGGCCAGCCAAAGT
ATTAGCAACAGCCTACACTGGTATCAACAAAAATCACATGAGTCTCCAAGGCTTCTCATCAAGTATGCTTCCCAGTCCATCTCTG
GAATCCCCTCTAGGTTCAGTGGCAGTGGATCAGGGACAGATTTCACtCTCAGTATCAACAGTGTGGAGACTGAAGATTTTGGA
ATGTATTTCTGTCAACAGAGTTACAGCTGGCCTCTCACGTTCGGTGCTGGGTCCAAGCTGGAGCTGAAACGGGCTGATGCT
GCACCAACTGTATCCATCTTCCCACCATCCAGTGAGCAGTTAACATCTGGAGGTGCCTCAGTCGTGTGCT
TCTTGAACAACTTCTACCCCAAAGACATCAATGTCAAGTGGAAGATTGATGGCAGTGAACGACAAAATGG
CGTCCTGAACAGTTGGACTGATCAGGACAGCAAAGACAGCACCTACAGCATGAGCAGCACCCTCACGTTG
ACCAAGGACGAGTATGAACGACATAACAGCTATACCTGTGAGGCCACTCACAAGACATCAACTTCACCCA
TTGTCAAGAGCTTCAACAGGAATGAGTGT
```

Fig. 70

DIVLTQSPATLSVSPGDSVSLSCRASQSISNSLHWYQQKSHESPRLLIKYASQSISGIPSRFSGSGSGTDFTLSINSVETEDFGMYFCQQ
SYSWPLTFGAGSKLELKRADAAPTVSIFPPSSEQLTSGGASVVCFLNNFYPKDINVKWKIDGSERQNGVLNSWT
DQDSKDSTYSMSSTLTLTKDEYERHNSYTCEATHKTSTSPIVKSFNRNEC

Fig. 70 - continued

C106B9 MAGE-A4 TCRL

Heavy chain: DNA sequence

FR1-CDR1-FR2-CDR2-FR3-CDR3-FR4-Constant region

Nuc-seq:

CAGGTTCAACTGCAGCAGTCTGGAGGTGAGGTGATGAAGCCTGGGGCCTCAGTGAAGCTTTCCTGCAAGGCTACT
GGCTACACATTCACTGGCTACTGGATAGAGTGGATAAAACAGAGGCCTGGACATGGCCTTGAGTGGATTGGAGA
GATTTTACCTGGAAGTGGTGGTACTAACTACAATGAGAAATTCAAGGGCAAGGCCACATTCACTGCACATACATCC
TCCAACACAGCCTACATGCAACTCAGCAGCCTGACAACTGAGGACTCTGCCATCTATTACTGTGCAAGGGATAGTA
ACTCCTTTACTTACTGGGGCCAAGGGACTCTGGTCACTGTCTCTTCAGCCAAAACGACACCCCCATCTGTCTATC
CACTGGCCCCTGGATCTGCTGCCCAAACTAACTCCATGGTGACCCTGGGATGCCTGGTCAAGGGCTATTT
CCCTGAGCCAGTGACAGTGACCTGGAACTCTGGATCCCTGTCAGCGGTGTGCACACCTTCCCAGCTGTC
CTGCAGTCTGACCTCTACACTCTGAGCAGCTCAGTGACTGTCCCCTCCAGCACCTGGCCCAGCGAGACCG
TCACCTGCAACGTTGCCCACCCGGCCAGCAGCACCAAGGTGGACAAGAAAATTGTGCCCAGGGATTGTGG
TTGTAAGCCTTGCATATGTACAGTCCCAGAAGTATCATCTGTCTTCATCTTCCCCCAAAGCCCAAGGAT
GTGCTCACCATTACTCTGACTCCTAAGGTCACGTGTGTTGTGGTAGACATCAGCAAGGATGATCCCGAGG
TCCAGTTCAGCTGGTTTGTAGATGATGTGGAGGTGCACACAGCTCAGACGCAACCCGGGAGGAGCAGTT
CAACAGCACTTTCCGCTCAGTCAGTGAACTTCCCATCATGCACCAGGACTGGCTCAATGGCAAGGAGTTC
AAATGCAGGGTCAACAGTGCAGCTTTCCCTGCCCCCATCGAGAAAACCATCTCCAAAACCAAAGGCAGAC
CGAAGGCTCCACAGGTGTACACCATTCCACCTCCCAAGGAGCAGATGGCCAAGGATAAAGTCAGTCTGAC
CTGCATGATAACAGACTTCTTCCCTGAAGACATTACTGTGGAGTGGCAGTGGAATGGGCAGCCAGCGGAG
AACTACAAGAACACTCAGCCCATCATGGACACAGATGGCTCTTACTTCGTCTACAGCAAGCTCAATGTGC
AGAAGAGCAACTGGGAGGCAGGAAATACTTTCACCTGCTCTGTGTTACATGAGGGCCTGCACAACCACCA
TACTGAGAAGAGCCTCTCCCACTCTCCTGGTAAA

AA-seq:

QVQLQQSGGEVMKPGASVKLSCKATGYTFTGYWIEWIKQRPGHGLEWIGEILPGSGGTNYNEKFKGKATFTAHTSSN
TAYMQLSSLTTEDSAIYYCARDSNSFTYWGQGTLVTVSSAKTTPPSVYPLAPGSAAQTNSMVTLGCLVKGYFPEP
VTVTWNSGSLSSGVHTFPAVLQSDLYTLSSSVTVPSSTWPSETVTCNVAHPASSTKVDKKIVPRDCGCKP
CICTVPEVSSVFIFPPKPKDVLTITLTPKVTCVVVDISKDDPEVQFSWFVDDVEVHTAQTQPREEQFNST
FRSVSELPIMHQDWLNGKEFKCRVNSAAFPAPIEKTISKTKGRPKAPQVYTIPPPKEQMAKDKVSLTCMI
TDFFPEDITVEWQWNGQPAENYKNTQPIMDTDGSYFVYSKLNVQKSNWEAGNTFTCSVLHEGLHNHHTEK
SLSHSPGK

Light Chain

Light chain: DNA sequence (705 bp)
FR1-CDR1-FR2-CDR2-FR3-CDR3-FR4-Constant region CAAATTGTTCTCACCCAGTCTCCAGCAATCATGTCTGCATCTCCAGGGGAGAAGGTCACCATAACCTGCAGTGTCA
GCTCAAGTGTAAGATTACATTCACTGGTTCCAGCAGAAGCCAGGCACTTCTCCCAAATTCTGGATTTATAGCACATCC
ATCCTGGCTTCTGGAGTCCCTGCTCGCTTCAGTGGCAGTGGATCTGGGACCTCTTACTCTCTCACAATCAGCCGAAT
GGAGGCTGAAGATGCTGCCACTTATTACTGCCAGCAAAGGAGtAGTTACCCACCCACgTCGGCTCGGGGACAAAGT

Fig. 71

```
TGGAAATAAAACGGGCTGATGCTGCACCAACTGTATCCATCTTCCCACCATCCAGTGAGCAGTTAACATCTG
GAGGTGCCTCAGTCGTGTGCTTCTTGAACAACTTCTACCCCAAAGACATCAATGTCAAGTGGAAGATTGA
TGGCAGTGAACGACAAAATGGCGTCCTGAACAGTTGGACTGATCAGGACAGCAAAGACAGTACCTACAGC
ATGAGCAGCACCCTCACGTTGACCAAGGACGAGTATGAACGACATAACAGCTATACCTGTGAGGCCACTC
ACAAGACATCAACTTCACCCATTGTCAAGAGCTTCAACAGGAATGAGTGT
```

AA-seq:

```
QIVLTQSPAIMSASPGEKVTITCSVSSSVDYIHWFQQKPGTSPKFWIYSTSILASGVPARFSGSGSGTSYSLTISRMEAEDA
ATYYCQQRSSYPPTFGSGTKLEIKRADAAPTVSIFPPSSEQLTSGGASVVCFLNNFYPKDINVKWKIDGSERQN
GVLNSWTDQDSKDSTYSMSSTLTLTKDEYERHNSYTCEATHKTSTSPIVKSFNRNEC
```

Fig. 71 - continued

F184C7 MAGE A9

Heavy chain: DNA sequence

FR1-CDR1-FR2-CDR2-FR3-CDR3-FR4-Constant region

Nuc-seq:

CAGGTTCAGCTGCAGCAGTCTGGACCTGAGATGGTGAAGCCTGGGGCCTCAGTGAAGATTCCCTGCAAGGCTTCT
GGCTACGCATTCAGTAGCTCCTGGATGAACTGGGTGAAGCAGAGGCCTGGAAAGGGTCTTGAGTGGATTGGACG
GATTTATCCTGGAGATGGAGATACTAACTACAATGAGAAGTTCAAGGGCAAGGCCACACTGACTGTAGACAAATC
CTCCAGCACAGTCTACATGCAACTCAGCAGCCTGACATCTGAGGACTCTGCGGTCTACTTCTGTGCAAGAGAGGCT
ACTACGGTAGTGGCCCCGTACTACTTTGACTACTGGGGCCAAGGCACCACTCTCACAGTCTCCTCAGCCAAAACGA
CACCCCCATCTGTCTATCCACTGGCCCCTGGATCTGCTGCCCAAACTAACTCCATGGTGACCCTGGGATG
CCTGGTCAAGGGCTATTTCCCTGAGCCAGTGACAGTGACCTGGAACTCTGGATCCTGTCCAGCGGTGTG
CACACCTTCCCAGCTGTCCTGCAGTCTGACCTCTACACTCTGAGCAGCTCAGTGACTGTCCCTCCAGCA
CCTGGCCCAGCGAGACCGTCACCTGCAACGTTGCCCACCCGGCCAGCAGCACCAAGGTGGACAAGAAAAT
TGTGCCCAGGGATTGTGGTTGTAAGCCTTGCATATGTACAGTCCAGAAGTATCATCTGTCTTCATCTTC
CCCCCAAAGCCCAAGGATGTGCTCACCATTACTCTGACTCCTAAGGTCACGTGTGTTGTGGTAGACATCA
GCAAGGATGATCCCGAGGTCCAGTTCAGCTGGTTTGTAGATGATGTGGAGGTGCACACAGCTCAGACGCA
ACCCCGGAGGAGCAGTTCAACAGCACTTTCCGCTCAGTCAGTGAACTTCCCATCATGCACCAGGACTGG
CTCAATGGCAAGGAGTTCAAATGCAGGGTCAACAGTGCAGCTTCCCTGCCCCATCGAGAAAACCATCT
CCAAAACCAAAGGCAGACCGAAGGCTCCACAGGTGTACACCATTCCACCTCCAAGGAGCAGATGGCCAA
GGATAAAGTCAGTCTGACCTGCATGATAACAGACTTCTTCCCTGAAGACATTACTGTGGAGTGGCAGTGG
AATGGGCAGCCAGCGGAGAACTACAAGAACACTCAGCCCATCATGGACACAGATGGCTCTTACTTCGTCT
ACAGCAAGCTCAATGTGCAGAAGAGCAACTGGGAGGCAGGAAATACTTTCACCTGCTCTGTGTTACATGA
GGGCCTGCACAACCACCATACTGAGAAGAGCCTCTCCCACTCTCCTGGTAAA

AA-seq:

QVQLQQSGPEMVKPGASVKIPCKASGYAFSSSWMNWVKQRPGKGLEWIGRIYPGDGDTNYNEKFKGKATLTVDKSS
STVYMQLSSLTSEDSAVYFCAREATTVVAPYYFDYWGQGTTLTVSSAKTTPPSVYPLAPGSAAQTNSMVTLGCLV
KGYFPEPVTVTWNSGSLSSGVHTFPAVLQSDLYTLSSSVTVPSSTWPSETVTCNVAHPASSTKVDKKIVP
RDCGCKPCICTVPEVSSVFIFPPKPKDVLTITLTPKVTCVVVDISKDDPEVQFSWFVDDVEVHTAQTQPR
EEQFNSTFRSVSELPIMHQDWLNGKEFKCRVNSAAFPAPIEKTISKTKGRPKAPQVYTIPPPKEQMAKDK
VSLTCMITDFFPEDITVEWQWNGQPAENYKNTQPIMDTDGSYFVYSKLNVQKSNWEAGNTFTCSVLHEGL
HNHHTEKSLSHSPGK

Light chain: DNA sequence

FR1-CDR1-FR2-CDR2-FR3-CDR3-FR4-Constant region

Nuq-seq:
GACATcCAGATGACTCAGTCTCCAGCCTCCCTATCTGTATCTGTGGGAGAAACTGTCACCATCACATGTCGAGCAA
GTGAGAATATTTACAGAAATTTAGCATGGTATCAGCAGAAACAGGGAAAATCTCCTCAACTCCTGGTCCATGCTGC
AACAAACTTAGCAGATGGTGTGCCATCAAGGTTCAGTGGCAGTGGATCAGACACACAGTATTCCCTCAAGATCAA
CAGCCTGCAGTCTGAAGATTTTGGGAATTATTACTGTCAACATTTTGGGGGACTCCGCTCACGTTCGGTGCTGGG

Fig. 72

ACCAAGCTGGAGCTGAAACGGGCTGATGCTGCACCAACTGTATCCATCTTCCCACCATCCAGTGAGCAGTT
AACATCTGGAGGTGCCTCAGTCGTGTGCTTCTTGAACAACTTCTACCCCAAAGACATCAATGTCAAGTGG
AAGATTGATGGCAGTGAACGACAAAATGGCGTCCTGAACAGTTGGACTGATCAGGACAGCAAAGACAGCA
CCTACAGCATGAGCAGCACCCTCACGTTGACCAAGGACGAGTATGAACGACATAACAGCTATACCTGTGA
GGCCACTCACAAGACATCAACTTCACCCATTGTCAAGAGCTTCAACAGGAATGAGTGT

AA-seq:
DIQMTQSPASLSVSVGETVTITCRASENIYRNLAWYQQKQGKSPQLLVHAATNLADGVPSRFSGSGSDTQYSLKINSLQ
SEDFGNYYCQHFWGTPLTFGAGTKLELKRADAAPTVSIFPPSSEQLTSGGASVVCFLNNFYPKDINVKWKIDG
SERQNGVLNSWTDQDSKDSTYSMSSTLTLTKDEYERHNSYTCEATHKTSTSPIVKSFNRNEC

Fig. 72 - continued

D10A3 PAP TCRL

Heavy chain: DNA sequence

FR1-CDR1-FR2-CDR2-FR3-CDR3-FR4-Constant region

Nuc seq

GAGGTCCAGCTGCAACAGTTTGGAACTGAGCTGGTGAAGCCTGGGGCTTCAGTGAAGATATCCTGCAA
GGCTTCTGGCTACACATTCACTGACTACAACATGGACTGGGTGAAGCAGAGCCATGGAAAGAGCCTTGA
GTGGATTGGAGATATTAATCCTAACTATGATACTACTACCTACAACCAGAAGTTCAAGGGAAAGGCCAC
ATTGACTGTAGACAAGTCCTCCAGCACAGCCTACATGGAGCTCCGCAGCCTGACTTCTGAGGACACTGC
AGTCTTTTACTGTGCAAGAAGGAACTATGGTAACTACGTGGGGTTTGACTTCTGGGGCCAAGGCACCAC
TCTCACAGTCTCCTCAGCCAAAACGACACCCCCATCTGTCTATCCACTGGCCCCTGGATCTGCTGCCCAAA
CTAACTCCATGGTGACCCTGGGATGCCTGGTCAAGGGCTATTTCCCTGAGCCAGTGACAGTGACCTGGAA
CTCTGGATCCCTGTCCAGCGGTGTGCACACCTTCCCAGCTGTCCTGCAGTCTGACCTCTACACTCTGAGC
AGCTCAGTGACTGTCCCCTCCAGCACCTGGCCCAGCGAGACCGTCACCTGCAACGTTGCCCACCCGGCCA
GCAGCACCAAGGTGGACAAGAAAATTGTGCCCAGGGATTGTGGTTGTAAGCCTTGCATATGTACAGTCCC
AGAAGTATCATCTGTCTTCATCTTCCCCCCAAAGCCCAAGGATGTGCTCACCATTACTCTGACTCCTAAG
GTCACGTGTGTTGTGGTAGACATCAGCAAGGATGATCCCGAGGTCCAGTTCAGCTGGTTTGTAGATGATG
TGGAGGTGCACACAGCTCAGACGCAACCCCGGGAGGAGCAGTTCAACAGCACTTTCCGCTCAGTCAGTGA
ACTTCCCATCATGCACCAGGACTGGCTCAATGGCAAGGAGTTCAAATGCAGGGTCAACAGTGCAGCTTTC
CCTGCCCCCATCGAGAAAACCATCTCCAAAACCAAAGGCAGACCGAAGGCTCCACAGGTGTACACCATTC
CACCTCCCAAGGAGCAGATGGCCAAGGATAAAGTCAGTCTGACCTGCATGATAACAGACTTCTTCCCTGA
AGACATTACTGTGGAGTGGCAGTGGAATGGGCAGCCAGCGGAGAACTACAAGAACACTCAGCCCATCATG
GACACAGATGGCTCTTACTTCGTCTACAGCAAGCTCAATGTGCAGAAGAGCAACTGGGAGGCAGGAAATA
CTTTCACCTGCTCTGTGTTACATGAGGGCCTGCACAACCACCATACTGAGAAGAGCCTCTCCCACTCTCC
TGGTAAA

AA-seq:

EVQLQQFGTELVKPGASVKISCKASGYTFTDYNMDWVKQSHGKSLEWIGDINPNYDTTTYNQKFKGKATLT
VDKSSSTAYMELRSLTSEDTAVFYCARRNYGNYVGFDFWGQGTTLTVSSAKTTPPSVYPLAPGSAAQTNSM
VTLGCLVKGYFPEPVTVTWNSGSLSSGVHTFPAVLQSDLYTLSSSVTVPSSTWPSETVTCNVAHPASSTK
VDKKIVPRDCGCKPCICTVPEVSSVFIFPPKPKDVLTITLTPKVTCVVVDISKDDPEVQFSWFVDDVEVH
TAQTQPREEQFNSTFRSVSELPIMHQDWLNGKEFKCRVNSAAFPAPIEKTISKTKGRPKAPQVYTIPPPK
EQMAKDKVSLTCMITDFFPEDITVEWQWNGQPAENYKNTQPIMDTDGSYFVYSKLNVQKSNWEAGNTFTC
SVLHEGLHNHHTEKSLSHSPGK

Light chain: DNA sequence

FR1-CDR1-FR2-CDR2-FR3-CDR3-FR4-Constant region
Nucseq:

AATATTGTGCTGACCCAGACTCCCAAATTCCTGCTTGTATCAGCAGGAGACAGGGTTTCCATAACCTGCA
AGGCCAGTCAGCGTGTGAATAATGATGTAGCTTGGTACCAACAGAAGCCAGGGCAGTCTCCTAAACTGC
TGATATACTATGCATCCAATCGCTACACTGGAGTCCCTGATCGCTTCACTGGCAGTGGATATGGGACGG

Fig. 73

ATTTCACTTTCACCATCAGCACTGTGCAGGCTGAAGACCTGGCAGTTTATTTCTGTCAGCAGGATTATAG
CTCTCCATTCACGTTCGGCTCGGGGACAAAGTTGGAAATAAAACGGGCTGATGCTGCACCAACTGTATCC
ATCTTCCCACCATCCAGTGAGCAGTTAACATCTGGAGGTGCCTCAGTCGTGTGCTTCTTGAACAACTTCT
ACCCCAAAGACATCAATGTCAAGTGGAAGATTGATGGCAGTGAACGACAAAATGGCGTCCTGAACAGTTG
GACTGATCAGGACAGCAAAGACAGCACCTACAGCATGAGTAGCACCCTCACGTTGACCAAGGACGAGTAT
GAACGACATAACAGCTATACCTGTGAGGCCACTCATAAGACATCAACTTCACCCATTGTCAAGAGCTTCA
ACAGGAATGAGTGT

AA-seq

NIVLTQTPKFLLVSAGDRVSITCKASQRVNNDVAWYQQKPGQSPKLLIYYASNRYTGVPDRFTGSGYGTD
FTFTISTVQAEDLAVYFCQQDYSSPFTFGSGTKLEIKRADAAPTVSIFPPSSEQLTSGGASVVCFLNNFYPKDI
NVKWKIDGSERQNGVLNSWTDQDSKDSTYSMSSTLTLTKDEYERHNSYTCEATHKTSTSPIVKSFNRNEC

Fig. 73 - continued

```
                       SEQUENCE LISTING

<160> NUMBER OF SEQ ID NOS: 384

<210> SEQ ID NO 1
    <211> LENGTH: 9
    <212> TYPE: PRT
    <213> ORGANISM: Artificial sequence
    <220> FEATURE:
    <223> OTHER INFORMATION: short peptide

<400> SEQUENCE: 1

Tyr Met Asp Gly Thr Met Ser Gln Val
    1               5

<210> SEQ ID NO 2
    <211> LENGTH: 9
    <212> TYPE: PRT
    <213> ORGANISM: Artificial sequence
    <220> FEATURE:
    <223> OTHER INFORMATION: short peptide

<400> SEQUENCE: 2

Tyr Leu Leu Pro Ala Ile Val His Ile
    1               5

<210> SEQ ID NO 3
    <211> LENGTH: 19
    <212> TYPE: PRT
    <213> ORGANISM: Artificial sequence
    <220> FEATURE:
    <223> OTHER INFORMATION: short peptide

<400> SEQUENCE: 3

Thr Thr Ala Gly Cys Ala Ala Ala Gly Cys Ala Thr Ala Cys Cys Ala
    1               5                   10                  15

Thr Cys Ala

<210> SEQ ID NO 4
    <211> LENGTH: 19
    <212> TYPE: PRT
    <213> ORGANISM: Artificial sequence
    <220> FEATURE:
    <223> OTHER INFORMATION: short peptide

<400> SEQUENCE: 4

Cys Cys Ala Gly Ala Cys Ala Ala Ala Gly Ala Gly Gly Thr Cys Ala
    1               5                   10                  15
```

Thr Ala Ala

<210> SEQ ID NO 5
<211> LENGTH: 18
<212> TYPE: PRT
<213> ORGANISM: Artificial sequence
<220> FEATURE:
<223> OTHER INFORMATION: short peptide

<400> SEQUENCE: 5

Ala Gly Gly Cys Thr Gly Cys Ala Ala Thr Ala Ala Gly Ala Gly Ala
1               5                  10                  15

Thr Ala

<210> SEQ ID NO 6
<211> LENGTH: 18
<212> TYPE: PRT
<213> ORGANISM: Artificial sequence
<220> FEATURE:
<223> OTHER INFORMATION: short peptide

<400> SEQUENCE: 6

Thr Thr Cys Gly Cys Thr Gly Ala Cys Ala Ala Gly Thr Thr Thr Thr
1               5                  10                  15

Ala Cys

<210> SEQ ID NO 7
<211> LENGTH: 10
<212> TYPE: PRT
<213> ORGANISM: Artificial sequence
<220> FEATURE:
<223> OTHER INFORMATION: short peptide

<400> SEQUENCE: 7

Glu Ala Ala Gly Ile Gly Ile Leu Thr Val
1               5                  10

<210> SEQ ID NO 8
<211> LENGTH: 163
<212> TYPE: PRT
<213> ORGANISM: homo sapiens

<400> SEQUENCE: 8

Met Lys Trp Lys Ala Leu Phe Thr Ala Ala Ile Leu Gln Ala Gln Leu
1               5                  10                  15

Pro Ile Thr Glu Ala Gln Ser Phe Gly Leu Leu Asp Pro Lys Leu Cys
                20                  25                  30

Tyr Leu Leu Asp Gly Ile Leu Phe Ile Tyr Gly Val Ile Leu Thr Ala
                35                  40                  45

Leu Phe Leu Arg Val Lys Phe Ser Arg Ser Ala Asp Ala Pro Ala Tyr
        50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Arg Arg Lys Asn Pro Gln Glu Gly Leu Tyr Asn Glu
                100                 105                 110

Leu Gln Lys Asp Lys Met Ala Glu Ala Tyr Ser Glu Ile Gly Met Lys
            115                 120                 125

Gly Glu Arg Arg Arg Gly Lys Gly His Asp Gly Leu Tyr Gln Gly Leu
        130                 135                 140

```
Ser Thr Ala Thr Lys Asp Thr Tyr Asp Ala Leu His Met Gln Ala Leu
145                 150                 155                 160

Pro Pro Arg

<210> SEQ ID NO 9
<211> LENGTH: 164
<212> TYPE: PRT
<213> ORGANISM: homo sapiens

<400> SEQUENCE: 9

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
                20                  25                  30

Tyr Leu Leu Asp Gly Ile Leu Phe Ile Tyr Gly Val Ile Leu Thr Ala
            35                  40                  45

Leu Phe Leu Arg Val Lys Phe Ser Arg Ser Ala Asp Ala Pro Ala Tyr
        50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 10
<211> LENGTH: 123
<212> TYPE: PRT
<213> ORGANISM: homo sapiens

<400> SEQUENCE: 10

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
                20                  25                  30

Asp Asn Ala Val Asn Leu Ser Trp Lys His Leu Cys Pro Ser Pro Leu
            35                  40                  45

Phe Pro Gly Pro Ser Lys Pro Phe Trp Val Leu Val Val Val Gly Gly
        50                  55                  60

Val Leu Ala Cys Tyr Ser Leu Leu Val Thr Val Ala Phe Ile Ile Phe
65                  70                  75                  80

Trp Val Arg Ser Lys Arg Ser Arg Leu Leu His Ser Asp Tyr Met Asn
                85                  90                  95

Met Thr Pro Arg Arg Pro Gly Pro Thr Arg Lys His Tyr Gln Pro Tyr
            100                 105                 110

Ala Pro Pro Arg Asp Phe Ala Ala Tyr Arg Ser
        115                 120
```

-continued

```
<210> SEQ ID NO 11
<211> LENGTH: 101
<212> TYPE: PRT
<213> ORGANISM: homo sapiens

<400> SEQUENCE: 11

Met Leu Arg Leu Leu Ala Leu Asn Leu Phe Pro Ser Ile Gln Val
1               5                   10                  15

Thr Gly Lys His Leu Cys Pro Ser Pro Leu Phe Pro Gly Pro Ser Lys
                20                  25                  30

Pro Phe Trp Val Leu Val Val Val Gly Gly Val Leu Ala Cys Tyr Ser
            35                  40                  45

Leu Leu Val Thr Val Ala Phe Ile Ile Phe Trp Val Arg Ser Lys Arg
    50                  55                  60

Ser Arg Leu Leu His Ser Asp Tyr Met Asn Met Thr Pro Arg Arg Pro
65                  70                  75                  80

Gly Pro Thr Arg Lys His Tyr Gln Pro Tyr Ala Pro Pro Arg Asp Phe
                85                  90                  95

Ala Ala Tyr Arg Ser
            100

<210> SEQ ID NO 12
<211> LENGTH: 220
<212> TYPE: PRT
<213> ORGANISM: homo sapiens

<400> SEQUENCE: 12

Met Leu Arg Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
                20                  25                  30

Asp Asn Ala Val Asn Leu Ser Cys Lys Tyr Ser Tyr Asn Leu Phe Ser
            35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Tyr Leu Asp Asn Glu Lys Ser
    115                 120                 125

Asn Gly Thr Ile Ile His Val Lys Gly Lys His Leu Cys Pro Ser Pro
130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
    195                 200                 205

Tyr Ala Pro Pro Arg Asp Phe Ala Ala Tyr Arg Ser
210                 215                 220
```

<210> SEQ ID NO 13
<211> LENGTH: 255
<212> TYPE: PRT
<213> ORGANISM: homo sapiens

<400> SEQUENCE: 13

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 14
<211> LENGTH: 199
<212> TYPE: PRT
<213> ORGANISM: homo sapiens

<400> SEQUENCE: 14

Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
        35                  40                  45

Gln Gln Phe Lys Met Gln Leu Leu Lys Gly Gly Gln Ile Leu Cys Asp
    50                  55                  60

Leu Thr Lys Thr Lys Gly Ser Gly Asn Thr Val Ser Ile Lys Ser Leu
65                  70                  75                  80

Lys Phe Cys His Ser Gln Leu Ser Asn Asn Ser Val Ser Phe Phe Leu

```
                    85                  90                  95

Tyr Asn Leu Asp His Ser His Ala Asn Tyr Tyr Phe Cys Asn Leu Ser
                100                 105                 110

Ile Phe Asp Pro Pro Phe Lys Val Thr Leu Thr Gly Gly Tyr Leu
            115                 120                 125

His Ile Tyr Glu Ser Gln Leu Cys Cys Gln Leu Lys Phe Trp Leu Pro
        130                 135                 140

Ile Gly Cys Ala Ala Phe Val Val Cys Ile Leu Gly Cys Ile Leu
145                 150                 155                 160

Ile Cys Trp Leu Thr Lys Lys Tyr Ser Ser Val His Asp Pro
                165                 170                 175

Asn Gly Glu Tyr Met Phe Met Arg Ala Val Asn Thr Ala Lys Lys Ser
                180                 185                 190

Arg Leu Thr Asp Val Thr Leu
                195

<210> SEQ ID NO 15
<211> LENGTH: 277
<212> TYPE: PRT
<213> ORGANISM: homo sapiens

<400> SEQUENCE: 15

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
                100                 105                 110

Thr Gln Pro Leu Asp Ser Tyr Lys Pro Gly Val Asp Cys Ala Pro Cys
            115                 120                 125

Pro Pro Gly His Phe Ser Pro Gly Asp Asn Gln Ala Cys Lys Pro Trp
        130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
                180                 185                 190

Glu Ala Trp Pro Arg Thr Ser Gln Gly Pro Ser Thr Arg Pro Val Glu
            195                 200                 205

Val Pro Gly Gly Arg Ala Val Ala Ala Ile Leu Gly Leu Gly Leu Val
        210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255
```

```
Gly Ser Phe Arg Thr Pro Ile Gln Glu Gln Ala Asp Ala His Ser
            260                 265                 270

Thr Leu Ala Lys Ile
            275

<210> SEQ ID NO 16
<211> LENGTH: 184
<212> TYPE: PRT
<213> ORGANISM: homo sapiens

<400> SEQUENCE: 16

Met Ala Pro Leu Leu Pro Ile Arg Thr Leu Pro Leu Ile Leu Ile Leu
1               5                   10                  15

Leu Ala Leu Leu Ser Pro Gly Ala Ala Asp Phe Asn Ile Ser Ser Leu
                20                  25                  30

Ser Gly Leu Leu Ser Pro Ala Leu Thr Glu Ser Leu Leu Val Ala Leu
            35                  40                  45

Pro Pro Cys His Leu Thr Gly Gly Asn Ala Thr Leu Met Val Arg Arg
        50                  55                  60

Ala Asn Asp Ser Lys Val Val Thr Ser Ser Phe Val Val Pro Pro Cys
65                  70                  75                  80

Arg Gly Arg Arg Glu Leu Val Ser Val Val Asp Ser Gly Ala Gly Phe
                85                  90                  95

Thr Val Thr Arg Leu Ser Ala Tyr Gln Val Thr Asn Leu Val Pro Gly
            100                 105                 110

Thr Lys Phe Tyr Ile Ser Tyr Leu Val Lys Lys Gly Thr Ala Thr Glu
        115                 120                 125

Ser Ser Arg Glu Ile Pro Met Ser Thr Leu Pro Arg Arg Asn Met Glu
130                 135                 140

Ser Ile Gly Leu Gly Met Ala Arg Thr Gly Gly Met Val Val Ile Thr
145                 150                 155                 160

Val Leu Leu Ser Val Ala Met Phe Leu Leu Val Leu Gly Phe Ile Ile
                165                 170                 175

Ala Leu Ala Leu Gly Ser Arg Lys
            180

<210> SEQ ID NO 17
<211> LENGTH: 273
<212> TYPE: PRT
<213> ORGANISM: homo sapiens

<400> SEQUENCE: 17

Met Ala Ser Ala Ala Ala Ala Glu Ala Glu Lys Gly Ser Pro Val Val
1               5                   10                  15

Val Gly Leu Leu Val Val Gly Asn Ile Ile Ile Leu Leu Ser Gly Leu
                20                  25                  30

Ser Leu Phe Ala Glu Thr Ile Trp Val Thr Ala Asp Gln Tyr Arg Val
            35                  40                  45

Tyr Pro Leu Met Gly Val Ser Gly Lys Asp Asp Val Phe Ala Gly Ala
        50                  55                  60

Trp Ile Ala Ile Phe Cys Gly Phe Ser Phe Met Val Ala Ser Phe
65                  70                  75                  80

Gly Val Gly Ala Ala Leu Cys Arg Arg Arg Ser Met Val Leu Thr Tyr
                85                  90                  95

Leu Val Leu Met Leu Ile Val Tyr Ile Phe Glu Cys Ala Ser Cys Ile
            100                 105                 110
```

Thr Ser Tyr Thr His Arg Asp Tyr Met Val Ser Asn Pro Ser Leu Ile
            115                 120                 125

Thr Lys Gln Met Leu Thr Phe Tyr Ser Ala Asp Thr Asp Gln Gly Gln
    130                 135                 140

Glu Leu Thr Arg Leu Trp Asp Arg Val Met Ile Glu Gln Glu Cys Cys
145                 150                 155                 160

Gly Thr Ser Gly Pro Met Asp Trp Val Asn Phe Thr Ser Ala Phe Arg
                165                 170                 175

Ala Ala Thr Pro Glu Val Val Phe Pro Trp Pro Leu Cys Cys Arg
            180                 185                 190

Arg Thr Gly Asn Phe Ile Pro Leu Asn Glu Glu Gly Cys Arg Leu Gly
            195                 200                 205

His Met Asp Tyr Leu Phe Thr Lys Ala Gly Val Gln Trp His Asn Leu
    210                 215                 220

Ser Ser Leu Gln Arg Leu Pro Pro Gly Phe Lys Gly Phe Ser His Leu
225                 230                 235                 240

Ser Phe Gln Ser Ser Trp Asp Tyr Arg Ala Ala Ser Asn Thr Ser Ala
                245                 250                 255

Thr Pro Ser Thr Ala Thr Arg Gly Val Ser Arg Gly Leu Gly Leu Pro
            260                 265                 270

Ser

<210> SEQ ID NO 18
<211> LENGTH: 258
<212> TYPE: PRT
<213> ORGANISM: homo sapiens

<400> SEQUENCE: 18

Met Ala Ser Ala Ala Ala Glu Ala Glu Lys Gly Ser Pro Val Val
1               5                   10                  15

Val Gly Leu Leu Val Val Gly Asn Ile Ile Ile Leu Leu Ser Gly Leu
                20                  25                  30

Ser Leu Phe Ala Glu Thr Ile Trp Val Thr Ala Asp Gln Tyr Arg Val
            35                  40                  45

Tyr Pro Leu Met Gly Val Ser Gly Lys Asp Asp Val Phe Ala Gly Ala
50                  55                  60

Trp Ile Ala Ile Phe Cys Gly Phe Ser Phe Phe Met Val Ala Ser Phe
65                  70                  75                  80

Gly Val Gly Ala Ala Leu Cys Arg Arg Arg Ser Met Val Leu Thr Tyr
                85                  90                  95

Leu Val Leu Met Leu Ile Val Tyr Ile Phe Glu Cys Ala Ser Cys Ile
            100                 105                 110

Thr Ser Tyr Thr His Arg Asp Tyr Met Val Ser Asn Pro Ser Leu Ile
            115                 120                 125

Thr Lys Gln Met Leu Thr Phe Tyr Ser Ala Asp Thr Asp Gln Gly Gln
    130                 135                 140

Glu Leu Thr Arg Leu Trp Asp Arg Val Met Ile Glu Gln Glu Cys Cys
145                 150                 155                 160

Gly Thr Ser Gly Pro Met Asp Trp Val Asn Phe Thr Ser Ala Phe Arg
                165                 170                 175

Ala Ala Thr Pro Glu Val Val Phe Pro Trp Pro Leu Cys Cys Arg
            180                 185                 190

Arg Thr Gly Asn Phe Ile Pro Leu Asn Glu Glu Gly Cys Arg Leu Gly
            195                 200                 205

```
His Met Asp Tyr Leu Phe Thr Lys Gly Cys Phe Glu His Ile Gly His
    210                 215                 220
Ala Ile Asp Ser Tyr Thr Trp Gly Ile Ser Trp Phe Gly Phe Ala Ile
    225                 230                 235                 240
Leu Met Trp Thr Leu Pro Val Met Leu Ile Ala Met Tyr Phe Tyr Thr
                    245                 250                 255
Met Leu
```

<210> SEQ ID NO 19
<211> LENGTH: 245
<212> TYPE: PRT
<213> ORGANISM: homo sapiens

<400> SEQUENCE: 19

```
Met Lys Gln Ser Phe Pro Leu Phe Leu Thr Pro Ser Pro Trp Lys Thr
1                   5                   10                  15
Thr Val Leu Leu Leu Tyr Met Arg Ile Cys Tyr Val Pro Ser Tyr Lys
                    20                  25                  30
Trp Asn Tyr Ser Ile Gly Leu Ile Tyr Leu Gly Ile Val Ser Glu Leu
                35                  40                  45
Pro His Met Val Gly Ile Gly Gln Asn Ser Ser Phe Asn Ser Trp Met
    50                  55                  60
Glu Ser Gln Phe Leu His Pro Ser Met Glu Pro Gly Gln Trp Leu Pro
65                  70                  75                  80
Tyr Ile Thr Ile Phe Arg Phe Thr His Ile Ile Arg Cys Val Arg Ile
                    85                  90                  95
Ser Phe Leu Phe Asn Ile Pro Trp Tyr Gly Tyr Pro His Phe Val Cys
                100                 105                 110
His Ser Ser Val Ser Gly His Leu Gly Tyr Phe Tyr Leu Leu Leu Leu
            115                 120                 125
Trp Leu Val Cys Cys Glu His Arg Cys Thr Asn Ile Cys Ser Arg Gln
    130                 135                 140
Thr Ser Phe Lys Arg Leu Phe Leu Lys Lys Tyr Val Ser Tyr Asn Ile
145                 150                 155                 160
Phe Leu Leu Cys Val Glu Ser Asp Ile Ser Ile Asp Leu Glu Gly Tyr
                    165                 170                 175
Gly Met Gly Cys Thr Asn Ile Cys Ser Arg Gln Thr Ser Phe Lys Arg
                180                 185                 190
Leu Phe Lys Arg Lys Tyr Arg Cys Leu Leu Asn Met Phe Leu Val Met
                195                 200                 205
Asn Val Glu Ser Gly Thr Asn Arg Tyr Met Glu Val Arg Arg Ala Trp
    210                 215                 220
Arg Gly Ser Lys Trp Glu Asp Glu Asn Trp Leu Gly Ile Asp Val
225                 230                 235                 240
Tyr Phe Glu Asp Arg
                245
```

<210> SEQ ID NO 20
<211> LENGTH: 114
<212> TYPE: PRT
<213> ORGANISM: homo sapiens

<400> SEQUENCE: 20

```
Met Ala Gly Leu Ala Leu Gln Pro Gly Thr Ala Leu Leu Cys Tyr Ser
1                   5                   10                  15
Cys Lys Ala Gln Val Ser Asn Glu Asp Cys Leu Gln Val Glu Asn Cys
```

```
                20                  25                  30
Thr Gln Leu Gly Glu Gln Cys Trp Thr Ala Arg Ile Arg Ala Val Gly
            35                  40                  45

Leu Leu Thr Val Ile Ser Lys Gly Cys Ser Leu Asn Cys Val Asp Asp
 50                  55                  60

Ser Gln Asp Tyr Tyr Val Gly Lys Lys Asn Ile Thr Cys Cys Asp Thr
 65                  70                  75                  80

Asp Leu Cys Asn Ala Ser Gly Ala His Ala Leu Gln Pro Ala Ala Ala
             85                  90                  95

Ile Leu Ala Leu Leu Pro Ala Leu Gly Leu Leu Trp Gly Pro Gly Gln
            100                 105                 110

Gln Leu

<210> SEQ ID NO 21
<211> LENGTH: 386
<212> TYPE: PRT
<213> ORGANISM: homo sapiens

<400> SEQUENCE: 21

Met Arg Ala Ala Pro Leu Leu Ala Arg Ala Ser Leu Ser Leu
 1               5                  10                  15

Gly Phe Leu Phe Leu Leu Phe Phe Trp Leu Asp Arg Ser Val Leu Ala
            20                  25                  30

Lys Glu Leu Lys Phe Val Thr Leu Val Phe Arg His Gly Asp Arg Ser
            35                  40                  45

Pro Ile Asp Thr Phe Pro Thr Asp Pro Ile Lys Glu Ser Ser Trp Pro
 50                  55                  60

Gln Gly Phe Gly Gln Leu Thr Gln Leu Gly Met Glu Gln His Tyr Glu
 65                  70                  75                  80

Leu Gly Glu Tyr Ile Arg Lys Arg Tyr Arg Lys Phe Leu Asn Glu Ser
            85                  90                  95

Tyr Lys His Glu Gln Val Tyr Ile Arg Ser Thr Asp Val Asp Arg Thr
            100                 105                 110

Leu Met Ser Ala Met Thr Asn Leu Ala Ala Leu Phe Pro Pro Glu Gly
            115                 120                 125

Val Ser Ile Trp Asn Pro Ile Leu Leu Trp Gln Pro Ile Pro Val His
130                 135                 140

Thr Val Pro Leu Ser Glu Asp Gln Leu Leu Tyr Leu Pro Phe Arg Asn
145                 150                 155                 160

Cys Pro Arg Phe Gln Glu Leu Glu Ser Glu Thr Leu Lys Ser Glu Glu
                165                 170                 175

Phe Gln Lys Arg Leu His Pro Tyr Lys Asp Phe Ile Ala Thr Leu Gly
            180                 185                 190

Lys Leu Ser Gly Leu His Gly Gln Asp Leu Phe Gly Ile Trp Ser Lys
            195                 200                 205

Val Tyr Asp Pro Leu Tyr Cys Glu Ser Val His Asn Phe Thr Leu Pro
210                 215                 220

Ser Trp Ala Thr Glu Asp Thr Met Thr Lys Leu Arg Glu Leu Ser Glu
225                 230                 235                 240

Leu Ser Leu Leu Ser Leu Tyr Gly Ile His Lys Gln Lys Glu Lys Ser
                245                 250                 255

Arg Leu Gln Gly Gly Val Leu Val Asn Glu Ile Leu Asn His Met Lys
            260                 265                 270

Arg Ala Thr Gln Ile Pro Ser Tyr Lys Lys Leu Ile Met Tyr Ser Ala
```

```
            275                 280                 285
His Asp Thr Thr Val Ser Gly Leu Gln Met Ala Leu Asp Val Tyr Asn
290                 295                 300

Gly Leu Leu Pro Pro Tyr Ala Ser Cys His Leu Thr Glu Leu Tyr Phe
305                 310                 315                 320

Glu Lys Gly Glu Tyr Phe Val Glu Met Tyr Tyr Arg Asn Glu Thr Gln
                325                 330                 335

His Glu Pro Tyr Pro Leu Met Leu Pro Gly Cys Ser Pro Ser Cys Pro
            340                 345                 350

Leu Glu Arg Phe Ala Glu Leu Val Gly Pro Val Ile Pro Gln Asp Trp
        355                 360                 365

Ser Thr Glu Cys Met Thr Thr Asn Ser His Gln Gly Thr Glu Asp Ser
370                 375                 380

Thr Asp
385

<210> SEQ ID NO 22
<211> LENGTH: 418
<212> TYPE: PRT
<213> ORGANISM: homo sapiens

<400> SEQUENCE: 22

Met Arg Ala Ala Pro Leu Leu Ala Arg Ala Ala Ser Leu Ser Leu
1               5                   10                  15

Gly Phe Leu Phe Leu Leu Phe Phe Trp Leu Asp Arg Ser Val Leu Ala
            20                  25                  30

Lys Glu Leu Lys Phe Val Thr Leu Val Phe Arg His Gly Asp Arg Ser
        35                  40                  45

Pro Ile Asp Thr Phe Pro Thr Asp Pro Ile Lys Glu Ser Ser Trp Pro
    50                  55                  60

Gln Gly Phe Gly Gln Leu Thr Gln Leu Gly Met Glu Gln His Tyr Glu
65                  70                  75                  80

Leu Gly Glu Tyr Ile Arg Lys Arg Tyr Arg Lys Phe Leu Asn Glu Ser
                85                  90                  95

Tyr Lys His Glu Gln Val Tyr Ile Arg Ser Thr Asp Val Asp Arg Thr
            100                 105                 110

Leu Met Ser Ala Met Thr Asn Leu Ala Ala Leu Phe Pro Pro Glu Gly
        115                 120                 125

Val Ser Ile Trp Asn Pro Ile Leu Leu Trp Gln Pro Ile Pro Val His
    130                 135                 140

Thr Val Pro Leu Ser Glu Asp Gln Leu Leu Tyr Leu Pro Phe Arg Asn
145                 150                 155                 160

Cys Pro Arg Phe Gln Glu Leu Glu Ser Glu Thr Leu Lys Ser Glu Glu
                165                 170                 175

Phe Gln Lys Arg Leu His Pro Tyr Lys Asp Phe Ile Ala Thr Leu Gly
            180                 185                 190

Lys Leu Ser Gly Leu His Gly Gln Asp Leu Phe Gly Ile Trp Ser Lys
        195                 200                 205

Val Tyr Asp Pro Leu Tyr Cys Glu Ser Val His Asn Phe Thr Leu Pro
    210                 215                 220

Ser Trp Ala Thr Glu Asp Thr Met Thr Lys Leu Arg Glu Leu Ser Glu
225                 230                 235                 240

Leu Ser Leu Leu Ser Leu Tyr Gly Ile His Lys Gln Lys Glu Lys Ser
                245                 250                 255
```

-continued

Arg Leu Gln Gly Gly Val Leu Val Asn Glu Ile Leu Asn His Met Lys
                260                 265                 270

Arg Ala Thr Gln Ile Pro Ser Tyr Lys Lys Leu Ile Met Tyr Ser Ala
            275                 280                 285

His Asp Thr Thr Val Ser Gly Leu Gln Met Ala Leu Asp Val Tyr Asn
        290                 295                 300

Gly Leu Leu Pro Pro Tyr Ala Ser Cys His Leu Thr Glu Leu Tyr Phe
305                 310                 315                 320

Glu Lys Gly Glu Tyr Phe Val Glu Met Tyr Tyr Arg Asn Glu Thr Gln
                325                 330                 335

His Glu Pro Tyr Pro Leu Met Leu Pro Gly Cys Ser Pro Ser Cys Pro
            340                 345                 350

Leu Glu Arg Phe Ala Glu Leu Val Gly Pro Val Ile Pro Gln Asp Trp
        355                 360                 365

Ser Thr Glu Cys Met Thr Thr Asn Ser His Gln Val Leu Lys Val Ile
370                 375                 380

Phe Ala Val Ala Phe Cys Leu Ile Ser Ala Val Leu Met Val Leu Leu
385                 390                 395                 400

Phe Ile His Ile Arg Arg Gly Leu Cys Trp Gln Arg Glu Ser Tyr Gly
                405                 410                 415

Asn Ile

<210> SEQ ID NO 23
<211> LENGTH: 353
<212> TYPE: PRT
<213> ORGANISM: homo sapiens

<400> SEQUENCE: 23

Met Arg Ala Ala Pro Leu Leu Leu Ala Arg Ala Ala Ser Leu Ser Leu
1               5                   10                  15

Gly Phe Leu Phe Leu Leu Phe Phe Trp Leu Asp Arg Ser Val Leu Ala
            20                  25                  30

Lys Glu Leu Lys Phe Val Thr Leu Val Phe Arg His Gly Asp Arg Ser
        35                  40                  45

Pro Ile Asp Thr Phe Pro Thr Asp Pro Ile Lys Glu Ser Ser Trp Pro
    50                  55                  60

Gln Gly Phe Gly Gln Leu Thr Gln Leu Gly Met Glu Gln His Tyr Glu
65                  70                  75                  80

Leu Gly Glu Tyr Ile Arg Lys Arg Tyr Arg Lys Phe Leu Asn Glu Ser
                85                  90                  95

Tyr Lys His Glu Gln Val Tyr Ile Arg Ser Thr Asp Val Asp Arg Thr
            100                 105                 110

Leu Met Ser Ala Met Thr Asn Leu Ala Ala Leu Phe Pro Pro Glu Gly
        115                 120                 125

Val Ser Ile Trp Asn Pro Ile Leu Leu Trp Gln Pro Ile Pro Val His
    130                 135                 140

Thr Val Pro Leu Ser Glu Asp Gln Asp Phe Ile Ala Thr Leu Gly Lys
145                 150                 155                 160

Leu Ser Gly Leu His Gly Gln Asp Leu Phe Gly Ile Trp Ser Lys Val
                165                 170                 175

Tyr Asp Pro Leu Tyr Cys Glu Ser Val His Asn Phe Thr Leu Pro Ser
            180                 185                 190

Trp Ala Thr Glu Asp Thr Met Thr Lys Leu Arg Glu Leu Ser Glu Leu
        195                 200                 205

```
Ser Leu Leu Ser Leu Tyr Gly Ile His Lys Gln Lys Glu Lys Ser Arg
    210                 215                 220

Leu Gln Gly Gly Val Leu Val Asn Glu Ile Leu Asn His Met Lys Arg
225                 230                 235                 240

Ala Thr Gln Ile Pro Ser Tyr Lys Lys Leu Ile Met Tyr Ser Ala His
                245                 250                 255

Asp Thr Thr Val Ser Gly Leu Gln Met Ala Leu Asp Val Tyr Asn Gly
            260                 265                 270

Leu Leu Pro Pro Tyr Ala Ser Cys His Leu Thr Glu Leu Tyr Phe Glu
        275                 280                 285

Lys Gly Glu Tyr Phe Val Glu Met Tyr Tyr Arg Asn Glu Thr Gln His
290                 295                 300

Glu Pro Tyr Pro Leu Met Leu Pro Gly Cys Ser Pro Ser Cys Pro Leu
305                 310                 315                 320

Glu Arg Phe Ala Glu Leu Val Gly Pro Val Ile Pro Gln Asp Trp Ser
                325                 330                 335

Thr Glu Cys Met Thr Thr Asn Ser His Gln Gly Thr Gly Asp Ser Thr
            340                 345                 350

Asp

<210> SEQ ID NO 24
<211> LENGTH: 335
<212> TYPE: PRT
<213> ORGANISM: homo sapiens

<400> SEQUENCE: 24

Met Pro Arg Pro Arg Leu Leu Ala Ala Leu Cys Gly Ala Leu Leu Cys
1               5                   10                  15

Ala Pro Ser Leu Leu Val Ala Leu Asp Ile Cys Ser Lys Asn Pro Cys
            20                  25                  30

His Asn Gly Gly Leu Cys Glu Glu Ile Ser Gln Glu Val Arg Gly Asp
        35                  40                  45

Val Phe Pro Ser Tyr Thr Cys Thr Cys Leu Lys Gly Tyr Ala Gly Asn
    50                  55                  60

His Cys Glu Thr Lys Cys Val Glu Pro Leu Gly Leu Glu Asn Gly Asn
65                  70                  75                  80

Ile Ala Asn Ser Gln Ile Ala Ala Ser Ser Val Arg Val Thr Phe Leu
                85                  90                  95

Gly Leu Gln His Trp Val Pro Glu Leu Ala Arg Leu Asn Arg Ala Gly
            100                 105                 110

Met Val Asn Ala Trp Thr Pro Ser Ser Asn Asp Asp Asn Pro Trp Ile
        115                 120                 125

Gln Val Asn Leu Leu Arg Arg Met Trp Val Thr Gly Val Val Thr Gln
130                 135                 140

Gly Ala Ser Arg Leu Ala Ser His Glu Tyr Leu Lys Ala Phe Lys Val
145                 150                 155                 160

Ala Tyr Ser Leu Asn Gly His Glu Phe Asp Phe Ile His Asp Val Asn
                165                 170                 175

Lys Lys His Lys Glu Phe Val Gly Asn Trp Asn Lys Asn Ala Val His
            180                 185                 190

Val Asn Leu Phe Glu Thr Pro Val Glu Ala Gln Tyr Val Arg Leu Tyr
        195                 200                 205

Pro Thr Ser Cys His Thr Ala Cys Thr Leu Arg Phe Glu Leu Leu Gly
    210                 215                 220
```

```
Cys Glu Leu Asn Gly Cys Ala Asn Pro Leu Gly Leu Lys Asn Asn Ser
225                 230                 235                 240

Ile Pro Asp Lys Gln Ile Thr Ala Ser Ser Tyr Lys Thr Trp Gly
                245                 250                 255

Leu His Leu Phe Ser Trp Asn Pro Ser Tyr Ala Arg Leu Asp Lys Gln
            260                 265                 270

Gly Asn Phe Asn Ala Trp Val Ala Gly Ser Tyr Gly Asn Asp Gln Trp
        275                 280                 285

Leu Gln Ile Phe Pro Gly Asn Trp Asp Asn His Ser His Lys Lys Asn
            290                 295                 300

Leu Phe Glu Thr Pro Ile Leu Ala Arg Tyr Val Arg Ile Leu Pro Val
305                 310                 315                 320

Ala Trp His Asn Arg Ile Ala Leu Arg Leu Glu Leu Leu Gly Cys
                325                 330                 335

<210> SEQ ID NO 25
<211> LENGTH: 264
<212> TYPE: PRT
<213> ORGANISM: homo sapiens

<400> SEQUENCE: 25

Met Thr Pro Gly Thr Gln Ser Pro Phe Phe Leu Leu Leu Leu Leu Thr
1               5                   10                  15

Val Leu Thr Ala Thr Thr Ala Pro Lys Pro Ala Thr Val Val Thr Gly
                20                  25                  30

Ser Gly His Ala Ser Ser Thr Pro Gly Gly Glu Lys Glu Thr Ser Ala
            35                  40                  45

Thr Gln Arg Ser Ser Val Pro Ser Ser Thr Glu Lys Asn Ala Phe Asn
    50                  55                  60

Ser Ser Leu Glu Asp Pro Ser Thr Asp Tyr Tyr Gln Glu Leu Gln Arg
65                  70                  75                  80

Asp Ile Ser Glu Met Phe Leu Gln Ile Tyr Lys Gln Gly Gly Phe Leu
                85                  90                  95

Gly Leu Ser Asn Ile Lys Phe Arg Pro Gly Ser Val Val Val Gln Leu
            100                 105                 110

Thr Leu Ala Phe Arg Glu Gly Thr Ile Asn Val His Asp Val Glu Thr
        115                 120                 125

Gln Phe Asn Gln Tyr Lys Thr Glu Ala Ala Ser Arg Tyr Asn Leu Thr
    130                 135                 140

Ile Ser Asp Val Ser Val Ser Asp Val Pro Phe Pro Phe Ser Ala Gln
145                 150                 155                 160

Ser Gly Ala Gly Val Pro Gly Trp Gly Ile Ala Leu Leu Val Leu Val
                165                 170                 175

Cys Val Leu Val Ala Leu Ala Ile Val Tyr Leu Ile Ala Leu Ala Val
            180                 185                 190

Cys Gln Cys Arg Arg Lys Asn Tyr Gly Gln Leu Asp Ile Phe Pro Ala
        195                 200                 205

Arg Asp Thr Tyr His Pro Met Ser Glu Tyr Pro Thr Tyr His Thr His
    210                 215                 220

Gly Arg Tyr Val Pro Pro Ser Ser Thr Asp Arg Ser Pro Tyr Glu Lys
225                 230                 235                 240

Val Ser Ala Gly Asn Gly Gly Ser Ser Leu Ser Tyr Thr Asn Pro Ala
                245                 250                 255

Val Ala Ala Thr Ser Ala Asn Leu
            260
```

<210> SEQ ID NO 26
<211> LENGTH: 203
<212> TYPE: PRT
<213> ORGANISM: homo sapiens

<400> SEQUENCE: 26

```
Met Thr Pro Gly Thr Gln Ser Pro Phe Phe Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Ile Pro Ala Pro Thr Thr Thr Lys Ser Cys Arg
    50                  55                  60

Glu Thr Phe Leu Lys Cys Phe Cys Arg Phe Ile Asn Lys Gly Val Phe
65                  70                  75                  80

Trp Ala Ser Pro Ile Leu Ser Ser Val Ser Asp Val Pro Phe Pro Phe
                85                  90                  95

Ser Ala Gln Ser Gly Ala Gly Val Pro Gly Trp Gly Ile Ala Leu Leu
            100                 105                 110

Val Leu Val Cys Val Leu Val Ala Leu Ala Ile Val Tyr Leu Ile Ala
        115                 120                 125

Leu Ala Val Cys Gln Cys Arg Arg Lys Asn Tyr Gly Gln Leu Asp Ile
    130                 135                 140

Phe Pro Ala Arg Asp Thr Tyr His Pro Met Ser Glu Tyr Pro Thr Tyr
145                 150                 155                 160

His Thr His Gly Arg Tyr Val Pro Pro Ser Ser Thr Asp Arg Ser Pro
                165                 170                 175

Tyr Glu Lys Val Ser Ala Gly Asn Gly Gly Ser Ser Leu Ser Tyr Thr
            180                 185                 190

Asn Pro Ala Val Ala Ala Thr Ser Ala Asn Leu
        195                 200
```

<210> SEQ ID NO 27
<211> LENGTH: 159
<212> TYPE: PRT
<213> ORGANISM: homo sapiens

<400> SEQUENCE: 27

```
Met Thr Pro Gly Thr Gln Ser Pro Phe Phe Leu Leu Leu Leu Thr
1               5                   10                  15

Val Leu Thr Ala Thr Ala Pro Lys Pro Ala Thr Val Val Thr Gly
            20                  25                  30

Ser Gly His Ala Ser Ser Thr Pro Gly Gly Glu Lys Glu Thr Ser Ala
        35                  40                  45

Thr Gln Arg Ser Ser Val Pro Ser Ser Thr Glu Lys Asn Ala Phe Asn
    50                  55                  60

Ser Ser Leu Glu Asp Pro Ser Thr Asp Tyr Tyr Gln Glu Leu Gln Arg
65                  70                  75                  80

Asp Ile Ser Glu Met Ala Val Cys Gln Cys Arg Arg Lys Asn Tyr Gly
                85                  90                  95

Gln Leu Asp Ile Phe Pro Ala Arg Asp Thr Tyr His Pro Met Ser Glu
            100                 105                 110

Tyr Pro Thr Tyr His Thr His Gly Arg Tyr Val Pro Pro Ser Ser Thr
        115                 120                 125
```

Asp Arg Ser Pro Tyr Glu Lys Val Ser Ala Gly Asn Gly Gly Ser Ser
            130                 135                 140

Leu Ser Tyr Thr Asn Pro Ala Val Ala Ala Thr Ser Ala Asn Leu
145                 150                 155

<210> SEQ ID NO 28
<211> LENGTH: 475
<212> TYPE: PRT
<213> ORGANISM: homo sapiens

<400> SEQUENCE: 28

Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Val Ser Met Thr Ser Ser Val Leu Ser Ser His
    50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Leu Gly Ser Thr Thr
            100                 105                 110

Pro Pro Ala His Asp Val Thr Ser Ala Pro Asp Asn Lys Pro Ala Pro
        115                 120                 125

Gly Ser Thr Ala Pro Pro Ala His Gly Val Thr Ser Ala Pro Asp Thr
    130                 135                 140

Arg Pro Ala Pro Gly Ser Thr Ala Pro Pro Ala His Gly Val Thr Ser
145                 150                 155                 160

Ala Pro Asp Asn Arg Pro Ala Leu Gly Ser Thr Ala Pro Pro Val His
                165                 170                 175

Asn Val Thr Ser Ala Ser Gly Ser Ala Ser Gly Ser Ala Ser Thr Leu
            180                 185                 190

Val His Asn Gly Thr Ser Ala Arg Ala Thr Thr Thr Pro Ala Ser Lys
        195                 200                 205

Ser Thr Pro Phe Ser Ile Pro Ser His His Ser Asp Thr Pro Thr Thr
    210                 215                 220

Leu Ala Ser His Ser Thr Lys Thr Asp Ala Ser Ser Thr His His Ser
225                 230                 235                 240

Thr Val Pro Pro Leu Thr Ser Ser Asn His Ser Thr Ser Pro Gln Leu
                245                 250                 255

Ser Thr Gly Val Ser Phe Phe Phe Leu Ser Phe His Ile Ser Asn Leu
            260                 265                 270

Gln Phe Asn Ser Ser Leu Glu Asp Pro Ser Thr Asp Tyr Tyr Gln Glu
        275                 280                 285

Leu Gln Arg Asp Ile Ser Glu Met Phe Leu Gln Ile Tyr Lys Gln Gly
    290                 295                 300

Gly Phe Leu Gly Leu Ser Asn Ile Lys Phe Arg Pro Gly Ser Val Val
305                 310                 315                 320

Val Gln Leu Thr Leu Ala Phe Arg Glu Gly Thr Ile Asn Val His Asp
                325                 330                 335

Val Glu Thr Gln Phe Asn Gln Tyr Lys Thr Glu Ala Ala Ser Arg Tyr

```
                    340                 345                 350
Asn Leu Thr Ile Ser Asp Val Ser Val Ser Asp Val Pro Phe Pro Phe
                355                 360                 365

Ser Ala Gln Ser Gly Ala Gly Val Pro Gly Trp Gly Ile Ala Leu Leu
            370                 375                 380

Val Leu Val Cys Val Leu Val Ala Leu Ala Ile Val Tyr Leu Ile Ala
385                 390                 395                 400

Leu Ala Val Cys Gln Cys Arg Arg Lys Asn Tyr Gly Gln Leu Asp Ile
                405                 410                 415

Phe Pro Ala Arg Asp Thr Tyr His Pro Met Ser Glu Tyr Pro Thr Tyr
            420                 425                 430

His Thr His Gly Arg Tyr Val Pro Pro Ser Ser Thr Asp Arg Ser Pro
        435                 440                 445

Tyr Glu Lys Val Ser Ala Gly Asn Gly Gly Ser Ser Leu Ser Tyr Thr
    450                 455                 460

Asn Pro Ala Val Ala Ala Thr Ser Ala Asn Leu
465                 470                 475

<210> SEQ ID NO 29
<211> LENGTH: 282
<212> TYPE: PRT
<213> ORGANISM: homo sapiens

<400> SEQUENCE: 29

Met Thr Pro Gly Thr Gln Ser Pro Phe Phe Leu Leu Leu Leu Leu Thr
1               5                   10                  15

Val Leu Thr Ala Thr Thr Ala Pro Lys Pro Ala Thr Val Val Thr Gly
            20                  25                  30

Ser Gly His Ala Ser Ser Thr Pro Gly Gly Glu Lys Glu Thr Ser Ala
        35                  40                  45

Thr Gln Arg Ser Ser Val Pro Ser Ser Thr Glu Lys Asn Ala Leu Ser
    50                  55                  60

Thr Gly Val Ser Phe Phe Phe Leu Ser Phe His Ile Ser Asn Leu Gln
65                  70                  75                  80

Phe Asn Ser Ser Leu Glu Asp Pro Ser Thr Asp Tyr Tyr Gln Glu Leu
                85                  90                  95

Gln Arg Asp Ile Ser Glu Met Phe Leu Gln Ile Tyr Lys Gln Gly Gly
            100                 105                 110

Phe Leu Gly Leu Ser Asn Ile Lys Phe Arg Pro Gly Ser Val Val Val
        115                 120                 125

Gln Leu Thr Leu Ala Phe Arg Glu Gly Thr Ile Asn Val His Asp Val
    130                 135                 140

Glu Thr Gln Phe Asn Gln Tyr Lys Thr Glu Ala Ala Ser Arg Tyr Asn
145                 150                 155                 160

Leu Thr Ile Ser Asp Val Ser Val Ser Asp Val Pro Phe Pro Phe Ser
                165                 170                 175

Ala Gln Ser Gly Ala Gly Val Pro Gly Trp Gly Ile Ala Leu Leu Val
            180                 185                 190

Leu Val Cys Val Leu Val Ala Leu Ala Ile Val Tyr Leu Ile Ala Leu
        195                 200                 205

Ala Val Cys Gln Cys Arg Arg Lys Asn Tyr Gly Gln Leu Asp Ile Phe
    210                 215                 220

Pro Ala Arg Asp Thr Tyr His Pro Met Ser Glu Tyr Pro Thr Tyr His
225                 230                 235                 240
```

```
Thr His Gly Arg Tyr Val Pro Pro Ser Ser Thr Asp Arg Ser Pro Tyr
            245                 250                 255

Glu Lys Val Ser Ala Gly Asn Gly Gly Ser Ser Leu Ser Tyr Thr Asn
            260                 265                 270

Pro Ala Val Ala Ala Thr Ser Ala Asn Leu
            275                 280
```

<210> SEQ ID NO 30
<211> LENGTH: 238
<212> TYPE: PRT
<213> ORGANISM: homo sapiens

<400> SEQUENCE: 30

```
Met Thr Pro Gly Thr Gln Ser Pro Phe Phe Leu Leu Leu Leu Leu Thr
1               5                   10                  15

Val Leu Thr Ala Thr Thr Ala Pro Lys Pro Ala Thr Val Val Thr Gly
            20                  25                  30

Ser Gly His Ala Ser Ser Thr Pro Gly Gly Glu Lys Glu Thr Ser Ala
            35                  40                  45

Thr Gln Arg Ser Ser Val Pro Ser Ser Thr Glu Lys Asn Ala Ile Tyr
        50                  55                  60

Lys Gln Gly Gly Phe Leu Gly Leu Ser Asn Ile Lys Phe Arg Pro Gly
65                  70                  75                  80

Ser Val Val Val Gln Leu Thr Leu Ala Phe Arg Glu Gly Thr Ile Asn
            85                  90                  95

Val His Asp Val Glu Thr Gln Phe Asn Gln Tyr Lys Thr Glu Ala Ala
            100                 105                 110

Ser Arg Tyr Asn Leu Thr Ile Ser Asp Val Ser Val Ser Asp Val Pro
            115                 120                 125

Phe Pro Phe Ser Ala Gln Ser Gly Ala Gly Val Pro Gly Trp Gly Ile
        130                 135                 140

Ala Leu Leu Val Leu Val Cys Val Leu Val Ala Leu Ala Ile Val Tyr
145                 150                 155                 160

Leu Ile Ala Leu Ala Val Cys Gln Cys Arg Arg Lys Asn Tyr Gly Gln
            165                 170                 175

Leu Asp Ile Phe Pro Ala Arg Asp Thr Tyr His Pro Met Ser Glu Tyr
            180                 185                 190

Pro Thr Tyr His Thr His Gly Arg Tyr Val Pro Pro Ser Ser Thr Asp
            195                 200                 205

Arg Ser Pro Tyr Glu Lys Val Ser Ala Gly Asn Gly Gly Ser Ser Leu
        210                 215                 220

Ser Tyr Thr Asn Pro Ala Val Ala Ala Thr Ser Ala Asn Leu
225                 230                 235
```

<210> SEQ ID NO 31
<211> LENGTH: 241
<212> TYPE: PRT
<213> ORGANISM: homo sapiens

<400> SEQUENCE: 31

```
Met Thr Pro Gly Thr Gln Ser Pro Phe Phe Leu Leu Leu Leu Leu Thr
1               5                   10                  15

Val Leu Thr Ala Thr Thr Ala Pro Lys Pro Ala Thr Val Val Thr Gly
            20                  25                  30

Ser Gly His Ala Ser Ser Thr Pro Gly Gly Glu Lys Glu Thr Ser Ala
            35                  40                  45
```

```
Thr Gln Arg Ser Ser Val Pro Ser Ser Thr Glu Lys Asn Ala Phe Leu
    50              55                  60
Gln Ile Tyr Lys Gln Gly Gly Phe Leu Gly Leu Ser Asn Ile Lys Phe
65              70                  75                  80
Arg Pro Gly Ser Val Val Gln Leu Thr Leu Ala Phe Arg Glu Gly
                85                  90                  95
Thr Ile Asn Val His Asp Val Glu Thr Gln Phe Asn Gln Tyr Lys Thr
            100                 105                 110
Glu Ala Ala Ser Arg Tyr Asn Leu Thr Ile Ser Asp Val Ser Val Ser
        115                 120                 125
Asp Val Pro Phe Pro Phe Ser Ala Gln Ser Gly Ala Gly Val Pro Gly
    130                 135                 140
Trp Gly Ile Ala Leu Leu Val Leu Val Cys Val Leu Ala Leu Ala
145                 150                 155                 160
Ile Val Tyr Leu Ile Ala Leu Ala Val Cys Gln Cys Arg Arg Lys Asn
                165                 170                 175
Tyr Gly Gln Leu Asp Ile Phe Pro Ala Arg Asp Thr Tyr His Pro Met
                180                 185                 190
Ser Glu Tyr Pro Thr Tyr His Thr His Gly Arg Tyr Val Pro Pro Ser
            195                 200                 205
Ser Thr Asp Arg Ser Pro Tyr Glu Lys Val Ser Ala Gly Asn Gly Gly
    210                 215                 220
Ser Ser Leu Ser Tyr Thr Asn Pro Ala Val Ala Ala Thr Ser Ala Asn
225                 230                 235                 240
Leu

<210> SEQ ID NO 32
<211> LENGTH: 198
<212> TYPE: PRT
<213> ORGANISM: homo sapiens

<400> SEQUENCE: 32

Met Thr Pro Gly Thr Gln Ser Pro Phe Phe Leu Leu Leu Leu Leu Thr
1               5                   10                  15
Val Leu Thr Val Val Thr Gly Ser Gly His Ala Ser Ser Thr Pro Gly
                20                  25                  30
Gly Glu Lys Glu Thr Ser Ala Thr Gln Arg Ser Ser Val Pro Ser Ser
            35                  40                  45
Thr Glu Lys Asn Ala Leu Ser Thr Gly Val Ser Phe Phe Phe Leu Ser
    50                  55                  60
Phe His Ile Ser Asn Leu Gln Phe Asn Ser Ser Leu Glu Asp Pro Ser
65              70                  75                  80
Thr Asp Tyr Tyr Gln Glu Leu Gln Arg Asp Ile Ser Glu Met Phe Leu
                85                  90                  95
Gln Ile Tyr Lys Gln Gly Gly Phe Leu Gly Leu Ser Asn Ile Lys Phe
                100                 105                 110
Arg Pro Gly Ser Val Val Gln Leu Thr Leu Ala Phe Arg Glu Gly
            115                 120                 125
Thr Ile Asn Val His Asp Val Glu Thr Gln Phe Asn Gln Tyr Lys Thr
    130                 135                 140
Glu Ala Ala Ser Arg Tyr Asn Leu Thr Ile Ser Asp Val Ser Gly Cys
145                 150                 155                 160
Leu Ser Val Pro Pro Lys Glu Leu Arg Ala Ala Gly His Leu Ser Ser
                165                 170                 175
```

```
Pro Gly Tyr Leu Pro Ser Tyr Glu Arg Val Pro His Leu Pro His Pro
            180                 185                 190

Trp Ala Leu Cys Ala Pro
        195
```

<210> SEQ ID NO 33
<211> LENGTH: 189
<212> TYPE: PRT
<213> ORGANISM: homo sapiens

<400> SEQUENCE: 33

```
Met Thr Pro Gly Thr Gln Ser Pro Phe Phe Leu Leu Leu Leu Leu Thr
1               5                   10                  15

Val Leu Thr Ala Thr Thr Ala Pro Lys Pro Ala Thr Val Val Thr Gly
            20                  25                  30

Ser Gly His Ala Ser Ser Thr Pro Gly Gly Glu Lys Glu Thr Ser Ala
        35                  40                  45

Thr Gln Arg Ser Ser Val Pro Ser Ser Thr Glu Lys Asn Ala Phe Asn
    50                  55                  60

Ser Ser Leu Glu Asp Pro Ser Thr Asp Tyr Tyr Gln Glu Leu Gln Arg
65                  70                  75                  80

Asp Ile Ser Glu Met Ser Gly Ala Gly Val Pro Gly Trp Gly Ile Ala
                85                  90                  95

Leu Leu Val Leu Val Cys Val Leu Val Ala Leu Ala Ile Val Tyr Leu
            100                 105                 110

Ile Ala Leu Ala Val Cys Gln Cys Arg Arg Lys Asn Tyr Gly Gln Leu
        115                 120                 125

Asp Ile Phe Pro Ala Arg Asp Thr Tyr His Pro Met Ser Glu Tyr Pro
    130                 135                 140

Thr Tyr His Thr His Gly Arg Tyr Val Pro Pro Ser Ser Thr Asp Arg
145                 150                 155                 160

Ser Pro Tyr Glu Lys Val Ser Ala Gly Asn Gly Gly Ser Ser Leu Ser
                165                 170                 175

Tyr Thr Asn Pro Ala Val Ala Ala Thr Ser Ala Asn Leu
            180                 185
```

<210> SEQ ID NO 34
<211> LENGTH: 177
<212> TYPE: PRT
<213> ORGANISM: homo sapiens

<400> SEQUENCE: 34

```
Met Thr Pro Gly Thr Gln Ser Pro Phe Phe Leu Leu Leu Leu Leu Thr
1               5                   10                  15

Val Leu Thr Ala Thr Thr Ala Pro Lys Pro Ala Thr Val Val Thr Gly
            20                  25                  30

Ser Gly His Ala Ser Ser Thr Pro Gly Gly Glu Lys Glu Thr Ser Ala
        35                  40                  45

Thr Gln Arg Ser Ser Val Pro Ser Ser Thr Glu Lys Asn Ala Leu Ser
    50                  55                  60

Thr Gly Val Ser Phe Phe Phe Leu Ser Phe His Ile Ser Asn Leu Gln
65                  70                  75                  80

Phe Asn Ser Ser Leu Glu Asp Pro Ser Thr Asp Tyr Tyr Gln Glu Leu
                85                  90                  95

Gln Arg Asp Ile Ser Glu Met Ala Val Cys Gln Cys Arg Arg Lys Asn
            100                 105                 110
```

```
Tyr Gly Gln Leu Asp Ile Phe Pro Ala Arg Asp Thr Tyr His Pro Met
            115                 120                 125

Ser Glu Tyr Pro Thr Tyr His Thr His Gly Arg Tyr Val Pro Pro Ser
130                 135                 140

Ser Thr Asp Arg Ser Pro Tyr Glu Lys Val Ser Ala Gly Asn Gly Gly
145                 150                 155                 160

Ser Ser Leu Ser Tyr Thr Asn Pro Ala Val Ala Ala Thr Ser Ala Asn
                165                 170                 175

Leu
```

<210> SEQ ID NO 35
<211> LENGTH: 255
<212> TYPE: PRT
<213> ORGANISM: homo sapiens

<400> SEQUENCE: 35

```
Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
                20                  25                  30

Gly Glu Lys Glu Thr Ser Ala Thr Gln Arg Ser Ser Val Pro Ser Ser
            35                  40                  45

Thr Glu Lys Asn Ala Phe Asn Ser Ser Leu Glu Asp Pro Ser Thr Asp
50                  55                  60

Tyr Tyr Gln Glu Leu Gln Arg Asp Ile Ser Glu Met Phe Leu Gln Ile
65                  70                  75                  80

Tyr Lys Gln Gly Gly Phe Leu Gly Leu Ser Asn Ile Lys Phe Arg Pro
                85                  90                  95

Gly Ser Val Val Val Gln Leu Thr Leu Ala Phe Arg Glu Gly Thr Ile
            100                 105                 110

Asn Val His Asp Val Glu Thr Gln Phe Asn Gln Tyr Lys Thr Glu Ala
            115                 120                 125

Ala Ser Arg Tyr Asn Leu Thr Ile Ser Asp Val Ser Val Ser Asp Val
130                 135                 140

Pro Phe Pro Phe Ser Ala Gln Ser Gly Ala Gly Val Pro Gly Trp Gly
145                 150                 155                 160

Ile Ala Leu Leu Val Leu Val Cys Val Leu Val Ala Leu Ala Ile Val
                165                 170                 175

Tyr Leu Ile Ala Leu Ala Val Cys Gln Cys Arg Arg Lys Asn Tyr Gly
            180                 185                 190

Gln Leu Asp Ile Phe Pro Ala Arg Asp Thr Tyr His Pro Met Ser Glu
            195                 200                 205

Tyr Pro Thr Tyr His Thr His Gly Arg Tyr Val Pro Pro Ser Ser Thr
210                 215                 220

Asp Arg Ser Pro Tyr Glu Lys Val Ser Ala Gly Asn Gly Gly Ser Ser
225                 230                 235                 240

Leu Ser Tyr Thr Asn Pro Ala Val Ala Ala Thr Ser Ala Asn Leu
                245                 250                 255
```

<210> SEQ ID NO 36
<211> LENGTH: 150
<212> TYPE: PRT
<213> ORGANISM: homo sapiens

<400> SEQUENCE: 36

```
Met Thr Pro Gly Thr Gln Ser Pro Phe Phe Leu Leu Leu Leu Leu Thr
```

-continued

```
                1               5                  10                 15
Val Leu Thr Val Val Thr Gly Ser Gly His Ala Ser Ser Thr Pro Gly
                    20                 25                 30

Gly Glu Lys Glu Thr Ser Ala Thr Gln Arg Ser Ser Val Pro Ser Ser
                    35                 40                 45

Thr Glu Lys Asn Ala Phe Asn Ser Ser Leu Glu Asp Pro Ser Thr Asp
            50                 55                 60

Tyr Tyr Gln Glu Leu Gln Arg Asp Ile Ser Glu Met Ala Val Cys Gln
65                  70                 75                 80

Cys Arg Arg Lys Asn Tyr Gly Gln Leu Asp Ile Phe Pro Ala Arg Asp
                    85                 90                 95

Thr Tyr His Pro Met Ser Glu Tyr Pro Thr Tyr His Thr His Gly Arg
                100                105                110

Tyr Val Pro Pro Ser Ser Thr Asp Arg Ser Pro Tyr Glu Lys Val Ser
                115                120                125

Ala Gly Asn Gly Gly Ser Ser Leu Ser Tyr Thr Asn Pro Ala Val Ala
                130                135                140

Ala Thr Ser Ala Asn Leu
145                 150
```

<210> SEQ ID NO 37
<211> LENGTH: 158
<212> TYPE: PRT
<213> ORGANISM: homo sapiens

<400> SEQUENCE: 37

```
Met Thr Pro Gly Thr Gln Ser Pro Phe Phe Leu Leu Leu Leu Leu Thr
1               5                  10                 15

Val Leu Thr Val Val Thr Gly Ser Gly His Ala Ser Ser Thr Pro Gly
                    20                 25                 30

Gly Glu Lys Glu Thr Ser Ala Thr Gln Arg Ser Ser Val Pro Ser Ser
                    35                 40                 45

Thr Glu Lys Asn Ala Ile Pro Ala Pro Thr Thr Thr Lys Ser Cys Arg
            50                 55                 60

Glu Thr Phe Leu Lys Cys Phe Cys Arg Phe Ile Asn Lys Gly Val Phe
65                  70                 75                 80

Trp Ala Ser Pro Ile Leu Ser Ser Val Trp Gly Trp Gly Ala Arg Leu
                    85                 90                 95

Gly His Arg Ala Ala Gly Ala Gly Leu Cys Ser Gly Cys Ala Gly His
                100                105                110

Cys Leu Ser His Cys Leu Gly Cys Leu Ser Val Pro Pro Lys Glu Leu
                115                120                125

Arg Ala Ala Gly His Leu Ser Ser Pro Gly Tyr Leu Pro Ser Tyr Glu
                130                135                140

Arg Val Pro His Leu Pro His Pro Trp Ala Leu Cys Ala Pro
145                 150                155
```

<210> SEQ ID NO 38
<211> LENGTH: 484
<212> TYPE: PRT
<213> ORGANISM: homo sapiens

<400> SEQUENCE: 38

```
Met Thr Pro Gly Thr Gln Ser Pro Phe Phe Leu Leu Leu Leu Leu Thr
1               5                  10                 15

Val Leu Thr Ala Thr Thr Ala Pro Lys Pro Ala Thr Val Val Thr Gly
```

```
                20              25              30
Ser Gly His Ala Ser Ser Thr Pro Gly Gly Glu Lys Glu Thr Ser Ala
                35              40              45
Thr Gln Arg Ser Ser Val Pro Ser Ser Thr Glu Lys Asn Ala Val Ser
    50              55              60
Met Thr Ser Ser Val Leu Ser Ser His Ser Pro Gly Ser Gly Ser Ser
65              70              75              80
Thr Thr Gln Gly Gln Asp Val Thr Leu Ala Pro Ala Thr Glu Pro Ala
                85              90              95
Ser Gly Ser Ala Ala Thr Trp Gly Gln Asp Val Thr Ser Val Pro Val
                100             105             110
Thr Arg Pro Ala Leu Gly Ser Thr Thr Pro Pro Ala His Asp Val Thr
            115             120             125
Ser Ala Pro Asp Asn Lys Pro Ala Pro Gly Ser Thr Ala Pro Pro Ala
            130             135             140
His Gly Val Thr Ser Ala Pro Asp Thr Arg Pro Ala Pro Gly Ser Thr
145             150             155             160
Ala Pro Pro Ala His Gly Val Thr Ser Ala Pro Asp Asn Arg Pro Ala
                165             170             175
Leu Gly Ser Thr Ala Pro Pro Val His Asn Val Thr Ser Ala Ser Gly
            180             185             190
Ser Ala Ser Gly Ser Ala Ser Thr Leu Val His Asn Gly Thr Ser Ala
        195             200             205
Arg Ala Thr Thr Thr Pro Ala Ser Lys Ser Thr Pro Phe Ser Ile Pro
        210             215             220
Ser His His Ser Asp Thr Pro Thr Thr Leu Ala Ser His Ser Thr Lys
225             230             235             240
Thr Asp Ala Ser Ser Thr His His Ser Thr Val Pro Pro Leu Thr Ser
            245             250             255
Ser Asn His Ser Thr Ser Pro Gln Leu Ser Thr Gly Val Ser Phe Phe
            260             265             270
Phe Leu Ser Phe His Ile Ser Asn Leu Gln Phe Asn Ser Ser Leu Glu
        275             280             285
Asp Pro Ser Thr Asp Tyr Tyr Gln Glu Leu Gln Arg Asp Ile Ser Glu
    290             295             300
Met Phe Leu Gln Ile Tyr Lys Gln Gly Gly Phe Leu Gly Leu Ser Asn
305             310             315             320
Ile Lys Phe Arg Pro Gly Ser Val Val Gln Leu Thr Leu Ala Phe
            325             330             335
Arg Glu Gly Thr Ile Asn Val His Asp Val Glu Thr Gln Phe Asn Gln
            340             345             350
Tyr Lys Thr Glu Ala Ala Ser Arg Tyr Asn Leu Thr Ile Ser Asp Val
        355             360             365
Ser Val Ser Asp Val Pro Phe Pro Phe Ser Ala Gln Ser Gly Ala Gly
        370             375             380
Val Pro Gly Trp Gly Ile Ala Leu Leu Val Leu Val Cys Val Leu Val
385             390             395             400
Ala Leu Ala Ile Val Tyr Leu Ile Ala Leu Ala Val Cys Gln Cys Arg
            405             410             415
Arg Lys Asn Tyr Gly Gln Leu Asp Ile Phe Pro Ala Arg Asp Thr Tyr
            420             425             430
His Pro Met Ser Glu Tyr Pro Thr Tyr His Thr His Gly Arg Tyr Val
            435             440             445
```

```
Pro Pro Ser Ser Thr Asp Arg Ser Pro Tyr Glu Lys Val Ser Ala Gly
    450                 455                 460

Asn Gly Gly Ser Ser Leu Ser Tyr Thr Asn Pro Ala Val Ala Ala Thr
465                 470                 475                 480

Ser Ala Asn Leu
```

<210> SEQ ID NO 39
<211> LENGTH: 219
<212> TYPE: PRT
<213> ORGANISM: homo sapiens

<400> SEQUENCE: 39

```
Met Thr Pro Gly Thr Gln Ser Pro Phe Phe Leu Leu Leu Leu Leu Thr
1               5                   10                  15

Val Leu Thr Ala Thr Thr Ala Pro Lys Pro Ala Thr Val Val Thr Gly
            20                  25                  30

Ser Gly His Ala Ser Ser Thr Pro Gly Gly Glu Lys Glu Thr Ser Ala
        35                  40                  45

Thr Gln Arg Ser Ser Val Pro Ser Ser Thr Glu Lys Asn Ala Phe Asn
    50                  55                  60

Ser Ser Leu Glu Asp Pro Ser Thr Asp Tyr Tyr Gln Glu Leu Gln Arg
65                  70                  75                  80

Asp Ile Ser Glu Met Phe Leu Gln Ile Tyr Lys Gln Gly Gly Phe Leu
                85                  90                  95

Gly Leu Ser Asn Ile Lys Phe Arg Pro Gly Ser Val Val Val Gln Leu
            100                 105                 110

Thr Leu Ala Phe Arg Glu Gly Thr Ile Asn Val His Asp Val Glu Thr
        115                 120                 125

Gln Phe Asn Gln Tyr Lys Thr Glu Ala Ala Ser Arg Tyr Asn Leu Thr
    130                 135                 140

Ile Ser Asp Val Ser Val Trp Gly Trp Gly Ala Arg Leu Gly His Arg
145                 150                 155                 160

Ala Ala Gly Ala Gly Leu Cys Ser Gly Cys Ala Gly His Cys Leu Ser
                165                 170                 175

His Cys Leu Gly Cys Leu Ser Val Pro Pro Lys Glu Leu Arg Ala Ala
            180                 185                 190

Gly His Leu Ser Ser Pro Gly Tyr Leu Pro Ser Tyr Glu Arg Val Pro
        195                 200                 205

His Leu Pro His Pro Trp Ala Leu Cys Ala Pro
    210                 215
```

<210> SEQ ID NO 40
<211> LENGTH: 217
<212> TYPE: PRT
<213> ORGANISM: homo sapiens

<400> SEQUENCE: 40

```
Met Thr Pro Gly Thr Gln Ser Pro Phe Phe Leu Leu Leu Leu Leu Thr
1               5                   10                  15

Val Leu Thr Gly Gly Glu Lys Glu Thr Ser Ala Thr Gln Arg Ser Ser
            20                  25                  30

Val Pro Ser Ser Thr Glu Lys Asn Ala Ile Tyr Lys Gln Gly Gly Phe
        35                  40                  45

Leu Gly Leu Ser Asn Ile Lys Phe Arg Pro Gly Ser Val Val Val Gln
    50                  55                  60
```

```
Leu Thr Leu Ala Phe Arg Glu Gly Thr Ile Asn Val His Asp Val Glu
 65                  70                  75                  80

Thr Gln Phe Asn Gln Tyr Lys Thr Glu Ala Ala Ser Arg Tyr Asn Leu
                 85                  90                  95

Thr Ile Ser Asp Val Ser Val Ser Asp Val Pro Phe Pro Phe Ser Ala
                100                 105                 110

Gln Ser Gly Ala Gly Val Pro Gly Trp Gly Ile Ala Leu Leu Val Leu
            115                 120                 125

Val Cys Val Leu Val Ala Leu Ala Ile Val Tyr Leu Ile Ala Leu Ala
130                 135                 140

Val Cys Gln Cys Arg Arg Lys Asn Tyr Gly Gln Leu Asp Ile Phe Pro
145                 150                 155                 160

Ala Arg Asp Thr Tyr His Pro Met Ser Glu Tyr Pro Thr Tyr His Thr
                165                 170                 175

His Gly Arg Tyr Val Pro Pro Ser Ser Thr Asp Arg Ser Pro Tyr Glu
            180                 185                 190

Lys Val Ser Ala Gly Asn Gly Ser Ser Leu Ser Tyr Thr Asn Pro
        195                 200                 205

Ala Val Ala Ala Thr Ser Ala Asn Leu
    210                 215

<210> SEQ ID NO 41
<211> LENGTH: 239
<212> TYPE: PRT
<213> ORGANISM: homo sapiens

<400> SEQUENCE: 41

Met Thr Pro Gly Thr Gln Ser Pro Phe Phe Leu Leu Leu Leu Leu Thr
  1               5                  10                  15

Val Leu Thr Ala Thr Thr Ala Pro Lys Pro Ala Thr Val Val Thr Gly
                 20                  25                  30

Ser Gly His Ala Ser Ser Thr Pro Gly Gly Glu Lys Glu Thr Ser Ala
             35                  40                  45

Thr Gln Arg Ser Ser Val Pro Ser Ser Thr Glu Lys Asn Ala Ile Pro
 50                  55                  60

Ala Pro Thr Thr Thr Lys Ser Cys Arg Glu Thr Phe Leu Lys Trp Pro
 65                  70                  75                  80

Gly Ser Val Val Val Gln Leu Thr Leu Ala Phe Arg Glu Gly Thr Ile
                 85                  90                  95

Asn Val His Asp Val Glu Thr Gln Phe Asn Gln Tyr Lys Thr Glu Ala
                100                 105                 110

Ala Ser Arg Tyr Asn Leu Thr Ile Ser Asp Val Ser Val Ser Asp Val
            115                 120                 125

Pro Phe Pro Phe Ser Ala Gln Ser Gly Ala Gly Val Pro Gly Trp Gly
130                 135                 140

Ile Ala Leu Leu Val Leu Val Cys Val Leu Val Ala Leu Ala Ile Val
145                 150                 155                 160

Tyr Leu Ile Ala Leu Ala Val Cys Gln Cys Arg Arg Lys Asn Tyr Gly
                165                 170                 175

Gln Leu Asp Ile Phe Pro Ala Arg Asp Thr Tyr His Pro Met Ser Glu
            180                 185                 190

Tyr Pro Thr Tyr His Thr His Gly Arg Tyr Val Pro Pro Ser Ser Thr
        195                 200                 205

Asp Arg Ser Pro Tyr Glu Lys Val Ser Ala Gly Asn Gly Gly Ser Ser
210                 215                 220
```

-continued

```
Leu Ser Tyr Thr Asn Pro Ala Val Ala Ala Thr Ser Ala Asn Leu
225                 230                 235

<210> SEQ ID NO 42
<211> LENGTH: 230
<212> TYPE: PRT
<213> ORGANISM: homo sapiens

<400> SEQUENCE: 42

Met Thr Pro Gly Thr Gln Ser Pro Phe Phe Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
            35                  40                  45

Thr Glu Lys Asn Ala Ile Pro Ala Pro Thr Thr Thr Lys Ser Cys Arg
        50                  55                  60

Glu Thr Phe Leu Lys Trp Pro Gly Ser Val Val Gln Leu Thr Leu
65                  70                  75                  80

Ala Phe Arg Glu Gly Thr Ile Asn Val His Asp Val Glu Thr Gln Phe
                85                  90                  95

Asn Gln Tyr Lys Thr Glu Ala Ala Ser Arg Tyr Asn Leu Thr Ile Ser
            100                 105                 110

Asp Val Ser Val Ser Asp Val Pro Phe Pro Phe Ser Ala Gln Ser Gly
            115                 120                 125

Ala Gly Val Pro Gly Trp Gly Ile Ala Leu Leu Val Leu Val Cys Val
130                 135                 140

Leu Val Ala Leu Ala Ile Val Tyr Leu Ile Ala Leu Ala Val Cys Gln
145                 150                 155                 160

Cys Arg Arg Lys Asn Tyr Gly Gln Leu Asp Ile Phe Pro Ala Arg Asp
                165                 170                 175

Thr Tyr His Pro Met Ser Glu Tyr Pro Thr Tyr His Thr His Gly Arg
            180                 185                 190

Tyr Val Pro Pro Ser Ser Thr Asp Arg Ser Pro Tyr Glu Lys Val Ser
            195                 200                 205

Ala Gly Asn Gly Gly Ser Ser Leu Ser Tyr Thr Asn Pro Ala Val Ala
210                 215                 220

Ala Thr Ser Ala Asn Leu
225                 230

<210> SEQ ID NO 43
<211> LENGTH: 212
<212> TYPE: PRT
<213> ORGANISM: homo sapiens

<400> SEQUENCE: 43

Met Thr Pro Gly Thr Gln Ser Pro Phe Phe Leu Leu Leu Leu Thr
1               5                   10                  15

Val Leu Thr Ala Thr Ala Pro Lys Pro Ala Thr Val Val Thr Gly
            20                  25                  30

Ser Gly His Ala Ser Ser Thr Pro Gly Gly Glu Lys Glu Thr Ser Ala
            35                  40                  45

Thr Gln Arg Ser Ser Val Pro Ser Ser Thr Glu Lys Asn Ala Ile Pro
        50                  55                  60

Ala Pro Thr Thr Thr Lys Ser Cys Arg Glu Thr Phe Leu Lys Cys Phe
65                  70                  75                  80
```

```
Cys Arg Phe Ile Asn Lys Gly Val Phe Trp Ala Ser Pro Ile Leu Ser
                85                  90                  95

Ser Val Ser Asp Val Pro Phe Pro Phe Ser Ala Gln Ser Gly Ala Gly
            100                 105                 110

Val Pro Gly Trp Gly Ile Ala Leu Leu Val Leu Val Cys Val Leu Val
        115                 120                 125

Ala Leu Ala Ile Val Tyr Leu Ile Ala Leu Ala Val Cys Gln Cys Arg
    130                 135                 140

Arg Lys Asn Tyr Gly Gln Leu Asp Ile Phe Pro Ala Arg Asp Thr Tyr
145                 150                 155                 160

His Pro Met Ser Glu Tyr Pro Thr Tyr His Thr His Gly Arg Tyr Val
                165                 170                 175

Pro Pro Ser Ser Thr Asp Arg Ser Pro Tyr Glu Lys Val Ser Ala Gly
            180                 185                 190

Asn Gly Gly Ser Ser Leu Ser Tyr Thr Asn Pro Ala Val Ala Ala Thr
        195                 200                 205

Ser Ala Asn Leu
    210

<210> SEQ ID NO 44
<211> LENGTH: 273
<212> TYPE: PRT
<213> ORGANISM: homo sapiens

<400> SEQUENCE: 44

Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Leu Ser Thr Gly Val Ser Phe Phe Phe Leu Ser
    50                  55                  60

Phe His Ile Ser Asn Leu Gln Phe Asn Ser Ser Leu Glu Asp Pro Ser
65                  70                  75                  80

Thr Asp Tyr Tyr Gln Glu Leu Gln Arg Asp Ile Ser Glu Met Phe Leu
                85                  90                  95

Gln Ile Tyr Lys Gln Gly Gly Phe Leu Gly Leu Ser Asn Ile Lys Phe
            100                 105                 110

Arg Pro Gly Ser Val Val Gln Leu Thr Leu Ala Phe Arg Glu Gly
        115                 120                 125

Thr Ile Asn Val His Asp Val Glu Thr Gln Phe Asn Gln Tyr Lys Thr
    130                 135                 140

Glu Ala Ala Ser Arg Tyr Asn Leu Thr Ile Ser Asp Val Ser Val Ser
145                 150                 155                 160

Asp Val Pro Phe Pro Phe Ser Ala Gln Ser Gly Ala Gly Val Pro Gly
                165                 170                 175

Trp Gly Ile Ala Leu Leu Val Leu Val Cys Val Leu Val Ala Leu Ala
            180                 185                 190

Ile Val Tyr Leu Ile Ala Leu Ala Val Cys Gln Cys Arg Arg Lys Asn
        195                 200                 205

Tyr Gly Gln Leu Asp Ile Phe Pro Ala Arg Asp Thr Tyr His Pro Met
    210                 215                 220

Ser Glu Tyr Pro Thr Tyr His Thr His Gly Arg Tyr Val Pro Pro Ser
```

```
225                 230                 235                 240

Ser Thr Asp Arg Ser Pro Tyr Glu Lys Val Ser Ala Gly Asn Gly Gly
                245                 250                 255

Ser Ser Leu Ser Tyr Thr Asn Pro Ala Val Ala Ala Thr Ser Ala Asn
                260                 265                 270

Leu

<210> SEQ ID NO 45
<211> LENGTH: 575
<212> TYPE: PRT
<213> ORGANISM: homo sapiens

<400> SEQUENCE: 45

Met Asp Leu Val Leu Lys Arg Cys Leu Leu His Leu Ala Val Ile Gly
1               5                   10                  15

Ala Leu Leu Ala Val Gly Ala Thr Lys Gly Ser Gln Val Trp Gly Gly
                20                  25                  30

Gln Pro Val Tyr Pro Gln Glu Thr Asp Asp Ala Cys Ile Phe Pro Asp
            35                  40                  45

Gly Gly Pro Cys Pro Ser Gly Ser Trp Ser Gln Lys Arg Ser Phe Val
        50                  55                  60

Tyr Val Trp Lys Thr Trp Gly Gln Tyr Trp Gln Val Leu Gly Gly Pro
65              70                  75                  80

Val Ser Gly Leu Ser Ile Gly Thr Gly Arg Ala Met Leu Gly Thr His
                85                  90                  95

Thr Met Glu Val Thr Val Tyr His Arg Arg Gly Ser Arg Ser Tyr Val
                100                 105                 110

Pro Leu Ala His Ser Ser Ser Ala Phe Thr Ile Thr Asp Gln Val Pro
            115                 120                 125

Phe Ser Val Ser Val Ser Gln Leu Arg Ala Leu Asp Gly Gly Asn Lys
        130                 135                 140

His Phe Leu Arg Asn Gln Pro Leu Thr Phe Ala Leu Gln Leu His Asp
145             150                 155                 160

Pro Ser Gly Tyr Leu Ala Glu Ala Asp Leu Ser Tyr Thr Trp Asp Phe
                165                 170                 175

Gly Asp Ser Ser Gly Thr Leu Ile Ser Arg Ala Leu Val Val Thr His
                180                 185                 190

Thr Tyr Leu Glu Pro Gly Pro Val Thr Ala Gln Val Val Leu Gln Ala
            195                 200                 205

Ala Ile Pro Leu Thr Ser Cys Gly Ser Ser Pro Val Pro Gly Thr Thr
        210                 215                 220

Asp Gly His Arg Pro Thr Ala Glu Ala Pro Asn Thr Thr Ala Gly Gln
225             230                 235                 240

Val Pro Thr Thr Glu Val Val Gly Thr Thr Pro Gly Gln Ala Pro Thr
                245                 250                 255

Ala Glu Pro Ser Gly Thr Thr Ser Val Gln Val Pro Thr Thr Glu Val
                260                 265                 270

Ile Ser Thr Ala Pro Val Gln Met Pro Thr Ala Glu Ser Thr Gly Met
            275                 280                 285

Thr Pro Glu Lys Val Pro Val Ser Glu Val Met Gly Thr Thr Leu Ala
        290                 295                 300

Glu Met Ser Thr Pro Glu Ala Thr Gly Met Thr Pro Ala Glu Val Ser
305             310                 315                 320

Ile Val Val Leu Ser Gly Thr Thr Ala Ala Gln Val Thr Thr Thr Glu
```

-continued

```
                    325                 330                 335
Trp Val Glu Thr Thr Ala Arg Glu Leu Pro Ile Pro Glu Pro Glu Gly
                340                 345                 350
Pro Asp Ala Ser Ser Ile Met Ser Thr Glu Ser Ile Thr Gly Ser Leu
            355                 360                 365
Gly Pro Leu Leu Asp Gly Thr Ala Thr Leu Arg Leu Val Lys Arg Gln
        370                 375                 380
Val Pro Leu Asp Cys Val Leu Tyr Arg Tyr Gly Ser Phe Ser Val Thr
385                 390                 395                 400
Leu Asp Ile Val Gln Gly Ile Glu Ser Ala Glu Ile Leu Gln Ala Val
                405                 410                 415
Pro Ser Gly Glu Gly Asp Ala Phe Glu Leu Thr Val Ser Cys Gln Gly
                420                 425                 430
Gly Leu Pro Lys Glu Ala Cys Met Glu Ile Ser Ser Pro Gly Cys Gln
            435                 440                 445
Pro Pro Ala Gln Arg Leu Cys Gln Pro Val Leu Pro Ser Pro Ala Cys
        450                 455                 460
Gln Leu Val Leu His Gln Ile Leu Lys Gly Gly Ser Gly Thr Tyr Cys
465                 470                 475                 480
Leu Asn Val Ser Leu Ala Asp Thr Asn Ser Leu Ala Val Val Ser Thr
                485                 490                 495
Gln Leu Ile Met Pro Gly Gln Glu Ala Gly Leu Gly Gln Val Pro Leu
                500                 505                 510
Ile Val Gly Ile Leu Leu Val Leu Met Ala Val Val Leu Ala Ser Leu
            515                 520                 525
Ile Tyr Arg Arg Arg Leu Met Lys Gln Asp Phe Ser Val Pro Gln Leu
        530                 535                 540
Pro His Ser Ser Ser His Trp Leu Arg Leu Pro Arg Ile Phe Cys Ser
545                 550                 555                 560
Cys Pro Ile Gly Glu Asn Ser Pro Leu Leu Ser Gly Gln Gln Val
                565                 570                 575

<210> SEQ ID NO 46
<211> LENGTH: 661
<212> TYPE: PRT
<213> ORGANISM: homo sapiens

<400> SEQUENCE: 46

Met Asp Leu Val Leu Lys Arg Cys Leu Leu His Leu Ala Val Ile Gly
1               5                   10                  15
Ala Leu Leu Ala Val Gly Ala Thr Lys Val Pro Arg Asn Gln Asp Trp
                20                  25                  30
Leu Gly Val Ser Arg Gln Leu Arg Thr Lys Ala Trp Asn Arg Gln Leu
            35                  40                  45
Tyr Pro Glu Trp Thr Glu Ala Gln Arg Leu Asp Cys Trp Arg Gly Gly
        50                  55                  60
Gln Val Ser Leu Lys Val Ser Asn Asp Gly Pro Thr Leu Ile Gly Ala
65                  70                  75                  80
Asn Ala Ser Phe Ser Ile Ala Leu Asn Phe Pro Gly Ser Gln Lys Val
                85                  90                  95
Leu Pro Asp Gly Gln Val Ile Trp Val Asn Asn Thr Ile Ile Asn Gly
                100                 105                 110
Ser Gln Val Trp Gly Gly Gln Pro Val Tyr Pro Gln Glu Thr Asp Asp
            115                 120                 125
```

```
Ala Cys Ile Phe Pro Asp Gly Gly Pro Cys Pro Ser Gly Ser Trp Ser
    130                 135                 140

Gln Lys Arg Ser Phe Val Tyr Val Trp Lys Thr Trp Gly Gln Tyr Trp
145                 150                 155                 160

Gln Val Leu Gly Gly Pro Val Ser Gly Leu Ser Ile Gly Thr Gly Arg
                165                 170                 175

Ala Met Leu Gly Thr His Thr Met Glu Val Thr Val Tyr His Arg Arg
                180                 185                 190

Gly Ser Arg Ser Tyr Val Pro Leu Ala His Ser Ser Ala Phe Thr
                195                 200                 205

Ile Thr Asp Gln Val Pro Phe Ser Val Ser Val Ser Gln Leu Arg Ala
    210                 215                 220

Leu Asp Gly Gly Asn Lys His Phe Leu Arg Asn Gln Pro Leu Thr Phe
225                 230                 235                 240

Ala Leu Gln Leu His Asp Pro Ser Gly Tyr Leu Ala Glu Ala Asp Leu
                245                 250                 255

Ser Tyr Thr Trp Asp Phe Gly Asp Ser Ser Gly Thr Leu Ile Ser Arg
                260                 265                 270

Ala Leu Val Val Thr His Thr Tyr Leu Glu Pro Gly Pro Val Thr Ala
                275                 280                 285

Gln Val Val Leu Gln Ala Ala Ile Pro Leu Thr Ser Cys Gly Ser Ser
                290                 295                 300

Pro Val Pro Gly Thr Thr Asp Gly His Arg Pro Thr Ala Glu Ala Pro
305                 310                 315                 320

Asn Thr Thr Ala Gly Gln Val Pro Thr Thr Glu Val Val Gly Thr Thr
                325                 330                 335

Pro Gly Gln Ala Pro Thr Ala Glu Pro Ser Gly Thr Thr Ser Val Gln
                340                 345                 350

Val Pro Thr Thr Glu Val Ile Ser Thr Ala Pro Val Gln Met Pro Thr
                355                 360                 365

Ala Glu Ser Thr Gly Met Thr Pro Glu Lys Val Pro Val Ser Glu Val
    370                 375                 380

Met Gly Thr Thr Leu Ala Glu Met Ser Thr Pro Glu Ala Thr Gly Met
385                 390                 395                 400

Thr Pro Ala Glu Val Ser Ile Val Val Leu Ser Gly Thr Thr Ala Ala
                405                 410                 415

Gln Val Thr Thr Thr Glu Trp Val Glu Thr Thr Ala Arg Glu Leu Pro
                420                 425                 430

Ile Pro Glu Pro Glu Gly Pro Asp Ala Ser Ser Ile Met Ser Thr Glu
                435                 440                 445

Ser Ile Thr Gly Ser Leu Gly Pro Leu Leu Asp Gly Thr Ala Thr Leu
    450                 455                 460

Arg Leu Val Lys Arg Gln Val Pro Leu Asp Cys Val Leu Tyr Arg Tyr
465                 470                 475                 480

Gly Ser Phe Ser Val Thr Leu Asp Ile Val Gln Gly Ile Glu Ser Ala
                485                 490                 495

Glu Ile Leu Gln Ala Val Pro Ser Gly Glu Gly Asp Ala Phe Glu Leu
                500                 505                 510

Thr Val Ser Cys Gln Gly Gly Leu Pro Lys Glu Ala Cys Met Glu Ile
                515                 520                 525

Ser Ser Pro Gly Cys Gln Pro Ala Gln Arg Leu Cys Gln Pro Val
530                 535                 540

Leu Pro Ser Pro Ala Cys Gln Leu Val Leu His Gln Ile Leu Lys Gly
```

```
                 545                 550                 555                 560
Gly Ser Gly Thr Tyr Cys Leu Asn Val Ser Leu Ala Asp Thr Asn Ser
                565                 570                 575

Leu Ala Val Val Ser Thr Gln Leu Ile Met Pro Gly Gln Glu Ala Gly
                580                 585                 590

Leu Gly Gln Val Pro Leu Ile Val Gly Ile Leu Leu Val Leu Met Ala
                595                 600                 605

Val Val Leu Ala Ser Leu Ile Tyr Arg Arg Arg Leu Met Lys Gln Asp
610                 615                 620

Phe Ser Val Pro Gln Leu Pro His Ser Ser His Trp Leu Arg Leu
625                 630                 635                 640

Pro Arg Ile Phe Cys Ser Cys Pro Ile Gly Glu Asn Ser Pro Leu Leu
                645                 650                 655

Ser Gly Gln Gln Val
                660

<210> SEQ ID NO 47
<211> LENGTH: 668
<212> TYPE: PRT
<213> ORGANISM: homo sapiens

<400> SEQUENCE: 47

Met Asp Leu Val Leu Lys Arg Cys Leu Leu His Leu Ala Val Ile Gly
1               5                   10                  15

Ala Leu Leu Ala Val Gly Ala Thr Lys Val Pro Arg Asn Gln Asp Trp
                20                  25                  30

Leu Gly Val Ser Arg Gln Leu Arg Thr Lys Ala Trp Asn Arg Gln Leu
            35                  40                  45

Tyr Pro Glu Trp Thr Glu Ala Gln Arg Leu Asp Cys Trp Arg Gly Gly
        50                  55                  60

Gln Val Ser Leu Lys Val Ser Asn Asp Gly Pro Thr Leu Ile Gly Ala
65                  70                  75                  80

Asn Ala Ser Phe Ser Ile Ala Leu Asn Phe Pro Gly Ser Gln Lys Val
                85                  90                  95

Leu Pro Asp Gly Gln Val Ile Trp Val Asn Asn Thr Ile Ile Asn Gly
            100                 105                 110

Ser Gln Val Trp Gly Gly Gln Pro Val Tyr Pro Gln Glu Thr Asp Asp
        115                 120                 125

Ala Cys Ile Phe Pro Asp Gly Gly Pro Cys Pro Ser Gly Ser Trp Ser
    130                 135                 140

Gln Lys Arg Ser Phe Val Tyr Val Trp Lys Thr Trp Gly Gln Tyr Trp
145                 150                 155                 160

Gln Val Leu Gly Gly Pro Val Ser Gly Leu Ser Ile Gly Thr Gly Arg
                165                 170                 175

Ala Met Leu Gly Thr His Thr Met Glu Val Thr Val Tyr His Arg Arg
            180                 185                 190

Gly Ser Arg Ser Tyr Val Pro Leu Ala His Ser Ser Ser Ala Phe Thr
        195                 200                 205

Ile Thr Asp Gln Val Pro Phe Ser Val Ser Val Ser Gln Leu Arg Ala
    210                 215                 220

Leu Asp Gly Gly Asn Lys His Phe Leu Arg Asn Gln Pro Leu Thr Phe
225                 230                 235                 240

Ala Leu Gln Leu His Asp Pro Ser Gly Tyr Leu Ala Glu Ala Asp Leu
                245                 250                 255
```

```
Ser Tyr Thr Trp Asp Phe Gly Asp Ser Ser Gly Thr Leu Ile Ser Arg
            260                 265                 270

Ala Leu Val Val Thr His Thr Tyr Leu Glu Pro Gly Pro Val Thr Ala
        275                 280                 285

Gln Val Val Leu Gln Ala Ala Ile Pro Leu Thr Ser Cys Gly Ser Ser
    290                 295                 300

Pro Val Pro Gly Thr Thr Asp Gly His Arg Pro Thr Ala Glu Ala Pro
305                 310                 315                 320

Asn Thr Thr Ala Gly Gln Val Pro Thr Thr Glu Val Val Gly Thr Thr
                325                 330                 335

Pro Gly Gln Ala Pro Thr Ala Glu Pro Ser Gly Thr Thr Ser Val Gln
            340                 345                 350

Val Pro Thr Thr Glu Val Ile Ser Thr Ala Pro Val Gln Met Pro Thr
        355                 360                 365

Ala Glu Ser Thr Gly Met Thr Pro Glu Lys Val Pro Val Ser Glu Val
    370                 375                 380

Met Gly Thr Thr Leu Ala Glu Met Ser Thr Pro Glu Ala Thr Gly Met
385                 390                 395                 400

Thr Pro Ala Glu Val Ser Ile Val Val Leu Ser Gly Thr Thr Ala Ala
                405                 410                 415

Gln Val Thr Thr Thr Glu Trp Val Glu Thr Thr Ala Arg Glu Leu Pro
            420                 425                 430

Ile Pro Glu Pro Glu Gly Pro Asp Ala Ser Ser Ile Met Ser Thr Glu
        435                 440                 445

Ser Ile Thr Gly Ser Leu Gly Pro Leu Leu Asp Gly Thr Ala Thr Leu
    450                 455                 460

Arg Leu Val Lys Arg Gln Val Pro Leu Asp Cys Val Leu Tyr Arg Tyr
465                 470                 475                 480

Gly Ser Phe Ser Val Thr Leu Asp Ile Val Gln Gly Ile Glu Ser Ala
                485                 490                 495

Glu Ile Leu Gln Ala Val Pro Ser Gly Glu Gly Asp Ala Phe Glu Leu
            500                 505                 510

Thr Val Ser Cys Gln Gly Gly Leu Pro Lys Glu Ala Cys Met Glu Ile
        515                 520                 525

Ser Ser Pro Gly Cys Gln Pro Pro Ala Gln Arg Leu Cys Gln Pro Val
    530                 535                 540

Leu Pro Ser Pro Ala Cys Gln Leu Val Leu His Gln Ile Leu Lys Gly
545                 550                 555                 560

Gly Ser Gly Thr Tyr Cys Leu Asn Val Ser Leu Ala Asp Thr Asn Ser
                565                 570                 575

Leu Ala Val Val Ser Thr Gln Leu Ile Met Pro Val Pro Gly Ile Leu
            580                 585                 590

Leu Thr Gly Gln Glu Ala Gly Leu Gly Gln Val Pro Leu Ile Val Gly
        595                 600                 605

Ile Leu Leu Val Leu Met Ala Val Val Leu Ala Ser Leu Ile Tyr Arg
    610                 615                 620

Arg Arg Leu Met Lys Gln Asp Phe Ser Val Pro Gln Leu Pro His Ser
625                 630                 635                 640

Ser Ser His Trp Leu Arg Leu Pro Arg Ile Phe Cys Ser Cys Pro Ile
                645                 650                 655

Gly Glu Asn Ser Pro Leu Leu Ser Gly Gln Gln Val
            660                 665
```

```
<210> SEQ ID NO 48
<211> LENGTH: 118
<212> TYPE: PRT
<213> ORGANISM: homo sapiens

<400> SEQUENCE: 48

Met Pro Arg Glu Asp Ala His Phe Ile Tyr Gly Tyr Pro Lys Lys Gly
1               5                   10                  15

His Gly His Ser Tyr Thr Thr Ala Glu Glu Ala Ala Gly Ile Gly Ile
                20                  25                  30

Leu Thr Val Ile Leu Gly Val Leu Leu Leu Ile Gly Cys Trp Tyr Cys
            35                  40                  45

Arg Arg Arg Asn Gly Tyr Arg Ala Leu Met Asp Lys Ser Leu His Val
        50                  55                  60

Gly Thr Gln Cys Ala Leu Thr Arg Arg Cys Pro Gln Glu Gly Phe Asp
65                  70                  75                  80

His Arg Asp Ser Lys Val Ser Leu Gln Glu Lys Asn Cys Glu Pro Val
                85                  90                  95

Val Pro Asn Ala Pro Pro Ala Tyr Glu Lys Leu Ser Ala Glu Gln Ser
            100                 105                 110

Pro Pro Pro Tyr Ser Pro
        115

<210> SEQ ID NO 49
<211> LENGTH: 1069
<212> TYPE: PRT
<213> ORGANISM: homo sapiens

<400> SEQUENCE: 49

Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
                20                  25                  30

Pro Gln Gly Trp Arg Leu Val Gln Arg Gly Asp Pro Ala Ala Phe Arg
            35                  40                  45

Ala Leu Val Ala Gln Cys Leu Val Cys Val Pro Trp Asp Ala Arg Pro
        50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
            115                 120                 125

Asp Ala Leu Arg Gly Ser Gly Ala Trp Gly Leu Leu Leu Arg Arg Val
        130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
```

-continued

```
            210                 215                 220
Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
                260                 265                 270

Val Ser Pro Ala Arg Pro Ala Glu Glu Ala Thr Ser Leu Glu Gly Ala
            275                 280                 285

Leu Ser Gly Thr Arg His Ser His Pro Ser Val Gly Arg Gln His His
            290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Ser Ser Leu Arg Pro
                340                 345                 350

Ser Leu Thr Gly Ala Arg Arg Leu Val Glu Thr Ile Phe Leu Gly Ser
            355                 360                 365

Arg Pro Trp Met Pro Gly Thr Pro Arg Arg Leu Pro Arg Leu Pro Gln
370                 375                 380

Arg Tyr Trp Gln Met Arg Pro Leu Phe Leu Glu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Asp Thr Asp Pro Arg Arg Leu
            435                 440                 445

Val Gln Leu Leu Arg Gln His Ser Ser Pro Trp Gln Val Tyr Gly Phe
450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
                500                 505                 510

Ser Val Arg Asp Cys Ala Trp Leu Arg Arg Ser Pro Gly Val Gly Cys
            515                 520                 525

Val Pro Ala Ala Glu His Arg Leu Arg Glu Glu Ile Leu Ala Lys Phe
530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
                580                 585                 590

Leu Lys Arg Val Gln Leu Arg Glu Leu Ser Glu Ala Glu Val Arg Gln
            595                 600                 605

His Arg Glu Ala Arg Pro Ala Leu Leu Thr Ser Arg Leu Arg Phe Ile
            610                 615                 620

Pro Lys Pro Asp Gly Leu Arg Pro Ile Val Asn Met Asp Tyr Val Val
625                 630                 635                 640
```

-continued

```
Gly Ala Arg Thr Phe Arg Arg Glu Lys Arg Ala Glu Arg Leu Thr Ser
                645                 650                 655
Arg Val Lys Ala Leu Phe Ser Val Leu Asn Tyr Glu Arg Ala Arg Arg
        660                 665                 670
Pro Gly Leu Leu Gly Ala Ser Val Leu Gly Leu Asp Asp Ile His Arg
            675                 680                 685
Ala Trp Arg Thr Phe Val Leu Arg Val Arg Ala Gln Asp Pro Pro
690                 695                 700
Glu Leu Tyr Phe Val Lys Val Asp Val Thr Gly Ala Tyr Asp Thr Ile
705                 710                 715                 720
Pro Gln Asp Arg Leu Thr Glu Val Ile Ala Ser Ile Ile Lys Pro Gln
                725                 730                 735
Asn Thr Tyr Cys Val Arg Arg Tyr Ala Val Val Gln Lys Ala Ala His
            740                 745                 750
Gly His Val Arg Lys Ala Phe Lys Ser His Val Ser Thr Leu Thr Asp
        755                 760                 765
Leu Gln Pro Tyr Met Arg Gln Phe Val Ala His Leu Gln Glu Thr Ser
770                 775                 780
Pro Leu Arg Asp Ala Val Val Ile Glu Gln Ser Ser Ser Leu Asn Glu
785                 790                 795                 800
Ala Ser Ser Gly Leu Phe Asp Val Phe Leu Arg Phe Met Cys His His
                805                 810                 815
Ala Val Arg Ile Arg Gly Lys Ser Tyr Val Gln Cys Gln Gly Ile Pro
            820                 825                 830
Gln Gly Ser Ile Leu Ser Thr Leu Leu Cys Ser Leu Cys Tyr Gly Asp
        835                 840                 845
Met Glu Asn Lys Leu Phe Ala Gly Ile Arg Arg Asp Gly Leu Leu Leu
850                 855                 860
Arg Leu Val Asp Asp Phe Leu Leu Val Thr Pro His Leu Thr His Ala
865                 870                 875                 880
Lys Thr Phe Leu Ser Tyr Ala Arg Thr Ser Ile Arg Ala Ser Leu Thr
                885                 890                 895
Phe Asn Arg Gly Phe Lys Ala Gly Arg Asn Met Arg Arg Lys Leu Phe
            900                 905                 910
Gly Val Leu Arg Leu Lys Cys His Ser Leu Phe Leu Asp Leu Gln Val
        915                 920                 925
Asn Ser Leu Gln Thr Val Cys Thr Asn Ile Tyr Lys Ile Leu Leu Leu
930                 935                 940
Gln Ala Tyr Arg Phe His Ala Cys Val Leu Gln Leu Pro Phe His Gln
945                 950                 955                 960
Gln Val Trp Lys Asn Pro Thr Phe Phe Leu Arg Val Ile Ser Asp Thr
                965                 970                 975
Ala Ser Leu Cys Tyr Ser Ile Leu Lys Ala Lys Asn Ala Gly Met Ser
            980                 985                 990
Leu Gly Ala Lys Gly Ala Ala Gly Pro Leu Pro Ser Glu Ala Val Gln
        995                 1000                1005
Trp Leu Cys His Gln Ala Phe Leu Leu Lys Leu Thr Arg His Arg
        1010                1015                1020
Val Thr Tyr Val Pro Leu Leu Gly Ser Leu Arg Thr Ala Gln Thr
        1025                1030                1035
Gln Leu Ser Arg Lys Leu Pro Gly Thr Thr Leu Thr Ala Leu Glu
        1040                1045                1050
```

-continued

Ala Ala Ala Asn Pro Ala Leu Pro Ser Asp Phe Lys Thr Ile Leu
      1055            1060              1065

Asp

<210> SEQ ID NO 50
<211> LENGTH: 1132
<212> TYPE: PRT
<213> ORGANISM: homo sapiens

<400> SEQUENCE: 50

Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

```
Ser Leu Thr Gly Ala Arg Arg Leu Val Glu Thr Ile Phe Leu Gly Ser
            355                 360                 365

Arg Pro Trp Met Pro Gly Thr Pro Arg Leu Pro Arg Leu Pro Gln
370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Asp Thr Asp Pro Arg Arg Leu
        435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
                500                 505                 510

Ser Val Arg Asp Cys Ala Trp Leu Arg Arg Ser Pro Gly Val Gly Cys
            515                 520                 525

Val Pro Ala Ala Glu His Arg Leu Arg Glu Glu Ile Leu Ala Lys Phe
        530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
                580                 585                 590

Leu Lys Arg Val Gln Leu Arg Glu Leu Ser Glu Ala Glu Val Arg Gln
            595                 600                 605

His Arg Glu Ala Arg Pro Ala Leu Leu Thr Ser Arg Leu Arg Phe Ile
610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
                660                 665                 670

Pro Gly Leu Leu Gly Ala Ser Val Leu Gly Leu Asp Asp Ile His Arg
            675                 680                 685

Ala Trp Arg Thr Phe Val Leu Arg Val Arg Ala Gln Asp Pro Pro Pro
            690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
                740                 745                 750

Gly His Val Arg Lys Ala Phe Lys Ser His Val Ser Thr Leu Thr Asp
            755                 760                 765

Leu Gln Pro Tyr Met Arg Gln Phe Val Ala His Leu Gln Glu Thr Ser
```

```
                770             775             780
Pro Leu Arg Asp Ala Val Val Ile Glu Gln Ser Ser Ser Leu Asn Glu
785             790             795             800

Ala Ser Ser Gly Leu Phe Asp Val Phe Leu Arg Phe Met Cys His His
            805             810             815

Ala Val Arg Ile Arg Gly Lys Ser Tyr Val Gln Cys Gln Gly Ile Pro
            820             825             830

Gln Gly Ser Ile Leu Ser Thr Leu Leu Cys Ser Leu Cys Tyr Gly Asp
            835             840             845

Met Glu Asn Lys Leu Phe Ala Gly Ile Arg Arg Asp Gly Leu Leu Leu
            850             855             860

Arg Leu Val Asp Asp Phe Leu Leu Val Thr Pro His Leu Thr His Ala
865             870             875             880

Lys Thr Phe Leu Arg Thr Leu Val Arg Gly Val Pro Glu Tyr Gly Cys
            885             890             895

Val Val Asn Leu Arg Lys Thr Val Val Asn Phe Pro Val Glu Asp Glu
            900             905             910

Ala Leu Gly Gly Thr Ala Phe Val Gln Met Pro Ala His Gly Leu Phe
            915             920             925

Pro Trp Cys Gly Leu Leu Leu Asp Thr Arg Thr Leu Glu Val Gln Ser
930             935             940

Asp Tyr Ser Ser Tyr Ala Arg Thr Ser Ile Arg Ala Ser Leu Thr Phe
945             950             955             960

Asn Arg Gly Phe Lys Ala Gly Arg Asn Met Arg Lys Leu Phe Gly
            965             970             975

Val Leu Arg Leu Lys Cys His Ser Leu Phe Leu Asp Leu Gln Val Asn
            980             985             990

Ser Leu Gln Thr Val Cys Thr Asn Ile Tyr Lys Ile Leu Leu Leu Gln
            995             1000            1005

Ala Tyr Arg Phe His Ala Cys Val Leu Gln Leu Pro Phe His Gln
    1010            1015            1020

Gln Val Trp Lys Asn Pro Thr Phe Phe Leu Arg Val Ile Ser Asp
    1025            1030            1035

Thr Ala Ser Leu Cys Tyr Ser Ile Leu Lys Ala Lys Asn Ala Gly
    1040            1045            1050

Met Ser Leu Gly Ala Lys Gly Ala Ala Gly Pro Leu Pro Ser Glu
    1055            1060            1065

Ala Val Gln Trp Leu Cys His Gln Ala Phe Leu Leu Lys Leu Thr
    1070            1075            1080

Arg His Arg Val Thr Tyr Val Pro Leu Leu Gly Ser Leu Arg Thr
    1085            1090            1095

Ala Gln Thr Gln Leu Ser Arg Lys Leu Pro Gly Thr Thr Leu Thr
    1100            1105            1110

Ala Leu Glu Ala Ala Ala Asn Pro Ala Leu Pro Ser Asp Phe Lys
    1115            1120            1125

Thr Ile Leu Asp
    1130

<210> SEQ ID NO 51
<211> LENGTH: 353
<212> TYPE: PRT
<213> ORGANISM: homo sapiens

<400> SEQUENCE: 51
```

```
Met Ala His Phe Pro Gly Phe Gly Gln Ser Leu Leu Phe Gly Tyr Pro
1               5                   10                  15

Val Tyr Val Phe Gly Asp Cys Val Gln Gly Asp Trp Cys Pro Ile Ser
            20                  25                  30

Gly Gly Leu Cys Ser Ala Arg Leu His Arg His Ala Leu Leu Ala Thr
            35                  40                  45

Cys Pro Glu His Gln Ile Thr Trp Asp Pro Ile Asp Gly Arg Val Ile
50                  55                  60

Gly Ser Ala Leu Gln Phe Leu Ile Pro Arg Leu Pro Ser Phe Pro Thr
65                  70                  75                  80

Gln Arg Thr Ser Lys Thr Leu Lys Val Leu Thr Pro Ile Thr His
                85                  90                  95

Thr Thr Pro Asn Ile Pro Pro Ser Phe Leu Gln Ala Met Arg Lys Tyr
                100                 105                 110

Ser Pro Phe Arg Asn Gly Tyr Met Glu Pro Thr Leu Gly Gln His Leu
                115                 120                 125

Pro Thr Leu Ser Phe Pro Asp Pro Gly Leu Arg Pro Gln Asn Leu Tyr
                130                 135                 140

Thr Leu Trp Gly Gly Ser Val Val Cys Met Tyr Leu Tyr Gln Leu Ser
145                 150                 155                 160

Pro Pro Ile Thr Trp Pro Leu Leu Pro His Val Ile Phe Cys His Pro
                165                 170                 175

Gly Gln Leu Gly Ala Phe Leu Thr Asn Val Pro Tyr Lys Arg Ile Glu
                180                 185                 190

Lys Leu Leu Tyr Lys Ile Ser Leu Thr Thr Gly Ala Leu Ile Ile Leu
                195                 200                 205

Pro Glu Asp Cys Leu Pro Thr Thr Leu Phe Gln Pro Ala Arg Ala Pro
210                 215                 220

Val Thr Leu Thr Ala Trp Gln Asn Gly Leu Leu Pro Phe His Ser Thr
225                 230                 235                 240

Leu Thr Thr Pro Gly Leu Ile Trp Thr Phe Thr Asp Gly Thr Pro Met
                245                 250                 255

Ile Ser Gly Pro Cys Pro Lys Asp Gly Gln Pro Ser Leu Val Leu Gln
                260                 265                 270

Ser Ser Ser Phe Ile Phe His Lys Phe Gln Thr Lys Ala Tyr His Pro
            275                 280                 285

Ser Phe Leu Leu Ser His Gly Leu Ile Gln Tyr Ser Ser Phe His Asn
                290                 295                 300

Leu His Leu Leu Phe Glu Glu Tyr Thr Asn Ile Pro Ile Ser Leu Leu
305                 310                 315                 320

Phe Asn Glu Lys Glu Ala Asp Asp Asn Asp His Glu Pro Gln Ile Ser
                325                 330                 335

Pro Gly Gly Leu Glu Pro Leu Ser Glu Lys His Phe Arg Glu Thr Glu
                340                 345                 350

Val

<210> SEQ ID NO 52
<211> LENGTH: 345
<212> TYPE: PRT
<213> ORGANISM: homo sapiens

<400> SEQUENCE: 52

Met Ala His Phe Pro Gly Phe Gly Gln Ser Leu Leu Tyr Gly Tyr Pro
1               5                   10                  15
```

```
Val Tyr Val Phe Gly Asp Cys Val Gln Ala Asp Trp Cys Pro Ile Ser
                20                  25                  30

Gly Gly Leu Cys Ser Pro Arg Leu His Arg His Ala Leu Leu Ala Thr
            35                  40                  45

Cys Pro Glu His Gln Ile Thr Trp Asp Pro Ile Asp Gly Arg Val Val
        50                  55                  60

Gly Ser Pro Leu Gln Tyr Leu Ile Pro Arg Leu Pro Ser Phe Pro Thr
65                  70                  75                  80

Gln Arg Thr Ser Lys Thr Leu Lys Val Leu Thr Pro Thr Thr Pro
                85                  90                  95

Val Thr Pro Lys Val Pro Pro Ser Phe Phe Gln Ser Val Arg Arg His
                100                 105                 110

Ser Pro Tyr Arg Asn Gly Cys Leu Glu Thr Thr Leu Gly Glu Gln Leu
            115                 120                 125

Pro Ser Leu Ala Phe Pro Glu Pro Gly Leu Arg Pro Gln Asn Val Tyr
        130                 135                 140

Thr Ile Trp Gly Lys Thr Ile Val Cys Leu Tyr Ile Tyr Gln Leu Ser
145                 150                 155                 160

Pro Pro Met Thr Trp Pro Leu Ile Pro His Val Ile Phe Cys Asn Pro
                165                 170                 175

Arg Gln Leu Gly Ala Phe Leu Ser Asn Val Pro Pro Lys Arg Leu Glu
            180                 185                 190

Glu Leu Leu Tyr Lys Leu Tyr Leu His Thr Gly Ala Ile Ile Ile Leu
        195                 200                 205

Pro Glu Asp Ala Leu Pro Thr Thr Leu Phe Gln Pro Val Arg Ala Pro
210                 215                 220

Cys Val Gln Thr Thr Trp Asn Thr Gly Leu Leu Pro Tyr Gln Pro Asn
225                 230                 235                 240

Leu Thr Thr Pro Gly Leu Ile Trp Thr Phe Asn Asp Gly Ser Pro Met
                245                 250                 255

Ile Ser Gly Pro Cys Pro Lys Ala Gly Gln Pro Ser Leu Val Val Gln
            260                 265                 270

Ser Ser Leu Leu Ile Phe Glu Arg Phe Gln Thr Lys Ala Tyr His Pro
        275                 280                 285

Ser Tyr Leu Leu Ser His Gln Leu Ile Gln Tyr Ser Ser Phe His His
290                 295                 300

Leu Tyr Leu Leu Phe Asp Glu Tyr Thr Thr Ile Pro Phe Ser Leu Leu
305                 310                 315                 320

Phe Lys Glu Lys Glu Gly Asp Asp Arg Asp Asn Asp Pro Leu Pro Gly
                325                 330                 335

Ala Thr Ala Ser Pro Gln Gly Gln Asn
            340                 345

<210> SEQ ID NO 53
<211> LENGTH: 180
<212> TYPE: PRT
<213> ORGANISM: homo sapiens

<400> SEQUENCE: 53

Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
            20                  25                  30

Gly Pro Gly Glu Ala Gly Ala Thr Gly Gly Arg Gly Pro Arg Gly Ala
        35                  40                  45
```

```
Gly Ala Ala Arg Ala Ser Gly Pro Gly Gly Ala Pro Arg Gly Pro
        50                  55                  60

His Gly Gly Ala Ala Ser Gly Leu Asn Gly Cys Cys Arg Cys Gly Ala
 65                  70                  75                  80

Arg Gly Pro Glu Ser Arg Leu Leu Glu Phe Tyr Leu Ala Met Pro Phe
                85                  90                  95

Ala Thr Pro Met Glu Ala Glu Leu Ala Arg Arg Ser Leu Ala Gln Asp
            100                 105                 110

Ala Pro Pro Leu Pro Val Pro Gly Val Leu Leu Lys Glu Phe Thr Val
            115                 120                 125

Ser Gly Asn Ile Leu Thr Ile Arg Leu Thr Ala Ala Asp His Arg Gln
130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Pro Pro Ser
                165                 170                 175

Gly Gln Arg Arg
            180

<210> SEQ ID NO 54
<211> LENGTH: 309
<212> TYPE: PRT
<213> ORGANISM: homo sapiens

<400> SEQUENCE: 54

Met Ser Leu Glu Gln Arg Ser Leu His Cys Lys Pro Glu Glu Ala Leu
 1               5                  10                  15

Glu Ala Gln Gln Glu Ala Leu Gly Leu Val Cys Val Gln Ala Ala Thr
            20                  25                  30

Ser Ser Ser Ser Pro Leu Val Leu Gly Thr Leu Glu Glu Val Pro Thr
        35                  40                  45

Ala Gly Ser Thr Asp Pro Pro Gln Ser Pro Gln Gly Ala Ser Ala Phe
    50                  55                  60

Pro Thr Thr Ile Asn Phe Thr Arg Gln Arg Gln Pro Ser Glu Gly Ser
 65                  70                  75                  80

Ser Ser Arg Glu Glu Glu Gly Pro Ser Thr Ser Cys Ile Leu Glu Ser
                85                  90                  95

Leu Phe Arg Ala Val Ile Thr Lys Lys Val Ala Asp Leu Val Gly Phe
            100                 105                 110

Leu Leu Leu Lys Tyr Arg Ala Arg Glu Pro Val Thr Lys Ala Glu Met
        115                 120                 125

Leu Glu Ser Val Ile Lys Asn Tyr Lys His Cys Phe Pro Glu Ile Phe
130                 135                 140

Gly Lys Ala Ser Glu Ser Leu Gln Leu Val Phe Gly Ile Asp Val Lys
145                 150                 155                 160

Glu Ala Asp Pro Thr Gly His Ser Tyr Val Leu Val Thr Cys Leu Gly
                165                 170                 175

Leu Ser Tyr Asp Gly Leu Leu Gly Asp Asn Gln Ile Met Pro Lys Thr
            180                 185                 190

Gly Phe Leu Ile Ile Val Leu Val Met Ile Ala Met Glu Gly Gly His
        195                 200                 205

Ala Pro Glu Glu Glu Ile Trp Glu Glu Leu Ser Val Met Glu Val Tyr
    210                 215                 220

Asp Gly Arg Glu His Ser Ala Tyr Gly Glu Pro Arg Lys Leu Leu Thr
```

```
                225                 230                 235                 240
        Gln Asp Leu Val Gln Glu Lys Tyr Leu Glu Tyr Arg Gln Val Pro Asp
                        245                 250                 255

Ser Asp Pro Ala Arg Tyr Glu Phe Leu Trp Gly Pro Arg Ala Leu Ala
                        260                 265                 270

Glu Thr Ser Tyr Val Lys Val Leu Glu Tyr Val Ile Lys Val Ser Ala
                        275                 280                 285

Arg Val Arg Phe Phe Phe Pro Ser Leu Arg Glu Ala Ala Leu Arg Glu
                        290                 295                 300

Glu Glu Glu Gly Val
        305

<210> SEQ ID NO 55
<211> LENGTH: 314
<212> TYPE: PRT
<213> ORGANISM: homo sapiens

<400> SEQUENCE: 55

Met Pro Leu Glu Gln Arg Ser Gln His Cys Lys Pro Glu Glu Gly Leu
1               5                   10                  15

Glu Ala Arg Gly Glu Ala Leu Gly Leu Val Gly Ala Gln Ala Pro Ala
                20                  25                  30

Thr Glu Glu Gln Glu Ala Ala Ser Ser Ser Thr Leu Val Glu Val
            35                  40                      45

Thr Leu Gly Glu Val Pro Ala Ala Glu Ser Pro Asp Pro Pro Gln Ser
        50                  55                  60

Pro Gln Gly Ala Ser Ser Leu Pro Thr Thr Met Asn Tyr Pro Leu Trp
65                  70                  75                  80

Ser Gln Ser Tyr Glu Asp Ser Ser Asn Gln Glu Glu Glu Gly Pro Ser
                85                  90                  95

Thr Phe Pro Asp Leu Glu Ser Glu Phe Gln Ala Ala Leu Ser Arg Lys
                100                 105                 110

Val Ala Glu Leu Val His Phe Leu Leu Leu Lys Tyr Arg Ala Arg Glu
                115                 120                 125

Pro Val Thr Lys Ala Glu Met Leu Gly Ser Val Val Gly Asn Trp Gln
                130                 135                 140

Tyr Phe Phe Pro Val Ile Phe Ser Lys Ala Ser Ser Ser Leu Gln Leu
145                 150                 155                 160

Val Phe Gly Ile Glu Leu Met Glu Val Asp Pro Ile Gly His Leu Tyr
                165                 170                 175

Ile Phe Ala Thr Cys Leu Gly Leu Ser Tyr Asp Gly Leu Leu Gly Asp
                180                 185                 190

Asn Gln Ile Met Pro Lys Ala Gly Leu Leu Ile Ile Val Leu Ala Ile
                195                 200                 205

Ile Ala Arg Glu Gly Asp Cys Ala Pro Glu Glu Lys Ile Trp Glu Glu
                210                 215                 220

Leu Ser Val Leu Glu Val Phe Glu Gly Arg Glu Asp Ser Ile Leu Gly
225                 230                 235                 240

Asp Pro Lys Lys Leu Leu Thr Gln His Phe Val Gln Glu Asn Tyr Leu
                245                 250                 255

Glu Tyr Arg Gln Val Pro Gly Ser Asp Pro Ala Cys Tyr Glu Phe Leu
                260                 265                 270

Trp Gly Pro Arg Ala Leu Val Glu Thr Ser Tyr Val Lys Val Leu His
                275                 280                 285
```

```
His Met Val Lys Ile Ser Gly Gly Pro His Ile Ser Tyr Pro Pro Leu
            290                 295                 300

His Glu Trp Val Leu Arg Glu Gly Glu Glu
305                 310
```

<210> SEQ ID NO 56
<211> LENGTH: 1225
<212> TYPE: PRT
<213> ORGANISM: homo sapiens

<400> SEQUENCE: 56

```
Met Lys Leu Arg Leu Pro Ala Ser Pro Glu Thr His Leu Asp Met Leu
1               5                   10                  15

Arg His Leu Tyr Gln Gly Cys Gln Val Val Gln Gly Asn Leu Glu Leu
            20                  25                  30

Thr Tyr Leu Pro Thr Asn Ala Ser Leu Ser Phe Leu Gln Asp Ile Gln
        35                  40                  45

Glu Val Gln Gly Tyr Val Leu Ile Ala His Asn Gln Val Arg Gln Val
    50                  55                  60

Pro Leu Gln Arg Leu Arg Ile Val Arg Gly Thr Gln Leu Phe Glu Asp
65                  70                  75                  80

Asn Tyr Ala Leu Ala Val Leu Asp Asn Gly Asp Pro Leu Asn Asn Thr
                85                  90                  95

Thr Pro Val Thr Gly Ala Ser Pro Gly Gly Leu Arg Glu Leu Gln Leu
            100                 105                 110

Arg Ser Leu Thr Glu Ile Leu Lys Gly Gly Val Leu Ile Gln Arg Asn
        115                 120                 125

Pro Gln Leu Cys Tyr Gln Asp Thr Ile Leu Trp Lys Asp Ile Phe His
    130                 135                 140

Lys Asn Asn Gln Leu Ala Leu Thr Leu Ile Asp Thr Asn Arg Ser Arg
145                 150                 155                 160

Ala Cys His Pro Cys Ser Pro Met Cys Lys Gly Ser Arg Cys Trp Gly
                165                 170                 175

Glu Ser Ser Glu Asp Cys Gln Ser Leu Thr Arg Thr Val Cys Ala Gly
            180                 185                 190

Gly Cys Ala Arg Cys Lys Gly Pro Leu Pro Thr Asp Cys Cys His Glu
        195                 200                 205

Gln Cys Ala Ala Gly Cys Thr Gly Pro Lys His Ser Asp Cys Leu Ala
    210                 215                 220

Cys Leu His Phe Asn His Ser Gly Ile Cys Glu Leu His Cys Pro Ala
225                 230                 235                 240

Leu Val Thr Tyr Asn Thr Asp Thr Phe Glu Ser Met Pro Asn Pro Glu
                245                 250                 255

Gly Arg Tyr Thr Phe Gly Ala Ser Cys Val Thr Ala Cys Pro Tyr Asn
            260                 265                 270

Tyr Leu Ser Thr Asp Val Gly Ser Cys Thr Leu Val Cys Pro Leu His
        275                 280                 285

Asn Gln Glu Val Thr Ala Glu Asp Gly Thr Gln Arg Cys Glu Lys Cys
    290                 295                 300

Ser Lys Pro Cys Ala Arg Val Cys Tyr Gly Leu Gly Met Glu His Leu
305                 310                 315                 320

Arg Glu Val Arg Ala Val Thr Ser Ala Asn Ile Gln Glu Phe Ala Gly
                325                 330                 335

Cys Lys Lys Ile Phe Gly Ser Leu Ala Phe Leu Pro Glu Ser Phe Asp
            340                 345                 350
```

```
Gly Asp Pro Ala Ser Asn Thr Ala Pro Leu Gln Pro Glu Gln Leu Gln
            355                 360                 365

Val Phe Glu Thr Leu Glu Glu Ile Thr Gly Tyr Leu Tyr Ile Ser Ala
370                 375                 380

Trp Pro Asp Ser Leu Pro Asp Leu Ser Val Phe Gln Asn Leu Gln Val
385                 390                 395                 400

Ile Arg Gly Arg Ile Leu His Asn Gly Ala Tyr Ser Leu Thr Leu Gln
                405                 410                 415

Gly Leu Gly Ile Ser Trp Leu Gly Leu Arg Ser Leu Arg Glu Leu Gly
            420                 425                 430

Ser Gly Leu Ala Leu Ile His His Asn Thr His Leu Cys Phe Val His
            435                 440                 445

Thr Val Pro Trp Asp Gln Leu Phe Arg Asn Pro His Gln Ala Leu Leu
            450                 455                 460

His Thr Ala Asn Arg Pro Glu Asp Glu Cys Val Gly Glu Gly Leu Ala
465                 470                 475                 480

Cys His Gln Leu Cys Ala Arg Gly His Cys Trp Gly Pro Gly Pro Thr
                485                 490                 495

Gln Cys Val Asn Cys Ser Gln Phe Leu Arg Gly Gln Glu Cys Val Glu
            500                 505                 510

Glu Cys Arg Val Leu Gln Gly Leu Pro Arg Glu Tyr Val Asn Ala Arg
            515                 520                 525

His Cys Leu Pro Cys His Pro Glu Cys Gln Pro Gln Asn Gly Ser Val
            530                 535                 540

Thr Cys Phe Gly Pro Glu Ala Asp Gln Cys Val Ala Cys Ala His Tyr
545                 550                 555                 560

Lys Asp Pro Pro Phe Cys Val Ala Arg Cys Pro Ser Gly Val Lys Pro
                565                 570                 575

Asp Leu Ser Tyr Met Pro Ile Trp Lys Phe Pro Asp Glu Glu Gly Ala
            580                 585                 590

Cys Gln Pro Cys Pro Ile Asn Cys Thr His Ser Cys Val Asp Leu Asp
            595                 600                 605

Asp Lys Gly Cys Pro Ala Glu Gln Arg Ala Ser Pro Leu Thr Ser Ile
            610                 615                 620

Ile Ser Ala Val Val Gly Ile Leu Leu Val Val Val Leu Gly Val Val
625                 630                 635                 640

Phe Gly Ile Leu Ile Lys Arg Arg Gln Gln Lys Ile Arg Lys Tyr Thr
                645                 650                 655

Met Arg Arg Leu Leu Gln Glu Thr Glu Leu Val Glu Pro Leu Thr Pro
            660                 665                 670

Ser Gly Ala Met Pro Asn Gln Ala Gln Met Arg Ile Leu Lys Glu Thr
            675                 680                 685

Glu Leu Arg Lys Val Lys Val Leu Gly Ser Gly Ala Phe Gly Thr Val
690                 695                 700

Tyr Lys Gly Ile Trp Ile Pro Asp Gly Glu Asn Val Lys Ile Pro Val
705                 710                 715                 720

Ala Ile Lys Val Leu Arg Glu Asn Thr Ser Pro Lys Ala Asn Lys Glu
                725                 730                 735

Ile Leu Asp Glu Ala Tyr Val Met Ala Gly Val Gly Ser Pro Tyr Val
            740                 745                 750

Ser Arg Leu Leu Gly Ile Cys Leu Thr Ser Thr Val Gln Leu Val Thr
            755                 760                 765
```

```
Gln Leu Met Pro Tyr Gly Cys Leu Leu Asp His Val Arg Glu Asn Arg
    770             775                 780
Gly Arg Leu Gly Ser Gln Asp Leu Leu Asn Trp Cys Met Gln Ile Ala
785                 790                 795                 800
Lys Gly Met Ser Tyr Leu Glu Asp Val Arg Leu Val His Arg Asp Leu
                805                 810                 815
Ala Ala Arg Asn Val Leu Val Lys Ser Pro Asn His Val Lys Ile Thr
            820                 825                 830
Asp Phe Gly Leu Ala Arg Leu Leu Asp Ile Asp Glu Thr Glu Tyr His
            835                 840                 845
Ala Asp Gly Gly Lys Val Pro Ile Lys Trp Met Ala Leu Glu Ser Ile
850                 855                 860
Leu Arg Arg Arg Phe Thr His Gln Ser Asp Val Trp Ser Tyr Gly Val
865                 870                 875                 880
Thr Val Trp Glu Leu Met Thr Phe Gly Ala Lys Pro Tyr Asp Gly Ile
                885                 890                 895
Pro Ala Arg Glu Ile Pro Asp Leu Leu Glu Lys Gly Glu Arg Leu Pro
            900                 905                 910
Gln Pro Pro Ile Cys Thr Ile Asp Val Tyr Met Ile Met Val Lys Cys
            915                 920                 925
Trp Met Ile Asp Ser Glu Cys Arg Pro Arg Phe Arg Glu Leu Val Ser
930                 935                 940
Glu Phe Ser Arg Met Ala Arg Asp Pro Gln Arg Phe Val Val Ile Gln
945                 950                 955                 960
Asn Glu Asp Leu Gly Pro Ala Ser Pro Leu Asp Ser Thr Phe Tyr Arg
                965                 970                 975
Ser Leu Leu Glu Asp Asp Asp Met Gly Asp Leu Val Asp Ala Glu Glu
            980                 985                 990
Tyr Leu Val Pro Gln Gln Gly Phe Phe Cys Pro Asp Pro Ala Pro Gly
            995                 1000                1005
Ala Gly Gly Met Val His His Arg His Arg Ser Ser Ser Thr Arg
    1010            1015                1020
Ser Gly Gly Gly Asp Leu Thr Leu Gly Leu Glu Pro Ser Glu Glu
    1025            1030                1035
Glu Ala Pro Arg Ser Pro Leu Ala Pro Ser Glu Gly Ala Gly Ser
    1040            1045                1050
Asp Val Phe Asp Gly Asp Leu Gly Met Gly Ala Ala Lys Gly Leu
    1055            1060                1065
Gln Ser Leu Pro Thr His Asp Pro Ser Pro Leu Gln Arg Tyr Ser
    1070            1075                1080
Glu Asp Pro Thr Val Pro Leu Pro Ser Glu Thr Asp Gly Tyr Val
    1085            1090                1095
Ala Pro Leu Thr Cys Ser Pro Gln Pro Glu Tyr Val Asn Gln Pro
    1100            1105                1110
Asp Val Arg Pro Gln Pro Pro Ser Pro Arg Glu Gly Pro Leu Pro
    1115            1120                1125
Ala Ala Arg Pro Ala Gly Ala Thr Leu Glu Arg Pro Lys Thr Leu
    1130            1135                1140
Ser Pro Gly Lys Asn Gly Val Val Lys Asp Val Phe Ala Phe Gly
    1145            1150                1155
Gly Ala Val Glu Asn Pro Glu Tyr Leu Thr Pro Gln Gly Gly Ala
    1160            1165                1170
Ala Pro Gln Pro His Pro Pro Pro Ala Phe Ser Pro Ala Phe Asp
```

```
        1175                1180                1185
Asn Leu Tyr Tyr Trp Asp Gln Asp Pro Pro Glu Arg Gly Ala Pro
    1190                1195                1200

Pro Ser Thr Phe Lys Gly Thr Pro Thr Ala Glu Asn Pro Glu Tyr
    1205                1210                1215

Leu Gly Leu Asp Val Pro Val
    1220                1225

<210> SEQ ID NO 57
<211> LENGTH: 1240
<212> TYPE: PRT
<213> ORGANISM: homo sapiens

<400> SEQUENCE: 57

Met Pro Arg Gly Ser Trp Lys Pro Gln Val Cys Thr Gly Thr Asp Met
1               5                   10                  15

Lys Leu Arg Leu Pro Ala Ser Pro Glu Thr His Leu Asp Met Leu Arg
                20                  25                  30

His Leu Tyr Gln Gly Cys Gln Val Val Gln Gly Asn Leu Glu Leu Thr
            35                  40                  45

Tyr Leu Pro Thr Asn Ala Ser Leu Ser Phe Leu Gln Asp Ile Gln Glu
    50                  55                  60

Val Gln Gly Tyr Val Leu Ile Ala His Asn Gln Val Arg Gln Val Pro
65                  70                  75                  80

Leu Gln Arg Leu Arg Ile Val Arg Gly Thr Gln Leu Phe Glu Asp Asn
                85                  90                  95

Tyr Ala Leu Ala Val Leu Asp Asn Gly Asp Pro Leu Asn Asn Thr Thr
            100                 105                 110

Pro Val Thr Gly Ala Ser Pro Gly Gly Leu Arg Glu Leu Gln Leu Arg
        115                 120                 125

Ser Leu Thr Glu Ile Leu Lys Gly Gly Val Leu Ile Gln Arg Asn Pro
130                 135                 140

Gln Leu Cys Tyr Gln Asp Thr Ile Leu Trp Lys Asp Ile Phe His Lys
145                 150                 155                 160

Asn Asn Gln Leu Ala Leu Thr Leu Ile Asp Thr Asn Arg Ser Arg Ala
                165                 170                 175

Cys His Pro Cys Ser Pro Met Cys Lys Gly Ser Arg Cys Trp Gly Glu
            180                 185                 190

Ser Ser Glu Asp Cys Gln Ser Leu Thr Arg Thr Val Cys Ala Gly Gly
        195                 200                 205

Cys Ala Arg Cys Lys Gly Pro Leu Pro Thr Asp Cys Cys His Glu Gln
    210                 215                 220

Cys Ala Ala Gly Cys Thr Gly Pro Lys His Ser Asp Cys Leu Ala Cys
225                 230                 235                 240

Leu His Phe Asn His Ser Gly Ile Cys Glu Leu His Cys Pro Ala Leu
                245                 250                 255

Val Thr Tyr Asn Thr Asp Thr Phe Glu Ser Met Pro Asn Pro Glu Gly
            260                 265                 270

Arg Tyr Thr Phe Gly Ala Ser Cys Val Thr Ala Cys Pro Tyr Asn Tyr
        275                 280                 285

Leu Ser Thr Asp Val Gly Ser Cys Thr Leu Val Cys Pro Leu His Asn
    290                 295                 300

Gln Glu Val Thr Ala Glu Asp Gly Thr Gln Arg Cys Glu Lys Cys Ser
305                 310                 315                 320
```

```
Lys Pro Cys Ala Arg Val Cys Tyr Gly Leu Gly Met Glu His Leu Arg
                325                 330                 335

Glu Val Arg Ala Val Thr Ser Ala Asn Ile Gln Glu Phe Ala Gly Cys
            340                 345                 350

Lys Lys Ile Phe Gly Ser Leu Ala Phe Leu Pro Glu Ser Phe Asp Gly
        355                 360                 365

Asp Pro Ala Ser Asn Thr Ala Pro Leu Gln Pro Glu Gln Leu Gln Val
    370                 375                 380

Phe Glu Thr Leu Glu Glu Ile Thr Gly Tyr Leu Tyr Ile Ser Ala Trp
385                 390                 395                 400

Pro Asp Ser Leu Pro Asp Leu Ser Val Phe Gln Asn Leu Gln Val Ile
                405                 410                 415

Arg Gly Arg Ile Leu His Asn Gly Ala Tyr Ser Leu Thr Leu Gln Gly
            420                 425                 430

Leu Gly Ile Ser Trp Leu Gly Leu Arg Ser Leu Arg Glu Leu Gly Ser
        435                 440                 445

Gly Leu Ala Leu Ile His His Asn Thr His Leu Cys Phe Val His Thr
    450                 455                 460

Val Pro Trp Asp Gln Leu Phe Arg Asn Pro His Gln Ala Leu Leu His
465                 470                 475                 480

Thr Ala Asn Arg Pro Glu Asp Glu Cys Val Gly Glu Gly Leu Ala Cys
                485                 490                 495

His Gln Leu Cys Ala Arg Gly His Cys Trp Gly Pro Gly Pro Thr Gln
            500                 505                 510

Cys Val Asn Cys Ser Gln Phe Leu Arg Gly Gln Glu Cys Val Glu Glu
        515                 520                 525

Cys Arg Val Leu Gln Gly Leu Pro Arg Glu Tyr Val Asn Ala Arg His
    530                 535                 540

Cys Leu Pro Cys His Pro Glu Cys Gln Pro Gln Asn Gly Ser Val Thr
545                 550                 555                 560

Cys Phe Gly Pro Glu Ala Asp Gln Cys Val Ala Cys Ala His Tyr Lys
                565                 570                 575

Asp Pro Pro Phe Cys Val Ala Arg Cys Pro Ser Gly Val Lys Pro Asp
            580                 585                 590

Leu Ser Tyr Met Pro Ile Trp Lys Phe Pro Asp Glu Glu Gly Ala Cys
        595                 600                 605

Gln Pro Cys Pro Ile Asn Cys Thr His Ser Cys Val Asp Leu Asp Asp
    610                 615                 620

Lys Gly Cys Pro Ala Glu Gln Arg Ala Ser Pro Leu Thr Ser Ile Ile
625                 630                 635                 640

Ser Ala Val Val Gly Ile Leu Leu Val Val Leu Gly Val Val Phe
                645                 650                 655

Gly Ile Leu Ile Lys Arg Arg Gln Gln Lys Ile Arg Lys Tyr Thr Met
            660                 665                 670

Arg Arg Leu Leu Gln Glu Thr Glu Leu Val Glu Pro Leu Thr Pro Ser
        675                 680                 685

Gly Ala Met Pro Asn Gln Ala Gln Met Arg Ile Leu Lys Glu Thr Glu
    690                 695                 700

Leu Arg Lys Val Lys Val Leu Gly Ser Gly Ala Phe Gly Thr Val Tyr
705                 710                 715                 720

Lys Gly Ile Trp Ile Pro Asp Gly Glu Asn Val Lys Ile Pro Val Ala
                725                 730                 735

Ile Lys Val Leu Arg Glu Asn Thr Ser Pro Lys Ala Asn Lys Glu Ile
```

```
                    740                 745                 750
Leu Asp Glu Ala Tyr Val Met Ala Gly Val Gly Ser Pro Tyr Val Ser
                755                 760                 765

Arg Leu Leu Gly Ile Cys Leu Thr Ser Thr Val Gln Leu Val Thr Gln
            770                 775                 780

Leu Met Pro Tyr Gly Cys Leu Leu Asp His Val Arg Glu Asn Arg Gly
785                 790                 795                 800

Arg Leu Gly Ser Gln Asp Leu Leu Asn Trp Cys Met Gln Ile Ala Lys
                805                 810                 815

Gly Met Ser Tyr Leu Glu Asp Val Arg Leu Val His Arg Asp Leu Ala
            820                 825                 830

Ala Arg Asn Val Leu Val Lys Ser Pro Asn His Val Lys Ile Thr Asp
            835                 840                 845

Phe Gly Leu Ala Arg Leu Leu Asp Ile Asp Thr Glu Tyr His Ala
            850                 855                 860

Asp Gly Gly Lys Val Pro Ile Lys Trp Met Ala Leu Glu Ser Ile Leu
865                 870                 875                 880

Arg Arg Arg Phe Thr His Gln Ser Asp Val Trp Ser Tyr Gly Val Thr
                885                 890                 895

Val Trp Glu Leu Met Thr Phe Gly Ala Lys Pro Tyr Asp Gly Ile Pro
            900                 905                 910

Ala Arg Glu Ile Pro Asp Leu Leu Glu Lys Gly Glu Arg Leu Pro Gln
            915                 920                 925

Pro Pro Ile Cys Thr Ile Asp Val Tyr Met Ile Met Val Lys Cys Trp
        930                 935                 940

Met Ile Asp Ser Glu Cys Arg Pro Arg Phe Arg Glu Leu Val Ser Glu
945                 950                 955                 960

Phe Ser Arg Met Ala Arg Asp Pro Gln Arg Phe Val Val Ile Gln Asn
                965                 970                 975

Glu Asp Leu Gly Pro Ala Ser Pro Leu Asp Ser Thr Phe Tyr Arg Ser
            980                 985                 990

Leu Leu Glu Asp Asp Asp Met Gly Asp Leu Val Asp Ala Glu Glu Tyr
        995                 1000                1005

Leu Val Pro Gln Gln Gly Phe Phe Cys Pro Asp Pro Ala Pro Gly
    1010                1015                1020

Ala Gly Gly Met Val His His Arg His Arg Ser Ser Ser Thr Arg
    1025                1030                1035

Ser Gly Gly Gly Asp Leu Thr Leu Gly Leu Glu Pro Ser Glu Glu
    1040                1045                1050

Glu Ala Pro Arg Ser Pro Leu Ala Pro Ser Glu Gly Ala Gly Ser
    1055                1060                1065

Asp Val Phe Asp Gly Asp Leu Gly Met Gly Ala Ala Lys Gly Leu
    1070                1075                1080

Gln Ser Leu Pro Thr His Asp Pro Ser Pro Leu Gln Arg Tyr Ser
    1085                1090                1095

Glu Asp Pro Thr Val Pro Leu Pro Ser Glu Thr Asp Gly Tyr Val
    1100                1105                1110

Ala Pro Leu Thr Cys Ser Pro Gln Pro Glu Tyr Val Asn Gln Pro
    1115                1120                1125

Asp Val Arg Pro Gln Pro Pro Ser Pro Arg Glu Gly Pro Leu Pro
    1130                1135                1140

Ala Ala Arg Pro Ala Gly Ala Thr Leu Glu Arg Pro Lys Thr Leu
    1145                1150                1155
```

```
Ser Pro Gly Lys Asn Gly Val Val Lys Asp Val Phe Ala Phe Gly
    1160                1165                1170

Gly Ala Val Glu Asn Pro Glu Tyr Leu Thr Pro Gln Gly Gly Ala
    1175                1180                1185

Ala Pro Gln Pro His Pro Pro Ala Phe Ser Pro Ala Phe Asp
    1190                1195                1200

Asn Leu Tyr Tyr Trp Asp Gln Asp Pro Pro Glu Arg Gly Ala Pro
    1205                1210                1215

Pro Ser Thr Phe Lys Gly Thr Pro Thr Ala Glu Asn Pro Glu Tyr
    1220                1225                1230

Leu Gly Leu Asp Val Pro Val
    1235                1240

<210> SEQ ID NO 58
<211> LENGTH: 1055
<212> TYPE: PRT
<213> ORGANISM: homo sapiens

<400> SEQUENCE: 58

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
```

```
                275                 280                 285
Tyr Thr Phe Gly Ala Ser Cys Val Thr Ala Cys Pro Tyr Asn Tyr Leu
            290                 295                 300
Ser Thr Asp Val Gly Ser Cys Thr Leu Val Cys Pro Leu His Asn Gln
305                 310                 315                 320
Glu Val Thr Ala Glu Asp Gly Thr Gln Arg Cys Glu Lys Cys Ser Lys
                325                 330                 335
Pro Cys Ala Arg Val Cys Tyr Gly Leu Gly Met Glu His Leu Arg Glu
            340                 345                 350
Val Arg Ala Val Thr Ser Ala Asn Ile Gln Glu Phe Ala Gly Cys Lys
                355                 360                 365
Lys Ile Phe Gly Ser Leu Ala Phe Leu Pro Glu Ser Phe Asp Gly Asp
        370                 375                 380
Pro Ala Ser Asn Thr Ala Pro Leu Gln Pro Glu Gln Leu Gln Val Phe
385                 390                 395                 400
Glu Thr Leu Glu Glu Ile Thr Gly Tyr Leu Tyr Ile Ser Ala Trp Pro
                405                 410                 415
Asp Ser Leu Pro Asp Leu Ser Val Phe Gln Asn Leu Gln Val Ile Arg
            420                 425                 430
Gly Arg Ile Leu His Asn Gly Ala Tyr Ser Leu Thr Leu Gln Gly Leu
        435                 440                 445
Gly Ile Ser Trp Leu Gly Leu Arg Ser Leu Arg Glu Leu Gly Ser Gly
        450                 455                 460
Leu Ala Leu Ile His His Asn Thr His Leu Cys Phe Val His Thr Val
465                 470                 475                 480
Pro Trp Asp Gln Leu Phe Arg Asn Pro His Gln Ala Leu Leu His Thr
                485                 490                 495
Ala Asn Arg Pro Glu Asp Glu Cys Val Gly Glu Gly Leu Ala Cys His
                500                 505                 510
Gln Leu Cys Ala Arg Gly His Cys Trp Gly Pro Gly Pro Thr Gln Cys
            515                 520                 525
Val Asn Cys Ser Gln Phe Leu Arg Gly Gln Glu Cys Val Glu Glu Cys
        530                 535                 540
Arg Val Leu Gln Gly Leu Pro Arg Glu Tyr Val Asn Ala Arg His Cys
545                 550                 555                 560
Leu Pro Cys His Pro Glu Cys Gln Pro Gln Asn Gly Ser Val Thr Cys
                565                 570                 575
Phe Gly Pro Glu Ala Asp Gln Cys Val Ala Cys Ala His Tyr Lys Asp
                580                 585                 590
Pro Pro Phe Cys Val Ala Arg Cys Pro Ser Gly Val Lys Pro Asp Leu
            595                 600                 605
Ser Tyr Met Pro Ile Trp Lys Phe Pro Asp Glu Glu Gly Ala Cys Gln
        610                 615                 620
Pro Cys Pro Ile Asn Cys Thr His Ser Cys Val Asp Leu Asp Asp Lys
625                 630                 635                 640
Gly Cys Pro Ala Glu Gln Arg Ala Ser Pro Leu Thr Ser Ile Ile Ser
                645                 650                 655
Ala Val Val Gly Ile Leu Leu Val Val Leu Gly Val Val Phe Gly
            660                 665                 670
Ile Leu Ile Lys Arg Arg Gln Gln Lys Ile Arg Lys Tyr Thr Met Arg
        675                 680                 685
Arg Leu Leu Gln Glu Thr Glu Leu Val Glu Pro Leu Thr Pro Ser Gly
        690                 695                 700
```

```
Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
    770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
    850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
    930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu  Asp Ser Thr Phe Tyr  Arg Ser Leu
    995                 1000                1005

Leu Glu  Asp Asp Asp Met Gly  Asp Leu Val Asp Ala  Glu Glu Tyr
    1010                1015                1020

Leu Val  Pro Gln Gln Gly Phe  Phe Cys Pro Asp Pro  Ala Pro Gly
    1025                1030                1035

Ala Gly  Gly Met Val His His  Arg His Arg Ser Ser  Ser Thr Arg
    1040                1045                1050

Asn Met
    1055

<210> SEQ ID NO 59
<211> LENGTH: 603
<212> TYPE: PRT
<213> ORGANISM: homo sapiens

<400> SEQUENCE: 59

Met Lys Leu Arg Leu Pro Ala Ser Pro Glu Thr His Leu Asp Met Leu
```

```
               1               5                  10                 15
            Arg His Leu Tyr Gln Gly Cys Gln Val Val Gln Gly Asn Leu Glu Leu
                            20                  25                  30

Thr Tyr Leu Pro Thr Asn Ala Ser Leu Ser Phe Leu Gln Asp Ile Gln
                            35                  40                  45

Glu Val Gln Gly Tyr Val Leu Ile Ala His Asn Gln Val Arg Gln Val
                            50                  55                  60

Pro Leu Gln Arg Leu Arg Ile Val Arg Gly Thr Gln Leu Phe Glu Asp
            65                  70                  75                  80

Asn Tyr Ala Leu Ala Val Leu Asp Asn Gly Asp Pro Leu Asn Asn Thr
                            85                  90                  95

Thr Pro Val Thr Gly Ala Ser Pro Gly Gly Leu Arg Glu Leu Gln Leu
                            100                 105                 110

Arg Ser Leu Thr Glu Ile Leu Lys Gly Gly Val Leu Ile Gln Arg Asn
                            115                 120                 125

Pro Gln Leu Cys Tyr Gln Asp Thr Ile Leu Trp Lys Asp Ile Phe His
                            130                 135                 140

Lys Asn Asn Gln Leu Ala Leu Thr Leu Ile Asp Thr Asn Arg Ser Arg
            145                 150                 155                 160

Ala Cys His Pro Cys Ser Pro Met Cys Lys Gly Ser Arg Cys Trp Gly
                            165                 170                 175

Glu Ser Ser Glu Asp Cys Gln Ser Leu Thr Arg Thr Val Cys Ala Gly
                            180                 185                 190

Gly Cys Ala Arg Cys Lys Gly Pro Leu Pro Thr Asp Cys Cys His Glu
                            195                 200                 205

Gln Cys Ala Ala Gly Cys Thr Gly Pro Lys His Ser Asp Cys Leu Ala
                            210                 215                 220

Cys Leu His Phe Asn His Ser Gly Ile Cys Glu Leu His Cys Pro Ala
            225                 230                 235                 240

Leu Val Thr Tyr Asn Thr Asp Thr Phe Glu Ser Met Pro Asn Pro Glu
                            245                 250                 255

Gly Arg Tyr Thr Phe Gly Ala Ser Cys Val Thr Ala Cys Pro Tyr Asn
                            260                 265                 270

Tyr Leu Ser Thr Asp Val Gly Ser Cys Thr Leu Val Cys Pro Leu His
                            275                 280                 285

Asn Gln Glu Val Thr Ala Glu Asp Gly Thr Gln Arg Cys Glu Lys Cys
                            290                 295                 300

Ser Lys Pro Cys Ala Arg Val Cys Tyr Gly Leu Gly Met Glu His Leu
            305                 310                 315                 320

Arg Glu Val Arg Ala Val Thr Ser Ala Asn Ile Gln Glu Phe Ala Gly
                            325                 330                 335

Cys Lys Lys Ile Phe Gly Ser Leu Ala Phe Leu Pro Glu Ser Phe Asp
                            340                 345                 350

Gly Asp Pro Ala Ser Asn Thr Ala Pro Leu Gln Pro Glu Gln Leu Gln
                            355                 360                 365

Val Phe Glu Thr Leu Glu Glu Ile Thr Gly Tyr Leu Tyr Ile Ser Ala
                            370                 375                 380

Trp Pro Asp Ser Leu Pro Asp Leu Ser Val Phe Gln Asn Leu Gln Val
            385                 390                 395                 400

Ile Arg Gly Arg Ile Leu His Asn Gly Ala Tyr Ser Leu Thr Leu Gln
                            405                 410                 415

Gly Leu Gly Ile Ser Trp Leu Gly Leu Arg Ser Leu Arg Glu Leu Gly
                            420                 425                 430
```

```
Ser Gly Leu Ala Leu Ile His His Asn Thr His Leu Cys Phe Val His
        435                 440                 445
Thr Val Pro Trp Asp Gln Leu Phe Arg Asn Pro His Gln Ala Leu Leu
450                 455                 460
His Thr Ala Asn Arg Pro Glu Asp Glu Cys Val Gly Glu Gly Leu Ala
465                 470                 475                 480
Cys His Gln Leu Cys Ala Arg Gly His Cys Trp Gly Pro Gly Pro Thr
            485                 490                 495
Gln Cys Val Asn Cys Ser Gln Phe Leu Arg Gly Gln Glu Cys Val Glu
            500                 505                 510
Glu Cys Arg Val Leu Gln Gly Leu Pro Arg Glu Tyr Val Asn Ala Arg
            515                 520                 525
His Cys Leu Pro Cys His Pro Glu Cys Gln Pro Gln Asn Gly Ser Val
            530                 535                 540
Thr Cys Phe Gly Pro Glu Ala Asp Gln Cys Val Ala Cys Ala His Tyr
545                 550                 555                 560
Lys Asp Pro Pro Phe Cys Val Ala Arg Cys Pro Ser Gly Val Lys Pro
                565                 570                 575
Asp Leu Ser Tyr Met Pro Ile Trp Lys Phe Pro Asp Glu Glu Gly Ala
            580                 585                 590
Cys Gln Pro Cys Pro Ile Asn Cys Thr His Ser
            595                 600
```

<210> SEQ ID NO 60
<211> LENGTH: 1255
<212> TYPE: PRT
<213> ORGANISM: homo sapiens
<400> SEQUENCE: 60

```
Met Glu Leu Ala Ala Leu Cys Arg Trp Gly Leu Leu Leu Ala Leu Leu
1               5                   10                  15
Pro Pro Gly Ala Ala Ser Thr Gln Val Cys Thr Gly Thr Asp Met Lys
            20                  25                  30
Leu Arg Leu Pro Ala Ser Pro Glu Thr His Leu Asp Met Leu Arg His
        35                  40                  45
Leu Tyr Gln Gly Cys Gln Val Val Gln Gly Asn Leu Glu Leu Thr Tyr
    50                  55                  60
Leu Pro Thr Asn Ala Ser Leu Ser Phe Leu Gln Asp Ile Gln Glu Val
65                  70                  75                  80
Gln Gly Tyr Val Leu Ile Ala His Asn Gln Val Arg Gln Val Pro Leu
                85                  90                  95
Gln Arg Leu Arg Ile Val Arg Gly Thr Gln Leu Phe Glu Asp Asn Tyr
            100                 105                 110
Ala Leu Ala Val Leu Asp Asn Gly Asp Pro Leu Asn Asn Thr Thr Pro
        115                 120                 125
Val Thr Gly Ala Ser Pro Gly Gly Leu Arg Glu Leu Gln Leu Arg Ser
    130                 135                 140
Leu Thr Glu Ile Leu Lys Gly Gly Val Leu Ile Gln Arg Asn Pro Gln
145                 150                 155                 160
Leu Cys Tyr Gln Asp Thr Ile Leu Trp Lys Asp Ile Phe His Lys Asn
                165                 170                 175
Asn Gln Leu Ala Leu Thr Leu Ile Asp Thr Asn Arg Ser Arg Ala Cys
            180                 185                 190
His Pro Cys Ser Pro Met Cys Lys Gly Ser Arg Cys Trp Gly Glu Ser
```

```
            195                 200                 205
Ser Glu Asp Cys Gln Ser Leu Thr Arg Thr Val Cys Ala Gly Gly Cys
210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620
```

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
            645                 650                 655

Ala Val Val Gly Ile Leu Leu Val Val Val Leu Gly Val Val Phe Gly
                660                 665                 670

Ile Leu Ile Lys Arg Arg Gln Gln Lys Ile Arg Lys Tyr Thr Met Arg
            675                 680                 685

Arg Leu Leu Gln Glu Thr Glu Leu Val Glu Pro Leu Thr Pro Ser Gly
        690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
            755                 760                 765

Asp Glu Ala Tyr Val Met Ala Gly Val Gly Ser Pro Tyr Val Ser Arg
770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
            930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
        995                 1000                1005

Leu Glu Asp Asp Asp Met Gly Asp Leu Val Asp Ala Glu Glu Tyr
    1010                1015                1020

Leu Val Pro Gln Gln Gly Phe Phe Cys Pro Asp Pro Ala Pro Gly
    1025                1030                1035

```
Ala Gly Gly Met Val His His Arg His Arg Ser Ser Ser Thr Arg
    1040                1045                1050

Ser Gly Gly Gly Asp Leu Thr Leu Gly Leu Glu Pro Ser Glu Glu
    1055                1060                1065

Glu Ala Pro Arg Ser Pro Leu Ala Pro Ser Glu Gly Ala Gly Ser
    1070                1075                1080

Asp Val Phe Asp Gly Asp Leu Gly Met Gly Ala Ala Lys Gly Leu
    1085                1090                1095

Gln Ser Leu Pro Thr His Asp Pro Ser Pro Leu Gln Arg Tyr Ser
    1100                1105                1110

Glu Asp Pro Thr Val Pro Leu Pro Ser Glu Thr Asp Gly Tyr Val
    1115                1120                1125

Ala Pro Leu Thr Cys Ser Pro Gln Pro Glu Tyr Val Asn Gln Pro
    1130                1135                1140

Asp Val Arg Pro Gln Pro Pro Ser Pro Arg Glu Gly Pro Leu Pro
    1145                1150                1155

Ala Ala Arg Pro Ala Gly Ala Thr Leu Glu Arg Pro Lys Thr Leu
    1160                1165                1170

Ser Pro Gly Lys Asn Gly Val Val Lys Asp Val Phe Ala Phe Gly
    1175                1180                1185

Gly Ala Val Glu Asn Pro Glu Tyr Leu Thr Pro Gln Gly Gly Ala
    1190                1195                1200

Ala Pro Gln Pro His Pro Pro Pro Ala Phe Ser Pro Ala Phe Asp
    1205                1210                1215

Asn Leu Tyr Tyr Trp Asp Gln Asp Pro Pro Glu Arg Gly Ala Pro
    1220                1225                1230

Pro Ser Thr Phe Lys Gly Thr Pro Thr Ala Glu Asn Pro Glu Tyr
    1235                1240                1245

Leu Gly Leu Asp Val Pro Val
    1250                1255

<210> SEQ ID NO 61
<211> LENGTH: 781
<212> TYPE: PRT
<213> ORGANISM: homo sapiens

<400> SEQUENCE: 61

Met Ala Thr Gln Ala Asp Leu Met Glu Leu Asp Met Ala Met Glu Pro
1               5                   10                  15

Asp Arg Lys Ala Ala Val Ser His Trp Gln Gln Gln Ser Tyr Leu Asp
                20                  25                  30

Ser Gly Ile His Ser Gly Ala Thr Thr Thr Ala Pro Ser Leu Ser Gly
            35                  40                  45

Lys Gly Asn Pro Glu Glu Glu Asp Val Asp Thr Ser Gln Val Leu Tyr
        50                  55                  60

Glu Trp Glu Gln Gly Phe Ser Gln Ser Phe Thr Gln Glu Gln Val Ala
65                  70                  75                  80

Asp Ile Asp Gly Gln Tyr Ala Met Thr Arg Ala Gln Arg Val Arg Ala
                85                  90                  95

Ala Met Phe Pro Glu Thr Leu Asp Glu Gly Met Gln Ile Pro Ser Thr
            100                 105                 110

Gln Phe Asp Ala Ala His Pro Thr Asn Val Gln Arg Leu Ala Glu Pro
        115                 120                 125

Ser Gln Met Leu Lys His Ala Val Val Asn Leu Ile Asn Tyr Gln Asp
    130                 135                 140
```

```
Asp Ala Glu Leu Ala Thr Arg Ala Ile Pro Glu Leu Thr Lys Leu Leu
145                 150                 155                 160

Asn Asp Glu Asp Gln Val Val Asn Lys Ala Ala Val Met Val His
            165                 170                 175

Gln Leu Ser Lys Lys Glu Ala Ser Arg His Ala Ile Met Arg Ser Pro
            180                 185                 190

Gln Met Val Ser Ala Ile Val Arg Thr Met Gln Asn Thr Asn Asp Val
            195                 200                 205

Glu Thr Ala Arg Cys Thr Ala Gly Thr Leu His Asn Leu Ser His His
        210                 215                 220

Arg Glu Gly Leu Leu Ala Ile Phe Lys Ser Gly Gly Ile Pro Ala Leu
225                 230                 235                 240

Val Lys Met Leu Gly Ser Pro Val Asp Ser Val Leu Phe Tyr Ala Ile
            245                 250                 255

Thr Thr Leu His Asn Leu Leu Leu His Gln Glu Gly Ala Lys Met Ala
        260                 265                 270

Val Arg Leu Ala Gly Gly Leu Gln Lys Met Val Ala Leu Leu Asn Lys
    275                 280                 285

Thr Asn Val Lys Phe Leu Ala Ile Thr Thr Asp Cys Leu Gln Ile Leu
290                 295                 300

Ala Tyr Gly Asn Gln Glu Ser Lys Leu Ile Ile Leu Ala Ser Gly Gly
305                 310                 315                 320

Pro Gln Ala Leu Val Asn Ile Met Arg Thr Tyr Thr Tyr Glu Lys Leu
            325                 330                 335

Leu Trp Thr Thr Ser Arg Val Leu Lys Val Leu Ser Val Cys Ser Ser
            340                 345                 350

Asn Lys Pro Ala Ile Val Glu Ala Gly Gly Met Gln Ala Leu Gly Leu
        355                 360                 365

His Leu Thr Asp Pro Ser Gln Arg Leu Val Gln Asn Cys Leu Trp Thr
    370                 375                 380

Leu Arg Asn Leu Ser Asp Ala Ala Thr Lys Gln Glu Gly Met Glu Gly
385                 390                 395                 400

Leu Leu Gly Thr Leu Val Gln Leu Leu Gly Ser Asp Asp Ile Asn Val
            405                 410                 415

Val Thr Cys Ala Ala Gly Ile Leu Ser Asn Leu Thr Cys Asn Asn Tyr
            420                 425                 430

Lys Asn Lys Met Met Val Cys Gln Val Gly Gly Ile Glu Ala Leu Val
        435                 440                 445

Arg Thr Val Leu Arg Ala Gly Asp Arg Glu Asp Ile Thr Glu Pro Ala
    450                 455                 460

Ile Cys Ala Leu Arg His Leu Thr Ser Arg His Gln Glu Ala Glu Met
465                 470                 475                 480

Ala Gln Asn Ala Val Arg Leu His Tyr Gly Leu Pro Val Val Val Lys
            485                 490                 495

Leu Leu His Pro Pro Ser His Trp Pro Leu Ile Lys Ala Thr Val Gly
        500                 505                 510

Leu Ile Arg Asn Leu Ala Leu Cys Pro Ala Asn His Ala Pro Leu Arg
    515                 520                 525

Glu Gln Gly Ala Ile Pro Arg Leu Val Gln Leu Leu Val Arg Ala His
    530                 535                 540

Gln Asp Thr Gln Arg Arg Thr Ser Met Gly Gly Thr Gln Gln Gln Phe
545                 550                 555                 560
```

Val Glu Gly Val Arg Met Glu Glu Ile Val Glu Gly Cys Thr Gly Ala
                565                 570                 575

Leu His Ile Leu Ala Arg Asp Val His Asn Arg Ile Val Ile Arg Gly
            580                 585                 590

Leu Asn Thr Ile Pro Leu Phe Val Gln Leu Leu Tyr Ser Pro Ile Glu
        595                 600                 605

Asn Ile Gln Arg Val Ala Ala Gly Val Leu Cys Glu Leu Ala Gln Asp
    610                 615                 620

Lys Glu Ala Ala Glu Ala Ile Glu Ala Glu Gly Ala Thr Ala Pro Leu
625                 630                 635                 640

Thr Glu Leu Leu His Ser Arg Asn Glu Gly Val Ala Thr Tyr Ala Ala
                645                 650                 655

Ala Val Leu Phe Arg Met Ser Glu Asp Lys Pro Gln Asp Tyr Lys Lys
            660                 665                 670

Arg Leu Ser Val Glu Leu Thr Ser Ser Leu Phe Arg Thr Glu Pro Met
        675                 680                 685

Ala Trp Asn Glu Thr Ala Asp Leu Gly Leu Asp Ile Gly Ala Gln Gly
    690                 695                 700

Glu Pro Leu Gly Tyr Arg Gln Asp Asp Pro Ser Tyr Arg Ser Phe His
705                 710                 715                 720

Ser Gly Gly Tyr Gly Gln Asp Ala Leu Gly Met Asp Pro Met Met Glu
                725                 730                 735

His Glu Met Gly Gly His His Pro Gly Ala Asp Tyr Pro Val Asp Gly
            740                 745                 750

Leu Pro Asp Leu Gly His Ala Gln Asp Leu Met Asp Gly Leu Pro Pro
        755                 760                 765

Gly Asp Ser Asn Gln Leu Ala Trp Phe Asp Thr Asp Leu
    770                 775                 780

<210> SEQ ID NO 62
<211> LENGTH: 781
<212> TYPE: PRT
<213> ORGANISM: homo sapiens

<400> SEQUENCE: 62

Met Ala Thr Gln Ala Asp Leu Met Glu Leu Asp Met Ala Met Glu Pro
1               5                   10                  15

Asp Arg Lys Ala Ala Val Ser His Trp Gln Gln Gln Ser Tyr Leu Asp
            20                  25                  30

Ser Gly Ile His Ser Gly Ala Thr Thr Thr Ala Pro Ser Leu Ser Gly
        35                  40                  45

Lys Gly Asn Pro Glu Glu Glu Asp Val Asp Thr Ser Gln Val Leu Tyr
    50                  55                  60

Glu Trp Glu Gln Gly Phe Ser Gln Ser Phe Thr Gln Glu Gln Val Ala
65                  70                  75                  80

Asp Ile Asp Gly Gln Tyr Ala Met Thr Arg Ala Gln Arg Val Arg Ala
                85                  90                  95

Ala Met Phe Pro Glu Thr Leu Asp Glu Gly Met Gln Ile Pro Ser Thr
            100                 105                 110

Gln Phe Asp Ala Ala His Pro Thr Asn Val Gln Arg Leu Ala Glu Pro
        115                 120                 125

Ser Gln Met Leu Lys His Ala Val Val Asn Leu Ile Asn Tyr Gln Asp
    130                 135                 140

Asp Ala Glu Leu Ala Thr Arg Ala Ile Pro Glu Leu Thr Lys Leu Leu
145                 150                 155                 160

-continued

Asn Asp Glu Asp Gln Val Val Asn Lys Ala Ala Val Met Val His
                165                 170                 175

Gln Leu Ser Lys Lys Glu Ala Ser Arg His Ala Ile Met Arg Ser Pro
            180                 185                 190

Gln Met Val Ser Ala Ile Val Arg Thr Met Gln Asn Thr Asn Asp Val
        195                 200                 205

Glu Thr Ala Arg Cys Thr Ala Gly Thr Leu His Asn Leu Ser His His
    210                 215                 220

Arg Glu Gly Leu Leu Ala Ile Phe Lys Ser Gly Ile Pro Ala Leu
225                 230                 235                 240

Val Lys Met Leu Gly Ser Pro Val Asp Ser Val Leu Phe Tyr Ala Ile
                245                 250                 255

Thr Thr Leu His Asn Leu Leu Leu His Gln Glu Gly Ala Lys Met Ala
            260                 265                 270

Val Arg Leu Ala Gly Gly Leu Gln Lys Met Val Ala Leu Leu Asn Lys
        275                 280                 285

Thr Asn Val Lys Phe Leu Ala Ile Thr Thr Asp Cys Leu Gln Ile Leu
    290                 295                 300

Ala Tyr Gly Asn Gln Glu Ser Lys Leu Ile Ile Leu Ala Ser Gly Gly
305                 310                 315                 320

Pro Gln Ala Leu Val Asn Ile Met Arg Thr Tyr Thr Tyr Glu Lys Leu
                325                 330                 335

Leu Trp Thr Thr Ser Arg Val Leu Lys Val Leu Ser Val Cys Ser Ser
            340                 345                 350

Asn Lys Pro Ala Ile Val Glu Ala Gly Gly Met Gln Ala Leu Gly Leu
        355                 360                 365

His Leu Thr Asp Pro Ser Gln Arg Leu Val Gln Asn Cys Leu Trp Thr
    370                 375                 380

Leu Arg Asn Leu Ser Asp Ala Ala Thr Lys Gln Glu Gly Met Glu Gly
385                 390                 395                 400

Leu Leu Gly Thr Leu Val Gln Leu Leu Gly Ser Asp Asp Ile Asn Val
                405                 410                 415

Val Thr Cys Ala Ala Gly Ile Leu Ser Asn Leu Thr Cys Asn Asn Tyr
            420                 425                 430

Lys Asn Lys Met Met Val Cys Gln Val Gly Gly Ile Glu Ala Leu Val
        435                 440                 445

Arg Thr Val Leu Arg Ala Gly Asp Arg Glu Asp Ile Thr Glu Pro Ala
    450                 455                 460

Ile Cys Ala Leu Arg His Leu Thr Ser Arg His Gln Glu Ala Glu Met
465                 470                 475                 480

Ala Gln Asn Ala Val Arg Leu His Tyr Gly Leu Pro Val Val Val Lys
                485                 490                 495

Leu Leu His Pro Pro Ser His Trp Pro Leu Ile Lys Ala Thr Val Gly
            500                 505                 510

Leu Ile Arg Asn Leu Ala Leu Cys Pro Ala Asn His Ala Pro Leu Arg
        515                 520                 525

Glu Gln Gly Ala Ile Pro Arg Leu Val Gln Leu Leu Val Arg Ala His
    530                 535                 540

Gln Asp Thr Gln Arg Arg Thr Ser Met Gly Gly Thr Gln Gln Gln Phe
545                 550                 555                 560

Val Glu Gly Val Arg Met Glu Glu Ile Val Glu Gly Cys Thr Gly Ala
                565                 570                 575

```
Leu His Ile Leu Ala Arg Asp Val His Asn Arg Ile Val Arg Gly
            580                 585                 590

Leu Asn Thr Ile Pro Leu Phe Val Gln Leu Leu Tyr Ser Pro Ile Glu
            595                 600                 605

Asn Ile Gln Arg Val Ala Ala Gly Val Leu Cys Glu Leu Ala Gln Asp
            610                 615                 620

Lys Glu Ala Ala Glu Ala Ile Glu Ala Glu Gly Ala Thr Ala Pro Leu
625                 630                 635                 640

Thr Glu Leu Leu His Ser Arg Asn Glu Gly Val Ala Thr Tyr Ala Ala
                    645                 650                 655

Ala Val Leu Phe Arg Met Ser Glu Asp Lys Pro Gln Asp Tyr Lys Lys
                660                 665                 670

Arg Leu Ser Val Glu Leu Thr Ser Ser Leu Phe Arg Thr Glu Pro Met
            675                 680                 685

Ala Trp Asn Glu Thr Ala Asp Leu Gly Leu Asp Ile Gly Ala Gln Gly
            690                 695                 700

Glu Pro Leu Gly Tyr Arg Gln Asp Asp Pro Ser Tyr Arg Ser Phe His
705                 710                 715                 720

Ser Gly Gly Tyr Gly Gln Asp Ala Leu Gly Met Asp Pro Met Met Glu
                    725                 730                 735

His Glu Met Gly Gly His His Pro Gly Ala Asp Tyr Pro Val Asp Gly
                740                 745                 750

Leu Pro Asp Leu Gly His Ala Gln Asp Leu Met Asp Gly Leu Pro Pro
            755                 760                 765

Gly Asp Ser Asn Gln Leu Ala Trp Phe Asp Thr Asp Leu
770                 775                 780

<210> SEQ ID NO 63
<211> LENGTH: 781
<212> TYPE: PRT
<213> ORGANISM: homo sapiens

<400> SEQUENCE: 63

Met Ala Thr Gln Ala Asp Leu Met Glu Leu Asp Met Ala Met Glu Pro
1               5                   10                  15

Asp Arg Lys Ala Ala Val Ser His Trp Gln Gln Gln Ser Tyr Leu Asp
            20                  25                  30

Ser Gly Ile His Ser Gly Ala Thr Thr Thr Ala Pro Ser Leu Ser Gly
            35                  40                  45

Lys Gly Asn Pro Glu Glu Glu Asp Val Asp Thr Ser Gln Val Leu Tyr
50                  55                  60

Glu Trp Glu Gln Gly Phe Ser Gln Ser Phe Thr Gln Glu Gln Val Ala
65                  70                  75                  80

Asp Ile Asp Gly Gln Tyr Ala Met Thr Arg Ala Gln Arg Val Arg Ala
                85                  90                  95

Ala Met Phe Pro Glu Thr Leu Asp Glu Gly Met Gln Ile Pro Ser Thr
            100                 105                 110

Gln Phe Asp Ala Ala His Pro Thr Asn Val Gln Arg Leu Ala Glu Pro
        115                 120                 125

Ser Gln Met Leu Lys His Ala Val Val Asn Leu Ile Asn Tyr Gln Asp
    130                 135                 140

Asp Ala Glu Leu Ala Thr Arg Ala Ile Pro Glu Leu Thr Lys Leu Leu
145                 150                 155                 160

Asn Asp Glu Asp Gln Val Val Val Asn Lys Ala Ala Val Met Val His
                165                 170                 175
```

```
Gln Leu Ser Lys Lys Glu Ala Ser Arg His Ala Ile Met Arg Ser Pro
            180                 185                 190

Gln Met Val Ser Ala Ile Val Arg Thr Met Gln Asn Thr Asn Asp Val
            195                 200                 205

Glu Thr Ala Arg Cys Thr Ala Gly Thr Leu His Asn Leu Ser His His
210                 215                 220

Arg Glu Gly Leu Leu Ala Ile Phe Lys Ser Gly Ile Pro Ala Leu
225                 230                 235                 240

Val Lys Met Leu Gly Ser Pro Val Asp Ser Val Leu Phe Tyr Ala Ile
                245                 250                 255

Thr Thr Leu His Asn Leu Leu His Gln Glu Gly Ala Lys Met Ala
            260                 265                 270

Val Arg Leu Ala Gly Gly Leu Gln Lys Met Val Ala Leu Leu Asn Lys
            275                 280                 285

Thr Asn Val Lys Phe Leu Ala Ile Thr Thr Asp Cys Leu Gln Ile Leu
            290                 295                 300

Ala Tyr Gly Asn Gln Glu Ser Lys Leu Ile Ile Leu Ala Ser Gly Gly
305                 310                 315                 320

Pro Gln Ala Leu Val Asn Ile Met Arg Thr Tyr Thr Tyr Glu Lys Leu
                325                 330                 335

Leu Trp Thr Thr Ser Arg Val Leu Lys Val Leu Ser Val Cys Ser Ser
            340                 345                 350

Asn Lys Pro Ala Ile Val Glu Ala Gly Gly Met Gln Ala Leu Gly Leu
            355                 360                 365

His Leu Thr Asp Pro Ser Gln Arg Leu Val Gln Asn Cys Leu Trp Thr
            370                 375                 380

Leu Arg Asn Leu Ser Asp Ala Ala Thr Lys Gln Glu Gly Met Glu Gly
385                 390                 395                 400

Leu Leu Gly Thr Leu Val Gln Leu Leu Gly Ser Asp Asp Ile Asn Val
                405                 410                 415

Val Thr Cys Ala Ala Gly Ile Leu Ser Asn Leu Thr Cys Asn Asn Tyr
            420                 425                 430

Lys Asn Lys Met Met Val Cys Gln Val Gly Gly Ile Glu Ala Leu Val
            435                 440                 445

Arg Thr Val Leu Arg Ala Gly Asp Arg Glu Asp Ile Thr Glu Pro Ala
            450                 455                 460

Ile Cys Ala Leu Arg His Leu Thr Ser Arg His Gln Glu Ala Glu Met
465                 470                 475                 480

Ala Gln Asn Ala Val Arg Leu His Tyr Gly Leu Pro Val Val Val Lys
                485                 490                 495

Leu Leu His Pro Pro Ser His Trp Pro Leu Ile Lys Ala Thr Val Gly
            500                 505                 510

Leu Ile Arg Asn Leu Ala Leu Cys Pro Ala Asn His Ala Pro Leu Arg
            515                 520                 525

Glu Gln Gly Ala Ile Pro Arg Leu Val Gln Leu Leu Val Arg Ala His
            530                 535                 540

Gln Asp Thr Gln Arg Arg Thr Ser Met Gly Gly Thr Gln Gln Gln Phe
545                 550                 555                 560

Val Glu Gly Val Arg Met Glu Glu Ile Val Glu Gly Cys Thr Gly Ala
                565                 570                 575

Leu His Ile Leu Ala Arg Asp Val His Asn Arg Ile Val Ile Arg Gly
            580                 585                 590
```

```
Leu Asn Thr Ile Pro Leu Phe Val Gln Leu Leu Tyr Ser Pro Ile Glu
            595                 600                 605

Asn Ile Gln Arg Val Ala Ala Gly Val Leu Cys Glu Leu Ala Gln Asp
        610                 615                 620

Lys Glu Ala Ala Glu Ala Ile Glu Ala Glu Gly Ala Thr Ala Pro Leu
625                 630                 635                 640

Thr Glu Leu Leu His Ser Arg Asn Glu Gly Val Ala Thr Tyr Ala Ala
                645                 650                 655

Ala Val Leu Phe Arg Met Ser Glu Asp Lys Pro Gln Asp Tyr Lys Lys
            660                 665                 670

Arg Leu Ser Val Glu Leu Thr Ser Ser Leu Phe Arg Thr Glu Pro Met
        675                 680                 685

Ala Trp Asn Glu Thr Ala Asp Leu Gly Leu Asp Ile Gly Ala Gln Gly
690                 695                 700

Glu Pro Leu Gly Tyr Arg Gln Asp Asp Pro Ser Tyr Arg Ser Phe His
705                 710                 715                 720

Ser Gly Gly Tyr Gly Gln Asp Ala Leu Gly Met Asp Pro Met Met Glu
                725                 730                 735

His Glu Met Gly Gly His His Pro Gly Ala Asp Tyr Pro Val Asp Gly
            740                 745                 750

Leu Pro Asp Leu Gly His Ala Gln Asp Leu Met Asp Gly Leu Pro Pro
        755                 760                 765

Gly Asp Ser Asn Gln Leu Ala Trp Phe Asp Thr Asp Leu
770                 775                 780

<210> SEQ ID NO 64
<211> LENGTH: 529
<212> TYPE: PRT
<213> ORGANISM: homo sapiens

<400> SEQUENCE: 64

Met Leu Leu Ala Val Leu Tyr Cys Leu Leu Trp Ser Phe Gln Thr Ser
1               5                   10                  15

Ala Gly His Phe Pro Arg Ala Cys Val Ser Ser Lys Asn Leu Met Glu
            20                  25                  30

Lys Glu Cys Cys Pro Pro Trp Ser Gly Asp Arg Ser Pro Cys Gly Gln
        35                  40                  45

Leu Ser Gly Arg Gly Ser Cys Gln Asn Ile Leu Leu Ser Asn Ala Pro
    50                  55                  60

Leu Gly Pro Gln Phe Pro Phe Thr Gly Val Asp Asp Arg Glu Ser Trp
65                  70                  75                  80

Pro Ser Val Phe Tyr Asn Arg Thr Cys Gln Cys Ser Gly Asn Phe Met
                85                  90                  95

Gly Phe Asn Cys Gly Asn Cys Lys Phe Gly Phe Trp Gly Pro Asn Cys
            100                 105                 110

Thr Glu Arg Arg Leu Leu Val Arg Arg Asn Ile Phe Asp Leu Ser Ala
        115                 120                 125

Pro Glu Lys Asp Lys Phe Phe Ala Tyr Leu Thr Leu Ala Lys His Thr
    130                 135                 140

Ile Ser Ser Asp Tyr Val Ile Pro Ile Gly Thr Tyr Gly Gln Met Lys
145                 150                 155                 160

Asn Gly Ser Thr Pro Met Phe Asn Asp Ile Asn Ile Tyr Asp Leu Phe
                165                 170                 175

Val Trp Met His Tyr Tyr Val Ser Met Asp Ala Leu Leu Gly Gly Ser
            180                 185                 190
```

```
Glu Ile Trp Arg Asp Ile Asp Phe Ala His Glu Ala Pro Ala Phe Leu
            195                 200                 205

Pro Trp His Arg Leu Phe Leu Leu Arg Trp Glu Gln Glu Ile Gln Lys
        210                 215                 220

Leu Thr Gly Asp Glu Asn Phe Thr Ile Pro Tyr Trp Asp Trp Arg Asp
225                 230                 235                 240

Ala Glu Lys Cys Asp Ile Cys Thr Asp Glu Tyr Met Gly Gly Gln His
                245                 250                 255

Pro Thr Asn Pro Asn Leu Leu Ser Pro Ala Ser Phe Phe Ser Ser Trp
            260                 265                 270

Gln Ile Val Cys Ser Arg Leu Glu Glu Tyr Asn Ser His Gln Ser Leu
        275                 280                 285

Cys Asn Gly Thr Pro Glu Gly Pro Leu Arg Arg Asn Pro Gly Asn His
290                 295                 300

Asp Lys Ser Arg Thr Pro Arg Leu Pro Ser Ser Ala Asp Val Glu Phe
305                 310                 315                 320

Cys Leu Ser Leu Thr Gln Tyr Glu Ser Gly Ser Met Asp Lys Ala Ala
                325                 330                 335

Asn Phe Ser Phe Arg Asn Thr Leu Glu Gly Phe Ala Ser Pro Leu Thr
            340                 345                 350

Gly Ile Ala Asp Ala Ser Gln Ser Ser Met His Asn Ala Leu His Ile
        355                 360                 365

Tyr Met Asn Gly Thr Met Ser Gln Val Gln Gly Ser Ala Asn Asp Pro
    370                 375                 380

Ile Phe Leu Leu His His Ala Phe Val Asp Ser Ile Phe Glu Gln Trp
385                 390                 395                 400

Leu Arg Arg His Arg Pro Leu Gln Glu Val Tyr Pro Glu Ala Asn Ala
                405                 410                 415

Pro Ile Gly His Asn Arg Glu Ser Tyr Met Val Pro Phe Ile Pro Leu
            420                 425                 430

Tyr Arg Asn Gly Asp Phe Phe Ile Ser Ser Lys Asp Leu Gly Tyr Asp
        435                 440                 445

Tyr Ser Tyr Leu Gln Asp Ser Asp Pro Asp Ser Phe Gln Asp Tyr Ile
    450                 455                 460

Lys Ser Tyr Leu Glu Gln Ala Ser Arg Ile Trp Ser Trp Leu Leu Gly
465                 470                 475                 480

Ala Ala Met Val Gly Ala Val Leu Thr Ala Leu Leu Ala Gly Leu Val
                485                 490                 495

Ser Leu Leu Cys Arg His Lys Arg Lys Gln Leu Pro Glu Glu Lys Gln
            500                 505                 510

Pro Leu Leu Met Glu Lys Glu Asp Tyr His Ser Leu Tyr Gln Ser His
        515                 520                 525

Leu

<210> SEQ ID NO 65
<211> LENGTH: 693
<212> TYPE: PRT
<213> ORGANISM: homo sapiens

<400> SEQUENCE: 65

Met Val Asp Pro Val Gly Phe Ala Glu Ala Trp Lys Ala Gln Phe Pro
1               5                   10                  15

Asp Ser Glu Pro Pro Arg Met Glu Leu Arg Ser Val Gly Asp Ile Glu
            20                  25                  30
```

```
Gln Glu Leu Glu Arg Cys Lys Ala Ser Ile Arg Arg Leu Glu Gln Glu
            35                  40                  45
Val Asn Gln Glu Arg Phe Arg Met Ile Tyr Leu Gln Thr Leu Leu Ala
 50                  55                  60
Lys Glu Lys Lys Ser Tyr Asp Arg Gln Arg Trp Gly Phe Arg Arg Ala
 65                  70                  75                  80
Ala Gln Ala Pro Asp Gly Ala Ser Glu Pro Arg Ala Ser Ala Ser Arg
                 85                  90                  95
Pro Gln Pro Ala Pro Ala Asp Gly Ala Asp Pro Pro Ala Glu Glu
            100                 105                 110
Pro Glu Ala Arg Pro Asp Gly Gly Ser Pro Gly Lys Ala Arg Pro
            115                 120                 125
Gly Thr Ala Arg Arg Pro Gly Ala Ala Ala Ser Gly Glu Arg Asp Asp
            130                 135                 140
Arg Gly Pro Pro Ala Ser Val Ala Ala Leu Arg Ser Asn Phe Glu Arg
145                 150                 155                 160
Ile Arg Lys Gly His Gly Gln Pro Gly Ala Asp Ala Glu Lys Pro Phe
                165                 170                 175
Tyr Val Asn Val Glu Phe His His Glu Arg Gly Leu Val Lys Val Asn
            180                 185                 190
Asp Lys Glu Val Ser Asp Arg Ile Ser Ser Leu Gly Ser Gln Ala Met
            195                 200                 205
Gln Met Glu Arg Lys Lys Ser Gln His Gly Ala Gly Ser Ser Val Gly
            210                 215                 220
Asp Ala Ser Arg Pro Pro Tyr Arg Gly Arg Ser Ser Glu Ser Ser Cys
225                 230                 235                 240
Gly Val Asp Gly Asp Tyr Glu Asp Ala Glu Leu Asn Pro Arg Phe Leu
                245                 250                 255
Lys Asp Asn Leu Ile Asp Ala Asn Gly Gly Ser Arg Pro Pro Trp Pro
            260                 265                 270
Pro Leu Glu Tyr Gln Pro Tyr Gln Ser Ile Tyr Val Gly Gly Met Met
            275                 280                 285
Glu Gly Glu Gly Lys Gly Pro Leu Leu Arg Ser Gln Ser Thr Ser Glu
            290                 295                 300
Gln Glu Lys Arg Leu Thr Trp Pro Arg Arg Ser Tyr Ser Pro Arg Ser
305                 310                 315                 320
Phe Glu Asp Cys Gly Gly Gly Tyr Thr Pro Asp Cys Ser Ser Asn Glu
                325                 330                 335
Asn Leu Thr Ser Ser Glu Glu Asp Phe Ser Ser Gly Gln Ser Ser Arg
            340                 345                 350
Val Ser Pro Ser Pro Thr Thr Tyr Arg Met Phe Arg Asp Lys Ser Arg
            355                 360                 365
Ser Pro Ser Gln Asn Ser Gln Gln Ser Phe Asp Ser Ser Ser Pro Pro
            370                 375                 380
Thr Pro Gln Cys His Lys Arg His Arg His Cys Pro Val Val Val Ser
385                 390                 395                 400
Glu Ala Thr Ile Val Gly Val Arg Lys Thr Gly Gln Ile Trp Pro Asn
                405                 410                 415
Asp Gly Glu Gly Ala Phe His Gly Asp Ala Asp Gly Ser Phe Gly Thr
            420                 425                 430
Pro Pro Gly Tyr Gly Cys Ala Ala Asp Arg Ala Glu Glu Gln Arg Arg
            435                 440                 445
```

-continued

```
His Gln Asp Gly Leu Pro Tyr Ile Asp Asp Ser Pro Ser Ser Ser Pro
    450                 455                 460
His Leu Ser Ser Lys Gly Arg Gly Ser Arg Asp Ala Leu Val Ser Gly
465                 470                 475                 480
Ala Leu Glu Ser Thr Lys Ala Ser Glu Leu Asp Leu Glu Lys Gly Leu
                485                 490                 495
Glu Met Arg Lys Trp Val Leu Ser Gly Ile Leu Ala Ser Glu Glu Thr
            500                 505                 510
Tyr Leu Ser His Leu Glu Ala Leu Leu Pro Met Lys Pro Leu Lys
            515                 520                 525
Ala Ala Ala Thr Thr Ser Gln Pro Val Leu Thr Ser Gln Gln Ile Glu
    530                 535                 540
Thr Ile Phe Phe Lys Val Pro Glu Leu Tyr Glu Ile His Lys Glu Phe
545                 550                 555                 560
Tyr Asp Gly Leu Phe Pro Arg Val Gln Gln Trp Ser His Gln Gln Arg
                565                 570                 575
Val Gly Asp Leu Phe Gln Lys Leu Ala Ser Gln Leu Gly Val Tyr Arg
            580                 585                 590
Ala Phe Val Asp Asn Tyr Gly Val Ala Met Glu Met Ala Glu Lys Cys
            595                 600                 605
Cys Gln Ala Asn Ala Gln Phe Ala Glu Ile Ser Glu Asn Leu Arg Ala
    610                 615                 620
Arg Ser Asn Lys Asp Ala Lys Asp Pro Thr Thr Lys Asn Ser Leu Glu
625                 630                 635                 640
Thr Leu Leu Tyr Lys Pro Val Asp Arg Val Thr Arg Ser Thr Leu Val
                645                 650                 655
Leu His Asp Leu Leu Lys His Thr Pro Ala Ser His Pro Asp His Pro
            660                 665                 670
Leu Leu Gln Asp Ala Leu Arg Ile Ser Gln Asn Phe Leu Ser Ser Ile
        675                 680                 685
Asn Glu Glu Ile Thr
        690

<210> SEQ ID NO 66
<211> LENGTH: 464
<212> TYPE: PRT
<213> ORGANISM: homo sapiens

<400> SEQUENCE: 66

Met Asp Phe Ser Arg Asn Leu Tyr Asp Ile Gly Glu Gln Leu Asp Ser
1               5                   10                  15
Glu Asp Leu Ala Ser Leu Lys Phe Leu Ser Leu Asp Tyr Ile Pro Gln
            20                  25                  30
Arg Lys Gln Glu Pro Ile Lys Asp Ala Leu Met Leu Phe Gln Arg Leu
        35                  40                  45
Gln Glu Lys Arg Met Leu Glu Glu Ser Asn Leu Ser Phe Leu Lys Glu
    50                  55                  60
Leu Leu Phe Arg Ile Asn Arg Leu Asp Leu Leu Ile Thr Tyr Leu Asn
65                  70                  75                  80
Thr Arg Lys Glu Glu Met Glu Arg Glu Leu Gln Thr Pro Gly Arg Ala
                85                  90                  95
Gln Ile Ser Ala Tyr Arg Val Met Leu Tyr Gln Ile Ser Glu Glu Val
            100                 105                 110
Ser Arg Ser Glu Leu Arg Ser Phe Lys Phe Leu Leu Gln Glu Glu Ile
        115                 120                 125
```

Ser Lys Cys Lys Leu Asp Asp Asp Met Asn Leu Leu Asp Ile Phe Ile
            130                 135                 140

Glu Met Glu Lys Arg Val Ile Leu Gly Glu Gly Lys Leu Asp Ile Leu
145                 150                 155                 160

Lys Arg Val Cys Ala Gln Ile Asn Lys Ser Leu Leu Lys Ile Ile Asn
                165                 170                 175

Asp Tyr Glu Glu Phe Ser Lys Gly Glu Glu Leu Cys Gly Val Met Thr
            180                 185                 190

Ile Ser Asp Ser Pro Arg Glu Gln Asp Ser Glu Ser Gln Thr Leu Asp
        195                 200                 205

Lys Val Tyr Gln Met Lys Ser Lys Pro Arg Gly Tyr Cys Leu Ile Ile
210                 215                 220

Asn Asn His Asn Phe Ala Lys Ala Arg Glu Lys Val Pro Lys Leu His
225                 230                 235                 240

Ser Ile Arg Asp Arg Asn Gly Thr His Leu Asp Ala Gly Ala Leu Thr
                245                 250                 255

Thr Thr Phe Glu Glu Leu His Phe Glu Ile Lys Pro His Asp Asp Cys
            260                 265                 270

Thr Val Glu Gln Ile Tyr Glu Ile Leu Lys Ile Tyr Gln Leu Met Asp
        275                 280                 285

His Ser Asn Met Asp Cys Phe Ile Cys Cys Ile Leu Ser His Gly Asp
290                 295                 300

Lys Gly Ile Ile Tyr Gly Thr Asp Gly Gln Glu Ala Pro Ile Tyr Glu
305                 310                 315                 320

Leu Thr Ser Gln Phe Thr Gly Leu Lys Cys Pro Ser Leu Ala Gly Lys
                325                 330                 335

Pro Lys Val Phe Phe Ile Gln Ala Cys Gln Gly Asp Asn Tyr Gln Lys
            340                 345                 350

Gly Ile Pro Val Glu Thr Asp Ser Glu Glu Gln Pro Tyr Leu Glu Met
        355                 360                 365

Asp Leu Ser Ser Pro Gln Thr Arg Tyr Ile Pro Asp Glu Ala Asp Phe
370                 375                 380

Leu Leu Gly Met Ala Thr Val Asn Asn Cys Val Ser Tyr Arg Asn Pro
385                 390                 395                 400

Ala Glu Gly Thr Trp Tyr Ile Gln Ser Leu Cys Gln Ser Leu Arg Glu
                405                 410                 415

Arg Cys Pro Arg Gly Asp Asp Ile Leu Thr Ile Leu Thr Glu Val Asn
            420                 425                 430

Tyr Glu Val Ser Asn Lys Asp Asp Lys Lys Asn Met Gly Lys Gln Met
        435                 440                 445

Pro Gln Pro Thr Phe Thr Leu Arg Lys Lys Leu Val Phe Pro Ser Asp
450                 455                 460

<210> SEQ ID NO 67
<211> LENGTH: 538
<212> TYPE: PRT
<213> ORGANISM: homo sapiens

<400> SEQUENCE: 67

Met Glu Gly Gly Arg Arg Ala Arg Val Val Ile Glu Ser Lys Arg Asn
1               5                   10                  15

Phe Phe Leu Gly Ala Phe Pro Thr Pro Phe Pro Ala Glu His Val Glu
            20                  25                  30

Leu Gly Arg Leu Gly Asp Ser Glu Thr Ala Met Val Pro Gly Lys Gly

```
                35                  40                  45
Gly Ala Asp Tyr Ile Leu Leu Pro Phe Lys Lys Met Asp Phe Ser Arg
 50                  55                  60
Asn Leu Tyr Asp Ile Gly Glu Gln Leu Asp Ser Glu Asp Leu Ala Ser
 65                  70                  75                  80
Leu Lys Phe Leu Ser Leu Asp Tyr Ile Pro Gln Arg Lys Gln Glu Pro
                 85                  90                  95
Ile Lys Asp Ala Leu Met Leu Phe Gln Arg Leu Gln Glu Lys Arg Met
                100                 105                 110
Leu Glu Glu Ser Asn Leu Ser Phe Leu Lys Glu Leu Leu Phe Arg Ile
                115                 120                 125
Asn Arg Leu Asp Leu Leu Ile Thr Tyr Leu Asn Thr Arg Lys Glu Glu
                130                 135                 140
Met Glu Arg Glu Leu Gln Thr Pro Gly Arg Ala Gln Ile Ser Ala Tyr
145                 150                 155                 160
Arg Val Met Leu Tyr Gln Ile Ser Glu Glu Val Ser Arg Ser Glu Leu
                165                 170                 175
Arg Ser Phe Lys Phe Leu Leu Gln Glu Glu Ile Ser Lys Cys Lys Leu
                180                 185                 190
Asp Asp Asp Met Asn Leu Leu Asp Ile Phe Ile Glu Met Glu Lys Arg
                195                 200                 205
Val Ile Leu Gly Glu Gly Lys Leu Asp Ile Leu Lys Arg Val Cys Ala
                210                 215                 220
Gln Ile Asn Lys Ser Leu Leu Lys Ile Ile Asn Asp Tyr Glu Glu Phe
225                 230                 235                 240
Ser Lys Glu Arg Ser Ser Leu Glu Gly Ser Pro Asp Glu Phe Ser
                245                 250                 255
Asn Gly Glu Glu Leu Cys Gly Val Met Thr Ile Ser Asp Ser Pro Arg
                260                 265                 270
Glu Gln Asp Ser Glu Ser Gln Thr Leu Asp Lys Val Tyr Gln Met Lys
                275                 280                 285
Ser Lys Pro Arg Gly Tyr Cys Leu Ile Ile Asn Asn His Asn Phe Ala
                290                 295                 300
Lys Ala Arg Glu Lys Val Pro Lys Leu His Ser Ile Arg Asp Arg Asn
305                 310                 315                 320
Gly Thr His Leu Asp Ala Gly Ala Leu Thr Thr Thr Phe Glu Glu Leu
                325                 330                 335
His Phe Glu Ile Lys Pro His Asp Asp Cys Thr Val Glu Gln Ile Tyr
                340                 345                 350
Glu Ile Leu Lys Ile Tyr Gln Leu Met Asp His Ser Asn Met Asp Cys
                355                 360                 365
Phe Ile Cys Cys Ile Leu Ser His Gly Asp Lys Gly Ile Ile Tyr Gly
                370                 375                 380
Thr Asp Gly Gln Glu Ala Pro Ile Tyr Glu Leu Thr Ser Gln Phe Thr
385                 390                 395                 400
Gly Leu Lys Cys Pro Ser Leu Ala Gly Lys Pro Lys Val Phe Phe Ile
                405                 410                 415
Gln Ala Cys Gln Gly Asp Asn Tyr Gln Lys Gly Ile Pro Val Glu Thr
                420                 425                 430
Asp Ser Glu Glu Gln Pro Tyr Leu Glu Met Asp Leu Ser Ser Pro Gln
                435                 440                 445
Thr Arg Tyr Ile Pro Asp Glu Ala Asp Phe Leu Leu Gly Met Ala Thr
                450                 455                 460
```

```
Val Asn Asn Cys Val Ser Tyr Arg Asn Pro Ala Glu Gly Thr Trp Tyr
465                 470                 475                 480

Ile Gln Ser Leu Cys Gln Ser Leu Arg Glu Arg Cys Pro Arg Gly Asp
                485                 490                 495

Asp Ile Leu Thr Ile Leu Thr Glu Val Asn Tyr Glu Val Ser Asn Lys
                500                 505                 510

Asp Asp Lys Lys Asn Met Gly Lys Gln Met Pro Gln Pro Thr Phe Thr
                515                 520                 525

Leu Arg Lys Lys Leu Val Phe Pro Ser Asp
                530                 535

<210> SEQ ID NO 68
<211> LENGTH: 496
<212> TYPE: PRT
<213> ORGANISM: homo sapiens

<400> SEQUENCE: 68

Met Asp Phe Ser Arg Asn Leu Tyr Asp Ile Gly Glu Gln Leu Asp Ser
1               5                   10                  15

Glu Asp Leu Ala Ser Leu Lys Phe Leu Ser Leu Asp Tyr Ile Pro Gln
                20                  25                  30

Arg Lys Gln Glu Pro Ile Lys Asp Ala Leu Met Leu Phe Gln Arg Leu
            35                  40                  45

Gln Glu Lys Arg Met Leu Glu Glu Ser Asn Leu Ser Phe Leu Lys Glu
        50                  55                  60

Leu Leu Phe Arg Ile Asn Arg Leu Asp Leu Leu Ile Thr Tyr Leu Asn
65                  70                  75                  80

Thr Arg Lys Glu Glu Met Glu Arg Glu Leu Gln Thr Pro Gly Arg Ala
                85                  90                  95

Gln Ile Ser Ala Tyr Arg Phe His Phe Cys Arg Met Ser Trp Ala Glu
            100                 105                 110

Ala Asn Ser Gln Cys Gln Thr Gln Ser Val Pro Phe Trp Arg Arg Val
        115                 120                 125

Asp His Leu Leu Ile Arg Val Met Leu Tyr Gln Ile Ser Glu Glu Val
        130                 135                 140

Ser Arg Ser Glu Leu Arg Ser Phe Lys Phe Leu Leu Gln Glu Glu Ile
145                 150                 155                 160

Ser Lys Cys Lys Leu Asp Asp Asp Met Asn Leu Leu Asp Ile Phe Ile
                165                 170                 175

Glu Met Glu Lys Arg Val Ile Leu Gly Glu Gly Lys Leu Asp Ile Leu
            180                 185                 190

Lys Arg Val Cys Ala Gln Ile Asn Lys Ser Leu Leu Lys Ile Ile Asn
        195                 200                 205

Asp Tyr Glu Glu Phe Ser Lys Gly Glu Glu Leu Cys Gly Val Met Thr
    210                 215                 220

Ile Ser Asp Ser Pro Arg Glu Gln Asp Ser Glu Ser Gln Thr Leu Asp
225                 230                 235                 240

Lys Val Tyr Gln Met Lys Ser Lys Pro Arg Gly Tyr Cys Leu Ile Ile
                245                 250                 255

Asn Asn His Asn Phe Ala Lys Ala Arg Glu Lys Val Pro Lys Leu His
            260                 265                 270

Ser Ile Arg Asp Arg Asn Gly Thr His Leu Asp Ala Gly Ala Leu Thr
        275                 280                 285

Thr Thr Phe Glu Glu Leu His Phe Glu Ile Lys Pro His Asp Asp Cys
```

```
                290             295             300
Thr Val Glu Gln Ile Tyr Glu Ile Leu Lys Ile Tyr Gln Leu Met Asp
305                 310                 315                 320

His Ser Asn Met Asp Cys Phe Ile Cys Cys Ile Leu Ser His Gly Asp
                325                 330                 335

Lys Gly Ile Ile Tyr Gly Thr Asp Gly Gln Glu Ala Pro Ile Tyr Glu
                340                 345                 350

Leu Thr Ser Gln Phe Thr Gly Leu Lys Cys Pro Ser Leu Ala Gly Lys
                355                 360                 365

Pro Lys Val Phe Phe Ile Gln Ala Cys Gln Gly Asp Asn Tyr Gln Lys
                370                 375                 380

Gly Ile Pro Val Glu Thr Asp Ser Glu Glu Gln Pro Tyr Leu Glu Met
385                 390                 395                 400

Asp Leu Ser Ser Pro Gln Thr Arg Tyr Ile Pro Asp Glu Ala Asp Phe
                405                 410                 415

Leu Leu Gly Met Ala Thr Val Asn Asn Cys Val Ser Tyr Arg Asn Pro
                420                 425                 430

Ala Glu Gly Thr Trp Tyr Ile Gln Ser Leu Cys Gln Ser Leu Arg Glu
                435                 440                 445

Arg Cys Pro Arg Gly Asp Asp Ile Leu Thr Ile Leu Thr Glu Val Asn
                450                 455                 460

Tyr Glu Val Ser Asn Lys Asp Asp Lys Lys Asn Met Gly Lys Gln Met
465                 470                 475                 480

Pro Gln Pro Thr Phe Thr Leu Arg Lys Lys Leu Val Phe Pro Ser Asp
                485                 490                 495

<210> SEQ ID NO 69
<211> LENGTH: 479
<212> TYPE: PRT
<213> ORGANISM: homo sapiens

<400> SEQUENCE: 69

Met Asp Phe Ser Arg Asn Leu Tyr Asp Ile Gly Glu Gln Leu Asp Ser
1               5                   10                  15

Glu Asp Leu Ala Ser Leu Lys Phe Leu Ser Leu Asp Tyr Ile Pro Gln
                20                  25                  30

Arg Lys Gln Glu Pro Ile Lys Asp Ala Leu Met Leu Phe Gln Arg Leu
                35                  40                  45

Gln Glu Lys Arg Met Leu Glu Glu Ser Asn Leu Ser Phe Leu Lys Glu
            50                  55                  60

Leu Leu Phe Arg Ile Asn Arg Leu Asp Leu Leu Ile Thr Tyr Leu Asn
65              70                  75                  80

Thr Arg Lys Glu Glu Met Glu Arg Glu Leu Gln Thr Pro Gly Arg Ala
                85                  90                  95

Gln Ile Ser Ala Tyr Arg Val Met Leu Tyr Gln Ile Ser Glu Glu Val
                100                 105                 110

Ser Arg Ser Glu Leu Arg Ser Phe Lys Phe Leu Leu Gln Glu Glu Ile
                115                 120                 125

Ser Lys Cys Lys Leu Asp Asp Asp Met Asn Leu Leu Asp Ile Phe Ile
                130                 135                 140

Glu Met Glu Lys Arg Val Ile Leu Gly Glu Gly Lys Leu Asp Ile Leu
145                 150                 155                 160

Lys Arg Val Cys Ala Gln Ile Asn Lys Ser Leu Leu Lys Ile Ile Asn
                165                 170                 175
```

-continued

Asp Tyr Glu Glu Phe Ser Lys Glu Arg Ser Ser Ser Leu Glu Gly Ser
                180                 185                 190

Pro Asp Glu Phe Ser Asn Gly Glu Leu Cys Gly Val Met Thr Ile
        195                 200                 205

Ser Asp Ser Pro Arg Glu Gln Asp Ser Glu Ser Gln Thr Leu Asp Lys
    210                 215                 220

Val Tyr Gln Met Lys Ser Lys Pro Arg Gly Tyr Cys Leu Ile Ile Asn
225                 230                 235                 240

Asn His Asn Phe Ala Lys Ala Arg Glu Lys Val Pro Lys Leu His Ser
                245                 250                 255

Ile Arg Asp Arg Asn Gly Thr His Leu Asp Ala Gly Ala Leu Thr Thr
            260                 265                 270

Thr Phe Glu Glu Leu His Phe Glu Ile Lys Pro His Asp Asp Cys Thr
        275                 280                 285

Val Glu Gln Ile Tyr Glu Ile Leu Lys Ile Tyr Gln Leu Met Asp His
    290                 295                 300

Ser Asn Met Asp Cys Phe Ile Cys Cys Ile Leu Ser His Gly Asp Lys
305                 310                 315                 320

Gly Ile Ile Tyr Gly Thr Asp Gly Gln Glu Ala Pro Ile Tyr Glu Leu
                325                 330                 335

Thr Ser Gln Phe Thr Gly Leu Lys Cys Pro Ser Leu Ala Gly Lys Pro
            340                 345                 350

Lys Val Phe Phe Ile Gln Ala Cys Gln Gly Asp Asn Tyr Gln Lys Gly
        355                 360                 365

Ile Pro Val Glu Thr Asp Ser Glu Glu Gln Pro Tyr Leu Glu Met Asp
370                 375                 380

Leu Ser Ser Pro Gln Thr Arg Tyr Ile Pro Asp Glu Ala Asp Phe Leu
385                 390                 395                 400

Leu Gly Met Ala Thr Val Asn Asn Cys Val Ser Tyr Arg Asn Pro Ala
                405                 410                 415

Glu Gly Thr Trp Tyr Ile Gln Ser Leu Cys Gln Ser Leu Arg Glu Arg
            420                 425                 430

Cys Pro Arg Gly Asp Asp Ile Leu Thr Ile Leu Thr Glu Val Asn Tyr
        435                 440                 445

Glu Val Ser Asn Lys Asp Asp Lys Lys Asn Met Gly Lys Gln Met Pro
    450                 455                 460

Gln Pro Thr Phe Thr Leu Arg Lys Lys Leu Val Phe Pro Ser Asp
465                 470                 475

<210> SEQ ID NO 70
<211> LENGTH: 464
<212> TYPE: PRT
<213> ORGANISM: homo sapiens

<400> SEQUENCE: 70

Met Asp Phe Ser Arg Asn Leu Tyr Asp Ile Gly Glu Gln Leu Asp Ser
1               5                   10                  15

Glu Asp Leu Ala Ser Leu Lys Phe Leu Ser Leu Asp Tyr Ile Pro Gln
            20                  25                  30

Arg Lys Gln Glu Pro Ile Lys Asp Ala Leu Met Leu Phe Gln Arg Leu
        35                  40                  45

Gln Glu Lys Arg Met Leu Glu Glu Ser Asn Leu Ser Phe Leu Lys Glu
    50                  55                  60

Leu Leu Phe Arg Ile Asn Arg Leu Asp Leu Leu Ile Thr Tyr Leu Asn
65                  70                  75                  80

Thr Arg Lys Glu Glu Met Glu Arg Glu Leu Gln Thr Pro Gly Arg Ala
            85                  90                  95

Gln Ile Ser Ala Tyr Arg Val Met Leu Tyr Gln Ile Ser Glu Glu Val
            100                 105                 110

Ser Arg Ser Glu Leu Arg Ser Phe Lys Phe Leu Leu Gln Glu Glu Ile
            115                 120                 125

Ser Lys Cys Lys Leu Asp Asp Met Asn Leu Leu Asp Ile Phe Ile
130                 135                 140

Glu Met Glu Lys Arg Val Ile Leu Gly Glu Gly Lys Leu Asp Ile Leu
145                 150                 155                 160

Lys Arg Val Cys Ala Gln Ile Asn Lys Ser Leu Leu Lys Ile Ile Asn
            165                 170                 175

Asp Tyr Glu Glu Phe Ser Lys Gly Glu Glu Leu Cys Gly Val Met Thr
            180                 185                 190

Ile Ser Asp Ser Pro Arg Glu Gln Asp Ser Glu Ser Gln Thr Leu Asp
            195                 200                 205

Lys Val Tyr Gln Met Lys Ser Lys Pro Arg Gly Tyr Cys Leu Ile Ile
            210                 215                 220

Asn Asn His Asn Phe Ala Lys Ala Arg Glu Lys Val Pro Lys Leu His
225                 230                 235                 240

Ser Ile Arg Asp Arg Asn Gly Thr His Leu Asp Ala Gly Ala Leu Thr
            245                 250                 255

Thr Thr Phe Glu Glu Leu His Phe Glu Ile Lys Pro His Asp Asp Cys
            260                 265                 270

Thr Val Glu Gln Ile Tyr Glu Ile Leu Lys Ile Tyr Gln Leu Met Asp
            275                 280                 285

His Ser Asn Met Asp Cys Phe Ile Cys Cys Ile Leu Ser His Gly Asp
            290                 295                 300

Lys Gly Ile Ile Tyr Gly Thr Asp Gly Gln Glu Ala Pro Ile Tyr Glu
305                 310                 315                 320

Leu Thr Ser Gln Phe Thr Gly Leu Lys Cys Pro Ser Leu Ala Gly Lys
            325                 330                 335

Pro Lys Val Phe Phe Ile Gln Ala Cys Gln Gly Asp Asn Tyr Gln Lys
            340                 345                 350

Gly Ile Pro Val Glu Thr Asp Ser Glu Glu Gln Pro Tyr Leu Glu Met
            355                 360                 365

Asp Leu Ser Ser Pro Gln Thr Arg Tyr Ile Pro Asp Glu Ala Asp Phe
370                 375                 380

Leu Leu Gly Met Ala Thr Val Asn Asn Cys Val Ser Tyr Arg Asn Pro
385                 390                 395                 400

Ala Glu Gly Thr Trp Tyr Ile Gln Ser Leu Cys Gln Ser Leu Arg Glu
            405                 410                 415

Arg Cys Pro Arg Gly Asp Asp Ile Leu Thr Ile Leu Thr Glu Val Asn
            420                 425                 430

Tyr Glu Val Ser Asn Lys Asp Asp Lys Lys Asn Met Gly Lys Gln Met
            435                 440                 445

Pro Gln Pro Thr Phe Thr Leu Arg Lys Lys Leu Val Phe Pro Ser Asp
450                 455                 460

<210> SEQ ID NO 71
<211> LENGTH: 235
<212> TYPE: PRT
<213> ORGANISM: homo sapiens

<400> SEQUENCE: 71

Met Asp Phe Ser Arg Asn Leu Tyr Asp Ile Gly Glu Gln Leu Asp Ser
1               5                   10                  15

Glu Asp Leu Ala Ser Leu Lys Phe Leu Ser Leu Asp Tyr Ile Pro Gln
            20                  25                  30

Arg Lys Gln Glu Pro Ile Lys Asp Ala Leu Met Leu Phe Gln Arg Leu
        35                  40                  45

Gln Glu Lys Arg Met Leu Glu Glu Ser Asn Leu Ser Phe Leu Lys Glu
    50                  55                  60

Leu Leu Phe Arg Ile Asn Arg Leu Asp Leu Leu Ile Thr Tyr Leu Asn
65                  70                  75                  80

Thr Arg Lys Glu Glu Met Glu Arg Glu Leu Gln Thr Pro Gly Arg Ala
                85                  90                  95

Gln Ile Ser Ala Tyr Arg Val Met Leu Tyr Gln Ile Ser Glu Glu Val
            100                 105                 110

Ser Arg Ser Glu Leu Arg Ser Phe Lys Phe Leu Leu Gln Glu Glu Ile
        115                 120                 125

Ser Lys Cys Lys Leu Asp Asp Met Asn Leu Leu Asp Ile Phe Ile
    130                 135                 140

Glu Met Glu Lys Arg Val Ile Leu Gly Glu Gly Lys Leu Asp Ile Leu
145                 150                 155                 160

Lys Arg Val Cys Ala Gln Ile Asn Lys Ser Leu Leu Lys Ile Ile Asn
                165                 170                 175

Asp Tyr Glu Glu Phe Ser Lys Glu Arg Ser Ser Ser Leu Glu Gly Ser
            180                 185                 190

Pro Asp Glu Phe Ser Asn Asp Phe Gly Gln Ser Leu Pro Asn Glu Lys
        195                 200                 205

Gln Thr Ser Gly Ile Leu Ser Asp His Gln Gln Ser Gln Phe Cys Lys
    210                 215                 220

Ser Thr Gly Glu Ser Ala Gln Thr Ser Gln His
225                 230                 235

<210> SEQ ID NO 72
<211> LENGTH: 9
<212> TYPE: PRT
<213> ORGANISM: Artificial sequence
<220> FEATURE:
<223> OTHER INFORMATION: short peptide

<400> SEQUENCE: 72

Ile Leu Lys Glu Pro Val His Gly Val
1               5

<210> SEQ ID NO 73
<211> LENGTH: 9
<212> TYPE: PRT
<213> ORGANISM: Artificial sequence
<220> FEATURE:
<223> OTHER INFORMATION: short peptide

<400> SEQUENCE: 73

Ser Leu Tyr Asn Thr Val Ala Thr Leu
1               5

<210> SEQ ID NO 74
<211> LENGTH: 8
<212> TYPE: PRT
<213> ORGANISM: Artificial sequence
<220> FEATURE:

<223> OTHER INFORMATION: short peptide

<400> SEQUENCE: 74

Ile Leu Glu Pro Val His Gly Val
1               5

<210> SEQ ID NO 75
<211> LENGTH: 9
<212> TYPE: PRT
<213> ORGANISM: Artificial sequence
<220> FEATURE:
<223> OTHER INFORMATION: short peptide

<400> SEQUENCE: 75

Gly Ile Leu Gly Phe Val Phe Thr Leu
1               5

<210> SEQ ID NO 76
<211> LENGTH: 252
<212> TYPE: PRT
<213> ORGANISM: Influenza A virus

<400> SEQUENCE: 76

Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asp Val Phe
                20                  25                  30

Ala Gly Lys Asn Thr Asp Leu Glu Ala Leu Met Glu Trp Leu Lys Thr
            35                  40                  45

Arg Pro Ile Leu Ser Pro Leu Thr Lys Gly Ile Leu Gly Phe Val Phe
50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Arg Ala
                85                  90                  95

Val Lys Leu Tyr Arg Lys Leu Lys Arg Glu Ile Thr Phe His Gly Ala
            100                 105                 110

Lys Glu Val Ala Leu Ser Tyr Ser Ala Gly Ala Leu Ala Ser Cys Met
        115                 120                 125

Gly Leu Ile Tyr Asn Arg Met Gly Ala Val Thr Thr Glu Val Ala Phe
    130                 135                 140

Ala Val Val Cys Ala Thr Cys Glu Gln Ile Ala Asp Ser Gln His Arg
145                 150                 155                 160

Ser His Arg Gln Met Val Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Gln
        195                 200                 205

Ala Arg Gln Met Val Gln Ala Met Arg Ala Ile Gly Thr Pro Pro Ser
    210                 215                 220

Ser Ser Ala Gly Leu Lys Asp Asp Leu Leu Glu Asn Leu Gln Ala Tyr
225                 230                 235                 240

Gln Lys Arg Met Gly Val Gln Met Gln Arg Phe Lys
                245                 250

<210> SEQ ID NO 77
<211> LENGTH: 584

-continued

```
<212> TYPE: PRT
<213> ORGANISM: Influenza A virus

<400> SEQUENCE: 77

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Gln Thr
    50                  55                  60

Arg Gly Lys Leu Cys Pro Asn Cys Phe Asn Cys Thr Asp Leu Asp Val
65                  70                  75                  80

Ala Leu Gly Arg Pro Lys Cys Met Gly Asn Thr Pro Ser Ala Lys Val
                85                  90                  95

Ser Ile Leu His Glu Val Lys Pro Ala Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu Asn Ile Arg Leu Ser Thr Ser Asn Val Ile Asn Thr Glu Thr
    130                 135                 140

Ala Pro Gly Gly Pro Tyr Lys Val Gly Thr Ser Gly Ser Cys Pro Asn
145                 150                 155                 160

Val Ala Asn Gly Asn Gly Phe Phe Asn Thr Met Ala Trp Val Ile Pro
                165                 170                 175

Lys Asp Asn Asn Lys Thr Ala Ile Asn Pro Val Thr Val Glu Val Pro
            180                 185                 190

Tyr Ile Cys Ser Glu Gly Glu Asp Gln Ile Thr Val Trp Gly Phe His
        195                 200                 205

Ser Asp Asp Lys Thr Gln Met Glu Arg Leu Tyr Gly Asp Ser Asn Pro
    210                 215                 220

Gln Lys Phe Thr Ser Ser Ala Asn Gly Val Thr Thr His Tyr Val Ser
225                 230                 235                 240

Gln Ile Gly Gly Phe Pro Asn Gln Thr Glu Asp Glu Gly Leu Lys Gln
                245                 250                 255

Ser Gly Arg Ile Val Val Asp Tyr Met Val Gln Lys Pro Gly Lys Thr
            260                 265                 270

Gly Thr Ile Val Tyr Gln Arg Gly Ile Leu Leu Pro Gln Lys Val Trp
        275                 280                 285

Cys Ala Ser Gly Arg Ser Lys Val Ile Lys Gly Ser Leu Pro Leu Ile
    290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
                325                 330                 335

Ile Trp Val Lys Thr Pro Leu Lys Leu Ala Asn Gly Thr Lys Tyr Arg
            340                 345                 350

Pro Pro Ala Lys Leu Leu Lys Glu Arg Gly Phe Phe Gly Ala Ile Ala
        355                 360                 365

Gly Phe Leu Glu Gly Gly Trp Glu Gly Met Ile Ala Gly Trp His Gly
    370                 375                 380

Tyr Thr Ser His Gly Ala His Gly Val Ala Val Ala Ala Asp Leu Lys
385                 390                 395                 400
```

```
Ser Thr Gln Glu Ala Ile Asn Lys Ile Thr Lys Asn Leu Asn Tyr Leu
                405                 410                 415

Ser Glu Leu Glu Val Lys Asn Leu Gln Arg Leu Ser Gly Ala Met Asn
            420                 425                 430

Glu Leu His Asp Glu Ile Leu Glu Leu Asp Glu Lys Val Asp Asp Leu
        435                 440                 445

Arg Ala Asp Thr Ile Ser Ser Gln Ile Glu Leu Ala Val Leu Leu Ser
    450                 455                 460

Asn Glu Gly Ile Ile Asn Ser Glu Asp Glu His Leu Leu Ala Leu Glu
465                 470                 475                 480

Arg Lys Leu Lys Lys Met Leu Gly Pro Ser Ala Val Glu Ile Gly Asn
                485                 490                 495

Gly Cys Phe Glu Thr Lys His Lys Cys Asn Gln Thr Cys Leu Asp Arg
            500                 505                 510

Ile Ala Ala Gly Thr Phe Asn Ala Gly Asp Phe Ser Leu Pro Thr Phe
        515                 520                 525

Asp Ser Leu Asn Ile Thr Ala Ala Ser Leu Asn Asp Asp Gly Leu Asp
    530                 535                 540

Asn His Thr Ile Leu Leu Tyr Tyr Ser Thr Ala Ala Ser Ser Leu Ala
545                 550                 555                 560

Val Thr Leu Met Ile Ala Ile Phe Ile Val Tyr Met Val Ser Arg Asp
                565                 570                 575

Asn Val Ser Cys Ser Ile Cys Leu
            580
```

<210> SEQ ID NO 78
<211> LENGTH: 566
<212> TYPE: PRT
<213> ORGANISM: Influenza A virus

<400> SEQUENCE: 78

```
Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Gly Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Lys Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Lys Phe Asp Lys
```

```
            180             185             190
Leu Tyr Ile Trp Gly Val His His Pro Gly Thr Asp Asn Asp Gln Ile
        195             200             205

Ser Leu Tyr Ala Gln Ala Ser Gly Arg Ile Thr Val Ser Thr Lys Arg
        210             215             220

Ser Gln Gln Thr Val Ile Pro Ser Ile Gly Ser Arg Pro Arg Ile Arg
225             230             235             240

Asp Val Pro Ser Arg Ile Ser Ile Tyr Trp Thr Ile Val Lys Pro Gly
            245             250             255

Asp Ile Leu Leu Ile Asn Ser Thr Gly Asn Leu Ile Ala Pro Arg Gly
            260             265             270

Tyr Phe Lys Ile Arg Ser Gly Lys Ser Ser Ile Met Arg Ser Asp Ala
            275             280             285

Pro Ile Gly Lys Cys Asn Ser Glu Cys Ile Thr Pro Asn Gly Ser Ile
            290             295             300

Pro Asn Asp Lys Pro Phe Gln Asn Val Asn Arg Ile Thr Tyr Gly Ala
305             310             315             320

Cys Pro Arg Tyr Val Lys Gln Asn Thr Leu Lys Leu Ala Thr Gly Met
                325             330             335

Arg Asn Val Pro Glu Lys Gln Thr Arg Gly Ile Phe Gly Ala Ile Ala
                340             345             350

Gly Phe Ile Glu Asn Gly Trp Glu Gly Met Val Asp Gly Trp Tyr Gly
            355             360             365

Phe Arg His Gln Asn Ser Glu Gly Thr Gly Gln Ala Ala Asp Leu Lys
            370             375             380

Ser Thr Gln Ala Ala Ile Asn Gln Ile Asn Gly Lys Leu Asn Arg Leu
385             390             395             400

Ile Gly Lys Thr Asn Glu Lys Phe His Gln Ile Glu Lys Glu Phe Ser
                405             410             415

Glu Val Glu Gly Arg Ile Gln Asp Leu Glu Lys Tyr Val Glu Asp Thr
                420             425             430

Lys Ile Asp Leu Trp Ser Tyr Asn Ala Glu Leu Leu Val Ala Leu Glu
            435             440             445

Asn Gln His Thr Ile Asp Leu Thr Asp Ser Glu Met Asn Lys Leu Phe
            450             455             460

Glu Arg Thr Lys Lys Gln Leu Arg Glu Asn Ala Glu Asp Met Gly Asn
465             470             475             480

Gly Cys Phe Lys Ile Tyr His Lys Cys Asp Asn Ala Cys Ile Gly Ser
                485             490             495

Ile Arg Asn Gly Thr Tyr Asp His Asp Val Tyr Arg Asp Glu Ala Leu
                500             505             510

Asn Asn Arg Phe Gln Ile Lys Gly Val Glu Leu Lys Ser Gly Tyr Lys
            515             520             525

Asp Trp Ile Leu Trp Ile Ser Phe Ala Ile Ser Cys Phe Leu Leu Cys
            530             535             540

Val Ala Leu Leu Gly Phe Ile Met Trp Ala Cys Gln Lys Gly Asn Ile
545             550             555             560

Arg Cys Asn Ile Cys Ile
                565

<210> SEQ ID NO 79
<211> LENGTH: 466
<212> TYPE: PRT
<213> ORGANISM: Influenza B virus
```

<400> SEQUENCE: 79

Met Leu Pro Ser Thr Val Gln Thr Leu Thr Leu Leu Thr Ser Gly
1               5                   10                  15

Gly Val Leu Leu Ser Leu Tyr Val Ser Ala Ser Leu Ser Tyr Leu Leu
            20                  25                  30

Tyr Ser Asp Val Leu Leu Lys Phe Ser Ser Thr Lys Thr Thr Ala Pro
                35                  40                  45

Thr Met Ser Leu Glu Cys Thr Asn Ala Ser Asn Ala Gln Thr Val Asn
    50                  55                  60

His Ser Ala Thr Lys Glu Met Thr Phe Pro Pro Glu Pro Glu Trp
65                  70                  75                  80

Thr Tyr Pro Arg Leu Ser Cys Gln Gly Ser Thr Phe Gln Lys Ala Leu
                85                  90                  95

Leu Ile Ser Pro His Arg Phe Gly Glu Ile Lys Gly Asn Ser Ala Pro
                100                 105                 110

Leu Ile Ile Arg Glu Pro Phe Val Ala Cys Gly Pro Lys Glu Cys Arg
            115                 120                 125

His Phe Ala Leu Thr His Tyr Ala Ala Gln Pro Gly Gly Tyr Tyr Asn
    130                 135                 140

Gly Thr Arg Lys Asp Arg Asn Lys Leu Arg His Leu Val Ser Val Lys
145                 150                 155                 160

Leu Gly Lys Ile Pro Thr Val Glu Asn Ser Ile Phe His Met Ala Ala
                165                 170                 175

Trp Ser Gly Ser Ala Cys His Asp Gly Arg Glu Trp Thr Tyr Ile Gly
            180                 185                 190

Val Asp Gly Pro Asp Asn Asp Ala Leu Val Lys Ile Lys Tyr Gly Glu
        195                 200                 205

Ala Tyr Thr Asp Thr Tyr His Ser Tyr Ala His Asn Ile Leu Arg Thr
    210                 215                 220

Gln Glu Ser Ala Cys Asn Cys Ile Gly Gly Asp Cys Tyr Leu Met Ile
225                 230                 235                 240

Thr Asp Gly Ser Ala Ser Gly Ile Ser Lys Cys Arg Phe Leu Lys Ile
                245                 250                 255

Arg Glu Gly Arg Ile Ile Lys Glu Ile Leu Pro Thr Gly Arg Val Glu
            260                 265                 270

His Thr Glu Glu Cys Thr Cys Gly Phe Ala Ser Asn Lys Thr Ile Glu
        275                 280                 285

Cys Ala Cys Arg Asp Asn Ser Tyr Thr Ala Lys Arg Pro Phe Val Lys
290                 295                 300

Leu Asn Val Glu Thr Asp Thr Ala Glu Ile Arg Leu Met Cys Thr Lys
305                 310                 315                 320

Thr Tyr Leu Asp Thr Pro Arg Pro Asp Asp Gly Ser Ile Ala Gly Pro
                325                 330                 335

Cys Glu Ser Asn Gly Asp Lys Trp Leu Gly Gly Ile Lys Gly Gly Phe
            340                 345                 350

Val His Gln Arg Met Ala Ser Lys Ile Gly Arg Trp Tyr Ser Arg Thr
    355                 360                 365

Met Ser Lys Thr Asn Arg Met Gly Met Glu Leu Tyr Val Lys Tyr Asp
370                 375                 380

Gly Asp Pro Trp Thr Asp Ser Asp Ala Leu Thr Leu Ser Gly Val Met
385                 390                 395                 400

Val Ser Ile Glu Glu Pro Gly Trp Tyr Ser Phe Gly Phe Glu Ile Lys 405 410 415

Asp Lys Lys Cys Asp Val Pro Cys Ile Gly Ile Glu Met Val His Asp
420 425 430

Gly Gly Lys Asp Thr Trp His Ser Ala Ala Thr Ala Ile Tyr Cys Leu
435 440 445

Met Gly Ser Gly Gln Leu Leu Trp Asp Thr Val Thr Gly Val Asp Met
450 455 460

Ala Leu
465

<210> SEQ ID NO 80
<211> LENGTH: 565
<212> TYPE: PRT
<213> ORGANISM: Influenza C virus

<400> SEQUENCE: 80

Met Ser Asp Arg Arg Gln Asn Arg Lys Thr Pro Asp Glu Gln Arg Lys
1 5 10 15

Ala Asn Ala Leu Ile Ile Asn Glu Asn Ile Glu Ala Tyr Ile Ala Ile
20 25 30

Cys Lys Glu Val Gly Leu Asn Gly Asp Glu Met Leu Ile Leu Glu Asn
35 40 45

Gly Ile Ala Ile Glu Lys Ala Ile Arg Ile Cys Cys Asp Gly Lys Tyr
50 55 60

Gln Glu Lys Arg Glu Lys Lys Ala Arg Glu Ala Gln Arg Ala Asp Ser
65 70 75 80

Asn Phe Asn Ala Asp Ser Ile Gly Ile Arg Leu Val Lys Arg Ala Gly
85 90 95

Ser Gly Thr Asn Ile Thr Tyr His Ala Val Val Glu Leu Thr Ser Arg
100 105 110

Ser Arg Ile Val Gln Ile Leu Lys Ser His Trp Gly Asn Glu Leu Asn
115 120 125

Arg Ala Lys Ile Ala Gly Lys Arg Leu Gly Phe Ser Ala Leu Phe Ala
130 135 140

Ser Asn Leu Glu Ala Ile Ile Tyr Gln Arg Gly Arg Asn Ala Ala Arg
145 150 155 160

Arg Asn Gly Ser Ala Glu Leu Phe Thr Leu Thr Gln Gly Ala Gly Ile
165 170 175

Glu Thr Arg Tyr Lys Trp Ile Met Glu Lys His Ile Gly Ile Gly Val
180 185 190

Leu Ile Ala Asp Ala Lys Gly Leu Ile Asn Gly Lys Arg Glu Gly Lys
195 200 205

Arg Gly Val Asp Ala Asn Val Lys Leu Arg Ala Gly Thr Thr Gly Ser
210 215 220

Pro Leu Glu Arg Ala Met Gln Gly Ile Glu Lys Lys Ala Phe Pro Gly
225 230 235 240

Pro Leu Arg Ala Leu Ala Arg Arg Val Val Lys Ala Asn Tyr Asn Asp
245 250 255

Ala Arg Glu Ala Leu Asn Val Ile Ala Glu Ala Ser Leu Leu Leu Lys
260 265 270

Pro Gln Ile Thr Asn Lys Met Thr Met Pro Trp Cys Met Trp Leu Ala
275 280 285

Ala Arg Leu Thr Leu Lys Asp Glu Phe Ala Asn Phe Cys Ala Tyr Ala
290 295 300

```
Gly Arg Arg Ala Phe Glu Val Phe Asn Ile Ala Met Glu Lys Ile Gly
305                 310                 315                 320

Ile Cys Ser Phe Gln Gly Thr Ile Met Asn Asp Asp Glu Ile Glu Ser
            325                 330                 335

Ile Glu Asp Lys Ala Gln Val Leu Met Met Ala Cys Phe Gly Leu Ala
            340                 345                 350

Tyr Glu Asp Phe Ser Leu Val Ser Ala Met Val Ser His Pro Leu Lys
            355                 360                 365

Leu Arg Asn Arg Met Lys Ile Gly Asn Phe Arg Val Gly Glu Lys Val
370                 375                 380

Ser Thr Val Leu Ser Pro Leu Leu Arg Phe Thr Arg Trp Ala Glu Phe
385                 390                 395                 400

Ala Gln Arg Phe Ala Leu Gln Ala Asn Thr Ser Arg Glu Gly Ala Gln
            405                 410                 415

Ile Ser Asn Ser Ala Val Phe Ala Val Glu Arg Lys Ile Thr Thr Asp
            420                 425                 430

Val Gln Arg Val Glu Glu Leu Leu Asn Lys Val Gln Ala His Glu Asp
            435                 440                 445

Glu Pro Leu Gln Thr Leu Tyr Lys Lys Val Arg Glu Gln Ile Ser Ile
450                 455                 460

Ile Gly Arg Asn Lys Ser Glu Ile Lys Glu Phe Leu Gly Ser Ser Met
465                 470                 475                 480

Tyr Asp Leu Asn Asp Gln Glu Lys Gln Asn Pro Ile Asn Phe Arg Ser
            485                 490                 495

Gly Ala His Pro Phe Phe Glu Phe Asp Pro Asp Tyr Asn Pro Ile
            500                 505                 510

Arg Val Lys Arg Pro Lys Lys Pro Ile Ala Lys Arg Asn Ser Asn Ile
            515                 520                 525

Ser Arg Leu Glu Glu Glu Gly Met Asp Glu Asn Ser Glu Ile Gly Gln
530                 535                 540

Ala Lys Lys Met Lys Pro Leu Asp Gln Leu Thr Ser Thr Ser Ser Asn
545                 550                 555                 560

Ile Pro Gly Lys Asn
            565

<210> SEQ ID NO 81
<211> LENGTH: 498
<212> TYPE: PRT
<213> ORGANISM: Influenza A virus

<400> SEQUENCE: 81

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Asp Gly Ile Gly Arg Phe Tyr Ile Gln Met Cys Thr Glu Leu Lys
            35                  40                  45

Leu Ser Asp Tyr Glu Gly Arg Leu Ile Gln Asn Ser Leu Thr Ile Glu
50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
            85                  90                  95

Tyr Lys Arg Val Asp Gly Lys Trp Met Arg Glu Leu Val Leu Tyr Asp
            100                 105                 110
```

Lys Glu Glu Ile Arg Arg Ile Trp Arg Gln Ala Asn Asn Gly Asp Asp
            115                 120                 125

Ala Thr Ala Gly Leu Thr His Met Met Ile Trp His Ser Asn Leu Asn
    130                 135                 140

Asp Thr Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
                180                 185                 190

Leu Ile Arg Met Ile Lys Arg Gly Ile Asn Asp Arg Asn Phe Trp Arg
            195                 200                 205

Gly Glu Asn Gly Arg Lys Thr Arg Ser Ala Tyr Glu Arg Met Cys Asn
210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
                260                 265                 270

Lys Ser Cys Leu Pro Ala Cys Val Tyr Gly Pro Ala Ile Ala Ser Gly
            275                 280                 285

Tyr Asn Phe Glu Lys Glu Gly Tyr Ser Leu Val Gly Ile Asp Pro Phe
            290                 295                 300

Lys Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys Asn Ser Ala
                325                 330                 335

Ala Phe Glu Asp Leu Arg Val Leu Ser Phe Ile Arg Gly Thr Lys Val
                340                 345                 350

Ser Pro Arg Gly Lys Leu Ser Thr Arg Gly Val Gln Ile Ala Ser Asn
            355                 360                 365

Glu Asn Met Asp Thr Met Glu Ser Ser Thr Leu Glu Leu Arg Ser Arg
            370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Val Gln Pro Ala Phe Ser Val Gln Arg
                405                 410                 415

Asn Leu Pro Phe Asp Lys Pro Thr Ile Met Ala Ala Phe Thr Gly Asn
                420                 425                 430

Thr Glu Gly Arg Thr Ser Asp Met Arg Ala Glu Ile Ile Arg Met Met
            435                 440                 445

Glu Gly Ala Lys Pro Glu Glu Met Ser Phe Gln Gly Arg Gly Val Phe
            450                 455                 460

Glu Leu Ser Asp Glu Lys Ala Thr Asn Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn

<210> SEQ ID NO 82
<211> LENGTH: 498
<212> TYPE: PRT

<213> ORGANISM: Influenza A virus

<400> SEQUENCE: 82

Met Ala Ser Gln Gly Thr Lys Arg Ser Tyr Glu Gln Met Glu Thr Gly
1               5                   10                  15

Gly Glu Arg Gln Asn Ala Thr Glu Ile Arg Ala Ser Val Gly Arg Met
            20                  25                  30

Val Gly Gly Ile Gly Arg Phe Tyr Val Gln Met Cys Thr Glu Leu Lys
        35                  40                  45

Leu Ser Asp Gln Glu Gly Arg Leu Ile Gln Asn Ser Ile Thr Ile Glu
    50                  55                  60

Arg Met Val Leu Ser Ala Phe Asp Glu Arg Arg Asn Arg Tyr Leu Glu
65                  70                  75                  80

Glu His Pro Ser Ala Gly Lys Asp Pro Lys Lys Thr Gly Gly Pro Ile
                85                  90                  95

Tyr Arg Arg Arg Asp Gly Lys Trp Val Arg Glu Leu Ile Leu Tyr Asp
            100                 105                 110

Lys Glu Glu Ile Arg Arg Ile Trp Arg Gln Ala Asn Asn Gly Glu Asp
        115                 120                 125

Ala Thr Ala Gly Leu Thr His Met Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Ile Lys Gly Val Gly Thr Met Val Met Glu
            180                 185                 190

Leu Ile Arg Met Ile Lys Arg Gly Ile Asn Asp Arg Asn Phe Trp Arg
        195                 200                 205

Gly Asp Asn Gly Arg Arg Thr Arg Ile Ala Tyr Glu Arg Met Cys Asn
    210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Leu Ala Val Ala Ser Gly
        275                 280                 285

Tyr Asp Phe Glu Arg Glu Gly Tyr Ser Leu Val Gly Ile Asp Pro Phe
    290                 295                 300

Arg Leu Leu Gln Asn Ser Gln Val Phe Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Ser Ser Phe Ile Arg Gly Thr Arg Val
            340                 345                 350

Ile Pro Arg Gly Gln Leu Ser Thr Arg Gly Val Gln Ile Ala Ser Asn
        355                 360                 365

Glu Asn Val Glu Ala Met Asp Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

```
Ala Ser Ala Gly Gln Ile Ser Val Gln Pro Thr Phe Ser Val Gln Arg
                405                 410                 415

Asn Leu Pro Phe Glu Arg Pro Thr Ile Met Ala Ala Phe Lys Gly Asn
            420                 425                 430

Thr Glu Gly Arg Thr Ser Asp Met Arg Thr Glu Ile Ile Arg Met Met
        435                 440                 445

Glu Ser Ala Arg Pro Glu Asp Val Ser Phe Gln Gly Arg Gly Val Phe
450                 455                 460

Glu Leu Ser Asp Glu Lys Ala Thr Asn Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn

<210> SEQ ID NO 83
<211> LENGTH: 560
<212> TYPE: PRT
<213> ORGANISM: Influenza B virus

<400> SEQUENCE: 83

Met Ser Asn Met Asp Ile Asp Ser Ile Asn Thr Gly Thr Ile Asp Lys
1               5                   10                  15

Thr Pro Glu Glu Leu Thr Pro Gly Thr Ser Gly Ala Thr Arg Pro Ile
            20                  25                  30

Ile Lys Pro Ala Thr Leu Ala Pro Pro Ser Asn Lys Arg Thr Arg Asn
        35                  40                  45

Pro Ser Pro Glu Arg Thr Thr Thr Ser Ser Glu Thr Asp Ile Gly Arg
50                  55                  60

Lys Ile Gln Lys Lys Gln Thr Pro Thr Glu Ile Lys Lys Ser Val Tyr
65                  70                  75                  80

Lys Met Val Val Lys Leu Gly Glu Phe Tyr Asn Gln Met Met Val Lys
                85                  90                  95

Ala Gly Leu Asn Asp Asp Met Glu Arg Asn Leu Ile Gln Asn Ala Gln
            100                 105                 110

Ala Val Glu Arg Ile Leu Leu Ala Ala Thr Asp Asp Lys Lys Thr Glu
        115                 120                 125

Tyr Gln Lys Lys Arg Asn Ala Arg Asp Val Lys Glu Gly Lys Glu Glu
130                 135                 140

Ile Asp His Asn Lys Thr Gly Gly Thr Phe Tyr Lys Met Val Arg Asp
145                 150                 155                 160

Asp Lys Thr Ile Tyr Phe Ser Pro Ile Lys Ile Thr Phe Leu Lys Glu
                165                 170                 175

Glu Val Lys Thr Met Tyr Lys Thr Thr Met Gly Ser Asp Gly Phe Ser
            180                 185                 190

Gly Leu Asn His Ile Met Ile Gly His Ser Gln Met Asn Asp Val Cys
        195                 200                 205

Phe Gln Arg Ser Lys Gly Leu Lys Arg Val Gly Leu Asp Pro Ser Leu
210                 215                 220

Ile Ser Thr Phe Ala Gly Ser Thr Leu Pro Arg Arg Ser Gly Thr Thr
225                 230                 235                 240

Gly Val Ala Ile Lys Gly Gly Thr Leu Val Asp Glu Ala Ile Arg
                245                 250                 255

Phe Ile Gly Arg Ala Met Ala Asp Arg Gly Leu Leu Arg Asp Ile Lys
            260                 265                 270
```

Ala Lys Thr Ala Tyr Glu Lys Ile Leu Leu Asn Leu Lys Asn Lys Cys
            275                 280                 285

Ser Ala Pro Gln Gln Lys Ala Leu Val Asp Gln Val Ile Gly Ser Arg
        290                 295                 300

Asn Pro Gly Ile Ala Asp Ile Glu Asp Leu Thr Leu Leu Ala Arg Ser
305                 310                 315                 320

Met Val Val Arg Pro Ser Val Ala Ser Lys Val Val Leu Pro Ile
                325                 330                 335

Ser Ile Tyr Ala Lys Ile Pro Gln Leu Gly Phe Asn Thr Glu Glu Tyr
                340                 345                 350

Ser Met Val Gly Tyr Glu Ala Met Ala Leu Tyr Asn Met Ala Thr Pro
            355                 360                 365

Val Ser Ile Leu Arg Met Gly Asp Asp Ala Lys Asp Lys Ser Gln Leu
        370                 375                 380

Phe Phe Met Ser Cys Phe Gly Ala Ala Tyr Glu Asp Leu Arg Val Leu
385                 390                 395                 400

Ser Ala Leu Thr Gly Thr Glu Phe Lys Pro Arg Ser Ala Leu Lys Cys
                405                 410                 415

Lys Gly Phe His Val Pro Ala Lys Glu Gln Val Glu Gly Met Gly Ala
                420                 425                 430

Ala Leu Met Ser Ile Lys Leu Gln Phe Trp Ala Pro Met Thr Arg Ser
            435                 440                 445

Gly Gly Asn Glu Val Ser Glu Gly Gly Ser Gly Gln Ile Ser Cys
        450                 455                 460

Ser Pro Val Phe Ala Val Glu Arg Pro Ile Ala Leu Ser Lys Gln Ala
465                 470                 475                 480

Val Arg Arg Met Leu Ser Met Asn Val Glu Gly Arg Asp Ala Asp Val
                485                 490                 495

Lys Gly Asn Leu Leu Lys Met Met Asn Asp Ser Met Ala Lys Lys Thr
                500                 505                 510

Ser Gly Asn Ala Phe Ile Gly Lys Lys Met Phe Gln Ile Ser Asp Lys
            515                 520                 525

Asn Lys Val Asn Pro Ile Glu Ile Pro Ile Lys Gln Thr Ile Pro Asn
        530                 535                 540

Phe Phe Phe Gly Arg Asp Thr Ala Glu Asp Tyr Asp Asp Leu Asp Tyr
545                 550                 555                 560

<210> SEQ ID NO 84
<211> LENGTH: 248
<212> TYPE: PRT
<213> ORGANISM: Influenza B virus

<400> SEQUENCE: 84

Met Ser Leu Phe Gly Asp Thr Ile Ala Tyr Leu Leu Ser Leu Ile Glu
1               5                   10                  15

Asp Gly Glu Gly Lys Ala Glu Leu Ala Glu Lys Leu His Cys Trp Phe
            20                  25                  30

Gly Gly Lys Glu Phe Asp Leu Asp Ser Ala Leu Glu Trp Ile Lys Asn
        35                  40                  45

Lys Arg Cys Leu Thr Asp Ile Gln Lys Ala Leu Ile Gly Ala Ser Ile
    50                  55                  60

Cys Phe Leu Lys Pro Lys Asp Gln Glu Arg Lys Arg Arg Phe Ile Thr
65                  70                  75                  80

Glu Pro Leu Ser Gly Met Gly Thr Thr Ala Thr Lys Lys Lys Gly Leu
                85                  90                  95

```
Ile Leu Ala Glu Arg Lys Met Arg Arg Cys Val Ser Phe His Glu Ala
            100                 105                 110

Phe Glu Ile Ala Glu Gly His Glu Ser Ser Ala Leu Leu Tyr Cys Leu
        115                 120                 125

Met Val Met Tyr Leu Asn Pro Glu Asn Tyr Ser Met Gln Val Lys Leu
    130                 135                 140

Gly Thr Leu Cys Ala Leu Cys Glu Lys Gln Ala Ser His Ser His Arg
145                 150                 155                 160

Ala His Ser Arg Ala Ala Arg Ser Ser Val Pro Gly Val Arg Arg Glu
                165                 170                 175

Met Gln Met Val Ser Ala Met Asn Thr Ala Lys Thr Met Asn Gly Met
            180                 185                 190

Gly Lys Gly Glu Asp Val Gln Lys Leu Ala Glu Glu Leu Gln Asn Asn
        195                 200                 205

Ile Gly Val Leu Arg Ser Leu Gly Ala Ser Gln Lys Asn Gly Glu Gly
    210                 215                 220

Ile Ala Lys Asp Val Met Glu Val Leu Lys Gln Ser Ser Met Gly Asn
225                 230                 235                 240

Ser Ala Leu Val Arg Lys Tyr Leu
                245

<210> SEQ ID NO 85
<211> LENGTH: 97
<212> TYPE: PRT
<213> ORGANISM: Influenza A virus

<400> SEQUENCE: 85

Met Ser Leu Leu Thr Glu Val Glu Thr Pro Ile Arg Asn Glu Trp Gly
1               5                   10                  15

Cys Arg Cys Asn Gly Ser Ser Asp Pro Leu Ala Ile Ala Ala Asn Ile
                20                  25                  30

Ile Gly Ile Leu His Leu Ile Leu Trp Ile Leu Asp Arg Leu Phe Phe
            35                  40                  45

Lys Cys Ile Tyr Arg Arg Phe Lys Tyr Gly Leu Lys Gly Gly Pro Ser
        50                  55                  60

Thr Glu Gly Val Pro Lys Ser Met Arg Glu Glu Tyr Arg Lys Glu Gln
65                  70                  75                  80

Gln Ser Ala Val Asp Ala Asp Asp Gly His Phe Val Ser Ile Glu Leu
                85                  90                  95

Glu

<210> SEQ ID NO 86
<211> LENGTH: 281
<212> TYPE: PRT
<213> ORGANISM: Influenza B virus

<400> SEQUENCE: 86

Met Ala Asp Asn Met Thr Thr Thr Gln Ile Glu Val Gly Pro Gly Ala
1               5                   10                  15

Thr Asn Ala Thr Ile Asn Phe Glu Ala Gly Ile Leu Glu Cys Tyr Glu
                20                  25                  30

Arg Phe Ser Trp Gln Arg Ala Leu Asp Tyr Pro Gly Gln Asp Arg Leu
            35                  40                  45

His Arg Leu Lys Arg Lys Leu Glu Ser Arg Ile Lys Thr His Asn Lys
        50                  55                  60
```

```
Ser Glu Pro Glu Asn Lys Arg Met Ser Leu Glu Arg Lys Ala Ile
 65                  70                  75                  80

Gly Val Lys Met Met Lys Val Leu Leu Phe Met Asp Pro Ser Ala Gly
                 85                  90                  95

Ile Glu Gly Phe Glu Pro Tyr Cys Val Lys Asn Pro Ser Thr Ser Lys
                100                 105                 110

Cys Pro Asn Tyr Asp Trp Thr Asp Tyr Pro Pro Thr Pro Gly Lys Tyr
                115                 120                 125

Leu Asp Asp Ile Glu Glu Pro Glu Asn Val Asp His Pro Ile Glu
                130                 135                 140

Val Val Leu Arg Asp Met Asn Asn Lys Asp Ala Arg Gln Lys Ile Lys
145                 150                 155                 160

Asp Glu Val Asn Thr Gln Lys Glu Gly Lys Phe Arg Leu Thr Ile Lys
                165                 170                 175

Arg Asp Ile Arg Asn Val Leu Ser Leu Arg Val Leu Val Asn Gly Thr
                180                 185                 190

Phe Leu Lys His Pro Asn Gly Asp Lys Ser Leu Ser Thr Leu His Arg
                195                 200                 205

Leu Asn Ala Tyr Asp Gln Asn Gly Gly Leu Val Ala Lys Leu Val Ala
                210                 215                 220

Thr Asp Asp Arg Thr Val Glu Asp Glu Lys Asp Gly His Arg Ile Leu
225                 230                 235                 240

Asn Ser Leu Phe Glu Arg Phe Asp Glu Gly His Ser Lys Pro Ile Arg
                245                 250                 255

Ala Ala Glu Thr Ala Val Gly Val Leu Ser Gln Phe Gly Gln Glu His
                260                 265                 270

Arg Leu Ser Pro Glu Glu Gly Asp Asn
                275                 280

<210> SEQ ID NO 87
<211> LENGTH: 122
<212> TYPE: PRT
<213> ORGANISM: Influenza B virus

<400> SEQUENCE: 87

Met Ala Asp Asn Met Thr Thr Thr Gln Ile Glu Trp Arg Met Lys Lys
  1               5                  10                  15

Met Ala Ile Gly Ser Ser Thr His Ser Ser Ser Val Leu Met Lys Asp
                 20                  25                  30

Ile Gln Ser Gln Phe Glu Gln Leu Lys Leu Arg Trp Glu Ser Tyr Pro
                 35                  40                  45

Asn Leu Val Lys Ser Thr Asp Tyr His Gln Lys Arg Glu Thr Ile Arg
 50                  55                  60

Leu Ala Thr Glu Glu Leu Tyr Leu Leu Ser Lys Arg Ile Asp Asp Ser
 65                  70                  75                  80

Ile Leu Phe His Lys Thr Val Ile Ala Asn Ser Ser Ile Ile Ala Asp
                 85                  90                  95

Met Ile Val Ser Leu Ser Leu Leu Glu Thr Leu Tyr Glu Met Lys Asp
                100                 105                 110

Val Val Glu Val Tyr Ser Arg Gln Cys Leu
                115                 120

<210> SEQ ID NO 88
<211> LENGTH: 716
<212> TYPE: PRT
<213> ORGANISM: Influenza A virus
```

<400> SEQUENCE: 88

| | | | | | | | | | | | | | | |
|---|---|---|---|---|---|---|---|---|---|---|---|---|---|---|
|Met|Glu|Asp|Phe|Val|Arg|Gln|Cys|Phe|Asn|Pro|Met|Ile|Val|Glu|Leu|
|1| | | |5| | | | |10| | | | |15| |

Ala Glu Lys Ala Met Lys Glu Tyr Gly Glu Asp Leu Lys Ile Glu Thr
                20                  25                  30

Asn Lys Phe Ala Ala Ile Cys Thr His Leu Glu Val Cys Phe Met Tyr
            35                  40                  45

Ser Asp Phe His Phe Ile Asn Glu Gln Gly Glu Ser Ile Ile Val Glu
    50                  55                  60

Pro Glu Asp Pro Asn Ala Leu Leu Lys His Arg Phe Glu Ile Ile Glu
65              70                  75                  80

Gly Arg Asp Arg Thr Met Ala Trp Thr Val Val Asn Ser Ile Cys Asn
                85                  90                  95

Thr Thr Gly Ala Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
            115                 120                 125

Ile Tyr Tyr Leu Glu Lys Ala Asn Lys Ile Lys Ser Glu Lys Thr His
130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Gly Leu Trp Asp Ser Phe Arg
            180                 185                 190

Gln Ser Glu Arg Gly Glu Glu Thr Ile Glu Glu Arg Phe Glu Ile Thr
        195                 200                 205

Gly Thr Met Arg Arg Leu Ala Asp Gln Ser Leu Pro Pro Asn Phe Ser
    210                 215                 220

Cys Leu Glu Asn Phe Arg Ala Tyr Val Asp Gly Phe Glu Pro Asn Gly
225                 230                 235                 240

Tyr Ile Glu Gly Lys Leu Ser Gln Met Ser Lys Glu Val Asn Ala Arg
                245                 250                 255

Ile Glu Pro Phe Leu Arg Thr Thr Pro Arg Pro Ile Arg Leu Pro Asp
            260                 265                 270

Gly Pro Pro Cys Phe Gln Arg Ser Lys Phe Leu Leu Met Asp Ser Leu
        275                 280                 285

Lys Leu Ser Ile Glu Asp Pro Ser His Glu Gly Glu Gly Ile Pro Leu
    290                 295                 300

Tyr Asp Ala Ile Lys Cys Met Arg Thr Phe Phe Gly Trp Lys Glu Pro
305                 310                 315                 320

Ser Val Val Lys Pro His Gly Lys Gly Ile Asn Pro Asn Tyr Leu Leu
                325                 330                 335

Ser Trp Lys Gln Val Leu Ala Glu Leu Gln Asp Ile Glu Ser Glu Glu
            340                 345                 350

Lys Ile Pro Arg Thr Lys Asn Met Lys Lys Thr Ser Gln Leu Lys Trp
        355                 360                 365

Ala Leu Gly Glu Asn Met Ala Pro Glu Lys Val Asp Phe Asp Asp Cys
    370                 375                 380

Lys Asp Ile Ser Asp Leu Lys Gln Tyr Asp Ser Asp Glu Pro Glu Leu
385                 390                 395                 400

Arg Ser Leu Ser Ser Trp Ile Gln Asn Glu Phe Asn Lys Ala Cys Glu

```
            405                 410                 415
Leu Thr Asp Ser Ile Trp Ile Glu Leu Asp Glu Ile Gly Glu Asp Val
            420                 425                 430

Ala Pro Ile Glu His Ile Ala Ser Met Arg Arg Asn Tyr Phe Thr Ala
            435                 440                 445

Glu Val Ser His Cys Arg Ala Thr Glu Tyr Ile Met Lys Gly Val Tyr
            450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
                500                 505                 510

Asn Asp Thr Asp Val Val Asn Phe Val Ser Met Glu Phe Ser Leu Thr
                515                 520                 525

Asp Pro Arg Leu Glu Pro His Lys Trp Glu Lys Tyr Cys Val Leu Glu
                530                 535                 540

Ile Gly Asp Met Leu Leu Arg Ser Ala Ile Gly Gln Val Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
                580                 585                 590

Glu Ser Met Ile Glu Ala Glu Ser Ser Val Lys Glu Lys Asp Met Thr
                595                 600                 605

Lys Glu Phe Phe Glu Asn Arg Ser Glu Thr Trp Pro Ile Gly Glu Ser
610                 615                 620

Pro Lys Gly Val Glu Glu Gly Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Ile Val Gln Ala Leu
                660                 665                 670

Arg Asp Asn Leu Glu Pro Gly Thr Phe Asp Leu Gly Gly Leu Tyr Glu
                675                 680                 685

Ala Ile Glu Glu Cys Leu Ile Asn Asp Pro Trp Val Leu Leu Asn Ala
                690                 695                 700

Ser Trp Phe Asn Ser Phe Leu Thr His Ala Leu Arg
705                 710                 715

<210> SEQ ID NO 89
<211> LENGTH: 752
<212> TYPE: PRT
<213> ORGANISM: Influenza B virus

<400> SEQUENCE: 89

Met Asn Ile Asn Pro Tyr Phe Leu Phe Ile Asp Val Pro Ile Gln Ala
1               5                   10                  15

Ala Ile Ser Thr Thr Phe Pro Tyr Thr Gly Val Pro Pro Tyr Ser His
                20                  25                  30

Gly Thr Gly Thr Gly Tyr Thr Ile Asp Thr Val Ile Arg Thr His Glu
                35                  40                  45

Tyr Ser Asn Lys Gly Lys Gln Tyr Ile Ser Asp Val Thr Gly Cys Val
                50                  55                  60
```

```
Met Val Asp Pro Thr Asn Gly Pro Leu Pro Glu Asp Asn Glu Pro Ser
 65                  70                  75                  80

Ala Tyr Ala Gln Leu Asp Cys Val Leu Glu Ala Leu Asp Arg Met Asp
                 85                  90                  95

Glu Glu His Pro Gly Leu Phe Gln Ala Gly Ser Gln Asn Ala Met Glu
            100                 105                 110

Ala Leu Met Val Thr Thr Val Asp Lys Leu Thr Gln Gly Arg Gln Thr
            115                 120                 125

Phe Asp Trp Thr Val Cys Arg Asn Gln Pro Ala Ala Thr Ala Leu Asn
    130                 135                 140

Thr Thr Ile Thr Ser Phe Arg Leu Asn Asp Leu Asn Gly Ala Asp Lys
145                 150                 155                 160

Gly Gly Leu Val Pro Phe Cys Gln Asp Ile Ile Asp Ser Leu Asp Lys
                165                 170                 175

Pro Glu Met Ile Phe Phe Thr Val Lys Asn Ile Lys Lys Lys Leu Pro
            180                 185                 190

Ala Lys Asn Arg Lys Gly Phe Leu Ile Lys Arg Ile Pro Met Lys Val
            195                 200                 205

Lys Asp Arg Ile Thr Arg Val Glu Tyr Ile Lys Arg Ala Leu Ser Leu
    210                 215                 220

Asn Thr Met Thr Lys Asp Ala Glu Arg Gly Lys Leu Lys Arg Arg Ala
225                 230                 235                 240

Ile Ala Thr Ala Gly Ile Gln Ile Arg Gly Phe Val Leu Val Val Glu
                245                 250                 255

Asn Leu Ala Lys Asn Ile Cys Glu Asn Leu Glu Gln Ser Gly Leu Pro
            260                 265                 270

Val Gly Gly Asn Glu Lys Lys Ala Lys Leu Ser Asn Ala Val Ala Lys
            275                 280                 285

Met Leu Ser Asn Cys Pro Pro Gly Gly Ile Ser Met Thr Val Thr Gly
            290                 295                 300

Asp Asn Thr Lys Trp Asn Glu Cys Leu Asn Pro Arg Ile Phe Leu Ala
305                 310                 315                 320

Met Thr Glu Arg Ile Thr Arg Asp Ser Pro Ile Trp Phe Arg Asp Phe
                325                 330                 335

Cys Ser Ile Ala Pro Val Leu Phe Ser Asn Lys Ile Ala Arg Leu Gly
            340                 345                 350

Lys Gly Phe Met Ile Thr Ser Lys Thr Lys Arg Leu Lys Ala Gln Ile
            355                 360                 365

Pro Cys Pro Asp Leu Phe Asn Ile Pro Leu Glu Arg Tyr Asn Glu Glu
    370                 375                 380

Thr Arg Ala Lys Leu Lys Lys Leu Lys Pro Phe Phe Asn Glu Glu Gly
385                 390                 395                 400

Thr Ala Ser Leu Ser Pro Gly Met Met Met Gly Met Phe Asn Met Leu
                405                 410                 415

Ser Thr Val Leu Gly Val Ala Ala Leu Gly Ile Lys Asn Ile Gly Asn
            420                 425                 430

Lys Glu Tyr Leu Trp Asp Gly Leu Gln Ser Ser Asp Asp Phe Ala Leu
            435                 440                 445

Phe Val Asn Ala Lys Asp Glu Glu Thr Cys Met Glu Gly Ile Asn Asp
    450                 455                 460

Phe Tyr Arg Thr Cys Lys Leu Leu Gly Ile Asn Met Ser Lys Lys Lys
465                 470                 475                 480

Ser Tyr Cys Asn Glu Thr Gly Met Phe Glu Phe Thr Ser Met Phe Tyr
```

```
            485                 490                 495
Arg Asp Gly Phe Val Ser Asn Phe Ala Met Glu Leu Pro Ser Phe Gly
                500                 505                 510

Val Ala Gly Val Asn Glu Ser Ala Asp Met Ala Ile Gly Met Thr Ile
                515                 520                 525

Ile Lys Asn Asn Met Ile Asn Asn Gly Met Gly Pro Ala Thr Ala Gln
            530                 535                 540

Thr Ala Ile Gln Leu Phe Ile Ala Asp Tyr Arg Tyr Thr Tyr Lys Cys
545                 550                 555                 560

His Arg Gly Asp Ser Lys Val Glu Gly Lys Arg Met Lys Ile Ile Lys
                565                 570                 575

Glu Leu Trp Glu Asn Thr Lys Gly Arg Asp Gly Leu Leu Val Ala Asp
                580                 585                 590

Gly Gly Pro Asn Leu Tyr Asn Leu Arg Asn Leu His Ile Pro Glu Ile
                595                 600                 605

Ile Leu Lys Tyr Asn Ile Met Asp Pro Glu Tyr Lys Gly Arg Leu Leu
            610                 615                 620

His Pro Gln Asn Pro Phe Val Gly His Leu Ser Ile Glu Gly Ile Lys
625                 630                 635                 640

Glu Ala Asp Ile Thr Pro Ala His Gly Pro Ile Lys Lys Met Asp Tyr
                645                 650                 655

Asp Ala Val Ser Gly Thr His Ser Trp Arg Thr Lys Arg Asn Arg Ser
                660                 665                 670

Ile Leu Asn Thr Asp Gln Arg Asn Met Ile Leu Glu Glu Gln Cys Tyr
            675                 680                 685

Ala Lys Cys Cys Asn Leu Phe Glu Ala Cys Phe Asn Ser Ala Ser Tyr
            690                 695                 700

Arg Lys Pro Val Gly Gln His Ser Met Leu Glu Ala Met Ala His Arg
705                 710                 715                 720

Leu Arg Met Asp Ala Arg Leu Asp Tyr Glu Ser Gly Arg Met Ser Lys
                725                 730                 735

Glu Asp Phe Glu Lys Ala Met Ala His Leu Gly Glu Ile Gly Tyr Met
                740                 745                 750

<210> SEQ ID NO 90
<211> LENGTH: 759
<212> TYPE: PRT
<213> ORGANISM: Influenza A virus

<400> SEQUENCE: 90

Met Glu Arg Ile Lys Glu Leu Arg Asn Leu Met Ser Gln Ser Arg Thr
1               5                   10                  15

Arg Glu Ile Leu Thr Lys Thr Thr Val Asp His Met Ala Ile Ile Lys
                20                  25                  30

Lys Tyr Thr Ser Gly Arg Gln Glu Lys Asn Pro Ala Leu Arg Met Lys
            35                  40                  45

Trp Met Met Ala Met Lys Tyr Pro Ile Thr Ala Asp Lys Arg Ile Thr
        50                  55                  60

Glu Met Ile Pro Glu Arg Asn Glu Gln Gly Gln Thr Leu Trp Ser Lys
65                  70                  75                  80

Met Asn Asp Ala Gly Ser Asp Arg Val Met Val Ser Pro Leu Ala Val
                85                  90                  95

Thr Trp Trp Asn Arg Asn Gly Pro Met Thr Asn Thr Val His Tyr Pro
                100                 105                 110
```

-continued

```
Lys Ile Tyr Lys Thr Tyr Phe Glu Arg Val Glu Arg Leu Lys His Gly
            115                 120                 125
Thr Phe Gly Pro Val His Phe Arg Asn Gln Val Lys Ile Arg Arg Arg
        130                 135                 140
Val Asp Ile Asn Pro Gly His Ala Asp Leu Ser Ala Lys Glu Ala Gln
145                 150                 155                 160
Asp Val Ile Met Glu Val Val Phe Pro Asn Glu Val Gly Ala Arg Ile
                165                 170                 175
Leu Thr Ser Glu Ser Gln Leu Thr Ile Thr Lys Glu Lys Lys Glu Glu
            180                 185                 190
Leu Gln Asp Cys Lys Ile Ser Pro Leu Met Val Ala Tyr Met Leu Glu
        195                 200                 205
Arg Glu Leu Val Arg Lys Thr Arg Phe Leu Pro Val Ala Gly Gly Thr
    210                 215                 220
Ser Ser Val Tyr Ile Glu Val Leu His Leu Thr Gln Gly Thr Cys Trp
225                 230                 235                 240
Glu Gln Met Tyr Thr Pro Gly Gly Glu Val Lys Asn Asp Asp Val Asp
                245                 250                 255
Gln Ser Leu Ile Ile Ala Ala Arg Asn Ile Val Arg Arg Ala Ala Val
            260                 265                 270
Ser Ala Asp Pro Leu Ala Ser Leu Leu Glu Met Cys His Ser Thr Gln
        275                 280                 285
Ile Gly Gly Ile Arg Met Val Asp Ile Leu Lys Gln Asn Pro Thr Glu
    290                 295                 300
Glu Gln Ala Val Gly Ile Cys Lys Ala Ala Met Gly Leu Arg Ile Ser
305                 310                 315                 320
Ser Ser Phe Ser Phe Gly Gly Phe Thr Phe Lys Arg Thr Ser Gly Ser
                325                 330                 335
Ser Val Lys Arg Glu Glu Val Leu Thr Gly Asn Leu Gln Thr Leu
            340                 345                 350
Lys Ile Arg Val His Glu Gly Tyr Glu Glu Phe Thr Met Val Gly Arg
    355                 360                 365
Arg Ala Thr Ala Ile Leu Arg Lys Ala Thr Arg Arg Leu Ile Gln Leu
370                 375                 380
Ile Val Ser Gly Arg Asp Glu Gln Ser Ile Ala Glu Ala Ile Ile Val
385                 390                 395                 400
Ala Met Val Phe Ser Gln Glu Asp Cys Met Ile Lys Ala Val Arg Gly
                405                 410                 415
Asp Leu Asn Phe Val Asn Arg Ala Asn Gln Arg Leu Asn Pro Met His
            420                 425                 430
Gln Leu Leu Arg His Phe Gln Lys Asp Ala Lys Val Leu Phe Gln Asn
        435                 440                 445
Trp Gly Val Glu Pro Ile Asp Asn Val Met Gly Met Ile Gly Ile Leu
    450                 455                 460
Pro Asp Met Thr Pro Ser Ile Glu Met Ser Met Arg Gly Val Arg Ile
465                 470                 475                 480
Ser Lys Met Gly Val Asp Glu Tyr Ser Ser Thr Glu Arg Val Val Val
                485                 490                 495
Ser Ile Asp Arg Phe Leu Arg Val Arg Asp Gln Arg Gly Asn Val Leu
            500                 505                 510
Leu Ser Pro Glu Glu Val Ser Glu Thr Gln Gly Thr Glu Lys Leu Thr
        515                 520                 525
Ile Thr Tyr Ser Ser Ser Met Met Trp Glu Ile Asn Gly Pro Glu Ser
```

```
        530                 535                 540
Val Leu Val Asn Thr Tyr Gln Trp Ile Ile Arg Asn Trp Glu Thr Val
545                 550                 555                 560

Lys Ile Gln Trp Ser Gln Asn Pro Thr Met Leu Tyr Asn Lys Met Glu
                565                 570                 575

Phe Glu Pro Phe Gln Ser Leu Val Pro Lys Ala Ile Arg Gly Gln Tyr
                580                 585                 590

Ser Gly Phe Val Arg Thr Leu Phe Gln Gln Met Arg Asp Val Leu Gly
            595                 600                 605

Thr Phe Asp Thr Ala Gln Ile Ile Lys Leu Leu Pro Phe Ala Ala Ala
        610                 615                 620

Pro Pro Lys Gln Ser Arg Met Gln Phe Ser Ser Phe Thr Val Asn Val
625                 630                 635                 640

Arg Gly Ser Gly Met Arg Ile Leu Val Arg Gly Asn Ser Pro Val Phe
                645                 650                 655

Asn Tyr Asn Lys Ala Thr Lys Arg Leu Thr Val Leu Gly Lys Asp Ala
                660                 665                 670

Gly Thr Leu Thr Glu Asp Pro Asp Glu Gly Thr Ala Gly Val Glu Ser
            675                 680                 685

Ala Val Leu Arg Gly Phe Leu Ile Leu Gly Lys Glu Asp Arg Arg Tyr
        690                 695                 700

Gly Pro Ala Leu Ser Ile Asn Glu Leu Ser Asn Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
                740                 745                 750

Arg Ile Arg Met Ala Ile Asn
                755

<210> SEQ ID NO 91
<211> LENGTH: 109
<212> TYPE: PRT
<213> ORGANISM: Influenza B virus

<400> SEQUENCE: 91

Met Leu Glu Pro Leu Gln Ile Leu Ser Ile Cys Ser Phe Ile Leu Ser
1               5                   10                  15

Ala Leu His Phe Met Ala Trp Thr Ile Gly His Leu Asn Gln Ile Lys
            20                  25                  30

Arg Gly Val Asn Leu Lys Ile Gln Ile Arg Asn Pro Asn Lys Glu Ala
        35                  40                  45

Ile Asn Arg Glu Val Ser Ile Leu Arg His Asn Tyr Gln Lys Glu Ile
    50                  55                  60

Gln Ala Lys Glu Thr Met Lys Lys Ile Leu Ser Asp Asn Met Glu Val
65                  70                  75                  80

Leu Gly Asp His Ile Val Val Glu Gly Leu Ser Thr Asp Glu Ile Ile
                85                  90                  95

Lys Met Gly Glu Thr Val Leu Glu Val Glu Glu Leu Gln
            100                 105

<210> SEQ ID NO 92
<211> LENGTH: 100
<212> TYPE: PRT
<213> ORGANISM: Influenza B virus
```

<400> SEQUENCE: 92

Met Asn Ala Thr Phe Asn Cys Thr Asn Ile Asn Pro Ile Thr His
1               5                   10                  15

Ile Arg Gly Ser Ile Ile Ile Thr Ile Cys Val Ser Leu Ile Val Ile
            20                  25                  30

Leu Ile Val Phe Gly Cys Ile Ala Lys Ile Phe Ile Asn Lys Asn Asn
                35                  40                  45

Cys Thr Asn Asn Val Ile Arg Val His Lys Arg Ile Lys Cys Pro Asp
            50                  55                  60

Cys Glu Pro Phe Cys Asn Lys Arg Asp Asp Ile Ser Thr Pro Arg Ala
65                  70                  75                  80

Gly Val Asp Ile Pro Ser Phe Ile Leu Pro Gly Leu Asn Leu Ser Glu
                85                  90                  95

Gly Thr Pro Asn
            100

<210> SEQ ID NO 93
<211> LENGTH: 498
<212> TYPE: PRT
<213> ORGANISM: Influenza A virus

<400> SEQUENCE: 93

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asn Gly Lys Trp Met Arg Glu Leu Ile Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Met Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Val Arg Met Ile Lys Arg Gly Ile Asn Asp Arg Asn Phe Trp Arg
        195                 200                 205

Gly Glu Asn Gly Arg Lys Thr Arg Ile Ala Tyr Glu Arg Met Cys Asn
    210                 215                 220

Ile Leu Lys Gly Lys Phe Gln Thr Ala Ala Gln Lys Ala Met Met Asp
225                 230                 235                 240

Gln Val Arg Glu Ser Arg Asp Pro Gly Asn Ala Glu Phe Glu Asp Leu
                245                 250                 255

```
Thr Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Ser Gly
        275                 280                 285

Tyr Asp Phe Glu Arg Glu Gly Tyr Ser Leu Val Gly Ile Asp Pro Phe
    290                 295                 300

Arg Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Leu Ser Phe Ile Lys Gly Thr Lys Val
            340                 345                 350

Val Pro Arg Gly Lys Leu Ser Thr Arg Gly Val Gln Ile Ala Ser Asn
        355                 360                 365

Glu Asn Met Glu Thr Met Glu Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Ile Gln Pro Thr Phe Ser Val Gln Arg
                405                 410                 415

Asn Leu Pro Phe Asp Arg Thr Thr Val Met Ala Ala Phe Thr Gly Asn
            420                 425                 430

Thr Glu Gly Arg Thr Ser Asp Met Arg Thr Glu Ile Ile Arg Met Met
        435                 440                 445

Glu Ser Ala Arg Pro Glu Asp Val Ser Phe Gln Gly Arg Gly Val Phe
    450                 455                 460

Glu Leu Ser Asp Glu Lys Ala Ala Ser Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn

<210> SEQ ID NO 94
<211> LENGTH: 548
<212> TYPE: PRT
<213> ORGANISM: Human herpesvirus 5

<400> SEQUENCE: 94

Met Glu Ser Arg Gly Arg Arg Cys Pro Glu Met Ile Ser Val Leu Gly
1               5                   10                  15

Pro Ile Ser Gly His Val Leu Lys Ala Val Phe Ser Arg Gly Asp Thr
            20                  25                  30

Pro Val Leu Pro His Glu Thr Arg Leu Leu Gln Thr Gly Ile His Val
        35                  40                  45

Arg Val Ser Gln Pro Ser Leu Ile Leu Val Ser Gln Tyr Thr Pro Asp
    50                  55                  60

Ser Thr Pro Cys His Arg Gly Asp Asn Gln Leu Gln Val Gln His Thr
65                  70                  75                  80

Tyr Phe Thr Gly Ser Glu Val Glu Asn Val Ser Val Asn Glu Pro Met
                85                  90                  95

Ser Ile Tyr Val Tyr Ala Leu Pro Leu Lys Met Leu Asn Ile Pro Ser
            100                 105                 110

Ile Asn Val His His Tyr Pro Ser Ala Ala Glu Arg Lys His Arg His
        115                 120                 125
```

```
Leu Pro Val Ala Asp Ala Val Ile His Ala Ser Gly Lys Gln Met Trp
130                 135                 140

Gln Ala Arg Leu Thr Val Ser Gly Leu Ala Trp Thr Arg Gln Gln Asn
145                 150                 155                 160

Gln Trp Lys Glu Pro Asp Val Tyr Tyr Thr Ser Ala Phe Val Phe Pro
                165                 170                 175

Thr Lys Asp Val Ala Leu Arg His Val Val Cys Ala His Glu Leu Val
                180                 185                 190

Cys Ser Met Glu Asn Thr Arg Ala Thr Lys Met Gln Val Ile Gly Asp
                195                 200                 205

Gln Tyr Val Lys Val Tyr Leu Glu Ser Phe Cys Glu Asp Val Pro Ser
210                 215                 220

Gly Lys Leu Phe Met His Val Thr Leu Gly Ser Asp Val Glu Glu Asp
225                 230                 235                 240

Leu Thr Met Thr Arg Asn Pro Gln Pro Phe Met Arg Pro His Glu Arg
                245                 250                 255

Asn Gly Phe Thr Val Leu Cys Pro Lys Asn Met Ile Ile Lys Pro Gly
                260                 265                 270

Lys Ile Ser His Ile Met Leu Asp Val Ala Phe Thr Ser His Glu His
                275                 280                 285

Phe Gly Leu Leu Cys Pro Lys Ser Ile Pro Gly Leu Ser Ile Ser Gly
                290                 295                 300

Asn Leu Leu Met Asn Gly Gln Gln Ile Phe Leu Glu Val Gln Ala Ile
305                 310                 315                 320

Arg Glu Thr Val Glu Leu Arg Gln Tyr Asp Pro Val Ala Ala Leu Phe
                325                 330                 335

Phe Phe Asp Ile Asp Leu Leu Leu Gln Arg Gly Pro Gln Tyr Ser Glu
                340                 345                 350

His Pro Thr Phe Thr Ser Gln Tyr Arg Ile Gln Gly Lys Leu Glu Tyr
                355                 360                 365

Arg His Thr Trp Asp Arg His Asp Glu Gly Ala Ala Gln Gly Asp Asp
                370                 375                 380

Asp Val Trp Thr Ser Gly Ser Asp Ser Asp Glu Glu Leu Val Thr Thr
385                 390                 395                 400

Glu Arg Lys Thr Pro Arg Val Thr Gly Gly Gly Ala Met Ala Gly Ala
                405                 410                 415

Ser Thr Ser Ala Gly Arg Lys Arg Lys Ser Ala Ser Ser Ala Thr Ala
                420                 425                 430

Cys Thr Ser Gly Val Met Thr Arg Gly Arg Leu Lys Ala Glu Ser Thr
                435                 440                 445

Val Ala Pro Glu Glu Asp Thr Asp Glu Asp Ser Asp Asn Glu Ile His
450                 455                 460

Asn Pro Ala Val Phe Thr Trp Pro Pro Trp Gln Ala Gly Ile Leu Ala
465                 470                 475                 480

Arg Asn Leu Val Pro Met Val Ala Thr Val Gln Gly Gln Asn Leu Lys
                485                 490                 495

Tyr Gln Glu Phe Phe Trp Asp Ala Asn Asp Ile Tyr Arg Ile Phe Ala
                500                 505                 510

Glu Leu Glu Gly Val Trp Gln Pro Ala Ala Gln Pro Lys Arg Arg Arg
                515                 520                 525

His Arg Gln Asp Ala Leu Pro Gly Pro Cys Ile Ala Ser Thr Pro Lys
                530                 535                 540

Lys His Arg Gly
```

545

```
<210> SEQ ID NO 95
<211> LENGTH: 561
<212> TYPE: PRT
<213> ORGANISM: Human herpesvirus 5

<400> SEQUENCE: 95
```

| | | | | | | | | | | | | | | |
|---|---|---|---|---|---|---|---|---|---|---|---|---|---|---|
| Met | Glu | Ser | Arg | Gly | Arg | Arg | Cys | Pro | Glu | Met | Ile | Ser | Val | Leu | Gly |
| 1 | | | | 5 | | | | | 10 | | | | | 15 | |
| Pro | Ile | Ser | Gly | His | Val | Leu | Lys | Ala | Val | Phe | Ser | Arg | Gly | Asp | Thr |
| | | | 20 | | | | | 25 | | | | | 30 | | |
| Pro | Val | Leu | Pro | His | Glu | Thr | Arg | Leu | Leu | Gln | Thr | Gly | Ile | His | Val |
| | | | 35 | | | | 40 | | | | | 45 | | | |
| Arg | Val | Ser | Gln | Pro | Ser | Leu | Ile | Leu | Val | Ser | Gln | Tyr | Thr | Pro | Asp |
| | 50 | | | | | 55 | | | | | 60 | | | | |
| Ser | Thr | Pro | Cys | His | Arg | Gly | Asp | Asn | Gln | Leu | Gln | Val | Gln | His | Thr |
| 65 | | | | | 70 | | | | 75 | | | | | 80 | |
| Tyr | Phe | Thr | Gly | Ser | Glu | Val | Glu | Asn | Val | Ser | Val | Asn | Val | His | Asn |
| | | | | 85 | | | | 90 | | | | | 95 | | |
| Pro | Thr | Gly | Arg | Ser | Ile | Cys | Pro | Ser | Gln | Glu | Pro | Met | Ser | Ile | Tyr |
| | | | 100 | | | | | 105 | | | | | 110 | | |
| Val | Tyr | Ala | Leu | Pro | Leu | Lys | Met | Leu | Asn | Ile | Pro | Ser | Ile | Asn | Val |
| | | 115 | | | | | 120 | | | | | 125 | | | |
| His | His | Tyr | Pro | Ser | Ala | Ala | Glu | Arg | Lys | His | Arg | His | Leu | Pro | Val |
| | 130 | | | | | 135 | | | | | 140 | | | | |
| Ala | Asp | Ala | Val | Ile | His | Ala | Ser | Gly | Lys | Gln | Met | Trp | Gln | Ala | Arg |
| 145 | | | | | 150 | | | | | 155 | | | | | 160 |
| Leu | Thr | Val | Ser | Gly | Leu | Ala | Trp | Thr | Arg | Gln | Gln | Asn | Gln | Trp | Lys |
| | | | | 165 | | | | | 170 | | | | | 175 | |
| Glu | Pro | Asp | Val | Tyr | Tyr | Thr | Ser | Ala | Phe | Val | Phe | Pro | Thr | Lys | Asp |
| | | | 180 | | | | | 185 | | | | | 190 | | |
| Val | Ala | Leu | Arg | His | Val | Val | Cys | Ala | His | Glu | Leu | Val | Cys | Ser | Met |
| | | 195 | | | | | 200 | | | | | 205 | | | |
| Glu | Asn | Thr | Arg | Ala | Thr | Lys | Met | Gln | Val | Ile | Gly | Asp | Gln | Tyr | Val |
| | 210 | | | | | 215 | | | | | 220 | | | | |
| Lys | Val | Tyr | Leu | Glu | Ser | Phe | Cys | Glu | Asp | Val | Pro | Ser | Gly | Lys | Leu |
| 225 | | | | | 230 | | | | | 235 | | | | | 240 |
| Phe | Met | His | Val | Thr | Leu | Gly | Ser | Asp | Val | Glu | Glu | Asp | Leu | Thr | Met |
| | | | | 245 | | | | | 250 | | | | | 255 | |
| Thr | Arg | Asn | Pro | Gln | Pro | Phe | Met | Arg | Pro | His | Glu | Arg | Asn | Gly | Phe |
| | | | 260 | | | | | 265 | | | | | 270 | | |
| Thr | Val | Leu | Cys | Pro | Lys | Asn | Met | Ile | Ile | Lys | Pro | Gly | Lys | Ile | Ser |
| | | 275 | | | | | 280 | | | | | 285 | | | |
| His | Ile | Met | Leu | Asp | Val | Ala | Phe | Thr | Ser | His | Glu | His | Phe | Gly | Leu |
| | 290 | | | | | 295 | | | | | 300 | | | | |
| Leu | Cys | Pro | Lys | Ser | Ile | Pro | Gly | Leu | Ser | Ile | Ser | Gly | Asn | Leu | Leu |
| 305 | | | | | 310 | | | | | 315 | | | | | 320 |
| Met | Asn | Gly | Gln | Gln | Ile | Phe | Leu | Glu | Val | Gln | Ala | Ile | Arg | Glu | Thr |
| | | | | 325 | | | | | 330 | | | | | 335 | |
| Val | Glu | Leu | Arg | Gln | Tyr | Asp | Pro | Val | Ala | Ala | Leu | Phe | Phe | Phe | Asp |
| | | | 340 | | | | | 345 | | | | | 350 | | |
| Ile | Asp | Leu | Leu | Leu | Gln | Arg | Gly | Pro | Gln | Tyr | Ser | Glu | His | Pro | Thr |
| | | 355 | | | | | 360 | | | | | 365 | | | |

```
Phe Thr Ser Gln Tyr Arg Ile Gln Gly Lys Leu Glu Tyr Arg His Thr
370                 375                 380

Trp Asp Arg His Asp Glu Gly Ala Ala Gln Gly Asp Asp Val Trp
385                 390                 395                 400

Thr Ser Gly Ser Asp Ser Asp Glu Glu Leu Val Thr Thr Glu Arg Lys
                405                 410                 415

Thr Pro Arg Val Thr Gly Gly Ala Met Ala Gly Ala Ser Thr Ser
                420                 425                 430

Ala Gly Arg Lys Arg Lys Ser Ala Ser Ser Ala Thr Ala Cys Thr Ser
            435                 440                 445

Gly Val Met Thr Arg Gly Arg Leu Lys Ala Glu Ser Thr Val Ala Pro
            450                 455                 460

Glu Glu Asp Thr Asp Glu Asp Ser Asp Asn Glu Ile His Asn Pro Ala
465                 470                 475                 480

Val Phe Thr Trp Pro Pro Trp Gln Ala Gly Ile Leu Ala Arg Asn Leu
                485                 490                 495

Val Pro Met Val Ala Thr Val Gln Gly Gln Asn Leu Lys Tyr Gln Glu
                500                 505                 510

Phe Phe Trp Asp Ala Asn Asp Ile Tyr Arg Ile Phe Ala Glu Leu Glu
                515                 520                 525

Gly Val Trp Gln Pro Ala Ala Gln Pro Lys Arg Arg Arg His Arg Gln
            530                 535                 540

Asp Ala Leu Pro Gly Pro Cys Ile Ala Ser Thr Pro Lys Lys His Arg
545                 550                 555                 560

Gly

<210> SEQ ID NO 96
<211> LENGTH: 551
<212> TYPE: PRT
<213> ORGANISM: Human herpesvirus 5

<400> SEQUENCE: 96

Met Ala Ser Val Leu Gly Pro Ile Ser Gly His Val Leu Lys Ala Val
1               5                   10                  15

Phe Ser Arg Gly Asp Thr Pro Val Leu Pro His Glu Thr Arg Leu Leu
                20                  25                  30

Gln Thr Gly Ile His Val Arg Val Ser Gln Pro Ser Leu Ile Leu Val
            35                  40                  45

Ser Gln Tyr Thr Pro Asp Ser Thr Pro Cys His Arg Gly Asp Asn Gln
    50                  55                  60

Leu Gln Val Gln His Thr Tyr Phe Thr Gly Ser Glu Val Glu Asn Val
65                  70                  75                  80

Ser Val Asn Val His Asn Pro Thr Gly Arg Ser Ile Cys Pro Ser Gln
                85                  90                  95

Glu Pro Met Ser Ile Tyr Val Tyr Ala Leu Pro Leu Lys Met Leu Asn
                100                 105                 110

Ile Pro Ser Ile Asn Val His His Tyr Pro Ser Ala Ala Glu Arg Lys
            115                 120                 125

His Arg His Leu Pro Val Ala Asp Ala Val Ile His Ala Ser Gly Lys
        130                 135                 140

Gln Met Trp Gln Ala Arg Leu Thr Val Ser Gly Leu Ala Trp Thr Arg
145                 150                 155                 160

Gln Gln Asn Gln Trp Lys Glu Pro Asp Val Tyr Tyr Thr Ser Ala Phe
                165                 170                 175
```

```
Val Phe Pro Thr Lys Asp Val Ala Leu Arg His Val Val Cys Ala His
            180                 185                 190

Glu Leu Val Cys Ser Met Glu Asn Thr Arg Ala Thr Lys Met Gln Val
            195                 200                 205

Ile Gly Asp Gln Tyr Val Lys Val Tyr Leu Glu Ser Phe Cys Glu Asp
            210                 215                 220

Val Pro Ser Gly Lys Leu Phe Met His Val Thr Leu Gly Ser Asp Val
225                 230                 235                 240

Glu Glu Asp Leu Thr Met Thr Arg Asn Pro Gln Pro Phe Met Arg Pro
                245                 250                 255

His Glu Arg Asn Gly Phe Thr Val Leu Cys Pro Lys Asn Met Ile Ile
            260                 265                 270

Lys Pro Gly Lys Ile Ser His Ile Met Leu Asp Val Ala Phe Thr Ser
            275                 280                 285

His Glu His Phe Gly Leu Leu Cys Pro Lys Ser Ile Pro Gly Leu Ser
            290                 295                 300

Ile Ser Gly Asn Leu Leu Met Asn Gly Gln Gln Ile Phe Leu Glu Val
305                 310                 315                 320

Gln Ala Ile Arg Glu Thr Val Glu Leu Arg Gln Tyr Asp Pro Val Ala
                325                 330                 335

Ala Leu Phe Phe Phe Asp Ile Asp Leu Leu Leu Gln Arg Gly Pro Gln
            340                 345                 350

Tyr Ser Glu His Pro Thr Phe Thr Ser Gln Tyr Arg Ile Gln Gly Lys
            355                 360                 365

Leu Glu Tyr Arg His Thr Trp Asp Arg His Asp Glu Gly Ala Ala Gln
            370                 375                 380

Gly Asp Asp Asp Val Trp Thr Ser Gly Ser Asp Ser Asp Glu Glu Leu
385                 390                 395                 400

Val Thr Thr Glu Arg Lys Thr Pro Arg Val Thr Gly Gly Ala Met
                405                 410                 415

Ala Gly Ala Ser Thr Ser Ala Gly Arg Lys Arg Lys Ser Ala Ser Ser
            420                 425                 430

Ala Thr Ala Cys Thr Ala Gly Val Met Thr Arg Gly Arg Leu Lys Ala
            435                 440                 445

Glu Ser Thr Val Ala Pro Glu Glu Asp Thr Asp Glu Asp Ser Asp Asn
450                 455                 460

Glu Ile His Asn Pro Ala Val Phe Thr Trp Pro Trp Gln Ala Gly
465                 470                 475                 480

Ile Leu Ala Arg Asn Leu Val Pro Met Val Ala Thr Val Gln Gly Gln
            485                 490                 495

Asn Leu Lys Tyr Gln Glu Phe Phe Trp Asp Ala Asn Asp Ile Tyr Arg
            500                 505                 510

Ile Phe Ala Glu Leu Glu Gly Val Trp Gln Pro Ala Ala Gln Pro Lys
            515                 520                 525

Arg Arg Arg His Arg Gln Asp Ala Leu Pro Gly Pro Cys Ile Ala Ser
            530                 535                 540

Thr Pro Lys Lys His Arg Gly
545                 550

<210> SEQ ID NO 97
<211> LENGTH: 551
<212> TYPE: PRT
<213> ORGANISM: Human herpesvirus 5

<400> SEQUENCE: 97
```

```
Met Ala Ser Val Leu Gly Pro Ile Ser Gly His Val Leu Lys Ala Val
1               5                   10                  15

Phe Ser Arg Gly Asp Thr Pro Val Leu Pro His Glu Thr Arg Leu Leu
            20                  25                  30

Gln Thr Gly Ile His Val Arg Val Ser Gln Pro Ser Leu Ile Leu Val
            35                  40                  45

Ser Gln Tyr Thr Pro Asp Ser Thr Pro Cys His Arg Gly Asp Asn Gln
50                      55                  60

Leu Gln Val Gln His Thr Tyr Phe Thr Gly Ser Glu Val Glu Asn Val
65                  70                  75                  80

Ser Val Asn Val His Asn Pro Thr Gly Arg Ser Ile Cys Pro Ser Gln
                85                  90                  95

Glu Pro Met Ser Ile Tyr Val Tyr Ala Leu Pro Leu Lys Met Leu Asn
                100                 105                 110

Ile Pro Ser Ile Asn Val His His Tyr Pro Ser Ala Ala Glu Arg Lys
            115                 120                 125

His Arg His Leu Pro Val Ala Asp Ala Val Ile His Ala Ser Gly Lys
        130                 135                 140

Gln Met Trp Gln Ala Arg Leu Thr Val Ser Gly Leu Ala Trp Thr Arg
145                 150                 155                 160

Gln Gln Asn Gln Trp Lys Glu Pro Asp Val Tyr Tyr Thr Ser Ala Phe
                165                 170                 175

Val Phe Pro Thr Lys Asp Val Ala Leu Arg His Val Val Cys Ala His
            180                 185                 190

Glu Leu Val Cys Ser Met Glu Asn Thr Arg Ala Thr Lys Met Gln Val
            195                 200                 205

Ile Gly Asp Gln Tyr Val Lys Val Tyr Leu Glu Ser Phe Cys Glu Asp
210                 215                 220

Val Pro Ser Gly Lys Leu Phe Met His Val Thr Leu Gly Ser Asp Val
225                 230                 235                 240

Glu Glu Asp Leu Thr Met Thr Arg Asn Pro Gln Pro Phe Met Arg Pro
            245                 250                 255

His Glu Arg Asn Gly Phe Thr Val Leu Cys Pro Lys Asn Met Ile Ile
            260                 265                 270

Lys Pro Gly Lys Ile Ser His Ile Met Leu Asp Val Ala Phe Thr Ser
275                 280                 285

His Glu His Phe Gly Leu Leu Cys Pro Lys Ser Ile Pro Gly Leu Ser
        290                 295                 300

Ile Ser Gly Asn Leu Leu Met Asn Gly Gln Gln Ile Phe Leu Glu Val
305                 310                 315                 320

Gln Ala Ile Arg Glu Thr Val Glu Leu Arg Gln Tyr Asp Pro Val Ala
                325                 330                 335

Ala Leu Phe Phe Phe Asp Ile Asp Leu Leu Gln Arg Gly Pro Gln
                340                 345                 350

Tyr Ser Glu His Pro Thr Phe Thr Ser Gln Tyr Arg Ile Gln Gly Lys
            355                 360                 365

Leu Glu Tyr Arg His Thr Trp Asp Arg His Asp Glu Gly Ala Ala Gln
        370                 375                 380

Gly Asp Asp Asp Val Trp Thr Ser Gly Ser Asp Ser Asp Glu Glu Leu
385                 390                 395                 400

Val Thr Thr Glu Arg Lys Thr Pro Arg Val Thr Gly Gly Gly Ala Met
                405                 410                 415
```

```
Ala Gly Ala Ser Thr Ser Ala Gly Arg Lys Arg Lys Ser Ala Ser Ser
            420                 425                 430

Ala Thr Ala Cys Thr Ala Gly Val Met Thr Arg Gly Arg Leu Lys Ala
            435                 440                 445

Glu Ser Thr Val Ala Pro Glu Glu Asp Thr Asp Glu Asp Ser Asp Asn
450                 455                 460

Glu Ile His Asn Pro Ala Val Phe Thr Trp Pro Pro Trp Gln Ala Gly
465                 470                 475                 480

Ile Leu Ala Arg Asn Leu Val Pro Met Val Ala Thr Val Gln Gly Gln
            485                 490                 495

Asn Leu Lys Tyr Gln Glu Phe Phe Trp Asp Ala Asn Asp Ile Tyr Arg
            500                 505                 510

Ile Phe Ala Glu Leu Glu Gly Val Trp Gln Pro Ala Ala Gln Pro Lys
            515                 520                 525

Arg Arg Arg His Arg Gln Asp Ala Leu Pro Gly Pro Cys Ile Ala Ser
            530                 535                 540

Thr Pro Lys Lys His Arg Gly
545                 550

<210> SEQ ID NO 98
<211> LENGTH: 353
<212> TYPE: PRT
<213> ORGANISM: Human T-lymphotropic virus 1]

<400> SEQUENCE: 98

Met Ala His Phe Pro Gly Phe Gly Gln Ser Leu Leu Phe Gly Tyr Pro
1               5                   10                  15

Val Tyr Val Phe Gly Asp Cys Val Gln Gly Asp Trp Cys Pro Ile Ser
            20                  25                  30

Gly Gly Leu Cys Ser Ala Arg Leu His Arg His Ala Leu Leu Ala Thr
            35                  40                  45

Cys Pro Glu His Gln Ile Thr Trp Asp Pro Ile Asp Gly Arg Val Ile
50                  55                  60

Gly Ser Ala Leu Gln Phe Leu Ile Pro Arg Leu Pro Ser Phe Pro Thr
65                  70                  75                  80

Gln Arg Thr Ser Lys Thr Leu Lys Val Leu Thr Pro Pro Ile Thr His
            85                  90                  95

Thr Thr Pro Asn Ile Pro Pro Ser Phe Leu Gln Ala Met Arg Lys Tyr
            100                 105                 110

Ser Pro Phe Arg Asn Gly Tyr Met Glu Pro Thr Leu Gly Gln His Leu
            115                 120                 125

Pro Thr Leu Ser Phe Pro Asp Pro Gly Leu Arg Pro Gln Asn Leu Tyr
            130                 135                 140

Thr Leu Trp Gly Gly Ser Val Val Cys Met Tyr Leu Tyr Gln Leu Ser
145                 150                 155                 160

Pro Pro Ile Thr Trp Pro Leu Leu Pro His Val Ile Phe Cys His Pro
            165                 170                 175

Gly Gln Leu Gly Ala Phe Leu Thr Asn Val Pro Tyr Lys Arg Ile Glu
            180                 185                 190

Lys Leu Leu Tyr Lys Ile Ser Leu Thr Thr Gly Ala Leu Ile Ile Leu
            195                 200                 205

Pro Glu Asp Cys Leu Pro Thr Thr Leu Phe Gln Pro Ala Arg Ala Pro
            210                 215                 220

Val Thr Leu Thr Ala Trp Gln Asn Gly Leu Leu Pro Phe His Ser Thr
225                 230                 235                 240
```

```
Leu Thr Thr Pro Gly Leu Ile Trp Thr Phe Thr Asp Gly Thr Pro Met
            245                 250                 255

Ile Ser Gly Pro Cys Pro Lys Asp Gly Gln Pro Ser Leu Val Leu Gln
            260                 265                 270

Ser Ser Ser Phe Ile Phe His Lys Phe Gln Thr Lys Ala Tyr His Pro
            275                 280                 285

Ser Phe Leu Leu Ser His Gly Leu Ile Gln Tyr Ser Ser Phe His Asn
            290                 295                 300

Leu His Leu Leu Phe Glu Glu Tyr Thr Asn Ile Pro Ile Ser Leu Leu
305                 310                 315                 320

Phe Asn Glu Lys Glu Ala Asp Asp Asn Asp His Glu Pro Gln Ile Ser
            325                 330                 335

Pro Gly Gly Leu Glu Pro Leu Ser Glu Lys His Phe Arg Glu Thr Glu
            340                 345                 350

Val

<210> SEQ ID NO 99
<211> LENGTH: 345
<212> TYPE: PRT
<213> ORGANISM: Human T-lymphotropic virus 1]

<400> SEQUENCE: 99

Met Ala His Phe Pro Gly Phe Gly Gln Ser Leu Leu Tyr Gly Tyr Pro
1               5                   10                  15

Val Tyr Val Phe Gly Asp Cys Val Gln Ala Asp Trp Cys Pro Ile Ser
            20                  25                  30

Gly Gly Leu Cys Ser Pro Arg Leu His Arg His Ala Leu Leu Ala Thr
            35                  40                  45

Cys Pro Glu His Gln Ile Thr Trp Asp Pro Ile Asp Gly Arg Val Val
        50                  55                  60

Gly Ser Pro Leu Gln Tyr Leu Ile Pro Arg Leu Pro Ser Phe Pro Thr
65                  70                  75                  80

Gln Arg Thr Ser Lys Thr Leu Lys Val Leu Thr Pro Pro Thr Thr Pro
            85                  90                  95

Val Thr Pro Lys Val Pro Ser Phe Phe Gln Ser Val Arg Arg His
            100                 105                 110

Ser Pro Tyr Arg Asn Gly Cys Leu Glu Thr Thr Leu Gly Glu Gln Leu
            115                 120                 125

Pro Ser Leu Ala Phe Pro Glu Pro Gly Leu Arg Pro Gln Asn Val Tyr
            130                 135                 140

Thr Ile Trp Gly Lys Thr Ile Val Cys Leu Tyr Ile Tyr Gln Leu Ser
145                 150                 155                 160

Pro Pro Met Thr Trp Pro Leu Ile Pro His Val Ile Phe Cys Asn Pro
            165                 170                 175

Arg Gln Leu Gly Ala Phe Leu Ser Asn Val Pro Pro Lys Arg Leu Glu
            180                 185                 190

Glu Leu Leu Tyr Lys Leu Tyr Leu His Thr Gly Ala Ile Ile Ile Leu
            195                 200                 205

Pro Glu Asp Ala Leu Pro Thr Thr Leu Phe Gln Pro Val Arg Ala Pro
            210                 215                 220

Cys Val Gln Thr Thr Trp Asn Thr Gly Leu Leu Pro Tyr Gln Pro Asn
225                 230                 235                 240

Leu Thr Thr Pro Gly Leu Ile Trp Thr Phe Asn Asp Gly Ser Pro Met
            245                 250                 255
```

Ile Ser Gly Pro Cys Pro Lys Ala Gly Gln Pro Ser Leu Val Val Gln
                260                 265                 270

Ser Ser Leu Leu Ile Phe Glu Arg Phe Gln Thr Lys Ala Tyr His Pro
            275                 280                 285

Ser Tyr Leu Leu Ser His Gln Leu Ile Gln Tyr Ser Ser Phe His His
        290                 295                 300

Leu Tyr Leu Leu Phe Asp Glu Tyr Thr Thr Ile Pro Phe Ser Leu Leu
305                 310                 315                 320

Phe Lys Glu Lys Glu Gly Asp Asp Arg Asp Asn Asp Pro Leu Pro Gly
                325                 330                 335

Ala Thr Ala Ser Pro Gln Gly Gln Asn
            340                 345

<210> SEQ ID NO 100

<400> SEQUENCE: 100

000

<210> SEQ ID NO 101
<211> LENGTH: 9
<212> TYPE: PRT
<213> ORGANISM: Artificial sequence
<220> FEATURE:
<223> OTHER INFORMATION: short peptide

<400> SEQUENCE: 101

Ser Thr Asn Arg Gln Ser Gly Arg Gln
1               5

<210> SEQ ID NO 102
<211> LENGTH: 9
<212> TYPE: PRT
<213> ORGANISM: Artificial sequence
<220> FEATURE:
<223> OTHER INFORMATION: short peptide

<400> SEQUENCE: 102

Leu Leu Phe Gly Tyr Pro Val Tyr Val
1               5

<210> SEQ ID NO 103
<211> LENGTH: 10
<212> TYPE: PRT
<213> ORGANISM: Artificial sequence
<220> FEATURE:
<223> OTHER INFORMATION: short peptide

<400> SEQUENCE: 103

Gly Leu Ser Pro Thr Val Trp Leu Ser Val
1               5                   10

<210> SEQ ID NO 104
<211> LENGTH: 9
<212> TYPE: PRT
<213> ORGANISM: Artificial sequence
<220> FEATURE:
<223> OTHER INFORMATION: short peptide

<400> SEQUENCE: 104

Ala Met Asp Gly Thr Met Ser Gln Val
1               5

```
<210> SEQ ID NO 105
<211> LENGTH: 9
<212> TYPE: PRT
<213> ORGANISM: Artificial sequence
<220> FEATURE:
<223> OTHER INFORMATION: short peptide

<400> SEQUENCE: 105

Tyr Ala Asp Gly Thr Met Ser Gln Val
1               5

<210> SEQ ID NO 106
<211> LENGTH: 9
<212> TYPE: PRT
<213> ORGANISM: Artificial sequence
<220> FEATURE:
<223> OTHER INFORMATION: short peptide

<400> SEQUENCE: 106

Tyr Met Ala Gly Thr Met Ser Gln Val
1               5

<210> SEQ ID NO 107
<211> LENGTH: 9
<212> TYPE: PRT
<213> ORGANISM: Artificial sequence
<220> FEATURE:
<223> OTHER INFORMATION: short peptide

<400> SEQUENCE: 107

Tyr Met Asp Ala Thr Met Ser Gln Val
1               5

<210> SEQ ID NO 108
<211> LENGTH: 9
<212> TYPE: PRT
<213> ORGANISM: Artificial sequence
<220> FEATURE:
<223> OTHER INFORMATION: short peptide

<400> SEQUENCE: 108

Tyr Met Asp Gly Ala Met Ser Gln Val
1               5

<210> SEQ ID NO 109
<211> LENGTH: 9
<212> TYPE: PRT
<213> ORGANISM: Artificial sequence
<220> FEATURE:
<223> OTHER INFORMATION: short peptide

<400> SEQUENCE: 109

Tyr Met Asp Gly Thr Ala Ser Gln Val
1               5

<210> SEQ ID NO 110
<211> LENGTH: 9
<212> TYPE: PRT
<213> ORGANISM: Artificial sequence
<220> FEATURE:
<223> OTHER INFORMATION: short peptide

<400> SEQUENCE: 110

Tyr Met Asp Gly Thr Met Ala Gln Val
1               5

<210> SEQ ID NO 111
```

```
<211> LENGTH: 9
<212> TYPE: PRT
<213> ORGANISM: Artificial sequence
<220> FEATURE:
<223> OTHER INFORMATION: short peptide

<400> SEQUENCE: 111

Tyr Met Asp Gly Thr Met Ser Ala Val
1               5

<210> SEQ ID NO 112
<211> LENGTH: 9
<212> TYPE: PRT
<213> ORGANISM: Artificial sequence
<220> FEATURE:
<223> OTHER INFORMATION: short peptide

<400> SEQUENCE: 112

Tyr Met Asp Gly Thr Met Ser Gln Ala
1               5

<210> SEQ ID NO 113
<211> LENGTH: 9
<212> TYPE: PRT
<213> ORGANISM: Artificial sequence
<220> FEATURE:
<223> OTHER INFORMATION: short peptide

<400> SEQUENCE: 113

Tyr Met Asp Gly Thr Met Ser Gln Val
1               5

<210> SEQ ID NO 114
<211> LENGTH: 9
<212> TYPE: PRT
<213> ORGANISM: Artificial sequence
<220> FEATURE:
<223> OTHER INFORMATION: short peptide

<400> SEQUENCE: 114

Tyr Met Asn Gly Thr Met Ser Gln Val
1               5

<210> SEQ ID NO 115
<211> LENGTH: 9
<212> TYPE: PRT
<213> ORGANISM: Artificial sequence
<220> FEATURE:
<223> OTHER INFORMATION: short peptide

<400> SEQUENCE: 115

Tyr Met Asp Asn Val Met Ser Glu Val
1               5

<210> SEQ ID NO 116
<211> LENGTH: 9
<212> TYPE: PRT
<213> ORGANISM: Artificial sequence
<220> FEATURE:
<223> OTHER INFORMATION: short peptide

<400> SEQUENCE: 116

Val Met Asp Ser Lys Ile Val Gln Val
1               5

<210> SEQ ID NO 117
<211> LENGTH: 9
```

```
<212> TYPE: PRT
<213> ORGANISM: Artificial sequence
<220> FEATURE:
<223> OTHER INFORMATION: short peptide

<400> SEQUENCE: 117

Leu Met Asn Gly Thr Leu Lys Gln Val
1               5

<210> SEQ ID NO 118
<211> LENGTH: 9
<212> TYPE: PRT
<213> ORGANISM: Artificial sequence
<220> FEATURE:
<223> OTHER INFORMATION: short peptide

<400> SEQUENCE: 118

Ser Gln Asp Gly Thr Arg Ser Gln Val
1               5

<210> SEQ ID NO 119
<211> LENGTH: 9
<212> TYPE: PRT
<213> ORGANISM: Artificial sequence
<220> FEATURE:
<223> OTHER INFORMATION: short peptide

<400> SEQUENCE: 119

Val Met Asp Thr Thr Lys Ser Gln Val
1               5

<210> SEQ ID NO 120
<211> LENGTH: 9
<212> TYPE: PRT
<213> ORGANISM: Artificial sequence
<220> FEATURE:
<223> OTHER INFORMATION: short peptide

<400> SEQUENCE: 120

Gly Met Asp Gly Thr Gln Gln Gln Ile
1               5

<210> SEQ ID NO 121
<211> LENGTH: 9
<212> TYPE: PRT
<213> ORGANISM: Artificial sequence
<220> FEATURE:
<223> OTHER INFORMATION: short peptide

<400> SEQUENCE: 121

Gly Met Val Gly Thr Met Thr Glu Val
1               5

<210> SEQ ID NO 122
<211> LENGTH: 9
<212> TYPE: PRT
<213> ORGANISM: Artificial sequence
<220> FEATURE:
<223> OTHER INFORMATION: short peptide

<400> SEQUENCE: 122

Met Met Asp Ala Thr Phe Ser Ala Val
1               5

<210> SEQ ID NO 123
<211> LENGTH: 9
<212> TYPE: PRT
```

```
<213> ORGANISM: Artificial sequence
<220> FEATURE:
<223> OTHER INFORMATION: short peptide

<400> SEQUENCE: 123

Gln Met Asp Pro Thr Gly Ser Gln Leu
1               5

<210> SEQ ID NO 124
<211> LENGTH: 9
<212> TYPE: PRT
<213> ORGANISM: Artificial sequence
<220> FEATURE:
<223> OTHER INFORMATION: short peptide

<400> SEQUENCE: 124

Ser Met Asp Gly Ser Met Arg Thr Val
1               5

<210> SEQ ID NO 125
<211> LENGTH: 9
<212> TYPE: PRT
<213> ORGANISM: Artificial sequence
<220> FEATURE:
<223> OTHER INFORMATION: short peptide

<400> SEQUENCE: 125

Trp Met Asp Gly Ile Ala Ser Gln Ile
1               5

<210> SEQ ID NO 126
<211> LENGTH: 9
<212> TYPE: PRT
<213> ORGANISM: Artificial sequence
<220> FEATURE:
<223> OTHER INFORMATION: short peptide

<400> SEQUENCE: 126

Tyr Leu Glu Gly Ile Leu Ser Gln Val
1               5

<210> SEQ ID NO 127
<211> LENGTH: 9
<212> TYPE: PRT
<213> ORGANISM: Artificial sequence
<220> FEATURE:
<223> OTHER INFORMATION: short peptide

<400> SEQUENCE: 127

Tyr Met Ala Ile Lys Met Ser Gln Leu
1               5

<210> SEQ ID NO 128
<211> LENGTH: 9
<212> TYPE: PRT
<213> ORGANISM: Artificial sequence
<220> FEATURE:
<223> OTHER INFORMATION: short peptide

<400> SEQUENCE: 128

Tyr Met Asp Ala Val Val Ser Leu Val
1               5

<210> SEQ ID NO 129
<211> LENGTH: 9
<212> TYPE: PRT
<213> ORGANISM: Artificial sequence
```

```
<220> FEATURE:
<223> OTHER INFORMATION: short peptide

<400> SEQUENCE: 129

Tyr Met Asp Gly Thr Asn Arg Arg Ile
1               5

<210> SEQ ID NO 130
<211> LENGTH: 9
<212> TYPE: PRT
<213> ORGANISM: Artificial sequence
<220> FEATURE:
<223> OTHER INFORMATION: short peptide

<400> SEQUENCE: 130

Tyr Met Asp Pro Ser Thr Tyr Gln Val
1               5

<210> SEQ ID NO 131
<211> LENGTH: 9
<212> TYPE: PRT
<213> ORGANISM: Artificial sequence
<220> FEATURE:
<223> OTHER INFORMATION: short peptide

<400> SEQUENCE: 131

Tyr Met Leu Gly Thr Asn His Gln Leu
1               5

<210> SEQ ID NO 132
<211> LENGTH: 9
<212> TYPE: PRT
<213> ORGANISM: Artificial sequence
<220> FEATURE:
<223> OTHER INFORMATION: short peptide

<400> SEQUENCE: 132

Tyr Met Pro Gly Thr Ala Ser Leu Ile
1               5

<210> SEQ ID NO 133
<211> LENGTH: 9
<212> TYPE: PRT
<213> ORGANISM: Artificial sequence
<220> FEATURE:
<223> OTHER INFORMATION: short peptide

<400> SEQUENCE: 133

Tyr Met Arg Glu Thr Arg Ser Gln Leu
1               5

<210> SEQ ID NO 134
<211> LENGTH: 9
<212> TYPE: PRT
<213> ORGANISM: Artificial sequence
<220> FEATURE:
<223> OTHER INFORMATION: short peptide

<400> SEQUENCE: 134

Met Met Asp Gly Ala Met Gly Tyr Val
1               5

<210> SEQ ID NO 135
<211> LENGTH: 9
<212> TYPE: PRT
<213> ORGANISM: Artificial sequence
<220> FEATURE:
```

```
<223> OTHER INFORMATION: short peptide

<400> SEQUENCE: 135

Asn Met Asp Ser Phe Met Ala Gln Val
1               5

<210> SEQ ID NO 136
<211> LENGTH: 9
<212> TYPE: PRT
<213> ORGANISM: Artificial sequence
<220> FEATURE:
<223> OTHER INFORMATION: short peptide

<400> SEQUENCE: 136

Gln Met Asp Phe Ile Met Ser Cys Val
1               5

<210> SEQ ID NO 137
<211> LENGTH: 9
<212> TYPE: PRT
<213> ORGANISM: Artificial sequence
<220> FEATURE:
<223> OTHER INFORMATION: short peptide

<400> SEQUENCE: 137

Tyr Glu Asp Leu Lys Met Tyr Gln Val
1               5

<210> SEQ ID NO 138
<211> LENGTH: 9
<212> TYPE: PRT
<213> ORGANISM: Artificial sequence
<220> FEATURE:
<223> OTHER INFORMATION: short peptide

<400> SEQUENCE: 138

Tyr Met Asp Thr Ile Met Glu Leu Val
1               5

<210> SEQ ID NO 139
<211> LENGTH: 9
<212> TYPE: PRT
<213> ORGANISM: Artificial sequence
<220> FEATURE:
<223> OTHER INFORMATION: short peptide

<400> SEQUENCE: 139

Tyr Thr Asp Leu Ala Met Ser Thr Val
1               5

<210> SEQ ID NO 140
<211> LENGTH: 9
<212> TYPE: PRT
<213> ORGANISM: Artificial sequence
<220> FEATURE:
<223> OTHER INFORMATION: short peptide

<400> SEQUENCE: 140

Tyr Val Asp Phe Val Met Ser Ser Val
1               5

<210> SEQ ID NO 141
<211> LENGTH: 9
<212> TYPE: PRT
<213> ORGANISM: Artificial sequence
<220> FEATURE:
<223> OTHER INFORMATION: short peptide
```

```
<400> SEQUENCE: 141

Arg Met Phe Pro Asn Ala Pro Tyr Leu
1               5

<210> SEQ ID NO 142
<211> LENGTH: 9
<212> TYPE: PRT
<213> ORGANISM: Artificial sequence
<220> FEATURE:
<223> OTHER INFORMATION: short peptide

<400> SEQUENCE: 142

Leu Asp Phe Pro Asn Leu Pro Tyr Leu
1               5

<210> SEQ ID NO 143
<211> LENGTH: 9
<212> TYPE: PRT
<213> ORGANISM: Artificial sequence
<220> FEATURE:
<223> OTHER INFORMATION: short peptide

<400> SEQUENCE: 143

Arg Cys Phe Pro Asn Cys Pro Phe Leu
1               5

<210> SEQ ID NO 144
<211> LENGTH: 9
<212> TYPE: PRT
<213> ORGANISM: Artificial sequence
<220> FEATURE:
<223> OTHER INFORMATION: short peptide

<400> SEQUENCE: 144

Leu Met Phe Glu Asn Ala Ala Tyr Leu
1               5

<210> SEQ ID NO 145
<211> LENGTH: 9
<212> TYPE: PRT
<213> ORGANISM: Artificial sequence
<220> FEATURE:
<223> OTHER INFORMATION: short peptide

<400> SEQUENCE: 145

Arg Met Phe Pro Asn Lys Tyr Ser Leu
1               5

<210> SEQ ID NO 146
<211> LENGTH: 9
<212> TYPE: PRT
<213> ORGANISM: Artificial sequence
<220> FEATURE:
<223> OTHER INFORMATION: short peptide

<400> SEQUENCE: 146

Arg Leu Phe Pro Asn Ala Lys Phe Leu
1               5

<210> SEQ ID NO 147
<211> LENGTH: 9
<212> TYPE: PRT
<213> ORGANISM: Artificial sequence
<220> FEATURE:
<223> OTHER INFORMATION: short peptide
```

```
<400> SEQUENCE: 147

Arg Leu Phe Pro Asn Leu Pro Glu Leu
1               5

<210> SEQ ID NO 148
<211> LENGTH: 9
<212> TYPE: PRT
<213> ORGANISM: Artificial sequence
<220> FEATURE:
<223> OTHER INFORMATION: short peptide

<400> SEQUENCE: 148

Arg Met Phe Pro Thr Pro Pro Ser Leu
1               5

<210> SEQ ID NO 149
<211> LENGTH: 9
<212> TYPE: PRT
<213> ORGANISM: Artificial sequence
<220> FEATURE:
<223> OTHER INFORMATION: short peptide

<400> SEQUENCE: 149

Arg Met Val Pro Arg Ala Val Tyr Leu
1               5

<210> SEQ ID NO 150
<211> LENGTH: 9
<212> TYPE: PRT
<213> ORGANISM: Artificial sequence
<220> FEATURE:
<223> OTHER INFORMATION: short peptide

<400> SEQUENCE: 150

Arg Met Phe Phe Asn Gly Arg Tyr Ile
1               5

<210> SEQ ID NO 151
<211> LENGTH: 9
<212> TYPE: PRT
<213> ORGANISM: Artificial sequence
<220> FEATURE:
<223> OTHER INFORMATION: short peptide

<400> SEQUENCE: 151

Arg Met Leu Pro His Ala Pro Gly Val
1               5

<210> SEQ ID NO 152
<211> LENGTH: 9
<212> TYPE: PRT
<213> ORGANISM: Artificial sequence
<220> FEATURE:
<223> OTHER INFORMATION: short peptide

<400> SEQUENCE: 152

Tyr Met Phe Pro Asn Ala Pro Tyr Leu
1               5

<210> SEQ ID NO 153
<211> LENGTH: 9
<212> TYPE: PRT
<213> ORGANISM: Artificial sequence
<220> FEATURE:
<223> OTHER INFORMATION: short peptide

<400> SEQUENCE: 153
```

```
Ala Met Asp Pro Asn Ala Ala Tyr Val
1               5

<210> SEQ ID NO 154
<211> LENGTH: 9
<212> TYPE: PRT
<213> ORGANISM: Artificial sequence
<220> FEATURE:
<223> OTHER INFORMATION: short peptide

<400> SEQUENCE: 154

Ile Cys Phe Pro Asn Ala Pro Lys Val
1               5

<210> SEQ ID NO 155
<211> LENGTH: 9
<212> TYPE: PRT
<213> ORGANISM: Artificial sequence
<220> FEATURE:
<223> OTHER INFORMATION: short peptide

<400> SEQUENCE: 155

Asn Met Phe Glu Asn Gly Cys Tyr Leu
1               5

<210> SEQ ID NO 156
<211> LENGTH: 9
<212> TYPE: PRT
<213> ORGANISM: Artificial sequence
<220> FEATURE:
<223> OTHER INFORMATION: short peptide

<400> SEQUENCE: 156

Asn Met Pro Pro Asn Phe Pro Tyr Ile
1               5

<210> SEQ ID NO 157
<211> LENGTH: 9
<212> TYPE: PRT
<213> ORGANISM: Artificial sequence
<220> FEATURE:
<223> OTHER INFORMATION: short peptide

<400> SEQUENCE: 157

Arg Glu Met Thr Gln Ala Pro Tyr Leu
1               5

<210> SEQ ID NO 158
<211> LENGTH: 9
<212> TYPE: PRT
<213> ORGANISM: Artificial sequence
<220> FEATURE:
<223> OTHER INFORMATION: short peptide

<400> SEQUENCE: 158

Arg Met Ala Pro Arg Ala Pro Trp Ile
1               5

<210> SEQ ID NO 159
<211> LENGTH: 9
<212> TYPE: PRT
<213> ORGANISM: Artificial sequence
<220> FEATURE:
<223> OTHER INFORMATION: short peptide

<400> SEQUENCE: 159
```

```
Arg Met Glu Pro Arg Ala Pro Trp Ile
1               5
```

<210> SEQ ID NO 160
<211> LENGTH: 9
<212> TYPE: PRT
<213> ORGANISM: Artificial sequence
<220> FEATURE:
<223> OTHER INFORMATION: short peptide

<400> SEQUENCE: 160

```
Arg Met Glu Pro Arg Ala Pro Trp Val
1               5
```

<210> SEQ ID NO 161
<211> LENGTH: 9
<212> TYPE: PRT
<213> ORGANISM: Artificial sequence
<220> FEATURE:
<223> OTHER INFORMATION: short peptide

<400> SEQUENCE: 161

```
Arg Met Phe Leu Asn Asn Pro Ser Ile
1               5
```

<210> SEQ ID NO 162
<211> LENGTH: 9
<212> TYPE: PRT
<213> ORGANISM: Artificial sequence
<220> FEATURE:
<223> OTHER INFORMATION: short peptide

<400> SEQUENCE: 162

```
Arg Met Phe Gln Gln Thr Phe Tyr Leu
1               5
```

<210> SEQ ID NO 163
<211> LENGTH: 9
<212> TYPE: PRT
<213> ORGANISM: Artificial sequence
<220> FEATURE:
<223> OTHER INFORMATION: short peptide

<400> SEQUENCE: 163

```
Arg Met Asn Pro Asn Ser Pro Ser Ile
1               5
```

<210> SEQ ID NO 164
<211> LENGTH: 9
<212> TYPE: PRT
<213> ORGANISM: Artificial sequence
<220> FEATURE:
<223> OTHER INFORMATION: short peptide

<400> SEQUENCE: 164

```
Arg Gln Phe Pro Asn Ala Ser Leu Ile
1               5
```

<210> SEQ ID NO 165
<211> LENGTH: 9
<212> TYPE: PRT
<213> ORGANISM: Artificial sequence
<220> FEATURE:
<223> OTHER INFORMATION: short peptide

<400> SEQUENCE: 165

Arg Gln Phe Pro Asn Lys Asp Ala Leu

```
<210> SEQ ID NO 166
<211> LENGTH: 9
<212> TYPE: PRT
<213> ORGANISM: Artificial sequence
<220> FEATURE:
<223> OTHER INFORMATION: short peptide

<400> SEQUENCE: 166

Arg Val Phe Pro Trp Ala Ser Ser Leu
1               5

<210> SEQ ID NO 167
<211> LENGTH: 9
<212> TYPE: PRT
<213> ORGANISM: Artificial sequence
<220> FEATURE:
<223> OTHER INFORMATION: short peptide

<400> SEQUENCE: 167

Arg Leu Phe Pro Trp Gly Asn Lys Leu
1               5

<210> SEQ ID NO 168
<211> LENGTH: 9
<212> TYPE: PRT
<213> ORGANISM: Artificial sequence
<220> FEATURE:
<223> OTHER INFORMATION: short peptide

<400> SEQUENCE: 168

Ala Met Phe Pro Asn Ala Pro Tyr Leu
1               5

<210> SEQ ID NO 169
<211> LENGTH: 9
<212> TYPE: PRT
<213> ORGANISM: Artificial sequence
<220> FEATURE:
<223> OTHER INFORMATION: short peptide

<400> SEQUENCE: 169

Arg Ala Phe Pro Asn Ala Pro Tyr Leu
1               5

<210> SEQ ID NO 170
<211> LENGTH: 9
<212> TYPE: PRT
<213> ORGANISM: Artificial sequence
<220> FEATURE:
<223> OTHER INFORMATION: short peptide

<400> SEQUENCE: 170

Arg Met Ala Pro Asn Ala Pro Tyr Leu
1               5

<210> SEQ ID NO 171
<211> LENGTH: 9
<212> TYPE: PRT
<213> ORGANISM: Artificial sequence
<220> FEATURE:
<223> OTHER INFORMATION: short peptide

<400> SEQUENCE: 171

Arg Met Phe Ala Asn Ala Pro Tyr Leu
1               5
```

```
<210> SEQ ID NO 172
<211> LENGTH: 9
<212> TYPE: PRT
<213> ORGANISM: Artificial sequence
<220> FEATURE:
<223> OTHER INFORMATION: short peptide

<400> SEQUENCE: 172

Arg Met Phe Pro Ala Ala Pro Tyr Leu
1               5

<210> SEQ ID NO 173
<211> LENGTH: 9
<212> TYPE: PRT
<213> ORGANISM: Artificial sequence
<220> FEATURE:
<223> OTHER INFORMATION: short peptide

<400> SEQUENCE: 173

Arg Met Phe Pro Asn Ala Ala Tyr Leu
1               5

<210> SEQ ID NO 174
<211> LENGTH: 9
<212> TYPE: PRT
<213> ORGANISM: Artificial sequence
<220> FEATURE:
<223> OTHER INFORMATION: short peptide

<400> SEQUENCE: 174

Arg Met Phe Pro Asn Ala Pro Ala Leu
1               5

<210> SEQ ID NO 175
<211> LENGTH: 9
<212> TYPE: PRT
<213> ORGANISM: Artificial sequence
<220> FEATURE:
<223> OTHER INFORMATION: short peptide

<400> SEQUENCE: 175

Arg Met Phe Pro Asn Ala Pro Tyr Ala
1               5

<210> SEQ ID NO 176
<211> LENGTH: 10
<212> TYPE: PRT
<213> ORGANISM: Artificial sequence
<220> FEATURE:
<223> OTHER INFORMATION: short peptide

<400> SEQUENCE: 176

Gly Val Tyr Asp Gly Arg Glu His Thr Val
1               5                   10

<210> SEQ ID NO 177
<211> LENGTH: 10
<212> TYPE: PRT
<213> ORGANISM: Artificial sequence
<220> FEATURE:
<223> OTHER INFORMATION: short peptide

<400> SEQUENCE: 177

Gly Leu Ala Asp Gly Arg Thr His Thr Val
1               5                   10
```

<210> SEQ ID NO 178
<211> LENGTH: 10
<212> TYPE: PRT
<213> ORGANISM: Artificial sequence
<220> FEATURE:
<223> OTHER INFORMATION: short peptide

<400> SEQUENCE: 178

Gly Val Ser Asp Gly Arg Trp His Ser Val
1               5                   10

<210> SEQ ID NO 179
<211> LENGTH: 10
<212> TYPE: PRT
<213> ORGANISM: Artificial sequence
<220> FEATURE:
<223> OTHER INFORMATION: short peptide

<400> SEQUENCE: 179

Gly Val Tyr Asp Gly Glu Glu His Ser Val
1               5                   10

<210> SEQ ID NO 180
<211> LENGTH: 9
<212> TYPE: PRT
<213> ORGANISM: Artificial sequence
<220> FEATURE:
<223> OTHER INFORMATION: short peptide

<400> SEQUENCE: 180

Gly Leu Tyr Asp Gly Met Glu His Leu
1               5

<210> SEQ ID NO 181
<211> LENGTH: 10
<212> TYPE: PRT
<213> ORGANISM: Artificial sequence
<220> FEATURE:
<223> OTHER INFORMATION: short peptide

<400> SEQUENCE: 181

Gly Val Ser Asp Gly Gln Trp His Thr Val
1               5                   10

<210> SEQ ID NO 182
<211> LENGTH: 10
<212> TYPE: PRT
<213> ORGANISM: Artificial sequence
<220> FEATURE:
<223> OTHER INFORMATION: short peptide

<400> SEQUENCE: 182

Gly Val Tyr Ala Gly Arg Glu His Phe Leu
1               5                   10

<210> SEQ ID NO 183
<211> LENGTH: 10
<212> TYPE: PRT
<213> ORGANISM: Artificial sequence
<220> FEATURE:
<223> OTHER INFORMATION: short peptide

<400> SEQUENCE: 183

Gly Leu Tyr Asp Gly Met Glu His Leu Ile
1               5                   10

```
<210> SEQ ID NO 184
<211> LENGTH: 10
<212> TYPE: PRT
<213> ORGANISM: Artificial sequence
<220> FEATURE:
<223> OTHER INFORMATION: short peptide

<400> SEQUENCE: 184

Ala Ser Tyr Asp Gly Thr Glu Val Thr Val
1               5                   10

<210> SEQ ID NO 185
<211> LENGTH: 10
<212> TYPE: PRT
<213> ORGANISM: Artificial sequence
<220> FEATURE:
<223> OTHER INFORMATION: short peptide

<400> SEQUENCE: 185

Ala Val Leu Asp Gly Arg Glu Leu Arg Val
1               5                   10

<210> SEQ ID NO 186
<211> LENGTH: 10
<212> TYPE: PRT
<213> ORGANISM: Artificial sequence
<220> FEATURE:
<223> OTHER INFORMATION: short peptide

<400> SEQUENCE: 186

Gly Leu Tyr Asp Gly Ile Glu His Phe Met
1               5                   10

<210> SEQ ID NO 187
<211> LENGTH: 10
<212> TYPE: PRT
<213> ORGANISM: Artificial sequence
<220> FEATURE:
<223> OTHER INFORMATION: short peptide

<400> SEQUENCE: 187

Gly Leu Tyr Asp Gly Pro Val His Glu Val
1               5                   10

<210> SEQ ID NO 188
<211> LENGTH: 10
<212> TYPE: PRT
<213> ORGANISM: Artificial sequence
<220> FEATURE:
<223> OTHER INFORMATION: short peptide

<400> SEQUENCE: 188

Gly Val Cys Ala Gly Arg Glu His Phe Ile
1               5                   10

<210> SEQ ID NO 189
<211> LENGTH: 10
<212> TYPE: PRT
<213> ORGANISM: Artificial sequence
<220> FEATURE:
<223> OTHER INFORMATION: short peptide

<400> SEQUENCE: 189

Gly Val Tyr Ala Gly Arg Pro Leu Ser Val
1               5                   10

<210> SEQ ID NO 190
```

<211> LENGTH: 10
<212> TYPE: PRT
<213> ORGANISM: Artificial sequence
<220> FEATURE:
<223> OTHER INFORMATION: short peptide

<400> SEQUENCE: 190

Thr Val Tyr Asp Leu Arg Glu Gln Ser Val
1               5                   10

<210> SEQ ID NO 191
<211> LENGTH: 10
<212> TYPE: PRT
<213> ORGANISM: Artificial sequence
<220> FEATURE:
<223> OTHER INFORMATION: short peptide

<400> SEQUENCE: 191

Val Val Asp Asp Gly Val Glu His Thr Ile
1               5                   10

<210> SEQ ID NO 192
<211> LENGTH: 9
<212> TYPE: PRT
<213> ORGANISM: Artificial sequence
<220> FEATURE:
<223> OTHER INFORMATION: short peptide

<400> SEQUENCE: 192

Gly Val Phe Asp Gly Leu His Thr Val
1               5

<210> SEQ ID NO 193
<211> LENGTH: 10
<212> TYPE: PRT
<213> ORGANISM: Artificial sequence
<220> FEATURE:
<223> OTHER INFORMATION: short peptide

<400> SEQUENCE: 193

Ala Val Tyr Asp Gly Arg Glu His Thr Val
1               5                   10

<210> SEQ ID NO 194
<211> LENGTH: 10
<212> TYPE: PRT
<213> ORGANISM: Artificial sequence
<220> FEATURE:
<223> OTHER INFORMATION: short peptide

<400> SEQUENCE: 194

Gly Ala Tyr Asp Gly Arg Glu His Thr Val
1               5                   10

<210> SEQ ID NO 195
<211> LENGTH: 10
<212> TYPE: PRT
<213> ORGANISM: Artificial sequence
<220> FEATURE:
<223> OTHER INFORMATION: short peptide

<400> SEQUENCE: 195

Gly Val Ala Asp Gly Arg Glu His Thr Val
1               5                   10

<210> SEQ ID NO 196
<211> LENGTH: 10

```
<212> TYPE: PRT
<213> ORGANISM: Artificial sequence
<220> FEATURE:
<223> OTHER INFORMATION: short peptide

<400> SEQUENCE: 196

Gly Val Tyr Ala Gly Arg Glu His Thr Val
1               5                   10

<210> SEQ ID NO 197
<211> LENGTH: 10
<212> TYPE: PRT
<213> ORGANISM: Artificial sequence
<220> FEATURE:
<223> OTHER INFORMATION: short peptide

<400> SEQUENCE: 197

Gly Val Tyr Asp Ala Arg Glu His Thr Val
1               5                   10

<210> SEQ ID NO 198
<211> LENGTH: 10
<212> TYPE: PRT
<213> ORGANISM: Artificial sequence
<220> FEATURE:
<223> OTHER INFORMATION: short peptide

<400> SEQUENCE: 198

Gly Val Tyr Asp Gly Ala Glu His Thr Val
1               5                   10

<210> SEQ ID NO 199
<211> LENGTH: 10
<212> TYPE: PRT
<213> ORGANISM: Artificial sequence
<220> FEATURE:
<223> OTHER INFORMATION: short peptide

<400> SEQUENCE: 199

Gly Val Tyr Asp Gly Arg Ala His Thr Val
1               5                   10

<210> SEQ ID NO 200
<211> LENGTH: 10
<212> TYPE: PRT
<213> ORGANISM: Artificial sequence
<220> FEATURE:
<223> OTHER INFORMATION: short peptide

<400> SEQUENCE: 200

Gly Val Tyr Asp Gly Arg Glu Ala Thr Val
1               5                   10

<210> SEQ ID NO 201
<211> LENGTH: 10
<212> TYPE: PRT
<213> ORGANISM: Artificial sequence
<220> FEATURE:
<223> OTHER INFORMATION: short peptide

<400> SEQUENCE: 201

Gly Val Tyr Asp Gly Arg Glu His Ala Val
1               5                   10

<210> SEQ ID NO 202
<211> LENGTH: 10
<212> TYPE: PRT
```

```
<213> ORGANISM: Artificial sequence
<220> FEATURE:
<223> OTHER INFORMATION: short peptide

<400> SEQUENCE: 202

Gly Val Tyr Asp Gly Arg Glu His Thr Ala
1               5                   10

<210> SEQ ID NO 203
<211> LENGTH: 9
<212> TYPE: PRT
<213> ORGANISM: Artificial sequence
<220> FEATURE:
<223> OTHER INFORMATION: short peptide

<400> SEQUENCE: 203

Ala Leu Ser Val Met Gly Val Tyr Val
1               5

<210> SEQ ID NO 204
<211> LENGTH: 9
<212> TYPE: PRT
<213> ORGANISM: Artificial sequence
<220> FEATURE:
<223> OTHER INFORMATION: short peptide

<400> SEQUENCE: 204

Ala Leu Ser Val Leu Gly Val Met Val
1               5

<210> SEQ ID NO 205
<211> LENGTH: 9
<212> TYPE: PRT
<213> ORGANISM: Artificial sequence
<220> FEATURE:
<223> OTHER INFORMATION: short peptide

<400> SEQUENCE: 205

Ala Leu Ser Arg Lys Gly Ile Tyr Val
1               5

<210> SEQ ID NO 206
<211> LENGTH: 9
<212> TYPE: PRT
<213> ORGANISM: Artificial sequence
<220> FEATURE:
<223> OTHER INFORMATION: short peptide

<400> SEQUENCE: 206

Ala Leu Ser Val Met Tyr Ser Tyr Leu
1               5

<210> SEQ ID NO 207
<211> LENGTH: 9
<212> TYPE: PRT
<213> ORGANISM: Artificial sequence
<220> FEATURE:
<223> OTHER INFORMATION: short peptide

<400> SEQUENCE: 207

Ala Val Ser His Met Gly Val Leu Val
1               5

<210> SEQ ID NO 208
<211> LENGTH: 9
<212> TYPE: PRT
<213> ORGANISM: Artificial sequence
```

```
<220> FEATURE:
<223> OTHER INFORMATION: short peptide

<400> SEQUENCE: 208

Leu Leu Ser Leu Met Gly Val Leu Val
1               5

<210> SEQ ID NO 209
<211> LENGTH: 9
<212> TYPE: PRT
<213> ORGANISM: Artificial sequence
<220> FEATURE:
<223> OTHER INFORMATION: short peptide

<400> SEQUENCE: 209

Val Leu Ser Ile Met Gly Val Tyr Ala
1               5

<210> SEQ ID NO 210
<211> LENGTH: 9
<212> TYPE: PRT
<213> ORGANISM: Artificial sequence
<220> FEATURE:
<223> OTHER INFORMATION: short peptide

<400> SEQUENCE: 210

Ala Leu Gln Val Arg Lys Val Tyr Val
1               5

<210> SEQ ID NO 211
<211> LENGTH: 9
<212> TYPE: PRT
<213> ORGANISM: Artificial sequence
<220> FEATURE:
<223> OTHER INFORMATION: short peptide

<400> SEQUENCE: 211

Ala Leu Gln Val Tyr Gly Val Glu Val
1               5

<210> SEQ ID NO 212
<211> LENGTH: 9
<212> TYPE: PRT
<213> ORGANISM: Artificial sequence
<220> FEATURE:
<223> OTHER INFORMATION: short peptide

<400> SEQUENCE: 212

Ala Leu Ser Val Ala Gly Gly Phe Val
1               5

<210> SEQ ID NO 213
<211> LENGTH: 9
<212> TYPE: PRT
<213> ORGANISM: Artificial sequence
<220> FEATURE:
<223> OTHER INFORMATION: short peptide

<400> SEQUENCE: 213

Ala Leu Ser Val Leu Gly Lys Val Val
1               5

<210> SEQ ID NO 214
<211> LENGTH: 9
<212> TYPE: PRT
<213> ORGANISM: Artificial sequence
<220> FEATURE:
```

<223> OTHER INFORMATION: short peptide

<400> SEQUENCE: 214

Ala Leu Ser Val Met Ile Pro Ala Val
1               5

<210> SEQ ID NO 215
<211> LENGTH: 9
<212> TYPE: PRT
<213> ORGANISM: Artificial sequence
<220> FEATURE:
<223> OTHER INFORMATION: short peptide

<400> SEQUENCE: 215

Asp Leu Ser Val Cys Ser Val Tyr Val
1               5

<210> SEQ ID NO 216
<211> LENGTH: 9
<212> TYPE: PRT
<213> ORGANISM: Artificial sequence
<220> FEATURE:
<223> OTHER INFORMATION: short peptide

<400> SEQUENCE: 216

Ile Leu Gly Val Met Gly Val Asp Val
1               5

<210> SEQ ID NO 217
<211> LENGTH: 9
<212> TYPE: PRT
<213> ORGANISM: Artificial sequence
<220> FEATURE:
<223> OTHER INFORMATION: short peptide

<400> SEQUENCE: 217

Leu Leu Ser Val Asn Gly Val Ser Val
1               5

<210> SEQ ID NO 218
<211> LENGTH: 9
<212> TYPE: PRT
<213> ORGANISM: Artificial sequence
<220> FEATURE:
<223> OTHER INFORMATION: short peptide

<400> SEQUENCE: 218

Ser Leu Ser Pro Met Gly Arg Tyr Val
1               5

<210> SEQ ID NO 219
<211> LENGTH: 10
<212> TYPE: PRT
<213> ORGANISM: Artificial sequence
<220> FEATURE:
<223> OTHER INFORMATION: short peptide

<400> SEQUENCE: 219

Ala Leu Ser Ala Val Met Gly Val Thr Leu
1               5                   10

<210> SEQ ID NO 220
<211> LENGTH: 10
<212> TYPE: PRT
<213> ORGANISM: Artificial sequence
<220> FEATURE:
<223> OTHER INFORMATION: short peptide

```
<400> SEQUENCE: 220

Ala Ile Leu Leu Val Met Gly Val Asp Val
1               5                   10

<210> SEQ ID NO 221
<211> LENGTH: 9
<212> TYPE: PRT
<213> ORGANISM: Artificial sequence
<220> FEATURE:
<223> OTHER INFORMATION: short peptide

<400> SEQUENCE: 221

Ala Leu Ser Asp His His Val Tyr Leu
1               5

<210> SEQ ID NO 222
<211> LENGTH: 9
<212> TYPE: PRT
<213> ORGANISM: Artificial sequence
<220> FEATURE:
<223> OTHER INFORMATION: short peptide

<400> SEQUENCE: 222

Ala Ala Ser Val Met Gly Val Tyr Val
1               5

<210> SEQ ID NO 223
<211> LENGTH: 9
<212> TYPE: PRT
<213> ORGANISM: Artificial sequence
<220> FEATURE:
<223> OTHER INFORMATION: short peptide

<400> SEQUENCE: 223

Ala Leu Ala Val Met Gly Val Tyr Val
1               5

<210> SEQ ID NO 224
<211> LENGTH: 9
<212> TYPE: PRT
<213> ORGANISM: Artificial sequence
<220> FEATURE:
<223> OTHER INFORMATION: short peptide

<400> SEQUENCE: 224

Ala Leu Ser Ala Met Gly Val Tyr Val
1               5

<210> SEQ ID NO 225
<211> LENGTH: 9
<212> TYPE: PRT
<213> ORGANISM: Artificial sequence
<220> FEATURE:
<223> OTHER INFORMATION: short peptide

<400> SEQUENCE: 225

Ala Leu Ser Val Ala Gly Val Tyr Val
1               5

<210> SEQ ID NO 226
<211> LENGTH: 9
<212> TYPE: PRT
<213> ORGANISM: Artificial sequence
<220> FEATURE:
<223> OTHER INFORMATION: short peptide
```

```
<400> SEQUENCE: 226

Ala Leu Ser Val Met Ala Val Tyr Val
1               5

<210> SEQ ID NO 227
<211> LENGTH: 9
<212> TYPE: PRT
<213> ORGANISM: Artificial sequence
<220> FEATURE:
<223> OTHER INFORMATION: short peptide

<400> SEQUENCE: 227

Ala Leu Ser Val Met Gly Ala Tyr Val
1               5

<210> SEQ ID NO 228
<211> LENGTH: 9
<212> TYPE: PRT
<213> ORGANISM: Artificial sequence
<220> FEATURE:
<223> OTHER INFORMATION: short peptide

<400> SEQUENCE: 228

Ala Leu Ser Val Met Gly Val Ala Val
1               5

<210> SEQ ID NO 229
<211> LENGTH: 9
<212> TYPE: PRT
<213> ORGANISM: Artificial sequence
<220> FEATURE:
<223> OTHER INFORMATION: short peptide

<400> SEQUENCE: 229

Ala Leu Ser Val Met Gly Val Tyr Ala
1               5

<210> SEQ ID NO 230
<211> LENGTH: 9
<212> TYPE: PRT
<213> ORGANISM: Artificial sequence
<220> FEATURE:
<223> OTHER INFORMATION: short peptide

<400> SEQUENCE: 230

Thr Leu Met Ser Ala Met Thr Asn Leu
1               5

<210> SEQ ID NO 231
<211> LENGTH: 9
<212> TYPE: PRT
<213> ORGANISM: Artificial sequence
<220> FEATURE:
<223> OTHER INFORMATION: short peptide

<400> SEQUENCE: 231

Thr Leu Met Ser Ala Glu Ala Asn Leu
1               5

<210> SEQ ID NO 232
<211> LENGTH: 9
<212> TYPE: PRT
<213> ORGANISM: Artificial sequence
<220> FEATURE:
<223> OTHER INFORMATION: short peptide

<400> SEQUENCE: 232
```

```
Gln Leu Cys Ser Ala Met Thr Gln Leu
1               5

<210> SEQ ID NO 233
<211> LENGTH: 9
<212> TYPE: PRT
<213> ORGANISM: Artificial sequence
<220> FEATURE:
<223> OTHER INFORMATION: short peptide

<400> SEQUENCE: 233

Arg Leu Met Ser Ala Leu Thr Gln Leu
1               5

<210> SEQ ID NO 234
<211> LENGTH: 9
<212> TYPE: PRT
<213> ORGANISM: Artificial sequence
<220> FEATURE:
<223> OTHER INFORMATION: short peptide

<400> SEQUENCE: 234

Gly Leu Met Ser Leu Thr Thr Asn Leu
1               5

<210> SEQ ID NO 235
<211> LENGTH: 9
<212> TYPE: PRT
<213> ORGANISM: Artificial sequence
<220> FEATURE:
<223> OTHER INFORMATION: short peptide

<400> SEQUENCE: 235

Gly Leu Met Ser Met Ala Thr Asn Leu
1               5

<210> SEQ ID NO 236
<211> LENGTH: 9
<212> TYPE: PRT
<213> ORGANISM: Artificial sequence
<220> FEATURE:
<223> OTHER INFORMATION: short peptide

<400> SEQUENCE: 236

Gly Leu Met Ser Met Thr Thr Asn Leu
1               5

<210> SEQ ID NO 237
<211> LENGTH: 9
<212> TYPE: PRT
<213> ORGANISM: Artificial sequence
<220> FEATURE:
<223> OTHER INFORMATION: short peptide

<400> SEQUENCE: 237

Leu Leu Met Ser Ile Ser Thr Asn Leu
1               5

<210> SEQ ID NO 238
<211> LENGTH: 9
<212> TYPE: PRT
<213> ORGANISM: Artificial sequence
<220> FEATURE:
<223> OTHER INFORMATION: short peptide

<400> SEQUENCE: 238
```

```
Gln Leu Pro Ser Thr Met Thr Asn Leu
1               5

<210> SEQ ID NO 239
<211> LENGTH: 9
<212> TYPE: PRT
<213> ORGANISM: Artificial sequence
<220> FEATURE:
<223> OTHER INFORMATION: short peptide

<400> SEQUENCE: 239

Thr Leu Ala Ser Ser Met Gly Asn Leu
1               5

<210> SEQ ID NO 240
<211> LENGTH: 9
<212> TYPE: PRT
<213> ORGANISM: Artificial sequence
<220> FEATURE:
<223> OTHER INFORMATION: short peptide

<400> SEQUENCE: 240

Thr Leu Phe Ser Ala Leu Thr Gly Leu
1               5

<210> SEQ ID NO 241
<211> LENGTH: 9
<212> TYPE: PRT
<213> ORGANISM: Artificial sequence
<220> FEATURE:
<223> OTHER INFORMATION: short peptide

<400> SEQUENCE: 241

Thr Leu Gly Ser Ala Thr Thr Glu Leu
1               5

<210> SEQ ID NO 242
<211> LENGTH: 9
<212> TYPE: PRT
<213> ORGANISM: Artificial sequence
<220> FEATURE:
<223> OTHER INFORMATION: short peptide

<400> SEQUENCE: 242

Thr Leu Met Arg Ala Met Thr Asp Cys
1               5

<210> SEQ ID NO 243
<211> LENGTH: 9
<212> TYPE: PRT
<213> ORGANISM: Artificial sequence
<220> FEATURE:
<223> OTHER INFORMATION: short peptide

<400> SEQUENCE: 243

Thr Leu Met Ser Met Val Ala Asn Leu
1               5

<210> SEQ ID NO 244
<211> LENGTH: 9
<212> TYPE: PRT
<213> ORGANISM: Artificial sequence
<220> FEATURE:
<223> OTHER INFORMATION: short peptide

<400> SEQUENCE: 244

Thr Leu Pro Ser Ala Glu Thr Ala Leu
```

```
1               5

<210> SEQ ID NO 245
<211> LENGTH: 9
<212> TYPE: PRT
<213> ORGANISM: Artificial sequence
<220> FEATURE:
<223> OTHER INFORMATION: short peptide

<400> SEQUENCE: 245

Thr Leu Pro Ser Arg Met Thr Val Leu
1               5

<210> SEQ ID NO 246
<211> LENGTH: 9
<212> TYPE: PRT
<213> ORGANISM: Artificial sequence
<220> FEATURE:
<223> OTHER INFORMATION: short peptide

<400> SEQUENCE: 246

Arg Leu Met Ser Ala Leu Thr Gln Val
1               5

<210> SEQ ID NO 247
<211> LENGTH: 9
<212> TYPE: PRT
<213> ORGANISM: Artificial sequence
<220> FEATURE:
<223> OTHER INFORMATION: short peptide

<400> SEQUENCE: 247

Ser Ile His Ser Gln Met Thr Asn Leu
1               5

<210> SEQ ID NO 248
<211> LENGTH: 9
<212> TYPE: PRT
<213> ORGANISM: Artificial sequence
<220> FEATURE:
<223> OTHER INFORMATION: short peptide

<400> SEQUENCE: 248

Ser Ile Met Phe Ala Met Thr Pro Leu
1               5

<210> SEQ ID NO 249
<211> LENGTH: 9
<212> TYPE: PRT
<213> ORGANISM: Artificial sequence
<220> FEATURE:
<223> OTHER INFORMATION: short peptide

<400> SEQUENCE: 249

Thr Ile Val Ala Ala Met Ser Asn Leu
1               5

<210> SEQ ID NO 250
<211> LENGTH: 9
<212> TYPE: PRT
<213> ORGANISM: Artificial sequence
<220> FEATURE:
<223> OTHER INFORMATION: short peptide

<400> SEQUENCE: 250

Thr Leu Ile Thr Ala Met Glu Gln Leu
1               5
```

```
<210> SEQ ID NO 251
<211> LENGTH: 9
<212> TYPE: PRT
<213> ORGANISM: Artificial sequence
<220> FEATURE:
<223> OTHER INFORMATION: short peptide

<400> SEQUENCE: 251

Thr Leu Thr Ser Asn Met Ser Gln Leu
1               5

<210> SEQ ID NO 252
<211> LENGTH: 9
<212> TYPE: PRT
<213> ORGANISM: Artificial sequence
<220> FEATURE:
<223> OTHER INFORMATION: short peptide

<400> SEQUENCE: 252

Ala Leu Met Ser Ala Met Thr Asn Leu
1               5

<210> SEQ ID NO 253
<211> LENGTH: 9
<212> TYPE: PRT
<213> ORGANISM: Artificial sequence
<220> FEATURE:
<223> OTHER INFORMATION: short peptide

<400> SEQUENCE: 253

Thr Leu Ala Ser Ala Met Thr Asn Leu
1               5

<210> SEQ ID NO 254
<211> LENGTH: 9
<212> TYPE: PRT
<213> ORGANISM: Artificial sequence
<220> FEATURE:
<223> OTHER INFORMATION: short peptide

<400> SEQUENCE: 254

Thr Leu Met Ala Ala Met Thr Asn Leu
1               5

<210> SEQ ID NO 255
<211> LENGTH: 9
<212> TYPE: PRT
<213> ORGANISM: Artificial sequence
<220> FEATURE:
<223> OTHER INFORMATION: short peptide

<400> SEQUENCE: 255

Thr Leu Met Ser Ala Ala Thr Asn Leu
1               5

<210> SEQ ID NO 256
<211> LENGTH: 9
<212> TYPE: PRT
<213> ORGANISM: Artificial sequence
<220> FEATURE:
<223> OTHER INFORMATION: short peptide

<400> SEQUENCE: 256

Thr Leu Met Ser Ala Met Ala Asn Leu
1               5
```

<210> SEQ ID NO 257
<211> LENGTH: 9
<212> TYPE: PRT
<213> ORGANISM: Artificial sequence
<220> FEATURE:
<223> OTHER INFORMATION: short peptide

<400> SEQUENCE: 257

Thr Leu Met Ser Ala Met Thr Ala Leu
1               5

<210> SEQ ID NO 258
<211> LENGTH: 9
<212> TYPE: PRT
<213> ORGANISM: Artificial sequence
<220> FEATURE:
<223> OTHER INFORMATION: short peptide

<400> SEQUENCE: 258

Thr Leu Met Ser Ala Met Thr Asn Ala
1               5

<210> SEQ ID NO 259
<211> LENGTH: 9
<212> TYPE: PRT
<213> ORGANISM: Artificial sequence
<220> FEATURE:
<223> OTHER INFORMATION: short peptide

<400> SEQUENCE: 259

Val Met Asp Ser Lys Ile Val Gln Val
1               5

<210> SEQ ID NO 260
<211> LENGTH: 9
<212> TYPE: PRT
<213> ORGANISM: Artificial sequence
<220> FEATURE:
<223> OTHER INFORMATION: short peptide

<400> SEQUENCE: 260

Arg Met Leu Pro His Ala Pro Gly Val
1               5

<210> SEQ ID NO 261
<211> LENGTH: 9
<212> TYPE: PRT
<213> ORGANISM: Artificial sequence
<220> FEATURE:
<223> OTHER INFORMATION: short peptide

<400> SEQUENCE: 261

Ala Met Asp Pro Asn Ala Ala Tyr Val
1               5

<210> SEQ ID NO 262
<211> LENGTH: 9
<212> TYPE: PRT
<213> ORGANISM: Artificial sequence
<220> FEATURE:
<223> OTHER INFORMATION: short peptide

<400> SEQUENCE: 262

Arg Met Asn Pro Asn Ser Pro Ser Ile
1               5

```
<210> SEQ ID NO 263
<211> LENGTH: 10
<212> TYPE: PRT
<213> ORGANISM: Artificial sequence
<220> FEATURE:
<223> OTHER INFORMATION: short peptide

<400> SEQUENCE: 263

Gly Leu Ala Asp Gly Arg Thr His Thr Val
1               5                   10

<210> SEQ ID NO 264
<211> LENGTH: 10
<212> TYPE: PRT
<213> ORGANISM: Artificial sequence
<220> FEATURE:
<223> OTHER INFORMATION: short peptide

<400> SEQUENCE: 264

Gly Leu Tyr Asp Gly Pro Val His Glu Val
1               5                   10

<210> SEQ ID NO 265
<211> LENGTH: 9
<212> TYPE: PRT
<213> ORGANISM: Artificial sequence
<220> FEATURE:
<223> OTHER INFORMATION: short peptide

<400> SEQUENCE: 265

Gly Val Phe Asp Gly Leu His Thr Val
1               5

<210> SEQ ID NO 266
<211> LENGTH: 9
<212> TYPE: PRT
<213> ORGANISM: Artificial sequence
<220> FEATURE:
<223> OTHER INFORMATION: short peptide

<400> SEQUENCE: 266

Ala Leu Ser Asp His His Val Tyr Leu
1               5

<210> SEQ ID NO 267
<211> LENGTH: 9
<212> TYPE: PRT
<213> ORGANISM: Artificial sequence
<220> FEATURE:
<223> OTHER INFORMATION: short peptide

<400> SEQUENCE: 267

Arg Leu Met Ser Ala Leu Thr Gln Leu
1               5

<210> SEQ ID NO 268
<211> LENGTH: 9
<212> TYPE: PRT
<213> ORGANISM: Artificial sequence
<220> FEATURE:
<223> OTHER INFORMATION: short peptide

<400> SEQUENCE: 268

Arg Leu Met Ser Ala Leu Thr Gln Val
1               5

<210> SEQ ID NO 269
```

```
<211> LENGTH: 10
<212> TYPE: PRT
<213> ORGANISM: Artificial sequence
<220> FEATURE:
<223> OTHER INFORMATION: short peptide

<400> SEQUENCE: 269

Glu Leu Ala Gly Ile Gly Ile Leu Thr Val
1               5                   10

<210> SEQ ID NO 270
<211> LENGTH: 9
<212> TYPE: PRT
<213> ORGANISM: Artificial sequence
<220> FEATURE:
<223> OTHER INFORMATION: short peptide

<400> SEQUENCE: 270

Asn Leu Val Pro Met Val Ala Thr Val
1               5

<210> SEQ ID NO 271
<211> LENGTH: 9
<212> TYPE: PRT
<213> ORGANISM: Artificial sequence
<220> FEATURE:
<223> OTHER INFORMATION: short peptide

<400> SEQUENCE: 271

Ser Leu Tyr Asn Thr Val Ala Thr Leu
1               5

<210> SEQ ID NO 272
<211> LENGTH: 9
<212> TYPE: PRT
<213> ORGANISM: Artificial sequence
<220> FEATURE:
<223> OTHER INFORMATION: short peptide

<400> SEQUENCE: 272

Tyr Met Asp Gly Thr Met Ser Gln Val
1               5

<210> SEQ ID NO 273
<211> LENGTH: 9
<212> TYPE: PRT
<213> ORGANISM: Artificial sequence
<220> FEATURE:
<223> OTHER INFORMATION: short peptide

<400> SEQUENCE: 273

Arg Met Phe Pro Asn Ala Pro Tyr Leu
1               5

<210> SEQ ID NO 274
<211> LENGTH: 10
<212> TYPE: PRT
<213> ORGANISM: Artificial sequence
<220> FEATURE:
<223> OTHER INFORMATION: short peptide

<400> SEQUENCE: 274

Gly Val Tyr Asp Gly Arg Glu His Thr Val
1               5                   10

<210> SEQ ID NO 275
<211> LENGTH: 9
```

```
<212> TYPE: PRT
<213> ORGANISM: Artificial sequence
<220> FEATURE:
<223> OTHER INFORMATION: short peptide

<400> SEQUENCE: 275

Thr Leu Met Ser Ala Met Thr Asn Leu
1               5

<210> SEQ ID NO 276
<211> LENGTH: 9
<212> TYPE: PRT
<213> ORGANISM: Artificial sequence
<220> FEATURE:
<223> OTHER INFORMATION: short peptide

<400> SEQUENCE: 276

Ala Leu Ser Val Met Gly Val Tyr Val
1               5

<210> SEQ ID NO 277
<211> LENGTH: 9
<212> TYPE: PRT
<213> ORGANISM: Artificial sequence
<220> FEATURE:
<223> OTHER INFORMATION: short peptide

<400> SEQUENCE: 277

Lys Ala Ser Glu Lys Ile Phe Tyr Val
1               5

<210> SEQ ID NO 278
<211> LENGTH: 9
<212> TYPE: PRT
<213> ORGANISM: Artificial sequence
<220> FEATURE:
<223> OTHER INFORMATION: short peptide

<400> SEQUENCE: 278

Ser Leu Leu Met Trp Ile Thr Gln Cys
1               5

<210> SEQ ID NO 279
<211> LENGTH: 9
<212> TYPE: PRT
<213> ORGANISM: Artificial sequence
<220> FEATURE:
<223> OTHER INFORMATION: short peptide

<400> SEQUENCE: 279

Thr Leu Phe Asp Tyr Glu Val Arg Leu
1               5

<210> SEQ ID NO 280
<211> LENGTH: 702
<212> TYPE: DNA
<213> ORGANISM: Artificial sequence
<220> FEATURE:
<223> OTHER INFORMATION: Nucleic Acid sequence of D11 light chain

<400> SEQUENCE: 280
atgagaccgt ctattcagtt cctggggctc ttgttgttct ggcttcatgg tgctcagtgt     60
gacatccaga tgacacagtc tccatcctca ctgtctgcat ctctgggagg caaagtcacc    120
atcacatgca aggcaagcca agacattcac aactatatag cttggtacca acacaagcct    180
gtaaaaggtc ctaggctgct catacattac acatctacat tacagccagg cacccccatca   240
```

```
aggttcagtg gaagtgggtc tgggagagat tattccttca gcatcagcaa cctggagcct    300
gaagatattg caacttatta ttgtctacag tatgataatc tgtggacgtt cggtggaggc    360
accaagctgg aaatcaaacg ggctgatgct gcaccaactg tatccatctt cccaccatcc    420
agtgagcagt taacatctgg aggtgcctca gtcgtgtgct tcttgaacaa cttctacccc    480
aaagacatca atgtcaagtg gaagattgat ggcagtgaac gacaaaatgg cgtcctgaac    540
agttggactg atcaggacag caaagacagc acctacagca tgagcagcac cctcacgttg    600
accaaggacg agtatgaacg acataacagc tatacctgtg aggccactca caagacatca    660
acttcaccca ttgtcaagag cttcaacagg aatgagtgtt ag                       702
```

<210> SEQ ID NO 281
<211> LENGTH: 233
<212> TYPE: PRT
<213> ORGANISM: Artificial sequence
<220> FEATURE:
<223> OTHER INFORMATION: Amino Acid sequence of D11 light chain

<400> SEQUENCE: 281

```
Met Arg Pro Ser Ile Gln Phe Leu Gly Leu Leu Leu Phe Trp Leu His
1               5                   10                  15

Gly Ala Gln Cys Asp Ile Gln Met Thr Gln Ser Pro Ser Ser Leu Ser
            20                  25                  30

Ala Ser Leu Gly Gly Lys Val Thr Ile Thr Cys Lys Ala Ser Gln Asp
        35                  40                  45

Ile His Asn Tyr Ile Ala Trp Tyr Gln His Lys Pro Val Lys Gly Pro
    50                  55                  60

Arg Leu Leu Ile His Tyr Thr Ser Thr Leu Gln Pro Gly Thr Pro Ser
65                  70                  75                  80

Arg Phe Ser Gly Ser Gly Ser Gly Arg Asp Tyr Ser Phe Ser Ile Ser
                85                  90                  95

Asn Leu Glu Pro Glu Asp Ile Ala Thr Tyr Tyr Cys Leu Gln Tyr Asp
            100                 105                 110

Asn Leu Trp Thr Phe Gly Gly Gly Thr Lys Leu Glu Ile Lys Arg Ala
        115                 120                 125

Asp Ala Ala Pro Thr Val Ser Ile Phe Pro Pro Ser Ser Glu Gln Leu
    130                 135                 140

Thr Ser Gly Gly Ala Ser Val Val Cys Phe Leu Asn Asn Phe Tyr Pro
145                 150                 155                 160

Lys Asp Ile Asn Val Lys Trp Lys Ile Asp Gly Ser Glu Arg Gln Asn
                165                 170                 175

Gly Val Leu Asn Ser Trp Thr Asp Gln Asp Ser Lys Asp Ser Thr Tyr
            180                 185                 190

Ser Met Ser Ser Thr Leu Thr Leu Thr Lys Asp Glu Tyr Glu Arg His
        195                 200                 205

Asn Ser Tyr Thr Cys Glu Ala Thr His Lys Thr Ser Thr Ser Pro Ile
    210                 215                 220

Val Lys Ser Phe Asn Arg Asn Glu Cys
225                 230
```

<210> SEQ ID NO 282
<211> LENGTH: 1398
<212> TYPE: DNA
<213> ORGANISM: Artificial sequence
<220> FEATURE:
<223> OTHER INFORMATION: Nucleic Acid sequence of D11 heavy chain

<400> SEQUENCE: 282

```
atggacaggc ttacttcctc attcctgctg ctgattgtcc ctgcatatgt cctttcccag    60
gtaactctga aagagtctgg ccctgggata ttgcagccct cccagaccct cagtctgact   120
tgttctttct ctgggttttc actgaccact tctggtatgg gtgtgagctg gattcgtcag   180
ccttcaggaa agggtctgga gtggctggca cacatttact gggatgatga caagcgctat   240
aacccatccc tgaagagccg actcacaatc tccaaggata cctccagaaa ccaggtattc   300
ctcaagatca ccagtgtgga cgctgcagat actgccacat actactgtgc tcgaaaggac   360
tacggtagta gcttctatgc tatgcactac tggggtcaag aacctcagt caccgtctcc    420
tcagccaaaa cgacaccccc atctgtctat ccactggccc ctggatctgc tgcccaaact   480
aactccatgg tgaccctggg atgcctggtc aagggctatt ccctgagcc agtgacagtg   540
acctggaact ctggatccct gtccagcggt gtgcacacct cccagctgt cctgcagtct    600
gacctctaca ctctgagcag ctcagtgact gtcccctcca gcacctggcc cagcgagacc   660
gtcacctgca acgttgccca cccggccagc agcaccaagg tggacaagaa aattgtgccc   720
agggattgtg gttgtaagcc ttgcatatgt acagtcccag aagtatcatc tgtcttcatc   780
ttccccccaa agcccaagga tgtgctcacc attactctga ctcctaaggt cacgtgtgtt   840
gtggtagaca tcagcaagga tgatcccgag gtccagttca gctggtttgt agatgatgtg   900
gaggtgcaca cagctcagac gcaaccccgg gaggagcagt tcaacagcac tttccgctca   960
gtcagtgaac ttcccatcat gcaccaggac tggctcaatg gcaaggagtt caaatgcagg  1020
gtcaacagtg cagctttccc tgcccccatc gagaaaacca tctccaaaac caaaggcaga  1080
ccgaaggctc cacaggtgta caccattcca cctcccaagg agcagatggc caaggataaa  1140
gtcagtctga cctgcatgat aacagacttc ttccctgaag acattactgt ggagtggcag  1200
tggaatgggc agccagcgga gaactacaag aacactcagc ccatcatgga cacagatggc  1260
tcttacttcg tctacagcaa gctcaatgtg cagaagagca ctgggaggc aggaaatact  1320
ttcacctgct ctgtgttaca tgagggcctg cacaaccacc atactgagaa gagcctctcc  1380
cactctcctg gtaaatga                                                 1398
```

<210> SEQ ID NO 283
<211> LENGTH: 465
<212> TYPE: PRT
<213> ORGANISM: Artificial sequence
<220> FEATURE:
<223> OTHER INFORMATION: Amino Acid sequence of D11 heavy chain

<400> SEQUENCE: 283

```
Met Asp Arg Leu Thr Ser Ser Phe Leu Leu Ile Val Pro Ala Tyr
1               5                   10                  15

Val Leu Ser Gln Val Thr Leu Lys Glu Ser Gly Pro Gly Ile Leu Gln
            20                  25                  30

Pro Ser Gln Thr Leu Ser Leu Thr Cys Ser Phe Ser Gly Phe Ser Leu
        35                  40                  45

Thr Thr Ser Gly Met Gly Val Ser Trp Ile Arg Gln Pro Ser Gly Lys
    50                  55                  60

Gly Leu Glu Trp Leu Ala His Ile Tyr Trp Asp Asp Asp Lys Arg Tyr
65                  70                  75                  80

Asn Pro Ser Leu Lys Ser Arg Leu Thr Ile Ser Lys Asp Thr Ser Arg
                85                  90                  95
```

-continued

```
Asn Gln Val Phe Leu Lys Ile Thr Ser Val Asp Ala Ala Asp Thr Ala
                100                 105                 110
Thr Tyr Tyr Cys Ala Arg Lys Asp Tyr Gly Ser Ser Phe Tyr Ala Met
            115                 120                 125
His Tyr Trp Gly Gln Gly Thr Ser Val Thr Val Ser Ser Ala Lys Thr
        130                 135                 140
Thr Pro Pro Ser Val Tyr Pro Leu Ala Pro Gly Ser Ala Ala Gln Thr
145                 150                 155                 160
Asn Ser Met Val Thr Leu Gly Cys Leu Val Lys Gly Tyr Phe Pro Glu
                165                 170                 175
Pro Val Thr Val Thr Trp Asn Ser Gly Ser Leu Ser Ser Gly Val His
            180                 185                 190
Thr Phe Pro Ala Val Leu Gln Ser Asp Leu Tyr Thr Leu Ser Ser Ser
        195                 200                 205
Val Thr Val Pro Ser Ser Thr Trp Pro Ser Glu Thr Val Thr Cys Asn
210                 215                 220
Val Ala His Pro Ala Ser Ser Thr Lys Val Asp Lys Lys Ile Val Pro
225                 230                 235                 240
Arg Asp Cys Gly Cys Lys Pro Cys Ile Cys Thr Val Pro Glu Val Ser
                245                 250                 255
Ser Val Phe Ile Phe Pro Pro Lys Pro Lys Asp Val Leu Thr Ile Thr
            260                 265                 270
Leu Thr Pro Lys Val Thr Cys Val Val Val Asp Ile Ser Lys Asp Asp
        275                 280                 285
Pro Glu Val Gln Phe Ser Trp Phe Val Asp Asp Val Glu Val His Thr
290                 295                 300
Ala Gln Thr Gln Pro Arg Glu Glu Gln Phe Asn Ser Thr Phe Arg Ser
305                 310                 315                 320
Val Ser Glu Leu Pro Ile Met His Gln Asp Trp Leu Asn Gly Lys Glu
                325                 330                 335
Phe Lys Cys Arg Val Asn Ser Ala Ala Phe Pro Ala Pro Ile Glu Lys
            340                 345                 350
Thr Ile Ser Lys Thr Lys Gly Arg Pro Lys Ala Pro Gln Val Tyr Thr
        355                 360                 365
Ile Pro Pro Pro Lys Glu Gln Met Ala Lys Asp Lys Val Ser Leu Thr
370                 375                 380
Cys Met Ile Thr Asp Phe Phe Pro Glu Asp Ile Thr Val Glu Trp Gln
385                 390                 395                 400
Trp Asn Gly Gln Pro Ala Glu Asn Tyr Lys Asn Thr Gln Pro Ile Met
                405                 410                 415
Asp Thr Asp Gly Ser Tyr Phe Val Tyr Ser Lys Leu Asn Val Gln Lys
            420                 425                 430
Ser Asn Trp Glu Ala Gly Asn Thr Phe Thr Cys Ser Val Leu His Glu
        435                 440                 445
Gly Leu His Asn His His Thr Glu Lys Ser Leu Ser His Ser Pro Gly
        450                 455                 460
Lys
465

<210> SEQ ID NO 284
<211> LENGTH: 33
<212> TYPE: DNA
<213> ORGANISM: Artificial sequence
<220> FEATURE:
<223> OTHER INFORMATION: Nucleic Acid sequence of D11 light chain CDR
```

<400> SEQUENCE: 284
aaggcaagcc aagacattca caactatata gct                              33

<210> SEQ ID NO 285
<211> LENGTH: 21
<212> TYPE: DNA
<213> ORGANISM: Artificial sequence
<220> FEATURE:
<223> OTHER INFORMATION: Nucleic Acid sequence of D11 light chain CDR

<400> SEQUENCE: 285
tacacatcta cattacagcc a                                            21

<210> SEQ ID NO 286
<211> LENGTH: 24
<212> TYPE: DNA
<213> ORGANISM: Artificial sequence
<220> FEATURE:
<223> OTHER INFORMATION: Nucleic Acid sequence of D11 light chain CDR

<400> SEQUENCE: 286
ctacagtatg ataatctgtg gacg                                         24

<210> SEQ ID NO 287
<211> LENGTH: 11
<212> TYPE: PRT
<213> ORGANISM: Artificial sequence
<220> FEATURE:
<223> OTHER INFORMATION: Amino Acid sequence of D11 light chain CDR

<400> SEQUENCE: 287

Lys Ala Ser Gln Asp Ile His Asn Tyr Ile Ala
1               5                   10

<210> SEQ ID NO 288
<211> LENGTH: 7
<212> TYPE: PRT
<213> ORGANISM: Artificial sequence
<220> FEATURE:
<223> OTHER INFORMATION: Amino Acid sequence of D11 light chain CDR

<400> SEQUENCE: 288

Tyr Thr Ser Thr Leu Gln Pro
1               5

<210> SEQ ID NO 289
<211> LENGTH: 8
<212> TYPE: PRT
<213> ORGANISM: Artificial sequence
<220> FEATURE:
<223> OTHER INFORMATION: Amino Acid sequence of D11 light chain CDR

<400> SEQUENCE: 289

Leu Gln Tyr Asp Asn Leu Trp Thr
1               5

<210> SEQ ID NO 290
<211> LENGTH: 21
<212> TYPE: DNA
<213> ORGANISM: Artificial sequence
<220> FEATURE:
<223> OTHER INFORMATION: Nucleic Acid sequence of D11 heavy chain CDR

<400> SEQUENCE: 290
acttctggta tgggtgtgag c                                            21

<210> SEQ ID NO 291
<211> LENGTH: 48
<212> TYPE: DNA
<213> ORGANISM: Artificial sequence
<220> FEATURE:
<223> OTHER INFORMATION: Nucleic Acid sequence of D11 heavy chain CDR

<400> SEQUENCE: 291
cacatttact gggatgatga caagcgctat aacccatccc tgaagagc         48

<210> SEQ ID NO 292
<211> LENGTH: 36
<212> TYPE: DNA
<213> ORGANISM: Artificial sequence
<220> FEATURE:
<223> OTHER INFORMATION: Nucleic Acid sequence of D11 heavy chain CDR

<400> SEQUENCE: 292
aaggactacg gtagtagctt ctatgctatg cactac                     36

<210> SEQ ID NO 293
<211> LENGTH: 7
<212> TYPE: PRT
<213> ORGANISM: Artificial sequence
<220> FEATURE:
<223> OTHER INFORMATION: Amino Acid sequence of D11 heavy chain CDR

<400> SEQUENCE: 293

Thr Ser Gly Met Gly Val Ser
1               5

<210> SEQ ID NO 294
<211> LENGTH: 16
<212> TYPE: PRT
<213> ORGANISM: Artificial sequence
<220> FEATURE:
<223> OTHER INFORMATION: Amino Acid sequence of D11 heavy chain CDR

<400> SEQUENCE: 294

His Ile Tyr Trp Asp Asp Asp Lys Arg Tyr Asn Pro Ser Leu Lys Ser
1               5                   10                  15

<210> SEQ ID NO 295
<211> LENGTH: 12
<212> TYPE: PRT
<213> ORGANISM: Artificial sequence
<220> FEATURE:
<223> OTHER INFORMATION: Amino Acid sequence of D11 heavy chain CDR

<400> SEQUENCE: 295

Lys Asp Tyr Gly Ser Ser Phe Tyr Ala Met His Tyr
1               5                   10

<210> SEQ ID NO 296
<211> LENGTH: 705
<212> TYPE: DNA
<213> ORGANISM: Artificial sequence
<220> FEATURE:
<223> OTHER INFORMATION: Nucleic Acid sequence of D7 light chain

<400> SEQUENCE: 296
atgagtgtgc ccactcaggt cctggggttg ctgctgctgt ggcttacaga tgccagatgt    60
gacatccaga tgactcagtc tccagcctcc tatctgtat ctgtgggaga aactgtcacc   120
atcacatgtc gagcaagtga tattatttac agtaatttag catggtatca gcagaaacag   180

```
ggaaaatctc ctcagctcct ggtctatgct gcaacaaact tagcagctgg tgtgccatca      240
aggttcagtg gcagtggatc aggcacacag tattccctca agatcaatag cctgcagtct      300
gaagattttg ggacttatta ctgtcaacat ttttggggta gttcaatctc gttcggctcg      360
gggacaaagt tggaaataaa acgggctgat gctgcaccaa ctgtatccat cttcccacca      420
tccagtgagc agttaacatc tggaggtgcc tcagtcgtgt gcttcttgaa caacttctac      480
cccaaagaca tcaatgtcaa gtggaagatt gatggcagtg aacgacaaaa tggcgtcctg      540
aacagttgga ctgatcagga cagcaaagac agcacctaca gcatgagcag cacccteacg      600 ttgaccaagg acgagtatga acgacataac agctatacct gtgaggccac tcacaagaca      660
tcaacttcac ccattgtcaa gagcttcaac aggaatgagt gttag                      705
```

<210> SEQ ID NO 297
<211> LENGTH: 234
<212> TYPE: PRT
<213> ORGANISM: Artificial sequence
<220> FEATURE:
<223> OTHER INFORMATION: Amino Acid sequence of D7 light chain

<400> SEQUENCE: 297

```
Met Ser Val Pro Thr Gln Val Leu Gly Leu Leu Leu Leu Trp Leu Thr
1               5                   10                  15

Asp Ala Arg Cys Asp Ile Gln Met Thr Gln Ser Pro Ala Ser Leu Ser
                20                  25                  30

Val Ser Val Gly Glu Thr Val Thr Ile Thr Cys Arg Ala Ser Asp Ile
            35                  40                  45

Ile Tyr Ser Asn Leu Ala Trp Tyr Gln Gln Lys Gln Gly Lys Ser Pro
        50                  55                  60

Gln Leu Leu Val Tyr Ala Ala Thr Asn Leu Ala Ala Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Ser Glu Asp Phe Gly Thr Tyr Tyr Cys Gln His Phe Trp
            100                 105                 110

Gly Ser Ser Ile Ser Phe Gly Ser Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230
```

<210> SEQ ID NO 298
<211> LENGTH: 1380
<212> TYPE: DNA
<213> ORGANISM: Artificial sequence
<220> FEATURE:
<223> OTHER INFORMATION: Nucleic Acid sequence of D7 heavy chain

<400> SEQUENCE: 298

```
atggctgtcc tggtgctgtt cctctgcctg gttgcatttc caagctgtgt cctgtcccag    60
gtgcaactga aggaatcagg acctggtctg gtggcgccct cacagagcct gtccatcact   120
tgcactgtct ctgggttttc attaaccagc tatggtgtac actgggttcg ccagcctcca   180
ggaaagggtc tggagtggct gggagtaata tgggctggtg aaccacaaa ttataattcg    240
gctctcatgt ccagactgag catcagcaga gacaactcca agagccaagt tttcttagaa   300
atgaacagtc tgcaaactga tgacacagcc atttactact gtgccagaga tggtcacttc   360
cactttgact tctggggcca aggcaccact ctcacagtct cctcagccaa aacgacaccc   420
ccatctgtct atccactggc cctggatctg ctgcccaaa ctaactccat ggtgaccctg    480
ggatgcctgg tcaagggcta tttccctgag ccagtgacag tgacctggaa ctctggatcc   540
ctgtccagcg gtgtgcacac cttcccagct gtcctgcagt ctgacctcta cactctgagc   600
agctcagtga ctgtcccctc agcacctgg cccagcgaga ccgtcacctg caacgttgcc    660
cacccggcca gcagcaccaa ggtggacaag aaaattgtgc ccagggattg tggttgtaag   720
ccttgcatat gtacagtccc agaagtatca tctgtcttca tcttcccccc aaagcccaag   780
gatgtgctca ccattactct gactcctaag gtcacgtgtg ttgtggtaga catcagcaag   840
gatgatcccg aggtccagtt cagctggttt gtagatgatg tggaggtgca cacagctcag   900
acgcaacccc gggaggagca gttcaacagc actttccgct cagtcagtga acttcccatc   960
atgcaccagg actggctcaa tggcaaggag ttcaaatgca gggtcaacag tgcagctttc  1020
cctgcccca tcgagaaaac catctccaaa accaaaggca gaccgaaggc tccacaggtg   1080
tacaccattc cacctcccaa ggagcagatg gccaaggata agtcagtct gacctgcatg   1140
ataacagact tcttccctga agacattact gtggagtggc agtggaatgg cagccagcg   1200
gagaactaca agaacactca gcccatcatg gacacagatg gctcttactt cgtctacagc  1260
aagctcaatg tgcagaagag caactgggag gcaggaaata ctttcacctg ctctgtgtta  1320
catgagggcc tgcacaacca ccatactgag aagagcctct cccactctcc tggtaaatga  1380
```

<210> SEQ ID NO 299
<211> LENGTH: 459
<212> TYPE: PRT
<213> ORGANISM: Artificial sequence
<220> FEATURE:
<223> OTHER INFORMATION: Amino Acid sequence of D7 heavy chain

<400> SEQUENCE: 299

```
Met Ala Val Leu Val Leu Phe Leu Cys Leu Val Ala Phe Pro Ser Cys
 1               5                  10                  15

Val Leu Ser Gln Val Gln Leu Lys Glu Ser Gly Pro Gly Leu Val Ala
            20                  25                  30

Pro Ser Gln Ser Leu Ser Ile Thr Cys Thr Val Ser Gly Phe Ser Leu
        35                  40                  45

Thr Ser Tyr Gly Val His Trp Val Arg Gln Pro Pro Gly Lys Gly Leu
    50                  55                  60

Glu Trp Leu Gly Val Ile Trp Ala Gly Gly Thr Thr Asn Tyr Asn Ser
65                  70                  75                  80

Ala Leu Met Ser Arg Leu Ser Ile Ser Arg Asp Asn Ser Lys Ser Gln
                85                  90                  95
```

Val Phe Leu Glu Met Asn Ser Leu Gln Thr Asp Thr Ala Ile Tyr
            100                 105                 110

Tyr Cys Ala Arg Asp Gly His Phe His Phe Asp Phe Trp Gly Gln Gly
            115                 120                 125

Thr Thr Leu Thr Val Ser Ser Ala Lys Thr Thr Pro Pro Ser Val Tyr
130                 135                 140

Pro Leu Ala Pro Gly Ser Ala Ala Gln Thr Asn Ser Met Val Thr Leu
145                 150                 155                 160

Gly Cys Leu Val Lys Gly Tyr Phe Pro Glu Pro Val Thr Val Thr Trp
                165                 170                 175

Asn Ser Gly Ser Leu Ser Ser Gly Val His Thr Phe Pro Ala Val Leu
            180                 185                 190

Gln Ser Asp Leu Tyr Thr Leu Ser Ser Val Thr Val Pro Ser Ser
            195                 200                 205

Thr Trp Pro Ser Glu Thr Val Thr Cys Asn Val Ala His Pro Ala Ser
            210                 215                 220

Ser Thr Lys Val Asp Lys Lys Ile Val Pro Arg Asp Cys Gly Cys Lys
225                 230                 235                 240

Pro Cys Ile Cys Thr Val Pro Glu Val Ser Ser Val Phe Ile Phe Pro
            245                 250                 255

Pro Lys Pro Lys Asp Val Leu Thr Ile Thr Leu Thr Pro Lys Val Thr
            260                 265                 270

Cys Val Val Asp Ile Ser Lys Asp Asp Pro Glu Val Gln Phe Ser
            275                 280                 285

Trp Phe Val Asp Asp Val Glu Val His Thr Ala Gln Thr Gln Pro Arg
290                 295                 300

Glu Glu Gln Phe Asn Ser Thr Phe Arg Ser Val Ser Glu Leu Pro Ile
305                 310                 315                 320

Met His Gln Asp Trp Leu Asn Gly Lys Glu Phe Lys Cys Arg Val Asn
            325                 330                 335

Ser Ala Ala Phe Pro Ala Pro Ile Glu Lys Thr Ile Ser Lys Thr Lys
            340                 345                 350

Gly Arg Pro Lys Ala Pro Gln Val Tyr Thr Ile Pro Pro Lys Glu
            355                 360                 365

Gln Met Ala Lys Asp Lys Val Ser Leu Thr Cys Met Ile Thr Asp Phe
370                 375                 380

Phe Pro Glu Asp Ile Thr Val Glu Trp Gln Trp Asn Gly Gln Pro Ala
385                 390                 395                 400

Glu Asn Tyr Lys Asn Thr Gln Pro Ile Met Asp Thr Asp Gly Ser Tyr
            405                 410                 415

Phe Val Tyr Ser Lys Leu Asn Val Gln Lys Ser Asn Trp Glu Ala Gly
            420                 425                 430

Asn Thr Phe Thr Cys Ser Val Leu His Glu Gly Leu His Asn His His
            435                 440                 445

Thr Glu Lys Ser Leu Ser His Ser Pro Gly Lys
            450                 455

<210> SEQ ID NO 300
<211> LENGTH: 33
<212> TYPE: DNA
<213> ORGANISM: Artificial sequence
<220> FEATURE:
<223> OTHER INFORMATION: Nucleic Acid sequence of D7 light chain CDR

<400> SEQUENCE: 300

```
cgagcaagtg atattattta cagtaattta gca                          33
```

<210> SEQ ID NO 301
<211> LENGTH: 21
<212> TYPE: DNA
<213> ORGANISM: Artificial sequence
<220> FEATURE:
<223> OTHER INFORMATION: Nucleic Acid sequence of D7 light chain CDR

<400> SEQUENCE: 301

```
gctgcaacaa acttagcagc t                                       21
```

<210> SEQ ID NO 302
<211> LENGTH: 27
<212> TYPE: DNA
<213> ORGANISM: Artificial sequence
<220> FEATURE:
<223> OTHER INFORMATION: Nucleic Acid sequence of D7 light chain CDR

<400> SEQUENCE: 302

```
caacattttt ggggtagttc aatctcg                                 27
```

<210> SEQ ID NO 303
<211> LENGTH: 11
<212> TYPE: PRT
<213> ORGANISM: Artificial sequence
<220> FEATURE:
<223> OTHER INFORMATION: Amino Acid sequence of D7 light chain CDR

<400> SEQUENCE: 303

Arg Ala Ser Asp Ile Ile Tyr Ser Asn Leu Ala
1               5                   10

<210> SEQ ID NO 304
<211> LENGTH: 7
<212> TYPE: PRT
<213> ORGANISM: Artificial sequence
<220> FEATURE:
<223> OTHER INFORMATION: Amino Acid sequence of D7 light chain CDR

<400> SEQUENCE: 304

Ala Ala Thr Asn Leu Ala Ala
1               5

<210> SEQ ID NO 305
<211> LENGTH: 9
<212> TYPE: PRT
<213> ORGANISM: Artificial sequence
<220> FEATURE:
<223> OTHER INFORMATION: Amino Acid sequence of D7 light chain CDR

<400> SEQUENCE: 305

Gln His Phe Trp Gly Ser Ser Ile Ser
1               5

<210> SEQ ID NO 306
<211> LENGTH: 15
<212> TYPE: DNA
<213> ORGANISM: Artificial sequence
<220> FEATURE:
<223> OTHER INFORMATION: Nucleic Acid sequence of D7 heavy chain CDR

<400> SEQUENCE: 306

```
agctatggtg tacac                                              15
```

<210> SEQ ID NO 307

```
<211> LENGTH: 48
<212> TYPE: DNA
<213> ORGANISM: Artificial sequence
<220> FEATURE:
<223> OTHER INFORMATION: Nucleic Acid sequence of D7 heavy chain CDR

<400> SEQUENCE: 307
gtaatatggg ctggtggaac cacaaattat aattcggctc tcatgtcc        48

<210> SEQ ID NO 308
<211> LENGTH: 24
<212> TYPE: DNA
<213> ORGANISM: Artificial sequence
<220> FEATURE:
<223> OTHER INFORMATION: Nucleic Acid sequence of D7 heavy chain CDR

<400> SEQUENCE: 308
gatggtcact tccactttga cttc        24

<210> SEQ ID NO 309
<211> LENGTH: 5
<212> TYPE: PRT
<213> ORGANISM: Artificial sequence
<220> FEATURE:
<223> OTHER INFORMATION: Amino Acid sequence of D7 heavy chain CDR

<400> SEQUENCE: 309

Ser Tyr Gly Val His
1               5

<210> SEQ ID NO 310
<211> LENGTH: 16
<212> TYPE: PRT
<213> ORGANISM: Artificial sequence
<220> FEATURE:
<223> OTHER INFORMATION: Amino Acid sequence of D7 heavy chain CDR

<400> SEQUENCE: 310

Val Ile Trp Ala Gly Gly Thr Thr Asn Tyr Asn Ser Ala Leu Met Ser
1               5                   10                  15

<210> SEQ ID NO 311
<211> LENGTH: 8
<212> TYPE: PRT
<213> ORGANISM: Artificial sequence
<220> FEATURE:
<223> OTHER INFORMATION: Amino Acid sequence of D7 heavy chain CDR

<400> SEQUENCE: 311

Asp Gly His Phe His Phe Asp Phe
1               5

<210> SEQ ID NO 312
<211> LENGTH: 642
<212> TYPE: DNA
<213> ORGANISM: Artificial sequence
<220> FEATURE:
<223> OTHER INFORMATION: Nucleic Acid sequence of B47B6 light chain

<400> SEQUENCE: 312
gatattgtgc tcactcagtc tccagccacc ctgtctgtga gtccaggaga tagcgtcagt     60
ctttcctgca gggccagcca agtattagc aacagcctac actggtatca acaaaaatca    120
catgagtctc caaggcttct catcaagtat gcttcccagt ccatctctgg aatcccctct    180
aggttcagtg gcagtggatc aggacagat ttcactctca gtatcaacag tgtggagact    240
```

```
gaagattttg gaatgtattt ctgtcaacag agttacagct ggcctctcac gttcggtgct      300
gggtccaagc tggagctgaa acgggctgat gctgcaccaa ctgtatccat cttcccacca      360
tccagtgagc agttaacatc tggaggtgcc tcagtcgtgt gcttcttgaa caacttctac      420
cccaaagaca tcaatgtcaa gtggaagatt gatggcagtg aacgacaaaa tggcgtcctg      480
aacagttgga ctgatcagga cagcaaagac agcacctaca gcatgagcag caccctcacg      540
ttgaccaagg acgagtatga acgacataac agctatacct gtgaggccac tcacaagaca      600
tcaacttcac ccattgtcaa gagcttcaac aggaatgagt gt                        642
```

<210> SEQ ID NO 313
<211> LENGTH: 214
<212> TYPE: PRT
<213> ORGANISM: Artificial sequence
<220> FEATURE:
<223> OTHER INFORMATION: Amino Acid sequence of B47B6 light chain

<400> SEQUENCE: 313

```
Asp Ile Val Leu Thr Gln Ser Pro Ala Thr Leu Ser Val Ser Pro Gly
1               5                   10                  15

Asp Ser Val Ser Leu Ser Cys Arg Ala Ser Gln Ser Ile Ser Asn Ser
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Tyr Ser Trp Pro Leu
                85                  90                  95

Thr Phe Gly Ala Gly Ser Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 314
<211> LENGTH: 1323
<212> TYPE: DNA
<213> ORGANISM: Artificial sequence
<220> FEATURE:
<223> OTHER INFORMATION: Nucleic Acid sequence of B47B6 heavy chain

<400> SEQUENCE: 314

```
gaagtgcagt tggtggagtc ggggggaggc ttagtgaagc ctggagggtc cctgaaactc       60
tcctgtgcag cctctggatt cgttttcagt agctatgaca tgtcttgggt tcgccaggct      120
```

```
caggagaaga ggctggagtg ggtcgcatac atgagtagtg gtggcggcac ctactatcca    180
gacactgtga agggccgatt caccatctcc agagacaatg ccaagaacac cctgcacctg    240
caaatgagca gcctgaagtc tgaggacaca gccatgtatt actgtgcaag acatgatgag    300
attactaact ttgactactg gggccaaggc accactctca cagtctcctc agccaaaacg    360
acacccccat ctgtctatcc actggcccct ggatctgctg cccaaactaa ctccatggtg    420
accctgggat gcctggtcaa gggctatttc cctgagccag tgacagtgac ctggaactct    480
ggatccctgt ccagcggtgt gcacaccttc ccagctgtcc tgcagtctga cctctacact    540
ctgagcagct cagtgactgt cccctccagc acctggccca gcgagaccgt cacctgcaac    600
gttgcccacc cggccagcag caccaaggtg gacaagaaaa ttgtgcccag ggattgtggt    660
tgtaagcctt gcatatgtac agtcccagaa gtatcatctg tcttcatctt cccccccaag    720
cccaaggatg tgctcaccat tactctgact cctaaggtca cgtgtgttgt ggtagacatc    780
agcaaggatg atcccgaggt ccagttcagc tggtttgtag atgatgtgga ggtgcacaca    840
gctcagacgc aaccccggga ggagcagttc aacagcactt tccgctcagt cagtgaactt    900
cccatcatgc accaggactg gctcaatggc aaggagttca aatgcagggt caacagtgca    960
gctttccctg cccccatcga gaaaaccatc tccaaaacca aaggcagacc gaaggctcca   1020
caggtgtaca ccattccacc tcccaaggag cagatggcca aggataaagt cagtctgacc   1080
tgcatgataa cagacttctt ccctgaagac attactgtgg agtggcagtg gaatgggcag   1140
ccagcggaga actacaagaa cactcagccc atcatggaca gagtggctc ttacttcgtc   1200 tacagcaagc tcaatgtgca gaagagcaac tgggaggcag gaaatacttt cacctgctct   1260
gtgttacatg agggcctgca caaccaccat actgagaaga gcctctccca ctctcctggt   1320
aaa                                                                  1323

<210> SEQ ID NO 315
<211> LENGTH: 441
<212> TYPE: PRT
<213> ORGANISM: Artificial sequence
<220> FEATURE:
<223> OTHER INFORMATION: Amino Acid sequence of B47B6 heavy chain

<400> SEQUENCE: 315

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Val Phe Ser Ser Tyr
            20                  25                  30

Asp Met Ser Trp Val Arg Gln Ala Gln Glu Lys Arg Leu Glu Trp Val
        35                  40                  45

Ala Tyr Met Ser Ser Gly Gly Gly Thr Tyr Tyr Pro Asp Thr Val Lys
    50                  55                  60

Gly Arg Phe Thr Ile Ser Arg Asp Asn Ala Lys Asn Thr Leu His Leu
65                  70                  75                  80

Gln Met Ser Ser Leu Lys Ser Glu Asp Thr Ala Met Tyr Tyr Cys Ala
                85                  90                  95

Arg His Asp Glu Ile Thr Asn Phe Asp Tyr Trp Gly Gln Gly Thr Thr
            100                 105                 110

Leu Thr Val Ser Ser Ala Lys Thr Thr Pro Pro Ser Val Tyr Pro Leu
        115                 120                 125

Ala Pro Gly Ser Ala Ala Gln Thr Asn Ser Met Val Thr Leu Gly Cys
    130                 135                 140
```

Leu Val Lys Gly Tyr Phe Pro Glu Pro Val Thr Val Thr Trp Asn Ser
145                 150                 155                 160

Gly Ser Leu Ser Ser Gly Val His Thr Phe Pro Ala Val Leu Gln Ser
            165                 170                 175

Asp Leu Tyr Thr Leu Ser Ser Ser Val Thr Val Pro Ser Ser Thr Trp
        180                 185                 190

Pro Ser Glu Thr Val Thr Cys Asn Val Ala His Pro Ala Ser Ser Thr
    195                 200                 205

Lys Val Asp Lys Ile Val Pro Arg Asp Cys Gly Cys Lys Pro Cys
210                 215                 220

Ile Cys Thr Val Pro Glu Val Ser Ser Val Phe Ile Phe Pro Pro Lys
225                 230                 235                 240

Pro Lys Asp Val Leu Thr Ile Thr Leu Thr Pro Lys Val Thr Cys Val
                245                 250                 255

Val Val Asp Ile Ser Lys Asp Asp Pro Glu Val Gln Phe Ser Trp Phe
            260                 265                 270

Val Asp Asp Val Glu Val His Thr Ala Gln Thr Gln Pro Arg Glu Glu
        275                 280                 285

Gln Phe Asn Ser Thr Phe Arg Ser Val Ser Glu Leu Pro Ile Met His
    290                 295                 300

Gln Asp Trp Leu Asn Gly Lys Glu Phe Lys Cys Arg Val Asn Ser Ala
305                 310                 315                 320

Ala Phe Pro Ala Pro Ile Glu Lys Thr Ile Ser Lys Thr Lys Gly Arg
                325                 330                 335

Pro Lys Ala Pro Gln Val Tyr Thr Ile Pro Pro Lys Glu Gln Met
            340                 345                 350

Ala Lys Asp Lys Val Ser Leu Thr Cys Met Ile Thr Asp Phe Phe Pro
            355                 360                 365

Glu Asp Ile Thr Val Glu Trp Gln Trp Asn Gly Gln Pro Ala Glu Asn
370                 375                 380

Tyr Lys Asn Thr Gln Pro Ile Met Asp Thr Asp Gly Ser Tyr Phe Val
385                 390                 395                 400

Tyr Ser Lys Leu Asn Val Gln Lys Ser Asn Trp Glu Ala Gly Asn Thr
                405                 410                 415

Phe Thr Cys Ser Val Leu His Glu Gly Leu His Asn His His Thr Glu
            420                 425                 430

Lys Ser Leu Ser His Ser Pro Gly Lys
            435                 440

<210> SEQ ID NO 316
<211> LENGTH: 33
<212> TYPE: DNA
<213> ORGANISM: Artificial sequence
<220> FEATURE:
<223> OTHER INFORMATION: Nucleic Acid sequence of B47B6 light chain CDR

<400> SEQUENCE: 316
agggccagcc aaagtattag caacagccta cac                                    33

<210> SEQ ID NO 317
<211> LENGTH: 21
<212> TYPE: DNA
<213> ORGANISM: Artificial sequence
<220> FEATURE:
<223> OTHER INFORMATION: Nucleic Acid sequence of B47B6 light chain CDR

<400> SEQUENCE: 317

```
tatgcttccc agtccatctc t                                           21
```

<210> SEQ ID NO 318
<211> LENGTH: 27
<212> TYPE: DNA
<213> ORGANISM: Artificial sequence
<220> FEATURE:
<223> OTHER INFORMATION: Nucleic Acid sequence of B47B6 light chain CDR

<400> SEQUENCE: 318

```
caacagagtt acagctggcc tctcacg                                     27
```

<210> SEQ ID NO 319
<211> LENGTH: 11
<212> TYPE: PRT
<213> ORGANISM: Artificial sequence
<220> FEATURE:
<223> OTHER INFORMATION: Amino Acid sequence of B47B6 light chain CDR

<400> SEQUENCE: 319

Arg Ala Ser Gln Ser Ile Ser Asn Ser Leu His
1               5                   10

<210> SEQ ID NO 320
<211> LENGTH: 7
<212> TYPE: PRT
<213> ORGANISM: Artificial sequence
<220> FEATURE:
<223> OTHER INFORMATION: Amino Acid sequence of B47B6 light chain CDR

<400> SEQUENCE: 320

Tyr Ala Ser Gln Ser Ile Ser
1               5

<210> SEQ ID NO 321
<211> LENGTH: 9
<212> TYPE: PRT
<213> ORGANISM: Artificial sequence
<220> FEATURE:
<223> OTHER INFORMATION: Amino Acid sequence of B47B6 light chain CDR

<400> SEQUENCE: 321

Gln Gln Ser Tyr Ser Trp Pro Leu Thr
1               5

<210> SEQ ID NO 322
<211> LENGTH: 15
<212> TYPE: DNA
<213> ORGANISM: Artificial sequence
<220> FEATURE:
<223> OTHER INFORMATION: Nucleic Acid sequence of B47B6  heavy chain CDR

<400> SEQUENCE: 322

```
agctatgaca tgtct                                                  15
```

<210> SEQ ID NO 323
<211> LENGTH: 48
<212> TYPE: DNA
<213> ORGANISM: Artificial sequence
<220> FEATURE:
<223> OTHER INFORMATION: Nucleic Acid sequence of B47B6  heavy chain CDR

<400> SEQUENCE: 323

```
tacatgagta gtggtggcgg cacctactat ccagacactg tgaagggc              48
```

-continued

```
<210> SEQ ID NO 324
<211> LENGTH: 27
<212> TYPE: DNA
<213> ORGANISM: Artificial sequence
<220> FEATURE:
<223> OTHER INFORMATION: Nucleic Acid sequence of B47B6 heavy chain CDR

<400> SEQUENCE: 324
catgatgaga ttactaactt tgactac                                              27

<210> SEQ ID NO 325
<211> LENGTH: 5
<212> TYPE: PRT
<213> ORGANISM: Artificial sequence
<220> FEATURE:
<223> OTHER INFORMATION: Amino Acid sequence of B47B6 heavy chain CDR

<400> SEQUENCE: 325

Ser Tyr Asp Met Ser
1               5

<210> SEQ ID NO 326
<211> LENGTH: 16
<212> TYPE: PRT
<213> ORGANISM: Artificial sequence
<220> FEATURE:
<223> OTHER INFORMATION: Amino Acid sequence of B47B6 heavy chain CDR

<400> SEQUENCE: 326

Tyr Met Ser Ser Gly Gly Gly Thr Tyr Tyr Pro Asp Thr Val Lys Gly
1               5                   10                  15

<210> SEQ ID NO 327
<211> LENGTH: 9
<212> TYPE: PRT
<213> ORGANISM: Artificial sequence
<220> FEATURE:
<223> OTHER INFORMATION: Amino Acid sequence of B47B6 heavy chain CDR

<400> SEQUENCE: 327

His Asp Glu Ile Thr Asn Phe Asp Tyr
1               5

<210> SEQ ID NO 328
<211> LENGTH: 639
<212> TYPE: DNA
<213> ORGANISM: Artificial sequence
<220> FEATURE:
<223> OTHER INFORMATION: Nucleic Acid sequence of C106B9 light chain

<400> SEQUENCE: 328
caaattgttc tcacccagtc tccagcaatc atgtctgcat ctccagggga gaaggtcacc        60
ataacctgca gtgtcagctc aagtgtagat tacattcact ggttccagca gaagccaggc       120
acttctccca aattctggat ttatagcaca tccatcctgg cttctggagt ccctgctcgc       180
ttcagtggca gtggatctgg gacctcttac tctctcacaa tcagccgaat ggaggctgaa       240
gatgctgcca cttattactg ccagcaaagg agtagttacc cacccacgtt cggctcgggg       300
acaaagttgg aaataaaacg ggctgatgct gcaccaactg tatccatctt cccaccatcc       360
agtgagcagt taacatctgg aggtgcctca gtcgtgtgct tcttgaacaa cttctacccc       420
aaagacatca atgtcaagtg gaagattgat ggcagtgaac gacaaaatgg cgtcctgaac       480
agttggactg atcaggacag caaagacagc acctacagca tgagcagcac cctcacgttg       540
accaaggacg agtatgaacg acataacagc tatacctgtg aggccactca caagacatca       600
``` acttcacccca ttgtcaagag cttcaacagg aatgagtgt                        639

<210> SEQ ID NO 329
<211> LENGTH: 213
<212> TYPE: PRT
<213> ORGANISM: Artificial sequence
<220> FEATURE:
<223> OTHER INFORMATION: Amino Acid sequence of C106B9 light chain

<400> SEQUENCE: 329

Gln Ile Val Leu Thr Gln Ser Pro Ala Ile Met Ser Ala Ser Pro Gly
1               5                   10                  15

Glu Lys Val Thr Ile Thr Cys Ser Val Ser Ser Val Asp Tyr Ile
            20                  25                  30

His Trp Phe Gln Gln Lys Pro Gly Thr Ser Pro Lys Phe Trp Ile Tyr
        35                  40                  45

Ser Thr Ser Ile Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Pro Thr
                85                  90                  95

Phe Gly Ser Gly Thr Lys Leu Glu Ile Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 330
<211> LENGTH: 1320
<212> TYPE: DNA
<213> ORGANISM: Artificial sequence
<220> FEATURE:
<223> OTHER INFORMATION: Nucleic Acid sequence of C106B9 heavy chain

<400> SEQUENCE: 330
caggttcaac tgcagcagtc tggaggtgag gtgatgaagc tggggcctc agtgaagctt       60 tcctgcaagg ctactggcta cacattcact ggctactgga tagagtggat aaaacagagg     120
cctggacatg gccttgagtg gattggagag atttttacctg gaagtggtgg tactaactac   180
aatgagaaat tcaagggcaa ggccacattc actgcacata catcctccaa cacagcctac    240
atgcaactca gcagcctgac aactgaggac tctgccatct attactgtgc aagggatagt    300 aactcctttta cttactgggg ccaagggact ctggtcactg tctcttcagc caaaacgaca    360
cccccatctg tctatccact ggcccctgga tctgctgccc aaactaactc catggtgacc    420

```
ctgggatgcc tggtcaaggg ctatttccct gagccagtga cagtgacctg gaactctgga   480
tccctgtcca gcggtgtgca caccttccca gctgtcctgc agtctgacct ctacactctg   540
agcagctcag tgactgtccc ctccagcacc tggcccagcg agaccgtcac ctgcaacgtt   600
gcccacccgg ccagcagcac caaggtggac aagaaaattg tgcccaggga ttgtggttgt   660
aagccttgca tatgtacagt cccagaagta tcatctgtct tcatcttccc cccaaagccc   720
aaggatgtgc tcaccattac tctgactcct aaggtcacgt gtgttgtggt agacatcagc   780
aaggatgatc ccgaggtcca gttcagctgg tttgtagatg atgtggaggt gcacacagct   840
cagacgcaac cccgggagga gcagttcaac agcactttcc gctcagtcag tgaacttccc   900
atcatgcacc aggactggct caatggcaag gagttcaaat gcagggtcaa cagtgcagct   960
ttccctgccc ccatcgagaa aaccatctcc aaaaccaaag cagaccgaa ggctccacag   1020 gtgtacacca ttccacctcc caaggagcag atggccaagg ataaagtcag tctgacctgc   1080
atgataacag acttcttccc tgaagacatt actgtggagt ggcagtggaa tgggcagcca   1140
gcggagaact acaagaacac tcagcccatc atggacacag atggctctta cttcgtctac   1200
agcaagctca atgtgcagaa gagcaactgg gaggcaggaa atactttcac ctgctctgtg   1260
ttacatgagg gcctgcacaa ccaccatact gagaagagcc tctcccactc tcctggtaaa   1320
```

<210> SEQ ID NO 331
<211> LENGTH: 440
<212> TYPE: PRT
<213> ORGANISM: Artificial sequence
<220> FEATURE:
<223> OTHER INFORMATION: Amino Acid sequence of C106B9 heavy chain

<400> SEQUENCE: 331

```
Gln Val Gln Leu Gln Gln Ser Gly Gly Glu Val Met Lys Pro Gly Ala
1               5                   10                  15

Ser Val Lys Leu Ser Cys Lys Ala Thr Gly Tyr Thr Phe Thr Gly Tyr
            20                  25                  30

Trp Ile Glu Trp Ile Lys Gln Arg Pro Gly His Gly Leu Glu Trp Ile
        35                  40                  45

Gly Glu Ile Leu Pro Gly Ser Gly Gly Thr Asn Tyr Asn Glu Lys Phe
    50                  55                  60

Lys Gly Lys Ala Thr Phe Thr Ala His Thr Ser Ser Asn Thr Ala Tyr
65                  70                  75                  80

Met Gln Leu Ser Ser Leu Thr Thr Glu Asp Ser Ala Ile Tyr Tyr Cys
                85                  90                  95

Ala Arg Asp Ser Asn Ser Phe Thr Tyr Trp Gly Gln Gly Thr Leu Val
            100                 105                 110

Thr Val Ser Ser Ala Lys Thr Thr Pro Pro Ser Val Tyr Pro Leu Ala
        115                 120                 125

Pro Gly Ser Ala Ala Gln Thr Asn Ser Met Val Thr Leu Gly Cys Leu
    130                 135                 140

Val Lys Gly Tyr Phe Pro Glu Pro Val Thr Val Thr Trp Asn Ser Gly
145                 150                 155                 160

Ser Leu Ser Ser Gly Val His Thr Phe Pro Ala Val Leu Gln Ser Asp
                165                 170                 175

Leu Tyr Thr Leu Ser Ser Ser Val Thr Val Pro Ser Ser Thr Trp Pro
            180                 185                 190

Ser Glu Thr Val Thr Cys Asn Val Ala His Pro Ala Ser Ser Thr Lys
        195                 200                 205
```

Val Asp Lys Lys Ile Val Pro Arg Asp Cys Gly Cys Lys Pro Cys Ile
210                 215                 220

Cys Thr Val Pro Glu Val Ser Ser Val Phe Ile Phe Pro Pro Lys Pro
225                 230                 235                 240

Lys Asp Val Leu Thr Ile Thr Leu Thr Pro Lys Val Thr Cys Val Val
            245                 250                 255

Val Asp Ile Ser Lys Asp Asp Pro Glu Val Gln Phe Ser Trp Phe Val
            260                 265                 270

Asp Asp Val Glu Val His Thr Ala Gln Thr Gln Pro Arg Glu Glu Gln
        275                 280                 285

Phe Asn Ser Thr Phe Arg Ser Val Ser Glu Leu Pro Ile Met His Gln
290                 295                 300

Asp Trp Leu Asn Gly Lys Glu Phe Lys Cys Arg Val Asn Ser Ala Ala
305                 310                 315                 320

Phe Pro Ala Pro Ile Glu Lys Thr Ile Ser Lys Thr Lys Gly Arg Pro
                325                 330                 335

Lys Ala Pro Gln Val Tyr Thr Ile Pro Pro Pro Lys Glu Gln Met Ala
            340                 345                 350

Lys Asp Lys Val Ser Leu Thr Cys Met Ile Thr Asp Phe Phe Pro Glu
            355                 360                 365

Asp Ile Thr Val Glu Trp Gln Trp Asn Gly Gln Pro Ala Glu Asn Tyr
        370                 375                 380

Lys Asn Thr Gln Pro Ile Met Asp Thr Asp Gly Ser Tyr Phe Val Tyr
385                 390                 395                 400

Ser Lys Leu Asn Val Gln Lys Ser Asn Trp Glu Ala Gly Asn Thr Phe
                405                 410                 415

Thr Cys Ser Val Leu His Glu Gly Leu His Asn His His Thr Glu Lys
            420                 425                 430

Ser Leu Ser His Ser Pro Gly Lys
        435                 440

<210> SEQ ID NO 332
<211> LENGTH: 30
<212> TYPE: DNA
<213> ORGANISM: Artificial sequence
<220> FEATURE:
<223> OTHER INFORMATION: Nucleic Acid sequence of C106B9 light chain CDR

<400> SEQUENCE: 332
agtgtcagct caagtgtaga ttacattcac                                    30

<210> SEQ ID NO 333
<211> LENGTH: 21
<212> TYPE: DNA
<213> ORGANISM: Artificial sequence
<220> FEATURE:
<223> OTHER INFORMATION: Nucleic Acid sequence of C106B9 light chain CDR

<400> SEQUENCE: 333
agcacatcca tcctggcttc t                                             21

<210> SEQ ID NO 334
<211> LENGTH: 27
<212> TYPE: DNA
<213> ORGANISM: Artificial sequence
<220> FEATURE:
<223> OTHER INFORMATION: Nucleic Acid sequence of C106B9 light chain CDR

<400> SEQUENCE: 334

```
cagcaaagga gtagttaccc acccacg                                          27
```

<210> SEQ ID NO 335
<211> LENGTH: 10
<212> TYPE: PRT
<213> ORGANISM: Artificial sequence
<220> FEATURE:
<223> OTHER INFORMATION: Amino Acid sequence of C106B9 light chain CDR

<400> SEQUENCE: 335

Ser Val Ser Ser Ser Val Asp Tyr Ile His
1               5                   10

<210> SEQ ID NO 336
<211> LENGTH: 7
<212> TYPE: PRT
<213> ORGANISM: Artificial sequence
<220> FEATURE:
<223> OTHER INFORMATION: Amino Acid sequence of C106B9 light chain CDR

<400> SEQUENCE: 336

Ser Thr Ser Ile Leu Ala Ser
1               5

<210> SEQ ID NO 337
<211> LENGTH: 9
<212> TYPE: PRT
<213> ORGANISM: Artificial sequence
<220> FEATURE:
<223> OTHER INFORMATION: Amino Acid sequence of C106B9 light chain CDR

<400> SEQUENCE: 337

Gln Gln Arg Ser Ser Tyr Pro Pro Thr
1               5

<210> SEQ ID NO 338
<211> LENGTH: 15
<212> TYPE: DNA
<213> ORGANISM: Artificial sequence
<220> FEATURE:
<223> OTHER INFORMATION: Nucleic Acid sequence of C106B9 heavy chain CDR

<400> SEQUENCE: 338

```
ggctactgga tagag                                                       15
```

<210> SEQ ID NO 339
<211> LENGTH: 51
<212> TYPE: DNA
<213> ORGANISM: Artificial sequence
<220> FEATURE:
<223> OTHER INFORMATION: Nucleic Acid sequence of C106B9 heavy chain CDR

<400> SEQUENCE: 339

```
gagattttac ctggaagtgg tggtactaac tacaatgaga aattcaaggg c               51
```

<210> SEQ ID NO 340
<211> LENGTH: 21
<212> TYPE: DNA
<213> ORGANISM: Artificial sequence
<220> FEATURE:
<223> OTHER INFORMATION: Nucleic Acid sequence of C106B9 heavy chain CDR

<400> SEQUENCE: 340

```
gatagtaact cctttactta c                                                21
```

<210> SEQ ID NO 341

```
<211> LENGTH: 5
<212> TYPE: PRT
<213> ORGANISM: Artificial sequence
<220> FEATURE:
<223> OTHER INFORMATION: Amino Acid sequence of C106B9 heavy chain CDR

<400> SEQUENCE: 341

Gly Tyr Trp Ile Glu
1               5

<210> SEQ ID NO 342
<211> LENGTH: 17
<212> TYPE: PRT
<213> ORGANISM: Artificial sequence
<220> FEATURE:
<223> OTHER INFORMATION: Amino Acid sequence of C106B9 heavy chain CDR

<400> SEQUENCE: 342

Glu Ile Leu Pro Gly Ser Gly Gly Thr Asn Tyr Asn Glu Lys Phe Lys
1               5                   10                  15

Gly

<210> SEQ ID NO 343
<211> LENGTH: 7
<212> TYPE: PRT
<213> ORGANISM: Artificial sequence
<220> FEATURE:
<223> OTHER INFORMATION: Amino Acid sequence of C106B9 heavy chain CDR

<400> SEQUENCE: 343

Asp Ser Asn Ser Phe Thr Tyr
1               5

<210> SEQ ID NO 344
<211> LENGTH: 642
<212> TYPE: DNA
<213> ORGANISM: Artificial sequence
<220> FEATURE:
<223> OTHER INFORMATION: Nucleic Acid sequence of F184C7 light chain

<400> SEQUENCE: 344
gacatccaga tgactcagtc tccagcctcc ctatctgtat ctgtgggaga aactgtcacc      60
atcacatgtc gagcaagtga gaatatttac agaaatttag catggtatca gcagaaacag     120
ggaaaatctc ctcaactcct ggtccatgct gcaacaaact agcagatgg tgtgccatca      180 aggttcagtg gcagtggatc agacacacag tattccctca agatcaacag cctgcagtct     240
gaagattttg gaattatta ctgtcaacat tttggggga ctccgctcac gttcggtgct       300
gggaccaagc tggagctgaa acgggctgat gctgcaccaa ctgtatccat cttcccacca     360
tccagtgagc agttaacatc tggaggtgcc tcagtcgtgt gcttcttgaa caacttctac     420
cccaaagaca tcaatgtcaa gtggaagatt gatggcagtg aacgacaaaa tggcgtcctg     480
aacagttgga ctgatcagga cagcaaagac agcacctaca gcatgagcag caccctcacg     540
ttgaccaagg acgagtatga acgacataac agctatacct gtgaggccac tcacaagaca     600
tcaacttcac ccattgtcaa gagcttcaac aggaatgagt gt                         642

<210> SEQ ID NO 345
<211> LENGTH: 214
<212> TYPE: PRT
<213> ORGANISM: Artificial sequence
<220> FEATURE:
<223> OTHER INFORMATION: Amino Acid sequence of F184C7 light chain
```

<400> SEQUENCE: 345

```
Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Arg Asn
            20                  25                  30

Leu Ala Trp Tyr Gln Gln Lys Gln Gly Lys Ser Pro Gln Leu Leu Val
        35                  40                  45

His Ala Ala Thr Asn Leu Ala Asp Gly Val Pro Ser Arg Phe Ser Gly
    50                  55                  60

Ser Gly Ser Asp Thr Gln Tyr Ser Leu Lys Ile Asn Ser Leu Gln Ser
65                  70                  75                  80

Glu Asp Phe Gly Asn Tyr Tyr Cys Gln His Phe Trp Gly Thr Pro Leu
                85                  90                  95

Thr Phe Gly Ala Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 346
<211> LENGTH: 1338
<212> TYPE: DNA
<213> ORGANISM: Artificial sequence
<220> FEATURE:
<223> OTHER INFORMATION: Nucleic Acid sequence of F184C7 heavy chain

<400> SEQUENCE: 346

```
caggttcagc tgcagcagtc tggacctgag atggtgaagc ctggggcctc agtgaagatt     60
ccctgcaagg cttctggcta cgcattcagt agctcctgga tgaactgggt gaagcagagg    120
cctggaaagg gtcttgagtg gattggacgg atttatcctg agatggaga tactaactac     180
aatgagaagt tcaagggcaa ggccacactg actgtagaca atcctccag cacagtctac     240
atgcaactca gcagcctgac atctgaggac tctgcggtct acttctgtgc aagagaggct    300
actacggtag tggccccgta ctactttgac tactggggcc aaggcaccac tctcacagtc    360
tcctcagcca aaacgacacc cccatctgtc tatccactgg ccctggatc tgctgcccaa    420
actaactcca tggtgaccct gggatgcctg gtcaagggct atttccctga ccagtgaca    480
gtgacctgga actctggatc cctgtccagc ggtgtgcaca ccttcccagc tgtcctgcag    540
tctgacctct acactctgag cagctcagtg actgtcccct ccagcacctg cccagcgag    600
accgtcacct gcaacgttgc ccacccggcc agcagcacca aggtggacaa gaaaattgtg    660
cccaggggat gtggttgtaa gccttgcata tgtacagtcc cagaagtatc atctgtcttc    720
atcttccccc caaagcccaa ggatgtgctc accattactc tgactcctaa ggtcacgtgt    780
```

-continued

```
gttgtggtag acatcagcaa ggatgatccc gaggtccagt tcagctggtt tgtagatgat      840
gtggaggtgc acacagctca gacgcaaccc cgggaggagc agttcaacag cactttccgc      900
tcagtcagtg aacttcccat catgcaccag gactggctca atggcaagga gttcaaatgc      960
agggtcaaca gtgcagcttt ccctgccccc atcgagaaaa ccatctccaa aaccaaaggc     1020
agaccgaagg ctccacaggt gtacaccatt ccacctccca aggagcagat ggccaaggat     1080
aaagtcagtc tgacctgcat gataacagac ttcttccctg aagacattac tgtggagtgg     1140
cagtggaatg ggcagccagc ggagaactac aagaacactc agcccatcat ggacacagat     1200
ggctcttact tcgtctacag caagctcaat gtgcagaaga gcaactggga ggcaggaaat     1260
actttcacct gctctgtgtt acatgagggc ctgcacaacc accatactga agagcctc      1320
tcccactctc ctggtaaa                                                   1338
```

<210> SEQ ID NO 347
<211> LENGTH: 446
<212> TYPE: PRT
<213> ORGANISM: Artificial sequence
<220> FEATURE:
<223> OTHER INFORMATION: Amino Acid sequence of F184C7 heavy chain

<400> SEQUENCE: 347

```
Gln Val Gln Leu Gln Gln Ser Gly Pro Glu Met Val Lys Pro Gly Ala
1               5                  10                  15

Ser Val Lys Ile Pro Cys Lys Ala Ser Gly Tyr Ala Phe Ser Ser Ser
            20                  25                  30

Trp Met Asn Trp Val Lys Gln Arg Pro Gly Lys Gly Leu Glu Trp Ile
        35                  40                  45

Gly Arg Ile Tyr Pro Gly Asp Gly Asp Thr Asn Tyr Asn Glu Lys Phe
    50                  55                  60

Lys Gly Lys Ala Thr Leu Thr Val Asp Lys Ser Ser Ser Thr Val Tyr
65                  70                  75                  80

Met Gln Leu Ser Ser Leu Thr Ser Glu Asp Ser Ala Val Tyr Phe Cys
                85                  90                  95

Ala Arg Glu Ala Thr Thr Val Val Ala Pro Tyr Tyr Phe Asp Tyr Trp
            100                 105                 110

Gly Gln Gly Thr Thr Leu Thr Val Ser Ser Ala Lys Thr Thr Pro Pro
        115                 120                 125

Ser Val Tyr Pro Leu Ala Pro Gly Ser Ala Ala Gln Thr Asn Ser Met
    130                 135                 140

Val Thr Leu Gly Cys Leu Val Lys Gly Tyr Phe Pro Glu Pro Val Thr
145                 150                 155                 160

Val Thr Trp Asn Ser Gly Ser Leu Ser Ser Gly Val His Thr Phe Pro
                165                 170                 175

Ala Val Leu Gln Ser Asp Leu Tyr Thr Leu Ser Ser Ser Val Thr Val
            180                 185                 190

Pro Ser Ser Thr Trp Pro Ser Glu Thr Val Thr Cys Asn Val Ala His
        195                 200                 205

Pro Ala Ser Ser Thr Lys Val Asp Lys Lys Ile Val Pro Arg Asp Cys
    210                 215                 220

Gly Cys Lys Pro Cys Ile Cys Thr Val Pro Glu Val Ser Ser Val Phe
225                 230                 235                 240

Ile Phe Pro Pro Lys Pro Lys Asp Val Leu Thr Ile Thr Leu Thr Pro
                245                 250                 255
```

```
Lys Val Thr Cys Val Val Asp Ile Ser Lys Asp Pro Glu Val
            260                 265                 270

Gln Phe Ser Trp Phe Val Asp Asp Val Glu Val His Thr Ala Gln Thr
        275                 280                 285

Gln Pro Arg Glu Glu Gln Phe Asn Ser Thr Phe Arg Ser Val Ser Glu
    290                 295                 300

Leu Pro Ile Met His Gln Asp Trp Leu Asn Gly Lys Glu Phe Lys Cys
305                 310                 315                 320

Arg Val Asn Ser Ala Ala Phe Pro Ala Pro Ile Glu Lys Thr Ile Ser
                325                 330                 335

Lys Thr Lys Gly Arg Pro Lys Ala Pro Gln Val Tyr Thr Ile Pro Pro
            340                 345                 350

Pro Lys Glu Gln Met Ala Lys Asp Lys Val Ser Leu Thr Cys Met Ile
        355                 360                 365

Thr Asp Phe Phe Pro Glu Asp Ile Thr Val Glu Trp Gln Trp Asn Gly
    370                 375                 380

Gln Pro Ala Glu Asn Tyr Lys Asn Thr Gln Pro Ile Met Asp Thr Asp
385                 390                 395                 400

Gly Ser Tyr Phe Val Tyr Ser Lys Leu Asn Val Gln Lys Ser Asn Trp
                405                 410                 415

Glu Ala Gly Asn Thr Phe Thr Cys Ser Val Leu His Glu Gly Leu His
            420                 425                 430

Asn His His Thr Glu Lys Ser Leu Ser His Ser Pro Gly Lys
        435                 440                 445
```

<210> SEQ ID NO 348
<211> LENGTH: 33
<212> TYPE: DNA
<213> ORGANISM: Artificial sequence
<220> FEATURE:
<223> OTHER INFORMATION: Nucleic Acid sequence of F184C7 light chain CDR

<400> SEQUENCE: 348
cgagcaagtg agaatattta cagaaattta gca                         33

<210> SEQ ID NO 349
<211> LENGTH: 21
<212> TYPE: DNA
<213> ORGANISM: Artificial sequence
<220> FEATURE:
<223> OTHER INFORMATION: Nucleic Acid sequence of F184C7 light chain CDR

<400> SEQUENCE: 349
gctgcaacaa acttagcaga t                                     21

<210> SEQ ID NO 350
<211> LENGTH: 27
<212> TYPE: DNA
<213> ORGANISM: Artificial sequence
<220> FEATURE:
<223> OTHER INFORMATION: Nucleic Acid sequence of F184C7 light chain CDR

<400> SEQUENCE: 350
caacattttt gggggactcc gctcacg                               27

<210> SEQ ID NO 351
<211> LENGTH: 11
<212> TYPE: PRT
<213> ORGANISM: Artificial sequence
<220> FEATURE:
<223> OTHER INFORMATION: Amino Acid sequence of F184C7 light chain CDR

<400> SEQUENCE: 351

Arg Ala Ser Glu Asn Ile Tyr Arg Asn Leu Ala
1               5                   10

<210> SEQ ID NO 352
<211> LENGTH: 7
<212> TYPE: PRT
<213> ORGANISM: Artificial sequence
<220> FEATURE:
<223> OTHER INFORMATION: Amino Acid sequence of F184C7 light chain CDR

<400> SEQUENCE: 352

Ala Ala Thr Asn Leu Ala Asp
1               5

<210> SEQ ID NO 353
<211> LENGTH: 9
<212> TYPE: PRT
<213> ORGANISM: Artificial sequence
<220> FEATURE:
<223> OTHER INFORMATION: Amino Acid sequence of F184C7 light chain CDR

<400> SEQUENCE: 353

Gln His Phe Trp Gly Thr Pro Leu Thr
1               5

<210> SEQ ID NO 354
<211> LENGTH: 22
<212> TYPE: DNA
<213> ORGANISM: Artificial sequence
<220> FEATURE:
<223> OTHER INFORMATION: Nucleic Acid sequence of F184C7 heavy chain CDR

<400> SEQUENCE: 354
attcagtagc tcctggatga ac                                            22

<210> SEQ ID NO 355
<211> LENGTH: 51
<212> TYPE: DNA
<213> ORGANISM: Artificial sequence
<220> FEATURE:
<223> OTHER INFORMATION: Nucleic Acid sequence of F184C7 heavy chain CDR

<400> SEQUENCE: 355
cggatttatc ctggagatgg agatactaac tacaatgaga agttcaaggg c            51

<210> SEQ ID NO 356
<211> LENGTH: 39
<212> TYPE: DNA
<213> ORGANISM: Artificial sequence
<220> FEATURE:
<223> OTHER INFORMATION: Nucleic Acid sequence of F184C7 heavy chain CDR

<400> SEQUENCE: 356
gaggctacta cggtagtggc cccgtactac tttgactac                          39

<210> SEQ ID NO 357
<211> LENGTH: 7
<212> TYPE: PRT
<213> ORGANISM: Artificial sequence
<220> FEATURE:
<223> OTHER INFORMATION: Amino Acid sequence of F184C7 heavy chain CDR

<400> SEQUENCE: 357

Phe Ser Ser Ser Trp Met Asn

```
<210> SEQ ID NO 358
<211> LENGTH: 17
<212> TYPE: PRT
<213> ORGANISM: Artificial sequence
<220> FEATURE:
<223> OTHER INFORMATION: Amino Acid sequence of F184C7 heavy chain CDR

<400> SEQUENCE: 358

Arg Ile Tyr Pro Gly Asp Gly Asp Thr Asn Tyr Asn Glu Lys Phe Lys
1               5                   10                  15

Gly

<210> SEQ ID NO 359
<211> LENGTH: 13
<212> TYPE: PRT
<213> ORGANISM: Artificial sequence
<220> FEATURE:
<223> OTHER INFORMATION: Amino Acid sequence of F184C7 heavy chain CDR

<400> SEQUENCE: 359

Glu Ala Thr Thr Val Val Ala Pro Tyr Tyr Phe Asp Tyr
1               5                   10

<210> SEQ ID NO 360
<211> LENGTH: 642
<212> TYPE: DNA
<213> ORGANISM: Artificial sequence
<220> FEATURE:
<223> OTHER INFORMATION: Nucleic Acid sequence of D10A3 light chain

<400> SEQUENCE: 360
aatattgtgc tgacccagac tcccaaattc ctgcttgtat cagcaggaga cagggtttcc        60
ataacctgca aggccagtca gcgtgtgaat aatgatgtag cttggtacca acagaagcca       120
gggcagtctc ctaaactgct gatatactat gcatccaatc gctacactgg agtccctgat       180
cgcttcactg gcagtggata tgggacggat ttcactttca ccatcagcac tgtgcaggct       240
gaagacctgg cagtttattt ctgtcagcag gattatagcc tcccattcac gttcggctcg       300
gggacaaagt tggaaataaa acgggctgat gctgcaccaa ctgtatccat cttcccacca       360
tccagtgagc agttaacatc tggaggtgcc tcagtcgtgt gcttcttgaa caacttctac       420
cccaaagaca tcaatgtcaa gtggaagatt gatggcagtg aacgacaaaa tggcgtcctg       480
aacagttgga ctgatcagga cagcaaagac agcacctaca gcatgagcag cacccctcacg     540
ttgaccaagg acgagtatga acgacataac agctatacct gtgaggccac tcacaagaca       600
tcaacttcac ccattgtcaa gagcttcaac aggaatgagt gt                          642

<210> SEQ ID NO 361
<211> LENGTH: 214
<212> TYPE: PRT
<213> ORGANISM: Artificial sequence
<220> FEATURE:
<223> OTHER INFORMATION: Amino Acid sequence of D10A3 light chain

<400> SEQUENCE: 361

Asn Ile Val Leu Thr Gln Thr Pro Lys Phe Leu Leu Val Ser Ala Gly
1               5                   10                  15

Asp Arg Val Ser Ile Thr Cys Lys Ala Ser Gln Arg Val Asn Asn Asp
            20                  25                  30

Val Ala Trp Tyr Gln Gln Lys Pro Gly Gln Ser Pro Lys Leu Leu Ile
```

```
                35                  40                  45
Tyr Tyr Ala Ser Asn Arg Tyr Thr Gly Val Pro Asp Arg Phe Thr Gly
 50                  55                  60

Ser Gly Tyr Gly Thr Asp Phe Thr Phe Thr Ile Ser Thr Val Gln Ala
 65                  70                  75                  80

Glu Asp Leu Ala Val Tyr Phe Cys Gln Gln Asp Tyr Ser Ser Pro Phe
                 85                  90                  95

Thr Phe Gly Ser Gly Thr Lys Leu Glu Ile Lys Arg Ala Asp Ala Ala
                100                 105                 110

Pro Thr Val Ser Ile Phe Pro Pro Ser Ser Glu Gln Leu Thr Ser Gly
                115                 120                 125

Gly Ala Ser Val Val Cys Phe Leu Asn Asn Phe Tyr Pro Lys Asp Ile
130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
                180                 185                 190

Thr Cys Glu Ala Thr His Lys Thr Ser Thr Ser Pro Ile Val Lys Ser
                195                 200                 205

Phe Asn Arg Asn Glu Cys
    210

<210> SEQ ID NO 362
<211> LENGTH: 1332
<212> TYPE: DNA
<213> ORGANISM: Artificial sequence
<220> FEATURE:
<223> OTHER INFORMATION: Nucleic Acid sequence of D10A3 heavy chain

<400> SEQUENCE: 362
gaggtccagc tgcaacagtt tggaactgag ctggtgaagc ctggggcttc agtgaagata     60
tcctgcaagg cttctggcta cacattcact gactacaaca tggactgggt gaagcagagc    120
catggaaaga gccttgagtg gattggagat attaatccta actatgatac tactacctac    180
aaccagaagt tcaagggaaa ggccacattg actgtagaca gtcctccag cacagcctac     240 atggagctcc gcagcctgac ttctgaggac actgcagtct tttactgtgc aagaaggaac    300
tatggtaact acgtggggtt tgacttctgg ggccaaggca ccactctcac agtctcctca    360
gccaaaacga caccccatc tgtctatcca ctggcccctg gatctgctgc ccaaactaac     420
tccatggtga ccctgggatg cctggtcaag ggctatttcc ctgagccagt gacagtgacc    480
tggaactctg gatccctgtc cagcggtgtg cacaccttcc cagctgtcct gcagtctgac    540
ctctacactc tgagcagctc agtgactgtc cctccagca cctggcccag cgagaccgtc     600
acctgcaacg ttgcccaccc ggccagcagc accaaggtgg acaagaaaat tgtgcccagg    660
gattgtggtt gtaagccttg catatgtaca gtcccagaag tatcatctgt cttcatcttc    720
cccccaaagc ccaaggatgt gctcaccatt actctgactc ctaaggtcac gtgtgttgtg    780
gtagacatca gcaaggatga tcccgaggtc cagttcagct ggtttgtaga tgatgtggag    840
gtgcacacag ctcagacgca acccgggag gagcagttca acagcacttt ccgctcagtc     900
agtgaacttc ccatcatgca ccaggactgg ctcaatggca aggagttcaa atgcagggtc    960
aacagtgcag ctttccctgc ccccatcgag aaaaccatct ccaaaaccaa aggcagaccg   1020
```

-continued

```
aaggctccac aggtgtacac cattccacct cccaaggagc agatggccaa ggataaagtc    1080
agtctgacct gcatgataac agacttcttc cctgaagaca ttactgtgga gtggcagtgg    1140
aatgggcagc cagcggagaa ctacaagaac actcagccca tcatggacac agatggctct    1200
tacttcgtct acagcaagct caatgtgcag aagagcaact gggaggcagg aaatactttc    1260
acctgctctg tgttacatga gggcctgcac aaccaccata ctgagaagag cctctcccac    1320
tctcctggta aa                                                        1332
```

<210> SEQ ID NO 363
<211> LENGTH: 444
<212> TYPE: PRT
<213> ORGANISM: Artificial sequence
<220> FEATURE:
<223> OTHER INFORMATION: Amino Acid sequence of D10A3 heavy chain

<400> SEQUENCE: 363

```
Glu Val Gln Leu Gln Gln Phe Gly Thr Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Asn Met Asp Trp Val Lys Gln Ser His Gly Lys Ser Leu Glu Trp Ile
        35                  40                  45

Gly Asp Ile Asn Pro Asn Tyr Asp Thr Thr Thr Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Thr Ala Val Phe Tyr Cys
                85                  90                  95

Ala Arg Arg Asn Tyr Gly Asn Tyr Val Gly Phe Asp Phe Trp Gly Gln
            100                 105                 110

Gly Thr Thr Leu Thr Val Ser Ser Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser
            180                 185                 190

Ser Thr Trp Pro Ser Glu Thr Val Thr Cys Asn Val Ala His Pro Ala
        195                 200                 205

Ser Ser Thr Lys Val Asp Lys Lys Ile Val Pro Arg Asp Cys Gly Cys
    210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Asp Ile Ser Lys Asp Asp Pro Glu Val Gln Phe
            260                 265                 270

Ser Trp Phe Val Asp Asp Val Glu Val His Thr Ala Gln Thr Gln Pro
        275                 280                 285

Arg Glu Glu Gln Phe Asn Ser Thr Phe Arg Ser Val Ser Glu Leu Pro
    290                 295                 300
```

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
            325                 330                 335

Lys Gly Arg Pro Lys Ala Pro Gln Val Tyr Thr Ile Pro Pro Pro Lys
            340                 345                 350

Glu Gln Met Ala Lys Asp Lys Val Ser Leu Thr Cys Met Ile Thr Asp
            355                 360                 365

Phe Phe Pro Glu Asp Ile Thr Val Glu Trp Gln Trp Asn Gly Gln Pro
370                 375                 380

Ala Glu Asn Tyr Lys Asn Thr Gln Pro Ile Met Asp Thr Asp Gly Ser
385                 390                 395                 400

Tyr Phe Val Tyr Ser Lys Leu Asn Val Gln Lys Ser Asn Trp Glu Ala
            405                 410                 415

Gly Asn Thr Phe Thr Cys Ser Val Leu His Glu Gly Leu His Asn His
            420                 425                 430

His Thr Glu Lys Ser Leu Ser His Ser Pro Gly Lys
            435                 440

<210> SEQ ID NO 364
<211> LENGTH: 33
<212> TYPE: DNA
<213> ORGANISM: Artificial sequence
<220> FEATURE:
<223> OTHER INFORMATION: Nucleic Acid sequence of D10A3 light chain CDR

<400> SEQUENCE: 364
aaggccagtc agcgtgtgaa taatgatgta gct                             33

<210> SEQ ID NO 365
<211> LENGTH: 21
<212> TYPE: DNA
<213> ORGANISM: Artificial sequence
<220> FEATURE:
<223> OTHER INFORMATION: Nucleic Acid sequence of D10A3 light chain CDR

<400> SEQUENCE: 365
tatgcatcca atcgctacac t                                          21

<210> SEQ ID NO 366
<211> LENGTH: 27
<212> TYPE: DNA
<213> ORGANISM: Artificial sequence
<220> FEATURE:
<223> OTHER INFORMATION: Nucleic Acid sequence of D10A3 light chain CDR

<400> SEQUENCE: 366
cagcaggatt atagctctcc attcacg                                    27

<210> SEQ ID NO 367
<211> LENGTH: 11
<212> TYPE: PRT
<213> ORGANISM: Artificial sequence
<220> FEATURE:
<223> OTHER INFORMATION: Amino Acid sequence of D10A3 light chain CDR

<400> SEQUENCE: 367

Lys Ala Ser Gln Arg Val Asn Asn Asp Val Ala
1               5                   10

<210> SEQ ID NO 368
<211> LENGTH: 7

```
<212> TYPE: PRT
<213> ORGANISM: Artificial sequence
<220> FEATURE:
<223> OTHER INFORMATION: Amino Acid sequence of D10A3 light chain CDR

<400> SEQUENCE: 368

Tyr Ala Ser Asn Arg Tyr Thr
1               5

<210> SEQ ID NO 369
<211> LENGTH: 9
<212> TYPE: PRT
<213> ORGANISM: Artificial sequence
<220> FEATURE:
<223> OTHER INFORMATION: Amino Acid sequence of D10A3 light chain CDR

<400> SEQUENCE: 369

Gln Gln Asp Tyr Ser Ser Pro Phe Thr
1               5

<210> SEQ ID NO 370
<211> LENGTH: 15
<212> TYPE: DNA
<213> ORGANISM: Artificial sequence
<220> FEATURE:
<223> OTHER INFORMATION: Nucleic Acid sequence of D10A3 heavy chain CDR

<400> SEQUENCE: 370
gactacaaca tggac                                                      15

<210> SEQ ID NO 371
<211> LENGTH: 51
<212> TYPE: DNA
<213> ORGANISM: Artificial sequence
<220> FEATURE:
<223> OTHER INFORMATION: Nucleic Acid sequence of D10A3 heavy chain CDR

<400> SEQUENCE: 371
gatattaatc ctaactatga tactactacc tacaaccaga agttcaaggg a              51

<210> SEQ ID NO 372
<211> LENGTH: 33
<212> TYPE: DNA
<213> ORGANISM: Artificial sequence
<220> FEATURE:
<223> OTHER INFORMATION: Nucleic Acid sequence of D10A3 heavy chain CDR

<400> SEQUENCE: 372
aggaactatg gtaactacgt ggggtttgac ttc                                  33

<210> SEQ ID NO 373
<211> LENGTH: 5
<212> TYPE: PRT
<213> ORGANISM: Artificial sequence
<220> FEATURE:
<223> OTHER INFORMATION: Amino Acid sequence of D10A3 heavy chain CDR

<400> SEQUENCE: 373

Asp Tyr Asn Met Asp
1               5

<210> SEQ ID NO 374
<211> LENGTH: 17
<212> TYPE: PRT
<213> ORGANISM: Artificial sequence
<220> FEATURE:
<223> OTHER INFORMATION: Amino Acid sequence of D10A3 heavy chain CDR
```

<400> SEQUENCE: 374

Asp Ile Asn Pro Asn Tyr Asp Thr Thr Thr Tyr Asn Gln Lys Phe Lys
1               5                   10                  15
Gly

<210> SEQ ID NO 375
<211> LENGTH: 11
<212> TYPE: PRT
<213> ORGANISM: Artificial sequence
<220> FEATURE:
<223> OTHER INFORMATION: Amino Acid sequence of D10A3 heavy chain CDR

<400> SEQUENCE: 375

Arg Asn Tyr Gly Asn Tyr Val Gly Phe Asp Phe
1               5                   10

<210> SEQ ID NO 376
<211> LENGTH: 163
<212> TYPE: PRT
<213> ORGANISM: homo sapiens

<400> SEQUENCE: 376

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
                20                  25                  30

Tyr Leu Leu Asp Gly Ile Leu Phe Ile Tyr Gly Val Ile Leu Thr Ala
            35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Arg Arg Lys Asn Pro Gln Glu Gly Leu Tyr Asn Glu
            100                 105                 110

Leu Gln Lys Asp Lys Met Ala Glu Ala Tyr Ser Glu Ile Gly Met Lys
        115                 120                 125

Gly Glu Arg Arg Arg Gly Lys Gly His Asp Gly Leu Tyr Gln Gly Leu
    130                 135                 140

Ser Thr Ala Thr Lys Asp Thr Tyr Asp Ala Leu His Met Gln Ala Leu
145                 150                 155                 160

Pro Pro Arg

<210> SEQ ID NO 377
<211> LENGTH: 164
<212> TYPE: PRT
<213> ORGANISM: homo sapiens

<400> SEQUENCE: 377

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
                20                  25                  30

Tyr Leu Leu Asp Gly Ile Leu Phe Ile Tyr Gly Val Ile Leu Thr Ala
            35                  40                  45

Leu Phe Leu Arg Val Lys Phe Ser Arg Ser Ala Asp Ala Pro Ala Tyr

```
                    50                  55                  60
Gln Gln Gly Gln Asn Gln Leu Tyr Asn Glu Leu Asn Leu Gly Arg Arg
 65                  70                  75                  80

Glu Glu Tyr Asp Val Leu Asp Lys Arg Arg Gly Arg Asp Pro Glu Met
                     85                  90                  95

Gly Gly Lys Pro Gln Arg Arg Lys Asn Pro Gln Glu Gly Leu Tyr Asn
                100                 105                 110

Glu Leu Gln Lys Asp Lys Met Ala Glu Ala Tyr Ser Glu Ile Gly Met
            115                 120                 125

Lys Gly Glu Arg Arg Arg Gly Lys Gly His Asp Gly Leu Tyr Gln Gly
        130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 378
<211> LENGTH: 123
<212> TYPE: PRT
<213> ORGANISM: homo sapiens

<400> SEQUENCE: 378

Met Leu Arg Leu Leu Leu Ala Leu Asn Leu Phe Pro Ser Ile Gln Val
 1               5                  10                  15

Thr Gly Asn Lys Ile Leu Val Lys Gln Ser Pro Met Leu Val Ala Tyr
                20                  25                  30

Asp Asn Ala Val Asn Leu Ser Trp Lys His Leu Cys Pro Ser Pro Leu
            35                  40                  45

Phe Pro Gly Pro Ser Lys Pro Phe Trp Val Leu Val Val Val Gly Gly
        50                  55                  60

Val Leu Ala Cys Tyr Ser Leu Leu Val Thr Val Ala Phe Ile Ile Phe
 65                  70                  75                  80

Trp Val Arg Ser Lys Arg Ser Arg Leu Leu His Ser Asp Tyr Met Asn
                85                  90                  95

Met Thr Pro Arg Arg Pro Gly Pro Thr Arg Lys His Tyr Gln Pro Tyr
                100                 105                 110

Ala Pro Pro Arg Asp Phe Ala Ala Tyr Arg Ser
            115                 120

<210> SEQ ID NO 379
<211> LENGTH: 101
<212> TYPE: PRT
<213> ORGANISM: homo sapiens

<400> SEQUENCE: 379

Met Leu Arg Leu Leu Leu Ala Leu Asn Leu Phe Pro Ser Ile Gln Val
 1               5                  10                  15

Thr Gly Lys His Leu Cys Pro Ser Pro Leu Phe Pro Gly Pro Ser Lys
                20                  25                  30

Pro Phe Trp Val Leu Val Val Val Gly Gly Val Leu Ala Cys Tyr Ser
            35                  40                  45

Leu Leu Val Thr Val Ala Phe Ile Ile Phe Trp Val Arg Ser Lys Arg
        50                  55                  60

Ser Arg Leu Leu His Ser Asp Tyr Met Asn Met Thr Pro Arg Arg Pro
 65                  70                  75                  80

Gly Pro Thr Arg Lys His Tyr Gln Pro Tyr Ala Pro Pro Arg Asp Phe
                85                  90                  95
```

Ala Ala Tyr Arg Ser
            100

<210> SEQ ID NO 380
<211> LENGTH: 220
<212> TYPE: PRT
<213> ORGANISM: homo sapiens

<400> SEQUENCE: 380

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220

<210> SEQ ID NO 381
<211> LENGTH: 255
<212> TYPE: PRT
<213> ORGANISM: homo sapiens

<400> SEQUENCE: 381

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

```
Ala Gly Cys Ser Met Cys Glu Gln Asp Cys Lys Gln Gly Gln Glu Leu
                100                 105                 110

Thr Lys Lys Gly Cys Lys Asp Cys Cys Phe Gly Thr Phe Asn Asp Gln
            115                 120                 125

Lys Arg Gly Ile Cys Arg Pro Trp Thr Asn Cys Ser Leu Asp Gly Lys
130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
                180                 185                 190

Ala Leu Thr Ser Thr Ala Leu Leu Phe Leu Leu Phe Phe Leu Thr Leu
                195                 200                 205

Arg Phe Ser Val Val Lys Arg Gly Arg Lys Lys Leu Leu Tyr Ile Phe
                210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 382
<211> LENGTH: 199
<212> TYPE: PRT
<213> ORGANISM: homo sapiens

<400> SEQUENCE: 382

Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
                20                  25                  30

Phe His Asn Gly Gly Val Gln Ile Leu Cys Lys Tyr Pro Asp Ile Val
                35                  40                  45

Gln Gln Phe Lys Met Gln Leu Leu Lys Gly Gly Gln Ile Leu Cys Asp
            50                  55                  60

Leu Thr Lys Thr Lys Gly Ser Gly Asn Thr Val Ser Ile Lys Ser Leu
65                  70                  75                  80

Lys Phe Cys His Ser Gln Leu Ser Asn Asn Ser Val Ser Phe Phe Leu
                85                  90                  95

Tyr Asn Leu Asp His Ser His Ala Asn Tyr Tyr Phe Cys Asn Leu Ser
                100                 105                 110

Ile Phe Asp Pro Pro Pro Phe Lys Val Thr Leu Thr Gly Gly Tyr Leu
                115                 120                 125

His Ile Tyr Glu Ser Gln Leu Cys Cys Gln Leu Lys Phe Trp Leu Pro
            130                 135                 140

Ile Gly Cys Ala Ala Phe Val Val Val Cys Ile Leu Gly Cys Ile Leu
145                 150                 155                 160

Ile Cys Trp Leu Thr Lys Lys Lys Tyr Ser Ser Ser Val His Asp Pro
                165                 170                 175

Asn Gly Glu Tyr Met Phe Met Arg Ala Val Asn Thr Ala Lys Lys Ser
                180                 185                 190

Arg Leu Thr Asp Val Thr Leu
            195
```

-continued

```
<210> SEQ ID NO 383
<211> LENGTH: 277
<212> TYPE: PRT
<213> ORGANISM: homo sapiens

<400> SEQUENCE: 383

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
                20                  25                  30

Gly Asp Thr Tyr Pro Ser Asn Asp Arg Cys Cys His Glu Cys Arg Pro
            35                  40                  45

Gly Asn Gly Met Val Ser Arg Cys Ser Arg Ser Gln Asn Thr Val Cys
        50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
                100                 105                 110

Thr Gln Pro Leu Asp Ser Tyr Lys Pro Gly Val Asp Cys Ala Pro Cys
            115                 120                 125

Pro Pro Gly His Phe Ser Pro Gly Asp Asn Gln Ala Cys Lys Pro Trp
        130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
                180                 185                 190

Glu Ala Trp Pro Arg Thr Ser Gln Gly Pro Ser Thr Arg Pro Val Glu
            195                 200                 205

Val Pro Gly Gly Arg Ala Val Ala Ala Ile Leu Gly Leu Gly Leu Val
        210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
                260                 265                 270

Thr Leu Ala Lys Ile
        275

<210> SEQ ID NO 384
<211> LENGTH: 9
<212> TYPE: PRT
<213> ORGANISM: Artificial Sequence
<220> FEATURE:
<223> OTHER INFORMATION: short peptide

<400> SEQUENCE: 384

Asp Leu Met Gly Tyr Ile Pro Leu Val
1               5
```

AFFINITY ENTITIES COMPRISING A TCR-LIKE ANTIBODY BINDING DOMAIN WITH HIGH AFFINITY AND FINE SPECIFICITY AND USES OF SAME

RELATED APPLICATIONS

This application is a divisional application of U.S. patent application Ser. No. 15/579,616 having a filing date of Dec. 5, 2017, which is a National Phase of PCT Patent Application No. PCT/IL2016/050600 having an International filing date of Jun. 8, 2016, which claims the benefit of priority of U.S. Provisional Patent Application No. 62/172,264 filed on Jun. 8, 2015, and Netherlands Patent Application No. N2014935 filed on Jun. 8, 2015. The contents of the above applications are all incorporated by reference as if fully set forth herein in their entirety.

SEQUENCE LISTING STATEMENT

The ASCII file, entitled 71619Sequence listing.txt, created on Dec. 5, 2017, comprising 440,897 bytes, submitted concurrently with the filing of this application is incorporated herein by reference. The sequence submitted herewith is identical to the sequence listing forming part of the international application.

FIELD AND BACKGROUND OF THE INVENTION

The present invention, in some embodiments thereof, relates to affinity entities comprising a TCR-like antibody binding domain with high affinity and fine specificity and uses of same.

Tumor and virus-infected cells are recognised by CD8+ cytotoxic T cells that, in response, are activated to eliminate these cells. In order to be activated, the clonotypic T-cell receptor (TCR) needs to encounter a specific peptide antigen presented by the membrane surface major histocompatibility complex (MHC) molecule. Cells that have undergone malignant transformation or viral infection present peptides derived from tumour-associated antigens or viral proteins on their MHC class I molecules. Therefore, disease-specific MHC-peptide complexes are desirable targets for immunotherapeutic approaches. One such approach transforms the unique fine specificity but low intrinsic affinity of TCRs to MHC-peptide complexes into high-affinity soluble antibody molecules endowed with a TCR-like specificity towards tumour or viral epitopes. These antibodies, termed TCR-like antibodies, are being developed as a new class of immunotherapeutics that can target tumour and virus-infected cells and mediate their specific killing. In addition to their therapeutic capabilities, TCR-like antibodies are being developed as diagnostic reagents for cancer and infectious diseases, and serve as valuable research tools for studying MHC class I antigen presentation.

SUMMARY OF THE INVENTION

According to an aspect of some embodiments of the present invention there is provided an affinity binding entity comprising an antigen binding domain comprising CDR sequences which are N—C ordered:

```
CDR1 Heavy
Chain (HC)
                                SEQ ID NO: 309
SYGVH

CDR2 HC
                                SEQ ID NO: 310
VIWAGGTTNYNSALMS

CDR3 HC
                                SEQ ID NO: 311
DGHFHFDF the CDR1 Light
Chain (LC)
                                SEQ ID NO: 303
RASDIIYSNLA

CDR2 LC
                                SEQ ID NO: 304
AATNLAA

CDR3 LC
                                SEQ ID NO: 305
QHFWGSSIS
``` the affinity binding entity capable of binding HLA-A2/TyrD$_{369-377}$ in an MHC restricted manner.

According to an aspect of some embodiments of the present invention there is provided an affinity binding entity comprising an antigen binding domain comprising CDR sequences which are N—C ordered:

```
CDR1 Heavy Chain
(HC)
                                SEQ ID NO: 293
TSGMGVS

CDR2 HC
                                SEQ ID NO: 294
HIYWDDDKRYNPSLKS

CDR3 HC
                                SEQ ID NO: 295
KDYGSSFYAMHY the the CDR1 Light
Chain (LC)
                                SEQ ID NO: 287
KASQDIHNYIA

CDR2 LC
                                SEQ ID NO: 288
YTSTLQP

CDR3 LC
                                SEQ ID NO: 289
LQYDNLWT
``` the affinity binding entity capable of binding HLA-A2/TyrD$_{369-377}$ in an MHC restricted manner.

According to an aspect of some embodiments of the present invention there is provided an affinity binding entity comprising an antigen binding domain comprising CDR sequences which are N—C ordered:

```
CDR1 HC
                                SEQ ID NO: 325
SYDMS

CDR2 HC
                                SEQ ID NO: 326
YMSSGGGTYYPDTVKG
```

-continued

CDR3 HC
SEQ ID NO: 327
HDEITNFDY

CDR1 LC
SEQ ID NO: 319
RASQSISNSLH

CDR2 LC
SEQ ID NO: 320
YASQSIS

CDR3 LC
SEQ ID NO: 321
QQSYSWPLT the affinity binding entity capable of binding HLA-A2/ WT1$_{126-134}$ in an MHC restricted manner.

According to an aspect of some embodiments of the present invention there is provided an affinity binding entity comprising an antigen binding domain comprising CDR sequences which are N—C ordered:

CDR1 HC
SEQ ID NO: 341
GYWIE

CDR2 HC
SEQ ID NO: 342
EILPGSGGTNYNEKFKG

CDR3 HC
SEQ ID NO: 343
DSNSFTY

CDR1 LC
SEQ ID NO: 335
SVSSSVDYIH

CDR2 LC
SEQ ID NO: 336
STSILAS

CDR3 LC
SEQ ID NO: 337
QQRSSYT the affinity binding entity capable of binding HLA-A2/ MAGE-A4$_{328-343}$ in an MHC restricted manner.

According to an aspect of some embodiments of the present invention there is provided an affinity binding entity comprising an antigen binding domain comprising CDR sequences which are N—C ordered:

CDR1 HC
SEQ ID NO: 357
FSSSWMN

CDR2 HC
SEQ ID NO: 358
RIYPGDGDTNYNEKFKG

CDR3 HC
SEQ ID NO: 359
EATTVVAPYYFDY

CDR1 LC
SEQ ID NO: 351
RASENIYRNLA

CDR2 LC
SEQ ID NO: 352
AATNLAD

-continued

CDR3 LC
SEQ ID NO: 353
QHFWGTPLT the affinity binding entity capable of binding HLA-A2/ MAGE-A9$_{344-359}$ in an MHC restricted manner.

According to an aspect of some embodiments of the present invention there is provided an affinity binding entity comprising an antigen binding domain comprising CDR sequences which are N—C ordered:

CDR1 HC
SEQ ID NO: 373
DYNMD

CDR2 HC
SEQ ID NO: 374
DINPNYDTTTYNQKFKG

CDR3 HC
SEQ ID NO: 375
RNYGNYVGFDF

CDR1 LC
SEQ ID NO: 367
KASQRVNNDVA

CDR2 LC
SEQ ID NO: 368
YASNRYT

CDR3 LC
SEQ ID NO: 369
QQDYSSPFT the affinity binding entity capable of binding HLA-A2/ PAP$_{360-375}$ in an MHC restricted manner.

According to some embodiments of the invention, the affinity binding entity is selected from the group consisting of an antibody, a CAR and a TCR.

According to some embodiments of the invention, the affinity binding entity is an antibody.

According to some embodiments of the invention, the affinity binding entity is a TCR.

According to some embodiments of the invention, the affinity binding entity is a CAR.

According to some embodiments of the invention, the affinity binding entity is a soluble entity.

According to some embodiments of the invention, the affinity binding entity is a humanized antibody.

According to some embodiments of the invention, the affinity binding entity comprises a therapeutic moiety.

According to some embodiments of the invention, the affinity binding entity comprises a detectable moiety.

According to some embodiments of the invention, the antibody is a single chain antibody, a bi-specific antibody or a full length antibody.

According to an aspect of some embodiments of the present invention there is provided an isolated polynucleotide comprising a nucleic acid sequence encoding the affinity binding entity.

According to an aspect of some embodiments of the present invention there is provided an expression vector comprising the polynucleotide operaly linked to a cis-acting regulatory element.

According to an aspect of some embodiments of the present invention there is provided a cell comprising the polynucleotide or the expression vector.

According to an aspect of some embodiments of the present invention there is provided a pharmaceutical composition comprising the affinity binding entity, the vector or the cell.

According to an aspect of some embodiments of the present invention there is provided a method of detecting a cancer cell, comprising contacting the cell with the antibody, under conditions which allow immunocomplex formation, wherein a presence of the immunocomplex or level thereof is indicative of the cancer cell.

According to an aspect of some embodiments of the present invention there is provided a method of diagnosing and treating cancer in a subject in need thereof, comprising:
(a) detecting the presence of cancer cells in the subject according to the method;
(b) diagnosing the subject as having cancer when cancer cells are detected;
(c) treating the subject with an anti-cancer therapy.

According to an aspect of some embodiments of the present invention there is provided a method of diagnosing cancer in a subject in need thereof, comprising contacting a cell of the subject with the antibody, under conditions which allow immunocomplex formation, wherein a presence of the immunocomplex or level thereof is indicative of the cancer.

According to some embodiments of the invention, the cell is a skin cell.

According to an aspect of some embodiments of the present invention there is provided a method of treating a cancer, comprising administering to a subject in need thereof a therapeutically effective amount of the affinity binding entity, the vector or the cell, thereby treating the cancer.

According to an aspect of some embodiments of the present invention there is provided use of the affinity binding entity, the vector or the cell in the manufacture of a medicament for treating cancer.

According to some embodiments of the invention, the affinity binding entity is for TyrD the cancer is selected from the group consisting of melanoma and glioblastoma.

According to some embodiments of the invention, the affinity binding entity is for WT1 the cancer is selected from the group consisting of chronic myelocytic leukemia, multiple myeloma (MM), acute lymphoblastic leukemia (ALL), acute myeloid/myelogenous leukemia (AML), myelodysplastic syndrome (MDS), mesothelioma, ovarian cancer, gastrointestinal cancers e.g., colorectal cancer adenocarcinoma, thyroid cancer, breast cancer, lung cancer (e.g., non small cell lung cancer), melanoma, osteosarcoma, endometrial cancer, prostate cancer and glioblastoma.

According to some embodiments of the invention, when the affinity binding entity is for MAGE-A4 the cancer is selected from the group consisting of melanoma, ovarian cancer, T cell leukemia/lymphoma (e.g., ATLL), testicular cancer, head and neck cancer, bladder cancer and esophagus cancer.

According to some embodiments of the invention, the affinity binding entity is for MAGE-A9 the cancer is selected from the group consisting of renal cell carcinoma, bladder cancer, breast cancer and hepatocellular carcinoma.

According to some embodiments of the invention, the affinity binding entity is for PAP the cancer is selected from the group consisting of prostate cancer.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Figure 1:
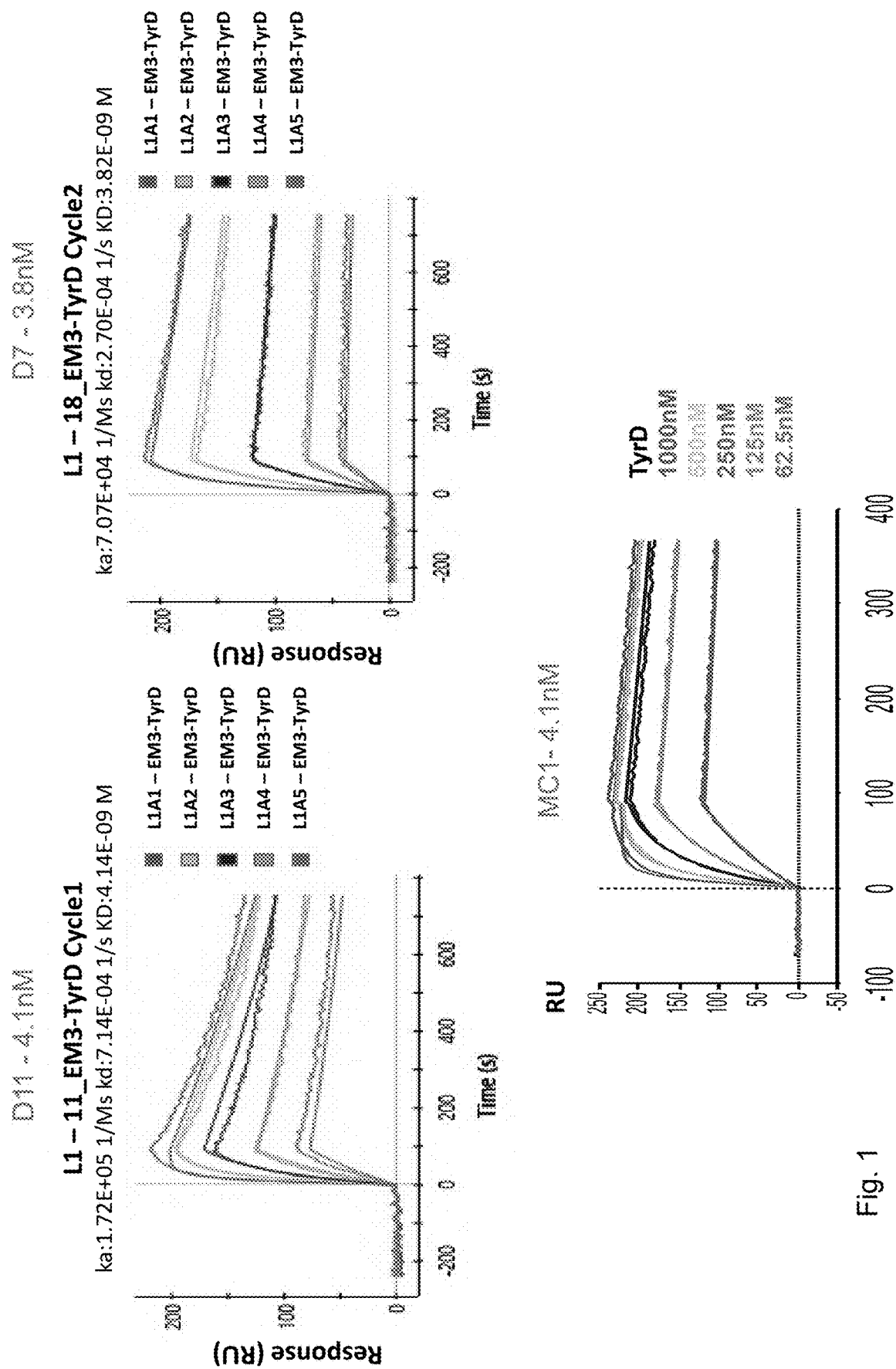

In the drawings:

FIG. 1: Apparent binding affinity determination of TCR-like antibodies targeting HLA-A2/Tyrosinase complexes. Purified IgGs were immobilized indirectly to the SPR sensor chip with anti-mouse or human IgG. Analyte was purified recombinant single-chain HLA-A2/Tyrosinase complexes generated by in vitro refolding of E. coli expressed scHLA-A2 complexes.

Figure 2:
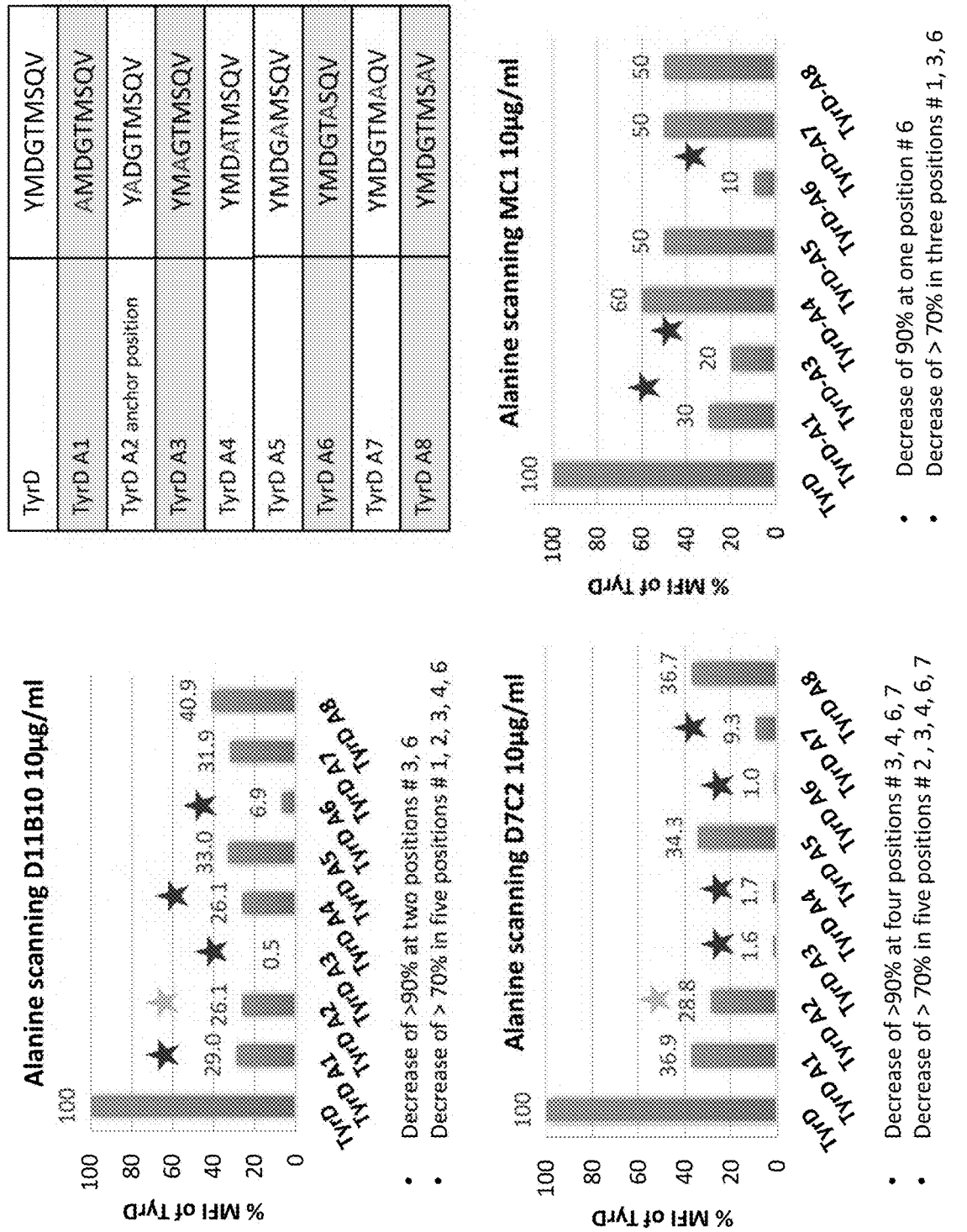

FIG. 2: Epitope specificity determination of TCR-like antibodies by Alanine scanning. The Tyrosinase peptide sequence was substituted with Alanine at positions 1, 2, 3, 4, 5, 6, 7, and 8. The Ala mutated peptides were synthesized and loaded onto T2 cells APCs at a concentration of $10^{-4}$-$10^{-5}$M for 12 hrs at 37° C. Binding of TCR-like antibodies at a concentration of 10 µg/ml was accessed by flow cytometry and binding intensity as measured by mean fluorescence intensity was measured and compared with the binding intensity to WT native Tyrosinase peptide. The relative effect of each position Ala substitution was evaluated as percentage to the binding to WT peptide.

FIG. 3: Binding of D11 and D7 TCR-like antibodies to T2 APCs loaded with tyrosinase peptide and control HLA-A2 restricted peptides. T2 cells were loaded with Tyrosinase peptide and indicated peptides at a concentration of $10^{-4}$-$10^{-5}$M for 12 hrs at 37° C. Binding was monitored by flow cytometry using secondary PE-labeled anti-mouse IgG. MAb BB7.2 was used to monitor expression of HLA-A2. Mean fluorescence intensity (MFI) is indicated.

FIG. 4: Binding of D11 and D7 TCR-like antibodies to T2 APCs loaded with tyrosinase peptide and control HLA-A2 restricted peptides. T2 cells were loaded with Tyrosinase peptide and indicated peptides at a concentration of $10^{-4}$-$10^{-5}$M for 12 hrs at 37° C. Binding was monitored by flow cytometry using secondary PE-labeled anti-mouse IgG. MAb BB7.2 was used to monitor expression of HLA-A2. Mean fluorescence intensity (MFI) is indicated.

FIG. 5: Binding of D11 TCR-like antibody to T2 APCs loaded with tyrosinase peptide and control HLA-A2 restricted peptides. T2 cells were loaded with Tyrosinase peptide and indicated peptides at a concentration of $10^{-4}$-$10^{-5}$ M for 12 hrs at 37° C. Binding was monitored by flow cytometry using secondary PE-labeled anti-mouse IgG. MAb BB7.2 was used to monitor expression of HLA-A2. Mean fluorescence intensity (MFI) is indicated.

FIG. 6: Binding of D7 TCR-like antibody to T2 APCs loaded with tyrosinase peptide and control HLA-A2 restricted peptides. T2 cells were loaded with Tyrosinase peptide and indicated peptides at a concentration of $10^{-4}$-$10^{-5}$M for 12 hrs at 37° C. Binding was monitored by flow cytometry using secondary PE-labeled anti-mouse IgG. MAb BB7.2 was used to monitor expression of HLA-A2. Mean fluorescence intensity (MFI) is indicated.

FIG. 7: Binding of MC1 TCR-like antibody to T2 APCs loaded with tyrosinase peptide and control HLA-A2 restricted peptides. T2 cells were loaded with Tyrosinase peptide and indicated peptides at a concentration of $10^{-4}$-$10^{-5}$ M for 12 hrs at 37° C. Binding was monitored by flow cytometry using secondary PE-labeled anti-mouse IgG. MAb BB7.2 was used to monitor expression of HLA-A2. Mean fluorescence intensity (MFI) is indicated.

FIG. 8: Binding of MC1 TCR-like antibody to melanoma cells that express HLA-A2 and Tyrosinase. Melanoma cells were monitored by flow cytometry for binding of TCR-like antibody MC1 using secondary PE-labeled anti-human IgG. MAb BB7.2 was used to monitor expression of HLA-A2. Mean fluorescence intensity (MFI) is indicated.

FIG. 9: Binding of MC1 TCR-like antibody to HLA-A2+ and Tyrosinase antigen positive or negative cells. Tumor cells that express HLA-A2 and are positive or negative for Tyrosinase were monitored by flow cytometry for binding of TCR-like antibody MC1 using secondary PE-labeled anti-human IgG. MAb BB7.2 was used to monitor expression of HLA-A2. Mean fluorescence intensity (MFI) is indicated.

FIG. 10: Binding of D11 and D7 TCR-like antibodies to HLA-A2+ and Tyrosinase antigen positive or negative cells. Tumor cells that express HLA-A2 and are positive or negative for Tyrosinase were monitored by flow cytometry for binding of TCR-like antibody MC1 using secondary PE-labeled anti-mouse IgG. MAb BB7.2 was used to monitor expression of HLA-A2. Mean fluorescence intensity (MFI) is indicated.

Figure 11:
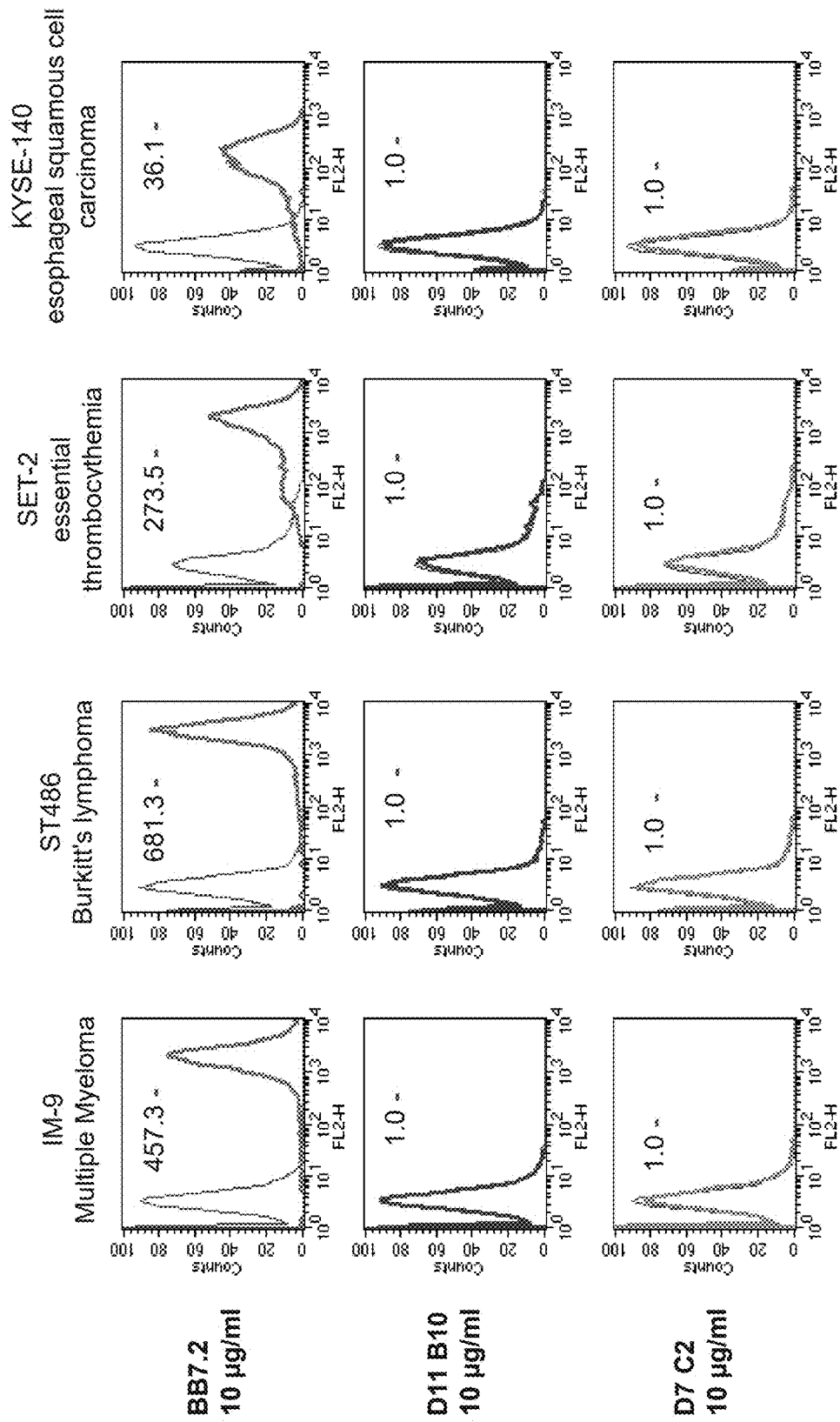

FIG. 11: Binding of D11 and D7 TCR-like antibodies to HLA-A2+ and Tyrosinase negative cells. Tumor cells that express HLA-A2 and are negative for Tyrosinase were monitored by flow cytometry for binding of TCR-like antibody MC1 using secondary PE-labeled anti-mouse IgG. MAb BB7.2 was used to monitor expression of HLA-A2. Mean fluorescence intensity (MFI) is indicated.

FIG. 12: Comparative Binding of D11, D7, and MC1 TCR-like antibodies to HLA-A2+ and Tyrosinase positive or negative cells. Tumor cells that express HLA-A2 and are positive or negative for Tyrosinase were monitored by flow cytometry for binding of TCR-like antibody D11, D7, and MC1 using secondary PE-labeled anti-mouse IgG.

FIG. 13: Binding of D11 TCR-like antibody to HLA-A2+/Tyrosinase negative normal primary cells. Primary normal cells of histological origin as indicated that express HLA-A2 and are negative for Tyrosinase were monitored by flow cytometry for binding of TCR-like antibody D11, using secondary PE-labeled anti-mouse IgG. MAb BB7.2 was used to monitor expression of HLA-A2.

Figure 14:
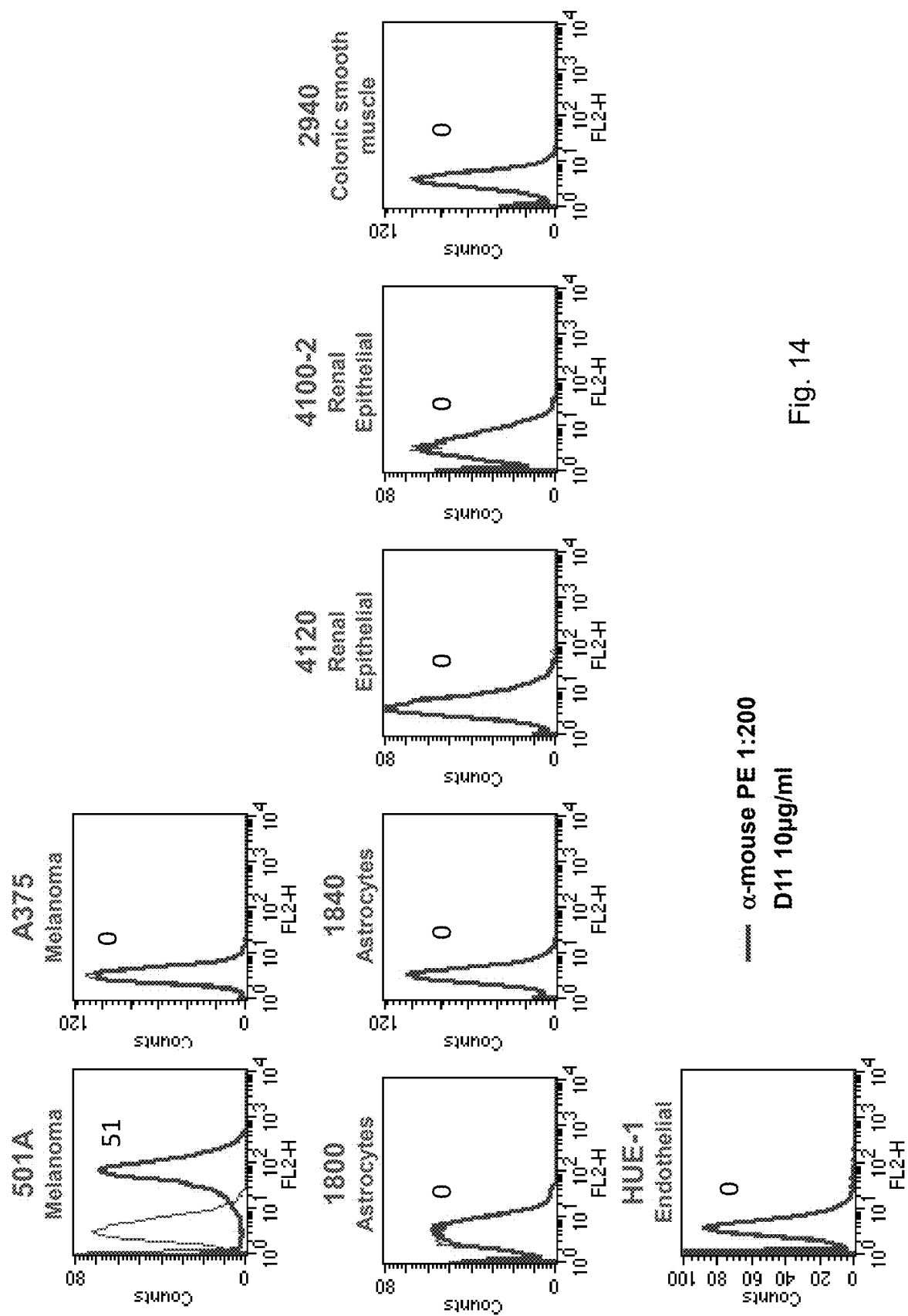

FIG. 14: Binding of D11 TCR-like antibody to HLA-A2+/Tyrosinase negative normal primary cells. Primary normal cells of histological origin as indicated that express HLA-A2 and are negative for Tyrosinase were monitored by flow cytometry for binding of TCR-like antibody D11, using secondary PE-labeled anti-mouse IgG.

Figure 15:
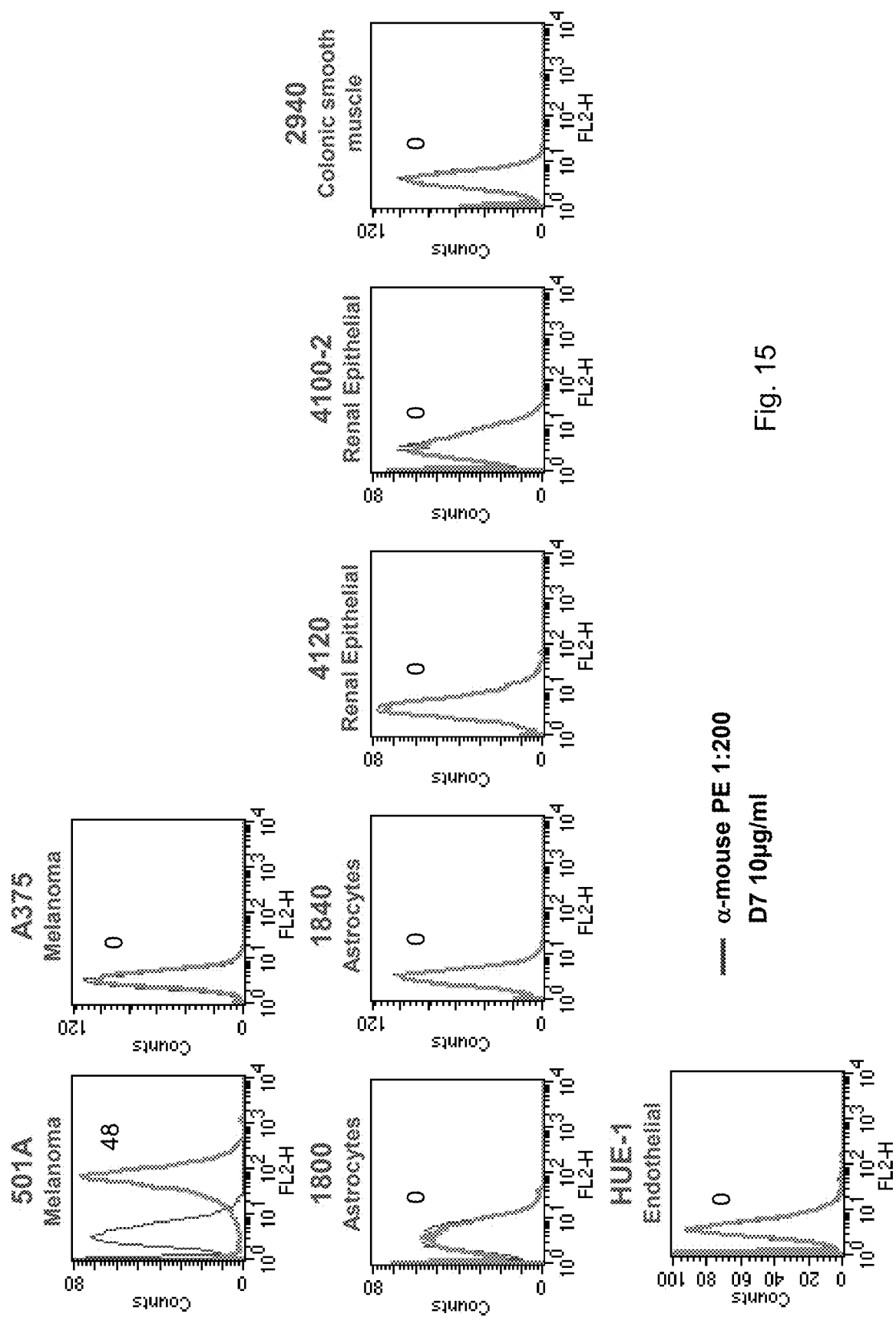

FIG. 15: Binding of D7 TCR-like antibody to HLA-A2+/Tyrosinase negative normal primary cells. Primary normal cells of histological origin as indicated that express HLA-A2 and are negative for Tyrosinase were monitored by flow cytometry for binding of TCR-like antibody D7, using secondary PE-labeled anti-mouse IgG.

Figure 16:
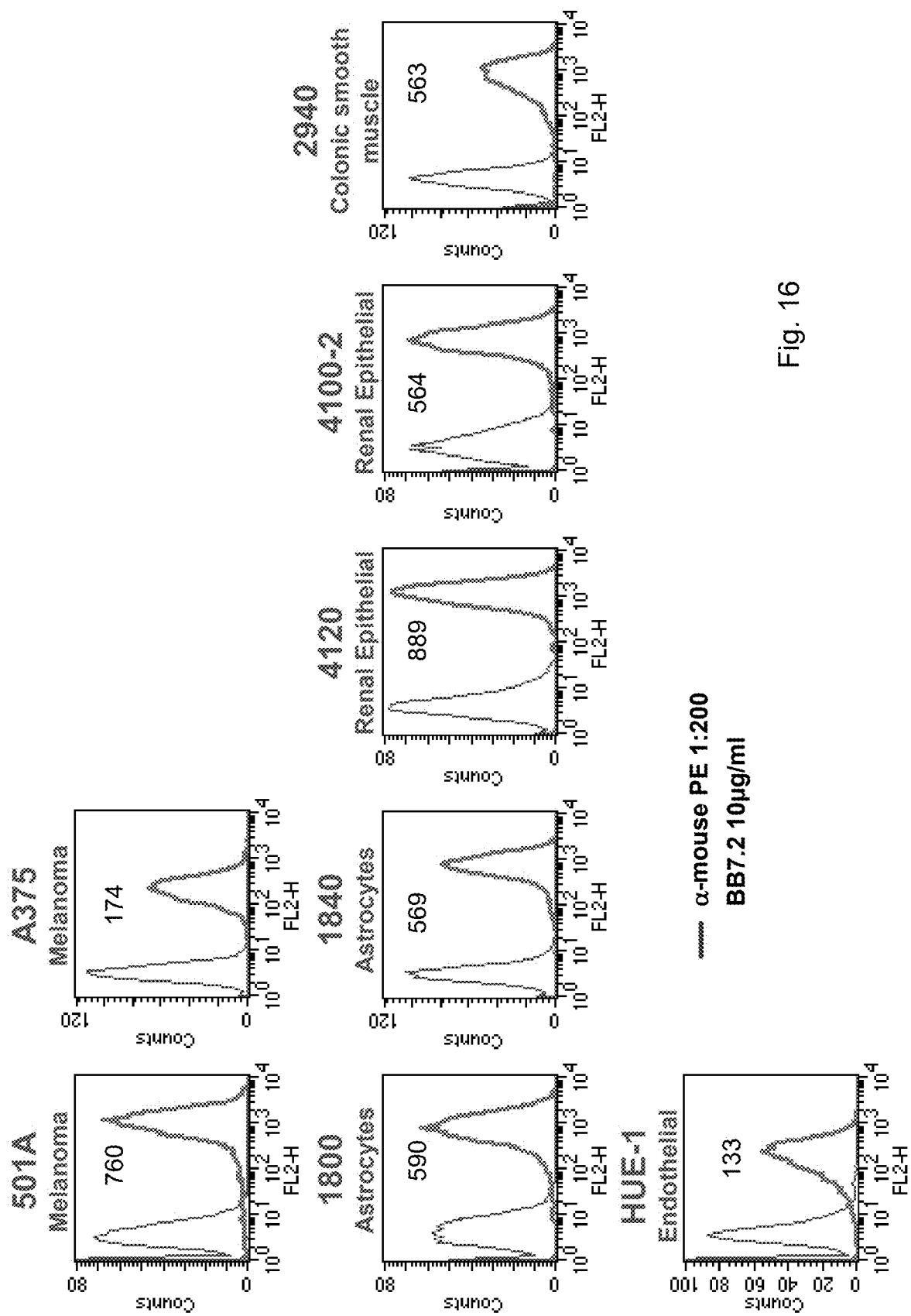

FIG. 16: Binding of BB7.2 to normal primary cells. Primary normal cells of histological origin were monitored by flow cytometry for expression of HLA-A2 using MAb BB7.2 and secondary PE-labeled anti-mouse IgG.

FIG. 17: Binding of MC1, D11 and D7 TCR-like antibodies to normal PBMCs. PBMCs were characterized for HLA-A2 homo or heterozygosity by PCR. Binding of TCR-like antibodies was monitored by PE-labeled secondary anti-mouse IgG.

Figure 18:
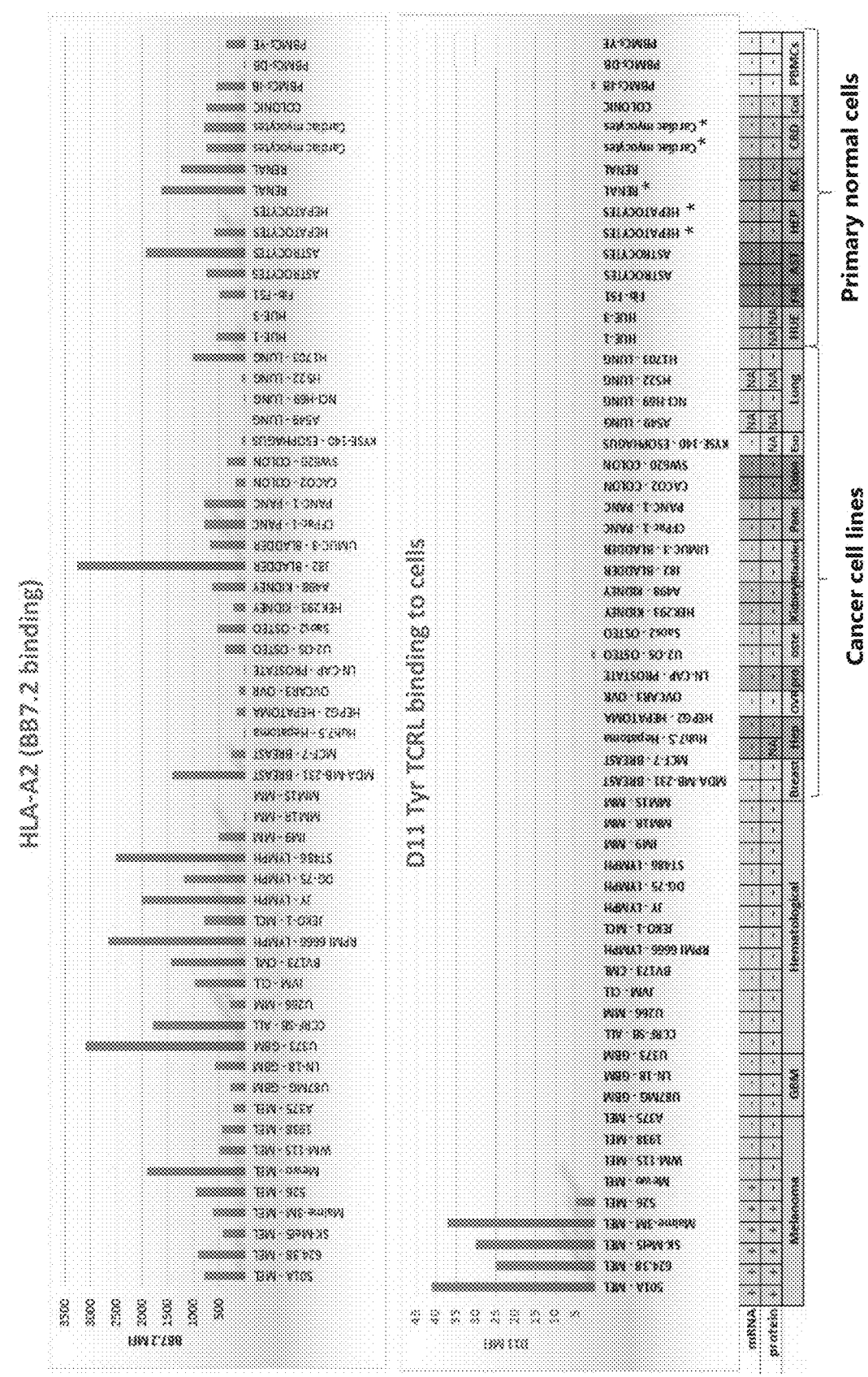

FIG. 18: Summary of D11 TCR-like antibody selectivity. Binding of D11 TCR-like antibodies to HLA-A2+ antigen positive and negative cells was monitored by using PE-labeled anti-mouse IgG. +/−indicate tyrosinase mRNA gene expression as measured by PCR. HLA-A2 expression was monitored with MAb BB7.2.

Figure 19:
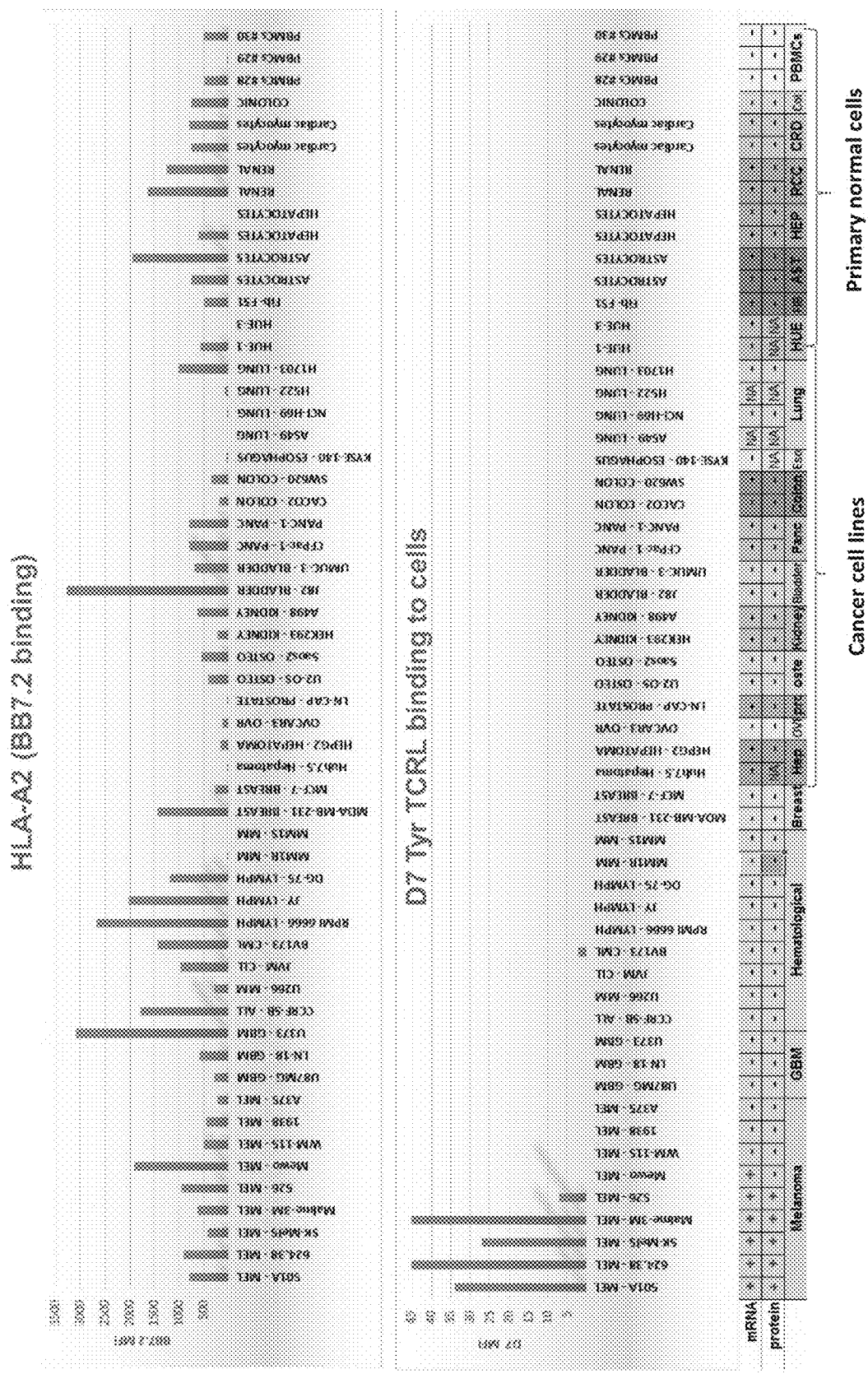

FIG. 19: Summary of D7 TCR-like antibody selectivity. Binding of D7 TCR-like antibodies to HLA-A2+ antigen positive and negative cells was monitored by using PE-labeled anti-mouse IgG. +/−indicate tyrosinase mRNA gene expression as measured by PCR. HLA-A2 expression was monitored with MAb BB7.2.

Figure 20:
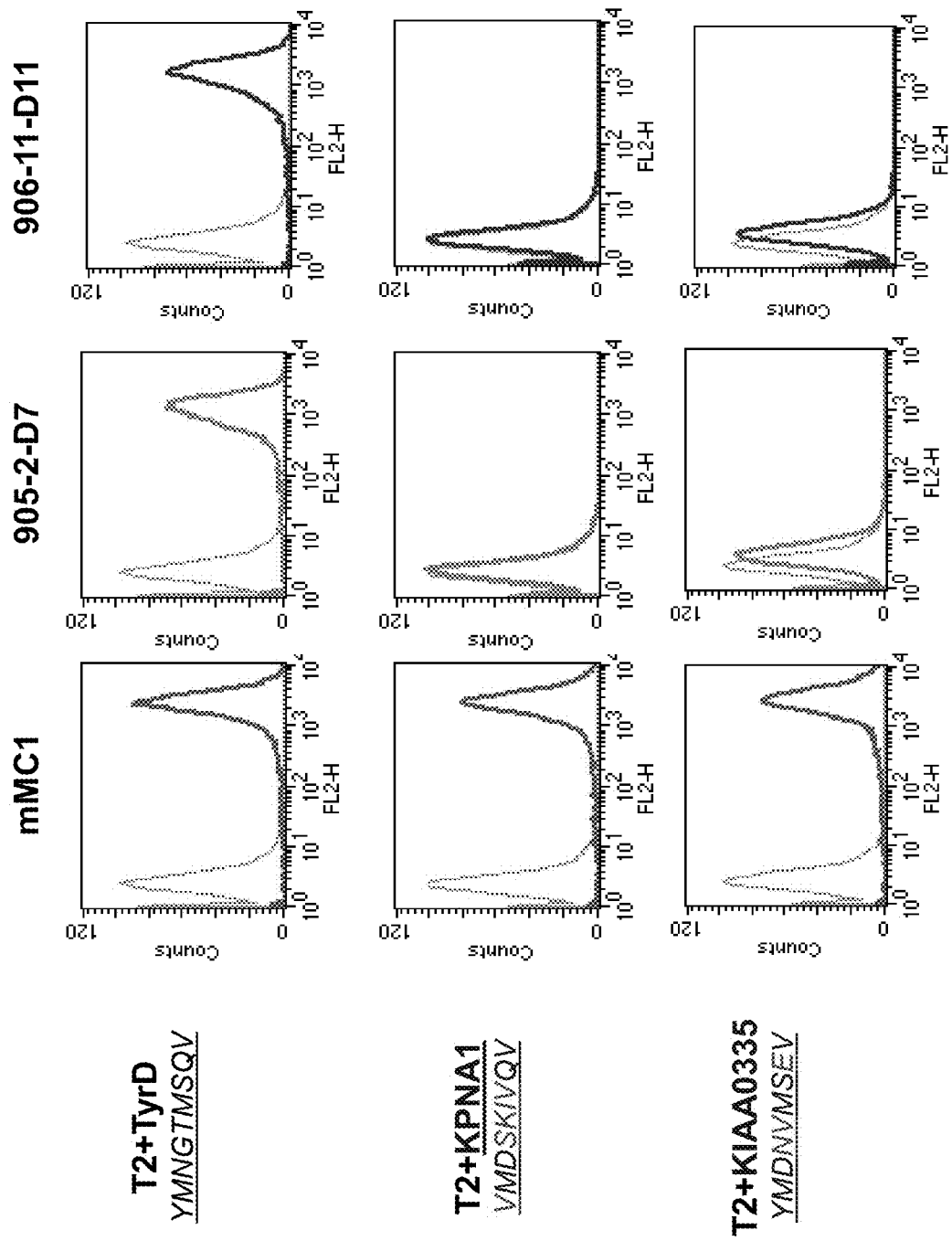

FIG. 20: Binding of MC1, D11, and D7 TCR-like antibodies to T2 APCs loaded with tyrosinase peptide and tyrosinase similar HLA-A2 restricted peptides. T2 cells were loaded with Tyrosinase peptide and indicated peptides at a concentration of $10^{-4}$M for 12 hrs at 37° C. Binding was monitored by flow cytometry using secondary PE-labeled anti-mouse IgG.

FIG. 21: Binding of D11 TCR-like antibody to T2 APCs loaded with tyrosinase peptide similar HLA-A2 restricted peptides. T2 cells were loaded with Tyrosinase peptide and indicated peptides at a concentration of $10^{-5}$M for 12 hrs at 37° C. Binding was monitored by flow cytometry using secondary PE-labeled anti-mouse IgG. Binding of MAb BB7.2 ensured measurement of peptide loading efficiency.

FIG. 22: Binding of D11 TCR-like antibody to T2 APCs loaded with tyrosinase peptide similar HLA-A2 restricted peptides. T2 cells were loaded with Tyrosinase peptide and indicated peptides at a concentration of $10^{-5}$M for 12 hrs at 37° C. Binding was monitored by flow cytometry using secondary PE-labeled anti-mouse IgG. Binding of MAb BB7.2 ensured measurement of peptide loading efficiency.

Figure 23:
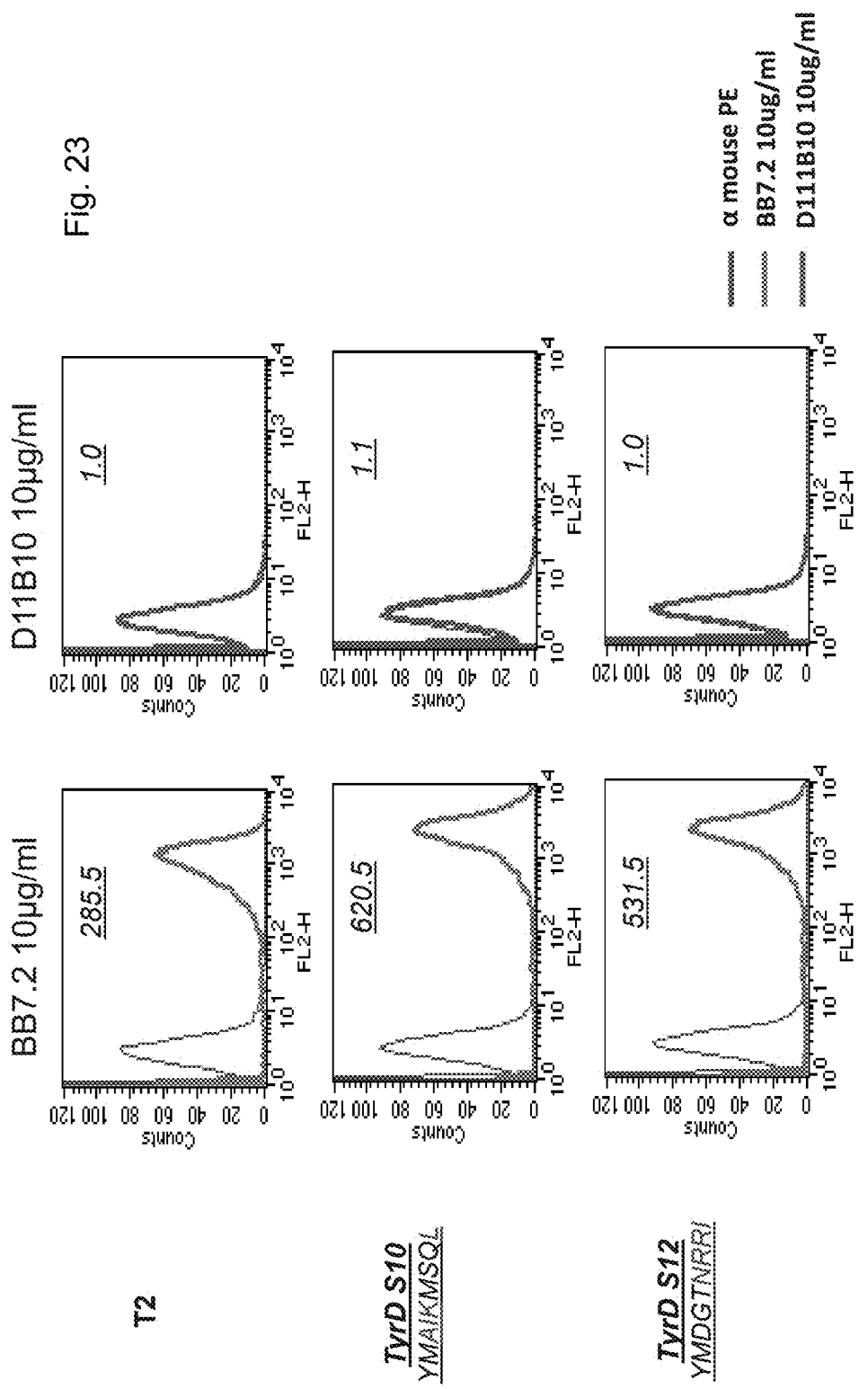

FIG. 23: Binding of D11 TCR-like antibody to T2 APCs loaded with tyrosinase peptide similar HLA-A2 restricted peptides. T2 cells were loaded with Tyrosinase peptide and indicated peptides at a concentration of $10^{-5}$M for 12 hrs at 37° C. Binding was monitored by flow cytometry using secondary PE-labeled anti-mouse IgG. Binding of MAb BB7.2 ensured measurement of peptide loading efficiency.

Figure 24:
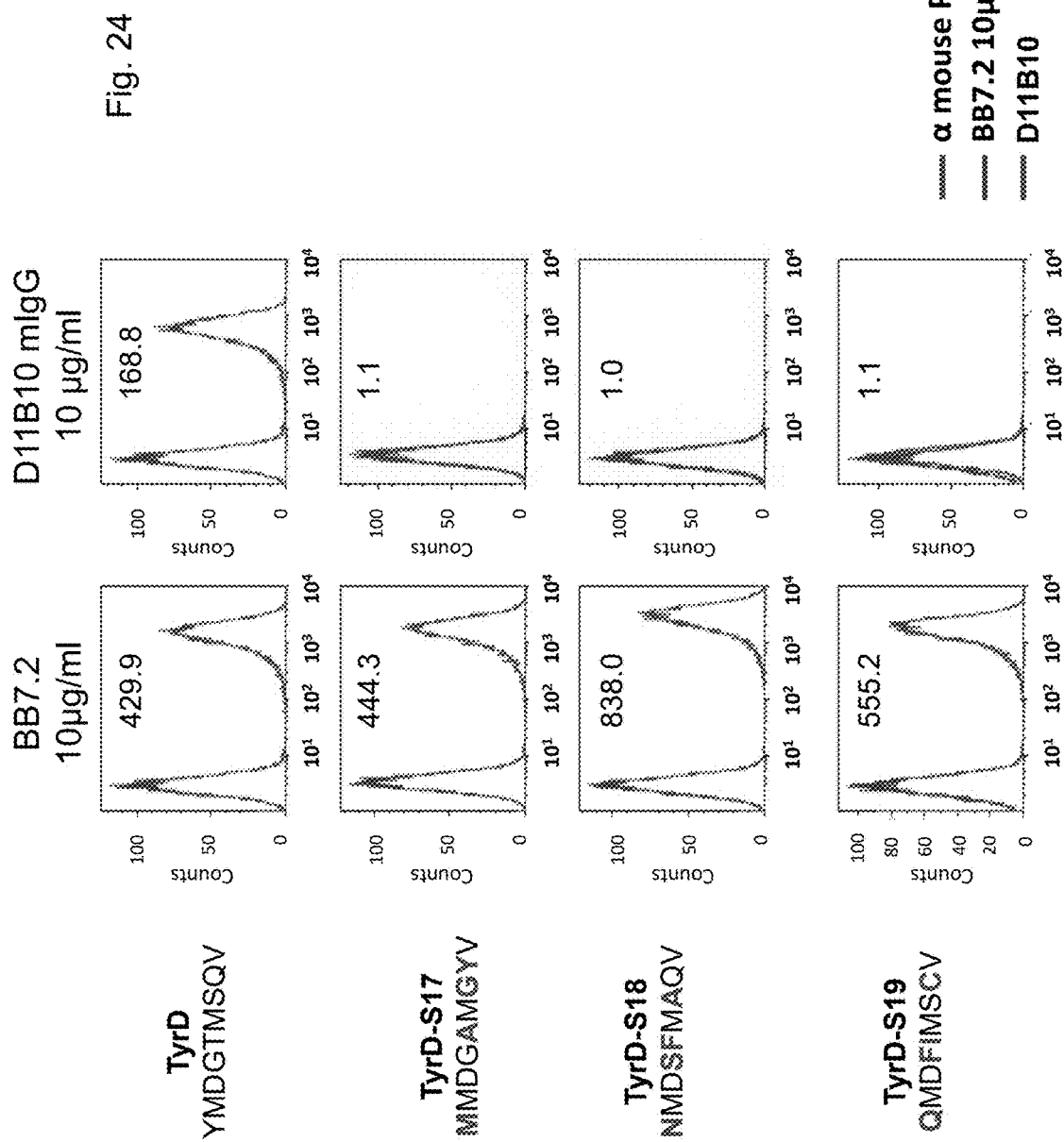

FIG. 24: Binding of D11 TCR-like antibody to T2 APCs loaded with tyrosinase similar HLA-A2 restricted peptides. T2 cells were loaded with Tyrosinase peptide and indicated peptides at a concentration of $-10^{-5}$M for 12 hrs at 37° C. Binding was monitored by flow cytometry using secondary PE-labeled anti-mouse IgG. Binding of MAb BB7.2 ensured measurement of peptide loading efficiency.

Figure 25:
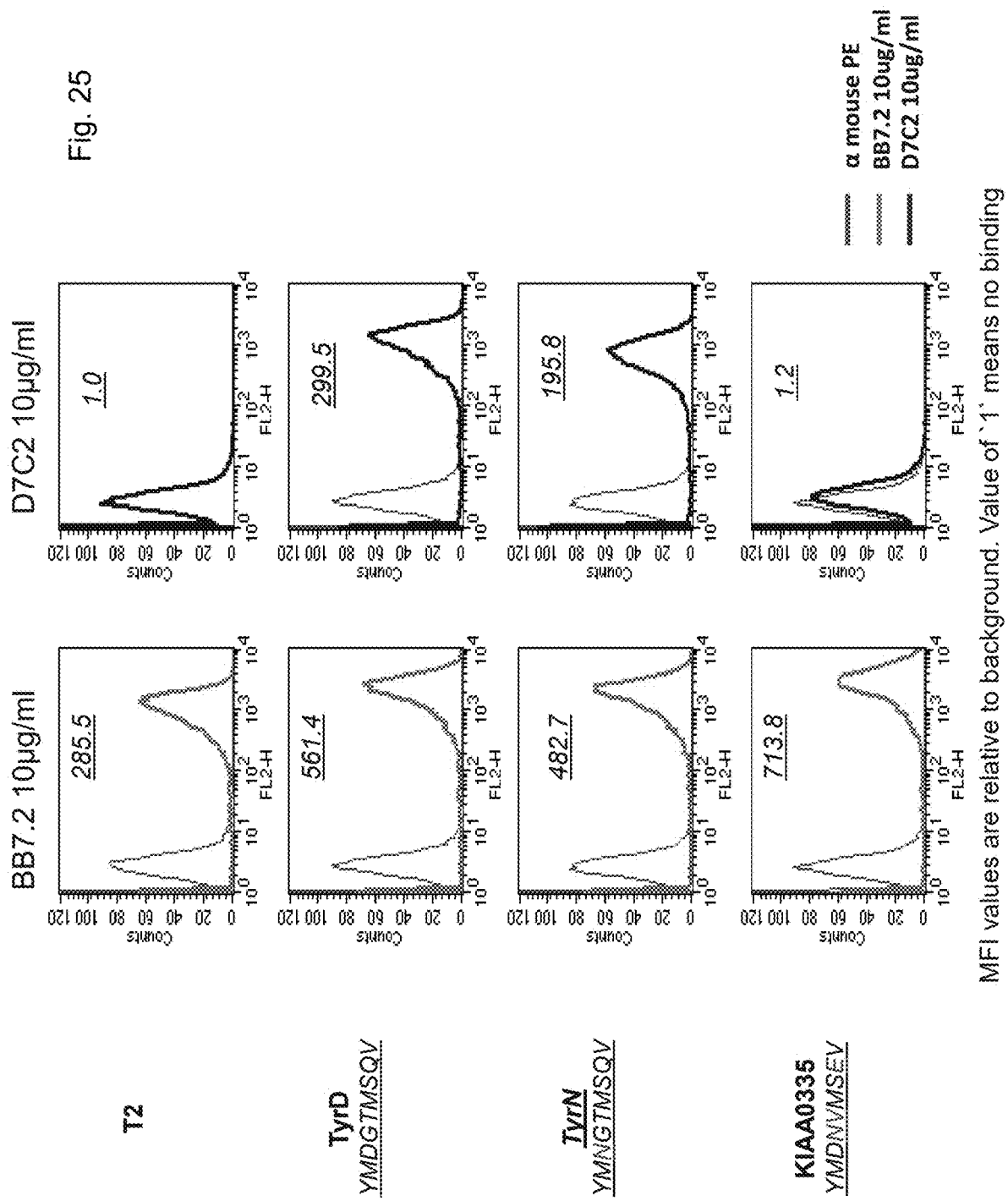

FIG. 25: Binding of D7 TCR-like antibody to T2 APCs loaded with tyrosinase similar HLA-A2 restricted peptides. T2 cells were loaded with Tyrosinase peptide and indicated peptides at a concentration of $10^{-5}$M for 12 hrs at 37° C. Binding was monitored by flow cytometry using secondary PE-labeled anti-mouse IgG. Binding of MAb BB7.2 ensured measurement of peptide loading efficiency.

FIG. 26: Binding of D7 TCR-like antibody to T2 APCs loaded with tyrosinase similar HLA-A2 restricted peptides. T2 cells were loaded with Tyrosinase peptide and indicated peptides at a concentration of $10^{-5}$M for 12 hrs at 37° C. Binding was monitored by flow cytometry using secondary PE-labeled anti-mouse IgG. Binding of MAb BB7.2 ensured measurement of peptide loading efficiency.

FIG. 27: Binding of D7 TCR-like antibody to T2 APCs loaded with tyrosinase similar HLA-A2 restricted peptides. T2 cells were loaded with Tyrosinase peptide and indicated peptides at a concentration of $10^{-5}$M for 12 hrs at 37° C. Binding was monitored by flow cytometry using secondary PE-labeled anti-mouse IgG. Binding of MAb BB7.2 ensured measurement of peptide loading efficiency.

Figure 28:
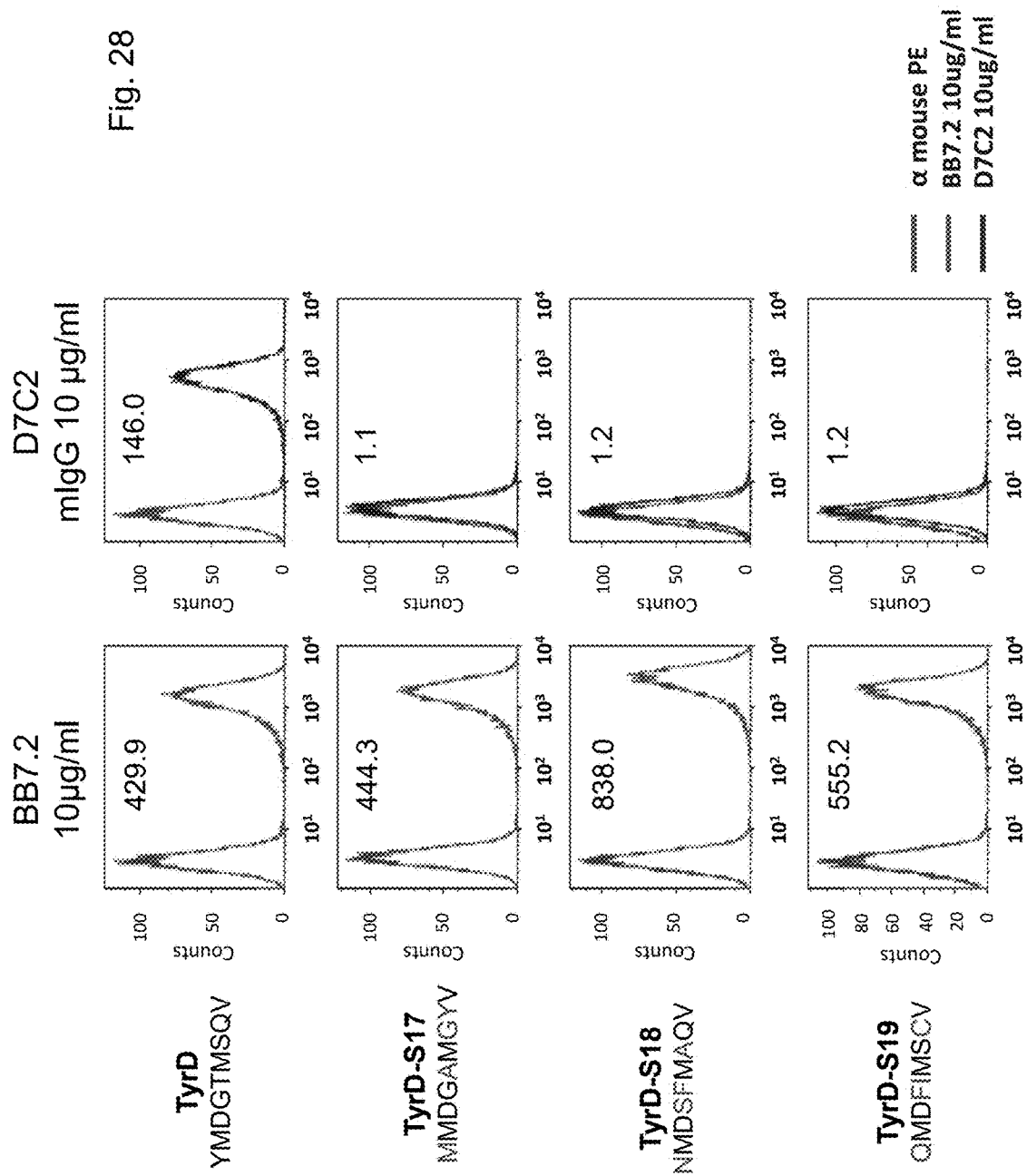

FIG. 28: Binding of D7 TCR-like antibody to T2 APCs loaded with tyrosinase similar HLA-A2 restricted peptides identified after alanine scanning. T2 cells were loaded with Tyrosinase peptide and indicated peptides which were selected according to epitope recognition specificity of by D7 of Ala mutated peptides at a concentration of $10^{-5}$M for 12 hrs at 37° C. Binding was monitored by flow cytometry using secondary PE-labeled anti-mouse IgG. Binding of MAb BB7.2 ensured measurement of peptide loading efficiency.

Figure 29:
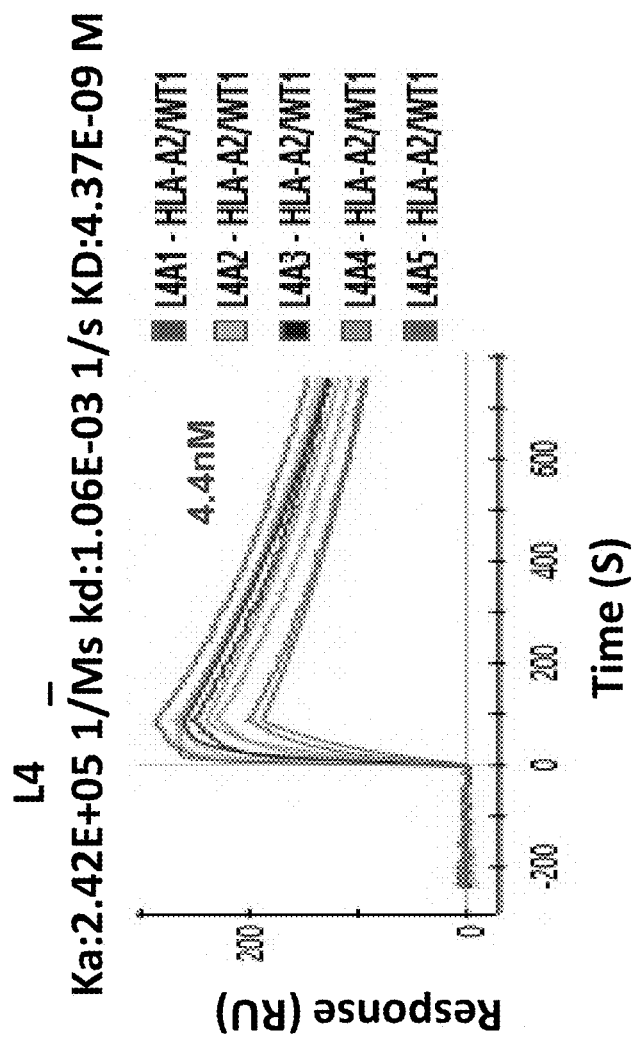

FIG. 29: Apparent binding affinity determination of TCR-like antibody B47B6 targeting HLA-A2/WT1 complexes. Purified IgGs were immobilized indirectly to the SPR sensor chip with anti-mouse. Analyte was purified recombinant single-chain HLA-A2/WT1 complexes generated by in vitro refolding of E. coli expressed scHLA-A2 complexes.

Figure 30:
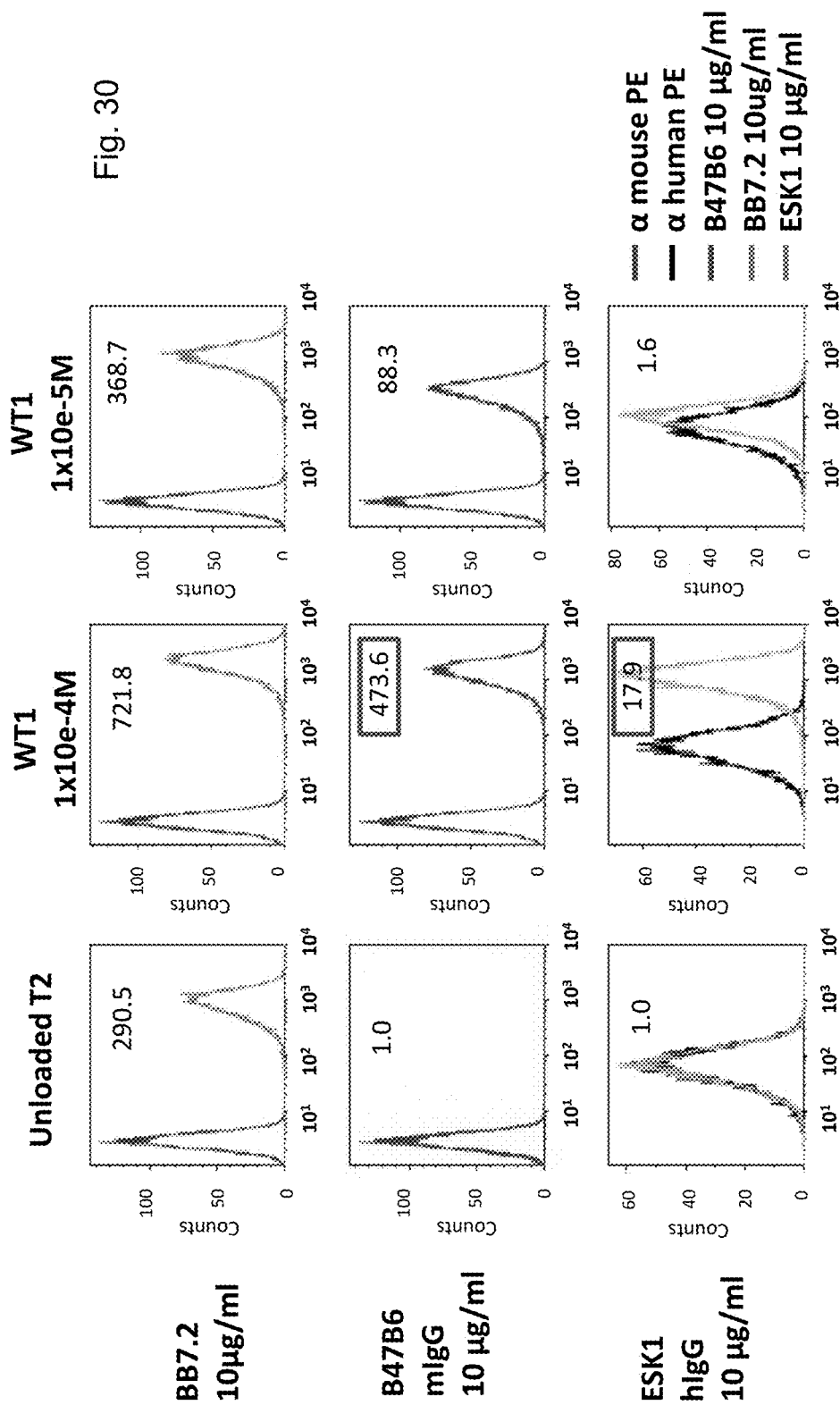

FIG. 30: Binding of B47 and ESK1 TCR-like antibodies to T2 APCs loaded with WT1 HLA-A2 restricted peptide. T2 cells were loaded with WT1 at a concentration of $10^{-4}$-$10^{-5}$M for 12 hrs at 37° C. Binding was monitored by flow cytometry using secondary PE-labeled anti-mouse IgG (for B47) or human IgG (for ESK1). MAb BB7.2 was used to monitor expression of HLA-A2. Mean fluorescence intensity (MFI) is indicated.

FIG. 31: Binding of B47 and ESK1 TCR-like antibodies to T2 APCs loaded with WT1 peptide and control HLA-A2 restricted peptides. T2 cells were loaded with WT1 peptide and indicated peptides at a concentration of $10^{-4}$M for 12 hrs at 37° C. Binding was monitored by flow cytometry using secondary PE-labeled anti-mouse IgG (for B47) or human IgG (for ESK1). MAb BB7.2 was used to monitor expression of HLA-A2. Mean fluorescence intensity (MFI) is indicated.

FIG. 32: Binding of B47 and ESK1 TCR-like antibodies to T2 APCs loaded with WT1 similar HLA-A2 restricted peptides. T2 cells were loaded with WT1 peptide and indicated peptides at a concentration of $10^{-4}$-$10^{-5}$M for 12 hrs at 37° C. Binding was monitored by flow cytometry using secondary PE-labeled anti-mouse IgG (for B47) or human IgG (for ESK1). Binding of MAb BB7.2 ensured measurement of peptide loading efficiency.

Figure 33:
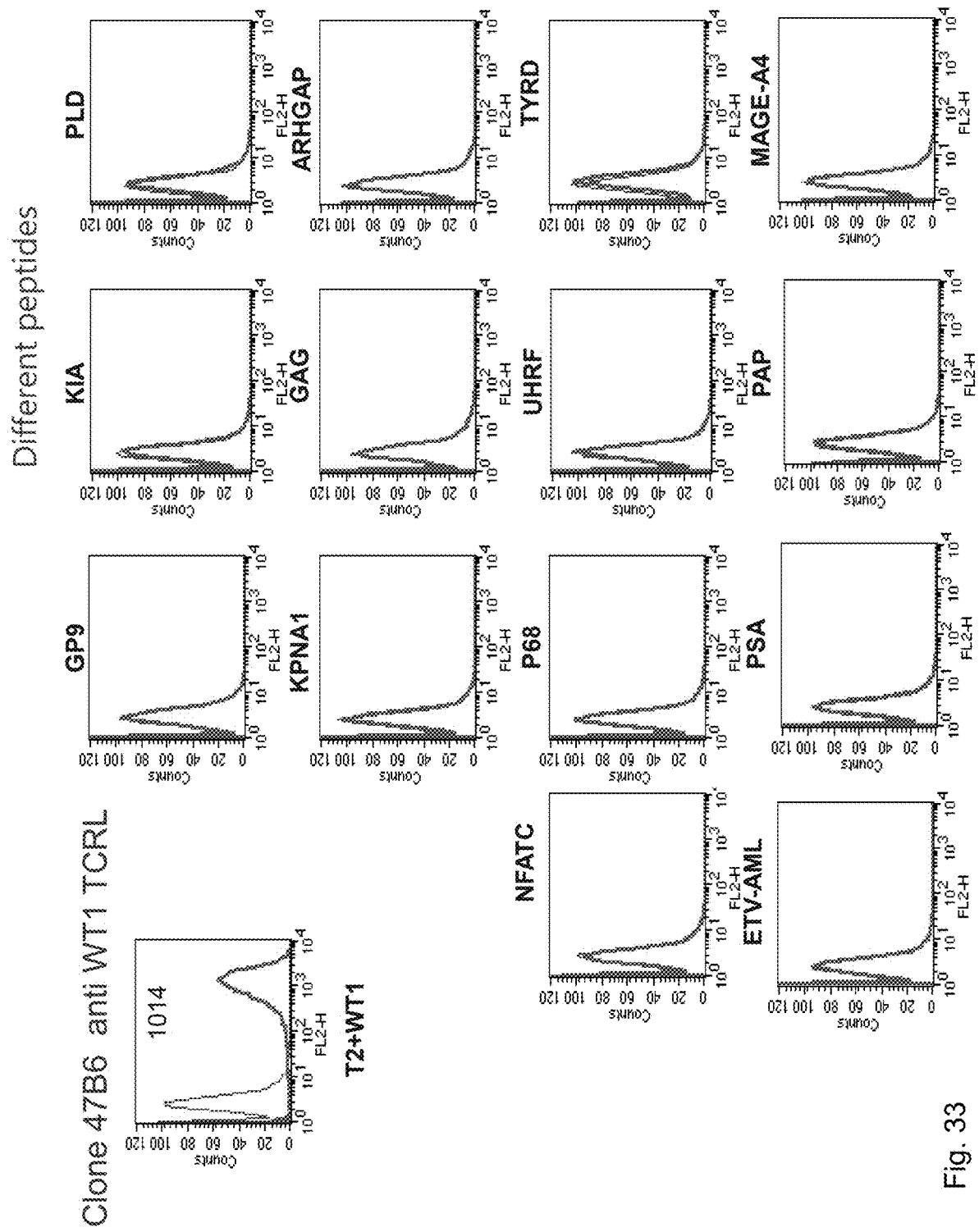

FIG. 33: Binding of B47 TCR-like antibody to T2 APCs loaded with WT1 peptide or control HLA-A2 restricted peptides. T2 cells were loaded with WT1 peptide and indicated peptides at a concentration of $10^{-4}$M for 12 hrs at 37° C. Binding was monitored by flow cytometry using secondary PE-labeled anti-mouse IgG. Binding of MAb BB7.2 ensured measurement of peptide loading efficiency.

FIG. 34: Binding of B47 TCR-like antibody to T2 APCs loaded with WT1 similar HLA-A2 restricted peptides. T2 cells were loaded with WT1 peptide and indicated peptides at a concentration of $10^{-4}$-$10^{-5}$M for 12 hrs at 37° C. Binding was monitored by flow cytometry using secondary PE-labeled anti-mouse IgG. Binding of MAb BB7.2 ensured measurement of peptide loading efficiency.

FIG. 35: Binding of B47 and ESK1 TCR-like antibodies to HLA-A2 positive cells that express or not express WT1. Binding was monitored by flow cytometry using secondary PE-labeled anti-mouse IgG (for B47) or human IgG (for ESK1). Expression of HLA-A2 was assessed with MAb BB7.2.

Figure 36:
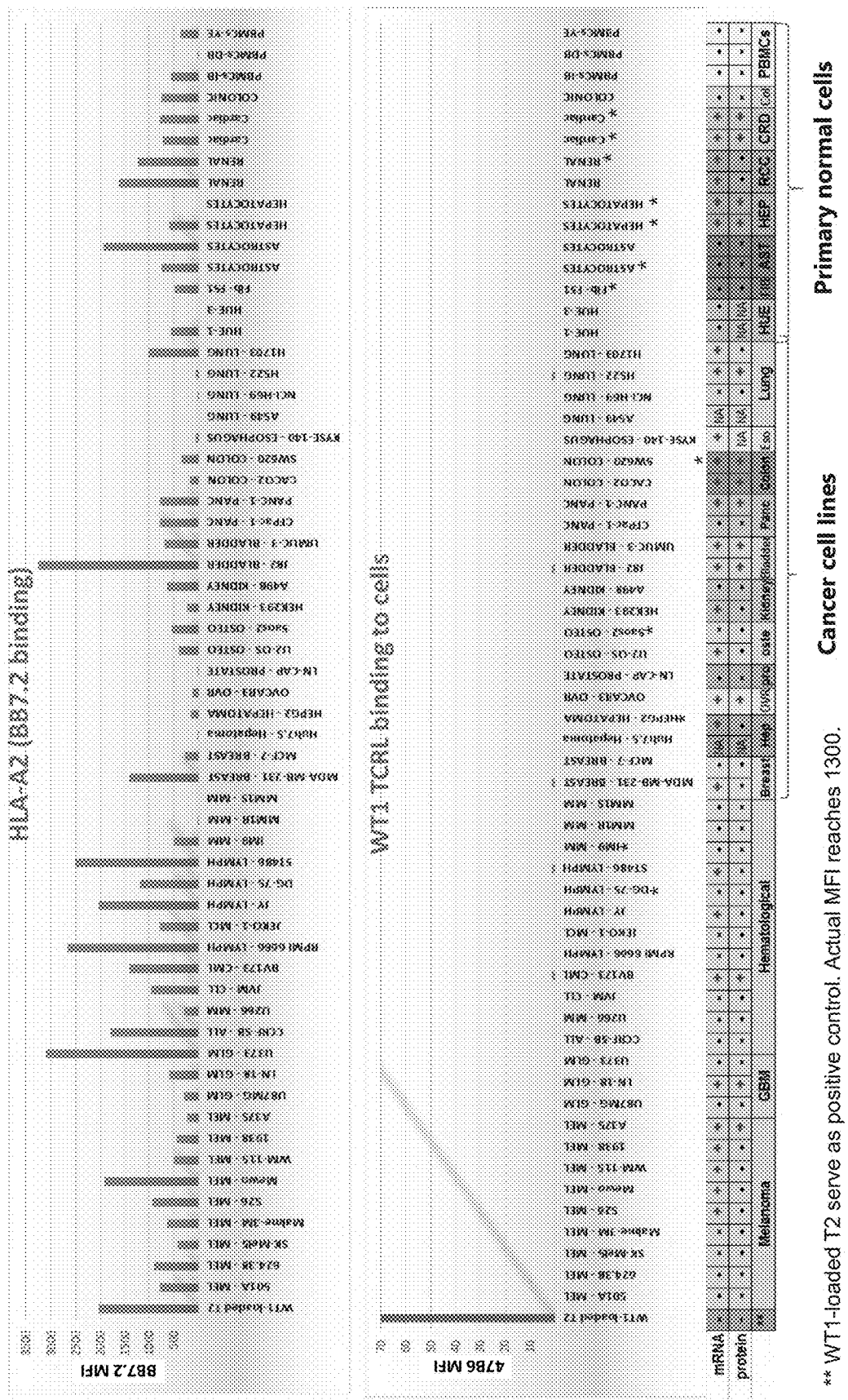

FIG. 36: Summary of B47 TCR-like antibody selectivity. Binding of B47 TCR-like antibodies to HLA-A2+ antigen positive and negative cells was monitored by using PE-labeled anti-mouse IgG. +/−indicate WT1 mRNA gene expression as measured by PCR. HLA-A2 expression was monitored with MAb BB7.2.

FIG. 37: Epitope specificity determination of TCR-like antibodies by Alanine scanning. The WT1 peptide sequence was substituted with Alanine at positions 1, 3, 4, 5, 7, and 8. The Ala mutated peptides were synthesized and loaded APCs Binding of TCR-like antibody ESK1 was accessed by flow cytometry and binding intensity as measured by mean fluorescence intensity was measured and compared with the binding intensity to WT native WT1 peptide. The relative effect of each position Ala substitution was evaluated as percentage to the binding to WT peptide. Data from Dao et al. Sci Transl Med 5, 176ra33 (2013).

Figure 38:
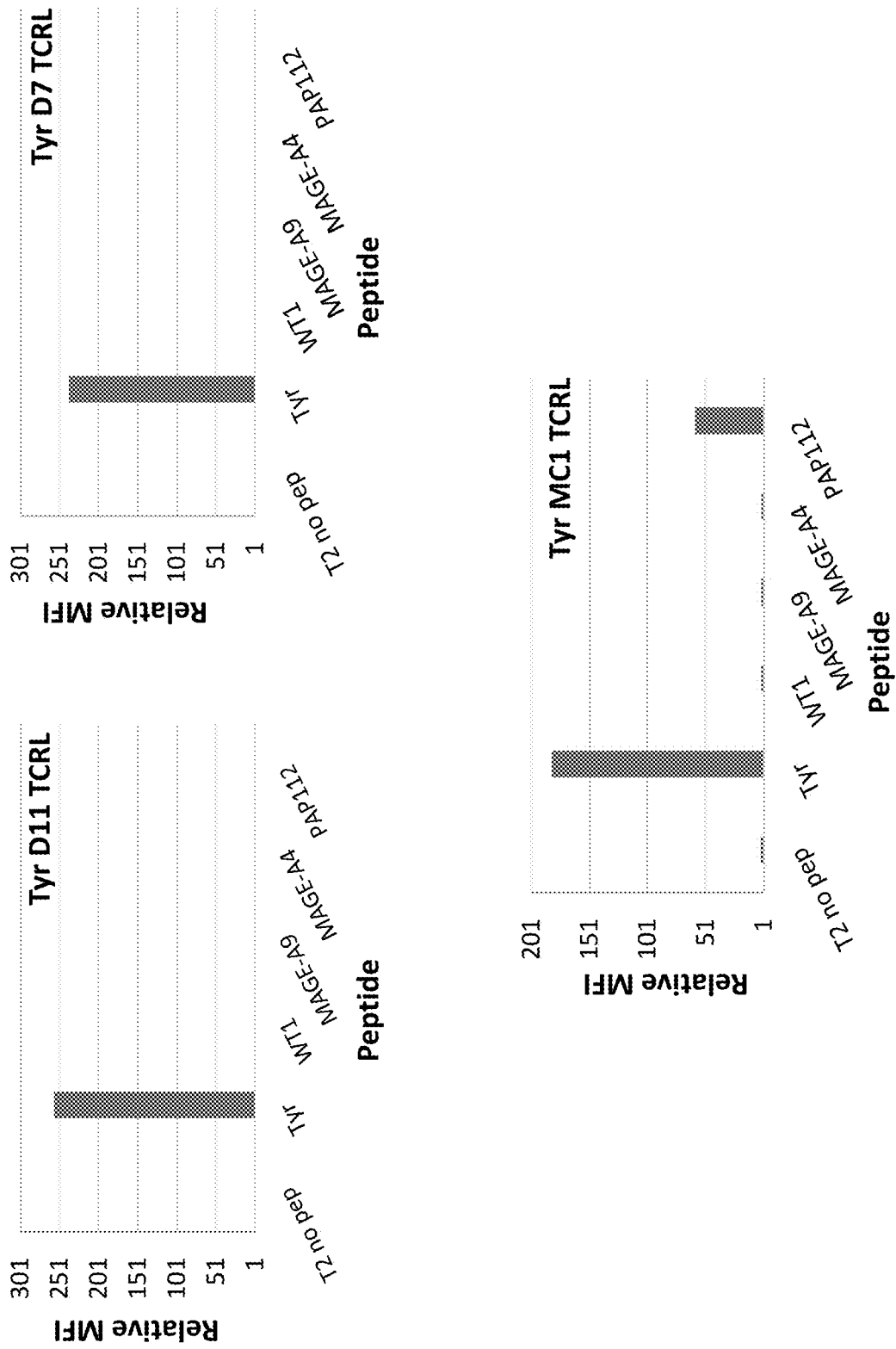

FIG. 38: Binding of D11, D7, and biotinylated MC1 to T2 APCs loaded with Tyrosinase peptide and Tyrosinase similar HLA-A2 restricted peptides. S17-S23 are Alanine-based similar peptides. T2 cells were loaded with Tyrosinase and indicated peptides at a concentration of $10^{-5}$ M for 12 hrs at 37° C. Cells were stained with TCRL antibodies at a concentration of 10 μg/ml followed by secondary PE-labeled streptavidin/anti-mouse antibody and analyzed by flow cytometry Mean fluorescence intensity (MFI) is indicated.

Figure 39:
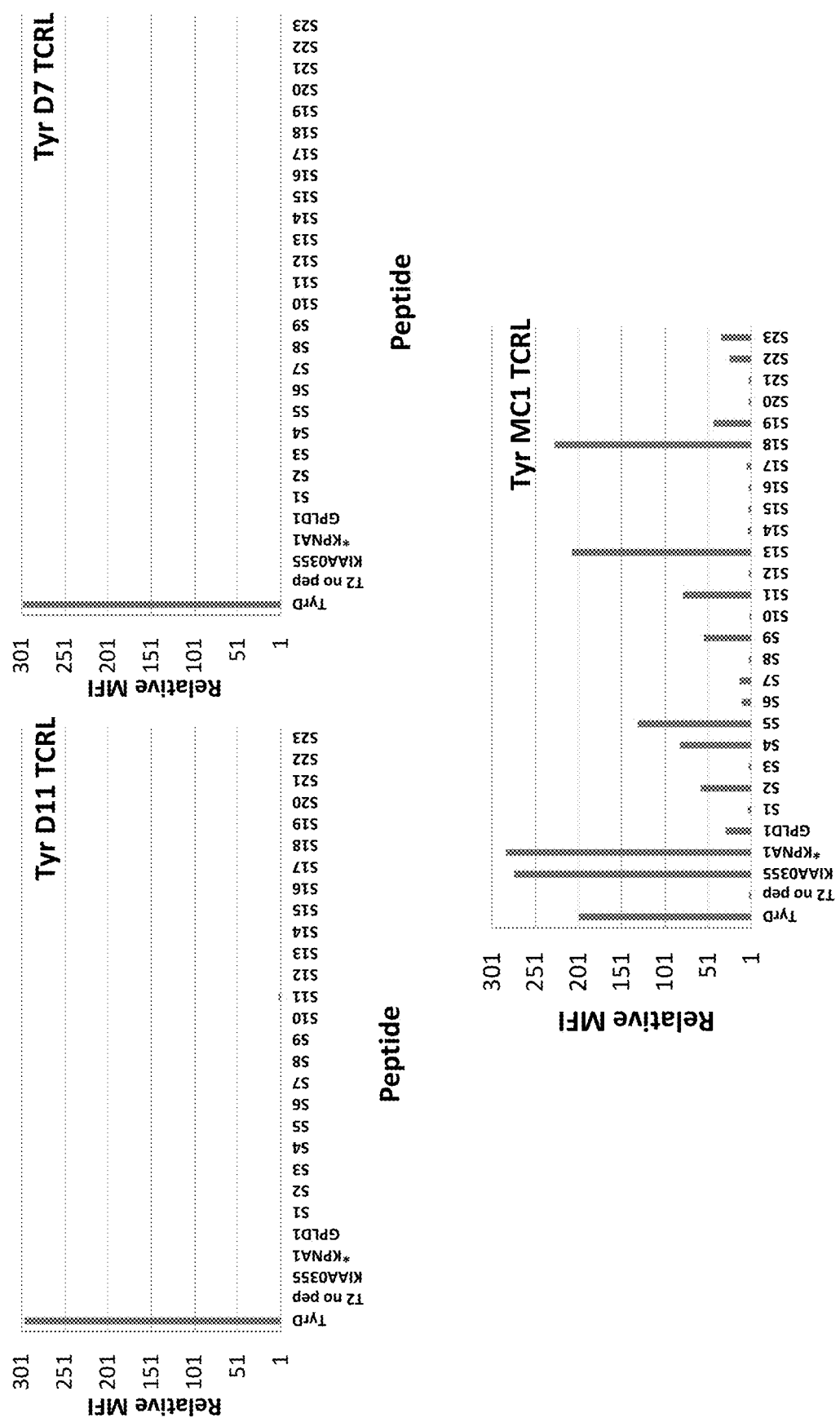

FIG. 39: Binding of D11, D7 and MC1 TCR-like antibodies to T2 APCs loaded with Tyrosinase peptide and Tyrosinase similar HLA-A2 restricted peptides. KIAA0355, S7, S17-S23 are Alanine-based similar peptides. T2 cells were loaded with Tyrosinase and indicated peptides at a concentration of $10^{-5}$ M for 12 hrs at 37° C. Cells were stained with TCRL antibodies at a concentration of 10 μg/ml followed by secondary PE-labeled streptavidin/anti-mouse antibody and analyzed by flow cytometry Mean fluorescence intensity (MFI) is indicated.

Figure 40A:
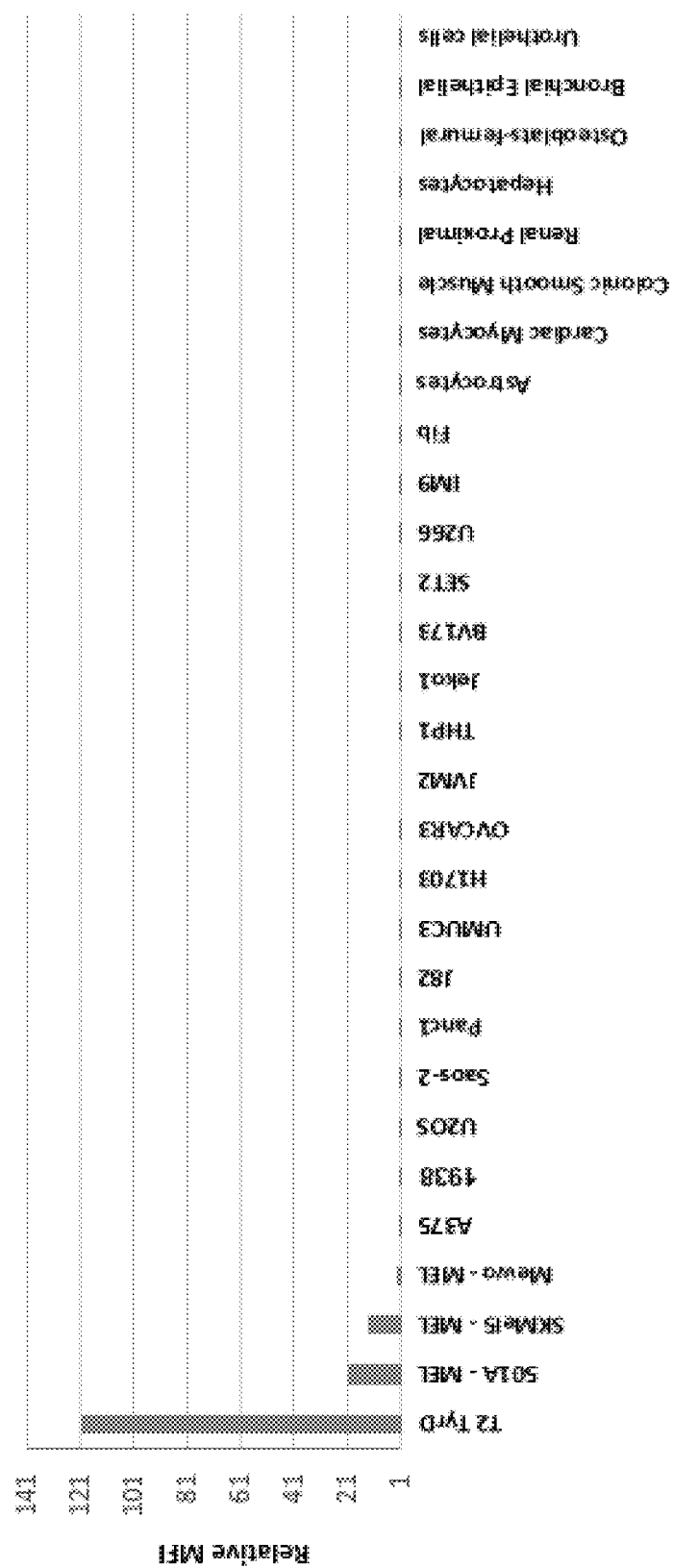
Figure 40C:
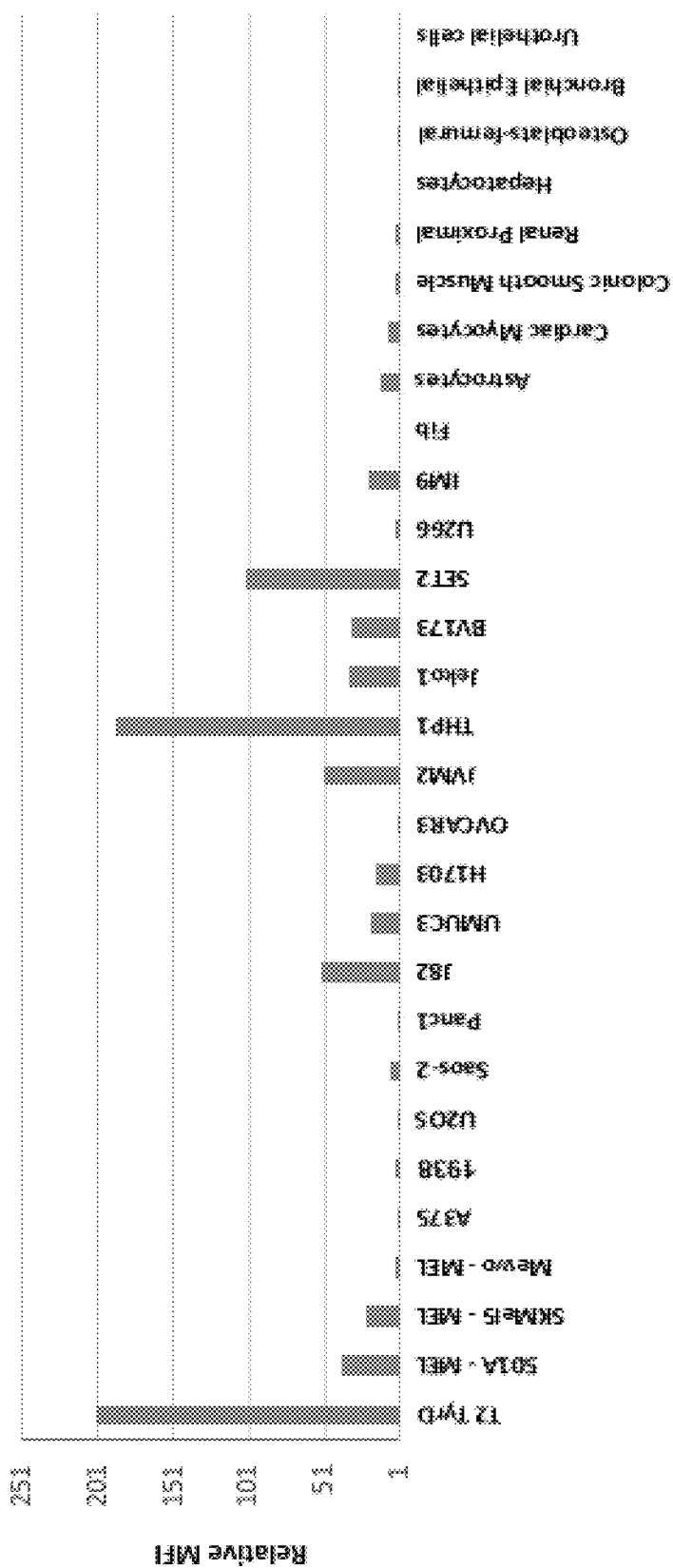

FIGS. 40A-C: Binding of D11 (FIG. 40A), D7 (FIG. 40B) and biotinylated MC1 (FIG. 40C) TCR-like antibodies to HLA-A2+, Tyrosinase antigen positive or negative cells. Tumor and normal primary cells that express HLA-A2 were tested by qPCR for Tyrosinase mRNA expression. Tumor cells were stained with the indicated TCR-like antibodies at a concentration of 10 μg/ml followed by secondary PE-labeled streptavidin/anti-mouse antibody and analyzed by flow cytometry. Mean fluorescence intensity (MFI) is indicated.

Figure 41:
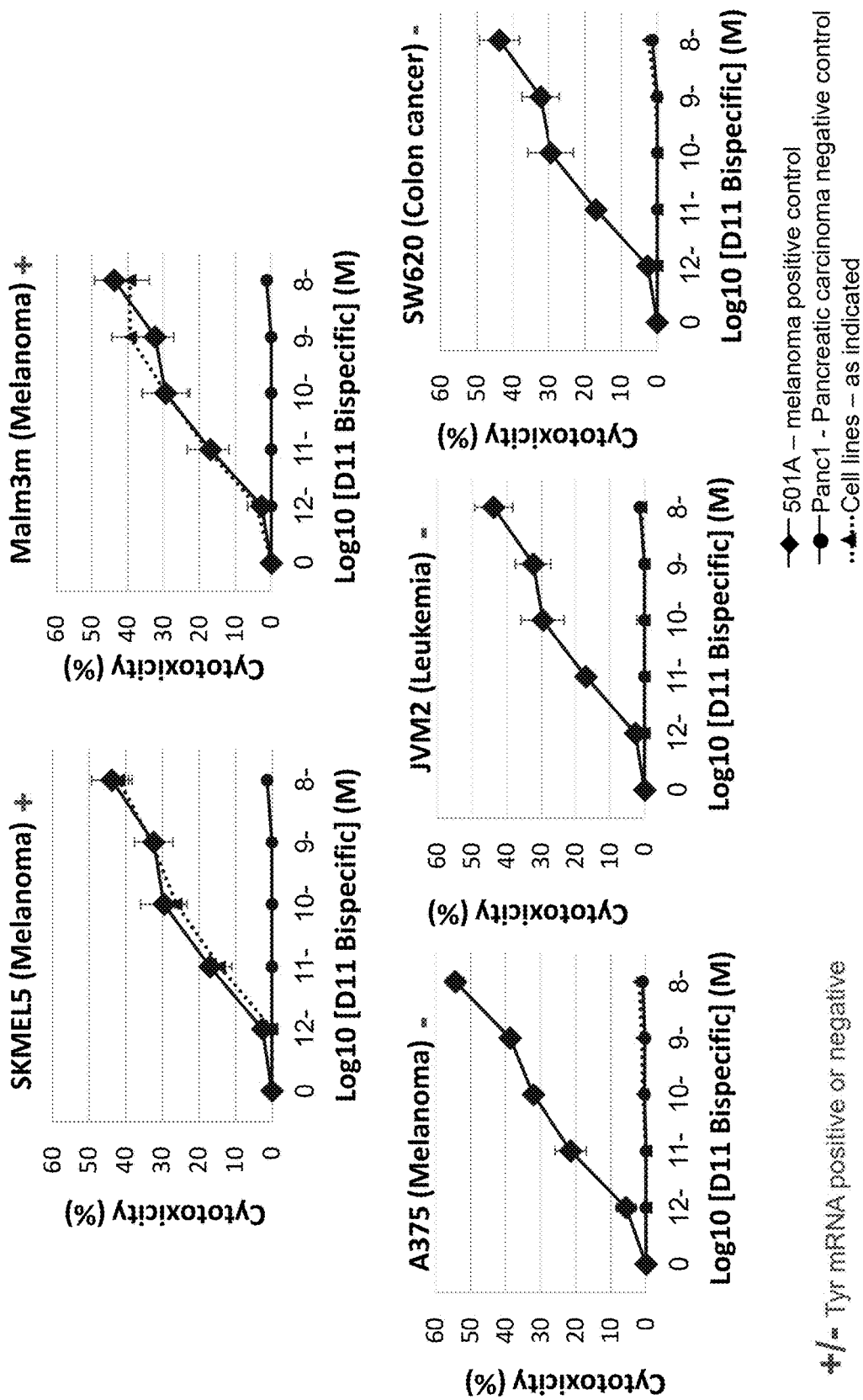

FIG. 41: Killing of HLA-A2+/Tyrosinase+ (positive) and HLA-A2+/Tyrosinase-(negative) cell lines by bi-specific (BS) TCRL having an anti CD-3 arm and a D11 arm, termed Tyr D11 BS TCRL. Tyr D11 BS TCRL was incubated with melanoma HLA-A2+/Tyrosinase+ cells and control tumor cells that are HLA-A2+/Tyrosinase-. Cells were incubated for 24 hrs with the Tyr D11 BS TCRL and with naïve PBMCs isolated from healthy individuals at 10:1 E:T ratio (10:1 effector:target ratio). Cytotoxicity determined by lactate dehydrogenase (LDH) release assay.

Figure 42:
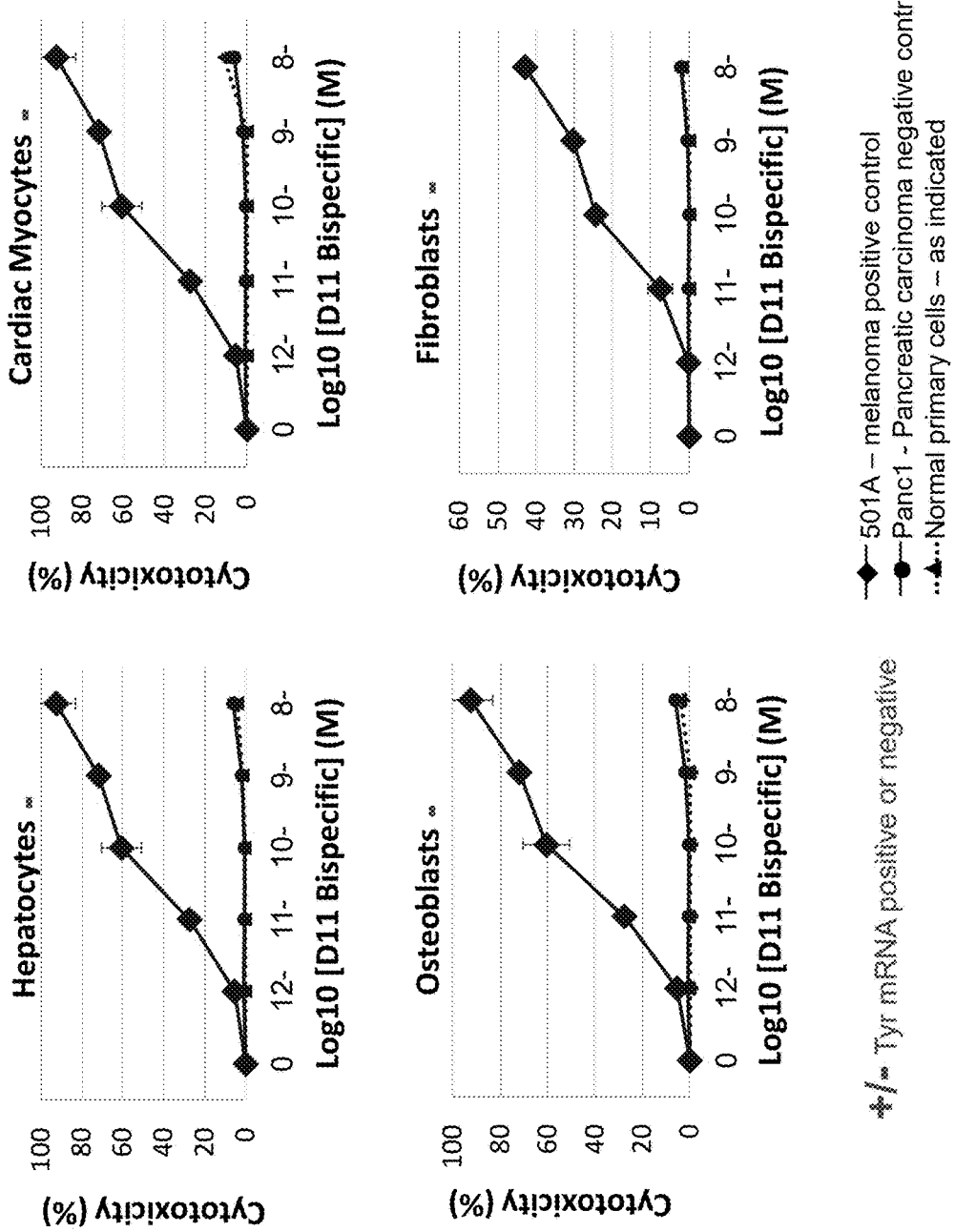

FIG. 42: Killing of HLA-A2+/Tyrosinase-normal primary cells by Tyr D11. BS D11 was incubated with melanoma HLA-A2+/Tyrosinase+ cells as control and normal primary cells that are HLA-A2+/Tyrosinase-. Cells were incubated for 24 hrs with the D11 BS TCRL and with naïve PBMCs isolated from healthy individuals at 10:1 E:T ratio.

Figure 43:
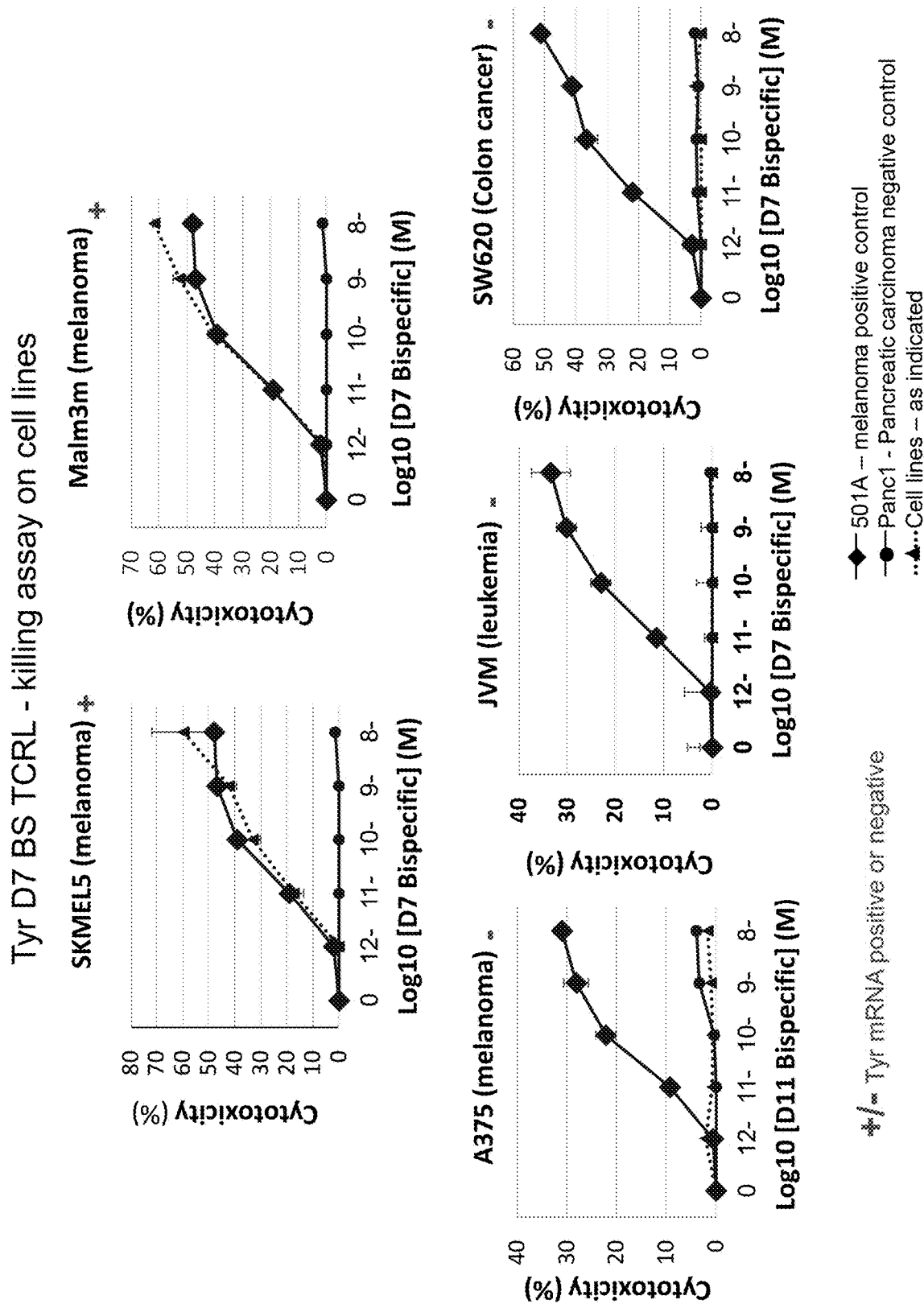

FIG. 43: Killing of HLA-A2+/Tyrosinase+ and HLA-A2+/Tyrosinase-cell lines by Tyr D7 BS TCRL. D7 BS was incubated with melanoma HLA-A2+/Tyrosinase+ cells and control tumor cells that are HLA-A2+/Tyrosinase-. Cells were incubated for 24 hrs with the D7 BS and with naïve PBMCs isolated from healthy individuals at 10:1 E:T ratio.

Figure 44:
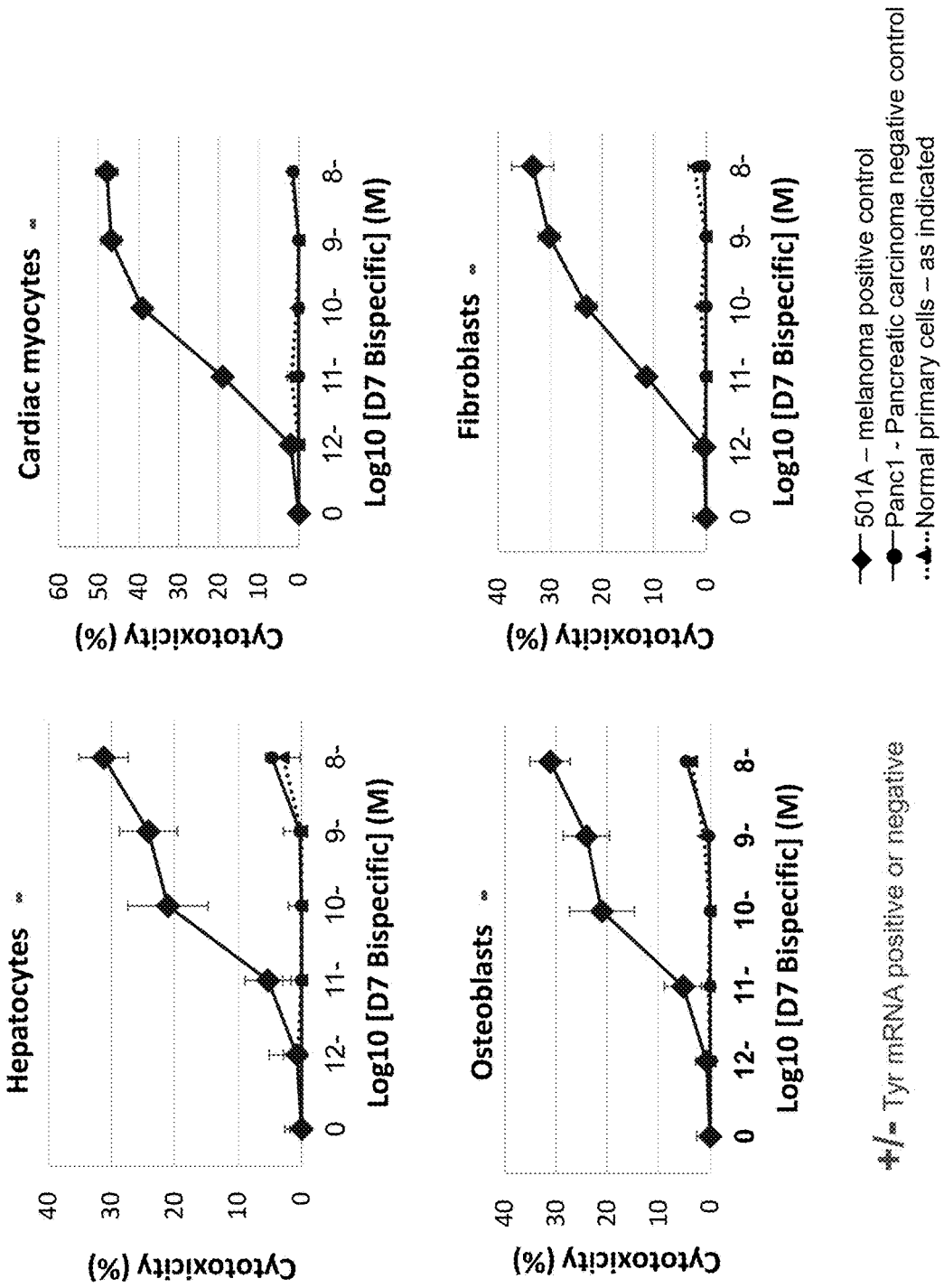

FIG. 44: Killing of HLA-A2+/Tyrosinase-normal primary cells by D7 BS. D7 BS was incubated with melanoma HLA-A2+/Tyrosinase+ cells as control and normal primary cells that are HLA-A2+/Tyrosinase-. Cells were incubated for 24 hrs with the D7 BS and with naïve PBMCs isolated from healthy individuals at 10:1 E:T ratio.

Figure 45:
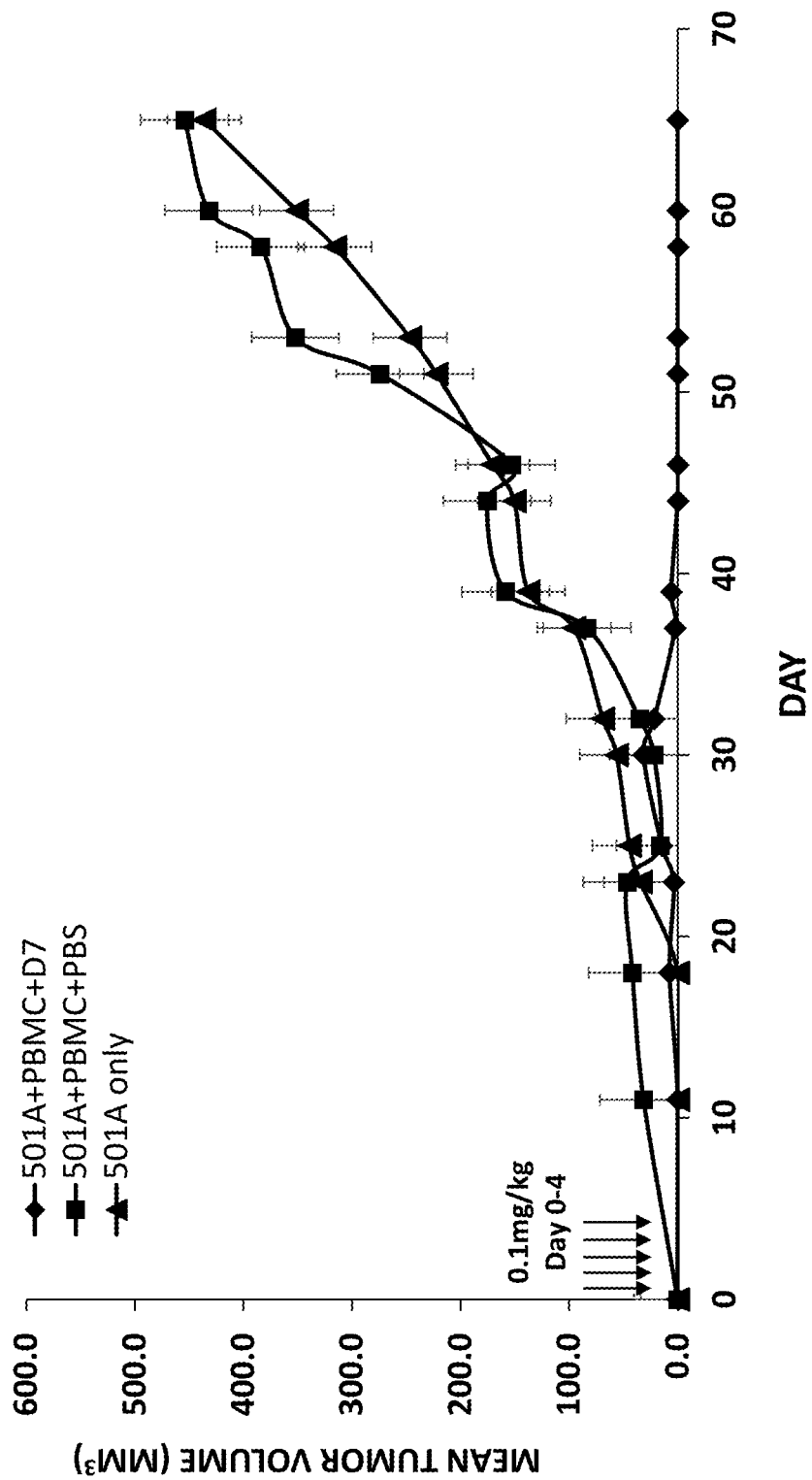

FIG. 45 In vivo efficacy of D7 BS in preventing an S.C. 501A melanoma tumor formation in NOD/SCID mice.

Figure 46:
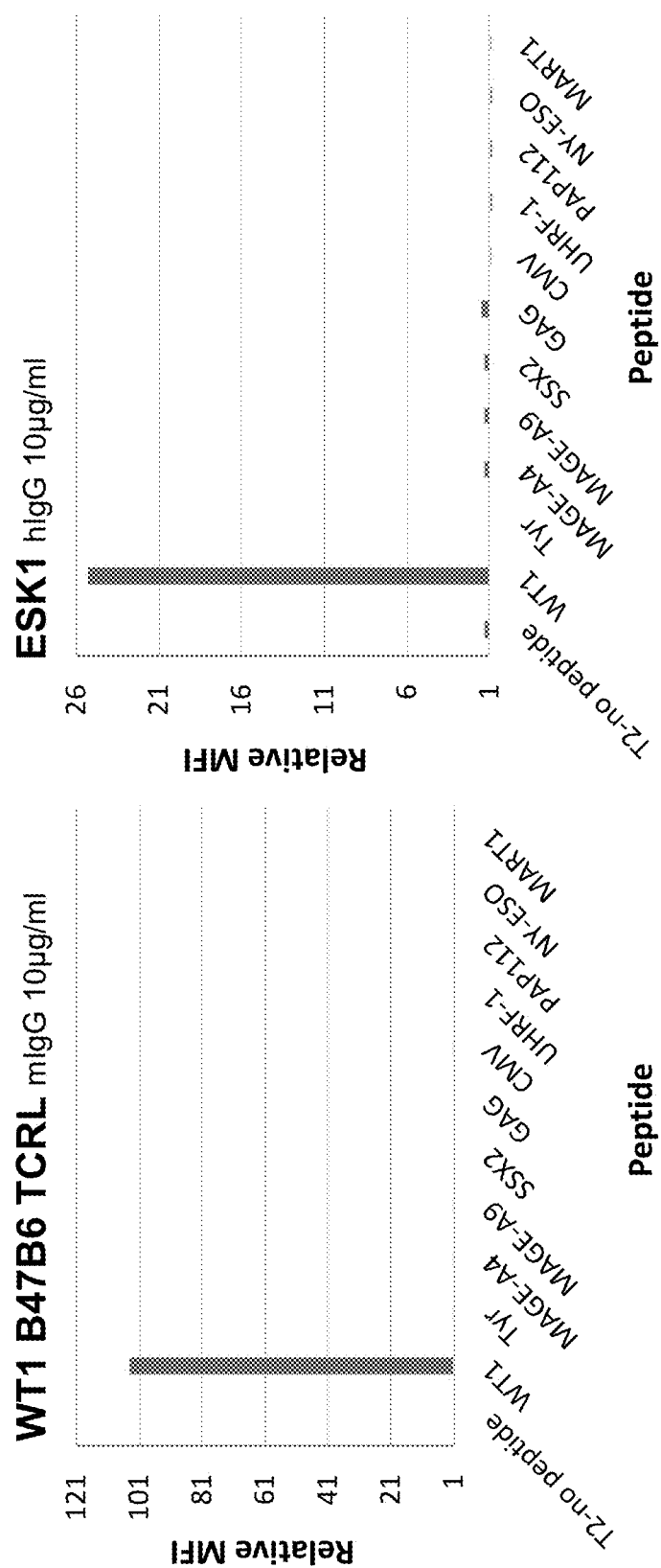

FIG. 46: Binding of biotinylated ESK1 and B47B6 TCR-like antibodies to T2 APCs loaded with WT1 peptide and other HLA-A2 restricted peptides. T2 cells were loaded with WT1 peptide and indicated peptides at a concentration of $10^{-5}$M for 12 hrs at 37° C. Cells were stained with ESK1 or B47B6 TCRL antibodies at a concentration of 10 µg/ml followed by secondary PE-labeled streptavidin/anti-mouse antibody and analyzed by flow cytometry Mean fluorescence intensity (MFI) is indicated.

Figure 47:
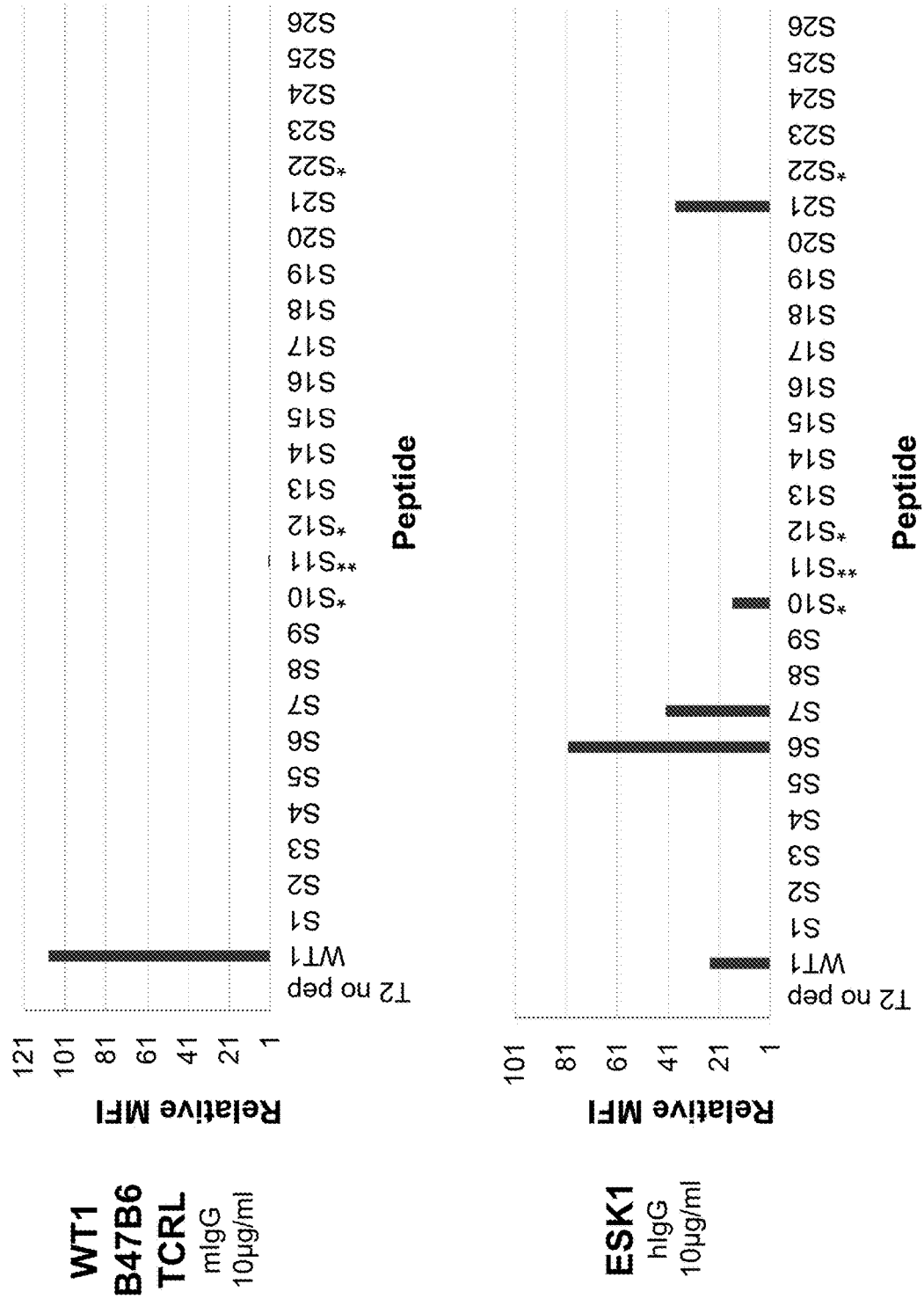

FIG. 47: Binding of ESK1 and B47B6 TCR-like antibodies to T2 APCs loaded with WT1 peptide and WT1 similar HLA-A2 restricted peptides. S2, S6 and S7 are Alanine-based similar peptides. S11 is a heteroclitic peptide. T2 cells were loaded with WT1 peptide and indicated peptides at a concentration of $10^{-5}$ M for 12 hrs at 37° C. Cells were stained with ESK1 or B47B6 TCRL antibodies at a concentration of 10 µg/ml followed by secondary PE-labeled streptavidin/anti-mouse antibody and analyzed by flow cytometry Mean fluorescence intensity (MFI) is indicated.

Figure 48:
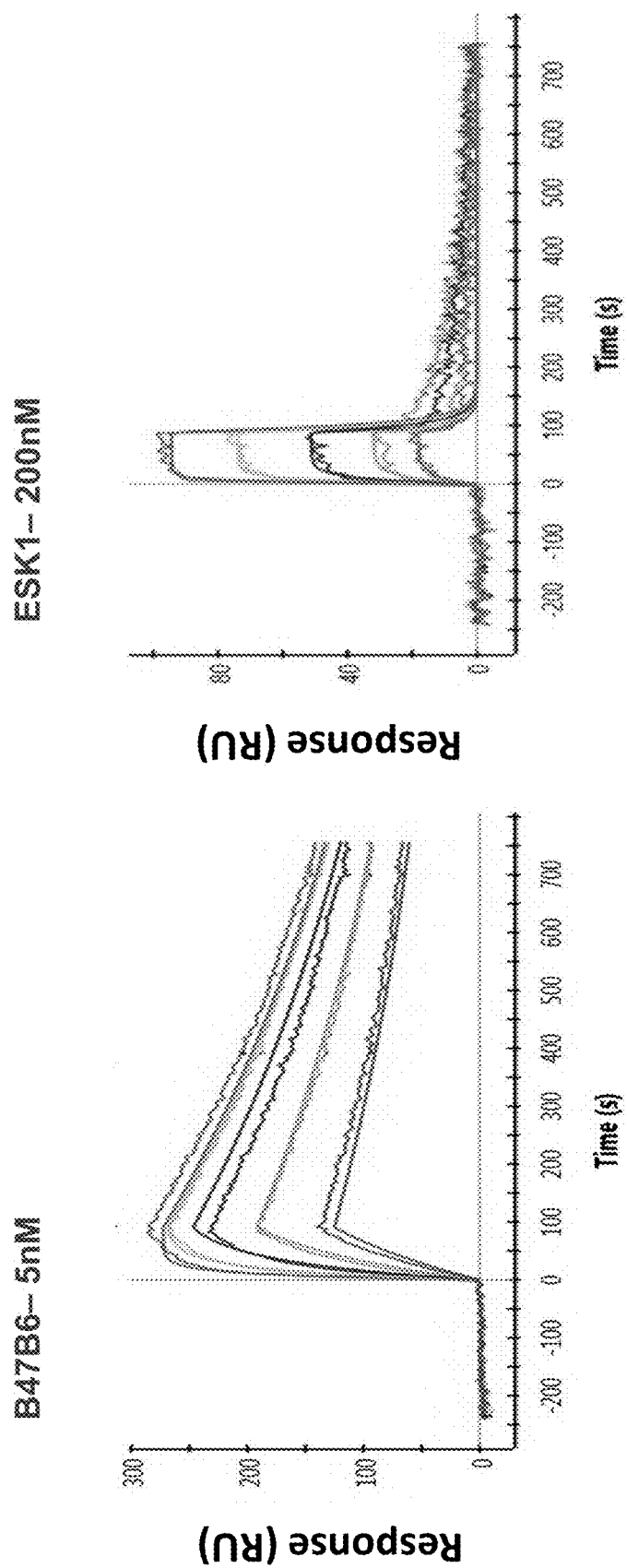

FIG. 48: Affinity by SPR—Apparent binding affinity determination of ESK1 and B47B6 TCR-like antibodies targeting HLA-A2/WT1 complexes. Purified recombinant biotinylated single-chain HLA-A2/WT1 complex generated by in vitro refolding of E. coli expressed scHLA-A2 complexes, was immobilized indirectly to the SPR sensor chip with NeutrAvidin. Purified ESK1 and B47B6 TCRL Fabs served as analytes.

Figure 49:
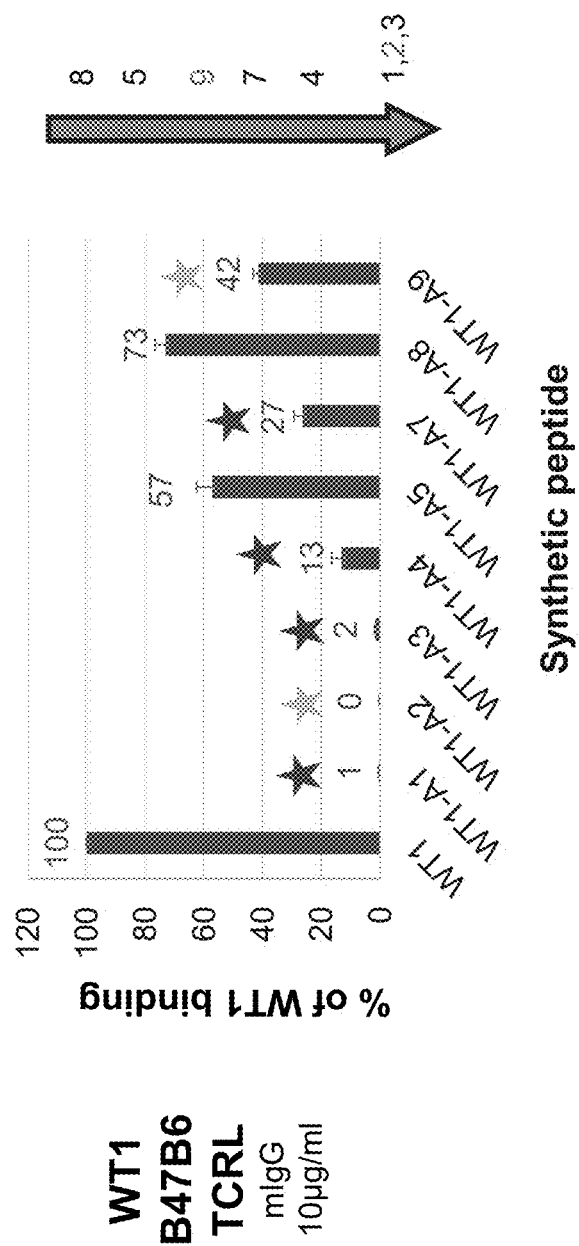

FIG. 49: Epitope specificity determination by Alanine scanning mutagenesis. The mutant WT1 peptides with Alanine substitutions at positions 1, 2, 3, 4, 5, 7, 8 and 9 were synthesized and loaded onto T2 cells APCs at a concentration of $10^{-5}$ M for 12 hrs at 37° C. Cells were stained with the B47B6 TCR-like antibody at a concentration of 10 µg/ml and analyzed by flow cytometry. The relative effect of Ala substitution at each position was expressed as percentage of the binding to wild-type peptide.

Figure 50:

FIG. 50: Binding of ESK1 and B47B6 TCR-like antibodies to HLA-A2+ and WT1 mRNA positive or negative cells. Tumor cells that express HLA-A2 were tested by qPCR for WT1 mRNA expression. Tumor cells were stained with biotinylated ESK1 and B47B6 TCRL antibodies at 10 µg/ml followed by secondary PE-labeled streptavidin. Mean fluorescence intensity (MFI) is indicated. Also shown are mRNA expression data and cell killing with the bispecific forms (with anti-CD3) of the antibodies, as described herein.

Figure 51A:
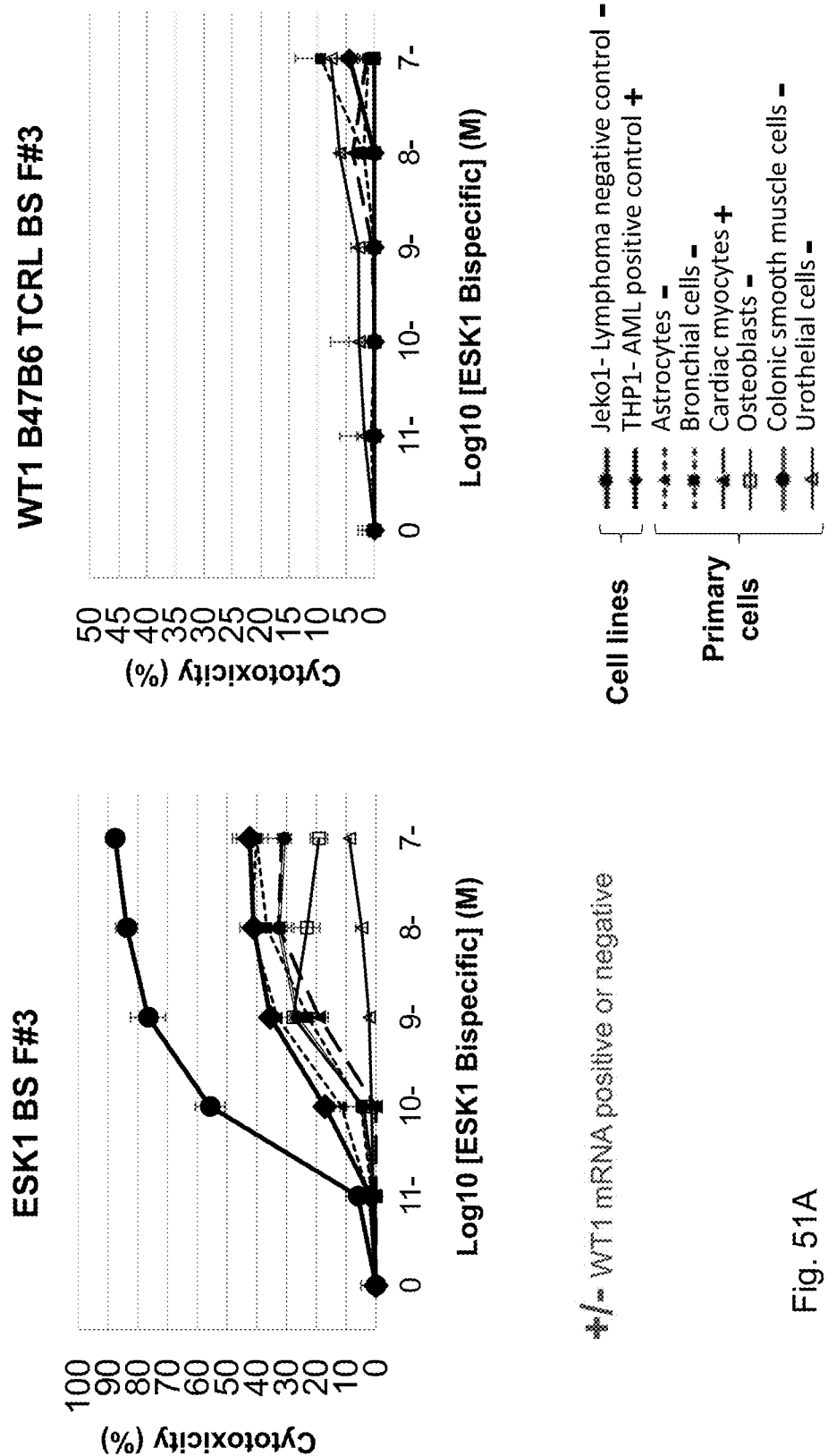

FIG. 51A: Killing of HLA-A2+/WT1+ and HLA-A2+/WT1- normal primary cells by B47B6 BS vs ESK1 BS. B47B6 BS and ESK1 BS were incubated with normal primary cells that are HLA-A2+/WT1+ or HLA-A2+/WT1-. Cells were incubated for 24 hrs with the B47B6 BS or ESK1 BS and with naïve PBMCs isolated from healthy individuals at 10:1 E:T ratio. Cytotoxicity was determined by LDH release assay.

Figure 51B:
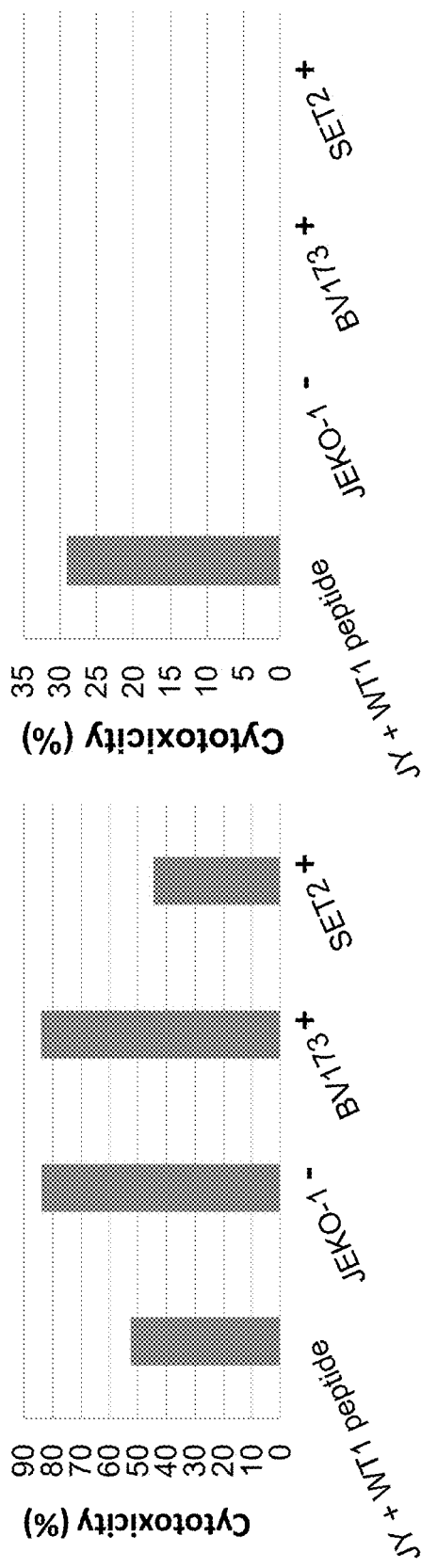

FIG. 51B: Killing of HLA-A2+/WT1+ and HLA-A2+/WT1- cell lines by B47B6 BS vs ESK1 BS. B47B6 BS and ESK1 BS were incubated with tumor cells that are HLA-A2+/WT1+ or HLA-A2+/WT1-. Cells were incubated for 24 hrs with the B47B6 BS or ESK1 BS and with naïve PBMCs isolated from healthy individuals at 10:1 E:T ratio (#F3-Format—in which the anti-CD3 scFv fragment was fused to the VLCL of the Fab).

Figure 52:
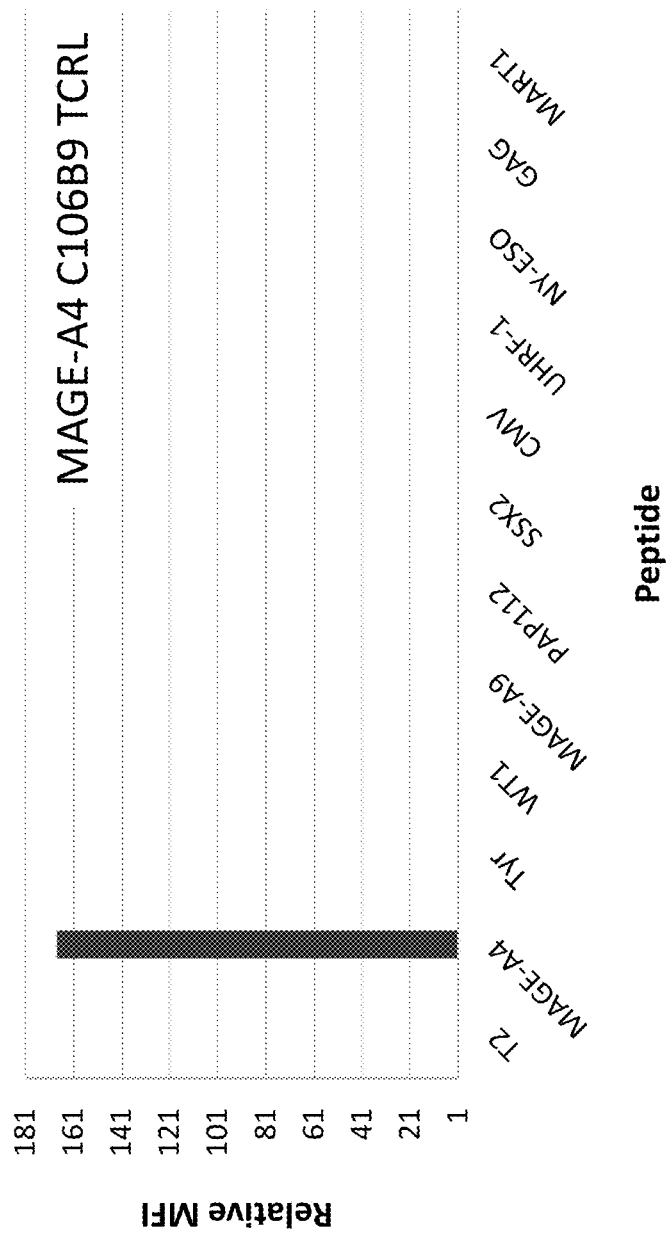

FIG. 52: Binding of C106B9 TCR-like antibody to T2 APCs loaded with MAGE-A4$_{230-239}$ (also referred to as MAGE-A4 peptide) peptide and other HLA-A2 restricted peptides. T2 cells were loaded with MAGE-A4 and indicated peptides at a concentration of $10^{-5}$M for 12 hrs at 37° C. Cells were stained with C106B9 TCRL antibody at 10 µg/ml followed by secondary PE-labeled anti-mouse antibody and analyzed by flow cytometry. Mean fluorescence intensity (MFI) is indicated.

Figure 53:
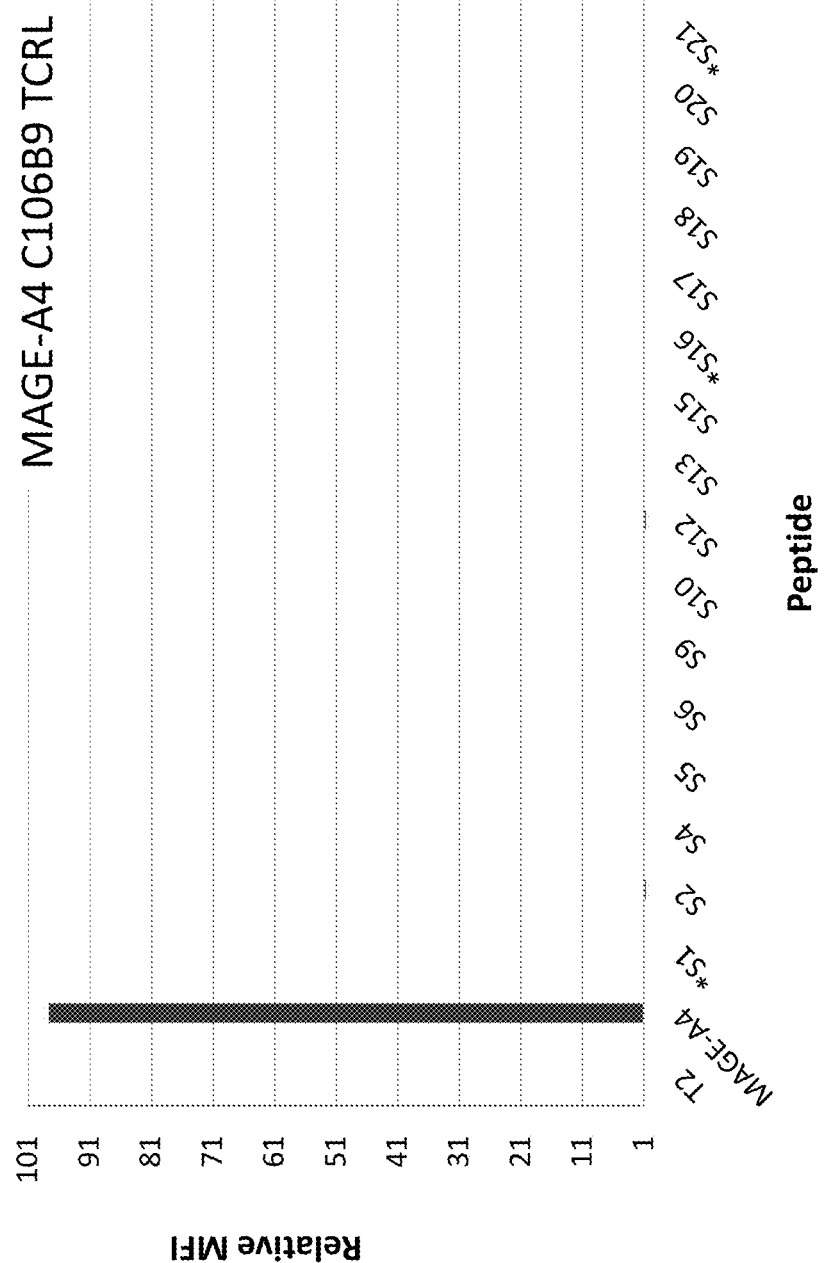

FIG. 53: Binding of C106B9 TCR-like antibody to T2 APCs loaded with MAGE-A4 peptide and MAGE-A4 similar HLA-A2 restricted peptides. T2 cells were loaded with MAGE-A4 and indicated peptides at a concentration of $10^{-5}$M for 12 hrs at 37° C. Cells were stained with C106B9 TCRL antibody at 10 µg/ml followed by secondary PE-labeled anti-mouse antibody and analyzed by flow cytometry.

Figure 54:
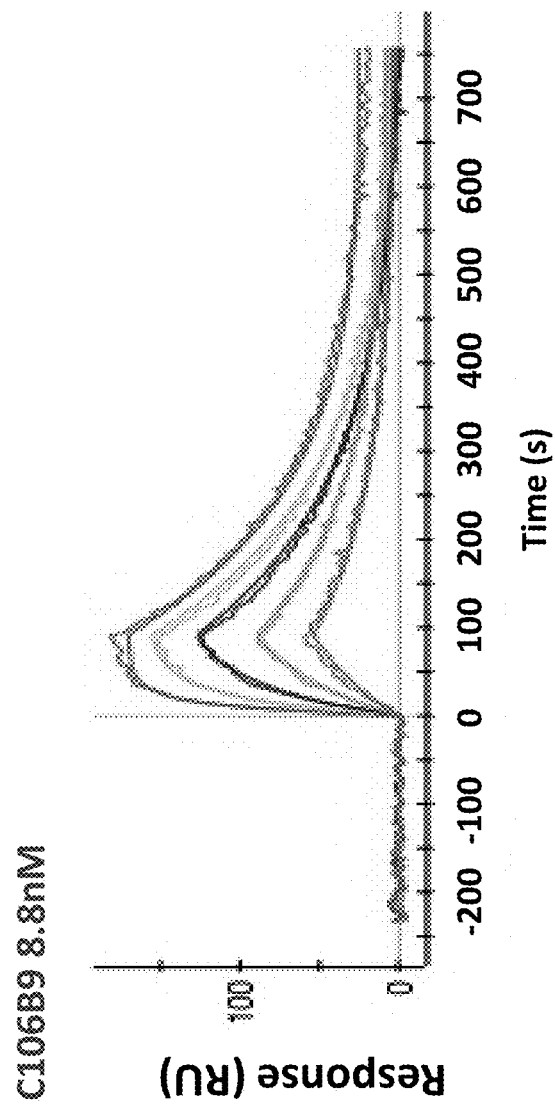

FIG. 54: Affinity by SPR—Apparent binding affinity determination of C106B9 TCR-like antibody targeting HLA-A2/MAGE-A4 complexes. Purified recombinant biotinylated single-chain HLA-A2/MAGE-A4 complex generated by in vitro refolding of E. coli expressed scHLA-A2 complexes, was immobilized indirectly to the SPR sensor chip with NeutrAvidin. Purified C106B9 TCRL Fab was used as the analyte.

Figure 55:
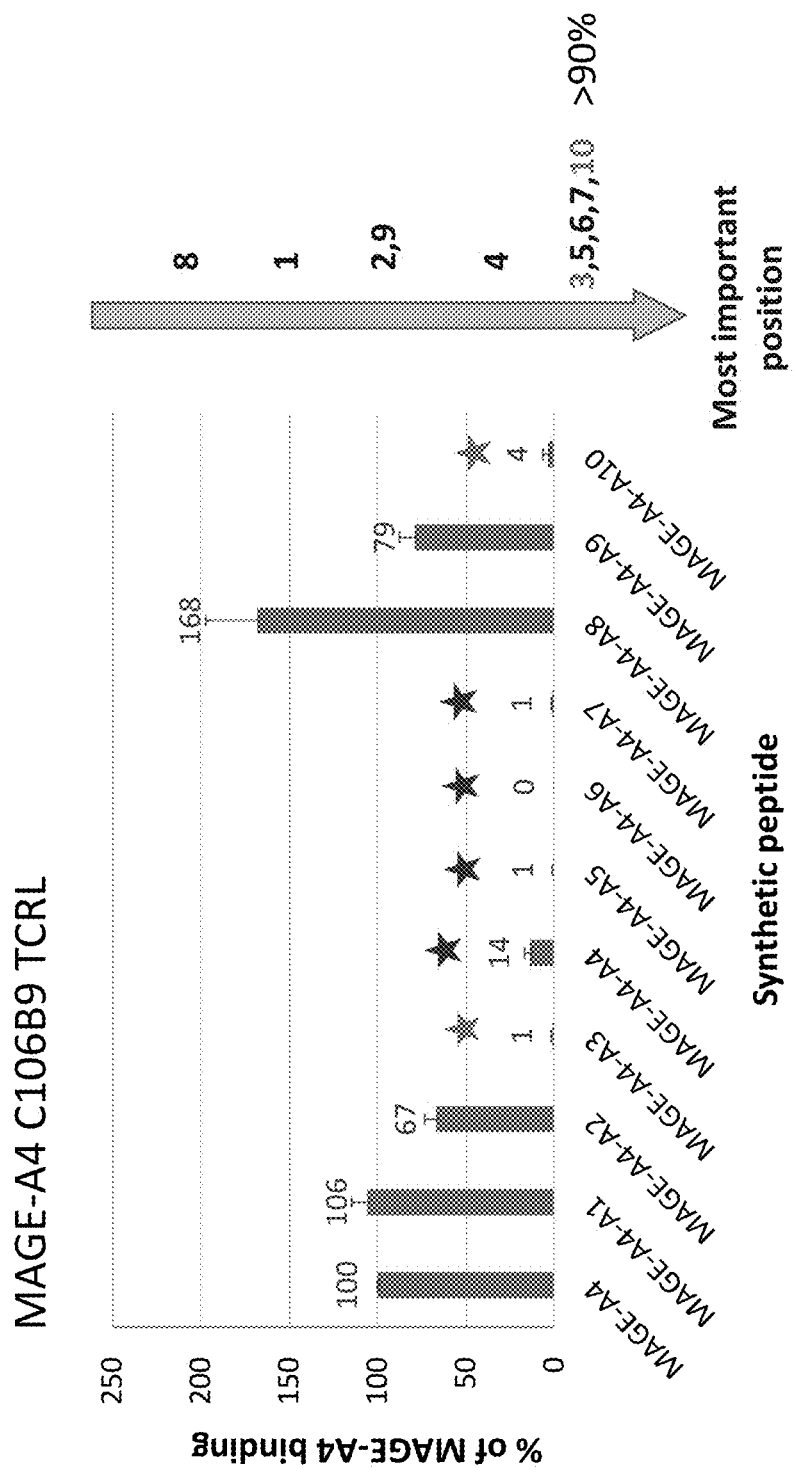

FIG. 55: Epitope specificity determination by Alanine scanning mutagenesis. The mutant MAGE-A4 peptides with alanine substitutions at positions 1, 2, 3, 4, 5, 6, 7, 8 and 9 were synthesized. Possible anchor positions are shown by a gray star. The native and mutant MAGE-A4 peptides were loaded onto T2 cells APCs at a concentration of $10^{-5}$M for 12 hrs at 37° C. Cells were stained with C106B9 TCR-like antibody at a concentration of 10 µg/ml and analyzed by flow cytometry. MFI values for cells loaded with mutant and wild type peptides were compared. The relative effect of each Ala substitution was expressed as percentage of the binding to native wild-type peptide.

Figure 56:
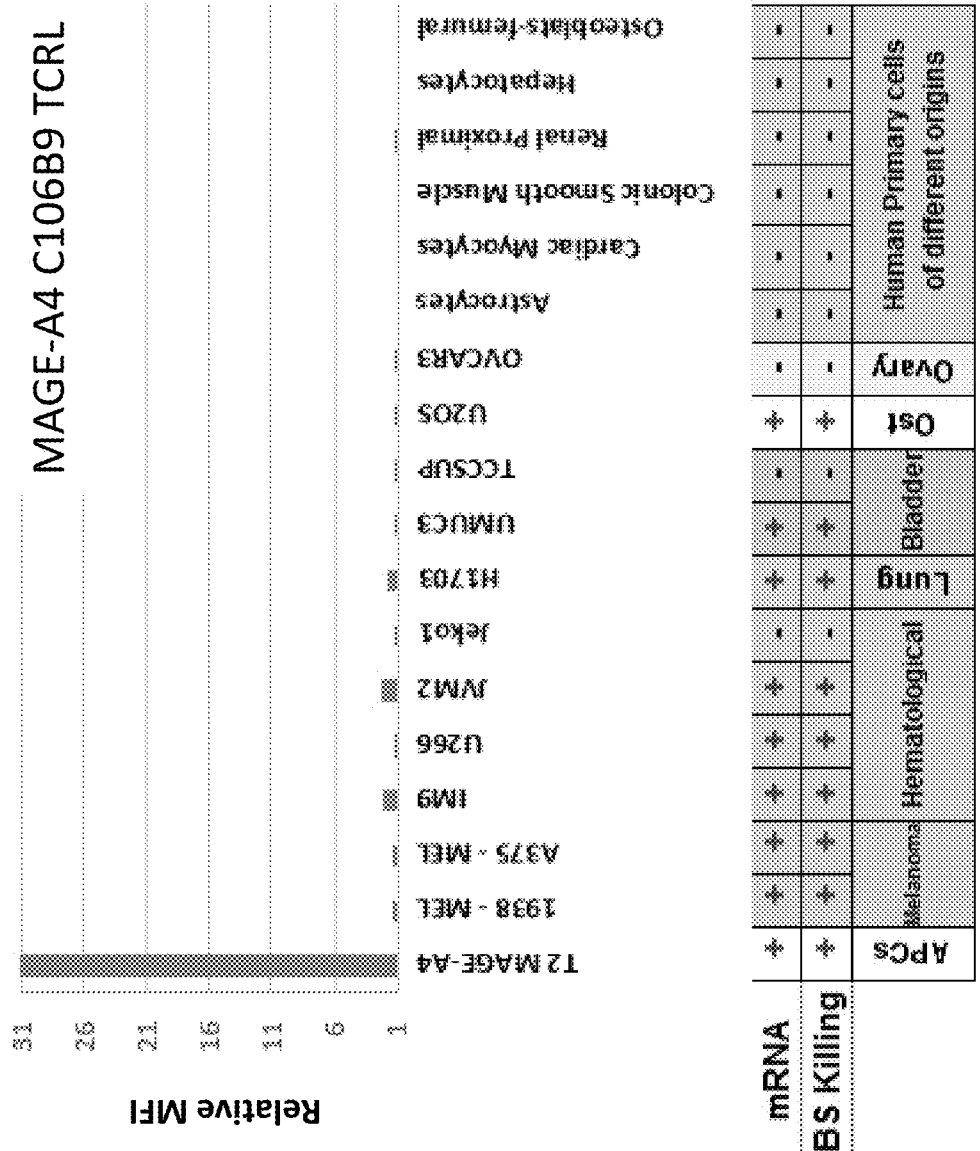

FIG. 56: Binding of C106B9 TCR-like antibody to HLA-A2+ and MAGE-A4 antigen positive or negative cells. Expression of MAGE-A4 mRNA in the cells was confirmed by qPCR. Tumor cells were stained with C106B9 at 10 µg/ml followed by secondary PE-labeled anti-mouse antibody and analyzed by flow cytometry. Mean fluorescence intensity (MFI) is indicated. Also shown are mRNA expression data and cell killing with the bispecific forms (with anti-CD3) of the antibodies, as described herein.

Figure 57:
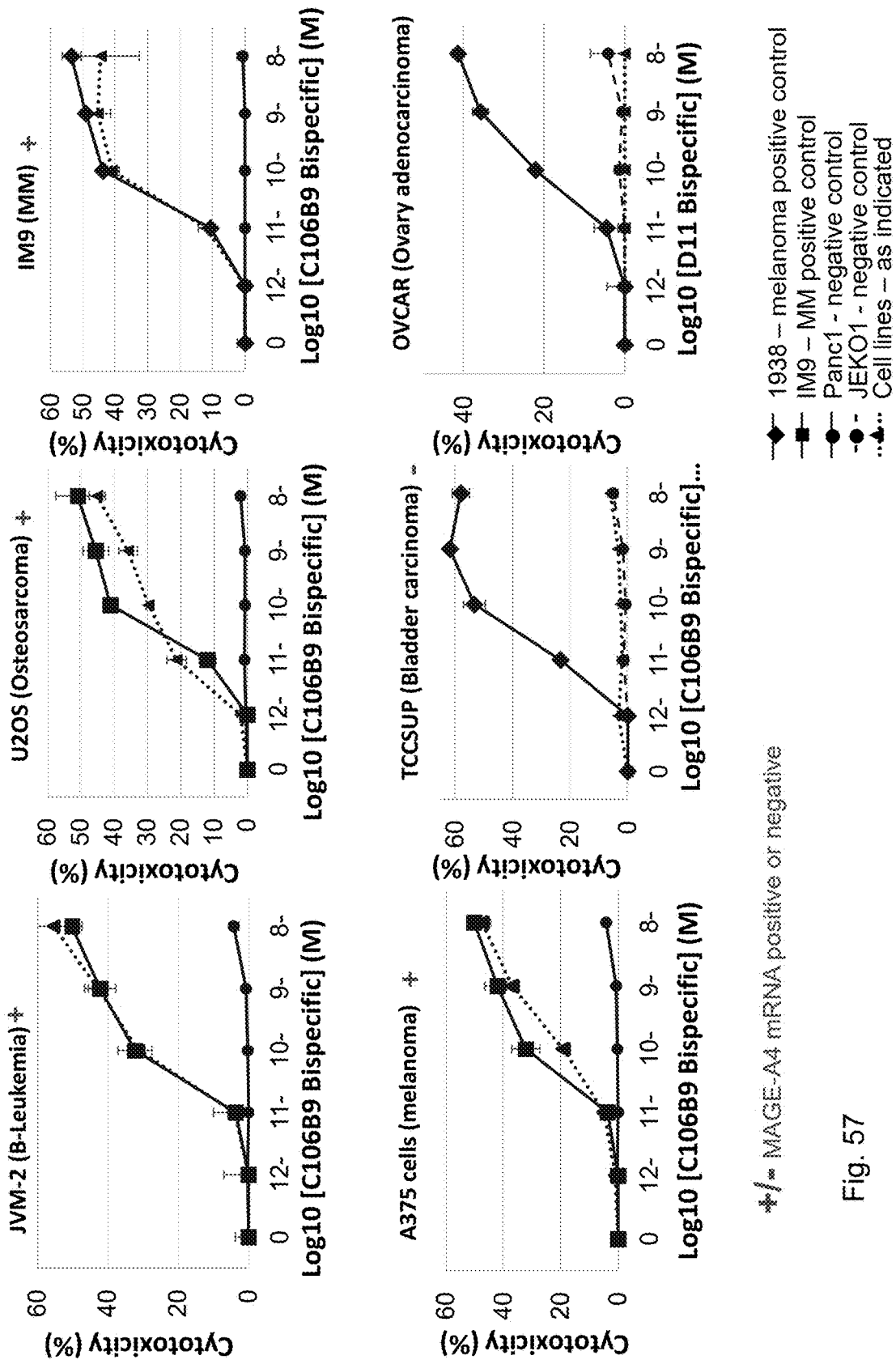

FIG. 57: Killing of HLA-A2+/MAGE-A4+ and HLA-A2+/MAGE-A4- cell lines by C106B9 BS. C106B9 BS was incubated with tumor cells that are HLA-A2+/MAGE-A4+ cells and control tumor cells that are HLA-A2+/MAGE-A4-. Cells were incubated for 24 hrs with the C106B9 BS and with naïve PBMCs isolated from healthy individuals at 10:1 E:T ratio.

Figure 58:
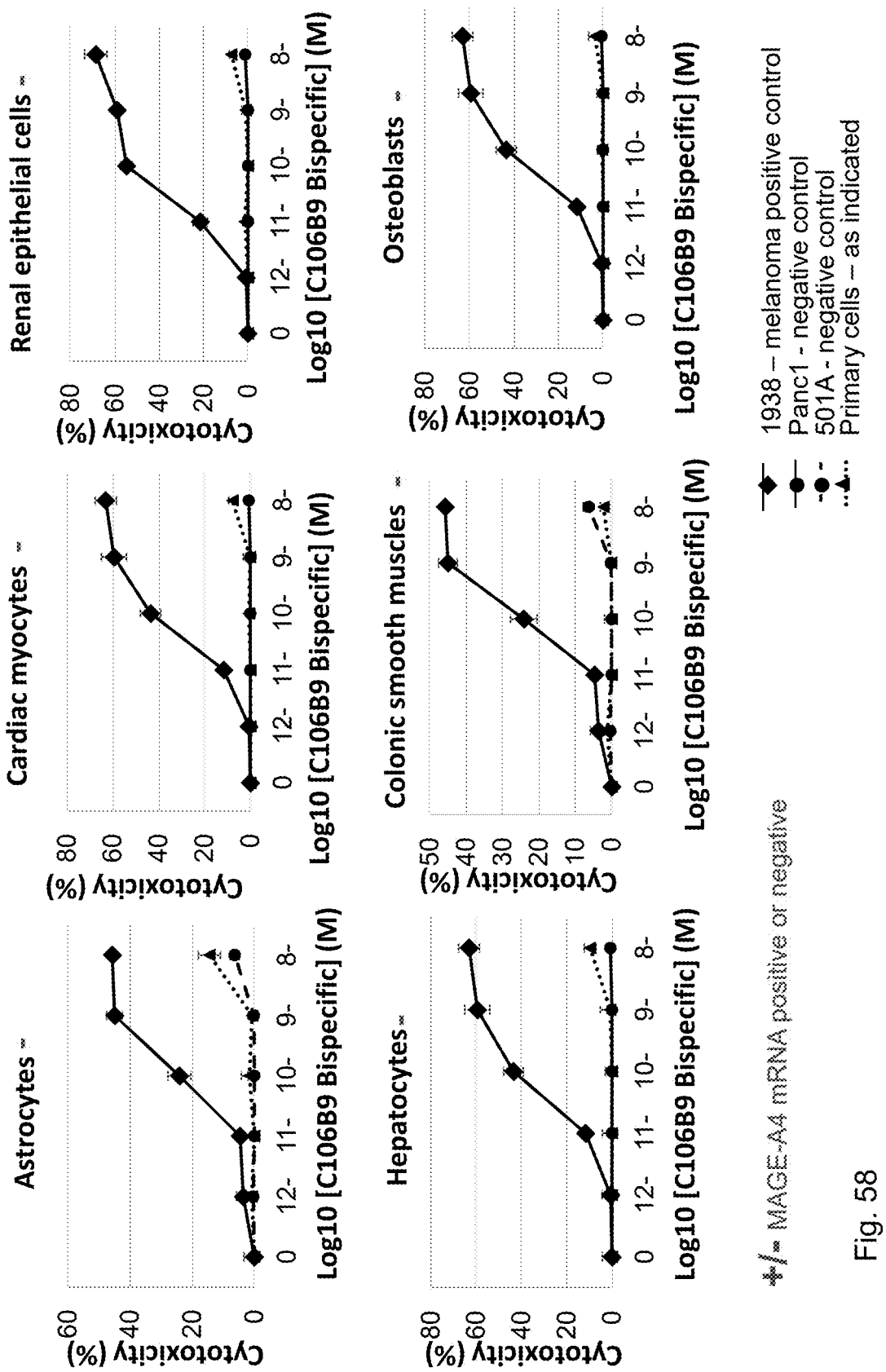

FIG. 58: Killing of HLA-A2+/MAGE-A4- normal primary cells by C106B9 BS. C106B9 BS was incubated with normal primary cells that are HLA-A2+/MAGE-A4-. Cells were incubated for 24 hrs with the C106B9 BS and with naïve PBMCs isolated from healthy individuals at 10:1 E:T ratio.

Figure 59:
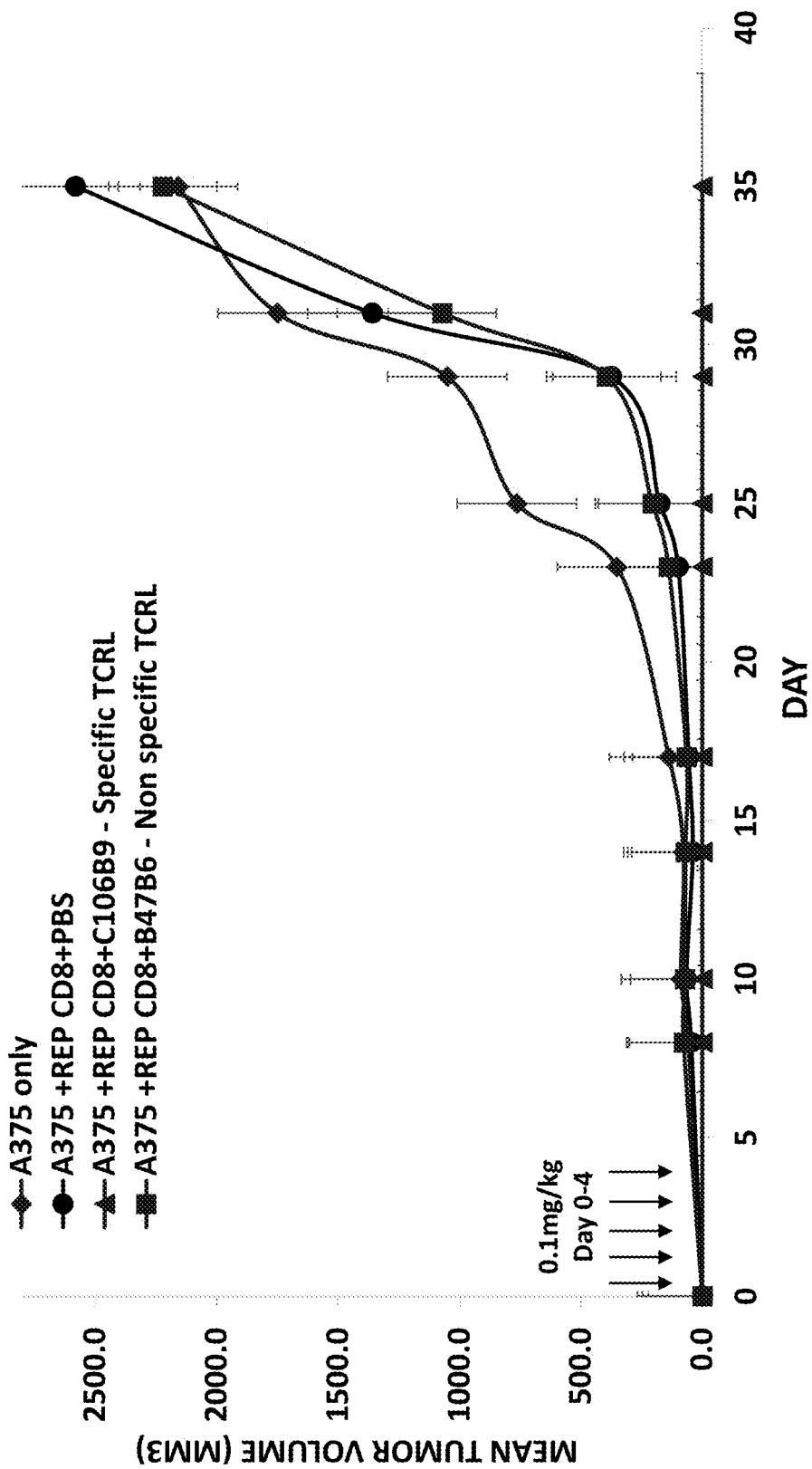

FIG. 59: In vivo efficacy of MAGE-A4 BS C106B9 BS in prevention of S.C. melanoma tumor formation in NOD/SCID mice.

Figure 60:
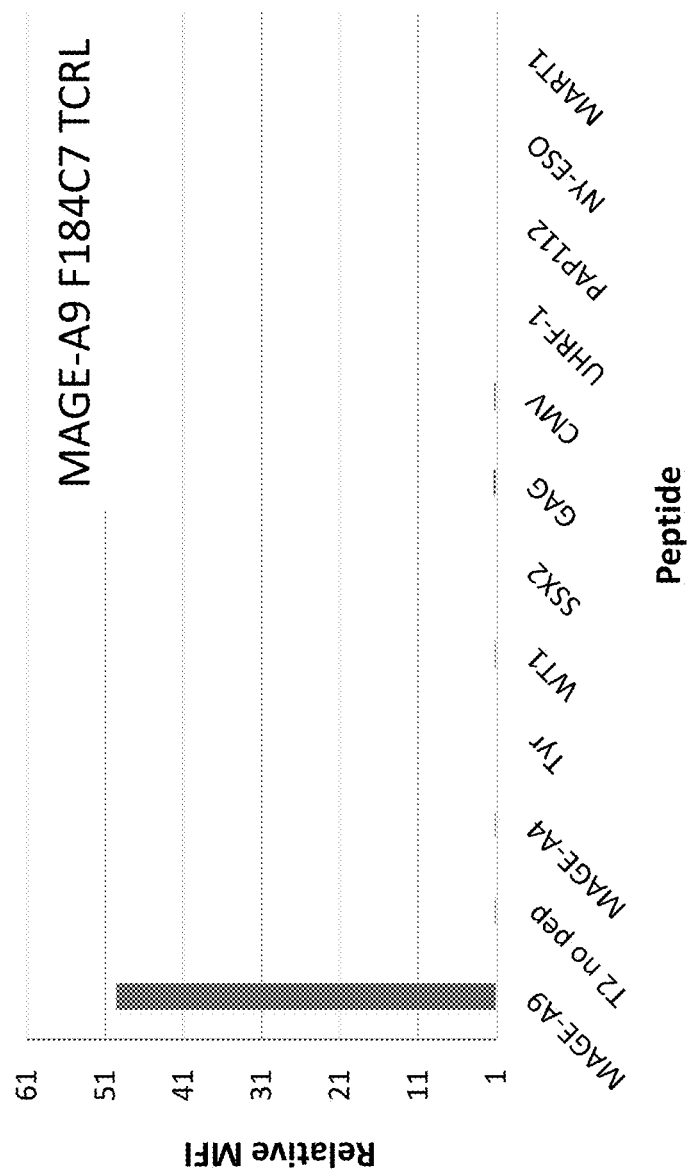

FIG. 60: Binding of F184C7 TCR-like antibody to T2 APCs loaded with MAGE-A9$_{223-231}$ peptide (also referred to as MAGE-A9 peptide) and other HLA-A2 restricted peptides. T2 cells were loaded with MAGE-A9 peptide and indicated peptides at a concentration of $10^{-5}$ M for 12 hrs at 37° C. Cells were stained with F184C7 TCRL antibody at 10 µg/ml followed by secondary PE-labeled anti-mouse antibody and analyzed by flow cytometry. Mean fluorescence intensity (MFI) is indicated.

Figure 61:
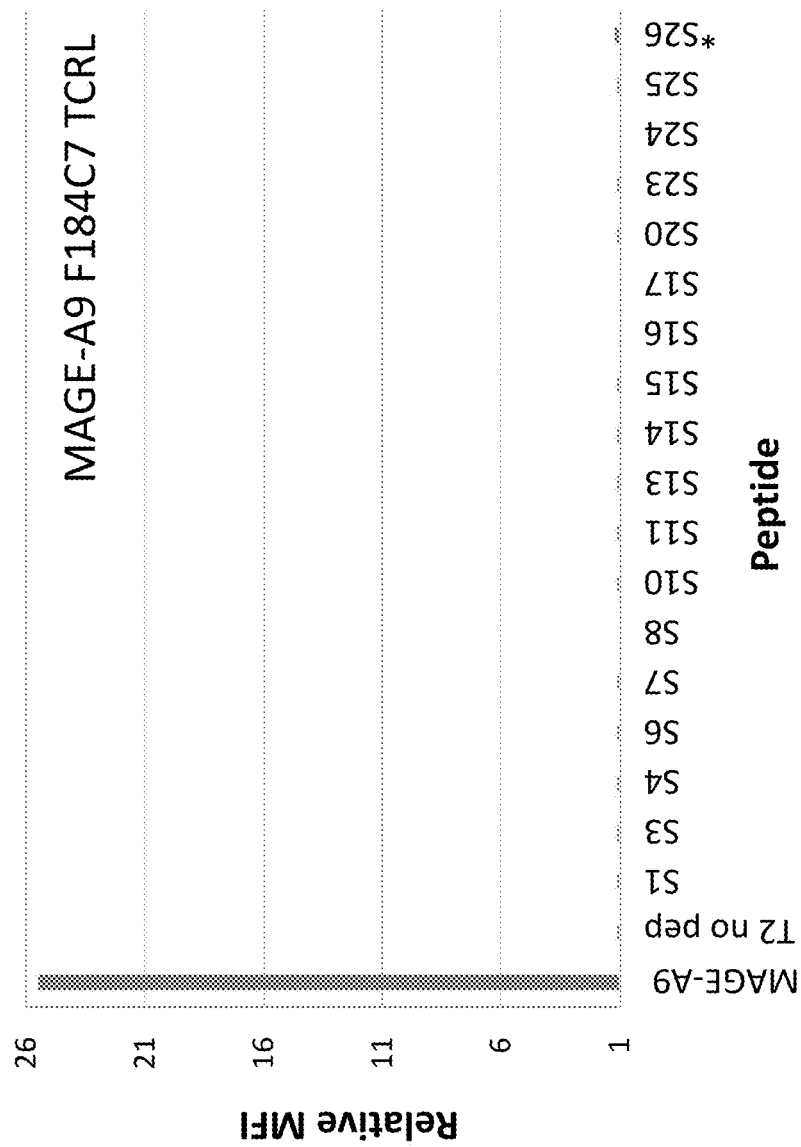

FIG. 61: Binding of F184C7 TCR-like antibodies to T2 APCs loaded with MAGE-A9 peptide and MAGE-A9 similar HLA-A2 restricted peptides. S8 is an Alanine-based similar peptide. T2 cells were loaded with MAGE-A9 peptide and indicated peptides at a concentration of $10^{-5}$M for 12 hrs at 37° C. Cells were stained with F184C7 TCRL antibody at 10 µg/ml followed by secondary PE-labeled anti-mouse antibody and analyzed by flow cytometry.

Figure 62:
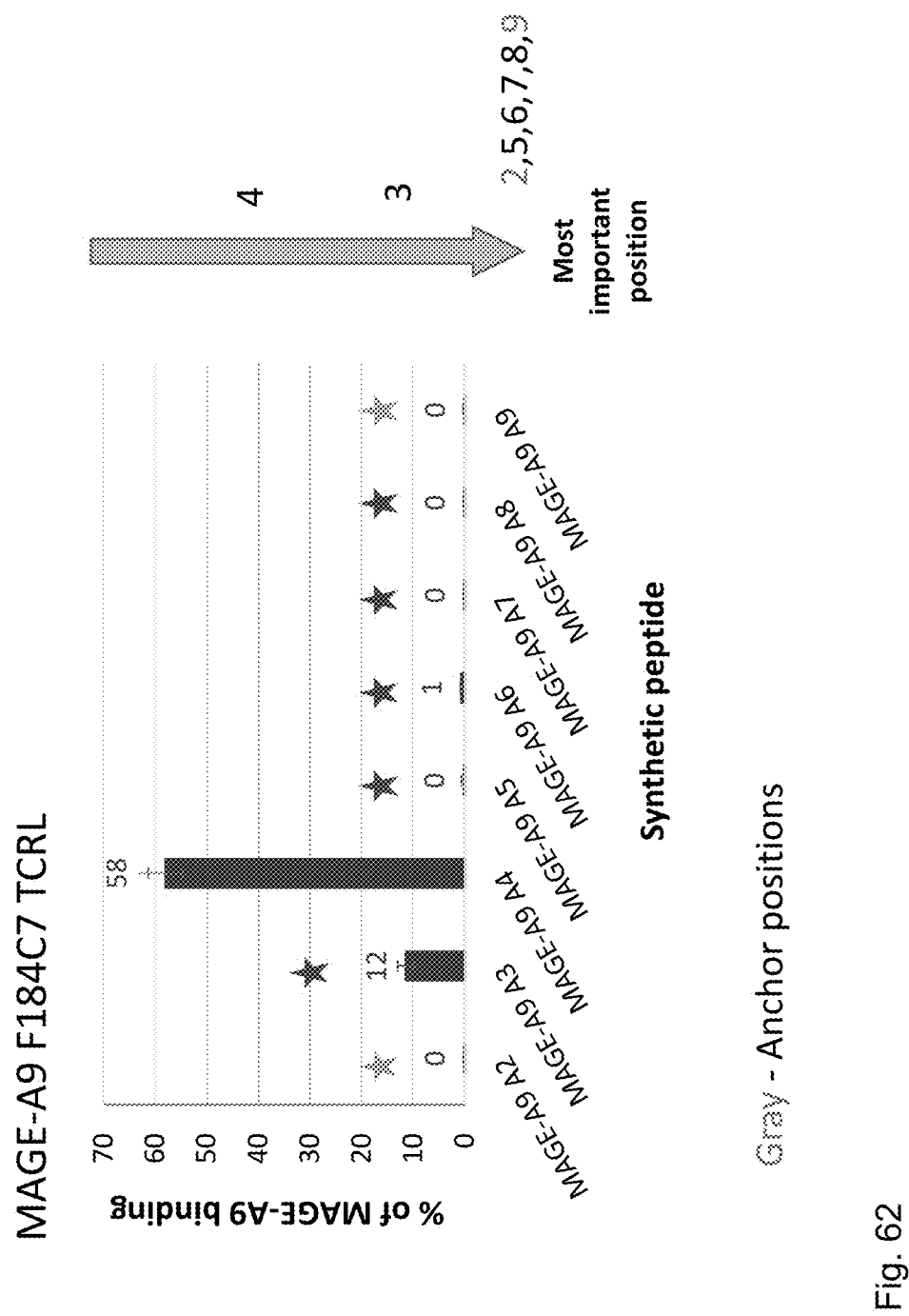

FIG. 62: Epitope specificity determination by Alanine scanning mutagenesis. The mutant MAGE-A9 peptides with alanine substitutions at positions 2, 3, 4, 5, 6, 7, 8 and 9 were synthesized. The Ala mutant and native peptides were loaded onto T2 cells APCs at a concentration of $10^{-5}$M for 12 hrs at 37° C. Cells were stained with F184C7 TCR-like antibody at a concentration of 10 µg/ml and analyzed by flow cytometry. MFI values for cells loaded with mutant and wild type peptides were compared. The relative effect of each Ala substitution was expressed as percentage of the binding to native peptide.

Figure 63:
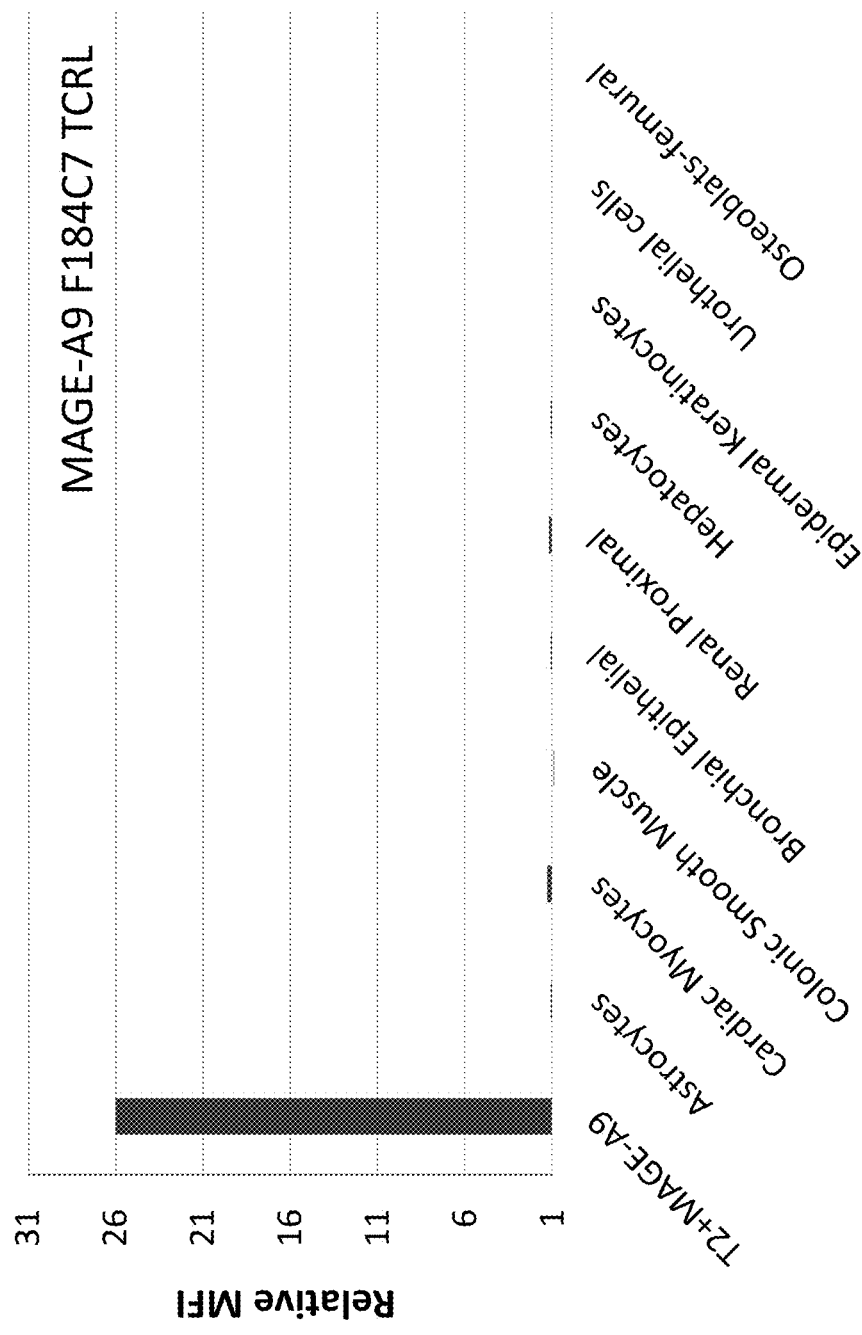

FIG. 63: Binding of F184C7 TCR-like antibody to HLA-A2+ normal primary cells. Normal primary cells were stained with F184C7 TCRL antibody at 10 µg/ml followed by secondary PE-labeled anti-mouse antibody. Mean fluorescence intensity (MFI) is indicated.

Figure 64:
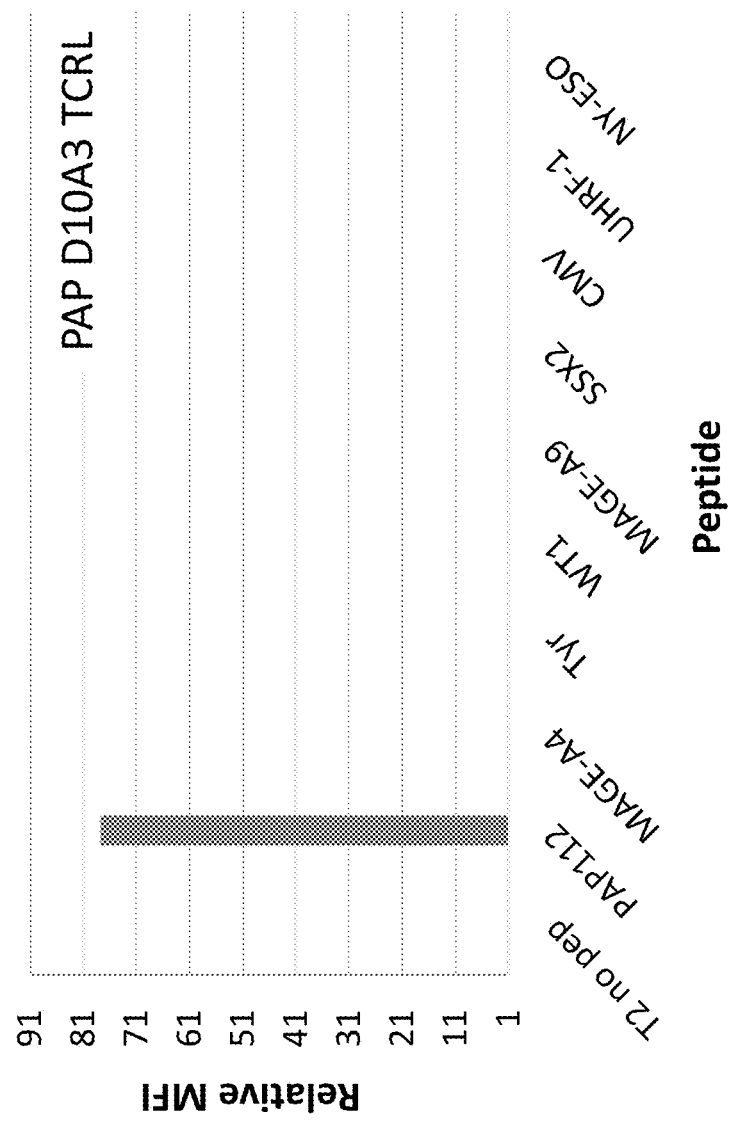

FIG. 64: Binding of D10A3 TCR-like antibody to T2 APCs loaded with $PAP_{112-120}$ peptide (also referred to as PAP peptide) and other HLA-A2 restricted peptides. T2 cells were loaded with PAP and indicated peptides at a concentration of $10^{-5}$M for 12 hrs at 37° C. Cells were stained with D10A3 TCRL antibody at 10 µg/ml followed by secondary PE-labeled anti-mouse antibody. Mean fluorescence intensity (MFI) is indicated.

Figure 65:
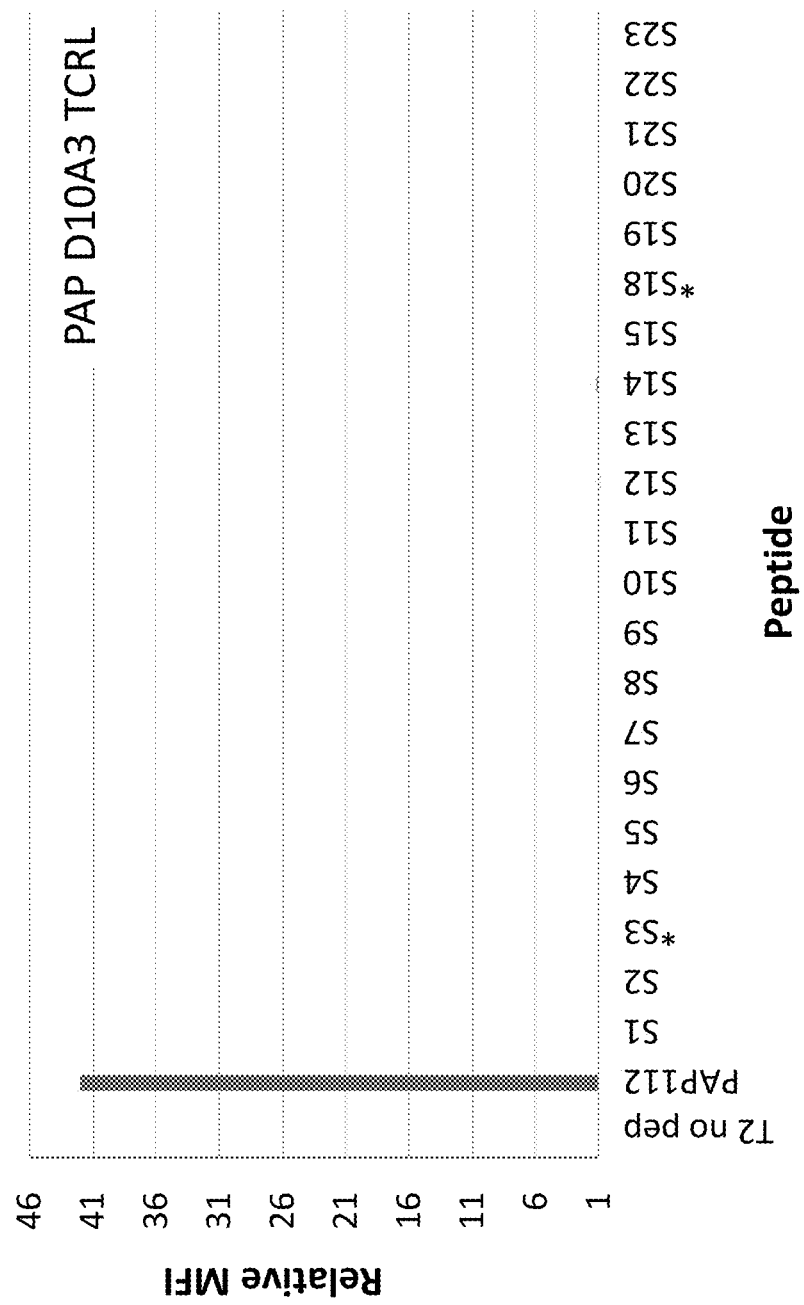

FIG. 65: Binding of D10A3 TCR-like antibodies to T2 APCs loaded with PAP peptide and PAP similar HLA-A2 restricted peptides. T2 cells were loaded with PAP and indicated peptides at a concentration of $10^{-5}$ M for 12 hrs at 37° C. Cells were stained with D10A3 TCRL antibody at 10 µg/ml followed by secondary PE-labeled anti-mouse antibody. Mean fluorescence intensity (MFI) is indicated.

Figure 66:
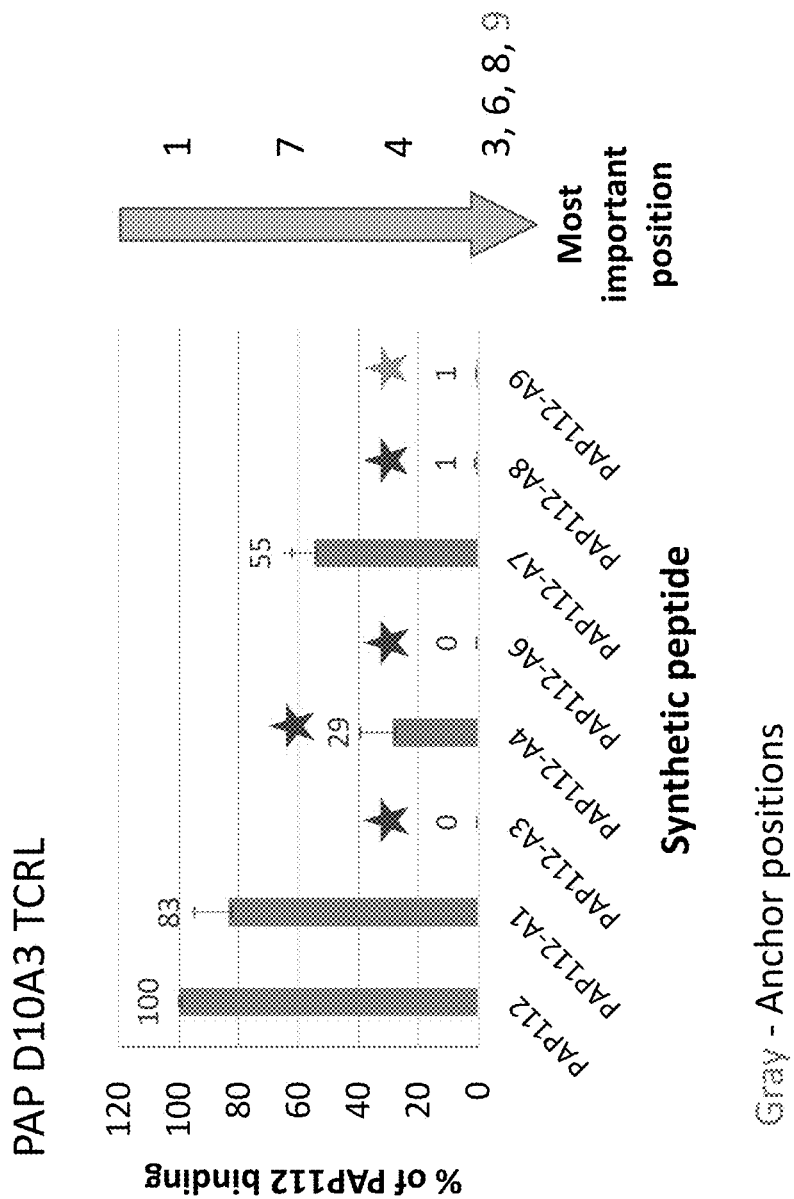

FIG. 66: Epitope specificity determination by Alanine scanning mutagenesis. The mutant PAP peptides with Alanine substitutions at positions 1, 3, 4, 6, 7, 8 and 9 were synthesized and loaded onto T2 cells APCs at a concentration of $10^{-5}$ M for 12 hrs at 37° C. Cells were stained with D10A3 TCR-like antibody at a concentration of 10 µg/ml. MFI values for cells loaded with mutant and wild type peptides were compared. The relative effect of each Ala substitution was expressed as percentage of the binding to WT peptide.

Figure 67:
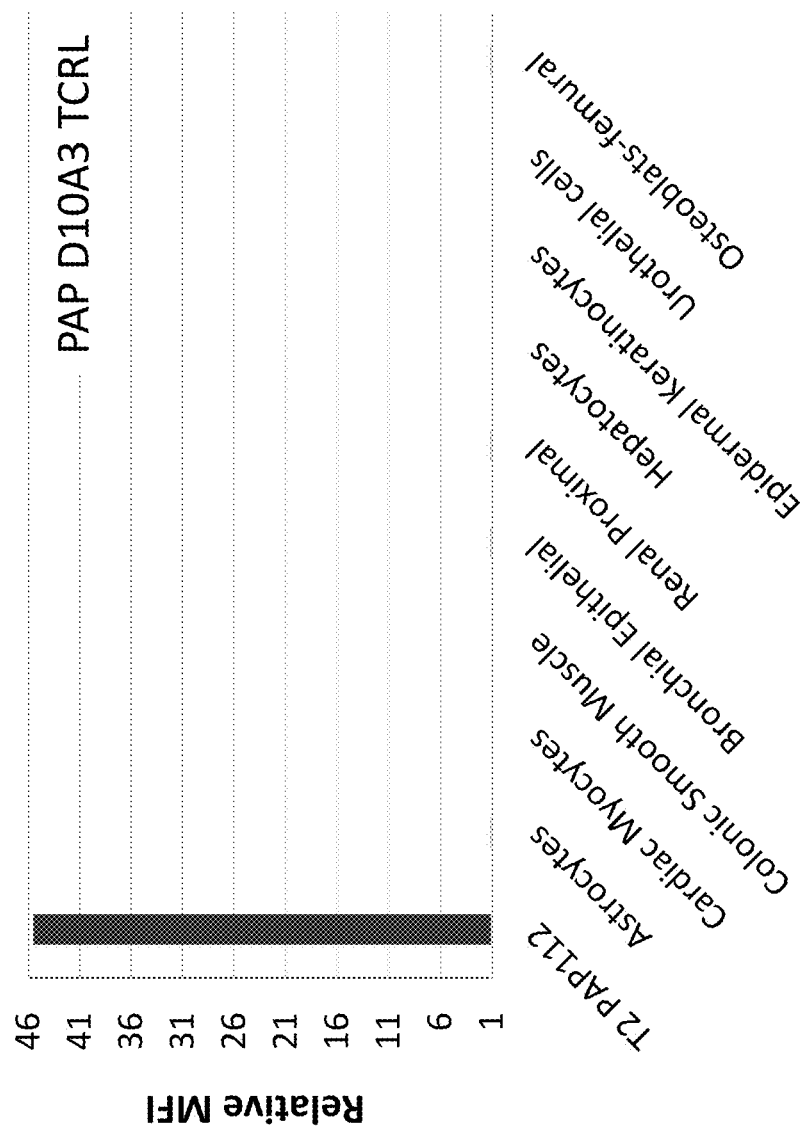

FIG. 67: Binding of D10A3 TCR-like antibody to HLA-A2+ normal primary cells. Normal primary cells were stained with D10A3 TCRL antibody at 10 µg/ml followed by secondary PE-labeled anti-mouse antibody. Mean fluorescence intensity (MFI) is indicated.

FIG. 68: Amino acids and nucleic acids of D11 antibody (SEQ ID NOs: 280-295).

FIG. 69: Amino acids and nucleic acids of D7 antibody (SEQ ID NOs: 296-311).

FIG. 70: Amino acids and nucleic acids of B47B6 antibody (SEQ ID NOs: 312-327).

FIG. 71: Amino acids and nucleic acids of C106B9 antibody (SEQ ID NOs: 328-343).

FIG. 72: Amino acids and nucleic acids of F184C7 antibody (SEQ ID NOs: 344-359).

FIG. 73: Amino acids and nucleic acids of D10A3 antibody (SEQ ID NOs: 360-375).

DESCRIPTION OF SPECIFIC EMBODIMENTS OF THE INVENTION

The present invention, in some embodiments thereof, relates to affinity entities comprising a TCR-like antibody binding domain with affinity and fine specificity and uses of same.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

T Cell Receptor (TCR)-like (TCRL) antibodies are endowed with a TCR-like specificity toward tumor epitopes. Unlike TCRs which exhibit low affinity to the MHC-peptide antigen complex, TCRLs are characterized by affinity even at their soluble form. TCRLs are being developed as a new therapeutic class for targeting tumor cells and mediating their specific killing. In addition, these antibodies are valuable research reagents enabling the study of human class I peptide-MHC ligand presentation and TCR-peptide-MHC interactions.

The present inventors have now indentified through a laborious screen and experimentation novel TCRLs which exhibit unprecedented fine specificity towards TyrD-HLA-A2 (D7 and D11), WT1-HLA-A2 (B47), MAGE-A4-HLA-A2 (C106B9), MAGE-A9-HLA-A2 (F184C7) and PAP (D10A3). The CDRs of these antibodies can be implanted in any affinity binding entity such as having an effector activity e.g., a CAR and TCR.

Thus, according to an aspect of the invention there is provided an affinity binding entity comprising an antigen binding domain comprising CDR sequences which are N—C ordered:

```
CDR1 Heavy
Chain (HC)
                              SEQ ID NO: 309
SYGVH

CDR2 HC
                              SEQ ID NO: 310
VIWAGGTTNYNSALMS

CDR3 HC
                              SEQ ID NO: 311
DGHFHFDF

CDR1 Light Chain
(LC)
                              SEQ ID NO: 303
RASDIIYSNLA

CDR2 LC
                              SEQ ID NO: 304
AATNLAA

CDR3 LC
                              SEQ ID NO: 305
QHFWGSSIS
``` the affinity binding entity capable of binding HLA-A2/ $Tyr_{D369-377}$ in an MHC restricted manner.

According to an aspect of the invention there is provided an affinity binding entity comprising an antigen binding domain comprising CDR sequences which are N—C ordered:

CDR1 Heavy Chain (HC)
SEQ ID NO: 293
TSGMGVS

CDR2 HC
SEQ ID NO: 294
HIYWDDDKRYNPSLKS

CDR3 HC
SEQ ID NO: 295
KDYGSSFYAMHY

CDR1 Light Chain (LC)
SEQ ID NO: 287
KASQDIHNYIA

CDR2 LC
SEQ ID NO: 288
YTSTLQP

CDR3 LC
SEQ ID NO: 289
LQYDNLWT the affinity binding entity capable of binding HLA-A2/TyrD$_{369\text{-}377}$ in an MHC restricted manner.

According to an aspect of the invention there is provided an affinity binding entity comprising an antigen binding domain comprising CDR sequences which are N—C ordered:

CDR1 HC
SEQ ID NO: 325
SYDMS

CDR2 HC
SEQ ID NO: 326
YMSSGGGTYYPDTVKG

CDR3 HC
SEQ ID NO: 327
HDEITNFDY

CDR1 LC
SEQ ID NO: 319
RASQSISNSLH

CDR2 LC
SEQ ID NO: 320
YASQSIS

CDR3 LC
SEQ ID NO: 321
QQSYSWPLT the affinity binding entity capable of binding HLA-A2/WT1$_{126\text{-}134}$ in an MHC restricted manner.

According to an aspect of the invention there is provided an affinity binding entity comprising an antigen binding domain comprising CDR sequences which are N—C ordered:

CDR1 HC
SEQ ID NO: 341
GYWIE

CDR2 HC
SEQ ID NO: 342
EILPGSGGTNYNEKFKG

CDR3 HC
SEQ ID NO: 343
DSNSFTY

CDR1 LC
SEQ ID NO: 335
SVSSSVDYIH

CDR2 LC
SEQ ID NO: 336
STSILAS

CDR3 LC
SEQ ID NO: 337
QQRSSYT the affinity binding entity capable of binding HLA-A2/MAGE-A4$_{328\text{-}343}$ in an MHC restricted manner.

According to an aspect of the invention there is provided an affinity binding entity comprising an antigen binding domain comprising CDR sequences which are N—C ordered:

CDR1 HC
SEQ ID NO: 357
FSSSWMN

CDR2 HC
SEQ ID NO: 358
RIYPGDGDTNYNEKFKG

CDR3 HC
SEQ ID NO: 359
EATTVVAPYYFDY

CDR1 LC
SEQ ID NO: 351
RASENIYRNLA

CDR2 LC
SEQ ID NO: 352
AATNLAD

CDR3 LC
SEQ ID NO: 353
QHFWGTPLT the affinity binding entity capable of binding HLA-A2/MAGE-A9$_{344\text{-}359}$ in an MHC restricted manner.

According to an aspect of the invention there is provided an affinity binding entity comprising an antigen binding domain comprising CDR sequences which are N—C ordered:

CDR1 HC
SEQ ID NO: 373
DYNMD

CDR2 HC
SEQ ID NO: 374
DINPNYDTTTYNQKFKG

CDR3 HC
SEQ ID NO: 375
RNYGNYVGFDF

CDR1 LC
SEQ ID NO: 367
KASQRVNNDVA

-continued

CDR2 LC

SEQ ID NO: 368

YASNRYT

CDR3 LC

SEQ ID NO: 369

QQDYSSPFT the affinity binding entity capable of binding HLA-A2/PAP$_{360-375}$ in an MHC restricted manner.

As used herein a "T Cell Receptor-like antibody" or "TCRL" refers to an antibody which binds an MHC being complexed with an HLA-restricted peptide antigen. Binding of the TCRL to its target is with an MHC-restricted specificity. The TCRL antibody does not bind said MHC in the absence of said complexed peptide, and the antibody does not bind said peptide in an absence of said MHC.

As used herein "binding" or "binds" refers to an antibody-antigen mode of binding, which is generally, in the case of clinically relevant TCRLs, in the range of KD below 20 nM, as determined by Surface Plasmon Resonance assay (SPR).

The affinity of the antigen binding domain to its antigen is determined using the soluble form of the antibody from which the CDRs of the antigen binding domain of the antibody are derived. For affinity evaluation, the antigen is used in its soluble form e.g., as a single chain MHC-peptide complex as further described hereinbelow.

As used herein the term "KD" refers to the equilibrium dissociation constant between the antigen binding domain and its respective antigen.

It will be appreciated that the affinity of the affinity binding entity is determined by the CDRs. However, the affinity may be improved using methods known in the art, such as affinity maturation.

As used herein "affinity binding entity" refers to a binding moiety which binds to a specific antigen with a higher affinity than to a non-specific antigen and is endowed with an affinity of at least $10^{-6}$ M, as determined by assays which are well known in the art, including SPR.

According to a specific embodiment the affinity is 500 nM-0.5 nM, 100 nM-1 nM, 50 nM-1 nM, 20 nM-1 nM, 10 nM-1 nM.

The affinity moiety may be selected from the group consisting of TCR, CAR-T and an antibody.

According to a specific embodiment, the affinity binding entity is an antibody. Although the reference to antibodies is in more details as compared to other affinity binding entities, the description of this embodiment should not be construed as limiting and the present invention is equally related to binding entities as described herein especially in the sense of cell therapy as further described hereinbelow.

The term "antibody" as used in this invention includes intact molecules as well as functional fragments thereof, such as Fab, F(ab')2, Fv, scFv, dsFv, or single domain molecules such as VH and VL that are capable of binding to an epitope of an antigen in an MHC restricted manner. As a more general statement the term "antibody" aims to encompass any affinity binding entity which binds a cell surface presented molecule with an MHC restricted specificity. Thus, CDRs of the antibodies of some embodiments of the present invention may be implanted in artificial molecules such as T cell receptors or CARs as further described hereinbelow.

Suitable antibody fragments for practicing some embodiments of the invention include a complementarity-determining region (CDR) of an immunoglobulin light chain (referred to herein as "light chain"), a complementarity-determining region of an immunoglobulin heavy chain (referred to herein as "heavy chain"), a variable region of a light chain, a variable region of a heavy chain, a light chain, a heavy chain, an Fd fragment, and antibody fragments comprising essentially whole variable regions of both light and heavy chains such as an Fv, a single chain Fv Fv (scFv), a disulfide-stabilized Fv (dsFv), an Fab, an Fab', and an F(ab')2.

As used herein, the terms "complementarity-determining region" or "CDR" are used interchangeably to refer to the antigen binding regions found within the variable region of the heavy and light chain polypeptides. Generally, antibodies comprise three CDRs in each of the VH (CDR HI or HI; CDR H2 or H2; and CDR H3 or H3) and three in each of the VL (CDR LI or LI; CDR L2 or L2; and CDR L3 or L3). Examples of such CDR sequences are provide for D7 and D11-TCRLs produced according to Example I below. Additional examples include, WT1 B47B6, MAGE-A4 C106B9, MAGE-A9 F184C7, PAP D10A3 (shown in FIGS. 68-73).

The identity of the amino acid residues in a particular antibody that make up a variable region or a CDR can be determined using methods well known in the art and include methods such as sequence variability as defined by Kabat et al. (See, e.g., Kabat et al., 1992, Sequences of Proteins of Immunological Interest, 5th ed., Public Health Service, NIH, Washington D.C.), location of the structural loop regions as defined by Chothia et al. (see, e.g., Chothia et al., Nature 342:877-883, 1989.), a compromise between Kabat and Chothia using Oxford Molecular's AbM antibody modeling software (now Accelrys®, see, Martin et al., 1989, Proc. Natl Acad Sci USA. 86:9268; and world wide web site www(dot)bioinf-org(dot)uk/abs), available complex crystal structures as defined by the contact definition (see MacCallum et al., J. Mol. Biol. 262:732-745, 1996), the "conformational definition" (see, e.g., Makabe et al., Journal of Biological Chemistry, 283:1156-1166, 2008) and IMGT [Lefranc M P, et al. (2003) IMGT unique numbering for immunoglobulin and T cell receptor variable domains and Ig superfamily V-like domains. Dev Comp Immunol 27: 55-77].

As used herein, the "variable regions" and "CDRs" may refer to variable regions and CDRs defined by any approach known in the art, including combinations of approaches. According to a specific embodiment, the CDRs are determined according to Kabat et al. (supra).

Functional antibody fragments comprising whole or essentially whole variable regions of both light and heavy chains are defined as follows:

(i) Fv, defined as a genetically engineered fragment consisting of the variable region of the light chain (VL) and the variable region of the heavy chain (VH) expressed as two chains;

(ii) single chain Fv ("scFv"), a genetically engineered single chain molecule including the variable region of the light chain and the variable region of the heavy chain, linked by a suitable polypeptide linker as a genetically fused single chain molecule;

(iii) disulfide-stabilized Fv ("dsFv"), a genetically engineered antibody including the variable region of the light chain and the variable region of the heavy chain, linked by a genetically engineered disulfide bond;

(iv) Fab, a fragment of an antibody molecule containing a monovalent antigen-binding portion of an antibody molecule which can be obtained by treating whole antibody with the enzyme papain to yield the intact light chain and the Fd fragment of the heavy chain which consists of the variable and CH1 domains thereof;

(v) Fab', a fragment of an antibody molecule containing a monovalent antigen-binding portion of an antibody molecule which can be obtained by treating whole antibody with the enzyme pepsin, followed by reduction (two Fab' fragments are obtained per antibody molecule);

(vi) F(ab')2, a fragment of an antibody molecule containing a monovalent antigen-binding portion of an antibody molecule which can be obtained by treating whole antibody with the enzyme pepsin (i.e., a dimer of Fab' fragments held together by two disulfide bonds); and (vii) Single domain antibodies or nanobodies are composed of a single VH or VL domains which exhibit sufficient affinity to the antigen.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to some embodiments of the invention can be prepared by proteolytic hydrolysis of the antibody or by expression in *E. coli* or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

Humanized forms of non-human (e.g., murine) antibodies are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95

(1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

In an embodiment in which the antibody is a full length antibody, the heavy and light chains of an antibody of the invention may be full-length (e.g., an antibody can include at least one, and preferably two, complete heavy chains, and at least one, or two, complete light chains) or may include an antigen-binding portion (a Fab, F(ab').sub.2, Fv or a single chain Fv fragment ("scFv")). In other embodiments, the antibody heavy chain constant region is chosen from, e.g., IgG1, IgG2, IgG3, IgG4, IgM, IgA1, IgA2, IgD, and IgE. In some embodiments, the immunoglobulin isotype is selected from IgG1, IgG2, IgG3, and IgG4, more particularly, IgG1 (e.g., human IgG1) or IgG4 (e.g., human IgG4). The choice of antibody type will depend on the immune effector function that the antibody is designed to elicit.

Bispecific configurations of antibodies are also contemplated herein. A bispecific monoclonal antibody (BsMAb, BsAb) is an artificial protein that is composed of fragments of two different monoclonal antibodies and consequently binds to two different types of antigen. According to a specific embodiment the BsMAb is engineered to simultaneously bind to a cytotoxic cell (e.g., using a receptor like CD3) and a target like a tumor cell to be destroyed (further described hereinbelow).

As used herein the phrase "chimeric antigen receptor (CAR)" refers to a recombinant or synthetic molecule which combines antibody-based specificity for a desired antigen with a T cell receptor-activating intracellular domain to generate a chimeric protein that exhibits cellular immune activity to the specific antigen.

As used herein the phrase "T Cell Receptor" or "TCR" refers to soluble and non-soluble forms of recombinant T cell receptor.

As used herein the phrase "MHC (or HLA)-restricted peptide" refers to a peptide which is potentially presented on an MHC molecule. Such peptides may be identified by "wet" laboratory procedures such as Mass-Spectrometry or by in-silico analysis. An MHC (or HLA)-presented peptide refers to a peptide which is confirmed in vitro or in vivo as being presented by an MHC molecule.

According to a specific embodiment, the MHC restricted peptide is from WT1 and the affinity binding entity comprises the CDRs of B47B6.

According to a specific embodiment, the MHC restricted peptide is from TyrD and the affinity binding entity comprises the CDRs of D7 or D11.

According to a specific embodiment, the MHC restricted peptide is from MAGE-A4 and the affinity binding entity comprises the CDRs of C106B9.

According to a specific embodiment, the MHC restricted peptide is from MAGE-A9 and the affinity binding entity comprises the CDRs of F184C7.

According to a specific embodiment, the MHC restricted peptide is from PAP and the affinity binding entity comprises the CDRs of D10A3.

CDRs of the above mentioned affinity binding entities are described in FIGS. 68-73.

Also contemplated are homologous sequences e.g., at least 90% homology, 95% homology or even at least 99% homology as long as the binding affinity to the respective target and optionally specificity are maintained or even improved.

According to an aspect of the invention there is also provided an isolated polynucleotide comprising a nucleic acid sequence encoding the affinity binding entity as described herein.

Also provided is an expression vector, comprising the polynucleotide operably linked to a cis-acting regulatory element.

The nucleic acid construct (also referred to herein as an "expression vector") of some embodiments of the invention includes additional sequences which render this vector suitable for replication and integration in prokaryotes, eukaryotes, or preferably both (e.g., shuttle vectors). In addition, typical cloning vectors may also contain a transcription and translation initiation sequence, transcription and translation terminator and a polyadenylation signal. By way of example, such constructs will typically include a 5' LTR, a tRNA binding site, a packaging signal, an origin of second-strand DNA synthesis, and a 3' LTR or a portion thereof.

The nucleic acid construct of some embodiments of the invention typically includes a signal sequence for secretion or presentation of the affinity binding entity from a host cell in which it is placed. Preferably the signal sequence for this purpose is a mammalian signal sequence.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Preferably, the promoter utilized by the nucleic acid construct of some embodiments of the invention is active in the specific cell population transformed. Examples of cell type-specific and/or tissue-specific promoters include promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264,166).

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for some embodiments of the invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of TCRL mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for some embodiments of the invention include those derived from SV40.

In addition to the elements already described, the expression vector of some embodiments of the invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

Also provided are cells which comprise the polynucleotides/expression vectors as described herein.

Such cells are typically selected for high expression of recombinant proteins (e.g., bacterial, plant or eukaryotic cells e.g., CHO, HEK-293 cells), but may also be host cells having a specific immune effector activity (e.g., T cells or NK cells) when for instance the CDRs of the TCRL are implanted in a T Cell Receptor or CAR transduced in said cells which are used in adoptive cell therapy as further described hereinbelow.

The high specificity of the affinity binding entity renders it particularly suitable for diagnostic and therapeutic applications.

Thus, according to an aspect of the present invention, there is provided a method of detecting a cell presenting an HLA-restricted peptide antigen of interest. The method comprises contacting the cell with the affinity binding entity (e.g., antibody) of the present invention having specificity to the HLA-restricted peptide antigen of interest. The contacting is effected under conditions which allow immunocomplex formation, wherein a presence of the immunocomplex or level thereof is indicative of the cell presenting the HLA-restricted peptide antigen of interest.

The term "detecting", as used herein, refers to the act of detecting, perceiving, uncovering, exposing, visualizing or identifying a cell. The precise method of detecting is dependent on the detectable moiety (also referred to herein as identifiable moiety) to which the antibody is attached as further described herein below.

Single cells may be used in accordance with the teachings of the present invention as well as a plurality of cells. For instance the cells may be from any biological sample such as cell-lines, primary (e.g., tumor cultures) and cellular samples, e.g. surgical biopsies including incisional or excisional biopsy, fine needle aspirates and the like. Methods of biopsy retrieval are well known in the art.

The above-mentioned detection method can be harnessed to the diagnosis of diseases which are characterized by above normal presentation or different tissue distribution of the HLA-peptide complex.

As used herein the term "diagnosing" refers to classifying a disease, determining a severity of a disease (grade or stage), monitoring progression, forecasting an outcome of the disease and/or prospects of recovery.

The subject may be a healthy subject (e.g., human) undergoing a routine well-being check up. Alternatively, the subject may be at risk of the disease. Yet alternatively, the method may be used to monitor treatment efficacy.

The TCRL may comprise e.g., attached to an identifiable moiety. Alternatively or additionally, the TCRL (or a complex comprising same) may be identified indirectly such as by using a secondary antibody.

The contacting may be effected in vitro (i.e. in a cell line, primary cells), ex vivo or in vivo.

As mentioned, the method of the present invention is effected under conditions sufficient to form an immunocomplex (e.g. a complex between the antibodies of the present invention and the peptide complexed to the MHC, typically when the cells are not lysed); such conditions (e.g., appropriate concentrations, buffers, temperatures, reaction times) as well as methods to optimize such conditions are known to those skilled in the art, and examples are disclosed herein.

The affinity binding entities of the invention (e.g., antibodies) are especially useful for the treatment of cancer.

The term "cancer" as used herein is defined as disease characterized by the rapid and uncontrolled growth of aberrant cells. Cancer cells can spread locally or through the bloodstream and lymphatic system to other parts of the body.

The cancer may be a hematological malignancy, a solid tumor, a primary or a metatastizing tumor. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, Chronic Lymphocytic Leukemia (CLL), leukemia, lung cancer and the like. Additional non-limiting examples of cancers which can be treated by the method of some embodiments of the invention are provided in Table 1, above.

Cancers that may be treated include tumors that are not vascularized, or not yet substantially vascularized, as well as vascularized tumors. The cancers may comprise non-solid tumors (such as hematological tumors, for example, leukemias and lymphomas) or may comprise solid tumors. Types of cancers to be treated with the Antibodies of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

According to some embodiments of the invention, the pathology is a solid tumor.

According to some embodiments of the invention, the affinity binding entiry of the invention has an anti-tumor effect.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the medicament of the invention in prevention of the occurrence of tumor in the first place.

According to a specific embodiment, when the affinity binding entity is for Tyrosinase (TyrD) the cancer is selected from the group consisting of melanoma and glioblastoma.

According to a specific embodiment, when the affinity binding entity is for WT1 the cancer is selected from:

TABLE 1

Leukemia
multiple myeloma (MM)
acute lymphoblastic leukemia (ALL)
acute myeloid/myelogenous leukemia (AML)
myelodysplastic syndrome (MDS)
mesothelioma
ovarian cancer
gastrointestinal cancers e.g., colorectal cancer
adenocarcinoma, thyroid cancer
breast cancer
lung cancer (e.g., non small cell lung cancer)

TABLE 1-continued melanoma
osteosarcoma
endomentrial cancer

According to a specific embodiment, when said affinity binding entity is for MAGE said cancer is selected from:

TABLE 2

MAGE-A4

Ovarian cancer
T cell leukemia/lymphoma (e.g., ATLL)
Sarcoma
testicular cancer
head and neck cancer
bladder cancer
esophagus cancer.

TABLE 3

MAGE-A9 renal cell carcinoma
bladder cancer
breast cancer
hepatocellular carcinoma.

According to a specific embodiment, when said affinity binding entity is for PAP said cancer is prostate cancer.

The foregoing classifications are relevant for both diagnosis and treatment.

Determining a presence or level of the immunocomplex of the present invention is dependent on the detectable moiety to which the antibody is attached.

Examples of detectable moieties that can be used in the present invention include but are not limited to radioactive isotopes, phosphorescent chemicals, chemiluminescent chemicals, fluorescent chemicals, enzymes, fluorescent polypeptides and epitope tags. The detectable moiety can be a member of a binding pair, which is identifiable via its interaction with an additional member of the binding pair, and a label which is directly visualized. In one example, the member of the binding pair is an antigen which is identified by a corresponding labeled antibody. In one example, the label is a fluorescent protein or an enzyme producing a colorimetric reaction.

Further examples of detectable moieties, include those detectable by Positron Emission Tomagraphy (PET) and Magnetic Resonance Imaging (MRI), all of which are well known to those of skill in the art.

When the detectable moiety is a polypeptide, the immunolabel (i.e. the antibody conjugated to the detectable moiety) may be produced by recombinant means or may be chemically synthesized by, for example, the stepwise addition of one or more amino acid residues in defined order using solid phase peptide synthetic techniques. Examples of polypeptide detectable moieties that can be linked to the antibodies of the present invention using recombinant DNA technology (in which the polynucleotide encoding the TCRL is translationally fused to the detectable moiety) include fluorescent polypeptides, phosphorescent polypeptides, enzymes and epitope tags.

Alternatively, chemical attachment of a detectable moiety to the antibodies of the present invention can be effected using any suitable chemical linkage, direct or indirect, as via a peptide bond (when the detectable moiety is a polypeptide), or via covalent bonding to an intervening linker element, such as a linker peptide or other chemical moiety, such as an organic polymer. Such chimeric peptides may be linked via bonding at the carboxy (C) or amino (N) termini of the peptides, or via bonding to internal chemical groups such as straight, branched or cyclic side chains, internal carbon or nitrogen atoms, and the like. Such modified peptides can be easily identified and prepared by one of ordinary skill in the art, using well known methods of peptide synthesis and/or covalent linkage of peptides. Description of fluorescent labeling of antibodies is provided in details in U.S. Pat. Nos. 3,940,475, 4,289,747, and 4,376,110.

Exemplary methods for conjugating two peptide moieties are described herein below:

SPDP Conjugation:

Any SPDP conjugation method known to those skilled in the art can be used. For example, in one illustrative embodiment, a modification of the method of Cumber et al. (1985, Methods of Enzymology 112: 207-224) as described below, is used.

A peptide, such as an identifiable or therapeutic moiety, (1.7 mg/ml) is mixed with a 10-fold excess of SPDP (50 mM in ethanol) and the antibody is mixed with a 25-fold excess of SPDP in 20 mM sodium phosphate, 0.10 M NaCl pH 7.2 and each of the reactions incubated, e.g., for 3 hours at room temperature. The reactions are then dialyzed against PBS.

The peptide is reduced, e.g., with 50 mM DTT for 1 hour at room temperature. The reduced peptide is desalted by equilibration on G-25 column (up to 5% sample/column volume) with 50 mM $KH_2PO_4$ pH 6.5. The reduced peptide is combined with the SPDP-antibody in a molar ratio of 1:10 antibody:peptide and incubated at 4° C. overnight to form a peptide-antibody conjugate.

Glutaraldehyde Conjugation:

Conjugation of a peptide (e.g., an identifiable or therapeutic moiety) with an antibody can be accomplished by methods known to those skilled in the art using glutaraldehyde. For example, in one illustrative embodiment, the method of conjugation by G. T. Hermanson (1996, "Antibody Modification and Conjugation, in Bioconjugate Techniques, Academic Press, San Diego) described below, is used.

The antibody and the peptide (1.1 mg/ml) are mixed at a 10-fold excess with 0.05% glutaraldehyde in 0.1 M phosphate, 0.15 M NaCl pH 6.8, and allowed to react for 2 hours at room temperature. 0.01 M lysine can be added to block excess sites. After-the reaction, the excess glutaraldehyde is removed using a G-25 column equilibrated with PBS (10% v/v sample/column volumes).

Carbodiimide Conjugation:

Conjugation of a peptide with an antibody can be accomplished by methods known to those skilled in the art using a dehydrating agent such as a carbodiimide. Most preferably the carbodiimide is used in the presence of 4-dimethyl aminopyridine. As is well known to those skilled in the art, carbodiimide conjugation can be used to form a covalent bond between a carboxyl group of peptide and an hydroxyl group of an antibody (resulting in the formation of an ester bond), or an amino group of an antibody (resulting in the formation of an amide bond) or a sulfhydryl group of an antibody (resulting in the formation of a thioester bond).

Likewise, carbodiimide coupling can be used to form analogous covalent bonds between a carbon group of an antibody and an hydroxyl, amino or sulfhydryl group of the peptide. See, generally, J. March, Advanced Organic Chemistry: Reaction's, Mechanism, and Structure, pp. 349-50 & 372-74 (3d ed.), 1985. By means of illustration, and not limitation, the peptide is conjugated to an antibody via a covalent bond using a carbodiimide, such as dicyclohexylcarbodiimide. See generally, the methods of conjugation by B. Neises et al. (1978, Angew Chem., Int. Ed. Engl. 17:522; A. Hassner et al. (1978, Tetrahedron Lett. 4475); E. P. Boden et al. (1986, J. Org. Chem. 50:2394) and L. J. Mathias (1979, Synthesis 561). The level of immunocomplex may be compared to a control sample from a non-diseased subject, wherein an up-regulation of immunocomplex formation is indicative of melanoma. Preferably, the subject is of the same species e.g. human, preferably matched with the same age, weight, sex etc. It will be appreciated that the control sample may also be of the same subject from a healthy tissue, prior to disease progression or following disease remission.

According to a specific embodiment, the detection is effected by FACS.

As mentioned the antibodies of the present invention can also be used in therapeutics where the affinity binding entity e.g., antibody comprises a therapeutic moiety.

The therapeutic moiety can be an integral part of the antibody e.g., in the case of a whole antibody, the Fc domain, which activates antibody-dependent cell-mediated cytotoxicity (ADCC). ADCC is a mechanism of cell-mediated immune defense whereby an effector cell of the immune system actively lyses a target cell, whose membrane-surface antigens have been bound by specific antibodies. It is one of the mechanisms through which antibodies, as part of the humoral immune response, can act to limit and contain infection. Classical ADCC is mediated by natural killer (NK) cells; macrophages, neutrophils and eosinophils can also mediate ADCC. For example, eosinophils can kill certain parasitic worms known as helminths through ADCC mediated by IgE. ADCC is part of the adaptive immune response due to its dependence on a prior antibody response.

Alternatively or additionally, the antibody may be a bispecific antibody in which the therapeutic moiety is a T cell engager for example, such as an anti CD3 antibody or an anti CD16a alternatively the therapeutic moiety may be an anti immune checkpoint molecule (anti PD-1).

Alternatively or additionally the antibody may be attached to a heterologous therapeutic moiety (methods of conjugation are described hereinabove). The therapeutic moiety can be, for example, a cytotoxic moiety, a toxic moiety, a cytokine moiety, a drug.

The antibody may be in a soluble or insoluble form.

Insoluble forms may be those in which a molecule comprising the antibody's CDRs is anchored to or expressed by a cell or a particle (the latter can be used for therapeutic as well as diagnostic applications).

Examples of such cells include immune cells, T cells, B cells, dendritic cells, CIK, NKT, NK cells (autologous, allogeneic, xenogeneic).

According to a specific embodiment, the antibody (or actually CDRs thereof) form a CAR (as explained above) or an artificial T Cell Receptor. Thus a polynucleotide coding for such a molecule is transduced in a cell of interest.

According to some embodiments of the invention, the cell is a T cell, a natural killer cell, a cell that exerts effector killing function on a target cell, a cell that exerts a suppressive effect on effector T cells, an engineered cell with an effector killing function or an engineered cell with a suppressive function.

According to some embodiments of the invention, the cell is a T cell, or $\alpha\beta$T cell, or $\gamma\delta$T cell.

According to some embodiments of the invention, the cell is a natural killer (NK) cell.

According to some embodiments of the invention, the natural killer cell is used to target cancer.

According to some embodiments of the invention, the T cell is a cytotoxic T cell (effector T cell).

According to some embodiments of the invention, the cytotoxic T cell (effector T cell) is used to target cancer antigens.

According to some embodiments of the invention, the cytotoxic T cell is used to treat a pathology caused by or associated with cancer.

According to some embodiments of the invention, the T cell comprises a Treg (T regulatory cell).

According to some embodiments of the invention, the T cell comprises a CD3 T cell.

According to some embodiments of the invention, the T cell comprises a CD4 T cell.

According to some embodiments of the invention, the T cell comprises a CD8 T cell.

According to some embodiments of the invention, the antigen binding domain comprises a single chain Fv (scFv) molecule.

The cytoplasmic domain (also referred to as "intracellular signaling domain") of the CAR molecule of the invention is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Examples of intracellular signaling domains for use in the CAR molecule of the invention include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs (ITAMs).

Examples of ITAM containing primary cytoplasmic signaling sequences that are of particular use in the invention include those derived from TCR zeta, FcR gamma, FcR beta, CD3 gamma, CD3 delta, CD3 epsilon, CD5, CD22, CD79a, CD79b, and CD66d. It is particularly preferred that cytoplasmic signaling molecule in the CAR of the invention comprises a cytoplasmic signaling sequence derived from CD3 zeta.

In a preferred embodiment, the cytoplasmic domain of the CAR can be designed to comprise the CD3-zeta signaling domain by itself or combined with any other desired cytoplasmic domain(s) useful in the context of the CAR of the invention. For example, the cytoplasmic domain of the CAR can comprise a CD3 zeta chain portion and a costimulatory signaling region. The costimulatory signaling region refers to a portion of the CAR comprising the intracellular domain of a costimulatory molecule. A co-stimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Thus, while the invention in exemplified primarily with 4-1BB as the co-stimulatory signaling element, other costimulatory elements are within the scope of the invention.

According to some embodiments of the invention, the intracellular domain comprises, a co-stimulatory signaling region and a zeta chain portion. The co-stimulatory signaling region refers to a portion of the CAR molecule comprising the intracellular domain of a co-stimulatory molecule. Co-stimulatory molecules are cell surface molecules other than antigen receptors or their ligands that are required for an efficient response of lymphocytes to antigen.

"Co-stimulatory ligand," as the term is used herein, includes a molecule on an antigen presenting cell [e.g., an aAPC (artificial antigen presenting cell), dendritic cell, B cell, and the like] that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-IBB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class 1 molecule, BTLA and a Toll ligand receptor.

A "co-stimulatory signal", as used herein, refers to a signal, which in combination with a primary signal, such as TCR/CD3 ligation, leads to T cell proliferation and/or upregulation or down regulation of key molecules.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter cilia, an MHC Class I molecule loaded with a peptide, an anti-CD3 antibody, a superagonist anti-CD28 antibody, and a superagonist anti-CD2 antibody.

With respect to the cytoplasmic domain, the CAR molecule of some embodiments of the invention can be designed to comprise the CD28 and/or 4-1BB signaling domain by itself or be combined with any other desired cytoplasmic domain(s) useful in the context of the CAR molecule of some embodiments of the invention. In one embodiment, the cytoplasmic domain of the CAR can be designed to further comprise the signaling domain of CD3-zeta. For example, the cytoplasmic domain of the CAR can include but is not limited to CD3-zeta, 4-1BB and CD28 signaling modules and combinations thereof.

According to some embodiments of the invention, the intracellular domain comprises at least one, e.g., at least two, at least three, at least four, at least five, e.g., at least six of the polypeptides selected from the group consisting of: CD3ζ (CD247, CD3z), CD28, 41BB, ICOS, OX40, and CD137.

According to some embodiments of the invention, the intracellular domain comprises the CD3ζ-chain [CD247 molecule, also known as "CD3-ZETA" and "CD3z"; GenBank Accession NOs. NP_000725.1 and NP_932170.1], which is the primary transmitter of signals from endogenous TCRs.

According to some embodiments of the invention, the intracellular domain comprises various co-stimulatory protein receptors to the cytoplasmic tail of the CAR to provide additional signals to the T cell (second generation CAR). Examples include, but are not limited to, CD28 [e.g., GenBank Accession Nos. NP_001230006.1, NP_001230007.1, NP_006130.1], 4-1BB [tumor necrosis factor receptor superfamily, member 9 (TNFRSF9), also known as "CD137", e.g., GenBank Accession No. NP_001552.2], and ICOS [inducible T-cell co-stimulator, e.g., GenBank Accession No. NP_036224.1]. Preclinical studies have indicated that the second generation of CAR designs improves the antitumor activity of T cells.

According to some embodiments of the invention, the intracellular domain comprises multiple signaling domains, such as CD3z-CD28-41BB or CD3z-CD28-OX40, to further augment potency. The term "OX40" refers to the tumor necrosis factor receptor superfamily, member 4 (TNFRSF4), e.g., GenBank Accession No. NP_003318.1 ("third-generation" CARs).

According to some embodiments of the invention, the intracellular domain comprises CD28-CD3z, CD3z, CD28-CD137-CD3z. The term "CD137" refers to tumor necrosis factor receptor superfamily, member 9 (TNFRSF9), e.g., GenBank Accession No. NP_001552.2.

According to some embodiments of the invention, when the CAR molecule is designed for a natural killer cell, then the signaling domain can be CD28 and/or CD3ζ. The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. Alternatively the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

According to some embodiments of the invention, the transmembrane domain comprised in the CAR molecule of some embodiments of the invention is a transmembrane domain that is naturally associated with one of the domains in the CAR. According to some embodiments of the invention, the transmembrane domain can be selected or modified by amino acid substitution to avoid binding of such domains to the transmembrane domains of the same or different surface membrane proteins to minimize interactions with other members of the receptor complex.

According to some embodiments, between the extracellular domain and the transmembrane domain of the CAR molecule, or between the cytoplasmic domain and the transmembrane domain of the CAR molecule, there may be incorporated a spacer domain. As used herein, the term "spacer domain" generally means any oligo- or polypeptide that functions to link the transmembrane domain to, either the extracellular domain or, the cytoplasmic domain in the polypeptide chain. A spacer domain may comprise up to 300 amino acids, preferably 10 to 100 amino acids and most preferably 25 to 50 amino acids.

According to an aspect of some embodiments of the invention, there is provided a method of treating cancer in a subject in need thereof, comprising administering to the subject the affinity binding entity, thereby treating the cancer in the subject.

Also provided is a use of the affinity binding entity as defined herein in the manufacture of a medicament for treating a pathology e.g., cancer.

The selection of the TCRL will naturally depend on its presentation in the pathology. Exemplary TCRLs and their association with pathologies are provided in the Tables hereinabove.

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein, the term "subject" includes mammals, preferably human beings at any age which suffer from the pathology.

The antibodies of some embodiments of the invention can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the antibody accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, PA, latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

The term "tissue" refers to part of an organism consisting of cells designed to perform a function or functions. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue, hematopoietic tissue.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients (TCRL-antibody) effective to prevent, alleviate or ameliorate symptoms of a disorder (e.g., cancer) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide TCRL (the TCRL tissue) levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit (diagnostic or therapeutic), which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

It is expected that during the life of a patent maturing from this application many relevant TCRLs will be developed and the scope of the term TCRLs is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Methods

Production of Biotinylated Single-Chain MHC-Peptide Complexes

Single-chain MHC (scMHC)$^3$-peptide complexes were produced by in vitro refolding of inclusion bodies produced in *Escherichia coli* upon isopropyl β-D-thiogalactoside (IPTG) induction. Briefly, a scMHC, which contains the $β_2$-microglobulin and the extracellular domains of the HLA A2 gene connected to each other by a flexible linker, was engineered to contain the BirA recognition sequence for site-specific biotinylation at the C terminus (scMHC-BirA). In vitro refolding was performed in the presence of peptides as described. Correctly folded MHC-peptide complexes were isolated and purified by anion exchange Q-Sepharose chromatography (GE Healthcare Life Sciences), followed by site-specific biotinylation using the BirA enzyme (Avidity). A more detailed description for the production of single chain-MHC peptide complexes is provided in Denkberg, et al. (2002) PNAS. 99:9421-9426.

Flow Cytometry

T-B hybrid T2 cells were washed with serum-free RPMI 1640 medium and incubated overnight with medium containing $10^{-4}$-$10^{-5}$M tyrosinase$_{369-377}$YMDGTMSQV (SEQ ID NO: 1)/WT1$_{126-434}$ (RMFPNAPYL, SEQ ID NO: 141) peptide/MAGE-A4$_{230-239}$ SEQ ID NO: 176/MAGE-A9$_{223-231}$ 203/PAP$_{112-120}$ SEQ ID NO: 230 peptide or relevant control peptides (listed in the Table 15 below). Peptide loading efficiency was verified by using the ratio between MFI of HLA-A2-binding antibody BB7.2 on peptide-loaded T2 cells and MFI of unloaded T2 cells (>1) data not shown.

T2 or primary cells or cell lines ($10^6$) were incubated with 10 μg/ml of specific Ab (with or without biotinylation) for 1 h at 4° C., followed by incubation with PE-labeled anti-mouse/human/steptavidin Ab for 45 min at 4° C. It will be appreciated that the work with anti mouse secondary antibody or with streptavidin gave similar results for D11 and B47B6. Cells were finally washed and analyzed by: FACS 1:
  Machine: BD FACS calibur
  Analysis software: CELLQuest
  FACS 2:
  Machine: Beckman Coulter NAVIOS
  Analysis software: Kaluza version 1.3

Production of TCR-Like Antibodies to HLA-A2/Tyrosinase369-377/WT1$_{126-134}$/MAGE-A4$_{230-239}$/MAGE-A9$_{223-231}$/PAP$_{112-120}$ Using the Hybridoma Technique HHD mice were immunized by 5-6 injections of HLA-A2-peptide complex 50 μg/mouse. 2-3 first injections were administrated s.c with addition of QuilA adjuvant. Hybridoma clones were generated by fusion of splenocytes isolated from mice immunized with the above complex (as previously described e.g., Weidanz et al. 2011 Int. Rev. Immunol. 30:328-340) with NSO myeloma cells and were screened and isolated by differential ELISA assays as described below. For example, for Tyrosinase TCRLs selection the relevant TyrD369-377 peptide HLA-A2 complexes were used and compared to the non relevant p68-DDX5 control peptide (SEQ ID NO: 2 YLLPAIVHI) HLA-A2 complexes. ELISA with purified HLA-A2-Tyr complexes as well as with control HLA-A2 complex displaying other HLA-A2-restricted peptide (Table 15) was used to select specific clones Isolated hybridoma clones were sub-cloned and were sequenced. Two clones 906-11-D11 (termed D11, FIG. 68) and 905-2-D7 (termed D7, FIG. 69) were characterized.

Hybridomas were grown to >80% confluency in HAT DMEM or serum free DCCM2 medium and supernatant was collected. Purified IgG was isolated from culture supernatant by affinity chromatography using Protein A column. SDS-PAGE analysis of the purified protein revealed homogenous, pure IgG with the expected molecular mass of ~150 kDa.

Construction of Whole IgG Ab

The H and L Fab genes (only for MC1) were cloned for expression as human IgG1 Ab into the eukaryotic expression vectors the eukaryotic expression vectors pOptiVEC and pcDNA3.3-TOPO respectively. Each shuttle expression vector carries a different gene selection (for pOptiVEC the DHFR/HT- and for pcDNA3.3 Geneticin). Expression was facilitated by co-transfection of the two constructs into the dihydrofolate reductase (DHFR)-deficient, Chinese hamster ovary (CHO)-derived DG44 cells in suspension culture by using the FreeStyle MAX reagent (Invitrogen). After co-transfection, cells were grown on selective medium. Clones that reacted specifically with JY T2 cells pulsed with tyrosinase 369-377 peptide were adapted to growth in 0.5% serum and were further purified using protein A affinity chromatography. SDS-PAGE analysis of the purified protein revealed homogenous, pure IgG with the expected molecular mass of ~150 kDa.

ELISA with Supernatant or Purified Abs

The binding specificities of individual supernatant or purified TCRL antibodies were determined by ELISA using biotinylated scMHC-peptide complexes. Maxi sorp 96 wells ELISA plates (Nunc #442404) were coated overnight with BSA-biotin (1 μg/well). After having been washed, the plates were incubated (1 h, RT) with streptavidin (1 μg/well), washed extensively, and further incubated (1 h, RT) with 0.25 μg of MI-IC/peptide complexes. The plates were blocked for 30 min at RT with PBS/2% skim milk and subsequently were incubated for 1 h at RT with 1 μg/well supernatant or purified TCRL antibodies. After having been washed, the plates were incubated with HRP-conjugated/anti-human or mouse Ab. Detection was performed using TMB tetramethylbenzidine reagent (DAKO, S1599). The HLA-A2-restricted peptides used for specificity studies of the purified supernatant or purified TCRL antibodies.

Proteon XPR36 Surface Plasmon Resonance (SPR) Binding Analysis

Immobilization of IgG TCR-like antibody was performed on a GLM (General Layer Medium) chip (Bio-Rad Laboratories, Hercules, Calif., USA) at 25° C. in the vertical orientation and the continuous running buffer was PBST (10 mM Na-phosphate, 150 mM NaCl, and 0.005% Tween 20, pH 7.4). Five channels were activated with 50 μl of a mixture of 0.04 M N-ethyl-N'-(3-dimethylaminopropyl) carbodiimide (EDC) and 0.01 M sulfo-N-hydroxysuccinimide (Sulfo-NHS) at a flow rate of 30 μl/min. The anti-mouse or human IgG/NeutrAvidin was diluted in 10 mM sodium acetate buffer pH 4.5 to a final concentration of 25 μg/ml and 150 μl were injected followed by an injection of 150 μl of 1 M ethanolamine-HCl pH 8.5. The IgG TCRL antibody/purified biotinylated single-chain recombinant HLA-A2/Tyrosinase/WT1/MAGE-A4/MAGE-A9/PAP complex ligand was diluted in PBST to 5-10 μg/ml and 90 μl were injected in the vertical orientation with a flow rate of 30 μl/min. The sixth channel remained empty to serve as a reference. The analyte purified single-chain recombinant HLA-A2/Tyrosinase/WT1/MAGE-A4/MAGE-A9/PAP complex/Fab TCRL antibody was injected (75 μl at 50 μl/min) in the horizontal orientation of the ProteOn using five different concentrations (1000, 500, 250, 125 and 62.5 nM). Running buffer was injected simultaneously in the sixth channel for double referencing to correct for loss of the captured antibodies from the chip sensor surface during the experiment. All binding sensorgrams were collected, processed and analyzed using the integrated ProteOn Manager (Bio-Rad Laboratories, Hercules, USA) software. Binding curves were fitted using the Langmuir model describing 1:1 binding stoichiometry, or with the Langmuir and mass transfer limitation model.

Functional Assays

LDH-Release Assay

Bispecific TCRL redirected target cell killing was measured in a non-radioactive cytotoxicity assay using Cyto-Tox96® (Promega). This assay quantitatively measures lactate dehydrogenase (LDH), an enzyme that is released upon cell lysis. Released LDH in culture supernatants is measured with a 10 minute coupled enzymatic assay, which results in the conversion of a tetrazolium salt (INT) into a red formazan product. The amount of color produced is proportional to the number of lysed cells.

Specifically, target cells and effector cells were washed, counted and resuspended in cRPMI medium (1% FBS) without phenol red. Target cells were adjusted to a cell density of $2.5 \times 10^5$ cells per ml and the effector cells at a cell density of $2.5 \times 10^6$ cells per ml. 40 μl ($1 \times 10^4$ cells) of target cells were cultured in a 96-well V-shaped plate. A 5 times concentrated stock of the Bispecific TCRL test reagent was prepared at the highest test concentration, which was serially diluted 1 in 10 in medium without phenol red in a separate plate to obtain other test concentrations. The Bispecific TCRL was then added to the target cells in the assay plate at 20 μl per well to give the final indicated titrated amounts. The assay plate containing the target cells mixed with the Bispecific TCRL was then incubated for 20 minutes at 37° C./5% $CO_2$. Following the incubation, 40 μl effector cells ($1 \times 10^5$ cells) were added to each well resulting in an effector to target (E:T) ratio of 10:1. Control wells were set up with effector cells alone to calculate effector spontaneous release, target cells alone to calculate target spontaneous release, and target cells with 80 μg/ml digitonin final to calculate maximum release. Each condition was assayed in triplicates in a final volume of 100 μl. The plate was incubated at 37° C./5% $CO_2$ for 24 hours. Following the incubation period, the plate was centrifuged at 700×g for 5 minutes and 50 μl transferred from each well to the corresponding well in a 96-well flat bottomed Maxisorb plate (Nunc). The CytoTox96® substrate mix was reconstituted using CytoTox96® assay buffer, as per manufacturer's instructions, and 50 μl added to each well of the plate. The plate was covered with aluminum foil and incubated at room temperature for 10 minutes. Then absorbance recorded at 490 nm on a plate reader. Percentage cytotoxicity was then calculated using the following equation: Specific lysis=[(Experimental−Effector Spontaneous−Target Spontaneous)/(Target Maximum−Target Spontaneous)]×100. PBMCs for killing assays are isolated from healthy volunteers and with all regulatory IRBs approvals and written consents. Effector PBMCs are isolated using the Lymphoprep procedure.

Tumor Cell Lines and Normal Primary Cells

Cells lines A375 (melanoma), U2OS (osteosarcoma), TCCSUP (bladder carcinoma) and Fib (fibroblasts) were cultured in complete DMEM supplemented with 10% FBS (all supplied by GIBCO). 501A, SKMe15, Mewo and 1938 (melanoma), Saos2 (osteosarcoma), Panc1 (pancreatic carcinoma), J82 and UMUC3 (bladder), H1703 (non-small cell lung adenocarcinoma), JVM2 (Mantle cell lymphoma), IM9 (multiple myeloma), U266 (myeloma) and SW620 (colorectal adenocarcinoma) were cultured in complete RPMI supplemented with 10% FBS (all supplied by GIBCO). Malme3m (melanoma), JEKO1 (mantle-cell lymphoma), SET2 (essential thrombocythemia) and BV173 (B cell precursor leukemia) were cultures in complete RPMI supplemented with 20% FBS (all supplied by GIBCO). THP-1 (AML) were cultured in complete RPMI supplemented with 10% FBS (all supplied by GIBCO) and 0.05 mM beta-mercaptoethanol (supplied by Thermo-fisher). OVCAR-3 (ovary adenocarcinoma) were cultured in complete RPMI supplemented with 20% FBS (all supplied by GIBCO) and 0.01 mg/ml bovine insulin (supplied by Sigma). All cell lines were maintained at 37° C. in a humidified atmosphere of 7.5% $CO_2$ and were purchased from American Type Culture Collection.

Normal primary hepatocytes, cardiac myocytes, osteoblasts, astrocytes, bronchial epithelial cells, colonic smooth muscle cells, urothelial cells and renal epithelial cells were obtained from Sciencell and cultured according to the manufacturer's instructions. All cell lines were maintained at 37° C. in a humidified atmosphere of 7.5% $CO_2$.

Expression and Purification of Soluble Recombinant Fab Abs in Expi293 System

The VH-CH1 and VL-CL genes of Tyr D11 and D7, MAGE-A4 C106B9, WT1 B47B6 and ESK1 IgGs were cloned for expression as Fab in the eukaryotic expression vector pcDNA3.4. His-tag was connected to the C-terminus of the CH1 region.

Expression was facilitated by co transfection of the two constructs (heavy and light chains) into the Expi293F human cells in Expi293 expression medium (both are components of the Expi293 expression system) by the Fectamine transfection reagent (Life technologies). Following co-transfection, cells were grown for 6 days. After 6 days cells were centrifuged at 700×g for 5 minutes. Following centrifugation, the supernatant containing the D11, D7, C106B9, B47B6 or ESK1 Fab was removed from cells and filtered through 0.22μ filter. The supernatant was then dialyzed overnight against PBS.

The D11, D7, C106B9, B47B6 or ESK1 Fab recombinant protein was purified by metal affinity column (Talon) and dialyzed overnight against PBS. The purified D11, D7, C106B9, B47B6 or ESK1 Fab were analyzed on reduced and non-reduced SDS-PAGE.

Construction, Expression and Purification of Bispecific TCRLs in Expi293 System

The VH-CH1 and VL-CL genes of Tyr D11 and D7, WT1 B47B6 and ESK1 and MAGE-A4 C106B9, IgGs were cloned for expression as bispecific (BS) in the eukaryotic expression vector pcDNA3.4 (sequences are shown in FIGS. 68-70, sequences of ESK1 is available from WO 2015/070061). For the light chain vector of Tyr D11, WT1 B47B6 and ESK1 and MAGE-A4 C106B9, anti CD3 (clone UCHT1) scFv was connected to the N-terminus of the VL region (BS format 3, #F3). For the heavy chain vector, His-tag was connected to the C-terminus of the CH1 region. For Tyr D7, anti CD3 (clone UCHT1) scFv was connected to the N-terminus of the VH region of the heavy chain (BS format 1, #F1) and His-tag was connected to the C-terminus of the CH1 region.

Expression was facilitated by co transfection of the two constructs into the Expi293F human cells in Expi293 expression medium (both are components of the Expi293 expression system) by the Fectamine transfection reagent (Life technologies). After co-transfection, cells were grown for 6 days. Following 6 days cells were centrifuged at 700×g for 5 minutes. Following centrifugation, the supernatant containing the TCRL bispecific antibodies were removed from cells and filtered through 0.22 nm filter. The supernatant was then dialyzed overnight against PBS.

The BS-TCRLs recombinant proteins were purified by two steps of metal affinity (Talon) and size exclusion chromatography (Superdex 200 10/300 GL GE). The purified BS-TCRLs were analyzed on SDS-PAGE.

In Vivo Assays for 501A Melanoma Cell Line (ATCC, Manassas Va., USA)

Cells were cultured in RPMI1640 growth medium (GIBCO, Waltham Mass., USA) supplemented with 10% fetal bovine serum (GIBCO, Waltham Mass., USA). Human peripheral blood mononuclear cells (PBMC) were prepared from healthy donors by using SepMateTM-50 tubes (Stemcell).

At day 0, eight to ten weeks old female NOD/SCID mice (Envigo, Israel; n=6-8) were inoculated subcutaneously (s.c.) in a single flank with $5\times10^6$ 501 A melanoma cells +/-$25\times10^6$ PBMCs (Effector:Tumor cell ratio 5:1) in a final volume of 0.25 ml phosphate-buffered saline (PBS); D7 bispecific TCRL (0.1 mg/kg) or vehicle (PBS) were administered i.v. one hour after the s.c. inoculation in a final volume of 0.2 ml, with 4 additional doses administered every 24 hours.

For A375 Melanoma Cell Line (ATCC, Manassas Va., USA)

Cells were cultured in RPMI1640 growth medium (GIBCO, Waltham Mass., USA) supplemented with 10% fetal bovine serum (GIBCO, Waltham Mass., USA).

Activated CD8 T-cells were prepared from human peripheral blood mononuclear cells (PBMC) using a rapid expansion protocol (REP). Naïve PBMCs were produced from healthy donor's peripheral blood using SepMateTM-50 tubes (Stemcell), following CD8 T cells enrichment using Dynabeads® Untouched™ Human CD8 T Cells kit (Invitrogen). Activation of the purified CD8 T cells was performed in flasks pre-coated with monoclonal antibodies against CD3 (OKT3) and CD28 for 72 hrs in media supplemented with 10% FBS and 100 IU/mL of 1(1 human IL-2. Activated cells were expanded over the period of 14 days in media supplemented with 10% FBS, 3000 IU/ml IL-2, 30 ng/ml OKT3 and $2\times10^8$ irradiated PBMCs.

At day 0, eight to ten weeks old female NOD/SCID mice (Envigo, Israel; n=6-8) were inoculated subcutaneously (s.c.) in a single flank with $5\times10^6$ A375 melanoma cells +/-$10\times10^6$ REP CD8 T-cells (Effector: Tumor cell ratio 2:1) in a final volume of 0.25 ml phosphate-buffered saline (PBS); MAGE-A4 C106B9 bispecific TCRL (0.1 mg/kg), WT1 B47B6 bispecific TCRL (0.1 mg/kg) or vehicle (PBS) were administered i.v. one hour after the s.c. inoculation in a final volume of 0.2 ml, with 4 additional doses administered every 24 hours.

In both cases (501A and A375) tumors were measured two times per week with calipers in two perpendicular dimensions and tumor volumes were calculated with the following formula:

$$\text{width} \times \left(\frac{501A}{2}\right)^2 \times 3.14$$

Other TCRL Antibodies Used in the Present Study

The generation of MC1 is described in WO2008/120202.

The generation of ESK1 (Dao T, Yan S, Veomett N, Pankov D, Zhou L, Korontsvit T, Scott A, Whitten J, Maslak P, Casey E, Tan T, Liu H, Zakhaleva V, Curcio M, Doubrovina E, O'Reilly R J, Liu C, Scheinberg D A. Targeting the intracellular WT1 oncogene product with a therapeutic human antibody. Sci Transl Med. 2013 Mar. 13; 5(176): 176ra33). ESK1 was thus generated by synthetic gene synthesis according to the published sequence WO 2015/070061 ESK1 full VH—SEQ ID NO:128 and ESK1 full VL—SEQ ID NO: 130 in the sequence listing of WO 2015/070061. The antibody was produced in HEK293 cells as IgG using the Expi293 system as described above and was purified from culture supernatants using protein A affinity chromatography.

Extraction of Nucleic Acids

Total RNA was extracted from $1*10^6$-$5*10^6$ cells cultured cells with RNeasy Plus Mini (Qiagen) according to the manufacturer's instructions.

cDNA Synthesis cDNA was synthesized from 1-5 µg RNA, using a combination of oligo dT and random hexamer (1:1) with SuperScript® III First-Strand Synthesis System (Invitrogen) according to the manufacturer's instructions. F or quantitative PCR, cDNA was diluted 1:5 with $H_2O$.

Conventional PCR (PCR)

The PCR cycling conditions were 95° C. for 2 minutes, followed by 40 cycles of 95° C. for 20 s, 60° C. for 1 min and 72° C. for 1 min. The PCR was ended with a final extension of 72° C. for 10 min. Reactions were performed with KAPA HiFi PCR Kit (Kapa Biosystems) according to the manufacturer's instructions.

Following primers were used:

TYR_S:
(SEQ ID NO: 3)
TTAGCAAAGCATACCATCA
and

TYR_AS:
(SEQ ID NO: 4)
CCAGACAAAGAGGTCATAA for tyrosinase expression (expected product size: 117 bp) and WT1 S: AGGCTGCAATAAGAGATA (SEQ ID NO: 5) and WT1_AS: TTCGCTGACAAGTTTTAC (SEQ ID NO: 6) for WT1 expression (expected product size: 188 bp).

To visualize the amplified products, 10 µl of samples were mixed with 2 µL of 6× loading buffer (New England Biolabs) and subjected to electrophoresis on 1.5% agarose gels stained with ethidium bromide with DNA markers (New England Biolabs). The presence and intensity of the PCR product bands was determined on an ImageQuant LAS 4000 (GE Healthcare Life Sciences).

Quantitative PCR (qPCR)

Quantitative PCR was carried out using TaqMan Gene Expression Master Mix on a ABI 7300 instrument (Applied Biosystems), according to the manufacturer's instructions. The cycle conditions for real-time PCR were 95° C. for 10 min, followed by 40 cycles of 95° C. for 15 sec, and 60° C. for 1 min. Probes for real-time PCR were purchased from Applied Biosystems; at the 5' end, they were conjugated to the fluorochrome FAM. Following assays (primers and probes) were used: for TYR (cat #Hs00165976), for MAGE A4 (cat #Hs00751150), and for WT1 (cat #Hs01103751). Beta-actin was used as a housekeeping gene for normalization (cat #Hs99999903).

Peptides Used in the Present Study

TABLE 4

| Ala Scan - TyrD | | |
|---|---|---|
| Peptide name | Peptide-HLA-A sequence | SEQ ID NO: |
| TyrD-A1 | AMDGTMSQV | 104 |
| TyrD-A2 | YADGTMSQV | 105 |

TABLE 4-continued

Ala Scan - TyrD

| Peptide name | Peptide-HLA-A sequence | SEQ ID NO: |
|---|---|---|
| TyrD-A3 | YMAGTMSQV | 106 |
| TyrD-A4 | YMDATMSQV | 107 |
| TyrD-A5 | YMDGAMSQV | 108 |
| TyrD-A6 | YMDGTASQV | 109 |
| TyrD-A7 | YMDGTMAQV | 110 |
| TyrD-A8 | YMDGTMSAV | 111 |
| TyrD-A9 | YMDGTMSQA | 112 |

TABLE 5

Similar peptides - TyrD

| Peptide name | Peptide-HLA-A2 sequence | SEQ ID NO: | Similar to |
|---|---|---|---|
| Tyrosinase D (Tyrosinase peptide) | YMDGTMSQV | 113 | |
| Tyrosinase N | YMNGTMSQV | 114 | |
| *KIAA0355 | YMDNVMSEV | 115 | TyrD |
| KPNA1 | VMDSKIVQV | 116 | TyrD |
| GPLD1 | LMNGTLKQV | 117 | TyrD |
| TyrD-S1 | SQDGTRSQV | 118 | TyrD |
| TyrD-S2 | VMDTTKSQV | 119 | TyrD |
| TyrD-S3 | GMDGTQQQI | 120 | TyrD |
| TyrD-S4 | GMVGTMTEV | 121 | TyrD |
| TyrD-S5 | MMDATFSAV | 122 | TyrD |
| TyrD-S6 | QMDPTGSQL | 123 | TyrD |
| *TyrD-S7 | SMDGSMRTV | 124 | TyrD |
| TyrD-S8 | WMDGIASQI | 125 | TyrD |
| TyrD-S9 | YLEGILSQV | 126 | TyrD |
| TyrD-S10 | YMAIKMSQL | 127 | TyrD |
| TyrD-S11 | YMDAVVSLV | 128 | TyrD |
| TyrD-S12 | YMDGTNRRI | 129 | TyrD |
| TyrD-S13 | YMDPSTYQV | 130 | TyrD |
| TyrD-S14 | YMLGTNHQL | 131 | TyrD |
| TyrD-S15 | YMPGTASLI | 132 | TyrD |
| TyrD-S16 | YMRETRSQL | 133 | TyrD |
| *TyrD-S17 | MMDGAMGYV | 134 | TyrD |
| *TyrD-S18 | NMDSFMAQV | 135 | TyrD |
| *TyrD-S19 | QMDFIMSCV | 136 | TyrD |
| *TyrD-S20 | YEDLKMYQV | 137 | TyrD |

TABLE 5-continued

Similar peptides - TyrD

| Peptide name | Peptide-HLA-A2 sequence | SEQ ID NO: | Similar to |
|---|---|---|---|
| *TyrD-S21 | YMDTIMELV | 138 | TyrD |
| *TyrD-S22 | YTDLAMSTV | 139 | TyrD |
| *TyrD-S23 | YVDFVMSSV | 140 | TyrD |

*Ala-based similar peptides

TABLE 6

Similar peptides - WT1

| Peptide name | Peptide-HLA-A2 sequence | SEQ ID NO: | Similar to |
|---|---|---|---|
| WT1 (WT1 peptide) | RMFPNAPYL | 141 | |
| WT1-S1 | LDFPNLPYL | 142 | WT1 |
| *WT1-S2 | RCFPNCPFL | 143 | WT1 |
| WT1-S3 | LMFENAAYL | 144 | WT1 |
| WT1-S4 | RMFPNKYSL | 145 | WT1 |
| WT1-S5 | RLFPNAKFL | 146 | WT1 |
| *WT1-S6 | RLFPNLPEL | 147 | WT1 |
| *WT1-S7 | RMFPTPPSL | 148 | WT1 |
| WT1-S8 | RMVPRAVYL | 149 | WT1 |
| WT1-S9 | RMFFNGRYI | 150 | WT1 |
| WT1-S10 | RMLPHAPGV | 151 | WT1 |
| WT1-S11 | YMFPNAPYL | 152 | WT1 |
| WT1-S12 | AMDPNAAYV | 153 | WT1 |
| WT1-S13 | ICFPNAPKV | 154 | WT1 |
| WT1-S14 | NMFENGCYL | 155 | WT1 |
| WT1-S15 | NMPPNFPYI | 156 | WT1 |
| WT1-S16 | REMTQAPYL | 157 | WT1 |
| WT1-S17 | RMAPRAPWI | 158 | WT1 |
| WT1-S18 | RMEPRAPWI | 159 | WT1 |
| WT1-S19 | RMEPRAPWV | 160 | WT1 |
| WT1-S20 | RMFLNNPSI | 161 | WT1 |
| WT1-S21 | RMFQQTFYL | 162 | WT1 |
| WT1-S22 | RMNPNSPSI | 163 | WT1 |
| WT1-S23 | RQFPNASLI | 164 | WT1 |
| WT1-S24 | RQFPNKDAL | 165 | WT1 |
| WT1-S25 | RVFPWASSL | 166 | WT1 |
| WT1-S26 | RLFPWGNKL | 167 | WT1 |

*Ala-based similar peptides

TABLE 7

Ala Scan - WT1

| Peptide name | Peptide-HLA-A2 sequence | SEQ ID NO: |
|---|---|---|
| WT1-A1 | AMFPNAPYL | 168 |
| WT1-A2 | RAFPNAPYL | 169 |
| WT1-A3 | RMAPNAPYL | 170 |
| WT1-A4 | RMFANAPYL | 171 |
| WT1-A5 | RMFPAAPYL | 172 |
| WT1-A7 | RMFPNAAYL | 173 |
| WT1-A8 | RMFPNAPAL | 174 |
| WT1-A9 | RMFPNAPYA | 175 |

TABLE 8

Similar peptides - MAGE-A4

| Peptide name | Peptide-HLA-A2 sequence | SEQ ID NO: | Similar to |
|---|---|---|---|
| MAGE-A4 (MAGE-A4 peptide) | GVYDGREHTV | 176 | |
| MAGE-A4-S1 | GLADGRTHTV | 177 | MAGE-A4 |
| MAGE-A4-S2 | GVSDGRWHSV | 178 | MAGE-A4 |
| MAGE-A4-S4 | GVYDGEEHSV | 179 | MAGE-A4 |
| MAGE-A4-S5 | GLYDGMEHL | 180 | MAGE-A4 |
| MAGE-A4-S6 | GVSDGQWHTV | 181 | MAGE-A4 |
| MAGE-A4-S9 | GVYAGREHFL | 182 | MAGE-A4 |
| MAGE-A4-S10 | GLYDGMEHLI | 183 | MAGE-A4 |
| MAGE-A4-S12 | ASYDGTEVTV | 184 | MAGE-A4 |
| MAGE-A4-S13 | AVLDGRELRV | 185 | MAGE-A4 |
| MAGE-A4-S15 | GLYDGIEHFM | 186 | MAGE-A4 |
| MAGE-A4-S16 | GLYDGPVHEV | 187 | MAGE-A4 |
| MAGE-A4-S17 | GVCAGREHFI | 188 | MAGE-A4 |
| MAGE-A4-S18 | GVYAGRPLSV | 189 | MAGE-A4 |
| MAGE-A4-S19 | TVYDLREQSV | 190 | MAGE-A4 |
| MAGE-A4-S20 | VVDDGVEHTI | 191 | MAGE-A4 |
| MAGE-A4-S21 | GVFDGLHTV | 192 | MAGE-A4 |

TABLE 9

Ala Scan - MAGE-A4

| Peptide name | Peptide-HLA-A2 sequence | SEQ ID NO: |
|---|---|---|
| MAGE-A4-A1 | AVYDGREHTV | 193 |
| MAGE-A4-A2 | GAYDGREHTV | 194 |
| MAGE-A4-A3 | GVADGREHTV | 195 |
| MAGE-A4-A4 | GVYAGREHTV | 196 |
| MAGE-A4-A5 | GVYDAREHTV | 197 |
| MAGE-A4-A6 | GVYDGAEHTV | 198 |
| MAGE-A4-A7 | GVYDGRAHTV | 199 |
| MAGE-A4-A8 | GVYDGREATV | 200 |
| MAGE-A4-A9 | GVYDGREHAV | 201 |
| MAGE-A4-A10 | GVYDGREHTA | 202 |

TABLE 10

Similar peptides - MAGE-A9

| Peptide name | Peptide-HLA-A2 sequence | SEQ ID NO: | Similar to |
|---|---|---|---|
| MAGE-A9 (MAGE-A9 peptide) | ALSVMGVYV | 203 | |
| MAGE-A9S1 | ALSVLGVMV | 204 | MAGE-A9 |
| MAGE-A9S3 | ALSRKGIYV | 205 | MAGE-A9 |
| MAGE-A9S4 | ALSVMYSYL | 206 | MAGE-A9 |
| MAGE-A9S6 | AVSHMGVLV | 207 | MAGE-A9 |
| MAGE-A9S7 | LLSLMGVLV | 208 | MAGE-A9 |
| *MAGE-A9S8 | VLSIMGVYA | 209 | MAGE-A9 |
| MAGE-A9S10 | ALQVRKVYV | 210 | MAGE-A9 |
| MAGE-A9S11 | ALQVYGVEV | 211 | MAGE-A9 |
| MAGE-A9S13 | ALSVAGGFV | 212 | MAGE-A9 |
| MAGE-A9S14 | ALSVLGKVV | 213 | MAGE-A9 |
| MAGE-A9S15 | ALSVMIPAV | 214 | MAGE-A9 |
| MAGE-A9S16 | DLSVCSVYV | 215 | MAGE-A9 |
| MAGE-A9S17 | ILGVMGVDV | 216 | MAGE-A9 |
| MAGE-A9S20 | LLSVNGVSV | 217 | MAGE-A9 |
| MAGE-A9S23 | SLSPMGRYV | 218 | MAGE-A9 |
| MAGE-A9S24 | ALSAVMGVTL | 219 | MAGE-A9 |
| MAGE-A9S25 | AILLVMGVDV | 220 | MAGE-A9 |
| MAGE-A9S26 | ALSDHHVYL | 221 | MAGE-A9 |

*Ala-based similar peptides

TABLE 11

Ala Scan - MAGE-A9

| Peptide name | Peptide-HLA-A2 sequence/ | SEQ ID NO: |
|---|---|---|
| MAGE-A9-A2 | AASVMGVYV | 222 |
| MAGE-A9-A3 | ALAVMGVYV | 223 |
| MAGE-A9-A4 | ALSAMGVYV | 224 |

TABLE 11-continued

Ala Scan - MAGE-A9

| Peptide name | Peptide-HLA-A2 sequence/ | SEQ ID NO: |
|---|---|---|
| MAGE-A9-A5 | ALSVAGVYV | 225 |
| MAGE-A9-A6 | ALSVMAVYV | 226 |
| MAGE-A9-A7 | ALSVMGAYV | 227 |
| MAGE-A9-A8 | ALSVMGVAV | 228 |
| MAGE-A9-A9 | ALSVMGVYA | 229 |

TABLE 12

Similar peptides - PAP

| Peptide name | Peptide-HLA-A2 sequence | SEQ ID NO: | Similar to |
|---|---|---|---|
| PAP (PAP peptide) | TLMSAMTNL | 230 | |
| PAP(TLM)S1 | TLMSAEANL | 231 | PAP |
| PAP(TLM)S2 | QLCSAMTQL | 232 | PAP |
| PAP(TLM)S3 | RLMSALTQL | 233 | PAP |
| PAP(TLM)S4 | GLMSLTTNL | 234 | PAP |
| PAP(TLM)S5 | GLMSMATNL | 235 | PAP |
| PAP(TLM)S6 | GLMSMTTNL | 236 | PAP |
| PAP(TLM)S7 | LLMSISTNL | 237 | PAP |
| PAP(TLM)S8 | QLPSTMTNL | 238 | PAP |
| PAP(TLM)S9 | TLASSMGNL | 239 | PAP |
| PAP(TLM)S10 | TLFSALTGL | 240 | PAP |
| PAP(TLM)S11 | TLGSATTEL | 241 | PAP |
| PAP(TLM)S12 | TLMRAMTDC | 242 | PAP |
| PAP(TLM)S13 | TLMSMVANL | 243 | PAP |
| PAP(TLM)S14 | TLPSAETAL | 244 | PAP |
| PAP(TLM)S15 | TLPSRMTVL | 245 | PAP |
| PAP(TLM)S18 | RLMSALTQV | 246 | PAP |
| PAP(TLM)S19 | SIHSQMTNL | 247 | PAP |
| PAP(TLM)S20 | SIMFAMTPL | 248 | PAP |
| PAP(TLM)S21 | TIVAAMSNL | 249 | PAP |
| PAP(TLM)S22 | TLITAMEQL | 250 | PAP |
| PAP(TLM)S23 | TLTSNMSQL | 251 | PAP |

TABLE 13

Ala Scan - PAP

| Peptide name | Peptide-HLA-A2 sequence | SEQ ID NO: |
|---|---|---|
| PAP A1 | ALMSAMTNL | 252 |
| PAP A3 | TLASAMTNL | 253 |
| PAP A4 | TLMAAMTNL | 254 |
| PAP A6 | TLMSAATNL | 255 |
| PAP A7 | TLMSAMANL | 256 |
| PAP A8 | TLMSAMTAL | 257 |
| PAP A9 | TLMSAMTNA | 258 |

TABLE 14

Similar peptides found in normal essential tissues by MS.

| Peptide name | Peptide sequence/SEQ ID NO: | Gene | Normal tissue in which peptide was found by MS |
|---|---|---|---|
| KPNA1 | VMDSKIVQV/259 | KPNA1, KPNA5, KPNA6 | Adrenal, bladder, brain cerebellum, brain cerebral cortex, brain cerebrum, colon, heart, intestine, kidney, liver, lung, mesothelial, nerve, pituitary, retina, spinal cord cervical, adipose, breast, duodenum, esophagus, gallbladder, ovary, pancreas, prostate, skin, spleen, stomach, testis, uterus |
| WT1-S10 | RMLPHAPGV/260 | HDAC1, HDAC2 | Adrenal, bladder, brain cerebellum, brain cerebral cortex, brain cerebrum, colon, heart, intestine, kidney, liver, lung, mesothelial, nerve, pituitary, retina, spinal cord cervical, adipose, breast, duodenum, esophagus, gallbladder, ovary, pancreas, |

TABLE 14-continued

Similar peptides found in normal essential tissues by MS.

| Peptide name | Peptide sequence/SEQ ID NO: | Gene | Normal tissue in which peptide was found by MS |
|---|---|---|---|
| | | | prostate, skin, spleen, stomach, testis, uterus |
| WT1-S12 | AMDPNAAYV/261 | SERPINA6 | Liver |
| WT1-S22 | RMNPNSPSI/262 | ERH | Colon, intestine, kidney, lung, duodenum, gallbladder, uterus |
| MAGE-A4-S1 | GLADGRTHTV/263 | THBS3 | Colon, endothelium, intestine, kidney, mesothelial, nerve, pituitary, duodenum, stomach |
| MAGE-A4-S16 | GLYDGPVHEV/264 | DPYSL4 | Brain cerebellum, brain cerebrum, intestine, lung, prostate, spleen |
| MAGE-A4-S21 | GVFDGLHTV/265 | BTD | Brain cerebral cortex, intestine, kidney, liver, lung, mesothelial, retina, breast, duodenum, stomach, testis, uterus |
| MAGE-A9-S26 | ALSDHHVYL/266 | ALDOC | Adrenal, bladder, brain cerebellum, brain cerebral cortex, brain cerebrum, colon, endothelium, heart, intestine, kidney, liver, lung, mesothelial, nerve, pituitary, retina, spinal cord cervical, breast, duodenum, esophagus, prostate skin, spleen, stomach, testis, uterus |
| PAP-S3 | RLMSALTQL/267 | DAB2IP | Brain cerebellum, brain cerebral cortex, brain cerebrum, colon, heart, intestine, kidney, lung, mesothelial, nerve, retina, spinal cord cervical, adipose, breast, duodenum, prostate, spleen, uterus |
| PAP-S18 | RLMSALTQV/268 | RASAL2 | Bladder, brain cerebellum, brain cerebral cortex, brain cerebrum, colon, endothelium, heart, intestine, kidney, liver, lung, mesothelial, nerve, pituitary, retina, spinal cord cervical, adipose, breast, duodenum, esophagus, gallbladder, ovary, prostate, skin, spleen, stomach, testis, uterus |

TABLE 15

Control peptides

| Peptide | Peptide-HLA-A2 sequence | SEQ ID NO: |
|---|---|---|
| MART1(26) | ELAGIGILTV | 269 |
| CMV | NLVPMVATV | 270 |
| Gag | SLYNTVATL | 271 |
| Tyrosinase D | YMDGTMSQV | 272 |
| WT-1 | RMFPNAPYL | 273 |
| MAGE-A4 | GVYDGREHTV | 274 |
| PAP | TLMSAMTNL | 275 |
| MAGE-A9 | ALSVMGVYV | 276 |
| SSX-2 | KASEKIFYV | 277 |

TABLE 15-continued

Control peptides

| Peptide | Peptide-HLA-A2 sequence | SEQ ID NO: |
|---|---|---|
| NY-ESO | SLLMWITQC | 278 |
| UHRF1 | TLFDYEVRL | 279 |

Example I

TCR-Like Antibodies for HLA-A2/Tyrosinase

Isolation of Abs with TCR-Like Specificity to HLA-A2/Tyrosinase369-377
Generation of MHC-TyrD369-377 Complex—

Previous studies performed by the present inventors have shown the generation of recombinant antibodies with peptide-specific, HLA-A2-restricted specificity to tumor and viral T cell epitopes using large antibody phage libraries. These molecules are termed TCR-like antibodies. To generate antibodies with a specificity to the HLA-A2/TyrD369-377 complex, recombinant peptide-HLA-A2 complexes were generated that present the Tyrosinase peptide (tyrosinase369-377YMDGTMSQV, SEQ ID NO: 1) using a single chain MHC construct. HHD mice were immunized by 5-6 injections of HLA-A2-peptide complex 50 µg/mouse. 2-3 first injections were administrated s.c with addition of QuilA adjuvant. Hybridoma clones were generated by fusion of splenocytes isolated from immunized mice (as previously described e.g., Weidanz et al. 2011 Int. Rev. Immunol. 30:328-340) with NSO myeloma cells and were screened and isolated by differential ELISA assays as described above using TyrD369-377 peptide and HLA-A2 complexes folded with p68-DDX5 control peptide. ELISA with purified HLA-A2-Tyr complexes as well as with control HLA-A2 complex displaying other HLA-A2-restricted peptide was used to select specific clones Isolated hybridoma clones were subcloned and were sequenced. Two clones 906-11-D11 (termed D11, FIG. 69) and 905-2-D7 (termed D7, FIG. 68) were characterized.

Characterization of TCR-Like Antibodies with Specificity to HLA A2/Tyrosinase 369-377

To determine the apparent affinity of isolated TCR-like antibodies, surface plasmon resonance (SPR) binding analysis was used in which the isolated purified IgG TCR-like antibody was immobilized to the SPR sensor chip by using anti-mouse IgG to indirectly immobilize the TCR-like antibodies on the chip surface. The analyte is the purified single-chain recombinant HLA-A2/Tyrosinase complex used at various concentrations. As shown in FIG. 1, the sensorgrams of SPR analysis revealed similar affinity for the HLA-A2/Tyrosinase specific TCR-like antibody clones MC1, D11, and D7 with corresponding affinity of 4.1 nM for MC1 and D11 and 3.8 nM for D7. These results indicate that all three TCR-like antibody clones exhibited similar high affinity of 4 nM towards the specific HLA-A2/peptide complex.

To investigate the fine peptide epitope specificity of the isolated TCR-like antibodies towards the Tyrosinase 369-377 peptide alanine scanning was performed in which specific residues in the peptide were mutated to alanine and the binding of the TCR-like antibodies to Ala mutated peptides was tested by their loading onto T2 antigen presenting cells. Binding was monitored by flow cytometry and extent of binding of TCR-like antibodies to the mutated presented peptides as measured by mean fluorescence intensity (MFI) was compared in comparison to T2 APCs loaded with the native unmutated Tyrosinase peptide. The proper loading of the various Ala mutated peptides (described in FIG. 2) was monitored by flow cytometry using BB7.2 a monoclonal antibody for HLA-A2.

All Ala mutated peptides were efficiently loaded onto T2 cells in comparison to the native un-mutated Tyrosinase peptide (data not shown). Peptide loading efficiency is verified using the ratio between MFI of HLA-A2-binding Ab BB7.2 on peptide-loaded T2 cells and MFI of unloaded T2 cells (>1).). As shown in FIG. 2, all three TCR-like antibodies exhibited peptide dependency binding as specific mutations affected the binding and induced a decrease in the binding intensity of the TCR-like antibody upon introduction of Ala at specific peptide positions. These results indicate that all three TCR-like antibodies exhibited peptide-specific and restricted binding in the context of HLA-A2 loaded with various Ala mutated Tyrosinase peptides, indicating that these antibodies are TCR-like in their binding properties, thus, they bind the MHC-peptide complex with MHC-restricted and peptide-specific manner.

However, the three TCR-like antibodies differ in their fine specificity and peptide-dependent reactivity with the number of positions in the peptide that were sensitive to Ala mutation and affected binding sensitivity. As MC1 exhibited a marked decrease of 90% in binding to a single Ala mutated peptide at one position #6, D11 and D7 exhibited a decrease of >90% at two positions #3, 6 for D11 and a decrease of >90% for D7 binding at four positions #3, 4, 6, 7. A milder but highly significant decrease of >70% in three positions #1, 3, 6 was further observed for MC1 binding to Ala mutated peptides while D11 and D7 exhibited significant decrease in binding of >70% when 5 peptide residues were mutated to Ala (positions #1, 2, 3, 4, 6 for D11 and positions #2, 3, 4, 6, 7 for D7).

Overall, the Alanine scanning analysis reveals that D11 and D7 are more influenced and sensitive to Ala mutations compared to MC1 as observed by the ability of the various Ala mutated Tyr peptide to bind properly the Tyr specific TCR-like antibodies. According to the data presented in FIG. 2, D11 and D7 are more peptide restricted and sensitive in their binding properties compared to MC1; they are sensitive (not including anchor positions) to Ala mutations in 4 out of 9 peptide residues while MC1 only to 3 positions. D11 and D7 are even sensitive in their binding properties in a 5th position 7, and 5, respectively. Specifically, D11 decrease the binding in 68% at position #7, 67% position #5, 59% position #8; D7 decrease the binding in 66% at position #5, 63% position #1, 63% position #8.

It is concluded that Ala scanning can be used as a measure to determine the selectivity and fine specificity of TCR-like antibodies. As more sensitivity to Ala mutations is exhibited the more specific and peptide-dependent binding will be observed. This strategy can be used to filter and select for the optimal TCR-like antibodies that exhibited the higher and optimized selectivity and specificity properties as MHC-restricted peptide-specific binders.

Binding Selectivity and Specificity of TCR-Like Antibodies Towards HLA-A2/Tyrosinase To characterize the binding specificity of the isolated TCR-like antibodies the reactivity and specificity of the purified IgGs were assessed by flow cytometry. T2 APCs were loaded with specific or control peptides and incubated with the Ab, followed by incubation with PE-labeled anti-human or mouse. Ab. As shown in FIGS. 3-7, the MC1 (FIG. 7), D11, and D7 (FIGS. 3-6) IgGs bound T2 cells loaded with the tyrosinase peptide but did not bind significantly to cells loaded with control peptides (Table 15). Very low background binding was observed on control peptides with MFIs ratio of 3-7 for MC1 (FIG. 7) while D11 and D7 did not exhibit any background binding (FIG. 3-6). The extent of loaded peptide presentation was monitored by binding of MAb BB7.2 which binds all HLA-A2 peptide complexes. These results indicate that all three TCR-like antibodies exhibited HLA-A2-restricted peptide-specific binding as they bound only to cells presenting the Tryosinase but no other HLA-A2 restricted peptides.

To explore whether the HLA-A2/tyrosinase TCR-like Abs are capable of binding endogenously derived MHC-tyrosinase complexes on the surface of tumor cells, flow cytometry analysis was done on lines derived from melanoma patients. Cells were incubated with anti-tyrosinase 369-377/ HLA-A2 TCR-like antibodies Ab followed by incubation with PE-labeled anti-human or anti-mouse Ab. As shown in FIGS. 8-12 the TCR-like antibodies recognized tyrosinase-positive and HLA-A2-positive cells with a very high intensity. As shown this indicates that large numbers of HLA-A2-tyrosinase complexes are presented on the surface of the melanoma cells. The staining with the TCR-like antibodies was very homogeneous; intracellular staining of these melanoma cells (for example 624.38, and 501A) with Ab against the tyrosinase protein revealed that ~95% of the cells in each line tested express the tyrosinase protein (data not shown). No reactivity was detected with tyrosinase-negative or HLA-A2-negative cells. The specificity of the anti-tyrosinase/HLA-A2 TCR-like Abs was verified by extensive flow cytometry analysis of multiple cell lines of various histological origins which are HLA-A2 positive and Ag (tyrosinase) negative. This analysis is shown in FIGS. 10-12. D11 and D7 reactivity was tested also on a panel of normal primary cells including endothelial cells, fibroblasts, astrocytes, hepatocytes, renal cells, cardiac myocytes, colonic muscle, and PBMCs (FIGS. 13-17). No binding to these HLA-A2+ and Tyr– normal primary cells was observed while background binding was observed when MC1 was tested on PBMCs (FIG. 17). Summary of the analysis of D11 and D7 reactivity with HLA-A2+/Tyrosinase+ melanoma cells as well as extensive panel of HLA-A2+/Tyrosinase– cells of various histological origins including the normal primary cells is presented in FIGS. 18-19. D11 and D7 TCR-like antibodies reactivity looks extremely specific only to melanoma cells expressing HLA-A2 and the antigen tyrosinase.

The overall conclusion from these studies is that the TCR-like Abs are specific and they recognize only the specific peptide-MHC complex presented on the cell surface when the adequate combination of HLA allele and Ag exist. However, careful evaluation of flow cytometry data exhibited results that demonstrate differential selectivity of MC1 compared to D11 and D7. For example, analysis of binding of MC1 to HLA-A2+ and Tyr– cell lines HepG2, SW620, and Loucy as shown in FIG. 9 reveals background binding as measured by MFI, however, similar analysis of D11 and D7 on these cells revealed no binding (FIGS. 10 and 12). Side by side comparison of the three TCR-like antibodies on these and additional cells (FIG. 12) revealed that MCI exhibited significant binding to HLA-A2+/Tyr+ melanoma cells but had background binding on a variety of HLA-A2+/ Tyr– cells (SW620, Colo205, HepG2, Panc1, RPMI, DG75, Jeko1, and Loucy) while D11 and D7 did not exhibit any background binding to these cells.

It may thus be concluded that D11 and D7 are more specific and selective compared to MC1 and that comprehensive flow cytometry studies as well as other assays, for example, functional assays utilizing a large panel of cells of different histological origins that express the appropriate HLA allele and are positive or negative for the antigen are useful tools to evaluate the selectivity of TCR-like antibodies.

To further evaluate the fine specificity of the Tyrosinase specific TCR-like antibodies their reactivity with peptides that exhibit sequence similarity to the native tyrosinase was evaluated (Table 5).

Thus, another round of similar peptides selection is performed when Alanine/Glycine scanning data are available as described above for a particular TCR-like antibody. Based on alanine scanning the contribution of each amino acid residue in the peptide antigen to TCRL binding is measured and evaluated. Similar peptides that preserve the critical positions are identified by the above described tools and are assigned higher priority. These peptides are synthesized and used for fine specificity evaluation as described above.

The strategy described here combines in silico analysis of peptide sequence similarity combined with Mass spectroscopy analysis of eluted HLA peptides, peptide data bases and alanine scanning provides a tool box to fully control peptide search parameters, more than other tools such as BLAST or ScanProsite provide. Additional parameters are employed including the range of allowed peptide lengths, the maximum allowed number or differences in sequence, and the requirement for HLA binding score. The tool also applies the ability to define certain amino acids as equivalent. Most important is the ability to highlight peptides that have been found by mass spectrometry or by peptide databases.

Applying the above tools, the fine specificity of the three TCR-like antibodies was evaluated by synthesizing a large panel of similar peptides that have been selected for evaluation according to the criteria described herein (Table 5). These similar peptides have been loaded on T2 APCs and the reactivity of the TCR-like antibodies was tested. As shown in FIG. 20, when MC1 was tested on a panel of similar peptides in comparison with binding to native tyrosinase peptide it was observed that it exhibits background binding to peptides with sequence similarity to Tyrosinase such as KIAA0335 and KPNA1. However, as shown in FIGS. 21-28, the D11 and D7 TCR-like antibodies did not bind any similar peptide from a large panel of such that were analyzed by peptide loading including no recognition of the KIAA0335 and KPNA1 peptides that exhibited background binding with MC1. These data demonstrate the superior selectivity and fine specificity of D11 and D7 in comparison to MC1 and demonstrates the usefulness of the similar peptide approach and tools developed as described above as important tools to evaluate the selectivity and fine specificity hierarchy when evaluating a panel of TCR-like antibodies for the best and optimal candidate for further evaluation.

Moreover, after alanine scanning of TCR-like antibodies additional similar peptides have been selected and tested. Since each amino acid within the TyrD peptide sequence is unlikely to contribute equally to Tyr TCRL binding, the peptide residues critical for recognition by the Tyr TCRL were identified. A set of synthetic peptides were produced in which each amino acid of the TyrD 9-mer was sequentially replaced by alanine. The ability of Tyr TCRL to bind cells pulsed with each of these alanine-substituted peptides was determined by FACS analysis and the binding results was compared to those obtained with the non-mutated peptide.

The residue at position that alanine substitution result in a large decrease in binding compared to the non-mutated peptide, was considered critical. A directed in-silico search was then carried out to identify protein sequences that contain only the critical positions motif. These peptides were also utilized for specificity evaluation of Tyr TCRLs (Table 5 S17-S23). These alanine scanning analysis-derived similar peptides were synthesized and loaded onto T2 APCs cells and the reactivity of D11 and D7 was tested. As show in FIG. 28, no binding to these peptides was observed, thereby further confirming and strengthening the fine specificity and selectivity of these TCR-like antibodies.

Example IA

Characterization of TCR-Like Antibodies for HLA-A2/Tyrosinase

Comparison of the Fine Specificity of Abs with TCR-Like Specificity to HLA-A2/Tyrosinase369-377

To characterize the binding specificity of the isolated TCR-like antibodies the reactivity and specificity of the purified IgGs (with or without biotinylation) were assessed by flow cytometry. T2 APCs were loaded with Tyrosinase peptide or control peptides (Table 15) and incubated with the Ab (D7, D11 or MC1), followed by incubation with PE-labeled streptavidin or PE-labeled anti mouse Abs. As shown in FIG. 38, D11, and D7 TCRLs bound T2 cells loaded with the tyrosinase peptide but showed no binding to cells loaded with control peptides. In contrast, MC1 TCRL showed binding to T2 cells loaded with both the Tyrosinase peptide and with the irrelevant peptide used as control.

To further evaluate the specificity of the D7 and D11 TCR-like antibodies their reactivity with peptides that exhibit sequence similarity to the tyrosinase peptide was evaluated. The peptides are shown in Table 5.

As shown in FIG. 39 MC1 TCRL exhibits readily detectable binding to various peptides with sequence similarity to Tyrosinase peptide such as KIAA0335 and KPNA1 (Table 14) as well as to peptides marked as S2, S4, S5, S9, S11, S13, S18, (S19, S22 and S23). D11 and D7 TCR-like antibodies did not bind any of the peptides from this same panel of similar peptides. These data demonstrate the superior selectivity and fine specificity of D11 and D7 TCRLs compared to MC1 TCRL and demonstrates the usefulness of the similar peptide approach and tools developed as described above to evaluate the selectivity and fine specificity hierarchy of TCRLs.

The present inventors explored binding specificity of the HLA-A2/tyrosinase TCR-like Abs to MHC-tyrosinase peptide complexes endogenously displayed on the surface of melanoma cell lines. Cells were incubated with anti-tyrosinase 369-377/HLA-A2 TCR-like antibodies Ab (with or without biotinylation) followed by incubation with PE-labeled streptavidin or anti-mouse Abs. A panel of tumor cells and normal primary cells that have been characterized for HLA-A2 (positive) and Tyrosinase (positive or negative) expression was used to compare the binding of the TCR-like antibodies. As shown in FIG. 40A-C, the TCR-like antibodies recognized tyrosinase-positive and HLA-A2-positive cells. The TCR-Like antibodies were tested on multiple HLA-A2-positive cell lines of various origin that do not show Tyr RNA expression (Tyr-negative). As shown in FIGS. 40A-B, D11 and D7 TCRLs did not bind any of these cells while MC1 readily stained various HLA-A2+/Tyr– cells. D7 and D11 TCRLs did not exhibit any binding to normal primary cells, while MC1 displayed detectable binding to some of them (FIG. 40C).

Overall, D7 and D11 TCRLs demonstrated superior specificity and selectivity recognizing tyrosinase peptide presented by HLA-A2 compared to MC1 TCRL.

Functional assays were used to further characterize the D7 and D11 TCR-like antibodies. TCRLs variable regions were fused to an anti-CD3 scFv which can re-target effector T cells to kill tumor target cell in a of bi-specific format. As shown in FIGS. 41-44, D7 and D11 CD3 Bi-specific TCR-like antibody constructs showed robust cytotoxicity against melanoma 501A cells in vitro in the presence of human PBMCs. Panc-1, Tyrosinase negative cell line served as negative control and demonstrated no cytotoxocitiy. No cytotoxicity was detected against a panel of HLA-A2+/Tyr– normal human primary cells with D7 and D11 TCRLs confirming their selectivity.

Example IB

In Vivo Efficacy of D7 BS TCRL in s.c. 501A Melanoma Tumor Formation Model in NOD/SCID Mice FIG. 45 shows in vivo efficacy of D7 BS TCRL in S.C. 501A melanoma tumor formation model in NOD/SCID mice. Clearly, administration of the bispecific antibody completely inhibited tumor formation over 65 days of the experiment, as evidenced by tumor volume. The results support the use of variable sequences of the TCRLs described herein in clinical settings.

Example II

TCR-Like Antibodies for HLA-A2/WT1

Isolation and Characterization of Abs with TCR-Like Specificity to HLA-A2/WT1

To generate such antibodies with a specificity to the HLA-A2/WT1 complex, recombinant peptide-HLA-A2 complexes were generated that present the WT1 peptide (RMFPNAPYL, SEQ ID NO: 151) using a single chain MHC construct. The generation of antibodies was as described in the general materials and methods as well as in Example I above, A TCR-like specific clone termed B47 (also referred to as B47B6) was isolated and characterized (FIG. 70).

As a comparison for TCR-like antibody binding selectivity, a TCR-like antibody termed ESK1 Dao T, Yan S, Veomett N, Pankov D, Zhou L, Korontsvit T, Scott A, Whitten J, Maslak P, Casey E, Tan T, Liu H, Zakhaleva V, Curcio M, Doubrovina E, O'Reilly R J, Liu C, Scheinberg D A.

The binding affinity of B47 was evaluated by surface plasmon resonance (SPR) binding analysis in which the isolated purified IgG TCR-like antibody was immobilized to the SPR sensor chip by using anti-mouse IgG to indirectly immobilize the TCR-like antibodies on the chip surface. The analyte is the purified single-chain recombinant HLA-A2/WT1 complex used at various concentrations. As shown in FIG. 29, the sensorgrams of SPR analysis revealed an affinity for the HLA-A2/WT1 specific TCR-like antibody clone B47 of 4.4 nM.

To characterize the binding specificity of the isolated TCR-like antibodies the reactivity and specificity of the purified IgGs were assessed by flow cytometry. T2 APCs were loaded with specific or control peptides (Table 15) and incubated with the Ab, followed by incubation with PE-labeled anti-human or mouse Ab. As shown in FIGS. 30 and 31, B47 and ESK1 bound T2 cells loaded with the WT1 peptide (FIG. 30) but did not bind to cells loaded with control peptides (FIG. 31). Of significance difference was the binding intensity observed for B47 and ESK1. While B47 bound intensely to T2 cells loaded with $10^{-4}$-$10^{-5}$M peptide, ESK1 bound much weaker to T2 cells loaded with $10^{-4}$M WT1 peptide (MFI 18 for ESK1 compared with 474 for B47). At peptide concentration of $10^{-5}$M B47 still bound significantly (MFI 88) while binding of ESK1 was almost undetectable or very low (FIG. 30). These results indicated marked differences in the affinity and binding sensitivity of B47 compared to ESK1 with sharp decrease in the binding intensity of ESK1 compared to B47 with 10× decreases in peptide concentration. B47 and ESK1 did not bind T2 APCs loaded with control HLA-A2 restricted peptides (FIG. 31). These results indicate that both TCR-like antibodies exhibited HLA-A2-restricted peptide-specific binding as they bound only to cells presenting the WT1 but no other HLA-A2 restricted peptides.

To further investigate the WT1 TCR-like antibodies fine specificity evaluation of binding to similar peptides identified in silico with the strategy described above was performed. As shown in FIGS. 32 and 33, B47 did not bind any similar peptide from a designed panel (Table 6). However, as shown in FIG. 32, ESK1 exhibited low background binding with two similar peptides. B47 was evaluated on additional control peptides and similar peptides (FIG. 34). Further analysis of these TCR-like antibodies was performed by flow cytometry using tumor cells that are HLA-A2 and express or not the WT1 antigen. As shown in FIG. 35, the ESK1 WT1 TCR-like antibody bound intensely to HLA-A2+/WT+ BV173 and SET2 cells however B47 did not exhibit any binding to these cells to the level of flow cytometry sensitivity. To further investigate specificity the reactivity of ESK1 and B47 was evaluated on cells that are HLA-A2 but do not express the WT1 gene as evaluated by PCR. As shown B47 did not bind to any of these cells while ESK1 bound to 501, A498, and SKMEL cells that were found to be WT1 negative. Other WT1 negative cells were not bound by ESK1. The level of HLA-A2 expression was monitored with MAb BB7.2 which recognizes all HLA-A2/peptide molecules on the cell surface. A summary of binding data for B47 WT-specific TCR-like antibody is shown in FIG. 36.

To further investigate the conflicting data of the binding of ESK1 and B47 to HLA-A2+/WT1+ BV173 and SET2 cells, i.e binding could be detected significantly by ESK1 but not B47 we employed direct biochemical means to evaluate actual WT1 presentation on these cells. We employed HLA peptide elution strategies from various tissues as well from BV173 and SET2 cells followed by MS analysis of eluted peptides. The data of these experiments indicate that the WT1 peptide has not been detected in any of the MS runs of clinical tissues or cell lines. In depth analysis of the BV173 or SET-2 cell lines (mRNA WT1-positive) failed to detect the peptide (Orbitrap or Q Exactive MS instruments). The WT1 peptide was detected by Orbi-Trap MS following direct elution from T2 peptide-loaded cells. These T2 cells were loaded with various WT1 peptide concentrations of $10^{-5}$, $10^{-7}$, $10^{-9}$ M and the peptide was detected by the MS in elutions from T2 APCs loaded with peptide concentration of $10^{-5}$ and $10^{-7}$M. Detecting the peptide from T2 cells loaded at $10^{-7}$M peptide by the MS corresponds to actual presentation of ~250 sites/cell (using the Orbitrap MS).

These data exemplifies the usefulness of the described binding tools towards peptide loaded cells that display similar peptides and cells of various histological origins to evaluate the specificity and selectivity of TCR-like antibodies.

To further investigate epitope specificity, alanine scanning mutagenesis was performed on the WT1 peptide sequence. As shown in FIG. 37 which demonstrates that only mutation in position 1 of the WT1 peptide influenced the binging intensity of ESK1 indicating that the binding selectivity and fine specificity of ESK1 is limited compared to B47 as also observed for the specificity pattern as observed for similar peptides and for cells that are HLA-A2+/WT1−/These data suggest that the selectivity and fine specificity of B47 is superior compared to ESK1 and that the tool box presented herein is a valuable tool to evaluate the selectivity and fine specificity of TCR-like antibodies in the process of their selection, characterization, and pre-clinical development.

Example IIA

TCR-Like Antibodies for HLA-A2/WT1

Comparison of Fine Specificity of Abs with TCR-Like Specificity to HLA-A2/WT1

The selectivity of TCR-like antibodies B47 and ESK1 both recognizing WT1 peptide was compared (Dao et al. Sci Transl Med. 2013 Mar. 13; 5(176):176ra33)

T2 APCs were loaded with specific (WT1, SEQ ID NO: 141) or control peptides (Table 15) and incubated with the B47 and ESK1 antibodies, followed by incubation with PE-labeled streptavidin or anti-mouse Abs. Both B47 and ESK1 TCRLs bound T2 cells loaded with the WT1 peptide but did not bind to cells loaded with control peptides (FIG. 46). A panel of similar peptides (Table 6) was synthesized to further characterize specificity of the WT1 TCRLs. The B47 TCRL did not bind to any of the similar peptides loaded onto T2 cells while ESK1 showed detectable binding to several similar peptides (FIG. 47). ESK1 TCRL showed binding to a similar peptide derived from HDAC2 (Histone deacetylase 2, Table 14) that is ubiquitously presented by many normal cells. WT1-S10 (SEQ ID NO: 151) is presented in normal tissues as evidenced by mass spectrometry in brain, cerebral cortex, heart, kidney, liver, lung, and other normal tissues (Table 14).

Further characterization of binding of B47 and ESK1 TCRLs by SPR showed that affinity of B47 (5 nM) is much stronger than that of ESK1 (200 nM) mainly due to faster dissociation rate of ESK1 and MHC-WT1 peptide complexes (FIG. 48).

Additional alanine scanning mutagenesis of the WT1 peptide was performed to refine peptide epitope specificity of B47 TCR-like antibodies (FIG. 49). The mutant peptides were loaded onto T2 cells and binding assay was performed as described above. The loading of the various Ala mutants was monitored by flow cytometry using BB7.2 monoclonal antibody against HLA-A2.

As shown in FIG. 49, substitutions to Ala at some positions significantly affected B47 binding to the mutated peptides. B47 TCRL exhibited greater sensitivity to positional substitutions (as compared to ESK1, FIG. 37). The B47 TCR-like antibody lost >73% of its binding to presented peptide with when 4 residues in the peptide were mutated to Alanine (positions 1, 3, 4, and 7). A 5th position sensitivity can be attributed to position number 5. For both B47 and ESK1 TCRLs position 2 was critical as it is expected to serve as anchor position for the peptides in the HLA-A2 peptide binding groove.

Further characterization and comparison between B47 and ESK1 TCRLs was done on tumor cell lines and primary cells of various origins. As shown in FIG. 50, B47 did not bind to a panel of cells that were all HLA-A2 positive and WT1 mRNA positive or negative cells. In contrast, ESK1 TCRL bound to a number of both tumor and normal primary cells (all HLA-A2+). For example, JVM2 and IM9 (both HLA-A2 positive and WT1 negative) as well as normal primary astrocytes showed binding. Cytotoxicity assays using TCRL-aCD3 bi-specific constructs and human PBMCs showed that B47 TCRL did not induce death of HLA-A2+/WT1+ or HLA-A2+/WT1− cells while ESK1 TCRL-aCD3 was cytotoxic to a number of cells, including WT-1 negative. Thus, B47 TCRL demonstrate superior specificity in both binding and functional activity in the bi-specific format compared to ESK1 that binds to and re-targets CD3 T-cells toward some cells, including normal primary cells, regardless of WT-1 expression.

Example III

TCR-Like Antibodies with Specificity to HLA-A2/MAGE-A4

Example IIIA

Isolation and Characterization of TCRL with Specificity to HLA-A2/MAGE-A4

To characterize the binding specificity of the isolated TCR-like antibodies the reactivity and specificity of the purified IgGs were assessed by flow cytometry. T2 APCs were loaded with MAGE-A4 peptide or control peptides (Table 15) and incubated with the TCRL Ab C106B, followed by incubation with PE-labeled streptavidin or PE-labeled anti mouse Abs. As shown in FIG. 52, C106B9 bound T2 cells loaded with the MAGE-A4 peptide but showed no binding to cells loaded with control peptides.

To further evaluate the specificity of the C106B9 TCR-like antibody its reactivity with peptides that exhibit sequence similarity to the MAGE-A4 peptide was evaluated. The peptides are shown in Table 8.

As shown in FIG. 53, C106B9 TCRL did not bind any of the peptides from this panel of similar peptides. These data demonstrate the high selectivity and fine specificity of C106B9 and demonstrates the usefulness of the similar peptide approach and tools developed as described above to evaluate the selectivity and fine specificity of TCRLs.

To determine the apparent affinity of the isolated TCR-like antibody, surface plasmon resonance (SPR) binding analysis was used in which the isolated purified IgG TCR-like antibody was immobilized to the SPR sensor chip by using anti-mouse IgG to indirectly immobilize the TCR-like antibodies on the chip surface. The analyte is the purified single-chain recombinant HLA-A2/MAGE-A4 complex used at various concentrations. As shown in FIG. 54, the sensorgrams of SPR analysis revealed affinity for the HLA-A2/MAGE-A4 specific TCR-like antibody clone C106B9 with corresponding affinity of 8.8 nM.

To investigate the fine peptide epitope specificity of the isolated TCR-like antibodies towards the MAGE-A4 peptide alanine scanning was performed in which specific residues in the peptide were mutated to alanine and the binding of the TCR-like antibody to Ala mutated peptides was tested by their loading onto T2 antigen presenting cells (Table 9). Binding was monitored by flow cytometry and extent of binding of TCR-like antibodies to the mutated presented peptides as measured by mean fluorescence intensity (MFI) was compared in comparison to T2 APCs loaded with the native unmutated MAGE-A4 peptide. The proper loading of the various Ala mutated peptides (described in FIG. 2) was monitored by flow cytometry using BB7.2 a monoclonal antibody for HLA-A2.

All Ala mutated peptides were efficiently loaded onto T2 cells in comparison to the native un-mutated MAGE-A4 peptide (data not shown). As shown in FIG. 55, The TCR-like antibody exhibited peptide dependent binding as specific mutations affected the binding and induced a decrease in the binding intensity of the TCR-like antibody upon introduction of Ala at specific peptide positions. These results indicate that MAGE-A4 TCR-like antibody exhibited peptide-specific and restricted binding in the context of HLA-A2 loaded with various Ala mutated MAGE-A4 peptides, indicating that this antibody is TCR-like in its binding properties, thus, it binds the MHC-peptide complex with MHC-restricted and peptide-specific manner.

The C106B9 TCR-like antibody exhibited a marked decrease of 90% in binding to Ala mutated peptide at four positions #4, 5, 6, and 7. A 5th position sensitivity can be attributed to position number 2 (decrease of 33%).

Overall, the Alanine scanning analysis reveals that Ala scanning can be used as a measure to determine the selectivity and fine specificity of TCR-like antibodies. As more sensitivity to Ala mutations is exhibited the more specific and peptide-dependent binding will be observed. This strategy can be used to filter and select for the optimal TCR-like antibodies that exhibited the higher and optimized selectivity and specificity properties as MHC-restricted peptide-specific binders.

The present inventors explored binding specificity of the HLA-A2/MAGE-A4 TCR-like Ab to MHC-MAGE-A4 peptide complexes endogenously displayed on the surface of tumor cell lines. Cells were incubated with anti-MAGE-A4–HLA-A2 TCR-like antibodies Ab followed by incubation with PE-labeled streptavidin or anti-mouse Abs. A panel of tumor cells and normal primary cells that have been characterized for HLA-A2 (positive) and MAGE-A4 (positive or negative) expression was used to compare the binding of the TCR-like antibodies. As shown in FIG. 56, the TCR-like antibody recognized with low intensity MAGE4-positive and HLA-A2-positive cells. The TCR-Like antibodies were tested on multiple HLA-A2-positive cell lines of various origin that do not show MAGE-A4 RNA expression (MAGE-A4-negative), killing activity of these cells with a MAGE-A4/HLA-A2 TCRL-Bispecific construct was also tested. As shown in FIG. 56, C106B9 TCRL did not bind any of these cells.

Functional assays were used to further characterize the C106B9 TCR-like antibody. TCRLs variable regions were fused to an anti-CD3 scFv which can re-target effector T cells to kill tumor target cell in a of bi-specific format. As shown in FIG. 57, the C106B9 Bi-specific TCR-like antibody constructs showed robust cytotoxicity against MAGE-A4 positive cells in vitro in the presence of human PBMCs. TCCSUP and OVCAR, MAGE-A4 negative cell line served as negative control and demonstrated no cytotoxicity. As further shown in FIG. 58, No cytotoxicity was detected against a panel of HLA-A2+/MAGE-A4− normal human primary cells with C106B9 TCRL confirming its selectivity.

Example IIIB

In Vivo Efficacy of MAGE-A4 C106B9 BS TCRL in s.c. A375 Melanoma Tumor Formation Model in NOD/SCID Mice FIG. 59 shows in vivo efficacy of C106B9 BS TCRL in S.C. A375 melanoma tumor formation model in NOD/SCID mice. Clearly, administration of the bispecific antibody completely inhibited tumor formation over 35 days of the experiment, as evidenced by tumor volume. The results support the use of variable sequences of the TCRLs described herein in clinical settings.

Example IV

TCR-Like Antibodies with Specificity to HLA-A2/MAGE-A9 Isolation and Characterization of TCRL with Specificity to HLA-A2/MAGE-A9

To characterize the binding specificity of the isolated TCR-like antibodies the reactivity and specificity of the purified IgGs were assessed by flow cytometry. T2 APCs were loaded with MAGE-A9 peptide or control peptides and incubated with the TCRL Ab F184C7, followed by incubation with PE-labeled streptavidin or PE-labeled anti mouse Abs. As shown in FIG. 60, F184C7 bound T2 cells loaded with the MAGE-A9 peptide but showed no binding to cells loaded with control peptides.

To further evaluate the specificity of the F184C7 TCR-like antibody its reactivity with peptides that exhibit sequence similarity to the MAGE-A9 peptide was evaluated. The peptides are shown in Table 10.

As shown in FIG. 61, F184C7 TCRL did not bind any of the peptides from this panel of similar peptides. These data demonstrate the high selectivity and fine specificity of F184C7 and demonstrates the usefulness of the similar peptide approach and tools developed as described above to evaluate the selectivity and fine specificity of TCRLs.

To investigate the fine peptide epitope specificity of the isolated TCR-like antibodies towards the MAGE-A9 peptide alanine scanning was performed in which specific residues in the peptide were mutated to alanine and the binding of the TCR-like antibody to Ala mutated peptides was tested by their loading onto T2 antigen presenting cells (Table 11). Binding was monitored by flow cytometry and extent of binding of TCR-like antibodies to the mutated presented peptides as measured by mean fluorescence intensity (MFI) was compared in comparison to T2 APCs loaded with the native unmutated MAGE-A9 peptide. The proper loading of the various Ala mutated peptides (described in FIG. 2) was monitored by flow cytometry using BB7.2 a monoclonal antibody for HLA-A2.

All Ala mutated peptides were efficiently loaded onto T2 cells in comparison to the native un-mutated MAGE-A9 peptide (data not shown). As shown in FIG. 62, The TCR-like antibody exhibited peptide dependency binding as specific mutations affected the binding and induced a decrease in the binding intensity of the TCR-like antibody upon introduction of Ala at specific peptide positions. These results indicate that MAGE-A9 TCR-like antibody exhibited peptide-specific and restricted binding in the context of HLA-A2 loaded with various Ala mutated MAGE-A9 peptides, indicating that this antibody is TCR-like in its binding properties, thus, it binds the MHC-peptide complex with MHC-restricted and peptide-specific manner.

The F184C7 TCR-like antibody exhibited a marked decrease of 90% in binding to five Ala mutated peptide at five positions #3, 5, 6, 7 and 8.

Overall, the Alanine scanning analysis reveals that Ala scanning can be used as a measure to determine the selectivity and fine specificity of TCR-like antibodies. As more sensitivity to Ala mutations is exhibited the more specific and peptide-dependent binding will be observed. This strategy can be used to filter and select for the optimal TCR-like antibodies that exhibited the higher and optimized selectivity and specificity properties as MHC-restricted peptide-specific binders.

The present inventors explored binding specificity of the HLA-A2/MAGE-A9 TCR-like Ab to a panel of normal primary cells of various origin that do not show MAGE-A9 RNA expression. As shown in FIG. 63, F184C7 TCRL did not bind any of these cells. Positive control was T2 cells loaded with the MAGE-A9 peptide to which F184C7 bound intensely.

Example V

TCR-Like Antibodies with Specificity to HLA-A2/PAP Isolation and Characterization of TCRL with Specificity to HLA-A2/PAP To characterize the binding specificity of the isolated TCR-like antibodies the reactivity and specificity of the purified IgGs were assessed by flow cytometry. T2 APCs were loaded with PAP peptide or control peptides and incubated with the TCRL Ab D10A3, followed by incubation with PE-labeled streptavidin or PE-labeled anti mouse Abs. As shown in FIG. 64, D10A3 bound T2 cells loaded with the PAP peptide but showed no binding to cells loaded with control peptides.

To further evaluate the specificity of the D10A3 TCR-like antibody its reactivity with peptides that exhibit sequence similarity to the PAP peptide was evaluated. The peptides are shown in Table 12.

As shown in FIG. 65, D10A3 TCRL did not bind any of the peptides from this panel of similar peptides. These data demonstrate the high selectivity and fine specificity of D10A3 and demonstrates the usefulness of the similar peptide approach and tools developed as described above to evaluate the selectivity and fine specificity of TCRLs.

To investigate the fine peptide epitope specificity of the isolated TCR-like antibodies towards the PAP peptide alanine scanning was performed in which specific residues in the peptide were mutated to alanine and the binding of the TCR-like antibody to Ala mutated peptides was tested by their loading onto T2 antigen presenting cells (Table 13). Binding was monitored by flow cytometry and extent of binding of TCR-like antibodies to the mutated presented peptides as measured by mean fluorescence intensity (MFI) was compared in comparison to T2 APCs loaded with the native unmutated PAP peptide. The proper loading of the various Ala mutated peptides (described in FIG. 2) was monitored by flow cytometry using BB7.2 a monoclonal antibody for HLA-A2.

All Ala mutated peptides were efficiently loaded onto T2 cells in comparison to the native un-mutated PAP peptide (data not shown). As shown in FIG. 66, The TCR-like antibody exhibited peptide dependency binding as specific mutations affected the binding and induced a decrease in the binding intensity of the TCR-like antibody upon introduction of Ala at specific peptide positions. These results indicate that PAP TCR-like antibody exhibited peptide-specific and restricted binding in the context of HLA-A2 loaded with various Ala mutated PAP peptides, indicating that this antibody is TCR-like in its binding properties, thus, it binds the MHC-peptide complex with MHC-restricted and peptide-specific manner.

The D10A3 TCR-like antibody exhibited a marked decrease of 90% in binding to three Ala mutated peptide at three positions #3, 6, and 8. Decrease of 70% in binding to one Ala mutated peptide at position #4 was also observed. A 5th position sensitivity can be attributed to position number 7 (decrease of 45%).

The present inventors explored binding specificity of the HLA-A2/PAP TCR-like Ab to a panel of normal primary cells of various origin that do not show PAP RNA expression. As shown in FIG. 67, D10A3 TCRL did not bind any of these cells. Positive control was T2 cells loaded with the PAP peptide to which D10A3 TCRL bound strongly.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An affinity binding entity comprising an antigen binding domain comprising:
   (i) CDR sequences of an immunoglobulin heavy chain which are N—C ordered:

```
   CDR1 HC
                              SEQ ID NO: 341
   GYWIE

CDR2 HC
                              SEQ ID NO: 342
   EILPGSGGTNYNEKFKG

CDR3 HC
                              SEQ ID NO: 343
   DSNSFTY;
   ``` and
   (ii) CDR sequences of an immunoglobulin light chain which are N—C ordered:

```
   CDR1 LC
                              SEQ ID NO: 335
   SVSSSVDYIH

CDR2 LC
                              SEQ ID NO: 336
   STSILAS

CDR3 LC
                              SEQ ID NO: 337
   QQRSSYPPT,
   ``` wherein said affinity binding entity is capable of binding HLA-A2/MAGE-A4$_{230\text{-}239}$ in an MHC restricted manner.

2. The affinity binding entity of claim 1, being selected from the group consisting of an antibody, a T-cell receptor (TCR), and a chimeric antigen receptor (CAR).

3. The affinity binding entity of claim 1, being an antibody.

4. The affinity binding entity of claim 1, being a TCR.

5. The affinity binding entity of claim 1, being a CAR.

6. The affinity binding entity of claim 1, being a soluble entity.

7. The affinity binding entity of claim 2, being a humanized antibody.

8. The affinity binding entity of claim 1, further comprising a therapeutic moiety.

9. The affinity binding entity of claim 2, further comprising a therapeutic moiety.

10. The affinity binding entity of claim 1, further comprising a detectable moiety.

11. The affinity binding entity of claim 2, wherein said antibody is a single chain Fv (scFv), a bi-specific antibody, or a full-length antibody.

12. An expression vector comprising a polynucleotide comprising a nucleic acid sequence encoding the affinity binding entity of claim 1 operably linked to a cis-acting regulatory element.

13. A cell comprising the expression vector of claim 12.

14. An in vitro method of detecting a cancer cell, comprising:
   contacting the cell with the antibody of claim 2, under conditions which allow immunocomplex formation, and
   detecting the presence or level thereof of said immunocomplex,
   wherein a presence of said immunocomplex, or level thereof, is indicative of the cancer cell,
   wherein the cancer is selected from the group consisting of melanoma, ovarian cancer, T cell leukemia/lymphoma, testicular cancer, head and neck cancer, bladder cancer, and esophagus cancer.

15. A method of diagnosing cancer in a subject in need thereof, comprising:
   contacting a cell of the subject with the antibody of claim 2, under ex vivo conditions which allow immunocomplex formation, and
   detecting the presence or level thereof of said immunocomplex,
   wherein a presence of said immunocomplex or level thereof is indicative of the cancer,
   wherein the cancer is selected from the group consisting of melanoma, ovarian cancer, T cell leukemia/lymphoma, testicular cancer, head and neck cancer, bladder cancer, and esophagus cancer.

16. A pharmaceutical composition comprising the affinity binding entity of claim 2, the expression vector of claim 12 or the cell of claim 13 and a carrier or excipient.

* * * * *